US011667723B2

(12) United States Patent
Zhao et al.

(10) Patent No.: US 11,667,723 B2
(45) Date of Patent: Jun. 6, 2023

(54) LYMPHOCYTES-ANTIGEN PRESENTING CELLS CO-STIMULATORS AND USES THEREOF

(71) Applicant: UTC Therapeutics (Shanghai) CO., LTD., Shanghai (CN)

(72) Inventors: Yangbing Zhao, Shanghai (CN); Xiaojun Liu, Shanghai (CN); Xiaodong Song, Shanghai (CN); Bin Li, Shanghai (CN); Jintao Feng, Shanghai (CN)

(73) Assignee: UTC Therapeutics (Shanghai) CO., LTD., Shanghai (CN)

( * ) Notice: Subject to any disclaimer, the term of this patent is extended or adjusted under 35 U.S.C. 154(b) by 0 days.

(21) Appl. No.: 17/821,182

(22) Filed: Aug. 21, 2022

(65) Prior Publication Data

US 2023/0044380 A1 Feb. 9, 2023

Related U.S. Application Data

(63) Continuation of application No. PCT/CN2021/112742, filed on Aug. 16, 2021.

(30) Foreign Application Priority Data

Aug. 17, 2020 (WO) ................ PCT/CN2020/109484

(51) Int. Cl.
| | | |
|---|---|---|
| *C07K 16/28* | (2006.01) | |
| *A61P 35/00* | (2006.01) | |
| *A61K 35/17* | (2015.01) | |
| *C07K 14/725* | (2006.01) | |
| *C07K 14/705* | (2006.01) | |
| *C12N 5/0783* | (2010.01) | |
| *C12N 15/62* | (2006.01) | |
| *C12N 15/86* | (2006.01) | |
| *A61K 38/00* | (2006.01) | |
| *A61K 39/00* | (2006.01) | |

(52) U.S. Cl.
CPC .......... *C07K 16/2878* (2013.01); *A61K 35/17* (2013.01); *A61P 35/00* (2018.01); *C07K 14/7051* (2013.01); *C07K 14/70521* (2013.01); *C07K 14/70578* (2013.01); *C12N 5/0636* (2013.01); *C12N 15/625* (2013.01); *C12N 15/86* (2013.01); *A61K 38/00* (2013.01); *A61K 39/00* (2013.01); *C07K 2319/00* (2013.01); *C12N 2740/15043* (2013.01)

(58) Field of Classification Search
CPC .......... C07K 16/00–468; C07K 16/278; C07K 14/705–70596; C07K 14/7051; C07K 14/70521; C07K 2319/00–95
See application file for complete search history.

(56) References Cited

U.S. PATENT DOCUMENTS

| | | | |
|---|---|---|---|
| 6,132,992 A | 10/2000 | Ledbetter et al. | |
| 7,193,064 B2* | 3/2007 | Mikayama | A61P 37/08 435/69.6 |
| 10,174,121 B2* | 1/2019 | Benatuil | A61P 1/04 |
| 10,449,227 B2 | 10/2019 | McLaughlin et al. | |
| 10,583,181 B2 | 3/2020 | Ochi | |
| 10,662,249 B1 | 5/2020 | Hu et al. | |
| 10,703,794 B2 | 7/2020 | Maher et al. | |
| 2003/0223989 A1 | 12/2003 | Pluenneke | |
| 2005/0255106 A1 | 11/2005 | Diehl et al. | |
| 2007/0036783 A1 | 2/2007 | Humeau et al. | |
| 2013/0129723 A1 | 5/2013 | Blankenship et al. | |
| 2015/0307620 A1 | 10/2015 | Vella et al. | |
| 2017/0267756 A1 | 9/2017 | Riddell et al. | |
| 2017/0275375 A1 | 9/2017 | Rossi et al. | |
| 2018/0369411 A1 | 12/2018 | Yu et al. | |
| 2019/0202937 A1 | 7/2019 | Humphreys et al. | |
| 2019/0276511 A1 | 9/2019 | Sahin et al. | |
| 2020/0071400 A1 | 3/2020 | Cao et al. | |
| 2021/0046113 A1* | 2/2021 | Qian | C07K 14/70521 |

FOREIGN PATENT DOCUMENTS

| | | |
|---|---|---|
| CN | 1817909 A | 8/2006 |
| CN | 107428842 A | 12/2017 |
| CN | 110078830 A | 8/2019 |
| CN | 110669139 A | 1/2020 |
| JP | 2006265155 A | 10/2006 |

(Continued)

OTHER PUBLICATIONS

Azuma, M. "Co-signal Molecules in T-Cell Activation. In: Azuma, M., Yagita, H. (eds) Co-signal Molecules in T Cell Activation. Advances in Experimental Medicine and Biology," vol. 1189. Springer, Singapore (2019) doi.org/10.1007/978-981-32-9717-3_1 (Year: 2019).*

Djureinovic et al., Cancers 13:1302; doi.org/10.3390/cancers13061302 (Year: 2021).*

Drent E et al. Combined CD28 and 4-1BB Costimulation Potentiates Affinity-tuned Chimeric Antigen Receptor-engineered T Cells. Clin Cancer Res. Jul. 1, 2019;25(13):4014-4025. doi: 10.1158/1078-0432.CCR-18-2559. Epub Apr. 12, 2019. PMID: 30979735; PMCID: PMC7477921.

(Continued)

*Primary Examiner* — Jessica H Roark
(74) *Attorney, Agent, or Firm* — Lin Yu, Esq.; Juniv LLP

(57) ABSTRACT

Disclosed herein are fusion proteins having a first domain that activates an antigen-presenting cell (APC) (e.g., a dendritic cell) by binding to an activation receptor of the APC, and a second domain that activates an immune effector cell (e.g., a T cell) by targeting a co-stimulatory signaling pathway of the immune effector cell, as well as polynucleotides that encode such fusion proteins. Disclosed herein are also genetically engineered immune effector cells expressing such fusion protein, methods of their production, and their uses in treatment of diseases such as cancers.

36 Claims, 87 Drawing Sheets

Specification includes a Sequence Listing.

(56) References Cited

FOREIGN PATENT DOCUMENTS

| | | |
|---|---|---|
| WO | 1999042077 A2 | 8/1999 |
| WO | 2001049318 A1 | 7/2001 |
| WO | 2001056603 A1 | 8/2001 |
| WO | 2002036141 A2 | 5/2002 |
| WO | 2002066044 A2 | 8/2002 |
| WO | 2003057732 A3 | 10/2003 |
| WO | 2003084999 A1 | 10/2003 |
| WO | 2002072141 A9 | 9/2004 |
| WO | 2005092927 A1 | 10/2005 |
| WO | 2006045750 A2 | 7/2006 |
| WO | 2006074399 A2 | 7/2006 |
| WO | 2006114115 A1 | 11/2006 |
| WO | 2006138670 A2 | 12/2006 |
| WO | 2006115413 A3 | 4/2007 |
| WO | 2008051424 A2 | 5/2008 |
| WO | 2011090762 A1 | 7/2011 |
| WO | 2011130434 A9 | 7/2012 |
| WO | 2013123061 A1 | 8/2013 |
| WO | 2014028560 A2 | 2/2014 |
| WO | 2014116846 A2 | 7/2014 |
| WO | 2014134165 A1 | 9/2014 |
| WO | 2015095895 A1 | 6/2015 |
| WO | 2015142675 A2 | 9/2015 |
| WO | 2016019969 A1 | 2/2016 |
| WO | 2016023960 A1 | 2/2016 |
| WO | 2016070061 A1 | 5/2016 |
| WO | 2016110584 A1 | 7/2016 |
| WO | 2016118641 A1 | 7/2016 |
| WO | 2016122738 A1 | 8/2016 |
| WO | 2016126781 A1 | 8/2016 |
| WO | 2016145085 A2 | 9/2016 |
| WO | 2017027291 A1 | 2/2017 |
| WO | 2017034615 A1 | 3/2017 |
| WO | 2017077085 A2 | 5/2017 |
| WO | 2017151940 A2 | 9/2017 |
| WO | 2017162797 A1 | 9/2017 |
| WO | 2017167350 A1 | 10/2017 |
| WO | 2017176525 A1 | 10/2017 |
| WO | 2017180913 A9 | 11/2017 |
| WO | 2017185662 A1 | 11/2017 |
| WO | 2017205738 A1 | 11/2017 |
| WO | 2017210058 A1 | 12/2017 |
| WO | 2018011421 A1 | 1/2018 |
| WO | 2018064190 A1 | 4/2018 |
| WO | 2018075978 A1 | 4/2018 |
| WO | 2018083126 A1 | 5/2018 |
| WO | 2018099539 A1 | 6/2018 |
| WO | 2018119298 A1 | 6/2018 |
| WO | 2018129474 A1 | 7/2018 |
| WO | 2018132513 A1 | 7/2018 |
| WO | 2018140890 A1 | 8/2018 |
| WO | 2018182935 A1 | 10/2018 |
| WO | 2018213747 A1 | 11/2018 |
| WO | 2019005637 A2 | 1/2019 |
| WO | 2019032945 A1 | 2/2019 |
| WO | 2019037711 A1 | 2/2019 |
| WO | 2019067951 A2 | 4/2019 |
| WO | 2019116046 A1 | 6/2019 |
| WO | 2019129047 A1 | 7/2019 |
| WO | 2019129086 A1 | 7/2019 |
| WO | 2019129124 A1 | 7/2019 |
| WO | 2019129142 A1 | 7/2019 |
| WO | 2019129173 A1 | 7/2019 |
| WO | 2019129174 A1 | 7/2019 |
| WO | 2019129177 A1 | 7/2019 |
| WO | 2019129644 A1 | 7/2019 |
| WO | 2019136307 A1 | 7/2019 |
| WO | 2020042647 A1 | 3/2020 |
| WO | 2020070303 A1 | 4/2020 |
| WO | 2020088631 A1 | 5/2020 |
| WO | 2020104531 A1 | 5/2020 |
| WO | 2020118076 A1 | 6/2020 |
| WO | 2020127376 A2 | 6/2020 |
| WO | 2020131697 A2 | 6/2020 |
| WO | 2020152451 A1 | 7/2020 |
| WO | 2020163222 A1 | 8/2020 |

OTHER PUBLICATIONS

Houtenbos, Ilse, Saskia Santegoets, Theresia M. Westers, Quinten Waisfisz, Sergey Kipriyanov, Fedor Denkers, Rik J. Scheper, Tanja D. De Gruijl, Gert J. Ossenkoppele, and Arjan A. Van De Loosdrecht. "The novel bispecific diabody αCD40/αCD28 strengthens leukaemic dendritic cell-induced T-cell reactivity." British journal of haematology 142, No. 2 (2008): 273-283.

* cited by examiner

CD27-CAR:

A40C28-CD27-CAR:

SEQUENCE LISTING

Sequence total quantity: 225
SEQ ID NO: 1             moltype = AA  length = 27
FEATURE                  Location/Qualifiers
REGION                   1..27

```
                          note = T4 fibritin trimerization motif
source                    1..27
                          mol_type = protein
                          organism = synthetic construct
SEQUENCE: 1
GYIPEAPRDG QAYVRKDGEW VLLSTFL                                         27

SEQ ID NO: 2              moltype = AA  length = 30
FEATURE                   Location/Qualifiers
REGION                    1..30
                          note = Isoleucine Zipper (L)
source                    1..30
                          mol_type = protein
                          organism = synthetic construct
SEQUENCE: 2
EKKIEAIEKK IEAIEKKIEA IEAIEKKIEA                                      30

SEQ ID NO: 3              moltype = AA  length = 20
FEATURE                   Location/Qualifiers
REGION                    1..20
                          note = Isoleucine Zipper (S)
source                    1..20
                          mol_type = protein
                          organism = synthetic construct
SEQUENCE: 3
EKKIEAIEKK IEAIEKKIEA                                                 20

SEQ ID NO: 4              moltype = AA  length = 28
FEATURE                   Location/Qualifiers
REGION                    1..28
                          note = GCN4II
source                    1..28
                          mol_type = protein
                          organism = synthetic construct
SEQUENCE: 4
EDKIEEILSK IYHIENEIAR IKKLIGEA                                        28

SEQ ID NO: 5              moltype = AA  length = 28
FEATURE                   Location/Qualifiers
REGION                    1..28
                          note = Optimized GCN4II
source                    1..28
                          mol_type = protein
                          organism = synthetic construct
SEQUENCE: 5
EDKVEELLSK IYHIENRIAR IEKLVGEA                                        28

SEQ ID NO: 6              moltype = AA  length = 43
FEATURE                   Location/Qualifiers
REGION                    1..43
                          note = Matrilin -1 (L)
source                    1..43
                          mol_type = protein
                          organism = synthetic construct
SEQUENCE: 6
EEDPCECKSI VKFQTKVEEL INTLQQKLEA VAKRIEALEN KII                       43

SEQ ID NO: 7              moltype = AA  length = 26
FEATURE                   Location/Qualifiers
REGION                    1..26
                          note = Matrilin -1 (S)
source                    1..26
                          mol_type = protein
                          organism = synthetic construct
SEQUENCE: 7
EELINTLQQK LEAVAKRIEA LENKII                                          26

SEQ ID NO: 8              moltype = AA  length = 64
FEATURE                   Location/Qualifiers
REGION                    1..64
                          note = Human collagen XV trimerization domain
source                    1..64
                          mol_type = protein
                          organism = synthetic construct
SEQUENCE: 8
VTAFSNMDDM LQKAHLVIEG TFIYLRDSTE FFIRVRDGWK KLQLGELIPI PADSPPPPAL     60
SSNP                                                                  64

SEQ ID NO: 9              moltype = AA  length = 261
```

```
FEATURE                 Location/Qualifiers
REGION                  1..261
                        note = Human CD40L full length
source                  1..261
                        mol_type = protein
                        organism = Homo sapiens
SEQUENCE: 9
MIETYNQTSP RSAATGLPIS MKIFMYLLTV FLITQMIGSA LFAVYLHRRL DKIEDERNLH    60
EDFVFMKTIQ RCNTGERSLS LLNCEEIKSQ FEGFVKDIML NKEETKKENS FEMQKGDQNP   120
QIAAHVISEA SSKTTSVLQW AEKGYYTMSN NLVTLENGKQ LTVKRQGLYY IYAQVTFCSN   180
REASSQAPFI ASLCLKSPGR FERILLRAAN THSSAKPCGQ QSIHLGGVFE LQPGASVFVN   240
VTDPSQVSHG TGFTSFGLLK L                                             261

SEQ ID NO: 10           moltype = AA  length = 24
FEATURE                 Location/Qualifiers
REGION                  1..24
                        note = Human CD40L transmembrane domain
source                  1..24
                        mol_type = protein
                        organism = Homo sapiens
SEQUENCE: 10
IFMYLLTVFL ITQMIGSALF AVYL                                           24

SEQ ID NO: 11           moltype = AA  length = 22
FEATURE                 Location/Qualifiers
REGION                  1..22
                        note = Human CD40L intracellular domain
source                  1..22
                        mol_type = protein
                        organism = Homo sapiens
SEQUENCE: 11
MIETYNQTSP RSAATGLPIS MK                                             22

SEQ ID NO: 12           moltype = AA  length = 215
FEATURE                 Location/Qualifiers
REGION                  1..215
                        note = Human CD40L extracellular domain
source                  1..215
                        mol_type = protein
                        organism = Homo sapiens
SEQUENCE: 12
HRRLDKIEDE RNLHEDFVFM KTIQRCNTGE RSLSLLNCEE IKSQFEGFVK DIMLNKEETK    60
KENSFEMQKG DQNPQIAAHV ISEASSKTTS VLQWAEKGYY TMSNNLVTLE NGKQLTVKRQ   120
GLYYIYAQVT FCSNREASSQ APFIASLCLK SPGRFERILL RAANTHSSAK PCGQQSIHLG   180
GVFELQPGAS VFVNVTDPSQ VSHGTGFTSF GLLKL                              215

SEQ ID NO: 13           moltype = AA  length = 220
FEATURE                 Location/Qualifiers
REGION                  1..220
                        note = Human CD28 full length
source                  1..220
                        mol_type = protein
                        organism = Homo sapiens
SEQUENCE: 13
MLRLLLALNL FPSIQVTGNK ILVKQSPMLV AYDNAVNLSC KYSYNLFSRE FRASLHKGLD    60
SAVEVCVVYG NYSQQLQVYS KTGFNCDGKL GNESVTFYLQ NLYVNQTDIY FCKIEVMYPP   120
PYLDNEKSNG TIIHVKGKHL CPSPLFPGPS KPFWVLVVVG GVLACYSLLV TVAFIIFWVR   180
SKRSRLLHSD YMNMTPRRPG PTRKHYQPYA PPRDFAAYRS                         220

SEQ ID NO: 14           moltype = AA  length = 41
FEATURE                 Location/Qualifiers
REGION                  1..41
                        note = Human CD28 intracellular domain
source                  1..41
                        mol_type = protein
                        organism = Homo sapiens
SEQUENCE: 14
RSKRSRLLHS DYMNMTPRRP GPTRKHYQPY APPRDFAAYR S                        41

SEQ ID NO: 15           moltype = AA  length = 27
FEATURE                 Location/Qualifiers
REGION                  1..27
                        note = Human CD28 transmembrane domain
source                  1..27
                        mol_type = protein
                        organism = Homo sapiens
SEQUENCE: 15
FWVLVVVGGV LACYSLLVTV AFIIFWV                                        27
```

```
SEQ ID NO: 16              moltype = AA   length = 255
FEATURE                    Location/Qualifiers
REGION                     1..255
                           note = Human 4-1BB full length
source                     1..255
                           mol_type = protein
                           organism = Homo sapiens
SEQUENCE: 16
MGNSCYNIVA TLLLVLNFER TRSLQDPCSN CPAGTFCDNN RNQICSPCPP NSFSSAGGQR    60
TCDICRQCKG VFRTRKECSS TSNAECDCTP GFHCLGAGCS MCEQDCKQGQ ELTKKGCKDC   120
CFGTFNDQKR GICRPWTNCS LDGKSVLVNG TKERDVVCGP SPADLSPGAS SVTPPAPARE   180
PGHSPQIISF FLALTSTALL FLLFFLTLRF SVVKRGRKKL LYIFKQPFMR PVQTTQEEDG   240
CSCRFPEEEE GGCEL                                                   255

SEQ ID NO: 17              moltype = AA   length = 42
FEATURE                    Location/Qualifiers
REGION                     1..42
                           note = Human 4-1BB intracellular domain
source                     1..42
                           mol_type = protein
                           organism = Homo sapiens
SEQUENCE: 17
KRGRKKLLYI FKQPFMRPVQ TTQEEDGCSC RFPEEEEGGC EL                       42

SEQ ID NO: 18              moltype = AA   length = 27
FEATURE                    Location/Qualifiers
REGION                     1..27
                           note = Human 4-1BB transmembrane domain
source                     1..27
                           mol_type = protein
                           organism = Homo sapiens
SEQUENCE: 18
IISFFLALTS TALLFLLFFL TLRFSVV                                        27

SEQ ID NO: 19              moltype = AA   length = 199
FEATURE                    Location/Qualifiers
REGION                     1..199
                           note = Human ICOS full length
source                     1..199
                           mol_type = protein
                           organism = Homo sapiens
SEQUENCE: 19
MKSGLWYFFL FCLRIKVLTG EINGSANYEM FIFHNGGVQI LCKYPDIVQQ FKMQLLKGGQ    60
ILCDLTKTKG SGNTVSIKSL KFCHSQLSNN SVSFFLYNLD HSHANYYFCN LSIFDPPPFK   120
VTLTGGYLHI YESQLCCQLK FWLPIGCAAF VVVCILGCIL ICWLTKKKYS SSVHDPNGEY   180
MFMRAVNTAK KSRLTDVTL                                                199

SEQ ID NO: 20              moltype = AA   length = 38
FEATURE                    Location/Qualifiers
REGION                     1..38
                           note = Human ICOS intracellular domain
source                     1..38
                           mol_type = protein
                           organism = Homo sapiens
SEQUENCE: 20
CWLTKKKYSS SVHDPNGEYM FMRAVNTAKK SRLTDVTL                            38

SEQ ID NO: 21              moltype = AA   length = 21
FEATURE                    Location/Qualifiers
REGION                     1..21
                           note = Human ICOS transmembrane domain
source                     1..21
                           mol_type = protein
                           organism = Homo sapiens
SEQUENCE: 21
FWLPIGCAAF VVVCILGCIL I                                              21

SEQ ID NO: 22              moltype = AA   length = 260
FEATURE                    Location/Qualifiers
REGION                     1..260
                           note = CD27 full length
source                     1..260
                           mol_type = protein
                           organism = Homo sapiens
SEQUENCE: 22
MARPHPWWLC VLGTLVGLSA TPAPKSCPER HYWAQGKLCC QMCEPGTFLV KDCDQHRKAA    60
QCDPCIPGVS FSPDHHTRPH CESCRHCNSG LLVRNCTITA NAECACRNGW QCRDKECTEC   120
DPLPNPSLTA RSSQALSPHP QPTHLPYVSE MLEARTAGHM QTLADFRQLP ARTLSTHWPP   180
QRSLCSSDFI RILVIFSGMF LVFTLAGALF LHQRRKYRSN KGESPVEPAE PCHYSCPREE   240
```

```
EGSTIPIQED YRKPEPACSP                                                    260

SEQ ID NO: 23           moltype = AA  length = 48
FEATURE                 Location/Qualifiers
REGION                  1..48
                        note = CD27 intracellular domain
source                  1..48
                        mol_type = protein
                        organism = Homo sapiens
SEQUENCE: 23
QRRKYRSNKG ESPVEPAEPC HYSCPREEEG STIPIQEDYR KPEPACSP                     48

SEQ ID NO: 24           moltype = AA  length = 21
FEATURE                 Location/Qualifiers
REGION                  1..21
                        note = CD27 transmembrane domain
source                  1..21
                        mol_type = protein
                        organism = Homo sapiens
SEQUENCE: 24
ILVIFSGMFL VFTLAGALFL H                                                  21

SEQ ID NO: 25           moltype = AA  length = 277
FEATURE                 Location/Qualifiers
REGION                  1..277
                        note = OX40 full length
source                  1..277
                        mol_type = protein
                        organism = Homo sapiens
SEQUENCE: 25
MCVGARRLGR GPCAALLLLG LGLSTVTGLH CVGDTYPSND RCCHECRPGN GMVSRCSRSQ         60
NTVCRPCGPG FYNDVVSSKP CKPCTWCNLR SGSERKQLCT ATQDTVCRCR AGTQPLDSYK         120
PGVDCAPCPP GHFSPGDNQA CKPWTNCTLA GKHTLQPASN SSDAICEDRD PPATQPQETQ         180
GPPARPITVQ PTEAWPRTSQ GPSTRPVEVP GGRAVAAILG LGLVLGLLGP LAILLALYLL         240
RRDQRLPPDA HKPPGGGSFR TPIQEEQADA HSTLAKI                                 277

SEQ ID NO: 26           moltype = AA  length = 42
FEATURE                 Location/Qualifiers
REGION                  1..42
                        note = OX40 intracellular domain
source                  1..42
                        mol_type = protein
                        organism = Homo sapiens
SEQUENCE: 26
ALYLLRRDQR LPPDAHKPPG GGSFRTPIQE EQADAHSTLA KI                            42

SEQ ID NO: 27           moltype = AA  length = 21
FEATURE                 Location/Qualifiers
REGION                  1..21
                        note = OX40 transmembrane domain
source                  1..21
                        mol_type = protein
                        organism = Homo sapiens
SEQUENCE: 27
VAAILGLGLV LGLLGPLAIL L                                                  21

SEQ ID NO: 28           moltype = AA  length = 93
FEATURE                 Location/Qualifiers
REGION                  1..93
                        note = DAP10 full length
source                  1..93
                        mol_type = protein
                        organism = Homo sapiens
SEQUENCE: 28
MIHLGHILFL LLLPVAAAQT TPGERSSLPA FYPGTSGSCS GCGSLSLPLL AGLVAADAVA         60
SLLIVGAVFL CARPRRSPAQ EDGKVYINMP GRG                                     93

SEQ ID NO: 29           moltype = AA  length = 24
FEATURE                 Location/Qualifiers
REGION                  1..24
                        note = DAP10 intracellular domain
source                  1..24
                        mol_type = protein
                        organism = Homo sapiens
SEQUENCE: 29
LCARPRRSPA QEDGKVYINM PGRG                                               24

SEQ ID NO: 30           moltype = AA  length = 21
FEATURE                 Location/Qualifiers
```

| | | |
|---|---|---|
| REGION | 1..21 | |
| | note = DAP10 transmembrane domain | |
| source | 1..21 | |
| | mol_type = protein | |
| | organism = Homo sapiens | |

SEQUENCE: 30
LLAGLVAADA VASLLIVGAV F                                          21

| | | |
|---|---|---|
| SEQ ID NO: 31 | moltype = AA   length = 595 | |
| FEATURE | Location/Qualifiers | |
| REGION | 1..595 | |
| | note = CD30 full length | |
| source | 1..595 | |
| | mol_type = protein | |
| | organism = Homo sapiens | |

SEQUENCE: 31
MRVLLAALGL LFLGALRAFP QDRPFEDTCH GNPSHYYDKA VRRCCYRCPM GLFPTQQCPQ   60
RPTDCRKQCE PDYLDEADR CTACVTCSRD DLVEKTPCAW NSSRVCECRP GMFCSTSAVN  120
SCARCFFHSV CPAGMIVKFP GTAQKNTVCE PASPGVSPAC ASPENCKEPS SGTIPQAKPT  180
PVSPATSSAS TMPVRGGTRL AQEAASKLTR APDSPSSVGR PSSDPGLSPT QPCPEGSGDC  240
RKQCEPDYYL DEAGRCTACV SCSRDDLVEK TPCAWNSSRT CECRPGMICA TSATNSCARC  300
VPYPICAAET VTKPQDMAEK DTTFEAPPLG TQPDCNPTPE NGEAPASTSP TQSLLVDSQA  360
SKTLPIPTSA PVALSSTGKP VLDAGPVLFW VILVLVVVG SSAFLLCHRR ACRKRIRQKL  420
HLCYPVQTSQ PKLELVDSRP RRSSTQLRSG ASVTEPVAEE RGLMSQPLME TCHSVGAAYL  480
ESLPLQDASP AGGPSSPRDL PEPRVSTEHT NNKIEKIYIM KADTVIVGTV KAELPEGRGL  540
AGPAEPELEE ELEADHTPHY PEQETEPPLG SCSDVMLSVE EEGKEDPLPT AASGK       595

| | | |
|---|---|---|
| SEQ ID NO: 32 | moltype = AA   length = 189 | |
| FEATURE | Location/Qualifiers | |
| REGION | 1..189 | |
| | note = CD30 intracellular domain | |
| source | 1..189 | |
| | mol_type = protein | |
| | organism = Homo sapiens | |

SEQUENCE: 32
CHRRACRKRI RQKLHLCYPV QTSQPKLELV DSRPRRSSTQ LRSGASVTEP VAEERGLMSQ   60
PLMETCHSVG AAYLESLPLQ DASPAGGPSS PRDLPEPRVS TEHTNNKIEK IYIMKADTVI  120
VGTVKAELPE GRGLAGPAEP ELEEELEADH TPHYPEQETE PPLGSCSDVM LSVEEEGKED  180
PLPTAASGK                                                         189

| | | |
|---|---|---|
| SEQ ID NO: 33 | moltype = AA   length = 21 | |
| FEATURE | Location/Qualifiers | |
| REGION | 1..21 | |
| | note = CD30 transmembrane domain | |
| source | 1..21 | |
| | mol_type = protein | |
| | organism = Homo sapiens | |

SEQUENCE: 33
PVLFWVILVL VVVVGSSAFL L                                           21

| | | |
|---|---|---|
| SEQ ID NO: 34 | moltype = AA   length = 370 | |
| FEATURE | Location/Qualifiers | |
| REGION | 1..370 | |
| | note = 2B4 full length | |
| source | 1..370 | |
| | mol_type = protein | |
| | organism = Homo sapiens | |

SEQUENCE: 34
MLGQVVTLIL LLLLKVYQGK GCQGSADHVV SISGVPLQLQ PNSIQTKVDS IAWKKLLPSQ   60
NGFHHILKWE NGSLPSNTSN DRFSIVKNL SLLIKAAQQQ DSGLYCLEVT SISGKVQTAT  120
FQVFVFESLL PDKVEKPRLQ GQGKILDRGR CQVALSCLVS RDGNVSYAWY RGSKLIQTAG  180
NLTYLDEEVD INGTHTYTCN VSNPVSWESH TLNLTQDCQN AHQEFRFWPF LVIIVILSAL  240
FLGTLACFCV WRRKREKQS ETSPKEFLTI YEDVKDLKTR RNHEQEQTFP GGGSTIYSMI  300
QSQSSAPTSQ EPAYTLYSLI QPSRKSGSRK RNHSPSFNST IYEVIGKSQP KAQNPARLSR  360
KELENFDVYS                                                         370

| | | |
|---|---|---|
| SEQ ID NO: 35 | moltype = AA   length = 120 | |
| FEATURE | Location/Qualifiers | |
| REGION | 1..120 | |
| | note = 2B4 intracellular domain | |
| source | 1..120 | |
| | mol_type = protein | |
| | organism = Homo sapiens | |

SEQUENCE: 35
WRRKRKEKQS ETSPKEFLTI YEDVKDLKTR RNHEQEQTFP GGGSTIYSMI QSQSSAPTSQ   60
EPAYTLYSLI QPSRKSGSRK RNHSPSFNST IYEVIGKSQP KAQNPARLSR KELENFDVYS  120

| | | |
|---|---|---|
| SEQ ID NO: 36 | moltype = AA   length = 21 | |
| FEATURE | Location/Qualifiers | |

```
REGION                  1..21
                        note = 2B4 transmembrane domain
source                  1..21
                        mol_type = protein
                        organism = Homo sapiens
SEQUENCE: 36
FLVIIVILSA LFLGTLACFC V                                                    21

SEQ ID NO: 37           moltype = AA   length = 351
FEATURE                 Location/Qualifiers
REGION                  1..351
                        note = CD2 full length
source                  1..351
                        mol_type = protein
                        organism = Homo sapiens
SEQUENCE: 37
MSFPCKFVAS FLLIFNVSSK GAVSKEITNA LETWGALGQD INLDIPSFQM SDDIDDIKWE    60
KTSDKKKIAQ FRKEKETFKE KDTYKLFKNG TLKIKHLKTD DQDIYKVSIY DTKGKNVLEK   120
IFDLKIQERV SKPKISWTCI NTTLTCEVMN GTDPELNLYQ DGKHLKLSQR VITHKWTTSL   180
SAKFKCTAGN KVSKESSVEP VSCPEKGLDI YLIIGICGGG SLLMVFVALL VFYITKRKKQ   240
RSRRNDEELE TRAHRVATEE RGRKPHQIPA STPQNPATSQ HPPPPPGHRS QAPSHRPPPP   300
GHRVQHQPQK RPPAPSGTQV HQQKGPPLPR PRVQPKPPHG AAENSLSPSS N            351

SEQ ID NO: 38           moltype = AA   length = 116
FEATURE                 Location/Qualifiers
REGION                  1..116
                        note = CD2 intracellular domain
source                  1..116
                        mol_type = protein
                        organism = Homo sapiens
SEQUENCE: 38
KRKKQRSRRN DEELETRAHR VATEERGRKP HQIPASTPQN PATSQHPPPP PGHRSQAPSH    60
RPPPPGHRVQ HQPQKRPPAP SGTQVHQQKG PPLPRPRVQP KPPHGAAENS LSPSSN       116

SEQ ID NO: 39           moltype = AA   length = 26
FEATURE                 Location/Qualifiers
REGION                  1..26
                        note = CD2 transmembrane domain
source                  1..26
                        mol_type = protein
                        organism = Homo sapiens
SEQUENCE: 39
IYLIIGICGG GSLLMVFVAL LVFYIT                                                26

SEQ ID NO: 40           moltype = AA   length = 240
FEATURE                 Location/Qualifiers
REGION                  1..240
                        note = LIGHT full length
source                  1..240
                        mol_type = protein
                        organism = Homo sapiens
SEQUENCE: 40
MEESVVRPSV FVVDGQTDIP FTRLGRSHRR QSCSVARVGL GLLLLLMGAG LAVQGWFLLQ    60
LHWRLGEMVT RLPDGPAGSW EQLIQERRSH EVNPAAHLTG ANSSLTGSGG PLLWETQLGL   120
APLRGLSYHD GALVVTKAGY YYIYSKVQLG GVGCPLGLAS TITHGLYKRT PRYPEELELL   180
VSQQSPCGRA TSSSRVWWDS SFLGGVVHLE AGEKVVRVL DERLVRLRDG TRSYFGAFMV    240

SEQ ID NO: 41           moltype = AA   length = 37
FEATURE                 Location/Qualifiers
REGION                  1..37
                        note = LIGHT intracellular domain
source                  1..37
                        mol_type = protein
                        organism = Homo sapiens
SEQUENCE: 41
MEESVVRPSV FVVDGQTDIP FTRLGRSHRR QSCSVAR                                    37

SEQ ID NO: 42           moltype = AA   length = 21
FEATURE                 Location/Qualifiers
REGION                  1..21
                        note = LIGHT transmembrane domain
source                  1..21
                        mol_type = protein
                        organism = Homo sapiens
SEQUENCE: 42
VGLGLLLLLM GAGLAVQGWF L                                                     21

SEQ ID NO: 43           moltype = AA   length = 241
FEATURE                 Location/Qualifiers
```

```
REGION                    1..241
                          note = GITR full length
source                    1..241
                          mol_type = protein
                          organism = Homo sapiens
SEQUENCE: 43
MAQHGAMGAF RALCGLALLC ALSLGQRPTG GPGCGPGRLL LGTGTDARCC RVHTTRCCRD    60
YPGEECCSEW DCMCVQPEFH CGDPCCTTCR HHPCPPGQGV QSQGKFSFGF QCIDCASGTF   120
SGGHEGHCKP WTDCTQFGFL TVFPGNKTHN AVCVPGSPPA EPLGWLTVVL LAVAACVLLL   180
TSAQLGLHIW QLRSQCMWPR ETQLLLEVPP STEDARSCQF PEEERGERSA EEKGRLGDLW   240
V                                                                  241

SEQ ID NO: 44             moltype = AA  length = 58
FEATURE                   Location/Qualifiers
REGION                    1..58
                          note = GITR intracellular domain
source                    1..58
                          mol_type = protein
                          organism = Homo sapiens
SEQUENCE: 44
QLGLHIWQLR SQCMWPRETQ LLLEVPPSTE DARSCQFPEE ERGERSAEEK GRLGDLWV      58

SEQ ID NO: 45             moltype = AA  length = 21
FEATURE                   Location/Qualifiers
REGION                    1..21
                          note = GITR transmembrane domain
source                    1..21
                          mol_type = protein
                          organism = Homo sapiens
SEQUENCE: 45
LGWLTVVLLA VAACVLLLTS A                                             21

SEQ ID NO: 46             moltype = AA  length = 417
FEATURE                   Location/Qualifiers
REGION                    1..417
                          note = DR3 full length
source                    1..417
                          mol_type = protein
                          organism = Homo sapiens
SEQUENCE: 46
MEQRPRGCAA VAAALLLVLL GARAQGGTRS PRCDCAGDFH KKIGLFCCRG CPAGHYLKAP    60
CTEPCGNSTC LVCPQDTFLA WENHHNSECA RCQACDEQAS QVALENCSAV ADTRCGCKPG   120
WFVECQVSQC VSSSPFYCQP CLDCGALHRH TRLLCSRRDT DCGTCLPGFY EHGDGCVSCP   180
TSTLGSCPER CAAVCGWRQM FWVQVLLAGL VVPLLLGATL TYTYRHCWPH KPLVTADEAG   240
MEALTPPPAT HLSPLDSAHT LLAPPDSSEK ICTVQLVGNS WTPGYPETQE ALCPQVTWSW   300
DQLPSRALGP AAAPTLSPES PAGSPAMMLQ PGPQLYDVMD AVPARRWKEF VRTLGLREAE   360
IEAVEVEIGR FRDQQYEMLK RWRQQQPAGL GAVYAALERM GLDGCVEDLR SRLQRGP      417

SEQ ID NO: 47             moltype = AA  length = 197
FEATURE                   Location/Qualifiers
REGION                    1..197
                          note = DR3 intracellular domain
source                    1..197
                          mol_type = protein
                          organism = Homo sapiens
SEQUENCE: 47
TYTYRHCWPH KPLVTADEAG MEALTPPPAT HLSPLDSAHT LLAPPDSSEK ICTVQLVGNS    60
WTPGYPETQE ALCPQVTWSW DQLPSRALGP AAAPTLSPES PAGSPAMMLQ PGPQLYDVMD   120
AVPARRWKEF VRTLGLREAE IEAVEVEIGR FRDQQYEMLK RWRQQQPAGL GAVYAALERM   180
GLDGCVEDLR SRLQRGP                                                 197

SEQ ID NO: 48             moltype = AA  length = 21
FEATURE                   Location/Qualifiers
REGION                    1..21
                          note = DR3 transmembrane domain
source                    1..21
                          mol_type = protein
                          organism = Homo sapiens
SEQUENCE: 48
MFWVQVLLAG LVVPLLLGAT L                                             21

SEQ ID NO: 49             moltype = AA  length = 181
FEATURE                   Location/Qualifiers
REGION                    1..181
                          note = CD160 full length
source                    1..181
                          mol_type = protein
                          organism = Homo sapiens
SEQUENCE: 49
```

```
MLLEPGRGCC ALAILLAIVD IQSGGCINIT SSASQEGTRL NLICTVWHKK EEAEGFVVFL    60
CKDRSGDCSP ETSLKQLRLK RDPGIDGVGE ISSQLMFTIS QVTPLHSGTY QCCARSQKSG   120
IRLQGHFFSI LFTETGNYTV TGLKQRQHLE FSHNEGTLSS GFLQEKVWVM LVTSLVALQA   180
L                                                                  181

SEQ ID NO: 50              moltype = AA   length = 400
FEATURE                    Location/Qualifiers
REGION                     1..400
                           note = CD43 full length
source                     1..400
                           mol_type = protein
                           organism = Homo sapiens
SEQUENCE: 50
MATLLLLLGV LVVSPDALGS TTAVQTPTSG EPLVSTSEPL SSKMYTTSIT SDPKADSTGD    60
QTSALPPSTS INEGSPLWTS IGASTGSPLP EPTTYQEVSI KMSSVPQETP HATSHPAVPI   120
TANSLGSHTV TGGTITTNSP ETSSRTSGAP VTTAASSLET SRGTSGPPLT MATVSLETSK   180
GTSGPPVTMA TDSLETSTGT TGPPVTMTTG SLEPSSGASG PQVSSVKLST MMSPTTSTNA   240
STVPFRNPDE NSRGMLPVAV LVALLAVIVL VALLLLWRRR QKRRTGALVL SRGGKRNGVV   300
DAWAGPAQVP EEGAVTVTVG GSGGDKGSGF PDGEGSSRRP TLTTFFGRRK SRQGSLAMEE   360
LKSGSGPSLK GEEEPLVASE DGAVDAPAPD EPEGGDGAAP                         400

SEQ ID NO: 51              moltype = AA   length = 124
FEATURE                    Location/Qualifiers
REGION                     1..124
                           note = CD43 intracellular domain
source                     1..124
                           mol_type = protein
                           organism = Homo sapiens
SEQUENCE: 51
WRRRQKRRTG ALVLSRGGKR NGVVDAWAGP AQVPEEGAVT VTVGGSGGDK GSGFPDGEGS    60
SRRPTLTTFF GRRKSRQGSL AMEELKSGSG PSLKGEEEPL VASEDGAVDA PAPDEPEGGD   120
GAAP                                                                124

SEQ ID NO: 52              moltype = AA   length = 23
FEATURE                    Location/Qualifiers
REGION                     1..23
                           note = CD43 transmembrane domain
source                     1..23
                           mol_type = protein
                           organism = Homo sapiens
SEQUENCE: 52
GMLPVAVLVA LLAVIVLVAL LLL                                            23

SEQ ID NO: 53              moltype = AA   length = 243
FEATURE                    Location/Qualifiers
REGION                     1..243
                           note = CD48 full length
source                     1..243
                           mol_type = protein
                           organism = Homo sapiens
SEQUENCE: 53
MCSRGWDSCL ALELLLLPLS LLVTSIQGHL VHMTVVSGSN VTLNISESLP ENYKQLTWFY    60
TFDQKIVEWD SRKSKYFESK FKGRVRLDPQ SGALYISKVQ KEDNSTYIMR VLKKTGNEQE   120
WKIKLQVLDP VPKPVIKIEK IEDMDDNCYL KLSCVIPGES VNYTWYGDKR PFPKELQNSV   180
LETTLMPHNY SRCYTCQVSN SVSSKNGTVC LSPPCTLARS FGVEWIASWL VVTVPTILGL   240
LLT                                                                 243

SEQ ID NO: 54              moltype = AA   length = 288
FEATURE                    Location/Qualifiers
REGION                     1..288
                           note = CD80 full length
source                     1..288
                           mol_type = protein
                           organism = Homo sapiens
SEQUENCE: 54
MGHTRRQGTS PSKCPYLNFF QLLVLAGLSH FCSGVIHVTK EVKEVATLSC GHNVSVEELA    60
QTRIYWQKEK KMVLTMMSGD MNIWPEYKNR TIFDITNNLS IVILALRPSD EGTYECVVLK   120
YEKDAFKREH LAEVTLSVKA DFPTPSISDP EIPTSNIRRI ICSTSGGFPE PHLSWLENGE   180
ELNAINTTVS QDPETELYAV SSKLDFNMTT NHSFMCLIKY GHLRVNQTFN WNTTKQEHFP   240
DNLLPSWAIT LISVNGIFVI CCLTYCFAPR CRERRRNERL RRESVRPV                288

SEQ ID NO: 55              moltype = AA   length = 25
FEATURE                    Location/Qualifiers
REGION                     1..25
                           note = CD80 intracellular domain
source                     1..25
                           mol_type = protein
                           organism = Homo sapiens
SEQUENCE: 55
```

```
TYCFAPRCRE RRRNERLRRE SVRPV                                              25

SEQ ID NO: 56            moltype = AA  length = 21
FEATURE                  Location/Qualifiers
REGION                   1..21
                         note = CD 80 transmembrane domain
source                   1..21
                         mol_type = protein
                         organism = Homo sapiens
SEQUENCE: 56
LLPSWAITLI SVNGIFVICC L                                                  21

SEQ ID NO: 57            moltype = AA  length = 329
FEATURE                  Location/Qualifiers
REGION                   1..329
                         note = CD 86 full length
source                   1..329
                         mol_type = protein
                         organism = Homo sapiens
SEQUENCE: 57
MDPQCTMGLS NILFVMAFLL SGAAPLKIQA YFNETADLPC QFANSQNQSL SELVVFWQDQ   60
ENLVLNEVYL GKEKFDSVHS KYMGRTSFDS DSWTLRLHNL QIKDKGLYQC IIHHKKPTGM  120
IRIHQMNSEL SVLANFSQPE IVPISNITEN VYINLTCSSI HGYPEPKKMS VLLRTKNSTI  180
EYDGVMQKSQ DNVTELYDVS ISLSVSFPDV TSNMTIFCIL ETDKTRLLSS PFSIELEDPQ  240
PPPDHIPWIT AVLPTVIICV MVFCLILWKW KKKKRPRNSY KCGTNTMERE ESEQTKKREK  300
IHIPERSDEA QRVFKSSKTS SCDKSDTCF                                    329

SEQ ID NO: 58            moltype = AA  length = 61
FEATURE                  Location/Qualifiers
REGION                   1..61
                         note = CD 86 intracellular domain
source                   1..61
                         mol_type = protein
                         organism = Homo sapiens
SEQUENCE: 58
KWKKKKRPRN SYKCGTNTME REESEQTKKR EKIHIPERSD EAQRVFKSSK TSSCDKSDTC   60
F                                                                   61

SEQ ID NO: 59            moltype = AA  length = 21
FEATURE                  Location/Qualifiers
REGION                   1..21
                         note = CD 86 transmembrane domain
source                   1..21
                         mol_type = protein
                         organism = Homo sapiens
SEQUENCE: 59
WITAVLPTVI ICVMVFCLIL W                                                  21

SEQ ID NO: 60            moltype = AA  length = 4544
FEATURE                  Location/Qualifiers
REGION                   1..4544
                         note = CD 91/LRP1 full length
source                   1..4544
                         mol_type = protein
                         organism = Homo sapiens
SEQUENCE: 60
MLTPPLLLLL PLLSALVAAA IDAPKTCSPK QFACRDQITC ISKGWRCDGE RDCPDGSDEA   60
PEICPQSKAQ RCQPNEHNCL GTELCVPMSR LCNGVQDCMD GSDEGPHCRE LQGNCSRLGC  120
QHHCVPTLDG PTCYCNSSFQ LQADGKTCKD FDECSVYGTC SQLCTNTDGS FICGCVEGYL  180
LQPDNRSCKA KNEPVDRPPV LLIANSQNIL ATYLSGAQVS TITPTSTRQT TAMDFSYANE  240
TVCWVHVGDS AAQTQLKCAR MPGLKGFVDE HTINISLSLH HVEQMAIDWL TGNFYFVDDI  300
DDRIFVCNRN GDTCVTLLDL ELYNPKGIAL DPAMGKVFFT DYGQIPKVER CDMDGQNRTK  360
LVDSKIVFPH GITLDLVSRL VYWADAYLDY IEVVDYEGKG RQTIIQGILI EHLYGLTVFE  420
NYLYATNSDN ANAQQKTSVI RVNRFNSTEY QVVTRVDKGG ALHIYHQRRQ PRVRSHACEN  480
DQYGKPGGCS DICLLANSHK ARTCRCRSGF SLGSDGKSCK KPEHELFLVY GKGRPGIIRG  540
MDMGAKVPDE HMIPIENLMN PRALDFHAET GFIYFADTTS YLIGRQKIDG TERETILKDG  600
IHNVEGVAVD WMGDNLYWTD DGPKKTISVA RLEKAAQTRK TLIEGKMTHP RAIVVDPLNG  660
WMYWTDWEED PKDSRRGRLE RAWMDGSHRD IFVTSKTVLW PNGLSLDIPA GRLYWVDAFY  720
DRIETILLNG TDRKIVYEGP ELNHAFGLCH HGNYLFWTEY RSGSVYRLER GVGGAPPTVT  780
LLRSERPPIF EIRMYDAQQQ QVGTNKCRVN NGGCSSLCLA TPGSRQCACA EDQVLDADGV  840
TCLANPSYVP PPQCQPGEFA CANSRCIQER WKCDGDNDCL DNSDEAPALC HQHTCPSDRF  900
KCENNRCIPN RWLCDGDNDC GNSEDESNAT CSARTCPPNQ FSCASGRCIP ISWTCDLDDD  960
CGDRSDESAS CAYPTCFPLT QFTCNNGRCI NINWRCDNDN DCGDNSDEAG CSHSCSSTQF 1020
KCNSGRCIPE HWTCDGDNDC GDYSDETHAN CTNQATRPPG GCHTDEFQCR LDGLCIPLRW 1080
RCDGDTDCMD SSDEKSCEGV THVCDPSVKF GCKDSARCIS KAWVCDGDND CEDNSDEENC 1140
ESLACRPPSH PCANNTSVCL PPDKLCDGND DCGDGSDEGE LCDQCSLNNG GCSHNCSVAP 1200
GEGIVCSCPL GMELGPDNHT CQIQSYCAKH LKCSQKCDQN KFSVKCSCYE GWVLEPDGES 1260
CRSLDPPKPF IIFSNRHEIR RIDLHKGDYS VLVPGLRNTI ALDFHLSQSA LYWTDVVEDK 1320
IYRGKLLDNG ALTSFEVVIQ YGLATPEGLA VDWIAGNIYW VESNLDQIEV AKLDGTLRTT 1380
```

```
LLAGDIEHPR AIALDPRDGI LFWTDWDASL PRIEAASMSG AGRRTVHRET GSGGWPNGLT    1440
VDYLEKRILW IDARSDAIYS ARYDGSGHME VLRGHEFLSH PFAVTLYGGE VYWTDWRTNT    1500
LAKANKWTGH NVTVVQRTNT QPFDLQVYHP SRQPMAPNPC EANGGQGPCS HLCLINYNRT    1560
VSCACPHLMK LHKDNTTCYE FKKFLLYARQ MEIRGVDLDA PYYNYIISFT VPDIDNVTVL    1620
DYDAREQRVY WSDVRTQAIK RAFINGTGVE TVVSADLPNA HGLAVDWVSR NLFWTSYDTN    1680
KKQINVARLD GSFKNAVVQG LEQPHGLVVH PLRGKLYWTD GDNISMANMD GSNRTLLFSG    1740
QKGPVGLAID FPESKLYWIS SGNHTINRCN LDGSGLEVID AMRSQLGKAT ALAIMGDKLW    1800
WADQVSEKMG TCSKADGSGS VVLRNSTTLV MHMKVYDESI QLDHKGTNPC SVNNGDCSQL    1860
CLPTSETTRS CMCTAGYSLR SGQQACEGVG SFLLYSVHEG IRGIPLDPND KSDALVPVSG    1920
TSLAVGIDFH AENDTIYWVD MGLSTISRAK RDQTWREDVV TNGIGRVEGI AVDWIAGNIY    1980
WTDQGFDVIE VARLNGSFRY VVISQGLDKP RAITVHPEKG YLFWTEWGQY PRIERSRLDG    2040
TERVVLVNVS ISWPNGISVD YQDGKLYWCD ARTDKIERID LETGENREVV LSSNNMDMFS    2100
VSVFEDPIYW SDRTHANGSI KRGSKDNATD SVPLRTGIGV QLKDIKVFNR DRQKGTNVCA    2160
VANGGCQQLC LYRGRGQRAC ACAHGMLAED GASCREYAGY LLYSERTILK SIHLSDERNL    2220
NAPVQPFEDP EHMKNVIALA FDYRAGTSPG TPNRIFFSDI HFGNIQQIND DGSRRITIVE    2280
NVGSVEGLAY HRGWDTLYWT SYTTSTITRH TVDQTRPGAF ERETVITMSG DDHPRAFVLD    2340
ECQNLMFWTN WNEQHPSIMR AALSGANVLT LIEKDIRTPN GLAIDHRAEK LYFSDATLDK    2400
IERCEYDGSH RYVILKSEPV HPFGLAVYGE HIFWTDWVRR AVQRANKHVG SNMKLLRVDI    2460
PQQPMGIIAV ANDTNSCELS PCRINNGGCQ DLCLLTHQGH VNCSCRGGRI LQDDLTCRAV    2520
NSSCRAQDEF ECANGECINF SLTCDGVPHC KDKSDEKPSY CNSRRCKKTF RQCSNGRCVS    2580
NMLWCNGADD CGDGSDEIPC NKTACGVGEF RCRDGTCIGN SSRCNQFVDC EDASDEMNCS    2640
ATDCSSYFRL GVKGVLFQPC ERTSLCYAPS WVCDGANDCG DSDERDCPG VKRPRCPLNY    2700
FACPSGRCIP MSWTCDKEDD CEHGEDETHC NKFCSEAQFE CQNHRCISKQ WLCDGSDDCG    2760
DGSDEAAHCE GKTCGPSSFS CPGTHVCVPE RWLCDGDKDC ADGADESIAA GCLYNSTCDD    2820
REFMCQNRQC IPKHFVCDHD RDCADGSDES PECEYPTCGP SEFRCANGRC LSSRQWECDG    2880
ENDCHDQSDE APKNPHCTSQ EHKCNASSQF LCSSGRCVAE ALLCNGQDDC GDSSDERGCH    2940
INECLSRKLS GCSQDCEDLK IGFKCRCRPG FRLKDDGRTC ADVDECSTFF PCSQRCINTH    3000
GSYKCLCVEG YAPRGGDPHS CKAVTDEEPF LIFANRYYLR KLNLDGSNYT LLKQGLNNAV    3060
ALDFDYREQM IYWTDVTTQG SMIRRMHLNG SNVQVLHRTG LSNPDGLAVD WVGGNLYWCD    3120
KGRDTIEVSK LNGAYRTVLV SSGLREPRAL VVDVQNGYLY WTDWGDHSLI GRIGMDGSSR    3180
SVIVDTKITW PNGLTLDYVT ERIYWADARE DYIEFASLDG SNRHVVLSQD IPHIFALTLF    3240
EDYVYWTDWE TKSINRAHKT TGTNKTLLIS TLHRPMDLHV FHALRQPDVP NHPCKVNNGG    3300
CSNLCLLSPG GGHKCACPTN FYLGSDGRTC VSNCTASQFV CKNDKCIPFW WKCDTEDDCG    3360
DHSDEPPDCP EFKCRPGQFQ CSTGICTNPA FICDGDNDCQ DNSDEANCDI HVCLPSQFKC    3420
TNTNRCIPGI FRCNGQDNCG DGEDERDCPE VTCAPNQFQC SITKRCIPRV WVCDRDNDCV    3480
DGSDEPANCT QMTCGVDEFR CKDSGRCIPA RWKCDGEDDC GDNSDEPKEE CDERTCEPYQ    3540
FRCKNNRCVP GRWQCDYDND CGDNSDEESC TPRPCSESEF SCANGRCIAG RWKCDGDHDC    3600
ADGSDEKDCT PRCDMDQFQC KSGHCIPLRW RCDADADCMD GSDEEACGTG VRTCPLDEFQ    3660
CNNTLCKPLA WKCDGEDDCG DNSDENPEEC ARFVCPPNRP FRCKNDRVCL WIGRQCDGTD    3720
NCGDGTDEED CEPPTAHTTH CKDKKEFLCR NQRCLSSSLR CNMFDDCGDG SDEEDCSIDP    3780
KLTSCATNAS ICGDEARCVR TEKAAYCACR SGFHTVPGQP GCQDINECLR FGTCSQLCNN    3840
TKGGHLCSCA RNFMKTHNTC KAEGSEYQVL YIADDNEIRS LFPGHPHSAY EQAFQGDESV    3900
RIDAMDVHVK AGRVYWTNWH TGTISYRSLP PAAPPTTSNR HRRQIDRGVT HLNISGLKMP    3960
RGIAIDWVAG NVYWTDSGRD VIEVAQMKGE NRKTLISGMI DEPHAIVVDP LRGTMYWSDW    4020
GNHPKIETAA MDGTLRETLV QDNIQWPTGL AVDYHNERLY WADAKLSVIG SIRLNGTDPI    4080
VAADSKRGLS HPFSIDVFED YIYGVTYINN RVFKIHKFGH SPLVNLTGGL SHASDVVLYH    4140
QHKQPEVTNP CDRKKCEWLC LLSPSGPVCT CPNGKRLDNG TCVPVPSPTP PPDAPRPGTC    4200
NLQCFNGGSC FLNARRQPKC RCQPRYTGDK CELDQCWEHC RNGGTCAASP SGMPTCRCPT    4260
GFTGPKCTQQ VCAGYCANNS TCTVNQGNQP QCRCLPGFLG DRCQYRQCSG YCENFGTCQM    4320
AADGSRQCRC TAYFEGSRCE VNKCSRCLEG ACVVNKQSGD VTCNCTDGRV APSCLTCVGH    4380
CSNGGSCTMN SKMMPECQCP PHMTGPRCEE HVFSQQQPDI IASILIPLLL LLLLVLVAGV    4440
VFWYKRRVQG AKGFQHQRMT NGAMNVEIGN PTYKMYEGGE PDDVGGLLDA DFALDPDKPT    4500
NFTNPVYATL YMGGHGSRHS LASTDEKREL LGRGPEDEIG DPLA                   4544

SEQ ID NO: 61            moltype = AA   length = 100
FEATURE                  Location/Qualifiers
REGION                   1..100
                         note = CD 91 intracellular domain
source                   1..100
                         mol_type = protein
                         organism = Homo sapiens
SEQUENCE: 61
KRRVQGAKGF QHQRMTNGAM NVEIGNPTYK MYEGGEPDDV GGLLDADFAL DPDKPTNFTN    60
PVYATLYMGG HGSRHSLAST DEKRELLGRG PEDEIGDPLA                          100

SEQ ID NO: 62            moltype = AA   length = 25
FEATURE                  Location/Qualifiers
REGION                   1..25
                         note = CD 91 transmembrane domain
source                   1..25
                         mol_type = protein
                         organism = Homo sapiens
SEQUENCE: 62
HIASILIPLL LLLLVLVAG VVFWY                                           25

SEQ ID NO: 63            moltype = AA   length = 1722
FEATURE                  Location/Qualifiers
REGION                   1..1722
                         note = DEC-205 full length
```

```
source                  1..1722
                        mol_type = protein
                        organism = Homo sapiens
SEQUENCE: 63
MRTGWATPRR PAGLLMLLFW FFDLAEPSGR AANDPFTIVH GNTGKCIKPV YGWIVADDCD    60
ETEDKLWKWV SQHRLFHLHS QKCLGLDITK SVNELRMFSC DSSAMLWWKC EHHSLYGAAR   120
YRLALKDGHG TAISNASDVW KKGGSEESLC DQPYHEIYTR DGNSYGRPCE FPFLIDGTWH   180
HDCILDEDHS GPWCATTLNY EYDRKWGICL KPENGCEDNW EKNEQFGSCY QFNTQTALSW   240
KEAYVSCQNQ GADLLSINSA AELTYLKEKE GIAKIFWIGL NQLYSARGWE WSDHKPLNFL   300
NWDPDRPSAP TIGGSSCARM DAESGLWQSF SCEAQLPYVC RKPLNNTVEL TDVWTYSDTR   360
CDAGWLPNNG FCYLLVNESN SWDKAHAKCK AFSSDLISIH SLADVEVVVT KLHNEDIKEE   420
VWIGLKNINI PTLFQWSDGT EVTLTYWDEN EPNVPYNKTP NCVSYLGELG QWKVQSCEEK   480
LKYVCKRKGE KLNDASSDKM CPPDEGWKRH GETCYKIYED EVPFGTNCNL TITSRFEQEY   540
LNDLMKKYDK SLRKYFWTGL RDVDSCGEYN WATVGGRRRA VTFSNWNFLE PASPGGCVAM   600
STGKSVGKWE VKDCRSFKAL SICKKMSGPL GPEEASPKPD DPCPEGWQSF PASLSCYKVF   660
HAERIVRKRN WEEAERFCQA LGAHLSSFSH VDEIKEFLHF LTDQFSGQHW LWIGLNKRSP   720
DLQGSWQWSD RTPVSTIIMP NEFQQDYDIR DCAAVKVFPR PWRRGWHFYD DREFIYLRPF   780
ACDTKLEWVC QIPKGRTPKT PDWYNPDRAG IHGPPLIIEG SEYWFVADLH LNYEEAVLYC   840
ASNHSFLATI TSFVGLKAIK NKIANISGDG QKWWIRISEW PIDDHFTYSR YPWHRFPVTF   900
GEECLYMSAK TWLIDLGKPT DCSTKLPFIC EKYNVSSLEK YSPDSAAKVQ CSEQWIPFQN   960
KCFLKIKPVS LTFSQASDTC HSYGGTLPSV LSQIEQDFIT SLLPDMEATL WIGLRWTAYE  1020
KINKWTDNRE LTYSNFHPLL VSGRLRIPEN FFEEESRYHC ALILNLQKSP FTGTWNFTSC  1080
SERHFVSLCQ KYSEVKSRQT LQNASETVKY LNNLYKIIPK TLTWHSAKRE CLKSNMQLVS  1140
ITDPYQQAFL SVQALLHNSS LWIGLFSQDD ELNFGWSDGK RLHFSRWAET NGQLEDCVVL  1200
DTDGFWKTVD CNDNQPGAIC YYSGNETEKE VKPVDSVKCP SPVLNTPWIP FQNCCYNFII  1260
TKNRHMATTQ DEVHTKCQKL NPKSHILSIR DEKENNFVLE QLLYFNYMAS WVMLGITYRN  1320
KSLMWFDKTP LSYTHWRAGR PTIKNEKFLA GLSTDGFWDI QTFKVIEEAV YFHQHSILAC  1380
KIEMVDYKEE YNTTLPQFMP YEDGIYSVIQ KKVTWYEALN MCSQSGGHLA SVHNQNGQLF  1440
LEDIVKRDGF PLWVGLSSHD GSESSFEWSD GSTFDYIPWK GQTSPGNCVL LDPKGTWKHE  1500
KCNSVKDGAI CYKPTKSKKL SRLTYSSRCP AAKENGSRWI QYKGHCYKSD QALHSFSEAK  1560
KLCSKHDHSA TIVSIKDEDE NKFVSRLMRE NNNITMRVWL GLSQHSVDQS WSWLDGSEVT  1620
FVKWENKSKS GVGRCSMLIA SNETWKKVEC EHGFGRVVCK VPLGPDYTAI AIIVATLSIL  1680
VLMGGLIWFL FQRHRLHLAG FSSVRYAQGV NEDEIMLPSF HD                    1722

SEQ ID NO: 64           moltype = AA   length = 31
FEATURE                 Location/Qualifiers
REGION                  1..31
                        note = DEC-205 intracellular domain
source                  1..31
                        mol_type = protein
                        organism = Homo sapiens
SEQUENCE: 64
QRHRLHLAGF SSVRYAQGVN EDEIMLPSFH D                                  31

SEQ ID NO: 65           moltype = AA   length = 25
FEATURE                 Location/Qualifiers
REGION                  1..25
                        note = DEC-205 transmembrane domain
source                  1..25
                        mol_type = protein
                        organism = Homo sapiens
SEQUENCE: 65
YTAIAIIVAT LSILVLMGGL IWFLF                                         25

SEQ ID NO: 66           moltype = AA   length = 404
FEATURE                 Location/Qualifiers
REGION                  1..404
                        note = DC-SIGN full length
source                  1..404
                        mol_type = protein
                        organism = Homo sapiens
SEQUENCE: 66
MSDSKEPRLQ QLGLLEEEQL RGLGFRQTRG YKSLAGCLGH GPLVLQLLSF TLLAGLLVQV    60
SKVPSSISQE QSRQDAIYQN LTQLKAAVGE LSEKSKLQEI YQELTQLKAA VGELPEKSKL   120
QEIYQELTRL KAAVGELPEK SKLQEIYQEL TWLKAAVGEL PEKSKMQEIY QELTRLKAAV   180
GELPEKSKQQ EIYQELTRLK AAVGELPEKS KQQEIYQELT RLKAAVGELP EKSKQQEIYQ   240
ELTQLKAAVE RLCHPCPWEW TFFQGNCYFM SNSQRNWHDS ITACKEVGAQ LVVIKSAEEQ   300
NFLQLQSSRS NRFTWMGLSD LNQEGTWQWV DGSPLLPSFK QYWNRGEPNN VGEEDCAEFS   360
GNGWNDDKCN LAKFWICKKS AASCSRDEEQ FLSPAPATPN PPPA                   404

SEQ ID NO: 67           moltype = AA   length = 37
FEATURE                 Location/Qualifiers
REGION                  1..37
                        note = DC-SIGN intracellular domain
source                  1..37
                        mol_type = protein
                        organism = Homo sapiens
SEQUENCE: 67
MSDSKEPRLQ QLGLLEEEQL RGLGFRQTRG YKSLAGC                            37
```

```
SEQ ID NO: 68            moltype = AA  length = 21
FEATURE                  Location/Qualifiers
REGION                   1..21
                         note = DC-SIGN transmembrane domain
source                   1..21
                         mol_type = protein
                         organism = Homo sapiens
SEQUENCE: 68
LGHGPLVLQL LSFTLLAGLL V                                              21

SEQ ID NO: 69            moltype = AA  length = 45
FEATURE                  Location/Qualifiers
REGION                   1..45
                         note = CD8 hinge
source                   1..45
                         mol_type = protein
                         organism = Homo sapiens
SEQUENCE: 69
TTTPAPRPPT PAPTIASQPL SLRPEACRPA AGGAVHTRGL DFACD                    45

SEQ ID NO: 70            moltype = AA  length = 43
FEATURE                  Location/Qualifiers
REGION                   1..43
                         note = CD28 hinge
source                   1..43
                         mol_type = protein
                         organism = Homo sapiens
SEQUENCE: 70
VAAAIEVMYP PPYLDNEKSN GTIIHVKGKH LCPSPLFPGP SKP                      43

SEQ ID NO: 71            moltype = AA  length = 35
FEATURE                  Location/Qualifiers
REGION                   1..35
                         note = IgG Fc hinge
source                   1..35
                         mol_type = protein
                         organism = synthetic construct
SEQUENCE: 71
AKTTPPSVYG RVTVSSAEPK SCDKTHTCPP CPDPK                               35

SEQ ID NO: 72            moltype = AA  length = 266
FEATURE                  Location/Qualifiers
REGION                   1..266
                         note = 1412 scFV
source                   1..266
                         mol_type = protein
                         organism = synthetic construct
SEQUENCE: 72
ALPVTALLLP LALLLHAARP QVQLVQSGAE VKKPGASVKV SCKASGYTFT SYYIHWVRQA    60
PGQGLEWIGC IYPGNVNTNY NEKFKDRATL TVDTSISTAY MELSRLRSDD TAVYFCTRSH   120
YGLDWNFDVW GQGTTVTVSS VEGGSGGSGG SGGSGGVMDD IQMTQSPSSL SASVGDRVTI   180
TCHASQNIYV WLNWYQQKPG KAPKLLIYKA SNLHTGVPSR FSGSGSGTDF TLTISSLQPE   240
DFATYYCQQG QTYPYTFGGG TKVEIK                                        266

SEQ ID NO: 73            moltype = AA  length = 120
FEATURE                  Location/Qualifiers
REGION                   1..120
                         note = 1412 heavy chain variable domain
source                   1..120
                         mol_type = protein
                         organism = synthetic construct
SEQUENCE: 73
QVQLVQSGAE VKKPGASVKV SCKASGYTFT SYYIHWVRQA PGQGLEWIGC IYPGNVNTNY    60
NEKFKDRATL TVDTSISTAY MELSRLRSDD TAVYFCTRSH YGLDWNFDVW GQGTTVTVSS   120

SEQ ID NO: 74            moltype = AA  length = 110
FEATURE                  Location/Qualifiers
REGION                   1..110
                         note = 1412 light chain variable domain
source                   1..110
                         mol_type = protein
                         organism = synthetic construct
SEQUENCE: 74
VMDDIQMTQS PSSLSASVGD RVTITCHASQ NIYVWLNWYQ QKPGKAPKLL IYKASNLHTG    60
VPSRFSGSGS GTDFTLTISS LQPEDFATYY CQQGQTYPYT FGGGTKVEIK              110

SEQ ID NO: 75            moltype = AA  length = 249
FEATURE                  Location/Qualifiers
REGION                   1..249
                         note = F2.103 scFV
```

```
                        source              1..249
                                            mol_type = protein
                                            organism = synthetic construct
SEQUENCE: 75
EVQLVESGGG LVQPGGSLRL SCAVSGFTFS TYWMHWVRQA PGKGLVWVSR INSDGSSTTY    60
ADSVKGRFTI SRDNAKNTLY LQMNSLRAED TAVYYCARDR VLWIGELSYY GMDWGQGTT    120
VTVSSGGGGS GGGGSGGGGS DIQMTQSPST LSASVGDRVT ITCRASQSIS NWLAWYQQKP   180
GKAPKLLLYK ASGLESGVPS RFSGSGSGTE FTLTINSLQP DDFATYYCQQ SNSYSWTFGH   240
GTKVEIKRT                                                            249

SEQ ID NO: 76           moltype = AA   length = 125
FEATURE                 Location/Qualifiers
REGION                  1..125
                        note = F2.103 heavy chain variable domain
source                  1..125
                        mol_type = protein
                        organism = synthetic construct
SEQUENCE: 76
EVQLVESGGG LVQPGGSLRL SCAVSGFTFS TYWMHWVRQA PGKGLVWVSR INSDGSSTTY    60
ADSVKGRFTI SRDNAKNTLY LQMNSLRAED TAVYYCARDR VLWIGELSYY GMDWGQGTT    120
VTVSS                                                                125

SEQ ID NO: 77           moltype = AA   length = 109
FEATURE                 Location/Qualifiers
REGION                  1..109
                        note = F2.103 light chain variable domain
source                  1..109
                        mol_type = protein
                        organism = synthetic construct
SEQUENCE: 77
DIQMTQSPST LSASVGDRVT ITCRASQSIS NWLAWYQQKP GKAPKLLLYK ASGLESGVPS    60
RFSGSGSGTE FTLTINSLQP DDFATYYCQQ SNSYSWTFGH GTKVEIKRT                109

SEQ ID NO: 78           moltype = AA   length = 261
FEATURE                 Location/Qualifiers
REGION                  1..261
                        note = F5.157 scFV
source                  1..261
                        mol_type = protein
                        organism = synthetic construct
SEQUENCE: 78
EVQLLESGGG LVQPGGSLRL SCAASGFAFS SYAMSWVRQA PGKGLEWVSA ISGSGGSTYY    60
ADSVKGRFTI SRDNSKNTLY LQMNSLRPRT RPYITVRKMG GTMVRGVMGT LTTGAREPWS   120
PSPQGGGGSG GGGSGGGGSI QMTQSPSSVS ASAGDRVTIT CRASQGISSW LAWYQQKPGK   180
APKLLIYAGS SLQSGVPSRF SGSGFGTDFT LTIGSLQPED FATYYCQQAS SFPRTFGQGT   240
KVEIKRTVLH HLSSSSRHLM S                                              261

SEQ ID NO: 79           moltype = AA   length = 124
FEATURE                 Location/Qualifiers
REGION                  1..124
                        note = F5.157 heavy chain variable domain
source                  1..124
                        mol_type = protein
                        organism = synthetic construct
SEQUENCE: 79
EVQLLESGGG LVQPGGSLRL SCAASGFAFS SYAMSWVRQA PGKGLEWVSA ISGSGGSTYY    60
ADSVKGRFTI SRDNSKNTLY LQMNSLRPRT RPYITVRKMG GTMVRGVMGT LTTGAREPWS   120
PSPQ                                                                 124

SEQ ID NO: 80           moltype = AA   length = 122
FEATURE                 Location/Qualifiers
REGION                  1..122
                        note = F5.157 light chain variable domain
source                  1..122
                        mol_type = protein
                        organism = synthetic construct
SEQUENCE: 80
IQMTQSPSSV SASAGDRVTI TCRASQGISS WLAWYQQKPG KAPKLLIYAG SSLQSGVPSR    60
FSGSGFGTDF TLTIGSLQPE DFATYYCQQA SSFPRTFGQG TKVEIKRTVL HHLSSSSRHL   120
MS                                                                   122

SEQ ID NO: 81           moltype = AA   length = 248
FEATURE                 Location/Qualifiers
REGION                  1..248
                        note = F5.77 scFV
source                  1..248
                        mol_type = protein
                        organism = synthetic construct
SEQUENCE: 81
```

```
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAKDG GYYGSGSYGY FDYWGQGTLV   120
TVSSGGGGSG GGGSGGGGSD IQMTQSPSSV SGSVGDRVTI TCRASQGISS WLAWYQQKPG   180
KAPKLLIYAG SSLQSGVPSR FSGSGFGTDF TLTISSLQPE DFATYYCQQA SSFPRTFGQG   240
TKVEIKRT                                                           248

SEQ ID NO: 82           moltype = AA   length = 124
FEATURE                 Location/Qualifiers
REGION                  1..124
                        note = F5.77 heavy chain variable domain
source                  1..124
                        mol_type = protein
                        organism = synthetic construct
SEQUENCE: 82
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAKDG GYYGSGSYGY FDYWGQGTLV   120
TVSS                                                               124

SEQ ID NO: 83           moltype = AA   length = 109
FEATURE                 Location/Qualifiers
REGION                  1..109
                        note = F5.77 light chain variable domain
source                  1..109
                        mol_type = protein
                        organism = synthetic construct
SEQUENCE: 83
DIQMTQSPSS VSGSVGDRVT ITCRASQGIS SWLAWYQQKP GKAPKLLIYA GSSLQSGVPS    60
RFSGSGFGTD FTLTISSLQP EDFATYYCQQ ASSFPRTFGQ GTKVEIKRT               109

SEQ ID NO: 84           moltype = AA   length = 246
FEATURE                 Location/Qualifiers
REGION                  1..246
                        note = 4D11 scFV
source                  1..246
                        mol_type = protein
                        organism = synthetic construct
SEQUENCE: 84
QLQLQESGPG LLKPSETLSL TCTVSGGSIS SPGYYGGWIR QPPGKGLEWI GSIYKSGSTY    60
HNPSLKSRVT ISVDTSKNQF SLKLSSVTAA DTAVYYCTRP VVRYFGWFDP WGQGTLVTVS   120
SASGGGGSGG GGSGGGGSAI QLTQSPSSLS ASVGDRVTIT CRASQGISSA LAWYQQKPGK   180
APKLLIYDAS NLESGVPSRF SGSGSGTDFT LTISSLQPED FATYYCQQFN SYPTFGQGTK   240
VEIKRT                                                             246

SEQ ID NO: 85           moltype = AA   length = 121
FEATURE                 Location/Qualifiers
REGION                  1..121
                        note = 4D11 heavy chain variable domain
source                  1..121
                        mol_type = protein
                        organism = synthetic construct
SEQUENCE: 85
QLQLQESGPG LLKPSETLSL TCTVSGGSIS SPGYYGGWIR QPPGKGLEWI GSIYKSGSTY    60
HNPSLKSRVT ISVDTSKNQF SLKLSSVTAA DTAVYYCTRP VVRYFGWFDP WGQGTLVTVS   120
S                                                                  121

SEQ ID NO: 86           moltype = AA   length = 108
FEATURE                 Location/Qualifiers
REGION                  1..108
                        note = 4D11 light chain variable domain
source                  1..108
                        mol_type = protein
                        organism = synthetic construct
SEQUENCE: 86
AIQLTQSPSS LSASVGDRVT ITCRASQGIS SALAWYQQKP GKAPKLLIYD ASNLESGVPS    60
RFSGSGSGTD FTLTISSLQP EDFATYYCQQ FNSYPTFGQG TKVEIKRT                108

SEQ ID NO: 87           moltype = AA   length = 241
FEATURE                 Location/Qualifiers
REGION                  1..241
                        note = A40C scFV
source                  1..241
                        mol_type = protein
                        organism = synthetic construct
SEQUENCE: 87
QVQLVQSGAE VKKPGASVKV SCTASGFNIK DYYVHWVKQA PGQGLEWMGR IDPEDGDSKY    60
APKFQGKATM TADTSTSTVY MELSSLRSED TAVYYCTTSY YVGTYGYWGQ GTLVTVSSGG   120
GGSGGGGSGG GGSDIQMTQS PSSLSASVGD RVTITCSASS SVSYMLWFQQ KPGKAPKLLI   180
YSTSNLASGV PSRFSGSGSG TDFTLTISSL QPEDFATYYC QQRTFYPYTF GGGTKVEIKR   240
T                                                                  241
```

```
SEQ ID NO: 88              moltype = AA   length = 118
FEATURE                    Location/Qualifiers
REGION                     1..118
                           note = A40C heavy chain variable domain
source                     1..118
                           mol_type = protein
                           organism = synthetic construct
SEQUENCE: 88
QVQLVQSGAE VKKPGASVKV SCTASGFNIK DYYVHWVKQA PGQGLEWMGR IDPEDGDSKY    60
APKFQGKATM TADTSTSTVY MELSSLRSED TAVYYCTTSY YVGTYGYWGQ GTLVTVSS    118

SEQ ID NO: 89              moltype = AA   length = 108
FEATURE                    Location/Qualifiers
REGION                     1..108
                           note = A40C light chain variable domain
source                     1..108
                           mol_type = protein
                           organism = synthetic construct
SEQUENCE: 89
DIQMTQSPSS LSASVGDRVT ITCSASSSVS YMLWFQQKPG KAPKLLIYST SNLASGVPSR    60
FSGSGSGTDF TLTISSLQPE DFATYYCQQR TFYPYTFGGG TKVEIKRT               108

SEQ ID NO: 90              moltype = AA   length = 249
FEATURE                    Location/Qualifiers
REGION                     1..249
                           note = 119 scFV
source                     1..249
                           mol_type = protein
                           organism = synthetic construct
SEQUENCE: 90
QVQLQQSGPG LVKPSQTLSL TCAISGDSVS SNSATWNWIR QSPSRDLEWL GRTYYRSKWY    60
RDYVGSVKSR IIINPDTSNN QFSLQLNSVT PEDTAIYYCT RAQWLGGDYP YYYSMDVWGQ   120
GTTVTVSSGG GGSGGGGSGG GGSEIVLTQS PATLSLSPGE RATLSCRASQ SVSSYLAWYQ   180
QKPGQAPRLL IYDASNRATG IPARFSGSGS GTDFTLTISS LEPEDFAVYY CQQRSNTFGP   240
GTKVDIKRT                                                         249

SEQ ID NO: 91              moltype = AA   length = 128
FEATURE                    Location/Qualifiers
REGION                     1..128
                           note = 119 heavy chain variable domain
source                     1..128
                           mol_type = protein
                           organism = synthetic construct
SEQUENCE: 91
QVQLQQSGPG LVKPSQTLSL TCAISGDSVS SNSATWNWIR QSPSRDLEWL GRTYYRSKWY    60
RDYVGSVKSR IIINPDTSNN QFSLQLNSVT PEDTAIYYCT RAQWLGGDYP YYYSMDVWGQ   120
GTTVTVSS                                                          128

SEQ ID NO: 92              moltype = AA   length = 106
FEATURE                    Location/Qualifiers
REGION                     1..106
                           note = 119 light chain variable domain
source                     1..106
                           mol_type = protein
                           organism = synthetic construct
SEQUENCE: 92
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNTFGPGTK VDIKRT                 106

SEQ ID NO: 93              moltype = AA   length = 302
FEATURE                    Location/Qualifiers
REGION                     1..302
                           note = 40L.28.40L.40L (CD40L signal peptide-CD28
                             intracellularregion-CD40L transmembrane region - CD40L
                             cytoplasmic domain)
source                     1..302
                           mol_type = protein
                           organism = synthetic construct
SEQUENCE: 93
MIETYNQTSP RSAATGLPIS MKRSKRSRLL HSDYMNMTPR RPGPTRKHYQ PYAPPRDFAA    60
YRSIFMYLLT VFLITQMIGS ALFAVYLHRR LDKIEDERNL HEDFVFMKTI QRCNTGERSL   120
SLLNCEEIKS QFEGFVKDIM LNKEETKKEN SFEMQKGDQN PQIAAHVISE ASSKTTSVLQ   180
WAEKGYYTMS NNLVTLENGK QLTVKRQGLY YIYAQVTFCS NREASSQAPF IASLCLKSPG   240
RFERILLRAA NTHSSAKPCG QQSIHLGGVF ELQPGASVFV NVTDPSQVSH GTGFTSFGLL   300
KL                                                                302

SEQ ID NO: 94              moltype = AA   length = 440
FEATURE                    Location/Qualifiers
```

| | | |
|---|---|---|
| REGION | 1..440 | |
| | note = 1412-T4-CD40L (anti-CD28 scFv (1412)- T4 fibritin trimerizationmotif-CD40L extracellular region) | |
| source | 1..440 | |
| | mol_type = protein | |
| | organism = synthetic construct | |

SEQUENCE: 94
```
MALPVTALLL PLALLLHAAR PQVQLVQSGA EVKKPGASVK VSCKASGYTF TSYYIHWVRQ  60
APGQGLEWIG CIYPGNVNTN YNEKFKDRAT LTVDTSISTA YMELSRLRSD DTAVYFCTRS 120
HYGLDWNFDV WGQGTTVTVS SVEGGSGGSG GSGGSGGVMD DIQMTQSPSS LSASVGDRVT 180
ITCHASQNIY VWLNWYQQKP GKAPKLLIYK ASNLHTGVPS RFSGSGSGTD FTLTISSLQP 240
EDFATYYCQQ GQTYPYTFGG GTKVEIKGYI PEAPRDGQAY VRKDGEWVLL STFLGDQNPQ 300
IAAHVISEAS SKTTSVLQWA EKGYYTMSNN LVTLENGKQL TVKRQGLYYI YAQVTFCSNR 360
EASSQAPFIA SLCLKSPGRF ERILLRAANT HSSAKPCGQQ SIHLGGVFEL QPGASVFVNV 420
TDPSQVSHGT GFTSFGLLKL                                            440
```

| | | |
|---|---|---|
| SEQ ID NO: 95 | moltype = AA length = 521 | |
| FEATURE | Location/Qualifiers | |
| REGION | 1..521 | |
| | note = 1412-F2.103 (Anti-CD28/anti-CD40 bispecific Ab) | |
| source | 1..521 | |
| | mol_type = protein | |
| | organism = synthetic construct | |

SEQUENCE: 95
```
MALPVTALLL PLALLLHAAR PQVQLVQSGA EVKKPGASVK VSCKASGYTF TSYYIHWVRQ  60
APGQGLEWIG CIYPGNVNTN YNEKFKDRAT LTVDTSISTA YMELSRLRSD DTAVYFCTRS 120
HYGLDWNFDV WGQGTTVTVS SVEGGSGGSG GSGGSGGVMD DIQMTQSPSS LSASVGDRVT 180
ITCHASQNIY VWLNWYQQKP GKAPKLLIYK ASNLHTGVPS RFSGSGSGTD FTLTISSLQP 240
EDFATYYCQQ GQTYPYTFGG GTKVEIKGGG GSEVQLLESG GGLVQPGGSL RLSCAVSGFT 300
FSTYWMHWVR QAPGKGLVWV SRINSDGSST TYADSVKGRF TISRDNAKNT LYLQMNSLRA 360
EDTAVYYCAR DRVLWIGELS YYGMDVWGQG TTVTVSSGGG GSGGGGSGGG GSDIQMTQSP 420
STLSASVGDR VTITCRASQS ISNWLAWYQQ KPGKAPKLLL YKASGLESGV PSRFSGSGSG 480
TEFTLTINSL QPDDFATYYC QQSNSYSWTF GHGTKVEIKR T                    521
```

| | | |
|---|---|---|
| SEQ ID NO: 96 | moltype = AA length = 533 | |
| FEATURE | Location/Qualifiers | |
| REGION | 1..533 | |
| | note = 1412-F5.157 (Anti-CD28/anti-CD40 bispecific Ab) | |
| source | 1..533 | |
| | mol_type = protein | |
| | organism = synthetic construct | |

SEQUENCE: 96
```
MALPVTALLL PLALLLHAAR PQVQLVQSGA EVKKPGASVK VSCKASGYTF TSYYIHWVRQ  60
APGQGLEWIG CIYPGNVNTN YNEKFKDRAT LTVDTSISTA YMELSRLRSD DTAVYFCTRS 120
HYGLDWNFDV WGQGTTVTVS SVEGGSGGSG GSGGSGGVMD DIQMTQSPSS LSASVGDRVT 180
ITCHASQNIY VWLNWYQQKP GKAPKLLIYK ASNLHTGVPS RFSGSGSGTD FTLTISSLQP 240
EDFATYYCQQ GQTYPYTFGG GTKVEIKGGG GSEVQLLESG GGLVQPGGSL RLSCAASGFA 300
FSSYAMSWVR QAPGKGLEWV SAISGSGGST YYADSVKGRF TISRDNSKNT LYLQMNSLRP 360
RTRPYITVRK MGGTMVRGVM GTLTTGAREP WSPSPQGGGG SGGGGSGGGG SIQMTQSPSS 420
VSASAGDRVT ITCRASQGIS SWLAWYQQKP GKAPKLLIYA GSSLQSGVPS RFSGSGFGTD 480
FTLTIGSLQP EDFATYYCQQ ASSFPRTFGQ GTKVEIKRTV LHHLSSSSRH LMS        533
```

| | | |
|---|---|---|
| SEQ ID NO: 97 | moltype = AA length = 520 | |
| FEATURE | Location/Qualifiers | |
| REGION | 1..520 | |
| | note = 1412-F5.77 (Anti-CD28/anti-CD40 bispecific Ab) | |
| source | 1..520 | |
| | mol_type = protein | |
| | organism = synthetic construct | |

SEQUENCE: 97
```
MALPVTALLL PLALLLHAAR PQVQLVQSGA EVKKPGASVK VSCKASGYTF TSYYIHWVRQ  60
APGQGLEWIG CIYPGNVNTN YNEKFKDRAT LTVDTSISTA YMELSRLRSD DTAVYFCTRS 120
HYGLDWNFDV WGQGTTVTVS SVEGGSGGSG GSGGSGGVMD DIQMTQSPSS LSASVGDRVT 180
ITCHASQNIY VWLNWYQQKP GKAPKLLIYK ASNLHTGVPS RFSGSGSGTD FTLTISSLQP 240
EDFATYYCQQ GQTYPYTFGG GTKVEIKGGG GSEVQLLESG GGLVQPGGSL RLSCAASGFT 300
FSSYAMSWVR QAPGKGLEWV SAISGSGGST YYADSVKGRF TISRDNSKNT LYLQMNSLRA 360
EDTAVYYCAK DGGYYGSGSY GYFDYWGQGT LVTVSSGGGG SGGGGSGGGG SDIQMTQSPS 420
SVSGSVGDRV TITCRASQGI SSWLAWYQQK PGKAPKLLIY AGSSLQSGVP SRFSGSGFGT 480
DFTLTISSLQ PEDFATYYCQ QASSFPRTFG QGTKVEIKRT                      520
```

| | | |
|---|---|---|
| SEQ ID NO: 98 | moltype = AA length = 385 | |
| FEATURE | Location/Qualifiers | |
| REGION | 1..385 | |
| | note = F2.103.CD28: (Anti-CD40 scFv-CD28 membrane chimeric fusionprotein) | |
| source | 1..385 | |
| | mol_type = protein | |
| | organism = synthetic construct | |

SEQUENCE: 98

```
MALPVTALLL PLALLLHAAR PEVQLVESGG GLVQPGGSLR LSCAVSGFTF STYWMHWVRQ    60
APGKGLVWVS RINSDGSSTT YADSVKGRFT ISRDNAKNTL YLQMNSLRAE DTAVYYCARD   120
RVLWIGELSY YGMDVWGQGT TVTVSSGGGG SGGGGSGGGG SDIQMTQSPS TLSASVGDRV   180
TITCRASQSI SNWLAWYQQK PGKAPKLLLY KASGLESGVP SRFSGSGSGT EFTLTINSLQ   240
PDDFATYYCQ QSNSYSWTFG HGTKVEIKRT ASTTTPAPRP PTPAPTIASQ PLSLRPEACR   300
PAAGGAVHTR GLDFACDFWV LVVVGGVLAC YSLLVTVAFI IFWVRSKRSR LLHSDYMNMT   360
PRRPGPTRKH YQPYAPPRDF AAYRS                                         385

SEQ ID NO: 99           moltype = AA   length = 397
FEATURE                 Location/Qualifiers
REGION                  1..397
                        note = F5.157.CD28: (Anti-CD40 scFv-CD28 membrane chimeric
                        fusionprotein)
source                  1..397
                        mol_type = protein
                        organism = synthetic construct
SEQUENCE: 99
MALPVTALLL PLALLLHAAR PEVQLLESGG GLVQPGGSLR LSCAASGFAF SSYAMSWVRQ    60
APGKGLEWVS AISGSGGSTY YADSVKGRFT ISRDNSKNTL YLQMNSLRPR TRPYITVRKM   120
GGTMVRGVMG TLTTGAREPW SPSPQGGGGS GGGGSGGGGS IQMTQSPSSV SASAGDRVTI   180
TCRASQGISS WLAWYQQKPG KAPKLLIYAG SSLQSGVPSR FSGSGFGTDF TLTIGSLQPE   240
DFATYYCQQA SSFPRTFGQG TKVEIKRTVL HHLSSSSRHL MSASTTTPAP RPPTPAPTIA   300
SQPLSLRPEA CRPAAGGAVH TRGLDFACDF WVLVVVGGVL ACYSLLVTVA FIIFWVRSKR   360
SRLLHSDYMN MTPRRPGPTR KHYQPYAPPR DFAAYRS                            397

SEQ ID NO: 100          moltype = AA   length = 384
FEATURE                 Location/Qualifiers
REGION                  1..384
                        note = F5.77.CD28 (Anti-CD40 scFv-CD28 membrane chimeric
                        fusionprotein):
source                  1..384
                        mol_type = protein
                        organism = synthetic construct
SEQUENCE: 100
MALPVTALLL PLALLLHAAR PEVQLLESGG GLVQPGGSLR LSCAASGFTF SSYAMSWVRQ    60
APGKGLEWVS AISGSGGSTY YADSVKGRFT ISRDNSKNTL YLQMNSLRAE DTAVYYCAKD   120
GGYYGSGSYG YFDYWGQGTL VTVSSGGGGS GGGGSGGGGS DIQMTQSPSS VSGSVGDRVT   180
ITCRASQGIS SWLAWYQQKP GKAPKLLIYA GSSLQSGVPS RFSGSGFGTD FTLTISSLQP   240
EDFATYYCQQ ASSFPRTFGQ GTKVEIKRTA STTTPAPRPP TPAPTIASQP LSLRPEACRP   300
AAGGAVHTRG LDFACDFWVL VVVGGVLACY SLLVTVAFII FWVRSKRSRL LHSDYMNMTP   360
RRPGPTRKHY QPYAPPRDFA AYRS                                          384

SEQ ID NO: 101          moltype = AA   length = 379
FEATURE                 Location/Qualifiers
REGION                  1..379
                        note = F2.103.BB (Anti-CD40 scFv-4-1BB membrane chimeric
                        fusionprotein):
source                  1..379
                        mol_type = protein
                        organism = synthetic construct
SEQUENCE: 101
MALPVTALLL PLALLLHAAR PEVQLVESGG GLVQPGGSLR LSCAVSGFTF STYWMHWVRQ    60
APGKGLVWVS RINSDGSSTT YADSVKGRFT ISRDNAKNTL YLQMNSLRAE DTAVYYCARD   120
RVLWIGELSY YGMDVWGQGT TVTVSSGGGG SGGGGSGGGG SDIQMTQSPS TLSASVGDRV   180
TITCRASQSI SNWLAWYQQK PGKAPKLLLY KASGLESGVP SRFSGSGSGT EFTLTINSLQ   240
PDDFATYYCQ QSNSYSWTFG HGTKVEIKRT TTTPAPRPPT PAPTIASQPL SLRPEACRPA   300
AGGAVHTRGL DFACDIYIWA PLAGTCGVLL LSLVITLYCR GRKKLLYIFK QPFMRPVQTT   360
QEEDGCSCRF PEEEEGGCE                                                379

SEQ ID NO: 102          moltype = AA   length = 391
FEATURE                 Location/Qualifiers
REGION                  1..391
                        note = F5.157.BB(Anti-CD40 scFv-4-1BB membrane chimeric
                        fusion protein)
source                  1..391
                        mol_type = protein
                        organism = synthetic construct
SEQUENCE: 102
MALPVTALLL PLALLLHAAR PEVQLLESGG GLVQPGGSLR LSCAASGFAF SSYAMSWVRQ    60
APGKGLEWVS AISGSGGSTY YADSVKGRFT ISRDNSKNTL YLQMNSLRPR TRPYITVRKM   120
GGTMVRGVMG TLTTGAREPW SPSPQGGGGS GGGGSGGGGS IQMTQSPSSV SASAGDRVTI   180
TCRASQGISS WLAWYQQKPG KAPKLLIYAG SSLQSGVPSR FSGSGFGTDF TLTIGSLQPE   240
DFATYYCQQA SSFPRTFGQG TKVEIKRTVL HHLSSSSRHL MSTTTPAPRP PTPAPTIASQ   300
PLSLRPEACR PAAGGAVHTR GLDFACDIYI WAPLAGTCGV LLLSLVITLY CRGRKKLLYI   360
FKQPFMRPVQ TTQEEDGCSC RFPEEEEGGC E                                  391

SEQ ID NO: 103          moltype = AA   length = 378
FEATURE                 Location/Qualifiers
REGION                  1..378
```

-continued

```
                        note = F5.77.BB(Anti-CD40 scFv-4-1BB membrane chimeric
                         fusion protein)
source                  1..378
                        mol_type = protein
                        organism = synthetic construct
SEQUENCE: 103
MALPVTALLL PLALLLHAAR PEVQLLESGG GLVQPGGSLR LSCAASGFTF SSYAMSWVRQ       60
APGKGLEWVS AISGSGGSTY YADSVKGRFT ISRDNSKNTL YLQMNSLRAE DTAVYYCAKD      120
GGYYGSGSYG YFDYWGQGTL VTVSSGGGGS GGGGSGGGGS DIQMTQSPSS VSGSVGDRVT      180
ITCRASQGIS SWLAWYQQKP GKAPKLLIYA GSSLQSGVPS RFSGSGFGTD FTLTISSLQP      240
EDFATYYCQQ ASSFPRTFGQ GTKVEIKRTT TTPAPRPPTP APTIASQPLS LRPEACRPAA      300
GGAVHTRGLD FACDIYIWAP LAGTCGVLLL SLVITLYCRG RKKLLYIFKQ PFMRPVQTTQ      360
EEDGCSCRFP EEEEGGCE                                                   378

SEQ ID NO: 104          moltype = AA  length = 382
FEATURE                 Location/Qualifiers
REGION                  1..382
                        note = 4D11.CD28
source                  1..382
                        mol_type = protein
                        organism = synthetic construct
SEQUENCE: 104
MALPVTALLL PLALLLHAAR PQLQLQESGP GLLKPSETLS LTCTVSGGSI SSPGYYGGWI       60
RQPPGKGLEW IGSIYKSGST YHNPSLKSRV TISVDTSKNQ FSLKLSSVTA ADTAVYYCTR      120
PVVRYFGWFD PWGQGTLVTV SSASGGGGSG GGGSGGGGSA IQLTQSPSSL SASVGDRVTI      180
TCRASQGISS ALAWYQQKPG KAPKLLIYDA SNLESGVPSR FSGSGSGTDF TLTISSLQPE      240
DFATYYCQQF NSYPTFGQGT KVEIKRTAST TTPAPRPPTP APTIASQPLS LRPEACRPAA      300
GGAVHTRGLD FACDFWVLVV VGGVLACYSL LVTVAFIIFW VRSKRSRLLH SDYMNMTPRR      360
PGPTRKHYQP YAPPRDFAAY RS                                              382

SEQ ID NO: 105          moltype = AA  length = 377
FEATURE                 Location/Qualifiers
REGION                  1..377
                        note = A40C.CD28
source                  1..377
                        mol_type = protein
                        organism = synthetic construct
SEQUENCE: 105
MALPVTALLL PLALLLHAAR PQVQLVQSGA EVKKPGASVK VSCTASGFNI KDYVHWVKQ        60
APGQGLEWMG RIDPEDGDSK YAPKFQGKAT MTADTSTSTV YMELSSLRSE DTAVYYCTTS      120
YYVGTYGYWG QGTLVTVSSG GGGSGGGGSG GGGSDIQMTQ SPSSLSASVG DRVTITCSAS      180
SSVSYMLWFQ QKPGKAPKLL IYSTSNLASG VPSRFSGSGS GTDFTLTISS LQPEDFATYY      240
CQQRTFYPYT FGGGTKVEIK RTASTTTPAP RPPTPAPTIA SQPLSLRPEA CRPAAGGAVH      300
TRGLDFACDF WVLVVVGGVL ACYSLLVTVA FIIFWVRSKR SRLLHSDYMN MTPRRPGPTR      360
KHYQPYAPPR DFAAYRS                                                    377

SEQ ID NO: 106          moltype = AA  length = 385
FEATURE                 Location/Qualifiers
REGION                  1..385
                        note = 119.CD28
source                  1..385
                        mol_type = protein
                        organism = synthetic construct
SEQUENCE: 106
MALPVTALLL PLALLLHAAR PQVQLQQSGP GLVKPSQTLS LTCAISGDSV SSNSATWNWI       60
RQSPSRDLEW LGRTYYRSKW YRDYVGSVKS RIIINPDTSN NQFSLQLNSV TPEDTAIYYC      120
TRAQWLGGDY PYYYSMDVWG QGTTVTVSSG GGGSGGGGSG GGGSEIVLTQ SPATLSLSPG      180
ERATLSCRAS QSVSSYLAWY QQKPGQAPRL LIYDASNRAT GIPARFSGSG SGTDFTLTIS      240
SLEPEDFAVY YCQQRSNTFG PGTKVDIKRT ASTTTPAPRP PTPAPTIASQ PLSLRPEACR      300
PAAGGAVHTR GLDFACDFWV LVVVGGVLAC YSLLVTVAFI IFWVRSKRSR LLHSDYMNMT      360
PRRPGPTRKH YQPYAPPRDF AAYRS                                           385

SEQ ID NO: 107          moltype = AA  length = 489
FEATURE                 Location/Qualifiers
REGION                  1..489
                        note = 4D5.BBZ (Her2 CAR)
source                  1..489
                        mol_type = protein
                        organism = synthetic construct
SEQUENCE: 107
MDFQVQIFSF LLISASVIMS RGDIQMTQSP SSLSASVGDR VTITCRASQD VNTAVAWYQQ       60
KPGKAPKLLI YSASFLYSGV PSRFSGSRSG TDFTLTISSL QPEDFATYYC QQHYTTPPTF      120
GQGTKVEIKR TGSTSGSGKP GSGEGSEVQL VESGGGLVQP GGSLRLSCAA SGFNIKDTYI      180
HWVRQAPGKG LEWVARIYPT NGYTRYADSV KGRFTISADT SKNTAYLQMN SLRAEDTAVY      240
YCSRWGGDGF YAMDVWGQGT LVTVSSTTTP APRPPTPAPT IASQPLSLRP EACRPAAGGA      300
VHTRGLDFAC DIYIWAPLAG TCGVLLLSLV ITLYCKRGRK KLLYIFKQPF MRPVQTTQEE      360
DGCSCRFPEE EEGGCELRVK FSRSADAPAY KQGQNQLYNE LNLGRREEYD VLDKRRGRDP      420
EMGGKPRRKN PQEGLYNELQ KDKMAEAYSE IGMKGERRRG KGHDGLYQGL STATKDTYDA      480
LHMQALPPR                                                             489
```

```
SEQ ID NO: 108            moltype = AA   length = 486
FEATURE                   Location/Qualifiers
REGION                    1..486
                          note = FMC63.BBZ (CD19 CAR)
source                    1..486
                          mol_type = protein
                          organism = synthetic construct
SEQUENCE: 108
MALPVTALLL PLALLLHAAR PDIQMTQTTS SLSASLGDRV TISCRASQDI SKYLNWYQQK    60
PDGTVKLLIY HTSRLHSGVP SRFSGSGSGT DYSLTISNLE QEDIATYFCQ QGNTLPYTFG   120
GGTKLEITGG GGSGGGGSGG GGSEVKLQES GPGLVAPSQS LSVTCTVSGV SLPDYGVSWI   180
RQPPRKGLEW LGVIWGSETT YYNSALKSRL TIIKDNSKSQ VFLKMNSLQT DDTAIYYCAK   240
HYYYGGSYAM DYWGQGTSVT VSSTTTPAPR PPTPAPTIAS QPLSLRPEAC RPAAGGAVHT   300
RGLDFACDIY IWAPLAGTCG VLLLSLVITL YCKRGRKKLL YIFKQPFMRP VQTTQEEDGC   360
SCRFPEEEEG GCELRVKFSR SADAPAYKQG QNQLYNELNL GRREEYDVLD KRRGRDPEMG   420
GKPRRKNPQE GLYNELQKDK MAEAYSEIGM KGERRRGKGH DGLYQGLSTA TKDTYDALHM   480
QALPPR                                                              486

SEQ ID NO: 109            moltype = AA   length = 488
FEATURE                   Location/Qualifiers
REGION                    1..488
                          note = ss1.BBZ (mesothelin CAR)
source                    1..488
                          mol_type = protein
                          organism = synthetic construct
SEQUENCE: 109
MALPVTALLL PLALLLHAAR PGSQVQLQQS GPELEKPGAS VKISCKASGY SFTGYTMNWV    60
KQSHGKSLEW IGLITPYNGA SSYNQKFRGK ATLTVDKSSS TAYMDLLSLT SEDSAVYFCA   120
RGGYDGRGFD YWGQGTTVTV SSGGGGSGGG GSSGGGSIE LTQSPAIMSA SPGEKVTMTC   180
SASSSVSYMH WYQQKSGTSP KRWIYDTSKL ASGVPGRFSG SGSGNSYSLT ISSVEAEDDA   240
TYYCQQWSKH PLTYGAGTKL EIKASTTTPA PRPPTPAPTI ASQPLSLRPE ACRPAAGGAV   300
HTRGLDFACD IYIWAPLAGT CGVLLLSLVI TLYCKRGRKK LLYIFKQPFM RPVQTTQEED   360
GCSCRFPEEE EGGCELRVKF SRSADAPAYK QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                            488

SEQ ID NO: 110            moltype = AA   length = 461
FEATURE                   Location/Qualifiers
REGION                    1..461
                          note = J591.BBZ (PSMA CAR)
source                    1..461
                          mol_type = protein
                          organism = synthetic construct
SEQUENCE: 110
MTQSHKFMST SVGDRVSIIC KASQDVGTAV DWYQQKPGQS PKLLIYWAST RHTGVPDRFT    60
GSGSGTDFTL TITNVQSEDL ADYFCQQYNS YPLTFGAGTK LDLKGGGSGG GGSSGGGSE   120
VQLQQSGPEL VKPGTSVRIS CKTSGYTFTE YTIHWVKQSH GKSLEWIGNI NPNNGGTTYN   180
QKFEDKATLT VDKSSSTAYM ELRSLTSEDS AVYYCAAGWN FDYWGQGTTL TVSSASSGTT   240
TPAPRPPTPA PTIASQPLSL RPEACRPAAG GAVHTRGLDF ACDIYIWAPL AGTCGVLLLS   300
LVITLYCKRG RKKLLYIFKQ PFMRPVQTTQ EEDGCSCRFP EEEEGGCELR VKFSRSADAP   360
AYKQGQNQLY NELNLGRREE YDVLDKRRGR DPEMGGKPRR KNPQEGLYNE LQKDKMAEAY   420
SEIGMKGERR RGKGHDGLYQ GLSTATKDTY DALHMQALPP R                       461

SEQ ID NO: 111            moltype = AA   length = 532
FEATURE                   Location/Qualifiers
REGION                    1..532
                          note = c-Met CAR
source                    1..532
                          mol_type = protein
                          organism = synthetic construct
SEQUENCE: 111
MALPVTALLL PLALLLHAAR PGSDIQMTQS PSSVSASVGD RVTITCRASQ GINTWLAWYQ    60
QKPGKAPKLL IYAASSLKSG VPSRFSGSGS GADFTLTISS LQPEDFATYY CQQANSFPLT   120
FGGGTKVEIK GSTSGSGKPG SGEGSTKGQV QLVQSGAEVK KPGASVKVSC EASGYTFTSY   180
GFSWVRQAPG QGLEWMGWIS ASNGNTYYAQ KLQGRVTMTT DTSTSSAYME LRSLRSDDTA   240
VYYCARVYAD YADYWGQGTL VTVASTTTPA PRPPTPAPTI ASQPLSLRPE ACRPAAGGAV   300
HTRGLDFACD FWVLVVVGGV LACYSLLVTV AFIIFWVRSK RSRLLHSDYM NMTPRRPGPT   360
RKHYQPYAPP RDFAAYRSKR GRKKLLYIFK QPFMRPVQTT QEEDGCSCRF PEEEEGGCEL   420
RVKFSRSADA PAYKQGQNQL YNELNLGRRE EYDVLDKRRG RDPEMGGKPR RKNPQEGLYN   480
ELQKDKMAEA YSEIGMKGER RRGKGHDGLY QGLSTATKDT YDALHMQALP PR           532

SEQ ID NO: 112            moltype = AA   length = 483
FEATURE                   Location/Qualifiers
REGION                    1..483
                          note = BCMA CAR
source                    1..483
                          mol_type = protein
                          organism = synthetic construct
```

```
SEQUENCE: 112
MALPVTALLL PLALLLHAAR PEVQLVESGG GLVQPGGSLR LSCAVSGFAL SNHGMSWVRR    60
APGKGLEWVS GIVYSGSTYY AASVKGRFTI SRDNSRNTLY LQMNSLRPED TAIYYCSAHG   120
GESDVWGQGT TVTVSSASGG GGSGGRASGG GGSDIQLTQS PSSLSASVGD RVTITCRASQ   180
SISSYLNWYQ QKPGKAPKLL IYAASSLQSG VPSRFSGSGS GTDFTLTISS LQPEDFATYY   240
CQQSYSTPYT FGQGTKVEIK TTTPAPRPPT PAPTIASQPL SLRPEACRPA AGGAVHTRGL   300
DFACDIYIWA PLAGTCGVLL LSLVITLYCK RGRKKLLYIF KQPFMRPVQT TQEEDGCSCR   360
FPEEEEGGCE LRVKFSRSAD APAYKQGQNQ LYNELNLGRR EEYDVLDKRR GRDPEMGGKP   420
RRKNPQEGLY NELQKDKMAE AYSEIGMKGE RRRGKGHDGL YQGLSTATKD TYDALHMQAL   480
PPR                                                                 483

SEQ ID NO: 113         moltype = AA  length = 364
FEATURE                Location/Qualifiers
REGION                 1..364
                       note = FHVH33.BBZ (BCMA CAR)
source                 1..364
                       mol_type = protein
                       organism = synthetic construct
SEQUENCE: 113
MALPVTALLL PLALLLHAAR PEVQLLESGG GLVQPGGSLR LSCAASGFTF SSYAMSWVRQ    60
APGKGLEWVS SISGSGDYIY YADSVKGRFT ISRDISKNTL YLQMNSLRAE DTAVYYCAKE   120
GTGANSSLAD YRGQGTLVTV SSTTTPAPRP PTPAPTIASQ PLSLRPEACR PAAGGAVHTR   180
GLDFACDIYI WAPLAGTCGV LLLSLVITLY CRGRKKLLYI FKQPFMRPVQ TTQEEDGCSC   240
RFPEEEEGGC ELRVKFSRSA DAPAYKQGQN QLYNELNLGR REEYDVLDKR RGRDPEMGGK   300
PRRKNPQEGL YNELQKDKMA EAYSEIGMKG ERRRGKGHDG LYQGLSTATK DTYDALHMQA   360
LPPR                                                                364

SEQ ID NO: 114         moltype = AA  length = 488
FEATURE                Location/Qualifiers
REGION                 1..488
                       note = BCMA338.BBZ (BCMA CAR)
source                 1..488
                       mol_type = protein
                       organism = synthetic construct
SEQUENCE: 114
MALPVTALLL PLALLLHAAR PQVKLEESGG GLVQAGRSLR LSCAASEHTF SSHVMGWFRQ    60
APGKERESVA VIGWRDISTS YADSVKGRFT ISRDNAKKTL YLQMNSLKPE DTAVYYCAAR   120
RIDAADFDSW GQGTQVTVSS GGGGSEVQLV ESGGGLVQAG GSLRLSCAAS GRTFTMGWFR   180
QAPGKEREFV AAISLSPTLA YYAESVKGRF TISRDNAKNT VVLQMNSLKP EDTALYYCAA   240
DRKSVMSIRP DYWGQGTQVT VSSTSTTTPA PRPPTPAPTI ASQPLSLRPE ACRPAAGGAV   300
HTRGLDFACD IYIWAPLAGT CGVLLLSLVI TLYCKRGRKK LLYIFKQPFM RPVQTTQEED   360
GCSCRFPEEE EGGCELRVKF SRSADAPAYQ QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                            488

SEQ ID NO: 115         moltype = AA  length = 486
FEATURE                Location/Qualifiers
REGION                 1..486
                       note = G33.BBZ (GPC3 CAR)
source                 1..486
                       mol_type = protein
                       organism = synthetic construct
SEQUENCE: 115
MALPVTALLL PLALLLHAAR PQVQLQQSGA ELVRPGASVK LSCKASGYTF TDYEMHWVKQ    60
TPVHGLKWIG ALDPKTGDTA YSQKFKGKAT LTADKSSSTA YMELRSLTSE DSAVYYCTRF   120
YSYTYWGQGT LVTVSAGGGG SGGGGSGGGG SDVVMTQTPL SLPVSLGDQA SISCRSSQSL   180
VHSNGNTYLH WYLQKPGQSP KLLIYKVSNR FSGVPDRFSG SGSGTDFTLK ISRVEAEDLG   240
VYFCSQNTHV PPTFGSGTKL EIKTTTPAPR PPTPAPTIAS QPLSLRPEAC RPAAGGAVHT   300
RGLDFACDIY IWAPLAGTCG VLLLSLVITL YCKRGRKKLL YIFKQPFMRP VQTTQEEDGC   360
SCRFPEEEEG GCELRVKFSR SADAPAYKQG QNQLYNELNL GRREEYDVLD KRRGRDPEMG   420
GKPRRKNPQE GLYNELQKDK MAEAYSEIGM KGERRRGKGH DGLYQGLSTA TKDTYDALHM   480
QALPPR                                                              486

SEQ ID NO: 116         moltype = AA  length = 889
FEATURE                Location/Qualifiers
REGION                 1..889
                       note = IL13(EQ).BBZ (IL13ra2 car)
source                 1..889
                       mol_type = protein
                       organism = synthetic construct
SEQUENCE: 116
MLLLVTSLLL CELPHPAFLL IPGPVPPSTA LRYLIEELVN ITQNQKAPLC NGSMVWSINL    60
TAGMYCAALE SLINVSGCSA IEKTQRMLSG FCPHKVSAGQ FSSLHVRDTK IEVAQFVKDL   120
LLHLKKLFRE GRFNESKYGP CPPCPAPEF EGGPSVFLFP PKPKDTLMIS RTPEVTCVVV   180
DVSQEDPEVQ FNWYVDGVEV HNAKTKPREE QFQSTYRVVS VLTVLHQDWL NGKEYKCKVS   240
NKGLPSSIEK TISKAKGQPR EPQVYTLPPS QEEMTKNQVS LTCLVKGFYP SDIAVEWESN   300
GQPENNYKTT PPVLDSDGSF FLYSRLTVDK SRWQEGNVFS CSVMHEALHN HYTQKSLSLS   360
LGKMALIVLG GVAGLLLFIG LGIFFKRGRK KLLYIFKQPF MRPVQTTQEE DGCSCRFPEE   420
EEGGCELGGG RVKFSRSADA PAYQQGQNQL YNELNLGRRE EYDVLDKRRG RDPEMGGKPR   480
```

```
RKNPQEGLYN ELQKDKMAEA YSEIGMKGER RRGKGHDGLY QGLSTATKDT YDALHMQALP    540
PRLEGGGEGR GSLLTCGDVE ENPGPRMPPP RLLFFLLFLT PMEVRPEEPL VVKVEEGDNA    600
VLQCLKGTSD GPTQQLTWSR ESPLKPFLKL SLGLPGLGIH MRPLAIWLFI FNVSQQMGGF    660
YLCQPGPPSE KAWQPGWTVN VEGSGELFRW NVSDLGGLGC GLKNRSSEGP SSPSGKLMSP    720
KLYVWAKDRP EIWEGEPPCV PPRDSLNQSL SQDLTMAPGS TLWLSCGVPP DSVSRGPLSW    780
THVHPKGPKS LLSLELKDDR PARDMWVMET GLLLPRATAQ DAGKYYCHRG NLTMSFHLEI    840
TARPVLWHWL LRTGGWKVSA VTLAYLIFCL CSLVGILHLQ RALVLRRKR              889

SEQ ID NO: 117          moltype = AA  length = 479
FEATURE                 Location/Qualifiers
REGION                  1..479
                        note = C10.BBZ (EGFR CAR)
source                  1..479
                        mol_type = protein
                        organism = synthetic construct
SEQUENCE: 117
MGWSCIILFL VATATGVHSD YKDDDDKEVQ LVQSGAEVKK PGSSVKVSCK ASGGTFSSYA     60
ISWVRQAPGQ GLEWMGGIIP IFGTANYAQK FQGRVTITAD ESTSTAYMEL SSLRSEDTAV    120
YYCAREEGPY CSSTSCYGAF DIWGQGTLVT VSSGGGGSGG GGSGGGGSQS VLTQDPAVSV    180
ALGQTVKITC QGDSLRSYFA SWYQQKPGQA PTLVMYARND RPAGVPDRFS GSKSGTSASL    240
AISGLQSEDE ADYYCAAWDD SLNGYLFGAG TKLTVLGRVT VSSAEPKSCD KTHTCPPCPG    300
SIYIWAPLAG TCGVLLLSLV ITLYCKRGRK KLLYIFKQPF MRPVQTTQEE DGCSCRFPEE    360
EGGCELRVK FSRSADAPAY QQGQNQLYNE LNLGRREEYD VLDKRRGRDP EMGGKPRRKN    420
PQEGLYNELQ KDKMAEAYSE IGMKGERRRG KGHDGLYQGL STATKDTYDA LHMQALPPR    479

SEQ ID NO: 118          moltype = AA  length = 333
FEATURE                 Location/Qualifiers
REGION                  1..333
                        note = 7G3L.BBZ (CD123 CAR)
source                  1..333
                        mol_type = protein
                        organism = synthetic construct
SEQUENCE: 118
MTQSPDSLAV SLGERATINC KSSQSLLNSG NQKNYLTWYL QKPGQPPKLL IYWASTRESG     60
VPDRFSGSGS GTDFTLTISS LQAEDVAVYY CQNDYSYPYT FGQGTKLEIK RTTTPAPRPP    120
TPAPTIASQP LSLRPEACRP AAGGAVHTRG LDFACDIYIW APLAGTCGVL LLSLVITLYC    180
RGRKKLLYIF KQPFMRPVQT TQEEDGCSCR FPEEEEGGCE LRVKFSRSAD APAYKQGQNQ    240
LYNELNLGRR EEYDVLDKRR GRDPEMGGKP RRKNPQEGLY NELQKDKMAE AYSEIGMKGE    300
RRRGKGHDGL YQGLSTATKD TYDALHMQAL PPR                                333

SEQ ID NO: 119          moltype = AA  length = 508
FEATURE                 Location/Qualifiers
REGION                  1..508
                        note = 3A1e.BBZ (CD7 CAR)
source                  1..508
                        mol_type = protein
                        organism = synthetic construct
SEQUENCE: 119
MLEVKQTLNF DLLKLAGDVE SNPGPMALPV TALLLPLALL LHAARPQVKL QESGGGLVKP     60
GGSLKLSCAA SGFTFSSYAM SWVRQTPEKR LEWVATISSG GSYTYYPDSV KGRFTISRDN    120
AKNTLYLQMS SLRSEDTAMY YCARQDGYYP GWFANWGQGT TVTVSSGGGG SGGGGSGGGG    180
SDIELTQSPA IMSASLGEEI TLTCSASSSV SYMHWYQQKS GTSPKLLIYS TSNLASGVPS    240
RFSGSGSGTF YSLTISSVEA EDAADYYCHQ WSSYTFGGGT KLEIKRTTTP APRPPTPAPT    300
IASQPLSLRP EACRPAAGGA VHTRGLDFAC DIYIWAPLAG TCGVLLLSLV ITLYCRGRKK    360
LLYIFKQPFM RPVQTTQEED GCSCRFPEEE EGGCELRVKF SRSADAPAYK QGQNQLYNEL    420
NLGRREEYDV LDKRRGRDPE MGGKPRRKNP QEGLYNELQK DKMAEAYSEI GMKGERRRGK    480
GHDGLYQGLS TATKDTYDAL HMQALPPR                                     508

SEQ ID NO: 120          moltype = AA  length = 507
FEATURE                 Location/Qualifiers
REGION                  1..507
                        note = 14.g2a.BBZ (GD2 CAR)
source                  1..507
                        mol_type = protein
                        organism = synthetic construct
SEQUENCE: 120
MEFGLSWLFL VAILKGVQCS RDILLTQTPL SLPVSLGDQA SISCRSSQSL VHRNGNTYLH     60
WYLQKPGQSP KLLIHKVSNR FSGVPDRFSG SGSGTDFTLK ISRVEAEDLG VYFCSQSTHV    120
PPLTFGAGTK LELKRADAAP TVSIFPGSGG GGSGGEVKLQ QSGPSLVEPG ASVMISCKAS    180
GSSFTGYNMN WVRQNIGKSL EWIGAIDPYY GGTSYNQKFK GRATLTVDKS SSTAYMHLKS    240
LTSEDSAVYY CVSGMEYWGQ GTSVTVSSAK TTPPSVYGRV TVSSTTTPAP RPPTPAPTIA    300
SQPLSLRPEA CRPAAGGAVH TRGLDFACDI YIWAPLAGTC GVLLLSLVIT LYCKRGRKKL    360
LYIFKQPFMR PVQTTQEEDG CSCRFPEEEE GGCELRVKFS RSADAPAYKQ GQNQLYNELN    420
LGRREEYDVL DKRRGRDPEM GGKPRRKNPQ EGLYNELQKD KMAEAYSEIG MKGERRRGKG    480
HDGLYQGLST ATKDTYDALH MQALPPR                                      507

SEQ ID NO: 121          moltype = AA  length = 483
FEATURE                 Location/Qualifiers
REGION                  1..483
```

```
                          note     = 2B3.BBZ (PSCA CAR)
source                    1..483
                          mol_type = protein
                          organism = synthetic construct
SEQUENCE: 121
MALPVTALLL PLALLLHAAR PDIQLTQSPS SLSASVGDRV TITCSASSSV RFIHWYQQKP    60
GKAPKRLIYD TSKLASGVPS RFSGSGSGTD FTLTISSLQP EDFATYYCQQ WSSSPFTFGQ   120
GTKVEIKGST SGGGSGGGSG GGGSSEVQLV ESGGGLVQPG GSLRLSCAAS GFNIKDYYIH   180
WVRQAPGKGL EWVAWIDPEN GDTEFVPKFQ GRATISADTS KNTAYLQMNS LRAEDTAVYY   240
CKTGGFWGQG TLVTVSSAAG TTTPAPRPPT PAPTIASQPL SLRPEACRPA AGGAVHTRGL   300
DPFACDIYIWA PLAGTCGVLL LSLVITLYCK RGRKKLLYIF KQPFMRPVQT TQEEDGCSCR  360
FPEEEEGGCE LRVKFSRSAD APAYKQGQNQ LYNELNLGRR EEYDVLDKRR GRDPEMGGKP   420
RRKNPQEGLY NELQKDKMAE AYSEIGMKGE RRRGKGHDGL YQGLSTATKD TYDALHMQAL   480
PPR                                                                483

SEQ ID NO: 122            moltype = AA   length = 270
FEATURE                   Location/Qualifiers
REGION                    1..270
                          note     = NY-ESO-1 TCR alpha chain
source                    1..270
                          mol_type = protein
                          organism = synthetic construct
SEQUENCE: 122
METLLGVSLV ILWLQLARVN SQQGEEDPQA LSIQEGENAT MNCSYKTSIN NLQWYRQNSG    60
RGLVHLILIR SNEREKHSGR LRVTLDTSKK SSSLLITASR AADTASYFCA TDGAGKSTFG   120
DGTTLTVKPN IQKPDPAVYQ LRDSKSSDKS VCLFTDFDSQ TNVSQSKDSD VYITDKTVLD   180
MRSMDFKSNS AVAWSNKSDF ACANAFNNSI IPADTFFPSP ESSCDVKLVE KSFETDTNLN   240
FQNLSVIGFR ILLLKVAGFN LLMTLRLWSS                                    270

SEQ ID NO: 123            moltype = AA   length = 308
FEATURE                   Location/Qualifiers
REGION                    1..308
                          note     = NY-ESO-1 TCR beta chain
source                    1..308
                          mol_type = protein
                          organism = synthetic construct
SEQUENCE: 123
MDSWTLCCVS LCILVAKHTD AGVIQSPRHE VTEMGQEVTL RCKPISGHDY LFWYRQTMMR    60
GLELLIYFNN NVPIDDSGMP EDRFSAKMPN ASFSTLKIQP SEPRDSAVYF CASTIGAQPQ   120
HFGDGTRLSI LEDLNKVFPP EVAVFEPSEA EISHTQKATL VCLATGFFPD HVELSWWVNG   180
KEVHSGVSTD PQPLKEQPAL NDSRYCLSSR LRVSATFWQN PRNHFRCQVQ FYGLSENDEW   240
TQDRAKPVTQ IVSAEAWGRA DCGFTSVSYQ QGVLSATILY EILLGKATLY AVLVSALVLM   300
AMVKRKDF                                                           308

SEQ ID NO: 124            moltype = AA   length = 603
FEATURE                   Location/Qualifiers
REGION                    1..603
                          note     = EBV16-E7 TCR
source                    1..603
                          mol_type = protein
                          organism = synthetic construct
SEQUENCE: 124
MWGVFLLYVS MKMGGTTGQN IDQPTEMTAT EGAIVQINCT YQTSGFNGLF WYQQHAGEAP    60
TFLSYNVLDG LEEKGRFSSF LSRSKGYSYL LLKELQMKDS ASYLCASVDG NNRLAFGKGN   120
QVVVIPNIQN PDPAVYQLRD SKSSDKSVCL FTDFDSQTNV SQSKDSDVYI TDKCVLDMRS   180
MDFKSNSAVA WSNKSDFACA NAFNNSIIPE DTFFPSPESS CDVKLVEKSF ETDTNLNFQN   240
LSVIGFRILL LKVAGFNLLM TLRLWSSRAK REGRGSLLTC GDVEENPGPM GPGLLCWALL   300
CLLGAGLVDA GVTQSPTHLI KTRGQQVTLR CSPKSGHDTV SWYQQALGQG PQFIFQYYEE   360
EERQRGNFPD RFSGHQFPNY SSELNVNALL LGDSALYLCA SSLGWRGGRY NEQFFGPGTR   420
LTVLEDLKNV FPPEVAVFEP SEAEISHTQK ATLVCLATGF YPDHVELSWW VNGKEVHSGV   480
CTDPQPLKEQ PALNDSRYCL SSRLRVSATF WQNPRNHFRC QVQFYGLSEN DEWTQDRAKP   540
VTQIVSAEAW GRADCGFTSE SYQQGVLSAT ILYEILLGKA TLYAVLVSAL VLMAMVKRKD   600
SRG                                                                603

SEQ ID NO: 125            moltype = AA   length = 267
FEATURE                   Location/Qualifiers
REGION                    1..267
                          note     = EBV16-E7 TCR alpha chain
source                    1..267
                          mol_type = protein
                          organism = synthetic construct
SEQUENCE: 125
MWGVFLLYVS MKMGGTTGQN IDQPTEMTAT EGAIVQINCT YQTSGFNGLF WYQQHAGEAP    60
TFLSYNVLDG LEEKGRFSSF LSRSKGYSYL LLKELQMKDS ASYLCASVDG NNRLAFGKGN   120
QVVVIPNIQN PDPAVYQLRD SKSSDKSVCL FTDFDSQTNV SQSKDSDVYI TDKCVLDMRS   180
MDFKSNSAVA WSNKSDFACA NAFNNSIIPE DTFFPSPESS CDVKLVEKSF ETDTNLNFQN   240
LSVIGFRILL LKVAGFNLLM TLRLWSS                                      267

SEQ ID NO: 126            moltype = AA   length = 314
```

```
FEATURE                 Location/Qualifiers
REGION                  1..314
                        note = EBV16-E7 TCR beta
source                  1..314
                        mol_type = protein
                        organism = synthetic construct
SEQUENCE: 126
MGPGLLCWAL LCLLGAGLVD AGVTQSPTHL IKTRGQQVTL RCSPKSGHDT VSWYQQALGQ    60
GPQFIFQYYE EEERQRGNFP DRFSGHQFPN YSSELNVNAL LLGDSALYLC ASSLGWRGGR   120
YNEQFFGPGT RLTVLEDLKN VFPPEVAVFE PSEAEISHTQ KATLVCLATG FYPDHVELSW   180
WVNGKEVHSG VCTDPQPLKE QPALNDSRYC LSSRLRVSAT FWQNPRNHFR CQVQFYGLSE   240
NDEWTQDRAK PVTQIVSAEA WGRADCGFTS ESYQQGVLSA TILYEILLGK ATLYAVLVSA   300
LVLMAMVKRK DSRG                                                    314

SEQ ID NO: 127          moltype = AA  length = 606
FEATURE                 Location/Qualifiers
REGION                  1..606
                        note = H3.3K27M TCR
source                  1..606
                        mol_type = protein
                        organism = synthetic construct
SEQUENCE: 127
MLTASLLRAV IASICVVSSM AQKVTQAQTE ISVVEKEDVT LDCVYETRDT TYYLFWYKQP    60
PSGELVFLIR RNSFDEQNEI SGRYSWNFQK STSSFNFTIT ASQVVDSAVY FCALSEENDM   120
RFGAGTRLTV KPNIQNPDPA VYQLRDSKSS DKSVCLFTDF DSQTNVSQSK SDSDVYITDKT  180
VLDMRSMDFK SNSAVAWSNK SDFACANAFN NSIIPEDTFF PSPESSCDVK LVEKSFETDT   240
NLNFQNLSVI GFRILLLKVA GFNLLMTLRL WSSVKQTLNF DLLKLAGDVE SNPGPMGPQL   300
LGYVVLCLLG AGPLEAQVTQ NPRYLITVTG KKLTVTCSQN MNHEYMSWYR QDPGLGLRQI   360
YYSMNVEVTD KGDVPEGYKV SRKEKRNFPL ILESPNPNQT SLYFCASGWG GPFYEQYFGP   420
GTRLTVTEDL KNVFPPEVAV FEPSEAEISH TQKATLVCLA TGFYPDHVEL SWWVNGKEVH   480
SGVSTDPQPL KEQPALNDSR YCLSSRLRVS ATFWQNPRNH FRCQVQFYGL SENDEWTQDR   540
AKPVTQIVSA EAWGRADCGF TSESYQQGVL SATILYEILL GKATLYAVLV SALVLMAMVK   600
RKDSRG                                                             606

SEQ ID NO: 128          moltype = AA  length = 273
FEATURE                 Location/Qualifiers
REGION                  1..273
                        note = H3.3K27M TCR alpha chain
source                  1..273
                        mol_type = protein
                        organism = synthetic construct
SEQUENCE: 128
MLTASLLRAV IASICVVSSM AQKVTQAQTE ISVVEKEDVT LDCVYETRDT TYYLFWYKQP    60
PSGELVFLIR RNSFDEQNEI SGRYSWNFQK STSSFNFTIT ASQVVDSAVY FCALSEENDM   120
RFGAGTRLTV KPNIQNPDPA VYQLRDSKSS DKSVCLFTDF DSQTNVSQSK SDSDVYITDKT  180
VLDMRSMDFK SNSAVAWSNK SDFACANAFN NSIIPEDTFF PSPESSCDVK LVEKSFETDT   240
NLNFQNLSVI GFRILLLKVA GFNLLMTLRL WSS                                273

SEQ ID NO: 129          moltype = AA  length = 311
FEATURE                 Location/Qualifiers
REGION                  1..311
                        note = H3.3K27M TCR beta chain
source                  1..311
                        mol_type = protein
                        organism = synthetic construct
SEQUENCE: 129
MGPGLLGYVV LCLLGAGPLE AQVTQNPRYL ITVTGKKLTV TCSQNMNHEY MSWYRQDPGL    60
GLRQIYYSMN VEVTDKGDVP EGYKVSRKEK RNFPLILESP NPNQTSLYFC ASGWGGPFYE   120
QYFGPGTRLT VTEDLKNVFP PEVAVFEPSE AEISHTQKAT LVCLATGFYP DHVELSWWVN   180
GKEVHSGVST DPQPLKEQPA LNDSRYCLSS RLRVSATFWQ NPRNHFRCQV QFYGLSENDE   240
WTQDRAKPVT QIVSAEAWGR ADCGFTSESY QQGVLSATIL YEILLGKATL YAVLVSALVL   300
MAMVKRKDSR G                                                       311

SEQ ID NO: 130          moltype = AA  length = 533
FEATURE                 Location/Qualifiers
REGION                  1..533
                        note = CD19-CD3 BiTE
source                  1..533
                        mol_type = protein
                        organism = synthetic construct
SEQUENCE: 130
MGWSCIILFL VATATGVHSD YKDDDDKDIQ LTQSPASLAV SLGQRATISC KASQSVDYDG    60
DSYLNWYQQI PGQPPKLLIY DASNLVSGIP PRFSGSGSGT DFTLNIHPVE KVDAATYHCQ   120
QSTEDPWTFG GGTKLEIKGG GGSGGGGSGG GGSQVQLQQS GAELVRPGSS VKISCKASGY   180
AFSSYWMNWV KQRPGQGLEW IGQIWPGDGD TNYNGKFKGK ATLTADESSS TAYMQLSSLA   240
SEDSAVYFCA RRETTTVGRY YYAMDYWGQG TTVTVSSGGG GSDIKLQQSG AELARPGASV   300
KMSCKTSGYT FTRYTMHWVK QRPGQGLEWI GYINPSRGYT NYNQKFKDKA TLTTDKSSST   360
AYMQLSSLTS EDSAVYFCAR YYDDHYCLDY WGQGTTLTVS SVEGGSGGSG SGGGSGGVDD   420
AAIQLTQSPA IMSASPGEKV TMTCRASSSV SYMNWYQQKS GTSPKRWIYD TSKVASGVPY   480
```

```
RFSGSGSGTS YSLTISSMEA EDAATYYCQQ WSSNPLTFGA GTKLELKHHH HHH        533

SEQ ID NO: 131         moltype = AA   length = 521
FEATURE                Location/Qualifiers
REGION                 1..521
                       note = 139-CD3 (EGFRvIII BiTE)
source                 1..521
                       mol_type = protein
                       organism = synthetic construct
SEQUENCE: 131
MGWSCIILFL VATATGVHSD YKDDDDKDIQ MTQSPSSLSA SVGDRVTITC RASQGIRNNL   60
AWYQQKPGKA PKRLIYAASN LQSGVPSRFT GSGSGTEFTL IVSSLQPEDF ATYYCLQHHS  120
YPLTSGGGTK VEIKGGGSSG GGGSGGGGSE VQVLESGGGL VQPGGSLRLS CAASGFTFSS  180
YAMSWVRQAP GKGLEWVSAI SGSGGSTNYA DSVKGRFTIS RDNSKNTLYL QMNSLRAEDT  240
AVYYCAGSSG WSEYWGQGTL VTVSSGGGGS DIKLQQSGAE LARPGASVKM SCKTSGYTFT  300
RYTMHWVKQR PGQGLEWIGY INPSRGYTNY NQKFKDKATL TTDKSSSTAY MQLSSLTSED  360
SAVYYCARYY DDHYCLDYWG QGTTLTVSSV EGGSGGSGGS GGSGGVDDAA IQLTQSPAIM  420
SASPGEKVTM TCRASSSVSY MNWYQQKSGT SPKRWIYDTS KVASGVPYRF SGSGSGTSYS  480
LTISSMEAED AATYYCQQWS SNPLTFGAGT KLELKHHHHH H                     521

SEQ ID NO: 132         moltype = DNA   length = 909
FEATURE                Location/Qualifiers
misc_feature           1..909
                       note = 40L.28.40L.40L
source                 1..909
                       mol_type = other DNA
                       organism = synthetic construct
SEQUENCE: 132
atgatcgaaa catacaacca aacttctccc cgatctgcgg ccactggact gcccatcagc   60
atgaaaagga gtaagaggag caggctcctg cacagtgact acatgaacat gactcccgc   120
cgccccgggc ccacccgcaa gcattaccag ccctatgccc caccacgcga cttcgcagcc  180
tatcgctcca ttttatgta tttacttact gttttctta tcacccagat gattgggtca    240
gcacttttg ctgtgtatct tcatagaagg ttggacaaga tagaagatga aaggaatctt   300
catgaagatt ttgtattcat gaaaacgata cagagatgca acacaggaga aagatcctta   360
tccttactga actgtgagga gattaaaagc cagtttgaag ctttgtgaa ggatataatg    420
ttaaacaaag aggagacgaa gaaagaaaac agctttgaaa tgcaaaaagg tgatcagaat   480
cctcaaattg cggcacatgt cataagtgag gccagcagta aaacaacatc tgtgttacag   540
tgggctgaaa aaggatacta caccatgagc acaacttgg taaccctgga aatgggaaa    600
cagctgaccg ttaaaagaca aggactctat tatatctatg cccaagtcac cttctgttcc  660
aatcgggaag cttcgagtca agctccattt atagccagcc tctgcctaaa gtccccggt   720
agattgagaa gaatcttact cagagctgca atacccaca gttccgccaa accttgcggg   780
caacaatcca ttcacttggg aggagtattt gaattgcaac aggtgcttc ggtgtttgtc    840
aatgtgactg atccaagcca agtgagccat ggcactggct tcacgtcctt tggcttactc   900
aaactctga                                                          909

SEQ ID NO: 133         moltype = DNA   length = 1328
FEATURE                Location/Qualifiers
misc_feature           1..1328
                       note = 1412-T4-CD40L
source                 1..1328
                       mol_type = other DNA
                       organism = synthetic construct
SEQUENCE: 133
atggccctcc ccgtgacggc actgctgcta cctctggcac tgctgctgca cgccgcgcgt   60
ccccaggtgc agctggtgca gtccggagcc gaggtaaaga agccaggcgc ttccgtcaag  120
gtgtcatgca aggcctcagg ctacaccttc acaagctatt acatccactg ggtgcgccaa  180
gctcccggtc agggcttgga gtggatcggg tgcatttacc cagggaacgt caacacaaac  240
tacaacgaga agttcaagga tcgggcaacc ctgaccgtgg acacatccat ctctaccgcc  300
tacatggagc tgtcacgcct cgcgtctgat gacaccgcag tgtacttctg taccaggagt  360
cactacggcc tggactggaa ctttgatgtc tggggccagg gaaccaccgt gacggtgtcc  420
agtgtggagg gcggtagtgg cggctctggt gggtccggag gctcaggcgg cgtgatggat  480
gacattcaga tgacccagag tcctcctcc ctctccgctt ccgtcggaga ccgcgtgacc   540
atcacttgtc acgcctcaca gaatatctac gtgtggctga actggtacca acagaagccc  600
ggcaagccc ccaagtgctt tatctataaa gcgtccaaac tccacaggag agtccttcc    660
cgcttctccg gatccggcag tgggacggac ttcacactca caatctcgtc gctgcagcca  720
gaggactttg cgacgtacta ctgccagcag ggccagacct acccatatac tttcggcggc  780
gggaccaagg tggagattaa gggatacatc cccgaggccc cgcgcgacgg gcaggcatac  840
gtgaggaaag acggtgagtg ggtcctgctg agcaccttc tcggtgatca gaatcctcaa   900
attgcggcac atgtcataag tgaggccagc agtaaaacaa catctgtgtt acagtgtgtt   960
gaaaaaggat actacaccat gagcaacaac ttggtaaccc tggaaaatgg gaaacagctg  1020
accgttaaaa gacaaggact ctattatatc tatgcccaag tcaccttctg ttccaatcgg  1080
gaagcttcga gtcaagctcc atttatagcc agcctctgcc taaagtcccc cggtagattc  1140
gagagaatct tactcagagc tgcaaatacc cacagttccg ccaaaccttg cgggcaacaa  1200
tccattcact ggaggagt atttgaattg caacaggtgc ttcggtgtt tgtcaatgtg     1260
actgatccaa gccaagtgag ccatggcact ggcttcacgt cctttggctt actcaaactc  1320
tgagtcga                                                           1328

SEQ ID NO: 134         moltype = DNA   length = 1566
FEATURE                Location/Qualifiers
```

```
misc_feature            1..1566
                        note = 1412-F2.103
source                  1..1566
                        mol_type = other DNA
                        organism = synthetic construct
SEQUENCE: 134
atggccctcc ccgtgacggc actgctgcta cctctggcac tgctgctgca cgccgcgcgt   60
ccccaggtgc agctggtgca gtccggagcc gaggtaaaga agccaggcgc ttccgtcaag  120
gtgtcatgca aggcctcagg ctacaccttc acaagctatt acatccactg ggtgcgccaa  180
gctcccggtc agggcttgga gtggatcggg tgcatttacc cagggaacgt caacacaaac  240
tacaacgaga agttcaagga tcgggcaacc ctgaccgtgg acacatccat ctctaccgcc  300
tacatggagc tgtcacgcct gcgctctgat gacaccgcag tgtacttctg taccaggagt  360
cactacggcc tggactggaa cttttgatgtc tggggccagg gaaccaccgt gacggtgtcc  420
agtgtggagg gcggtagtgg cggctctggt gggtccggag gctcaggcgg cgtgatggat  480
gacattcaga tgacccagag tccctcctcc ctctccgctt ccgtcggaga ccgcgtgacc  540
atcacttgtc acgcctcaca gaatatctac gtgtggctga actggtacca acagaagccc  600
ggcaaggccc ccaagctgct tatctataaa gcgtccaacc tccacacggg agtcccttcc  660
cgcttctccg gatccggcag tgggacggac ttcacactca caatctcgtc gctgcagcca  720
gaggactttg cgacgtacta ctgccagcag ggccagacct acccatatac tttcggcggc  780
gggaccaagg tggagattaa gggaggtggt ggatccgagg tgcagctggt ggagtccggg  840
ggaggcttag ttcagcctgg ggggtccctg agactctcct gtgcagtctc tggattcacc  900
ttcagtacct actggatgca ctgggtccgc caagctccag ggaaggggct ggtgtgggtc  960
tcacgtatta atagtgatgg gagtagcaca acctacgcgg actccgtgaa gggccgattc 1020
accatctcca gagacaacgc caagaacacg ctgtatctgc aaatgaacag tctgagagcc 1080
gaggacacgg ctgtgtatta ctgtgcaaga gatagagtac tatggatcgg ggagttatcc 1140
tactacggta tggacgtctg ggggcaaggg accacggtca ccgtctcctc aggtggcggt 1200
ggctcgggcg gtggtgggtc gggtggcggc ggatctgaca tccagatgac ccagtctcct 1260
tccaccctgt ctgcatctgt aggagacaga gtcaccatca cttgccgggc cagtcagagt 1320
attagtaact ggttggcctg gtatcagcag aaaccaggga agcccctaa actcctgctc 1380
tataaggcat ctggtttaga aagtgggggtc ccatcaaggt tcagcggcag tggatctggg 1440
acagaattca ctctcaccat caacagcctg cagcctgatg atttttgcaac ttattactgc 1500
caacagtcta atagttattc gtggacgttc ggccacggga ccaaggtgga aatcaaacgt 1560
acgtaa                                                            1566

SEQ ID NO: 135          moltype = DNA   length = 1599
FEATURE                 Location/Qualifiers
misc_feature            1..1599
                        note = 1412-F5.157
source                  1..1599
                        mol_type = other DNA
                        organism = synthetic construct
SEQUENCE: 135
atggccctcc ccgtgacggc actgctgcta cctctggcac tgctgctgca cgccgcgcgt   60
ccccaggtgc agctggtgca gtccggagcc gaggtaaaga agccaggcgc ttccgtcaag  120
gtgtcatgca aggcctcagg ctacaccttc acaagctatt acatccactg ggtgcgccaa  180
gctcccggtc agggcttgga gtggatcggg tgcatttacc cagggaacgt caacacaaac  240
tacaacgaga agttcaagga tcgggcaacc ctgaccgtgg acacatccat ctctaccgcc  300
tacatggagc tgtcacgcct gcgctctgat gacaccgcag tgtacttctg taccaggagt  360
cactacggcc tggactggaa cttttgatgtc tggggccagg gaaccaccgt gacggtgtcc  420
agtgtggagg gcggtagtgg cggctctggt gggtccggag gctcaggcgg cgtgatggat  480
gacattcaga tgacccagag tccctcctcc ctctccgctt ccgtcggaga ccgcgtgacc  540
atcacttgtc acgcctcaca gaatatctac gtgtggctga actggtacca acagaagccc  600
ggcaaggccc ccaagctgct tatctataaa gcgtccaacc tccacacggg agtcccttcc  660
cgcttctccg gatccggcag tgggacggac ttcacactca caatctcgtc gctgcagcca  720
gaggactttg cgacgtacta ctgccagcag ggccagacct acccatatac tttcggcggc  780
gggaccaagg tggagattaa gggaggtggt ggatccgagg tgcagctgtt ggagtctggg  840
ggaggcttgg tacagcctgg ggggtccctg agactctcct gtgcagcctc tggattcgcc  900
tttagcagct atgccatgag ctgggtccgc caggctccag ggaaggggct ggagtgggtc  960
tcagctatta gtggtagtgg tggtagcaca tactacgcag actccgtgaa gggccggttc 1020
accatctcca gagacaattc caagaacacg ctgtatctgc aaatgaacag cctgagaccc 1080
aggacacggc cgtatattac tgtgcgaaag atggggggta ctatggttcg gggagttatg 1140
ggtactttga ctactgggc cagggaaccc tggtcaccgt ctcctcaggg tggcggtggc 1200
tcgggcggtg tgggtcggg tggcggcgga tctatccaga tgacccagtc tccatcttcc 1260
gtgtctgcat ctgcaggaga cagagtcacc atcacttgtc aggcgagtca ggattattac 1320
agctggttag cctggtatca acagaaacca gggaaagccc ctaagctcct gatctatgct 1380
ggatccagtt tgcaaagtgg ggtcccatca aggttcagcg gcagtggatt tgggacagat 1440
ttcactctca ccatcggcag cctgcagcct gaagattttg caacttacta ttgtcaacag 1500
gctagcagtt tccctcggac gttcggccaa gggaccaagg tggagatcaa acgtacggtg 1560
ctgcaccatc tgtcttcatc ttcccgccat ctgatgagc                       1599

SEQ ID NO: 136          moltype = DNA   length = 1560
FEATURE                 Location/Qualifiers
misc_feature            1..1560
                        note = 1412-F5.77
source                  1..1560
                        mol_type = other DNA
                        organism = synthetic construct
SEQUENCE: 136
atggccctcc ccgtgacggc actgctgcta cctctggcac tgctgctgca cgccgcgcgt   60
```

```
cccccaggtgc agctggtgca gtccggagcc gaggtaaaga agccaggcgc ttccgtcaag   120
gtgtcatgca aggcctcagg ctacaccttc acaagctatt acatccactg ggtgcgccaa   180
gctcccggtc agggcttgga gtggatcggg tgcatttacc cagggaacgt caacacaaac   240
tacaacgaga agttcaagga tcgggcaacc ctgaccgtgg acacatccat ctctaccgcc   300
tacatggagc tgtcacgcct gcgctctgat gacaccgcag tgtactttgt taccaggagt   360
cactacgacc tggactggaa cttgatgtc tggggccagg gaaccaccgt gacggtgtcc   420
agtgtggagg gcggtagtgg cggctctggt ggtccggag gctcaggcgg cgtgatggat   480
gacattcaga tgacccagag tccctcctcc ctctccgctt ccgtcggaga ccgcgtgacc   540
atcacttgtc acgcctcaca gaatatctac gtgtggctga actggtacca acagaagccc   600
ggcaaggccc ccaagctgct tatctataaa gcgtccaacc tccacacggg agtcccttcc   660
cgcttctccg gatccggcag tgggacggac ttcacactca caatctcgtc gctgcagcca   720
gaggactttg cgacgtacta ctgccagcag ggccagacct acccatatac tttcggcggc   780
gggaccaagg tggagattaa gggaggtggt ggatccgagg tgcagctgtt ggagtctggg   840
ggaggcttgg tacagcctgg ggggtccctg agactctctg tgtcagcctc tggattcacc   900
tttagcagct atgccatgag ctgggtccga caggctccag gaaggggct ggagtgggtc   960
tcagctatta gtggtagtgg tggtagcaca tactacgcag actccgtgaa gggccggttc  1020
accatctcca gagacaattc caagaacacg ctgtatctgc aaatgaacag cctgagagcc  1080
gaggacacgg ccgtatatta ctgtgcgaaa gatgggggt actatggttc gggaagttat  1140
gggtactttg actactgggg ccagggaacc ctggtcaccg tctcctcagg tggcggtggc  1200
tcgggcggtg tgggtcggg tggcggcgga tctgacatcc agatgaccca gtctccatct  1260
tccgtgtctg gatctgtagg agacagagtc accatcactt gtcgggcgag tcagggtatt  1320
agcagctggt tagcctggta tcagcagaaa ccagggaaag cccctaagct cctgatctat  1380
gctggatcca gtttgcaaag tggggtccca tcaaggttca gcggcagtgg atttgggaca  1440
gatttcactc tcaccatcag cagcctgcag cctgaagatt ttgcaacctta ctattgtcaa  1500
caggctagca gtttccctcg gacattcggc caagggacca aggtggagat caaacgtacg  1560

SEQ ID NO: 137          moltype = DNA   length = 1158
FEATURE                 Location/Qualifiers
misc_feature            1..1158
                        note = F2.103.CD28
source                  1..1158
                        mol_type = other DNA
                        organism = synthetic construct
SEQUENCE: 137
atggccttac cagtgaccgc cttgctcctg ccgctggcct tgctgctcca cgccgccagg    60
ccggaggtgc agctggtgga gtccggggga ggcttagttc agcctggggg gtccctgaga   120
ctctcctgtg cagtctctgg attcaccttc agtacctact ggatgcactg ggtccgccaa   180
gctccaggga aggggctggt gtgggtctca cgtattaata gtgatgggag tagcacaacc   240
tacgcggact ccgtgaaggg ccgattcacc atctccagag acaacgccaa gaacacgctg   300
tatctgcaaa tgaacagtct gagagccgag gacacggctg tgtattactg tgcaagagat   360
agagtactat ggatcgggga gttatcctac tacggtatgg acgtctgggg ccaagggacc   420
acggtcaccg tctcctcagg tggcggtggc tcgggcggtg tgggtcggg tggcggcgga   480
tctgacatcc agatgaccca gtctcctttcc accctgtctg catctgtagg agacagagtc   540
accatcactt gccgggccag tcagagtatt agtaactggt tggcctggta tcagcagaaa   600
ccagggaaag cccctaaact cctgctctat aaggcatctg gtttagaaag tggggtccca   660
tcaaggttca gcggcagtgg atctgggaca gaattcactc tcaccatcaa cagcctgcag   720
cctgatgatt ttgcaactta ttactgccaa cagtctaata gttattcgtc gacgttcggc   780
cacgggacca aggtgaaat caaacgtacg gctagcacca cgacgccagc cgcgcgacca   840
ccaacaccgg cgcccaccat cgcgtcgcag ccctgtccc tgcgcccaga ggcgtgccgg   900
ccagcggcg ggggcgcagt gcacacgagg gggctgact cgcctgtga ttttggtgtg   960
ctggtggtga ttggtgagt cctggcttgc tatagcttgc tagtaacagt ggcctttatt  1020
attttctggg tgaggagtaa gaggagcagg ctcctgcaca gtgactacat gaacatgact  1080
ccccgccgcc ccgggcccac ccgcaagcat taccagccct atgccccacc acgcgacttc  1140
gcagcctatc gctcctaa                                                1158

SEQ ID NO: 138          moltype = DNA   length = 1194
FEATURE                 Location/Qualifiers
misc_feature            1..1194
                        note = F5.157.CD28
source                  1..1194
                        mol_type = other DNA
                        organism = synthetic construct
SEQUENCE: 138
atggccttac cagtgaccgc cttgctcctg ccgctggcct tgctgctcca cgccgccagg    60
ccggaggtgc agctgttgga gtctggggga ggcttggtac agcctggggg gtccctgaga   120
ctctcctgtg cagcctctgg attcgccttt agcagctatg ccatgagctg ggtccgccag   180
gctccaggga aggggctgga gtgggtctca gctattagtg gtagtggtgg tagcacatac   240
tacgcagact ccgtgaaggg ccggttcacc atctccagag acaattccaa gaacacgctg   300
tatctgcaaa tgaacagcct gagaccgagg acacggctg tatattactg tgcgaaagatg   360
gggggtacta tggttcgggg agttatgggt actttgacta ctggggccag gaaccctgg   420
tcaccgtctc ctcaggtgg cggtggctcg gcggtggtg gtcggtgg cggcggatct   480
atccagatga cccagtctcc atcttccgtg tctgcatctg caggagacag agtcaccatc   540
acttgtcggg cgagtcaggg tattagcagc tggttagcct ggtatcaaca gaaaccaggg   600
aaagcccta agctcctgat ctatgctgga tccagtttgc aaagtggggt cccatcaagg   660
ttcagcggca gtggatttgg gacagatttc actctcacca tcggcagcct gcagcctgaa   720
gattttgcaa cttactattg tcaacaggct agcagtttcc ctcggacgtt cggccaaggg   780
accaaggtgg agatcaaacg tacggtgctg caccatctgt cttcatcttc cgccatctg   840
atgagcgcta gcaccacgac gccagcgccg gaccaccaa caccgcgcc caccatcgcg   900
tcgcagcccc tgtccctgcg cccagaggcg tgccggccag gcggggggg cgcagtgcac   960
```

```
acgagggggc tggacttcgc ctgtgatttt tgggtgctgg tggtggttgg tggagtcctg   1020
gcttgctata gcttgctagt aacagtggcc tttattattt tctgggtgag gagtaagagg   1080
agcaggctcc tgcacagtga ctacatgaac atgactcccc gccgcccggg cccacccgc    1140
aagcattacc agcccctatgc cccaccacgc gacttcgcag cctatcgctc ctaa         1194

SEQ ID NO: 139          moltype = DNA   length = 1155
FEATURE                 Location/Qualifiers
misc_feature            1..1155
                        note = F5.77.CD28
source                  1..1155
                        mol_type = other DNA
                        organism = synthetic construct
SEQUENCE: 139
atggccttac cagtgaccgc cttgctcctg ccgctggcct tgctgctcca cgccgccagg   60
ccggaggtgc agctgttgga gtctggggga ggcttggtac agcctggggg gtccctgaga   120
ctctcctgtg cagcctctgg attcaccttt agcagctatg ccatgagctg ggtccgccag   180
gctccaggga aggggctgga gtgggtctca gctattagtg gtagtggtgg tagcacatac   240
tacgcagact ccgtgaaggg ccggttcacc atctccagag acaattccaa gaacacgctg   300
tatctgcaaa tgaacagcct gagagccgag gacacggccg tatattactg tgcgaaagat   360
gggggggtact atggttcggg gagttatggg tactttgact actggggcca gggaaccctg   420
gtcaccgtct cctcaggtgg cggtggctcg gcggtggtgg ggtcgggtgg cggcggatct   480
gacatccaga tgacccagtc tccatcttcc gtgtctgtat ctgtaggaga cagagtcacc   540
atcacttgtc gggcgagtca gggtattagc agctggttag cctggtatca gcagaaacca   600
gggaaagccc ctaagctcct gatctatgct ggatccagtt tgcaaagtgg ggtcccatca   660
aggttcagcg gcagtggatt tgggacagat ttcactctca ccatcagcag cctgcagcct   720
gaagattttg caacttacta ttgtcaacag gctagcagtt tccctcggac attcggccaa   780
gggaccaagg tggagatcaa acgtacggct agcaccacga cgccagcgcc gcgaccacca   840
acaccggcgc caccatcgcg tcgcagcccc tgtccctgcc ccagaggc gtgccggcca    900
gcggcggggg gcgcagtgca cacgaggggg ctggacttcg cctgtgatt ttgggtgctg    960
gtgtggttg gtgaagtcct ggcttgctat agcttgctag taacagtggc ctttattatt   1020
ttctgggtga ggagtaagag gagcaggctc ctgcacagtg actacatgaa catgactccc   1080
cgccgcccccg ggcccacccg caagcattac cagcccctatg ccccaccacg cgacttcgca   1140
gcctatcgct cctaa                                                    1155

SEQ ID NO: 140          moltype = DNA   length = 1140
FEATURE                 Location/Qualifiers
misc_feature            1..1140
                        note = F2.103.BB
source                  1..1140
                        mol_type = other DNA
                        organism = synthetic construct
SEQUENCE: 140
atggccttac cagtgaccgc cttgctcctg ccgctggcct tgctgctcca cgccgccagg   60
ccggaggtgc agctggtgga gtccggggga ggcttagttc agcctggggg gtccctgaga   120
ctctcctgtg cagtctctgg attcaccttc agtacctact ggatgcactg ggtccgccaa   180
gctccaggga aggggctggt gtgggtctca cgtattaata gtgatgggag tagcacaacc   240
tacgcggact ccgtgaaggg ccgattcacc atctccagag acaacgccaa gaacacgctg   300
tatctgcaaa tgaacagtct gagagccgag gacacggctg tgtattactg tgcaagagat   360
agagtactat ggatcgggga gttatcctac tacggtatgg acgtctgggg ccaagggacc   420
acggtcaccg tctcctcagg tggcggtggc tcggcggtg gtgggtcggg tggcggcgga    480
tctgacatcc agatgaccca gtctcctttcc accctgtctg catctgtagg agacagagtc   540
accatcactt gccgggccag tcagagtatt agtaactggt tggcctggta tcagcagaaa   600
ccagggaaag cccctaaact cctgctctat aaggcatctg gtttagaaag tgggggtccca   660
tcaaggttca gcggcagtgg atctgggaca gaattcactc tcaccatcaa cagcctgcag   720
cctgatgatt ttgcaactta ttactgccaa cagtctaata gttattcgtg gacgttcggc   780
cacgggacca aggtggaaat caaacgtacg accacgacgc cagcgccgcg accaccaaca   840
ccggcgccca ccatcgcgtc gcagcccctg tccctgcgcc agaggcgtg ccggccagcg    900
gcggggggcg cagtgcacac gaggggctg gacttcgcct gtgatatcta catctgggcg     960
cccttggccg ggacttgtgg ggtccttctc ctgtcactgg ttatcaccct ttactgccgg   1020
ggcagaaaga aactcctgta tattcaaa caaccattta tgagaccagt acaaactact   1080
caagaggaag atggctgtag ctgccgattt ccagaagaag aagaaggagg atgtgaataa   1140

SEQ ID NO: 141          moltype = DNA   length = 1176
FEATURE                 Location/Qualifiers
misc_feature            1..1176
                        note = F5.157.BB
source                  1..1176
                        mol_type = other DNA
                        organism = synthetic construct
SEQUENCE: 141
atggccttac cagtgaccgc cttgctcctg ccgctggcct tgctgctcca cgccgccagg   60
ccggaggtgc agctgttgga gtctggggga ggcttggtac agcctggggg gtccctgaga   120
ctctcctgtg cagcctctgg attcgccttt agcagctatg ccatgagctg ggtccgccag   180
gctccaggga aggggctgga gtgggtctca gctattagtg gtagtggtgg tagcacatac   240
tacgcagact ccgtgaaggg ccggttcacc atctccagag acaattccaa gaacacgctg   300
tatctgcaaa tgaacagcct gagaccgagg acacggccgt atattactgt gcgaaagatg   360
ggggggtacta tggttcgggg agttatgggt actttgactac tggggccagg gaaccctgg   420
tcaccgtctc tcaggtgg cggtggctcg gcggtggtgg ggtcgggtgg cggcggatct    480
atccagatga cccagtctcc atcttccgtg tctgcatctg caggagacag agtcaccatc   540
```

```
acttgtcggg cgagtcaggg tattagcagc tggttagcct ggtatcaaca gaaaccaggg    600
aaagccccta agctcctgat ctatgctgga tccagtttgc aaagtggggt cccatcaagg    660
ttcagcggca gtggatttgg gacagatttc actctcacca tcggcagcct gcagcctgaa    720
gattttgcaa cttactattg tcaacaggct agcagtttcc ctcggacgtt cggccaaggg    780
accaaggtgg agatcaaacg tacggtgctg caccatctgt cttcatcttc ccgccatctg    840
atgagcacca cgacgccagc gccgcgacca ccaacaccgg cgcccaccat cgcgtcgcag    900
cccctgtccc tgcgcccaga ggcgtgccgg ccagcggcgg ggggcgcagt gcacacgagg    960
gggctggact cgcctgtga tatctacatc tgggcgccct tggccgggac ttgtggggtc    1020
cttctcctgt cactggttat caccctttac tgccggggca gaaagaaact cctgtatata    1080
ttcaaacaac catttatgag accagtacaa actactcaa aggaagatgg ctgtagctgc    1140
cgatttccag aagaagaaga aggaggatgt gaataa                             1176

SEQ ID NO: 142          moltype = DNA  length = 1137
FEATURE                 Location/Qualifiers
misc_feature            1..1137
                        note = F5.77.BB
source                  1..1137
                        mol_type = other DNA
                        organism = synthetic construct
SEQUENCE: 142
atggccttac cagtgaccgc cttgctcctg ccgctggcct tgctgctcca cgccgccagg    60
ccggaggtgc agctgttgga gtctggggga ggcttggtac agcctgggg gtccctgaga    120
ctctcctgtg cagcctctgg attcacctt agcagctatg ccatgagctg ggtccgccag    180
gctccaggga aggggctgga gtgggtctca gctattagtg gtagtggtgg tagcacatac    240
tacgcagact ccgtgaaggg ccggttcacc atctccagag acaattccaa gaacacgctg    300
tatctgcaaa tgaacagcct gagagccgag gacacgccta tattactg tgcgaaagat    360
gggggggtact atggttcggg gagttatggg tactttgact actggggcca gggaaccctg    420
gtcaccgtct cctcaggtgg cggtggctcg gcggtggtg gtcgggtgg cggcggatct    480
gacatccaga tgacccagtc tccatcttcc gtgtctggat ctgtaggaga cagagtcacc    540
atcacttgtc gggcgagtca gggtattagc agctggttag cctgtatca gcagaaacca    600
gggaaagccc ctaagctcct gatctatgct ggatccagtt tgcaaagtgg ggtcccatca    660
aggttcagcg gcagtggatt tgggacagat ttcactctca ccatcagcag cctgcagcct    720
gaagatttgg caacttacta ttgtcaacag gctagcagtt ccctcggac attcggccaa    780
gggaccaagg tggagatcaa acgtacgacc acgacgccag cgccgcgacc accaacaccg    840
gcgcccacca tcgcgtcgca gcccctgtcc ctgcgcccag aggcgtgccg gccagcggcg    900
gggggcgcag tgcacacgag ggggctggac ttcgcctgtg atatctacat ctgggcgccc    960
ttggccggga cttgtggggt ccttctcctg tcactggtta tcacccttta ctgccgggggc   1020
agaaagaaac tcctgtatat attcaaacaa ccatttatga ccagtacaa actactcaa    1080
gaggaagatg gctgtagctg ccgatttcca gaagaagaag aaggaggatg tgaataa      1137

SEQ ID NO: 143          moltype = DNA  length = 1149
FEATURE                 Location/Qualifiers
misc_feature            1..1149
                        note = 4D11.CD28
source                  1..1149
                        mol_type = other DNA
                        organism = synthetic construct
SEQUENCE: 143
atggccttac cagtgaccgc cttgctcctg ccgctggcct tgctgctcca cgccgccagg    60
ccgcagctgc agctgcagga gtcgggccca ggactactga agccttcgga ccctgtcc    120
ctctcctgca ctgtctctgg cggctccatc agcagtcctg gttactacgg gggctggatc    180
cgccagcccc cagggaaggg gctggagtgg attgggagta tctataaaag tgggagcacc    240
taccacaacc cgtccctcaa gagtcgagtc accatatccg tagacacgtc caagaaccag    300
ttctccctga agctgagctc tgtgaccgcc gcagacacgg ctgtgtatta ctgtacgaga    360
cctgtagtac gatatttggg tggttcgac ccctggggca gggaacccct ggtcaccgtc    420
tcctcagcta gcggtggctg cggtcgggc ggtgtgggt cgggtggcgg cggatctgct   480
atccagttga cccagtctcc atcccctg tctgcatctg taggagacag agtcaccatc    540
acttgccggg caagtcaggg cattagcagt gctttagcct ggtatcagca gaaaccaggg    600
aaagctccta agctcctgat ctatgatgcc tccaattgg aaagtggggt cccatcaagg    660
ttcagcggca gtggatctgg gacagatttc actctcacca tcagcagcct gcagcctgaa    720
gattttgcaa cttattactg tcaacagttt aatagttacc cgacgttcgg ccaagggacc    780
aaggtggaaa tcaaacgtac ggctagcacc acgacgccag cgccgcgacc accaacaccg    840
gcgcccacca tcgcgtcgca gcccctgtcc ctgcgcccag aggcgtgccg gccagcggcg    900
gggggcgcag tgcacacgag ggggctggac ttcgcctgtg attttttggg gttggtggag    960
tcctgccttg ctatagcttg ctagtaacag tggcctttat tattttctgg gtgaggagta    1020
agaggagcag gctcctgcac agtgactaca tgaacatgac tccccgccgc                1080
cccgggccca cccgcaagca ttaccagccc tatgccccac cacgcgactt cgcagcctat    1140
cgctcctaa                                                           1149

SEQ ID NO: 144          moltype = DNA  length = 1134
FEATURE                 Location/Qualifiers
misc_feature            1..1134
                        note = A40C.CD28
source                  1..1134
                        mol_type = other DNA
                        organism = synthetic construct
SEQUENCE: 144
atggccttac cagtgaccgc cttgctcctg ccgctggcct tgctgctcca cgccgccagg    60
ccgcaggtcc agctggtaca atctggtgct gaagtgaaga aaccaggagc gtcggtgaag    120
```

```
gtctcatgca cagcctcagg cttcaacatc aaggactact acgtgcactg ggtcaagcaa    180
gctcccggac aggggctgga gtggatgggg agaattgacc cggaagacgg cgactcgaaa    240
tacgcgccga agttccaggg caaggccacc atgacagccg ataccagtac atcgaccgtt    300
tacatggagc tgtccagcct ccgctcagag gataccgcgg tatactactg tacgacctcc    360
tactacgtcg gaacgtacgg ttactggggc cagggtaccc tggtgacagt gtcctcgggg    420
ggcggcgggt ctggcggggg aggcagcggg ggcggcgggt cggacatcca gatgactcaa    480
tccccctctt ccctgagtgc gtccgtgggg gacagggtga cgatcacttg tagcgcttcg    540
tcctcggtgt cgtatatgct gtggttccag cagaagcccg gtaaggcccc caaactgctc    600
atttattcca ccagcaacct cgccagtggc gtacccagtc gcttctccgg tagtggctct    660
ggtaccgatt tcacactgac catctccagt ctgcaacctg aagacttcgc aacgtactat    720
tgtcagcagc gcacattcta tccctatacg tttgggggcg ggaccaaggt cgagatcaag    780
cgcacagcta gcaccacgac gccagcgccg cgaccaccaa caccggcgcc caccatcgcg    840
tcgcagcccc tgtccctgcg cccagaggcg tgccggccag cggcgggggg cgcagtgcac    900
acgagggggc tggacttcgc ctgtgatttt tgggtgctgg tggtggttgg tggagtcctg    960
gcttgctata gcttgctagt aacagtggcc tttattattt tctgggtgag gagtaagagg   1020
agcaggctcc tgcacagtga ctacatgaac atgactcccc gccgcccggg cccaccccgc   1080
aagcattacc agccctatgc cccaccacgc gacttcgcag cctatcgctc ctaa         1134

SEQ ID NO: 145           moltype = DNA   length = 1158
FEATURE                  Location/Qualifiers
misc_feature             1..1158
                         note = 119.CD28
source                   1..1158
                         mol_type = other DNA
                         organism = synthetic construct
SEQUENCE: 145
atggccttac cagtgaccgc cttgctcctg ccgctggcct tgctgctcca cgccgccagg    60
ccgcaggtcc aactgcagca gtcaggtcca ggactggtga agccctcgca gacccctctca   120
ctcacctgtg ccatctccgg ggacagtgtc tctagcaaca gtgctacttg gaactggatc    180
aggcagtccc catcgagaga ccttgagtgg ctgggaagga catactacag gtccaagtgg    240
tatcgtgatt atgtaggatc tgtgaaaagt cgaataatca tcaacccaga cacatccaac    300
aaccagttct ccctgcagct gaactctgtg actcccgagg acacggctat atattactgt    360
acaagagcac agtggctggg agggattacc cctactact acagtatgga cgtctggggc    420
caagggacca cggtcaccgt ctcttcaggt ggcggtggct cgggcggtgg tgggtcgggt    480
ggcggcggat ctgagatcgt gctgacgcag agtcccgcca ccctgtccct gtcgcccggt    540
gagcgggcca ctctctcctg cagggccagt cagtccgtgt ccagttatct cgcatggtac    600
caacagaagc cagggcaggc ccctcggctg ctcatatacg acgcttcaaa tcgcgccacc    660
gggatccctg caaggttctc cggctccggc agtggcaccg atttcacccct cacaatttcc    720
tccctggagc cggaggactt cgccgtgtat tactgccaac agaggagtaa cacttccggc    780
cccggcacaa aggtcgacat taagcgcact gctagcacca cgacgccagc gccgcgacca    840
ccaacaccgg cgcccaccat cgcgtcgcag ccctgtccc tgcgcccaga ggcgtgccga    900
ccagcggcgg ggggcgcagt gcacacgagg gggctggact tcgcctgtga tttttgggtg    960
ctggtggtgg ttggtggagt cctggcttgc tatagcttgc tagtaacagt ggcctttatt   1020
attttctggg tgaggagtaa gaggagcagg ctcctgcaca gtgactacat gaacatgact   1080
ccccgccgcc ccgggcccac ccgcaagcat taccagcct atgcccccacc acgcgacttc   1140
gcagcctatc gctcctaa                                                 1158

SEQ ID NO: 146           moltype = DNA   length = 1470
FEATURE                  Location/Qualifiers
misc_feature             1..1470
                         note = 4D5.BBZ (Her2 CAR)
source                   1..1470
                         mol_type = other DNA
                         organism = synthetic construct
SEQUENCE: 146
atggacttcc aggttcagat cttttcgttc ctgctgatca gcgcctctgt tatcatgtcg    60
cgcggcgaca tccagatgac ccagtcccct tcctccctct ctgcctctgt gggagaccgc   120
gttaccatca catgccgagc ttcccaggac gtgaacacag ccgtggcctg gtaccagcag   180
aagcccggga aggcacccaa actcctcatc tactccgctc cttcctata cagtggcgtg   240
ccttcccgat tctccggctc caggagtggc acggactttta cgctcaccat tagtagcctg   300
cagcccgaag acttcgcgac ctactattgt cagcaacact acacgacgcc accaactttc   360
ggccaggtac caaggtcga gattaagcga accggcagta ccagtgggtc tggcaagccc   420
ggcagcggcg agggatccga ggtccagctg gtcgagtccg gcggggggcct ggtgcagccg   480
ggccgctcgc tgaggttatc ttgcgccgcc agtggcttca acattacatc   540
cactgggtga ggcaggctcc gggcaagggc ctggaatggg tggctaggat ctacccta ct   600
aacgggtaca cacgctacgc agattcggtg aaaggccgct tcactatctc cgccgacacc   660
tcgaagaaca ctgcttacct gcagatgaac tccctcaggg ccgaagatac tgcagtctac   720
tactgctccc gctgggggtgg ggacggcttc tacgccatgg acgtgtgggg tcagggcact   780
ctagttacag tgtcatccac cacgacgcca gccgcgca ccaacaccg gcgcccacc    840
atcgcgtcgc agcccctgtc cctgcgccca gaggcgtgcc ggccagcggc gggggggcgca    900
gtgcacacga gggggctgga cttcgcctgt gatatctaca tctgggcgcc cttgccgggg   960
acttgtgggg tccttctcct gtcactggtt atcaccctt actgcaaacg gggcagaaag   1020
aaactcctgt atatattcaa acaacctttt atgagaccca tacaaactac tcaagaggaa   1080
gatggctgta gctgccgatt tccagaagaa gaagaaggag gatgtgaact gagagtgaag   1140
ttcagcagga gcgcagacgc cccgcgtac aagcaggcc agaaccagct ctataacgag   1200
ctcaatctag gacgaagaga ggagtacgac gttttggaca gagacgtgg ccgggaccct   1260
gagatggggg gaaagccgag aaggaagaac cctcaggaag gcctgtacaa tgaactgcag   1320
aaagataaga tggcggaggc ctacagtgag attgggatga aggcgagcg ccggagggc   1380
aaggggcacg atggccttta ccagggtctc agtacagcca ccaaggacac ctacgacgcc   1440
```

```
cttcacatgc aggccctgcc ccctcgctaa                                        1470

SEQ ID NO: 147          moltype = DNA  length = 1461
FEATURE                 Location/Qualifiers
misc_feature            1..1461
                        note = FMC63.BBZ (CD19 CAR)
source                  1..1461
                        mol_type = other DNA
                        organism = synthetic construct
SEQUENCE: 147
atggccttac cagtgaccgc cttgctcctg ccgctggcct tgctgctcca cgccgccagg   60
ccggacatcc agatgacaca gactacatcc tccctgtctg cctctctggg agacagagtc   120
accatcagtt gcagggcaag tcaggacatt agtaaatatt taaattggta tcagcagaaa   180
ccagatggaa ctgttaaact cctgatctac catacatcaa gattacactc aggagtccca   240
tcaaggttca gtggcagtgg gtctggaaca gattattctc tcaccattag caacctggag   300
caagaagata ttgccactta cttttgccaa caggtaata cgcttccgta cacgttcgga   360
ggggggacca agctggagat cacaggtggc ggtggctcgg gcggtggtgg gtcgggtggc   420
ggcggatctg aggtgaaact gcaggagtca ggacctggcc tggtggcgcc ctcacagagc   480
ctgtccgtca catgcactgt ctcagggggtc tcattacccg actatggtgt aagctggatt   540
cgccagcctc cacgaaaggg tctgagtgg ctgggagtaa tatggggtag tgaaaccaca   600
tactataatt cagctctcaa atccagactg accatcatca aggacaactc caagagccaa   660
gttttcttaa aaatgaacag tctgcaaact gatgacacag ccatttacta ctgtgccaaa   720
cattattact acggtggtag ctatgctatg gactactggg gccaaggaac ctcagtcacc   780
gtctcctcaa ccacgacgcc agcgccgcga ccaccaacac cggcgcccac catcgcgtcg   840
cagcccctgt cctgcgccc agaggcgtgc cggccagcgg cgggggcgc agtgcacacg   900
aggggggctgg acttcgcctg tgatatctac atctgggcgc ccttgccggg gacttgtggg   960
gtccttctcc tgtcactggt tatcaccctt tactgcaaac ggggcagaaa gaaactcctg   1020
tatatattca acaaccatt tatgagacca gtacaaacta ctcaagagga gatggctgt    1080
agctgccgat ttcagaaga agaagaagga ggatgtgaac tgagagtgaa gttcagcagg   1140
agcgcagacg cccccgcgta caagcagggc cagaaccagc tctataacga gctcaatcta   1200
ggacgaagag aggagtacga tgtttggac aagagacgtg gccgggaccc tgagatgggg   1260
ggaaagccga aaggaagaa ccctcaggaa ggcctgtaca atgaactgca gaaagataag   1320
atggcggagg cctacagtga gattgggatg aaggcgagc gccggagggg caaggggcac   1380
gatggccttt accagggtct cagtacagcc accaaggaca cctacgacgc ccttcacatg   1440
caggccctgc ccctcgcta a                                              1461

SEQ ID NO: 148          moltype = DNA  length = 1467
FEATURE                 Location/Qualifiers
misc_feature            1..1467
                        note = ss1.BBZ (mesothelin CAR)
source                  1..1467
                        mol_type = other DNA
                        organism = synthetic construct
SEQUENCE: 148
atggccttac cagtgaccgc cttgctcctg ccgctggcct tgctgctcca cgccgccagg   60
ccgggatccc aggtacaact gcagcagtct gggcctgagc tggagaagcc tggcgcttca   120
gtgaagatat cctgcaaggc ttctggttac tcattcactg gctacaccat gaactgggtg   180
aagcagagcc atggaaagag ccttgagtgg attggactta ttactcctta caatggtgct   240
tctagctaca accagaagtt caggggcaag gccacattaa ctgtagacaa gtcatccagc   300
acagcctaca tggacctcct cagtctgaca tctgaagact ctgcagtcta tttctgtgca   360
aggggggggt acgacgggag ggggttttgac tactgggggcc aagggaccac ggtcaccgtc   420
tcctcaggtg gaggcggttc aggcggcggt ggctctagcg gtggcggatc ggacatcgag   480
ctcactcagt ctccagcaat catgtctgca tctccagggg agaaggtcac catgacctgc   540
agtgccagct caagtgtaag ttacatgcac tggtaccagc agaagtcagg cacctccccc   600
aaaagatgga tttatgacac atccaaactg gcttctggag tcccaggtcg cttcagtgga   660
agtgggtctg gaaactctta ctctctcaca atcagcagcg tggaggctga agatgatgca   720
acttattact gccagcagtg gagtaagcac cctctcacgt acggtgctgg gacaaagttg   780
gaaatcaaag ctagcaccac gacgccagcg ccgcgaccac caacaccggc gcccaccatc   840
gcgtcgcagc ccctgtccct gcgcccagag gcgtgccgcc cagcgcggg ggcgcagtgc   900
acacgagggg ggctggactt cgcctgtgat atctacatct gggcgccctt gccgggggact   960
tgtgggggtcc ttctcctgtc actggttatc acccttttact gcaaacgggg cagaaagaaa   1020
ctcctgtata tattcaaaca accatttatg agaccagtac aaactactca agaggaagat   1080
ggctgtagct gccgatttcc agaagaagaa gaaggaggat gtgaactgag agtgaagttc   1140
agcaggagcg cagacgcccc cgcgtacaag cagggccaga accagctcta taacgagctc   1200
aatctaggac gaagagagga gtacgatgtt ttggacaaga cgtggccg ggaccctgag   1260
atgggggaa agccgagaag gaagaaccct caggaaggcc tgtacaatga actgcagaaa   1320
gataagatgc ggaggccta cagtgagatt gggatgaaag gcgagcgccg gaggggcaag   1380
gggcacgatg gcctttacca gggtctcagt acagccacca aggacaccta cgacgccctt   1440
cacatgcagg ccctgccccc tcgctaa                                       1467

SEQ ID NO: 149          moltype = DNA  length = 1386
FEATURE                 Location/Qualifiers
misc_feature            1..1386
                        note = J591.BBZ (PSMA CAR)
source                  1..1386
                        mol_type = other DNA
                        organism = synthetic construct
SEQUENCE: 149
atgacccagt ctcacaaatt catgtccaca tcagtaggag acagggtcag catcatctgt   60
```

```
aaggccagtc aagatgtggg tactgctgta gactggtatc aacagaaacc aggacaatct    120
cctaaactac tgatttattg ggcatccact cggcacactg gagtccctga tcgcttcaca    180
ggcagtggat ctgggacaga cttcactctc accattacta acgttcagtc tgaagacttg    240
gcagattatt tctgtcagca atataacagc tatcctctca cgttcggtgc tgggaccatg    300
ctggacctga aaggaggcgg aggatctggc ggcggaggaa gttctggcgg aggcagcgag    360
gtgcagctgc agcagagcgg acccgagctc gtgaagcctg gaacaagcgt gcggatcagc    420
tgcaagacca cgggctacac cttcaccgag tacaccatcc actgggtcaa gcagtcccac    480
ggcaagagcc tggagtggat cggcaatatc aaccccaaca cggcggcac cacctacaac    540
cagaagttcg aggacaaggc caccctgacc gtggacagca gcagcagcac cgcctacatg    600
gaactgcgga gcctgaccag cgaggacagc gccgtgtact attgtgccgc cggttggaac    660
ttcgactact ggggccaggg cacaaccctg acagtgtcta gcgctagctc cggaaccacg    720
acgccagcgc cgcgaccacc aacaccggcg cccaccatcg cgtcgcagcc cctgtccctg    780
cgcccagagg cgtgccggcc agcggcgggg ggcgcagtgc acacgagggg gctggacttc    840
gcctgtgata tctacatctg ggcgcccttg gccgggactt gtgggtcctt tctcctgtca    900
ctggttatca ccctttactg caaacggggc agaaagaaac tcctgtatat attcaaacaa    960
ccatttatga gaccagtaca aactactcaa gaggaagacg gctgtagctg ccgatttcca   1020
gaagaagaag aggaggatg tgaactgaga gtgaagttca gcaggagcgc agacgccccc   1080
gcgtacaagc agggccagaa ccagctctat aacgagctca atctaggacg aagagaggag   1140
tacgacgttt tggacaagag acgtggccgg gaccctgaga tgggggggaa gccgagaagg   1200
aagaaccctc aggaaggcct gtacaacgaa ctgcagaaaa taagatggcg ggaggcctac   1260
agtgagattg ggatgaaagg cgagcgccgg aggggcaagg ggcacgacgg cctttaccag   1320
ggtctcagta cagccaccaa ggacacctac gacgcccttc acatgcaggc cctgccccct   1380
cgctaa                                                               1386

SEQ ID NO: 150         moltype = DNA  length = 1599
FEATURE                Location/Qualifiers
misc_feature           1..1599
                       note = c-Met CAR
source                 1..1599
                       mol_type = other DNA
                       organism = synthetic construct
SEQUENCE: 150
atggccttac cagtgaccgc cttgctcctg ccgctggcct tgctgctcca cgccgccagg    60
ccgggatccg acatccagat gacccagagc cccagcagcg tgagcgccag cgtgggcgac   120
cgggtgacca tcacctgccg ggcagccag ggcatcaaca cctggctggc ctggtatcag   180
cagaagcccg gcaaggcccc caagctgctg atctacgccg ccagcagcct gaagagcggc   240
gtgcccagcc ggtttagcgg ctctggctct ggcgccgact tcaccctgac catcagcagc   300
ctgcagcccg aggacttcgc cacctactac tgccagcagg ccaacagctt cccctgacc   360
tttggcggcg gaacaaaggt ggagatcaag ggcagcacct caagcctggc   420
agcggcgagg gcagcaccaa gggcaggtg cagctggtgc agagcggagc cgaggtgaag   480
aagcctgcc cctccgtcaa ggtgtcctgc gaggccagcg gctacacctt caccagctac   540
ggcttcagct gggtgcggca ggcaccaggc cagggcctcg agtggatggg ctggatcagc   600
gccagcaacg gcaacaccta ctacgcccag aagttcgacg gcagggtcac catgaccacc   660
gacaccagca ccagcagcgc ctacatggaa ctgcggagcc tgagaagcga cgacaccgcc   720
gtgtactact gcgccagggt gtacgccgac tacgccgatt actggggcca gggcaccctg   780
gtgaccgtgt ctagcaccac gacgccagcg ccgcgaccac caacaccggc gcccaccatc   840
gcgtcgcagc cctgtccct gcgcccagag gcgtgccggc cagcggcggg ggcgcagtg   900
cacacgaggg ggctggactt cgcctgtgat ttttggggtgc tggtggtggt tggtggagtc   960
ctggcttgct atagcttgct agtaacagtg gcctttatta ttttctgggt gaggagtaag  1020
aggagcaggc tcctgcacag tgactacatg aacatgactc ccgcccgccc ggggccacc  1080
cgcaagcatt accagcccta tgccccacca cgcgcgactt cagcctatcg ctccaaacgg  1140
ggcagaaaga aactcctgta tatattcaaa caaccattta tgagaccagt acaaactact  1200
caagaggaag atggctgtag ctgccgattt ccagaagaag aagaaggagg atgtgaactg  1260
agagtgaagt tcagcaggag cgcagacgcc ccgcgtaca gcagggcca gaaccagctc  1320
tataacgaga gcttaggg acgaagagag gagtacgacg tttttggacaa gagacgtggc  1380
cgggaccctg agatgggggg aaagccgaga aggaagaacc ctcaggaagg cctgtacaat  1440
gaactgcaga agataagat ggcggaggcc tacagtgaga ttgggatgaa aggcgagcgc  1500
cggagggggca aggggcacga tggccttta cagggtctca gtacagccac caaggacacc  1560
tacgacgccc ttcacatgca ggccctgccc ctcgctaa                           1599

SEQ ID NO: 151         moltype = DNA  length = 1452
FEATURE                Location/Qualifiers
misc_feature           1..1452
                       note = BCMA CAR
source                 1..1452
                       mol_type = other DNA
                       organism = synthetic construct
SEQUENCE: 151
atggccttac cagtgaccgc cttgctcctg ccgctggcct tgctgctcca cgccgccagg    60
ccggaagtgc aattggtgga atcagggga ggacttgtgc agcctggagg atcgctgaga   120
ctgtcatgtg ccgtgtccgg cttttgccctg tccaaccacg gatgtcctg ggtccgccgc   180
gcgcctggaa aggcctcga atgggtgtcg ggtattgtgt acagcggtag cacctactat   240
gccgcatccg tgaaggggag attcaccatc agccgggaca actccaggaa cactctgtac   300
ctccaaatga attcgctgag accagaggac actgccatct actactgcgc cgcgcatgga   360
ggagagtccc acgtctgggg acaggggacc accgtgaccg tgtctagcgc gtccggcgga   420
ggcggcagcg ggggtcgggc atcaggggggc ggcgatcgg acatccagct cacccagtcc   480
ccagctcgc tgtccgcctc cgtgggagat cgggtcacca tcacgtgccg cgccagccag   540
tcgatttcct cctacctgaa ctggtaccaa cagaagcccg gaaagccccc gaagcttctc   600
atctacgccg cctcgagcct gcagtcagga gtgccctcac ggttctccgg ctccggttcc   660
```

```
ggtactgatt tcaccctgac catttcctcc ctgcaaccgg aggacttcgc tacttactac    720
tgccagcagt cgtactccac cccctacact ttcggacaag gcaccaaggt cgaaatcaag    780
accacgacgc cagcgccgcg accaccaaca ccggcgccca ccatcgcgtc gcagcccctg    840
tccctgcgcc cagaggcgtg ccggccagcg gcggggggcg cagtgcacac gagggggctg    900
gacttcgcct gtgatatcta catctgggcg cccttgtcg  ggacttgtgg ggtccttctc    960
ctgtcactgg ttatcaccct ttactgcaaa cggggcagaa agaaactcct gtatatattc   1020
aaacaaccat ttatgagacc agtacaaact actcaagagg aagatggctg tagctgccga   1080
tttccagaag aagaagaagg aggatgtgaa ctgagagtga agttcagcag gagcgcagac   1140
gccccgcgt  acaagcaggg ccagaaccag ctctataacg agctcaatct aggacgaaga   1200
gaggagtacg atgttttgga caagagacgt ggccgggacc ctgagatggg gggaaagccg   1260
agaaggaaga accctcagga aggcctgtac aatgaactgc agaaagataa gatggcggag   1320
gcctacagtg agattgggat gaaaggcgag cgccggaggg caaggggca  cgatggcctt   1380
taccagggtc tcagtacagc caccaaggac acctacgacg cccttcacat gcaggccctg   1440
cccccctcgct aa                                                      1452

SEQ ID NO: 152          moltype = DNA  length = 1095
FEATURE                 Location/Qualifiers
misc_feature            1..1095
                        note = FHVH33.BBZ (BCMA CAR)
source                  1..1095
                        mol_type = other DNA
                        organism = synthetic construct
SEQUENCE: 152
atggcactcc cagtaaccgc gctgttgctc cctctggccc tgctgctgca cgctgcgcgc     60
cctgaggttc agctgctgga gtccgggggc gggttagtcc agcccggcgg aagcctcgcg    120
ctgtcctgcg ccgcatccgg attcaccttc agttcgtacg ccatgagttg ggttcggcag    180
gctcccggaa agggtctgga gtgggtgtca agcatcagtg gaagtggtga ttacatctac    240
tacgccgaca gcgtcaaggg acgcttcact atcagtcggg acatctctaa gaacaccctg    300
tacctccaga tgaattccct gagggccgag gacaccgccg tctattactg cgccaaggag    360
gggaccggtg ctaactcttc cttggccgac tatcgcagct agggcaccct agtgactgtt    420
tcgtccacca cgacgccagc gccgcgacca caacaccgg  cgccaccatc gcgtcgcag    480
ccctgtccc  tgcgcccaga ggcgtgccgg ccagcggcgg ggggcgcagt gcacacgagg    540
gggctggact tcgcctgtga tatctacatc tgggcgccct tggccgggac ttgtggggtc    600
cttctcctgt cactggttat cacccttac  tgcggggca  gaaagaaact cctgtatata    660
ttcaaacaac catttatgag accagtacaa actactcaag aggaagatgg ctgtagctgc    720
cgatttccag aagaagaaga aggaggatgt gaactgagag tgaagttcag caggagcgca    780
gacgcccccg cgtacaagca gggccagaac cagctctata acgagctcaa tctaggacga    840
agagaggagt acgatgtttt ggacaagaga cgtggccggg accctgagat gggggggaaag   900
ccgagaagga agaaccctca ggaaggcctg tacaatgaac tgcagaaaga taagatggcg    960
gaggcctaca gtgagattgg gatgaaaggc gagcgccgga gggcaaggg  cgcacgatggc   1020
ctttaccagg gtctcagtac agccaccaag gacacctacg acgcccttca catgcaggcc   1080
ctgcccccctc gctaa                                                   1095

SEQ ID NO: 153          moltype = DNA  length = 1467
FEATURE                 Location/Qualifiers
misc_feature            1..1467
                        note = BCMA338.BBZ (BCMA CAR)
source                  1..1467
                        mol_type = other DNA
                        organism = synthetic construct
SEQUENCE: 153
atggctctgc ccgtcaccgc tctgctgctg cctctggctc tgctgctgca cgctgctcgc     60
cctcaggtca aactggaaga atctggcgga ggcctggtgc aggcaggacg gagcctgcgc    120
ctgagctgcg cagcatccga gcacaccttc agctcccacg tgatgggctg gtttcggcag    180
gccccaggca aggagagaga gagcgtggcc gtgatcgctg gagggacat  ctccacatct    240
tacgccgatt ccgtgaaggg ccggttcacc atcagccggg acaacgccaa gaagacactg    300
tatctgcaga tgaacagcct gaagcccgag gacaccgccg tgtactattg cgcagcaagg    360
agaatcgacg cagcagactt tgattcctgg ggccagggca cccaggtgac agtgtctagc    420
ggaggaggag gatctgaggt gcagctggtg gagagcggag cggcctggt  gcaggccgga    480
ggctctctga ggctgagctg tgcagcatcc ggaagaacct tcacaatgcg ctggtttagg    540
caggcaccag gaaaggagag ggagttcgtg gcagcaatca gcctgtcccc taccctggcc    600
tactatgccg agagcgtgaa gggcaggttt accatctccc gcgataacgc caagaataca    660
gtggtgctgc agatgaactc cctgaaacct gaggacacag ccctgtacta ttgtgccgcc    720
gatcggaaga gcgtgatgag cattagacca gactattggg gcagggaac  acaggtgacc    780
gtgagcagca ctagtaccac gacgccagcg ccgcgaccac caacaccggc gccaccatc    840
gcgtcgcagc cctgtccct  gcgcccagag gcgtgccggc cagcggcggg ggcgcagtg    900
cacacgaggg ggctggactt cgcctgtgat atctacatct gggcgccct  ggccgggact    960
tgtggggtcc ttctcctgt  actggttatc accctttact gcaaacgggg cagaaagaat   1020
ctcctgtata ttcaaaaca aacatttatg agaccagtac aaactactca agaggaagat   1080
ggctgtagct gccgatttcc agaagaagaa gaaggaggat gtgaactgag agtgaagttc   1140
agcaggagcg cagacgcccc cgcgtaccag caggcagga  accagctcta taacgagctc   1200
aatctaggac gaagagagga gtacgatgtt ttggacaaga gacgtggccg ggaccctgag   1260
atggggggaa agccgagaag gaagaaccct caggaaggcc tgtacaatga actgcagaaa   1320
gataagatgg cggaggccta cagtgagatt gggatgaaag gcgagcgccg gagggggcaag   1380
ggcacgatg  cctttaccag ggtctcagt  acagccacca aggacaccta cgacgccctt   1440
cacatgcagg ccctgccccc tcgctaa                                        1467

SEQ ID NO: 154          moltype = DNA  length = 1461
FEATURE                 Location/Qualifiers
```

```
misc_feature            1..1461
                        note = G33.BBZ (GPC3 CAR)
source                  1..1461
                        mol_type = other DNA
                        organism = synthetic construct
SEQUENCE: 154
atggctctcc ctgtgaccgc cctcttgctg ccgctggccc tcctgctgca cgccgcacgg     60
ccgcaggtgc agctgcagca gtcggggggcc gagctggtgc ggcccggggc ctccgtcaag    120
ctgtcctgca aggccagtgg gtacaccttc actgattatg agatgcactg ggtgaagcag    180
accctgtgc atggcctgaa atggatcggc gctctcgacc ccaagacagg tgacaccgcc     240
tacagtcaga agtttaaggg caaagcaacc ctcaccgccg acaagtcgtc ctcgaccgcc    300
tacatggagc tgaggtccct gacctccgag gattcggccg tctactactg cacccgcttc    360
tactcctaca catactgggg ccagggtacc ttagtgaccg tctcggcagg cggggggggc    420
tccggggggtg gcggcagtgg tgggggggggc tccgacgtgg tgatgacaca gaccccctgg    480
tccctcccag tttcgctcgg tgaccaggca tcgatctcgt gccgctcctc acagagtctg    540
gtgcactcca acggcaacac atatctgcac tggtacctcc agaagccggg gcagtcacct    600
aagctcctca tctacaaggt gagtaatcga ttcagtggcg tgccagacag gttctccggc    660
tccgggagtg gaacggattt cacccctgaag atctcccgcc tggaggcgga ggacctggga    720
gtctacttct gctcgcagaa cacccacgtc ccgccacgt ttggcagtgg cactaagctc    780
gagatcaaaa ccacgacgcc agcgccgcga ccccccaccc cggcgccgac aatcgcatcg    840
cagcccctga gcctgaggcc cgaggcatgt aggcccgccg caggcggagc cgtccacacc    900
aggggggtcg acttttgcatg cgatatctac atttgggcc ctctgccgg cacctgcgga    960
gtgctcctcc tcagtctggt gatcacactc tactgtaaga gggccgcaa gaagctgctg   1020
tacatcttca gcagccctt catgcgcccc gtccagacca cccaggaaga agatgggtgc   1080
agctgcagat tccccgagga ggaggaaggg gggtgcgaat tgcgcgttaa gttctcgcgt   1140
tccgccgacg cccagtcta caagcagggc cagaaccagc tttataacga gctcaatttg   1200
ggccggaggg aggagtacga cgtactcgac aagcgccgcg gccgcgaccc cgaaatgggt   1260
ggaaagcccc ggcgcaaaaa ccccccaggag gggctgtaca cgagctgca gaaggataag   1320
atggctgagg cctactctga gatcggtatg aagggcgagc ggcgccgcgg caaggacac    1380
gatggcctgt accaggggct gtccacggcc acaaaggata cgtacgacgc tctgcacatg   1440
caggccctgc ccccccgcta a                                             1461

SEQ ID NO: 155          moltype = DNA  length = 1440
FEATURE                 Location/Qualifiers
misc_feature            1..1440
                        note = C10.BBZ (EGFR CAR)
source                  1..1440
                        mol_type = other DNA
                        organism = synthetic construct
SEQUENCE: 155
atgggttggt cgtgcattat cctcttcctc gtcgcaaccg ctaccggcgt tcactcggat     60
tacaaggatg acgacgacaa agaggtacag ctggtgcaga gcggggccga ggttaagaag    120
cccggggtctt ccgtaaaggt gtcctgcaag gcctcgggag gcaattctc atcgtacgca   180
atatcgtggg tgcggcaggc ccccgggcag gggctggaat ggatgggcgg aattatccca   240
atcttcggga ccgccaacta tgcccagaag tttcagggtc gtgtgaccat tactgccgac   300
gagtccacca gtacgcccta catggagctg agtagtctgc gtagcgagga tactgccgtt   360
tattattgcg cccgggaaga gggaccgtac tgctcgtcga ctcatgttg cggcgccttc    420
gacatctggg gccaaggcac cctggtgacg gtgtcctccg gtggtgggcg aagtggcggc    480
ggggggtccg gcggggggcgg ttcacagtcc gtcctgaccc aggatcccgc ggtgtcggtc    540
gcgctgggtc agacagtaaa gataacatgc caggggcgat tctgcgcag ttatttcgcc    600
tcgtgatacc agcagaaacc cggccaggct cctaccctg ttatgtacga gcgcaatgac    660
agacccgcgg gcgtgcccga ccgcttctcc ggctcaaaga gcgggacctc cgcctccctg    720
gccatctccg gctccagtc tgaggatgag gccgattact actgcgctgc ttgggacgac    780
tccctcaatg gctatctgtt tggcgcaggc acaaagctga ccgtgctcgg aagggtcacc    840
gtctcttcag cggagcccaa atcttgtgac aaaactcaca ctgcccacc gtgcccagga    900
tccatctaca tctgggcccc tctgccggc acctgtggcg tgctgctgct gtccctggtc    960
atcacctgt actgcaagcg ggggcagaaa aagctgctgt acatcttcaa gcagccttc   1020
atgcggcctg tgcagaccac acaggaagag gacggctgta gctgtagatt ccccgaggaa   1080
gaggaaggcg gctgcgagct gagagtgaag ttcagcagaa gcgccgacgc ccctgcctat   1140
cagcagggcc agaaccagct gtacaacag ctgaacctgg gcagacggga ggaatacgac   1200
gtgctggaca gagaagagg ccggaccct gagatgggcg gcaagccag acggaagaac   1260
ccccaggaag gcctgtataa cgaactgcag aaagacaaga tggccgaggc ctacagcgag   1320
atcggcatga gggcgagcg gagaagaggc aaggccatg acgcctgta ccagggcctg   1380
agcaccgcca ccaaggacac ctacgacgcc ctgcacatgc aggccctgcc tccaagatga   1440

SEQ ID NO: 156          moltype = DNA  length = 1452
FEATURE                 Location/Qualifiers
misc_feature            1..1452
                        note = 2B3.BBZ (PSCA CAR)
source                  1..1452
                        mol_type = other DNA
                        organism = synthetic construct
SEQUENCE: 156
atggcgctac cggtgaccgc actcctgctg ccactcgccc tcctgctcca cgccgcccgc     60
cccgatatcc agctgaccca atcaccgtcg tccctgtctg cctccgtggg cgaccgggtg    120
acgatcacct gtagtgcctc gagcagtgta cggttcatcc actggtacca acagaagccc    180
ggcaaggcac caaagcggct gatctacgac accagcaagc tggcgtctgg ggtgcccagc    240
aggttctcgg gaagtggtag tggcacagac ttcactctca ccatcagttc actccagccg    300
gaggactttg ccacctacta ttgccagcag tggtcctcgt ccccctttac cttcggccag    360
```

```
ggaacaaagg tggaaattaa gggttcgacc tccggggggg gctccggtgg gggctccggc    420
ggggggggct catcggaggt tcagctggtg gagagcggcg gcggcctggt gcagcccggc    480
gggagtctgc ggctgtcctg tgccgccagc ggcttcaaca tcaaggacta ctacattcac    540
tgggtgcgga agccccagg caagggtctg gagtgggtgg cttggattga ccctgaaaac    600
ggcgacactg agttcgtgcc aaaattccag gggcgggca ccatctccgc cgacacctcc    660
aagaatacgg cctacctgca gatgaactcc ctgcgcgccg aagacacagc ggtctactac    720
tgcaagacag ggggtttctg gggccagggc accctcgtga ccgtttcgag tgccgccggc    780
accacgacgc cagcgccgcg accaccaaca ccggcgccca ccatcgcgtc gcagcccctg    840
tccctgcgcc cagaggcgtg ccggccagcg gcgggggcg cagtgcacac gagggggctg    900
gacttcgcct gtgatatcta catctgggcg cccttggccg ggacttgtgg ggtccttctc    960
ctgtcactgg ttatcaccct ttactgcaaa cggggcagaa agaaactcct gtatatattc   1020
aaacaaccat ttatgagacc agtacaaact actcaagagg aagatggctg tagctgccga   1080
tttccagaag aagaagaagg aggatgtgaa ctgagagtga agttcagcag gagcgcagac   1140
gcccccgcgt acaagcaggg ccagaaccag ctctataacg agctcaatct aggacgaaga   1200
gaggagtacg acgttttgga caagagacgt ggccgggacc ctgagatggg gggaaagccg   1260
agaaggaaga accctcagga aggcctgtac aatgaactgc agaaagataa gatggcggag   1320
gcctacagtg agattgggat gaaaggcgag cgccggaggg gcaaggggca cgatggcctt   1380
taccagggtc tcagtacagc caccaaggac acctacgacg cccttcacat gcaggccctg   1440
ccccctcgct aa                                                        1452

SEQ ID NO: 157          moltype = DNA   length = 1002
FEATURE                 Location/Qualifiers
misc_feature            1..1002
                        note = 7G3L.BBZ (CD123 CAR)
source                  1..1002
                        mol_type = other DNA
                        organism = synthetic construct
SEQUENCE: 157
atgcacacagt cgccagactc gctcgcggtt agcctcgggg agcgcgctac tatcaactgt     60
aagtcgtccc agtccctgct gaactcgggg aaccagaaga actacctcac ctggtacctg    120
cagaagcctg gtcagccccc aaaactgttg atctactggg ctagcacgcg ggagtcgggc    180
gtcccagacc gcttcagtgg tagcggcagt gggaccgact tcacactgac aatctcgtcg    240
cttcaggctg aggatgtggc ggtctattac tgtcagaacg actattcata cccctatacg    300
ttcggccagg gcaccaagct ggaaatcaag aggccagca cgccagcgcc gcgaccacca    360
acaccggcgc ccaccatcgc gtcgcagccc ctgtccctgc gcccagaggc gtgccggca    420
gcggcggggg cgcagtgca cacgagggg ctggacttcg cctgtgatat ctacatctgg    480
gcgcccttgg ccgggacttg tggggtcctt ctcctgtcac tggttatcac cctttactgc    540
cggggcagaa agaaactcct gtatatattc aaacaaccat ttatgagacc agtacaaact    600
actcaagagg aagatggctg tagctgccga tttccagaag aagaagaagg aggatgtgaa    660
ctgagagtga agttcagcag gagcgcagac gcccccgcgt acaagcaggg ccagaaccag    720
ctctataacg agctcaatct aggacgaaga gaggagtacg atgttttgga caagagacgt    780
ggccgggacc ctgagatggg gggaaagccg agaaggaaga accctcagga aggcctgtac    840
aatgaactgc agaaagataa gatggcggag gcctacagtg agattgggat gaaaggcgag    900
cgccggaggg gcaaggggca cgatggcctt taccagggtc tcagtacagc caccaaggac   960
acctacgacg cccttcacat gcaggccctg ccccctcgct aa                      1002

SEQ ID NO: 158          moltype = DNA   length = 1524
FEATURE                 Location/Qualifiers
misc_feature            1..1524
                        note = 14.g2a.BBZ (GD2 CAR)
source                  1..1524
                        mol_type = other DNA
                        organism = synthetic construct
SEQUENCE: 158
atggagttcg gcctctcctg gctctttctg gtcgcgatcc tgaaaggtgt gcagtgttcc     60
agggacatcc tgctgacgca gactcccctg tctctgcccg tgtcgctggg cgaccaggcc    120
tctatctcct gcagatcatc tcagtccctg gtgcacagga atggcaatac ctacctccac    180
tggtatctgc agaagcccgg ccagtcaccc aagttgctga tccacaaggt gtccaatcgt    240
ttctcggggg tccctgaccg cttctcgggg tccggcagtg gcaccgattt caccctgaag    300
atttcccgcg tggaggccga ggacctcggt gtctactct gttcccagtc cacccacgtg    360
ccccactca cctttggcgc cggtaccaaa ctcgaactca agcgcgcgga cgcagccccc    420
acggtgtcaa tcttccccgg ttcgggcggt ggggctccg gggagaggt gaagctgcag    480
cagagcggcc cctcgctcgt cgagccaggt gcgtccgtga tgatctcctg caaggcctcg    540
gggtcatcgt tcactggcta caacatgaac tgggtgcgac agaacattgg caagtcgctc    600
gagtggattg ggctcatcga cccctattac ggggcacctc ctacaaccga agttcaaa    660
ggccgggcca ccctgactgt ggataagagc tcgtccacgg cctacatgca cctgaagtcc    720
ctgacttcag aggattcggc ggtgtactac tgcgtgagtg gcatggagta ctgggggcag    780
gggacttcgg tcaccgtctc gtccgctaag acgaccccc catccgtcta cggcgagtt    840
acagtctcta gtaccacgac gccagcgccg cgaccaccaa caccggcgcc caccatcgcg    900
tcgcagcccc tgtccctgcg cccagaggcg tgccggccag cggcgggggg cgcagtgcac    960
acgagggggc tggacttcgc ctgtgatatc tacatctggg cgccttggc ggggacttgt   1020
ggggtccttc tcctgtcact ggttatcacc ctttactgca acggggcag aagaaactc   1080
ctgtatatat tcaaacaacc atttatgaga ccagtacaaa ctactcaaga ggaagatggc   1140
tgtagctgcc gatttccaga agaagaagaa ggaggatgtg aactgagagt gaagttcagc   1200
aggagcgcag acgcccccgc gtacaagcag ggccagaacc agctctataa cgagctcaat   1260
ctaggacgaa gagaggagta cgatgttttg acaagagac gtggccggga ccctgagatg   1320
gggggaaagc cgagaaggaa gaaccctcag gaaggcctgt acaatgaact gcagaaagat   1380
aagatggcgg aggcctacag tgagattggg atgaaaggcg agcgccggag gggcaagggg   1440
cacgatggcc tttaccaggg tctcagtaca gccaccaagg acacctacga cgcccttcac   1500
```

```
atgcaggccc tgcccctcg ctaa                                          1524
```

SEQ ID NO: 159          moltype = DNA   length = 1527
FEATURE                 Location/Qualifiers
misc_feature            1..1527
                        note = 3A1e.BBZ (CD7 CAR)
source                  1..1527
                        mol_type = other DNA
                        organism = synthetic construct
SEQUENCE: 159
```
atgctcgagg tgaaacagac tttgaatttt gaccttctca agttggcggg agacgtggag   60
tccaacccag ggccgatggc cttaccagtg accgccttgc tcctgccgct ggccttgctg  120
ctccacgccg ccaggccgca ggtgaaactg caggagtccg gcggcggtct ggtcaaaccg  180
ggcggctccc tgaagttgag ctgtgcggca tccgggttca cattctcgtc atacgcaatg  240
tcctgggtcc gccagacccc cgagaagcgc ctcgaatggg tggccaccat ctcctccggt  300
ggcagttata cgtactatcc ggactcggtg aagggccggt tcaccatctc tcgcgacaac  360
gccaagaaca ctctgtacct ccagatgtcc agcctgcgct ctgaagacac agcgatgtac  420
tactgcgcgc gccaggacgg ttattaccct ggatggttcg ccaattgggg ccagggcacg  480
actgtgaccg tgagtagtgg aggcggcggg tcaggcggcg ggggctcggg gggcggcgga  540
tcggacatcg agctgacaca atcgcccgct atcatgagtg cctcgctcgg agaggagatc  600
accctgactt gttctgcctc cagctccgtc tcatacatgc actggtatca gcagaagagc  660
ggcacctccc ccaagctcct catctactcc acaagcaacc tggcgtccgg ggtgccgtcc  720
cgcttctctg gctcgggctc aggaaccttc tattcactca ccatctcttc cgtggaggct  780
gaagatgcag ccgactacta ctgccatcag tggtcgtcgt acactttcgg cggcgggacc  840
aagctagaga tcaagcgcac cacgacgcca gcgccgcgac caccaacacc ggcgcccacc  900
atcgcgtcgc agccccctgtc cctgcgccca gaggcgtgcc ggcccgcggc ggggggcgca  960
gtgcacacga gggggctgga cttcgcctgt gatatctaca tctgggcgcc cttggccggg 1020
acttgtgggg tccttctcct gtcactggtt atcacccttt actgccgggg cagaaagaaa 1080
ctcctgtata tattcaaaca accatttatg agaccagtac aaactactca agaggaagat 1140
ggctgtagct gccgatttcc agaagaagaa gaaggaggat gtgaactgag agtgaagttc 1200
agcaggagcg cagacgcccc cgcgtacaag cagggccaga ccagctcta taacgagctc 1260
aatctaggac gaagagagga gtacgatgtt ttggacaaga cgtggccg ggaccctgag 1320
atgggggga agccgagaag gaagaaccct caggaaggcc tgtacaatga actgcagaaa 1380
gataagatgg cggaggccta cagtgagatt gggatgaaag cgagcgccg gaggggcaag 1440
gggcacgatg gcctttacca gggtctcagt acagccacca aggacaccta cgacgccctt 1500
cacatgcagg ccctgccccc tcgctaa                                    1527
```

SEQ ID NO: 160          moltype = DNA   length = 810
FEATURE                 Location/Qualifiers
misc_feature            1..810
                        note = NY-ESO-1 TCR alpha chain
source                  1..810
                        mol_type = other DNA
                        organism = synthetic construct
SEQUENCE: 160
```
atggagaccc tgctcggggt ctcactggtc atcctgtggc tgcagctggc cagggtgaac   60
tcgcagcagg ggggaggga cccccaggcc ctgtccatcc aggaggggga gaatgccatc  120
atgaattgca gttacaagac ttccataaac aacctgcagt ggtaccgcca gaactccggc  180
cgcggcctgg tgcacctgat cctcatccgg tcgaatgaaa gggaaaagca ctcgggacgc  240
ctgcgagtga ctctggacac gtccaagaag tcgtccagtc tcttaatcac cgcctctcgc  300
gcagccgata ccgcatcgta cttctgtgca accgacgggg cgggcaagag tacattcggc  360
gacggcacta ccctgaccgt gaagccaaat atccagaagc tgatccagc tgtctatcag  420
ttgcgcgatt ccaaatcgtc tgacaaatct gtgtgcctgt tcaccgactt cgactcccag  480
acgaacgtgt cccagagtaa agacagcgac gtgtacatca ctgataagac cgtgctggac  540
atgcgctcca tggactttaa aagtaacagc gctgtagcgt ggagcaacaa gagtgacttc  600
gcctgcgcca acgccttcaa taactctatc atacctgccg atacccttctt cccgagcccc  660
gaatccagtt gcgacgtgaa gctcgtggag aagagctttg agacagacac caacctgaac  720
ttccaaaacc tgtccgtcat tggcttcagg atcctcctcc tcaaggtggc cggcttcaac  780
ttgctcatga cgctgagact ctggagttca                                  810
```

SEQ ID NO: 161          moltype = DNA   length = 927
FEATURE                 Location/Qualifiers
misc_feature            1..927
                        note = NY-ESO-1 beta chain
source                  1..927
                        mol_type = other DNA
                        organism = synthetic construct
SEQUENCE: 161
```
atggactcgt ggaccttatg ctgcgtgtcc ctgtgcatac tggttgccaa gcacacagac   60
gccgggtga tccagagccc ccggcacgaa gttaccgaga tgggccagga ggtgacgctc  120
cgatgcaagc ccatcagtgg ccacgattat ctcttctggt accgcaaac catgatgcgc  180
ggcttggaac tcctcatcta cttcaacaac acgtcccca tcgatgactc cggcatgcct  240
gaggacaggt tcagtgcgaa gatgccgaat gcatccttct cccaccctga gatacagccg  300
agtgagcgc gcgactccgc tgtgtacttc tgcgcctcta tatcggcgc ccagctcaa  360
catttcggcg acggcacgcg cctcagtatc ctgaggacc tgaacaaggt gttccctccg  420
gaagtgcgct gtgtttgagcc ctcgaggca gaaatctcac acacacagaa ggcaaccctc  480
gtgtgtctgg caacagggtt cttcccgat cacgtggagc tgagttggtg ggtcaacggc  540
aaggaggtcc atagcggggt gagtaccgac ccacagcctc tcaaggagca gcctgccctc  600
aacgacagta ggtactgcct gtcctcgcgc ctccgcgtgt ccgcaacgtt ctggcagaat  660
```

```
cccccgcaacc acttccggtg ccaggtccaa ttctacggcc tgagtgagaa cgatgagtgg   720
acacaggata gggccaagcc cgtgacccag atcgtgtccg ccgaggcctg ggccgcgct    780
gactgcggct tcacctccgt gtcgtatcag cagggcgtat tatcagccac cattctttac   840
gaaatcctcc tcggcaaggc cacactatac gccgtgctgg tgtcggcgct ggtgttaatg   900
gcgatggtca agcgaaagga tttctaa                                       927

SEQ ID NO: 162           moltype = DNA   length = 1818
FEATURE                  Location/Qualifiers
misc_feature             1..1818
                         note = EBV16-E7 TCR
source                   1..1818
                         mol_type = other DNA
                         organism = synthetic construct
SEQUENCE: 162
atgtggggcg tgttccttct ctacgtgtcg atgaagatgg gtggcaccac aggacagaat   60
atcgaccagc ccactgagat daccgcaacc gagggagcga tcgtgcagat caactgcacc   120
taccagacat ccgggttcaa cgggctgttc tggtaccagc agcacgcagg ggaggcacct   180
accttcctgt cctacaatgt tctggacggc ctggaagaga aaggccgctt ctcttcattc   240
ctcagtcgct cgaagggcta ctcctacttg ctgctcaagg agttgcagat gaaggacagc   300
gcgtcctacc tctgcgcttc cgtggacggc aacaaccgtc tggcgttcgg caaaggcaac   360
caagtggtgg tgatcccgaa catccagaat cccgacccgg ctgtttacca gctgagagac   420
tccaaatcca gtgacaaatc tgtgtgtctg ttcaccgact tcgactccca aaccaacgtg   480
tctcagagta aggactctga cgtgtatatt acggataagt gcgtgctgga catgcgttca   540
atggacttca aaagcaattc cgccgtggca tggtccaaca agtcagactt cgcgtgtgcg   600
aacgccttca ataactcaat tatccccgag gataccttct tccctttccc agagagctct   660
tgcgatgtta agctccgtcg agaagtcgttc gagactgata ccaacctgta cttccagaac   720
ctgtcagtga tcggattccg tatactcctt ctgaaggtgg ccggcttcaa cctgctgatg   780
acactgagac tgtggagcag tcgagcgaag cgcgagggaa ggggcagtct gctcacctgc   840
ggcgacgtgg aggagaaccc cggccctatg gccccggac tgctgtgctg ggcactcctg   900
tgcctgctcg gggccggcct cgtcgatgct ggcgtgaccc agtcgcccac ccacctagtc   960
aagacgagag gacagcaagt gacgcttagg tgctcccccga agtcgggcca cgatacagtg  1020
agctggtacc agcaggccct ggggcaggc cccaattca tcttccaata ctatgaggag   1080
gaaagcgcc agcgaggcaa cttccctgac cgattcagcg gcatcagtt ccctaattac   1140
tcctcggagc tcaatgtgaa cgccctgctc tcggagact cggcactgta cctctgcgct   1200
tccagtctgg ggtgcgggg cggaagatac aatgaacagt tcttcgggcc aggcacccgc   1260
ttgaccgtgc tggaggacct caagaacgtg ttccccccag aggtggctgt gttcgagccg   1320
tcggaggcgg agatctcgca tacccagaag gctaccctgg tgtgccttgc taccggattc   1380
tatccggatc atgtggagct atcatggtgg gtcaacggga aggaggtgca ctccggggtg   1440
tgcaccgatc cacaacccct gaaggaacag cccgcactga atgatagcag gtactgcctc   1500
tccagtcgcc tgcgggtgtc agcaacattc tggcagaacc cccgcaacca ctttcgctgt   1560
caggtgcaat tttacggtct gtccgagaac acgaatgga ctcaggaccg tgccaaaccc   1620
gtgacacaga tcgtgtccgc agaagcgtgg ggccgtgccg actgcgggtt caccagcgag   1680
tcctaccagc agggcgtgct gtctgccact atcttgtacg agatcctcct gggcaaggca   1740
actctgtacg cagtactggt gtcggcgctg gtcctgatgg ccatggtgaa agcgtaaggac  1800
tctcgcgggt aataataa                                                1818

SEQ ID NO: 163           moltype = DNA   length = 1821
FEATURE                  Location/Qualifiers
misc_feature             1..1821
                         note = H3.3K27M TCR
source                   1..1821
                         mol_type = other DNA
                         organism = synthetic construct
SEQUENCE: 163
atgctgactg ccagcctgtt gagggcagtc atagcctcca tctgtgttgt atccagcatg   60
gctcagaagg taactcaagc gcagactgaa atttctgtgg tggagaagga ggatgtgacc   120
ttggactgtg tgtatgaaac ccgtgatact acttattact tattctggta caagcaacca   180
ccaagtggag aattggtttt ccttattcgt cggaactctt ttgatgagca aaatgaaata   240
agtggtcggt attcttggaa cttccagaaa tccaccagtt ccttcaactt caccatcaca   300
gcctcacaag tcgtggactc agcagtatac ttctgtctc tgagtgagga gaatgcatg   360
cgctttggag cagggaccag actgacagta aaaccaaata tccagaaccc tgaccctgcc   420
gtgtaccagc tgagagactc taaatccagt gacaagtctg tctgcctatt caccgatttt   480
gattctcaaa caaatgtgtc acaaagtaag gattctgatg tgtatatcac agacaaaact   540
gtcctagaca tgaggtctat ggacttcaag agcaacagtg ctgtggcctg gagcaacaaa   600
tctgactttg catgtgcaaa cgccttcaac aacagcatta ttccagaaga cactttcttc   660
cccagcccag aaagttcctg tgatgtcaag ctggtcgaga aaagctttga aacagatacg   720
aacctaaact tcaaaacct gtcagtgatt gggttccgaa tcctcctcct gaaagtggcc   780
ggatttaatc tgctcatgac gctgcggctg tggtccagcg tgaaacagca tttgaatttt   840
gaccttctca gttggcgggg agacgtggga tccaacccag gccgatggg ccccccagctc   900
cttggctatg tggtcctttg ccttctagga gcaggccccc tggaagccca agtgacccag   960
aacccaagat acctcatcac agtgactgga agaagttaa cagtgacttg ttctcagaat  1020
atgaaccatg agtatatgtc ctggtatcga caagacccag gctgggctt aaggcagatc  1080
tactattcaa tgaatgttga ggtgactgat aagggagatg ttcctgaagg gtacaaagtc  1140
tctcgaaaag agaagaggaa tttccccctg atcctggagt cagccaacca caacctgtgt  1200
tctctgtact ctgtgccag cggctggggt ggtccattct acgagcagta cttcgggccg  1260
ggcaccaggc tcacggtcac agaggacctg aaaaacgtgt tcccaccgga ggtgctgtg  1320
tttgagccat cagaagcaga gatctcccac acccaaaagg ccacactggt atgcctggcc  1380
acaggcttct ccccgaccca cgtggagctg agctggtggg tgaatgggaa ggaggtgcac  1440
agtgggtca gcacagaccc gcagcccctc aaggagcagc ccgccctcaa cgactccaga  1500
```

```
tactgcctga gcagccgcct gagggtctcg gccaccttct ggcagaaccc ccgcaaccac   1560
ttccgctgtc aagtccagtt ctacgggctc tcggagaacg acgagtggac ccaggatagg   1620
gccaaacccg tcacccagat cgtcagcgcc gaggcctggg gtagagcaga ctgtggcttc   1680
acctccgagt cttaccagca aggggtcctg tctgccacca tcctctatga gatcttgcta   1740
gggaaggcca ccttgtatgc cgtgctggtc agtgccctcg tgctgatggc catggtcaag   1800
agaaaggatt ccagaggcta g                                             1821

SEQ ID NO: 164         moltype = DNA  length = 1605
FEATURE                Location/Qualifiers
misc_feature           1..1605
                       note = CD19-CD3 BiTE
source                 1..1605
                       mol_type = other DNA
                       organism = synthetic construct
SEQUENCE: 164
atgggatgga gctgtatcat cctcttcttg gtagcaacag ctacaggtgt ccactccgac    60
tacaaagatg atgacgataa ggatatccag ctgacccagt ctccagcttc tttggctgtg   120
tctctagggc agagggccac catctcctgc aaggccagcc aaagtgttga ttatgatggt   180
gatagttatt tgaactggta ccaacagatt ccaggacagc cacccaaact cctcatctat   240
gatgcatcca atcagtttc tgggatccca cccaggttta gtggcagtgg gtctgggaca   300
gacttcaccc tcaacatcca tcctgtggag aaggtggatg ctgcaaccta tcactgtcag   360
caaagtactg aggatccgtg gacgttcggt ggagggacca agctcgagat caaaggtggt   420
ggtggttctg gcggcggcgg ctccggtggt ggtggttctc aggtgcagct gcagcagtct   480
ggggctgagc tggtgaggcc tgggtcctca gtgaagattt cctgcaaggc ttctggctat   540
gcattcagta gctactggat gaactgggtg aagcagaggc ctgacaggg tcttgagtgg   600
attggacaga tttggcctgg agatggtgat actaactaca atggaaagtt caagggtaaa   660
gccactctga ctgcagacga atcctccagc acagcctaca tgcaactcag cagcctagca   720
tctgaggact ctgcggtcta tttctgtgca agacggagga ctacgacggt aggccgttat   780
tactatgcta tggactactg gggccaaggg accacggtca ccgtctcctc cggaggtggt   840
ggatccgata tcaaactgca gcagtcaggg gctgaactgg caagacctgg ggcctcagtg   900
aagatgtcct gcaagacttc tggctacacc tttactaggt acacgatgca ctgggtaaaa   960
cagaggcctg gacagggtct ggaatggatt ggatacatta atcctagccg tggttatact  1020
aattacaatc agaagttcaa ggacaaggcc acattgacta gacaaatc tccagcaca   1080
gcctacatgc aactgagcag cctgacatct gaggactctg cggtctattt ctgtgcaaga  1140
tattatgatg atcattactg ccttgactac tggggccaag gcaccactct cacagtctcc  1200
tcagtcgaag tgaagtgg aggttctggt ggaagtggag gttcaggtgg agtcgacgac  1260
gccgccattc agctgaccca gtctccagca atcatgtctg catctccagg ggagaaggtc  1320
accatgacct gcagagccag ttcaagtgta agttacatga actggtacca gcagaagtca  1380
ggcacctccc ccaaaagatg gatttatgac acatccaaac tggcttctgg agtccctat  1440
cgcttcagtg gcagtgggtc tgggacctca tactctctca caatcagcag catggaggct  1500
gaagatgctg ccacttatta ctgccaacag tggagtagta cccgctcac gttcggtgct  1560
gggaccaagc tggagctgaa acatcatcac catcatcatt aataa                   1605

SEQ ID NO: 165         moltype = DNA  length = 1569
FEATURE                Location/Qualifiers
misc_feature           1..1569
                       note = 139-CD3 (EGFRvIII BiTE)
source                 1..1569
                       mol_type = other DNA
                       organism = synthetic construct
SEQUENCE: 165
atgggctgga gctgtatcat tctgttcctg gtggccacag ccactggcgt gcattcggat    60
tacaaggatg acgatgacaa ggatatccag atgacccaga gtccatcgtc cctgtccgcc   120
tcggtggaga ccgggtgac catcacttgc agagcatccc aaggcatccg caacaacctc   180
gcctggtacc agcagaagcc cggcaaggcc cccaagagcc tgatctatgc ggcatccaac   240
ctgcagtccg gcgtcccaag tcgcttcaca ggctcgggtt ccggcacaga gttcacttta   300
atcgtgtcct cgctccagcc agaggactt gcaacatact actgcctgca gcaccactcg   360
tatccctga cctcgggcgg cgggaccaag gtggagatca aggagggtgg cgggtctggt   420
ggcggaggtt ccggcggcgg ggctccgag gtacaggtac tcgagagtgg tggggcctg   480
gtgcagcccg gggctccct tagactctcg tgcgcggcca gcggattcac cttcagtcgc   540
tacgccatgt catgggtgcg acaggcgccc ggcaagggtc tcgagtgggt atcgccatt   600
tcgggctccg gcgggtcgac caactacgcc gatagtgtga agggccgttt caccatctcc   660
cgggacaaca gtaagaacac cctctacctg cagatgaaca gtctgagagc ggaggacacc   720
gcagtgtact actgcgcgcg gctcctcggg ggtccagat actggggcca gggcaccctg   780
gtgactgtgt ctagcggagg tggtggatcc gatatcaaac tgcagcagtc aggggctgaa   840
ctggcaagac tgggccctc agtgaagatg tcctgcaaga cttctggcta cacctttact   900
aggtacacga tgcactgggt aaaacagagg cctggacagg tctgaatg gattggatac   960
attaatccta gccgtggtta tactaattac aatcagaagt tcaaggacaa ggccacattg  1020
actacagaca aatcctccag cacagcctac atgcaactga gcagcctgac atctgaggac  1080
tctgcagtct attactgtgc aagatattat gatgatcatt actgccttga ctactggggc  1140
caaggcacca ctctcacagt ctcctcagtc gaaggtggaa gtggaggttc tggtggaagt  1200
ggaggttcag gtggagtcga cgacgccgcc attcagctga cccagtctcc agcaatcatg  1260
tctgcatctc caggggagaa ggtcaccatg acctgcagag ccagttcaag tgtaagttac  1320
atgaactggt accagcagaa gtcaggcacc tcccccaaaa gatggattta tgacacatcc  1380
aaactggcca ctctggagtc ccttatcgct tcagtggcag tggtctggac ctcatatctct  1440
ctcacaatca gcagcatgga ggctgaagat gctgccactt attactgcca acagtggagt  1500
agtaacccgc tcacgttcgg tgctgggacc aagctggagc tgaaacatca tcaccatcat  1560
cattaataa                                                           1569
```

| | | |
|---|---|---|
| SEQ ID NO: 166 | moltype = AA length = 277 | |
| FEATURE | Location/Qualifiers | |
| REGION | 1..277<br>note = Human CD40 | |
| source | 1..277<br>mol_type = protein<br>organism = Homo sapiens | |
| SEQUENCE: 166 | | |
| MVRLPLQCVL WGCLLTAVHP EPPTACREKQ YLINSQCCSL CQPGQKLVSD CTEFTETECL | | 60 |
| PCGESEFLDT WNRETHCHQH KYCDPNLGLR VQQKGTSETD TICTCEEGWH CTSEACESCV | | 120 |
| LHRSCSPGFG VKQIATGVSD TICEPCPVGF FSNVSSAFEK CHPWTSCETK DLVVQQAGTN | | 180 |
| KTDVVCGPQD RLRALVVIPI IFGILFAILL VLVFIKKVAK KPTNKAPHPK QEPQEINFPD | | 240 |
| DLPGSNTAAP VQETLHGCQP VTQEDGKESR ISVQERQ | | 277 |
| | | |
| SEQ ID NO: 167 | moltype = AA length = 357 | |
| FEATURE | Location/Qualifiers | |
| REGION | 1..357<br>note = Human RAP1 | |
| source | 1..357<br>mol_type = protein<br>organism = Homo sapiens | |
| SEQUENCE: 167 | | |
| MAPRRVRSFL RGLPALLLLL LFLGPWPAAS HGGKYSREKN QPKPSPKRES GEEFRMEKLN | | 60 |
| QLWEKAQRLH LPPVRLAELH ADLKIQERDE LAWKKLKLDG LDEDGEKEAR LIRNLNVILA | | 120 |
| KYGLDGKKDA RQVTSNSLSG TQEDGLDDPR LEKLWHKAKT SGKFSGEELD KLWREFLHHK | | 180 |
| EKVHEYNVLL ETLSRTEEIH ENVISPSDLS DIKGSVLHSR HTELKEKLRS INQGLDRLRR | | 240 |
| VSHQGYSTEA EFEEPRVIDL WDLAQSANLT DKELEAFREE LKHFEAKIEK HNHYQKQLEI | | 300 |
| AHEKLRHAES VGDGERVSRS REKHALLEGR TKELGYTVKK HLQDLSGRIS RARHNEL | | 357 |
| | | |
| SEQ ID NO: 168 | moltype = AA length = 105 | |
| FEATURE | Location/Qualifiers | |
| REGION | 1..105<br>note = Human RAP1 Domain 3 | |
| source | 1..105<br>mol_type = protein<br>organism = Homo sapiens | |
| SEQUENCE: 168 | | |
| SRHTELKEKL RSINQGLDRL RRVSHQGYST EAEFEEPRVI DLWDLAQSAN LTDKELEAFR | | 60 |
| EELKHFEAKI EKHNHYQKQL EIAHEKLRHA ESVGDGERVS RSREK | | 105 |
| | | |
| SEQ ID NO: 169 | moltype = AA length = 275 | |
| FEATURE | Location/Qualifiers | |
| REGION | 1..275<br>note = Human ICAM2 | |
| source | 1..275<br>mol_type = protein<br>organism = Homo sapiens | |
| SEQUENCE: 169 | | |
| MSSFGYRTLT VALFTLICCP GSDEKVFEVH VRPKKLAVEP KGSLEVNCST TCNQPEVGGL | | 60 |
| ETSLDKILLD EQAQWKHYLV SNISHDTVLQ CHFTCSGKQE SMNSNVSVYQ PPRQVILTLQ | | 120 |
| PTLVAVGKSF TIECRVPTVE PLDSLTLFLF RGNETLHYET FGKAAPAPQE ATATFNSTAD | | 180 |
| REDGHRNFSC LAVLDLMSRG GNIFHKHSAP KMLEIYEPVS DSQMVIIVTV VSVLLSLFVT | | 240 |
| SVLLCFIFGQ HLRQQRMGTY GVRAAWRRLP QAFRP | | 275 |
| | | |
| SEQ ID NO: 170 | moltype = AA length = 547 | |
| FEATURE | Location/Qualifiers | |
| REGION | 1..547<br>note = Human ICAM3 | |
| source | 1..547<br>mol_type = protein<br>organism = Homo sapiens | |
| SEQUENCE: 170 | | |
| MATMVPSVLW PRACWTLLVC CLLTPGVQGQ EFLLRVEPQN PVLSAGGSLF VNCSTDCPSS | | 60 |
| EKIALETSLS KELVASGMGW AAFNLSNVTG NSRILCSVYC NGSQITGSSN ITVYRLPERV | | 120 |
| ELAPLPPWQP VGQNFTLRCQ VEDGSPRTSL TVVLLRWEEE LSRQPAVEEP AEVTATVLAS | | 180 |
| RDDHGAPFSC RTELDMQPQG LGLFVNTSAP RQLRTFVLPV TPPRLVAPRF LEVETSWPVD | | 240 |
| CTLDGLFPAS EAQVYLALGD QMLNATVMNH GDTLTATATA TARADQEGAR EIVCNVTLGG | | 300 |
| ERREARENLT VFSFLGPIVN LSEPTAHEGS TVTVSCMAGA RVQVTLDGVP AAAPGQPAQL | | 360 |
| QLNATESDDG RSFFCSATLE VDGEFLHRNS SVQLRVLYGP KIDRATCPQH LKWKDKTRHV | | 420 |
| LQCQARGNPY PELRCLKEGS SREVPVGIPF FVNVTHNGTY QCQASSSRGK YTLVVVMDIE | | 480 |
| AGSSHFVPVF VAVLLTLGVV TIVLALMYVF REHQRSGSYH VREESTYLPL TSMQPTEAMG | | 540 |
| EEPSRAE | | 547 |
| | | |
| SEQ ID NO: 171 | moltype = AA length = 769 | |
| FEATURE | Location/Qualifiers | |
| REGION | 1..769<br>note = Human CD18 | |
| source | 1..769<br>mol_type = protein | |

```
                        organism = Homo sapiens
SEQUENCE: 171
MLGLRPPLLA LVGLLSLGCV LSQECTKFKV SSCRECIESG PGCTWCQKLN FTGPGDPDSI    60
RCDTRPQLLM RGCAADDIMD PTSLAETQED HNGGQKQLSP QKVTLYLRPG QAAAFNVTFR   120
RAKGYPIDLY YLMDLSYSML DDLRNVKKLG GDLLRALNEI TESGRIGFGS FVDKTVLPFV   180
NTHPDKLRNP CPNKEKECQP PFAFRHVLKL TNNSNQFQTE VGKQLISGNL DAPEGGLDAM   240
MQVAACPEEI GWRNVTRLLV FATDDGFHFA GDGKLGAILT PNDGRCHLED NLYKRSNEFD   300
YPSVGQLAHK LAENNIQPIF AVTSRMVKTY EKLTEIIPKS AVGELSEDSS NVVQLIKNAY   360
NKLSSRVFLD HNALPDTLKV TYDSFCSNGV THRNQPRGDC DGVQINVPIT PQVKVTATEC   420
IQEQSFVIRA LGFTDIVTVQ VLPQCECRCR DQSRDRSLCH GKGFLECGIC RCDTGYIGKN   480
CECQTQGRSS QELEGSCRKD NNSIICSGLG DCVCGQCLCH TSDVPGKLIY GQYCECDTIN   540
CERYNGQVCG GPGRGLCFCG KCRCHPGFEG SACQCERTTE GCLNPRRVEC SGRGRCRCNV   600
CECHSGYQLP LCQECPGCPS PCGKYISCAE CLKFEKGPFG KNCSAACPGL QLSNNPVKGR   660
TCKERDSEGC WVAYTLEQQD GMDRYLIYVD ESRECVAGPN IAAIVGGTVA GIVLIGILLL   720
VIWKALIHLS DLREYRRFEK EKLKSQWNND NPLFKSATTT VMNPKFAES              769

SEQ ID NO: 172          moltype = AA  length = 468
FEATURE                 Location/Qualifiers
REGION                  1..468
                        note = Human CEACAM1
source                  1..468
                        mol_type = protein
                        organism = Homo sapiens
SEQUENCE: 172
MGHLSAPLHR VRVPWQGLLL TASLLTFWNP PTTAQLTTES MPFNVAEGKE VLLLVHNLPQ    60
QLFGYSWYKG ERVDGNRQIV GYAIGTQQAT PGPANSGRET IYPNASLLIQ NVTQNDTGFY   120
TLQVIKSDLV NEEATGQFHV YPELPKPSIS SNNSNPVEDK DAVAFTCEPE TQDTTYLWWI   180
NNQSLPVSPR LQLSNGNRTL TLLSVTRNDT GPYECEIQNP VSANRSDPVT LNVTYGPDTP   240
TISPSDTYYR PGANLSLSCY AASNPPAQYS WLINGTFQQS TQELFIPNIT VNNSGSYTCH   300
ANNSVTGCNR TTVKTIIVTE LSPVVAKPQI KASKTTVTGD KDSVNLTCST NDTGISIRPW   360
FKNQSLPSSE RMKLSQGNTT LSINPVKRED AGTYWCEVFN PISKNQSDPI MLNVNYNALP   420
QENGLSPGAI AGIVIGVVAL VALIAVALAC FLHFGKTGRT TPMTHLTR                468

SEQ ID NO: 173          moltype = AA  length = 164
FEATURE                 Location/Qualifiers
REGION                  1..164
                        note = CD3zeta polypeptide
source                  1..164
                        mol_type = protein
                        organism = Homo sapiens
SEQUENCE: 173
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP QRRKNPQEGL YNELQKDKMA   120
EAYSEIGMKG ERRRGKGHDG LYQGLSTATK DTYDALHMQA LPPR                    164

SEQ ID NO: 174          moltype = AA  length = 86
FEATURE                 Location/Qualifiers
REGION                  1..86
                        note = FcRgamma polypeptide
source                  1..86
                        mol_type = protein
                        organism = Homo sapiens
SEQUENCE: 174
MIPAVVLLLL LLVEQAAALG EPQLCYILDA ILFLYGIVLT LLYCRLKIQV RKAAITSYEK    60
SDGVYTGLST RNQETYETLK HEKPPQ                                        86

SEQ ID NO: 175          moltype = AA  length = 113
FEATURE                 Location/Qualifiers
REGION                  1..113
                        note = DAP12
source                  1..113
                        mol_type = protein
                        organism = Homo sapiens
SEQUENCE: 175
MGGLEPCSRL LLLPLLLAVS GLRPVQAQAQ SDCSCSTVSP GVLAGIVMGD LVLTVLIALA    60
VYFLGRLVPR GRGAAEAATR KQRITETESP YQELQGQRSD VYSDLNTQRP YYK          113

SEQ ID NO: 176          moltype = AA  length = 235
FEATURE                 Location/Qualifiers
REGION                  1..235
                        note = CD8
source                  1..235
                        mol_type = protein
                        organism = Homo sapiens
SEQUENCE: 176
MALPVTALLL PLALLLHAAR PSQFRVSPLD RTWNLGETVE LKCQVLLSNP TSGCSWLFQP    60
RGAAASPTFL LYLSQNKPKA AEGLDTQRFS GKRLGDTFVL TLSDFRRENE GYYFCSALSN   120
SIMYFSHFVP VFLPAKPTTT PAPRPPTPAP TIASQPLSLR PEACRPAAGG AVHTRGLDFA   180
CDIYIWAPLA GTCGVLLLSL VITLYCNHRN RRRVCKCPRP VVKSGDKPSL SARYV        235
```

```
SEQ ID NO: 177          moltype = AA  length = 458
FEATURE                 Location/Qualifiers
REGION                  1..458
                        note = CD4
source                  1..458
                        mol_type = protein
                        organism = Homo sapiens
SEQUENCE: 177
MNRGVPFRHL LLVLQLALLP AATQGKKVVL GKKGDTVELT CTASQKKSIQ FHWKNSNQIK   60
ILGNQGSFLT KGPSKLNDRA DSRRSLWDQG NFPLIIKNLK IEDSDTYICE VEDQKEEVQL  120
LVFGLTANSD THLLQGQSLT LTLESPPGSS PSVQCRSPRG KNIQGGKTLS VSQLELQDSG  180
TWTCTVLQNQ KKVEFKIDIV VLAFQKASSI VYKKEGEQVE FSFPLAFTVE KLTGSGELWW  240
QAERASSSKS WITFDLKNKE VSVKRVTQDP KLQMGKKLPL HLTLPQALPQ YAGSGNLTLA  300
LEAKTGKLHQ EVNLVVMRAT QLQKNLTCEV WGPTSPKLML SLKLENKEAK VSKREKAVWV  360
LNPEAGMWQC LLSDSGQVLL ESNIKVLPTW STPQVPMALI VLGGVAGLLL FIGLGIFFCV  420
RCRHRRRQAE RMSQIKRLLS EKKTCQCPHR FQKTCSPI                         458

SEQ ID NO: 178          moltype = AA  length = 250
FEATURE                 Location/Qualifiers
REGION                  1..250
                        note = CD58
source                  1..250
                        mol_type = protein
                        organism = Homo sapiens
SEQUENCE: 178
MVAGSDAGRA LGVLSVVCLL HCFGFISCFS QQIYGVVYGN VTFHVPSNVP LKEVLWKKQK   60
DKVAELENSE FRAFSSFKNR VYLDTVSGSL TIYNLTSSDE DEYEMESPNI TDTMKFFLYV  120
LESLPSPTLT CALTNGSIEV QCMIPEHYNS HRGLIMYSWD CPMEQCKRNS TSIYFKMEND  180
LPQKIQCTLS NPLFNTTSSI ILTTCIPSSG HSRHRYALIP IPLAVITTCI VLYMNGILKC  240
DRKPDRTNSN                                                        250

SEQ ID NO: 179          moltype = AA  length = 193
FEATURE                 Location/Qualifiers
REGION                  1..193
                        note = CD70
source                  1..193
                        mol_type = protein
                        organism = Homo sapiens
SEQUENCE: 179
MPEEGSGCSV RRRPYGCVLR AALVPLVAGL VICLVVCIQR FAQAQQQLPL ESLGWDVAEL   60
QLNHTGPQQD PRLYWQGGPA LGRSFLHGPE LDKGQLRIHR DGIYMVHIQV TLAICSSTTA  120
SRHHPTTLAV GICSPASRSI SLLRLSFHQG CTIASQRLTP LARGDTLCTN LTGTLLPSRN  180
TDETFFGVQW VRP                                                    193

SEQ ID NO: 180          moltype = AA  length = 205
FEATURE                 Location/Qualifiers
REGION                  1..205
                        note = CD83
source                  1..205
                        mol_type = protein
                        organism = Homo sapiens
SEQUENCE: 180
MSRGLQLLLL SCAYSLAPAT PEVKVACSED VDLPCTAPWD PQVPYTVSWV KLLEGGEERM   60
ETPQEDHLRG QHYHQKGQNG SFDAPNERPY SLKIRNTTSC NSGTYRCTLQ DPDGQRNLSG  120
KVILRVTGCP AQRKEETFKK YRAEIVLLLA LVIFYLTLII FTCKFARLQS IFPDFSKAGM  180
ERAFLPVTSP NKHLGLVTPH KTELV                                       205

SEQ ID NO: 181          moltype = AA  length = 254
FEATURE                 Location/Qualifiers
REGION                  1..254
                        note = CD137L
source                  1..254
                        mol_type = protein
                        organism = Homo sapiens
SEQUENCE: 181
MEYASDASLD PEAPWPPAPR ARACRVLPWA LVAGLLLLLL LAAACAVFLA CPWAVSGARA   60
SPGSAASPRL REGPELSPDD PAGLLDLRQG MFAQLVAQNV LLIDGPLSWY SDPGLAGVSL  120
TGGLSYKEDT KELVVAKAGV YYVFFQLELR RVVAGEGSGS VSLALHLQPL RSAAGAAALA  180
LTVDLPPASS EARNSAFGFQ GRLLHLSAGQ RLGVHLHTEA RARHAWQLTQ GATVLGLFRV  240
TPEIPAGLPS PRSE                                                   254

SEQ ID NO: 182          moltype = AA  length = 183
FEATURE                 Location/Qualifiers
REGION                  1..183
                        note = CD252
source                  1..183
                        mol_type = protein
                        organism = Homo sapiens
```

```
SEQUENCE: 182
MERVQPLEEN VGNAARPRFE RNKLLLVASV IQGLGLLLCF TYICLHFSAL QVSHRYPRIQ    60
SIKVQFTEYK KEKGFILTSQ KEDEIMKVQN NSVIINCDGF YLISLKGYFS QEVNISLHYQ   120
KDEEPLFQLK KVRSVNSLMV ASLTYKDKVY LNVTTDNTSL DDFHVNGGEL ILIHQNPGEF   180
CVL                                                                183

SEQ ID NO: 183            moltype = AA   length = 302
FEATURE                   Location/Qualifiers
REGION                    1..302
                          note = CD275
source                    1..302
                          mol_type = protein
                          organism = Homo sapiens
SEQUENCE: 183
MRLGSPGLLF LLFSSLRADT QEKEVRAMVG SDVELSCACP EGSRFDLNDV YVYWQTSESK    60
TVVTYHIPQN SSLENVDSRY RNRALMSPAG MLRGDFSLRL FNVTPQDEQK FHCLVLSQSL   120
GFQEVLSVEV TLHVAANFSV PVVSAPHSPS QDELTFTCTS INGYPRPNVY WINKTDNSLL   180
DQALQNDTVF LNMRGLYDVV SVLRIARTPS VNIGCCIENV LLQQNLTVGS QTGNDIGERD   240
KITENPVSTG EKNAATWSIL AVLCLLVVVA VAIGWVCRDR CLQHSYAGAW AVSPETELTG   300
HV                                                                 302

SEQ ID NO: 184            moltype = AA   length = 532
FEATURE                   Location/Qualifiers
REGION                    1..532
                          note = CD54
source                    1..532
                          mol_type = protein
                          organism = Homo sapiens
SEQUENCE: 184
MAPSSPRPAL PALLVLLGAL FPGPGNAQTS VSPSKVILPR GGSVLVTCST SCDQPKLLGI    60
ETPLPKKELL LPGNNRKVYE LSNVQEDSQP MCYSNCPDGQ STAKTFLTVY WTPERVELAP   120
LPSWQPVGKN LTLRCQVEGG APRANLTVVL LRGEKELKRE PAVGEPAEVT TTVLVRRDHH   180
GANFSCRTEL DLRPQGLELF ENTSAPYQLQ TFVLPATPPQ LVSPRVLEVD TQGTVVCSLD   240
GLFPVSEAQV HLALGDQRLN PTVTYGNDSF SAKASVSVTA EDEGTQRLTC AVILGNQSQE   300
TLQTVTIYSF PAPNVILTKP EVSEGTEVTV KCEAHPRAKV TLNGVPAQPL GPRAQLLLKA   360
TPEDNGRSFS CSATLEVAGQ LIHKNQTREL RVLYGPRLDE RDCPGNWTWP ENSQQTPMCQ   420
AWGNPLPELK CLKDGTFPLP IGESVTVTRD LEGTYLCRAR STQGEVTRKV TVNVLSPRYE   480
IVIITVVAAA VIMGTAGLST YLYNRQRKIK KYRLQQAQKG TPMKPNTQAT PP           532

SEQ ID NO: 185            moltype = AA   length = 1179
FEATURE                   Location/Qualifiers
REGION                    1..1179
                          note = CD49a
source                    1..1179
                          mol_type = protein
                          organism = Homo sapiens
SEQUENCE: 185
MAPRPRARPG VAVACCWLLT VVLRCCVSFN VDVKNSMTFS GPVEDMFGYT VQQYENEEGK    60
WVLIGSPLVG QPKNRTGDVY KCPVGRGESL PCVKLDLPVN TSIPNVTEVK ENMTFGSTLV   120
TNPNGGFLAC GPLYAYRCGH LHYTTGICSD VSPTFQVVNS IAPVQECSTQ LDIVIVLDGS   180
NSIYPWDSVT AFLNDLLERM DIGPKQTQVG IVQYGENEVH EFNLNKYSST EEVLVAAKKI   240
VQRGGRQTMT ALGIDTARKE AFTEARGARR GVKKVMVIVT DGESHDNHRL KKVIQDCEDE   300
NIQRFSIAIL GSYNRGNLST EKFVEEIKSI ASEPTEKHFF NVSDELALVT IVKTLGERIF   360
ALEATADQSA ASFEMEMSQT GFSAHYSQDW VMLGAVGAYD WNGTVVMQKA SQIIIPRNTT   420
FNVESTKKNE PLASYLGYTV NSATASSGDV LYIAGQPRYN HTGQVIIYRM EDGNIKILQT   480
LSGEQIGSYF GSILTTTDID KDSNTDILLV GAPMYMGTEK EEQGKVYVYA LNQTRFEYQM   540
SLEPIKQTCC SSRQHNSCTT ENKNEPCGAR FGTAIAAVKD LNLDGFNDIV IGAPLEDDHG   600
GAVYIYHGSG KTIRKEYAQR IPSGGDGKTL KFFGQSIHGE MDLNGDGLTD VTIGGLGGAA   660
LFWSRDVAVV KVTMNFEPNK VNIQKKNCHM EGKETVCINA TVCFDVKLKS KEDTIYEADL   720
QYRVTLDSLR QISRSFFSGT QERKVQRNIT VRKSECTKHS FYMLDKHDFQ DSVRITLDFN   780
LTDPENGPVL DDSLPNSVHE YIPFAKDCGN KEKCISDLSL HVATTEKDLL IVRSQNDKFN   840
VSLTVKNTKD SAYNTRTIVH YSPNLVFSGI EAIQKDSCES NHNITCKVGY PFLRRGEMVT   900
FKILFQFNTS YLMENVTIYL SATSDSEEPP ETLSDNVVNI SIPVLYEVGL QFYSSASEYH   960
ISIAANETVP EVINSTEDIG NEINIFYLIR KSGSFPMPEL KLSISFPNMT SNGYPVLYPT  1020
GLSSSENANC RPHIFEDPFS INSGKKMTTS TDHLKRGTIL DCNTCKFATI TCNLTSSDIS  1080
QVNVSLILWK PTFIKSYFSS LNLTIRGELR SENASLVLSS SNQKRELAIQ ISKDGLPGRV  1140
PLWVILLSAF AGLLLLMLLI LALWKIGFFK RPLKKKMEK                         1179

SEQ ID NO: 186            moltype = AA   length = 538
FEATURE                   Location/Qualifiers
REGION                    1..538
                          note = CD112
source                    1..538
                          mol_type = protein
                          organism = Homo sapiens
SEQUENCE: 186
MARAAALLPS RSPPTPLLWP LLLLLLLETG AQDVRVQVLP EVRGQLGGTV ELPCHLLPPV    60
PGLYISLVTW QRPDAPANHQ NVAAFHPKMG PSFPSPKPGS ERLSFVSAKQ STGQDTEAEL   120
QDATLALHGL TVEDEGNYTC EFATFPKGSV RGMTWLRVIA KPKNQAEAQK VTFSQDPTTV   180
```

```
ALCISKEGRP PARISWLSSL DWEAKETQVS GTLAGTVTVT SRFTLVPSGR ADGVTVTCKV     240
EHESFEEPAL IPVTLSVRYP PEVSISGYDD NWYLGRTDAT LSCDVRSNPE PTGYDWSTTS     300
GTFPTSAVAQ GSQLVIHAVD SLFNTTFVCT VTNAVGMGRA EQVIFVRETP NTAGAGATGG     360
IIGGIIAAII ATAVAATGIL ICRQQRKEQT LQGAEEDEDL EGPPSYKPPT PKAKLEAQEM     420
PSQLFTLGAS EHSPLKTPYF DAGASCTEQE MPRYHELPTL EERSGPLHPG ATSLGSPIPV     480
PPGPPAVEDV SLDLEDEEGE EEEEYLDKIN PIYDALSYSS PSDSYQGKGF VMSRAMYV      538

SEQ ID NO: 187          moltype = AA   length = 335
FEATURE                 Location/Qualifiers
REGION                  1..335
                        note = CD150
source                  1..335
                        mol_type = protein
                        organism = Homo sapiens
SEQUENCE: 187
MDPKGLLSLT FVLFLSLAFG ASYGTGGRMM NCPKILRQLG SKVLLPLTYE RINKSMNKSI     60
HIVVTMAKSL ENSVENKIVS LDPSEAGPPR YLGDRYKFYL ENLTLGIRES RKEDEGWYLM    120
TLEKNVSVQR FCLQLRLYEQ VSTPEIKVLN KTQENGTCTL ILGCTVEKGD HVAYSWSEKA    180
GTHPLNPANS SHLLSLTLGP QHADNIYICT VSNPISNNSQ TFSPWPGCRT DPSETKPWAV    240
YAGLLGGVIM ILIMVVILQL RRRGKTNHYQ TTVEKKSLTI YAQVQKPGPL QKKLDSFPAQ    300
DPCTTIYVAA TEPVPESVQE TNSITVYASV TLPES                               335

SEQ ID NO: 188          moltype = AA   length = 417
FEATURE                 Location/Qualifiers
REGION                  1..417
                        note = CD155
source                  1..417
                        mol_type = protein
                        organism = Homo sapiens
SEQUENCE: 188
MARAMAAAWP LLLVALLVLS WPPPGTGDVV VQAPTQVPGF LGDSVTLPCY LQVPNMEVTH     60
VSQLTWARHG ESGSMAVFHQ TQGPSYSESK RLEFVAARLG AELRNASLRM FGLRVEDEGN    120
YTCLFVTFPQ GSRSVDIWLR VLAKPQNTAE VQKVQLTGEP VPMARCVSTG GRPPAQITWH    180
SDLGGMPNTS QVPGFLSGTV TVTSLWILVP SSQVDGKNVT CKVEHESFEK PQLLTVNLTV    240
YYPPEVSISG YDNNWYLGQN EATLTCDARS NPEPTGYNWS TTMGPLPPFA VAQGAQLLIR    300
PVDKPINTTL ICNVTNALGA RQAELTVQVK EGPPSEHSGM SRNAIIFLVL GILVFLILLG    360
IGIYFYWSKC SREVLWHCHL CPSSTEHASA SANGHVSYSA VSRENSSSQD PQTEGTR       417

SEQ ID NO: 189          moltype = AA   length = 616
FEATURE                 Location/Qualifiers
REGION                  1..616
                        note = CD265
source                  1..616
                        mol_type = protein
                        organism = Homo sapiens
SEQUENCE: 189
MAPRARRRRP LFALLLLCAL LARLQVALQI APPCTSEKHY EHLGRCCNKC EPGKYMSSKC     60
TTTSDSVCLP CGPDEYLDSW NEEDKCLLHK VCDTGKALVA VVAGNSTTPR RCACTAGYHW    120
SQDCECCRRN TECAPGLGAQ HPLQLNKDTV CKPCLAGYFS DAFSSTDKCR PWTNCTFLGK    180
RVEHHGTEKS DAVCSSSLPA RKPPNEPHVY LPGLIILLLF ASVALVAAII FGVCYRKKGK    240
ALTANLWHWI NEACGRLSGD KESSGDSCVS THTANFGQQG ACEGVLLLTL EEKTFPEDMC    300
YPDQGGVCQG TCVGGGPYAQ GEDARMLSLV SKTEIEEDSF RQMPTEDEYM DRPSQPTDQL    360
LFLTEPGSKS TPPFSEPLEV GENDSLSQCF TGTQSTVGSE SCNCTEPLCR TDWTPMSSEN    420
YLQKEVDSGH CPHWAASPSP NWADVCTGCR NPPGEDCEPL VGSPKRGPLP QCAYGMGLPP    480
EEEASRTEAR DQPEDGADGR LPSSARAGAG SGSSPGGQSP ASGNVTGNSN STFISSGQVM    540
NFKGDIIVVY VSQTSQEGAA AAAEPMGRPV QEETLARRDS FAGNGPRFPD PCGGPEGLRE    600
PEKASRPVQE QGGAKA                                                    616

SEQ ID NO: 190          moltype = AA   length = 283
FEATURE                 Location/Qualifiers
REGION                  1..283
                        note = CD270
source                  1..283
                        mol_type = protein
                        organism = Homo sapiens
SEQUENCE: 190
MEPPGDWGPP PWRSTPKTDV LRLVLYLTFL GAPCYAPALP SCKEDEYPVG SECCPKCSPG     60
YRVKEACGEL TGTVCEPCPP GTYIAHLNGL SKCLQCQMCD PAMGLRASRN CSRTENAVCG    120
CSPGHFCIVQ DGDHCAACRA YATSSPGQRV QKGGTESQDT LCQNCPPGTF SPNGTLEECQ    180
HQTKCSWLVT KAGAGTSSSH WVWWFLSGSL VIVIVCSTVG LIICVKRRKP RGDVVKVIVS    240
VQRKRQEAEG EATVIEALQA PPDVTTVAVE ETIPSFTGRS PNH                      283

SEQ ID NO: 191          moltype = AA   length = 251
FEATURE                 Location/Qualifiers
REGION                  1..251
                        note = TL1A
source                  1..251
                        mol_type = protein
                        organism = Homo sapiens
```

```
SEQUENCE: 191
MAEDLGLSFG ETASVEMLPE HGSCRPKARS SSARWALTCC LVLLPFLAGL TTYLLVSQLR      60
AQGEACVQFQ ALKGQEFAPS HQQVYAPLRA DGDKPRAHLT VVRQTPTQHF KNQFPALHWE     120
HELGLAFTKN RMNYTNKFLL IPESGDYFIY SQVTFRGMTS ECSEIRQAGR PNKPDSITVV     180
ITKVTDSYPE PTQLLMGTKS VCEVGSNWFQ PIYLGAMFSL QEGDKLMVNV SDISLVDYTK     240
EDKTFFGAFL L                                                          251

SEQ ID NO: 192          moltype = AA  length = 459
FEATURE                 Location/Qualifiers
REGION                  1..459
                        note = CD127
source                  1..459
                        mol_type = protein
                        organism = Homo sapiens
SEQUENCE: 192
MTILGTTFGM VFSLLQVVSG ESGYAQNGDL EDAELDDYSF SCYSQLEVNG SQHSLTCAFE      60
DPDVNITNLE FEICGALVEV KCLNFRKLQE IYFIETKKFL LIGKSNICVK VGEKSLTCKK     120
IDLTTIVKPE APFDLSVVYR EGANDFVVTF NTSHLQKKYV KVLMHDVAYR QEKDENKWTH     180
VNLSSTKLTL LQRKLQPAAM YEIKVRSIPD HYFKGFWSEW SPSYYFRTPE INNSSGEMDP     240
ILLTISILSF FSVALLVILA CVLWKKRIKP IVWPSLPDHK KTLEHLCKKP RKNLNVSFNP     300
ESFLDCQIHR VDDIQARDEV EGFLQDTFPQ QLEESEKQRL GGDVQSPNCP SEDVVITPES     360
FGRDSSLTCL AGNVSACDAP ILSSSRSLDC RESGKNGPHV YQDLLLSLGT TNSTLPPPFS     420
LQSGILTLNP VAQGQPILTS LGSNQEEAYV TMSSFYQNQ                            459

SEQ ID NO: 193          moltype = AA  length = 825
FEATURE                 Location/Qualifiers
REGION                  1..825
                        note = IL-4R
source                  1..825
                        mol_type = protein
                        organism = Homo sapiens
SEQUENCE: 193
MGWLCSGLLF PVSCLVLLQV ASSGNMKVLQ EPTCVSDYMS ISTCEWKMNG PTNCSTELRL      60
LYQLVFLLSE AHTCIPENNG GAGCVCHLLM DDVVSADNYT LDLWAGQQLL WKGSFKPSEH     120
VKPRAPGNLT VHTNVSDTLL LTWSNPYPPD NYLYNHLTYA VNIWSENDPA DFRIYNVTYL     180
EPSLRIAAST LKSGISYRAR VRAWAQCYNT TWSEWSPSTK WHNSYREPFE QHLLLGVSVS     240
CIVILAVCLL CYVSITKIKK EWWDQIPNPA RSRLVAIIIQ DAQGSQWEKR SRGQEPAKCP     300
HWKNCLTKLL PCFLEHNMKR DEDPHKAAKE MPFQGSGKSA WCPVEISKTV LWPESISVVR     360
CVELFEAPVE CEEEEVEEE KGSFCASPES SRDDFQEGRE GIVARLTESL FLDDLLGEENG     420
GFCQQDMGES CLLPPSGSTS AHMPWDEFPS AGPKEAPPWG KEQPLHLEPS PPASPTQSPD     480
NLTCTETPLV IAGNPAYRSF SNSLSQSPCP RELGPDPLLA RHLEEVEPEM PCVPQLSEPT     540
TVPQPEPETW EQILRRNVLQ HGAAAAPVSA PTSGYQEFVH AVEQGGTQAS AVVGLGPPGE     600
AGYKAFSSLL ASSAVSPEKC GFGASSGEEG YKPFQDLIPG CPGDPAPVPV PLFTFGLDRE     660
PPRSPQSSHL PSSSPEHLGL EPGEKVEDMP KPPLPQEQAT DPLVDSLGSG IVYSALTCHL     720
CGHLKQCHGQ EDGGQTPVMA SPCCGCCCGD RSSPPTTPLR APDPSPGGVP LEASLCPASL     780
APSGISEKSK SSSSFHPAPG NAQSSSQTPK IVNFVSVGPT YMRVS                     825

SEQ ID NO: 194          moltype = AA  length = 199
FEATURE                 Location/Qualifiers
REGION                  1..199
                        note = GITR-L
source                  1..199
                        mol_type = protein
                        organism = Homo sapiens
SEQUENCE: 194
MTLHPSPITC EFLFSTALIS PKMCLSHLEN MPLSHSRTQG AQRSSWKLWL FCSIVMLLFL      60
CSFSWLIFIF LQLETAKEPC MAKFGPLPSK WQMASSEPPC VNKVSDWKLE ILQNGLYLIY     120
GQVAPNANYN DVAPFEVRLY KNKDMIQTLT NKSKIQNVGG TYELHVGDTI DLIFNSEHQV     180
LKNNTYWGII LLANPQFIS                                                  199

SEQ ID NO: 195          moltype = AA  length = 378
FEATURE                 Location/Qualifiers
REGION                  1..378
                        note = TIM-4
source                  1..378
                        mol_type = protein
                        organism = Homo sapiens
SEQUENCE: 195
MSKEPLILWL MIEFWWLYLT PVTSETVVTE VLGHRVTLPC LYSSWSHNSN SMCWGKDQCP      60
YSGCKEALIR TDGMRVTSRK SAKYRLQGTI PRGDVSLTIL NPSESDSGVY CCRIEVPGWF     120
NDVKINVRLN LQRASTTTHR TATTTTRRTT TTSPTTTRQM TTTAAPLPTT VVTTPDLTTG     180
TPLQMTTIAV FTTANTCLSL TPSTLPEEAT GLLTPEPSKE GPILTAESET VLPSDSWSSV     240
ESTSADTVLL TSKESKVWDL PSTSHVSMWK TSDSVSSPQP GASDTAVPEQ NKTTKTGQMD     300
GIPMSMKNEM PISQLLMIIA PSLGFVLFAL FVAFLLRGKL METYCSQKHT RLDYIGDSKN     360
VLNDVQHGRE DEDGLFTL                                                   378

SEQ ID NO: 196          moltype = AA  length = 234
FEATURE                 Location/Qualifiers
REGION                  1..234
```

```
                        note = CD153
source                  1..234
                        mol_type = protein
                        organism = Homo sapiens
SEQUENCE: 196
MDPGLQQALN GMAPPGDTAM HVPAGSVASH LGTTSRSYFY LTTATLALCL VFTVATIMVL    60
VVQRTDSIPN SPDNVPLKGG NCSEDLLCIL KRAPFKKSWA YLQVAKHLNK TKLSWNKDGI   120
LHGVRYQDGN LVIQFPGLYF IICQLQFLVQ CPNNSVDLKL ELLINKHIKK QALVTVCESG   180
MQTKHVYQNL SQFLLDYLQV NTTISVNVDT FQYIDTSTFP LENVLSIFLY SNSD         234

SEQ ID NO: 197          moltype = AA  length = 325
FEATURE                 Location/Qualifiers
REGION                  1..325
                        note = CD200R
source                  1..325
                        mol_type = protein
                        organism = Homo sapiens
SEQUENCE: 197
MLCPWRTANL GLLLILTIFL VAASSSLCMD EKQITQNYSK VLAEVNTSWP VKMATNAVLC    60
CPPIALRNLI IITWEIILRG QPSCTKAYRK ETNETKETNC TDERITWVSR PDQNSDLQIR   120
PVAITHDGYY RCIMVTPDGN FHRGYHLQVL VTPEVTLFQN RNRTAVCKAV AGKPAAQISW   180
IPEGDCATKQ EYWSNGTVTV KSTCHWEVHN VSTVTCHVSH LTGNKSLYIE LLPVPGAKKS   240
AKLYIPYIIL TIIILTIVGF IWLLKVNGCR KYKLNKTEST PVVEEDEMQP YASYTEKNNP   300
LYDTTNKVKA SEALQSEVDT DLHTL                                        325

SEQ ID NO: 198          moltype = AA  length = 742
FEATURE                 Location/Qualifiers
REGION                  1..742
                        note = CD44
source                  1..742
                        mol_type = protein
                        organism = Homo sapiens
SEQUENCE: 198
MDKFWWHAAW GLCLVPLSLA QIDLNITCRF AGVFHVEKNG RYSISRTEAA DLCKAFNSTL    60
PTMAQMEKAL SIGFETCRYG FIEGHVVIPR IHPNSICAAN NTGVYILTSN TSQYDTYCFN   120
ASAPPEEDCT SVTDLPNAFD GPITITIVNR DGTRYVQKGE YRTNPEDIYP SNPTDDDVSS   180
GSSSERSSTS GGYIFYTFST VHPIPDEDSP WITDSTDRIP ATTLMSTSAT ATETATKRQE   240
TWDWFSWLFL PSESKNHLHT TTQMAGTSSN TISAGWEPNE ENEDERDRHL SFSGSGIDDD   300
EDFISSTIST TPRAFDHTKQ NQDWTQWNPS HSNPEVLLQT TTRMTDVDRN GTTAYEGNWN   360
PEAHPPLIHH EHHEEEETPH STSTIQATPS STTEETATQK EQWFGNRWHE GYRQTPKEDS   420
HSTTGTAAAS AHTSHPMQGR TTPSPEDSSW TDFFNPISHP MGRGHQAGRR MDMDSSHSIT   480
LQPTANPNTG LVEDLDRTGP LSMTTQQSNS QSFSTSHEGL EEDKDHPTTS TLTSSNRNDV   540
TGGRRDPNHS EGSTTLLEGY TSHYPHTKES RTFIPVTSAK TGSFGVTAVT VGDSNSNVNR   600
SLSGDQDTFH PSGGSHTTHG SESDGHSHGS QEGGANTTSG PIRTPQIPEW LIILASLLAL   660
ALILAVCIAV NSRRRCGQKK KLVINSGNGA VEDRKPSGLN GEASKSQEMV HLVNKESSET   720
PDQFMTADET RNLQNVDMKI GV                                           742

SEQ ID NO: 199          moltype = AA  length = 595
FEATURE                 Location/Qualifiers
REGION                  1..595
                        note = TriCD40L_8-28 AA
source                  1..595
                        mol_type = protein
                        organism = synthetic construct
SEQUENCE: 199
MALPVTALLL PLALLLHAAR PNPQIAAHVI SEASSKTTSV LQWAEKGYYT MSNNLVTLEN    60
GKQLTVKRQG LYYIYAQVTF CSNREASSQA PFIASLCLKS PGRFERILLR AANTHSSAKP   120
CGQQSIHLGG VFELQPGASV FVNVTDPSQV SHGTGFTSFG LLKLGGGGSG GGSNPQIAAH   180
VISEASSKTT SVLQWAEKGY YTMSNNLVTL ENGKQLTVKR QGLYYIYAQV TFCSNREASS   240
QAPFIASLCL KSPGRFERIL LRAANTHSSA KPCGQQSIHL GGVFELQPGA SVFVNVTDPS   300
QVSHGTGFTS FGLLKLGGGG SGGGSNPQIA AHVISEASSK TTSVLQWAEK GYYTMSNNLV   360
TLENGKQLTV KRQGLYYIYA QVTFCSNREA SSQAPFIASL CLKSPGRFER ILLRAANTHS   420
SAKPCGQQSI HLGGVFELQP GASVFVNVTD PSQVSHGTGF TSFGLLKLGG GGGSGGGGS   480
GGGSTTTPA PRPPTPAPTI ASQPLSLRPE ACRPAAGGAV HTRGLDFACD IYIWAPLAGT   540
CGVLLLSLVI TLYCRSKRSR LLHSDYMNMT PRRPGPTRKH YQPYAPPRDF AAYRS       595

SEQ ID NO: 200          moltype = DNA  length = 1788
FEATURE                 Location/Qualifiers
misc_feature            1..1788
                        note = TriCD40L_8-28 NT
source                  1..1788
                        mol_type = other DNA
                        organism = synthetic construct
SEQUENCE: 200
atggccttac cagtgaccgc cttgctcctg ccgctggcct tgctgctcca cgccgccagg    60
ccgaatcctc aaattgcggc acatgtcata agtgaggcca gcagtaaaac aacatctgtg   120
ttacagtggg ctgaaaaagg atactacacc atgagcaaca cttggtaac ctggaaaat    180
gggaaacagc tgaccgttaa aagacaagga ctctattata tctatgccca gtcaccttc   240
tgttccaatc gggaagcttc gagtcaagct ccatttatag ccagcctctg cctaaagtcc   300
```

```
cccggtagat tcgagagaat cttactcaga gctgcaaata cccacagttc cgccaaacct    360
tgcgggcaac aatccattca cttgggagga gtatttgaat tgcaaccagg tgcttccggtg   420
tttgtcaatg tgactgatcc aagccaagtg agccatggca ctggcttcac gtcctttggc   480
ttactcaaac tcggcggggg cggttctggg ggtggcagta atcccagat cgccgcacac    540
gtgatctccg aggctagctc taagaccacc agtgtgctgc agtgggccga aaagggatac   600
tatacaatga gcaataacct ggtgacactg gagaacggca aacagctcac cgtgaagagg   660
caaggtctgt actacatcta cgctcaggtc accttctgca gcaatcgaga agcaagtagt   720
caggcgccct tcattgccag tttatgtcta aagagcccag gccgctttga gcgtatcctc   780
ctccgcgccg ctaatacgca ctccagcgca aaacctgtg gccagcagtc aatccactc    840
ggcggggtgt tcgaactgca acctggcgct tccgtgttcg tgaatgtgac cgatccctca   900
caggtcagcc acggcacggg cttcacctcg ttcgggctgc tgaagctggg gggcggcggc   960
agtggcgggg ggagtaaccc ccagatcgcc gcacacgtga ttagtgaggc gtcctccaag  1020
acaacctccg tgctgcagtg ggccgagaag ggctactaca ccatgagtaa caacctcgta  1080
accctggaga acggaaagca gttaaccgtc aagcgccagg gcctgtacta catctacgcg  1140
caggtcacat tctgctcaaa cagggaggcc tcgtcccagg ccccctttat cgcttccctg  1200
tgcctgaagt ctccgggacg cttcgaacga atcctgctgc gtgcgccaa cacgcactcg  1260
tccgccaaac cgtgtggcca gcagtccata cacctcggcg gcgtgttcga gctgcaacct  1320
ggcgccagcg tgttcgtgaa cgtgacagac ccctcccagg tctcccacgg gacaggtttt  1380
accagtttcg gcctgcttaa gctcggatcc gggggcggcg gttccggcgg ggggggctct  1440
ggggggcggcg gctccaccac gacgccagcc cgcgaccac caacaccggc gcccaccatc  1500
gcgtcgcagc ccctgtccct gcgcccagag gcgtgccggc cagcggcggg gggcgcagtg  1560
cacacgaggg ggctggactt cgcctgtgat atctacatct ggccccttt ggccgggact  1620
tgtgggggtcc ttctcctgtc actggttatc ccccttact gcaggagtaa gaggagcagg  1680
ctcctgcaca gtgactacat gaacatgact ccccgccgcc ccgggcccac ccgcaagcat  1740
taccagcct atgcccacc acgcgacttc gcagcctatc gctcctaa              1788

SEQ ID NO: 201          moltype = AA  length = 592
FEATURE                 Location/Qualifiers
REGION                  1..592
                        note = TriCD40L_28-28 AA
source                  1..592
                        mol_type = protein
                        organism = synthetic construct
SEQUENCE: 201
MALPVTALLL PLALLLHAAR PNPQIAAHVI SEASSKTTSV LQWAEKGYYT MSNNLVTLEN    60
GKQLTVKRQG LYYIYAQVTF CSNREASSQA PFIASLCLKS PGRFERILLR AANTHSSAKP   120
CGQQSIHLGG VFELQPGASV FVNVTDPSQV SHGTGFTSFG LLKLGGGGSG GGSNPQIAAH   180
VISEASSKTT SVLQWAEKGY YTMSNNLVTL ENGKQLTVKR QGLYYIYAQV TFCSNREASS   240
QAPFIASLCL KSPGRFERIL LRAANTHSSA KPCGQQSIHL GGVFELQPGA SVFVNVTDPS   300
QVSHGTGFTS FGLLKLGGGG SGGGSNPQIA AHVISEASSK TTSVLQWAEK GYYTMSNNLV   360
TLENGKQLTV KRQGLYYIYA QVTFCSNREA SSQAPFIASL CLKSPGRFER ILLRAANTHS   420
SAKPCGQQSI HLGGVFELQP GASVFVNVTD PSQVSHGTGF TSFGLLKLGS GGGGSGGGGS   480
GGGGSIEVMY PPPYLDNEKS NGTIIHVKGK HLCPSPLFPG PSKPFWVLVV VGGVLACYSL   540
LVTVAFIIFW VRSKRSLLH SDYMNMTPRR PGPTRKHYQP YAPPRDFAAY RS            592

SEQ ID NO: 202          moltype = DNA  length = 1779
FEATURE                 Location/Qualifiers
misc_feature            1..1779
                        note = TriCD40L_28-28 NT
source                  1..1779
                        mol_type = other DNA
                        organism = synthetic construct
SEQUENCE: 202
atggccttac cagtgaccgc cttgctcctg ccgctggcct tgctgctcca cgccgccagg    60
ccgaatcctc aaattgcggc acatgtcata agtgaggccg gcagtaaaac aacatctgtg   120
ttacagtggg ctgaaaaagg atactacacc atgagcaaca acttggtaac cctggaaaat   180
gggaaacagc tgaccgttaa agacaagga ctctattata tctatgccca gtcaccttc    240
tgttccaatc gggaagcttc gagtcaagct ccatttatag ccagcctctg cctaaagtcc   300
cccggtagat tcgagagaat cttactcaga gctgcaaata cccacagttc cgccaaacct   360
tgcgggcaac aatccattca cttgggagga gtatttgaat tgcaaccagg tgcttccggtg   420
tttgtcaatg tgactgatcc aagccaagtg agccatggca ctggcttcac gtcctttggc   480
ttactcaaac tcggcggggg cggttctggg ggtggcagta atcccagat cgccgcacac    540
gtgatctccg aggctagctc taagaccacc agtgtgctgc agtgggccga aaagggatac   600
tatacaatga gcaataacct ggtgacactg gagaacggca aacagctcac cgtgaagagg   660
caaggtctgt actacatcta cgctcaggtc accttctgca gcaatcgaga agcaagtagt   720
caggcgccct tcattgccag tttatgtcta aagagcccag gccgctttga gcgtatcctc   780
ctccgcgccg ctaatacgca ctccagcgca aaacctgtg gccagcagtc aatccactc    840
ggcggggtgt tcgaactgca acctggcgct tccgtgttcg tgaatgtgac cgatccctca   900
caggtcagcc acggcacggg cttcacctcg ttcgggctgc tgaagctggg gggcggcggc   960
agtggcgggg ggagtaaccc ccagatcgcc gcacacgtga ttagtgaggc gtcctccaag  1020
acaacctccg tgctgcagtg ggccgagaag ggctactaca ccatgagtaa caacctcgta  1080
accctggaga acggaaagca gttaaccgtc aagcgccagg gcctgtacta catctacgcg  1140
caggtcacat tctgctcaaa cagggaggcc tcgtcccagg ccccctttat cgcttccctg  1200
tgcctgaagt ctccgggacg cttcgaacga atcctgctgc gtgcgccaa cacgcactcg  1260
tccgccaaac cgtgtggcca gcagtccata cacctcggcg gcgtgttcga gctgcaacct  1320
ggcgccagcg tgttcgtgaa cgtgacagac ccctcccagg tctcccacgg gacaggtttt  1380
accagtttcg gcctgcttaa gctcggatcc gggggcggcg gttccggcgg ggggggctct  1440
ggggggcggcg gctccattga agttatgtat cctcctcctt acctagacaa tgagaagagc  1500
aatggaacca ttatccatgt gaaagggaaa cacctttgtc caagtcccct atttcccgga  1560
```

```
cctcctaagc ccttttgggg gctggtggtg gttggtggag tcctggcttg ctatagcttg   1620
ctagtaacag tggcctttat tattttctgg gtgaggagta agaggagcag gctcctgcac   1680
agtgactaca tgaacatgac tccccgccgc cccgggccca cccgcaagca ttaccagccc   1740
tatgccccac cacgcgactt cgcagcctat cgctcctaa                          1779
```

```
SEQ ID NO: 203          moltype = AA   length = 372
FEATURE                 Location/Qualifiers
REGION                  1..372
                        note = CD27 CAR
source                  1..372
                        mol_type = protein
                        organism = synthetic construct
SEQUENCE: 203
MARPHPWWLC VLGTLVGLSA TPAPKSCPER HYWAQGKLCC QMCEPGTFLV KDCDQHRKAA    60
QCDPCIPGVS FSPDHHTRPH CESCRHCNSG LLVRNCTITA NAECACRNGW QCRDKECTEC   120
DPLPNPSLTA RSSQALSPHP QPTHLPYVSE MLEARTAGHM QTLADFRQLP ARTLSTHWPP   180
QRSLCSSDFI RILVIFSGMF LVFTLAGALF LHQRRKYRSN KGESPVEPAE PCRYSCPREE   240
EGSTIPIQED YRKPEPACSP RVKFSRSADA PAYQQGNQNL YNELNLGRRE EYDVLDKRRG   300
RDPEMGGKPR RKNPQEGLYN ELQKDKMAEA YSEIGMKGER RRGKGHDGLY QGLSTATKDT   360
YDALHMQALP PR                                                       372

SEQ ID NO: 204          moltype = AA   length = 771
FEATURE                 Location/Qualifiers
REGION                  1..771
                        note = A40C28 - CD27 CAR
source                  1..771
                        mol_type = protein
                        organism = synthetic construct
SEQUENCE: 204
MALPVTALLL PLALLLHAAR PQVQLVQSGA EVKKPGASVK VSCTASGFNI KDYYVHWVKQ    60
APGQGLEWMG RIDPEDGDSK YAPKFQGKAT MTADTSTSTV YMELSSLRSE DTAVYYCTTS   120
YYVGTYGYWG QGTLVTVSSG GGGSGGGGSG GGGSDIQMTQ SPSSLSASVG DRVTITCSAS   180
SSVSYMLWFQ QKPGKAPKLL IYSTSNLASG VPSRFSGSGS GTDFTLTISS LQPEDFATYY   240
CQQRTFYPYT FGGGTKVEIK RTASTTTPAP RPPTPAPTIA SQPLSLRPEA CRPAAGGAVH   300
TRGLDFACDF WVLVVVGGVL ACYSLLVTVA FIIFWVRSKR SRLLHSDYMN MTPRRPGPTR   360
KHYQPYAPPR DFAAYRSVKQ TLNFDLLKLA GDVESNPGPM ARPHPWWLCV LGTLVGLSAT   420
PAPKSCPERH YWAQGKLCCQ MCEPGTFLVK DCDQHRKAAQ CDPCIPGVSF SPDHHTRPHC   480
ESCRHCNSGL LVRNCTITAN AECACRNGWQ CRDKECTECD PLPNPSLTAR SSQALSPHPQ   540
PTHLPYVSEM LEARTAGHMQ TLADFRQLPA RTLSTHWPPQ RSLCSSDFIR ILVIFSGMFL   600
VFTLAGALFL HQRRKYRSNK GESPVEPAEP CRYSCPREEE GSTIPIQEDY RKPEPACSPR   660
VKFSRSADAP AYQQGNQLY NELNLGRREE YDVLDKRRGR DPEMGGKPRR KNPQEGLYNE   720
LQKDKMAEAY SEIGMKGERR RGKGHDGLYQ GLSTATKDTY DALHMQALPP R            771

SEQ ID NO: 205          moltype = AA   length = 486
FEATURE                 Location/Qualifiers
REGION                  1..486
                        note = Anti-BCMA CAR (BCMA31)
source                  1..486
                        mol_type = protein
                        organism = synthetic construct
SEQUENCE: 205
MLLLVTSLLL CELPHPAFLL IPQSALTQPP SASGSPGQSV TISCTGTSSD VGTYNYVSWY    60
QQHPGKAPKL MIYDVNQRPS GVPDRFSGSK SGNTASLTVS GLQAEDEADY YCSSYGGSNN   120
LVFGGGTKVT VLGGGGSGGG GSGGGGSEVQ LVESGGGLIQ PGGSLRLSCA ASGFTFSSYW   180
MSWVRQSPGK GLEWVANIKP DGSDKYYVDS VKGRFTISRD NAKNSLDLQM NSLRGEDTAI   240
YYCARGATTY GSWGQGTLVT VSSTTTPAPR PPTPAPTIAS QPLSLRPEAC RPAAGGAVHT   300
RGLDFACDIY IWAPLAGTCG VLLLSLVITL YCKRGRKKLL YIFKQPFMRP VQTTQEEDGC   360
SCRFPEEEEG GCELRVKFSR SADAPAYQQG QNLYNELNL GRREEYDVLD KRRGRDPEMG   420
GKPRRKNPQE GLYNELQKDK MAEAYSEIGM KGERRRGKGH DGLYQGLSTA TKDTYDALHM   480
QALPPR                                                              486

SEQ ID NO: 206          moltype = AA   length = 885
FEATURE                 Location/Qualifiers
REGION                  1..885
                        note = A40C.28-BCMA31.BBZ
source                  1..885
                        mol_type = protein
                        organism = synthetic construct
SEQUENCE: 206
MALPVTALLL PLALLLHAAR PQVQLVQSGA EVKKPGASVK VSCTASGFNI KDYYVHWVKQ    60
APGQGLEWMG RIDPEDGDSK YAPKFQGKAT MTADTSTSTV YMELSSLRSE DTAVYYCTTS   120
YYVGTYGYWG QGTLVTVSSG GGGSGGGGSG GGGSDIQMTQ SPSSLSASVG DRVTITCSAS   180
SSVSYMLWFQ QKPGKAPKLL IYSTSNLASG VPSRFSGSGS GTDFTLTISS LQPEDFATYY   240
CQQRTFYPYT FGGGTKVEIK RTASTTTPAP RPPTPAPTIA SQPLSLRPEA CRPAAGGAVH   300
TRGLDFACDF WVLVVVGGVL ACYSLLVTVA FIIFWVRSKR SRLLHSDYMN MTPRRPGPTR   360
KHYQPYAPPR DFAAYRSVKQ TLNFDLLKLA GDVESNPGPM LLLVTSLLLC ELPHPAFLLI   420
PQSALTQPPS ASGSPGQSVT ISCTGTSSDV GTYNYVSWYQ QHPGKAPKLM IYDVNQRPSG   480
VPDRFSGSKS GNTASLTVSG LQAEDEADYY CSSYGGSNNL VFGGGTKVTV LGGGGSGGGG   540
SGGGGSEVQL VESGGGLIQP GGSLRLSCAA SGFTFSSYWM SWVRQSPGKG LEWVANIKPD   600
```

```
GSDKYYVDSV KGRFTISRDN AKNSLDLQMN SLRGEDTAIY YCARGATTYG SWGQGTLVTV  660
SSTTTPAPRP PTPAPTIASQ PLSLRPEACR PAAGGAVHTR GLDFACDIYI WAPLAGTCGV  720
LLLSLVITLY CKRGRKKLLY IFKQPFMRPV QTTQEEDGCS CRFPEEEEGG CELRVKFSRS  780
ADAPAYQQGQ NQLYNELNLG RREEYDVLDK RRGRDPEMGG KPRRKNPQEG LYNELQKDKM  840
AEAYSEIGMK GERRRGKGHD GLYQGLSTAT KDTYDALHMQ ALPPR             885

SEQ ID NO: 207         moltype = AA  length = 885
FEATURE                Location/Qualifiers
REGION                 1..885
                       note = BCMA31.BBZ-A40C.28
source                 1..885
                       mol_type = protein
                       organism = synthetic construct
SEQUENCE: 207
MLLLVTSLLL CELPHPAFLL IPQSALTQPP SASGSPGQSV TISCTGTSSD VGTYNYVSWY  60
QQHPGKAPKL MIYDVNQRPS GVPDRFSGSK SGNTASLTVS GLQAEDEADY YCSSYGGSNN  120
LVFGGGTKVT VLGGGGSGGG GSGGGGSEVQ LVESGGGLIQ PGGSLRLSCA ASGFTFSSYW  180
MSWVRQSPGK GLEWVANIKP DGSDKYYVDS VKGRFTISRD NAKNSLDLQM NSLRGEDTAI  240
YYCARGATTY GSWGQGTLVT VSSTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYQQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPRVKQT LNFDLLKLAG DVESNPGPMA LPVTALLLPL ALLLHAARPQ VQLVQSGAEV  540
KKPGASVKVS CTASGFNIKD YYVHWVKQAP GQGLEWMGRI DPEDGDSKYA PKFQGKATMT  600
ADTSTSTVYM ELSSLRSEDT AVYYCTTSYY VGTYGYWGQG TLVTVSSGGG GSGGGGSGGG  660
GSDIQMTQSP SSLSASVGDR VTITCSASSS VSYMLWFQQK PGKAPKLLIY STSNLASGVP  720
SRFSGSGSGT DFTLTISSLQ PEDFATYYCQ QRTFYPYTFG GGTKVEIKRT ASTTTPAPRP  780
PTPAPTIASQ PLSLRPEACR PAAGGAVHTR GLDFACDFWV LVVVGGVLAC YSLLVTVAFI  840
IFWVRSKRSR LLHSDYMNMT PRRPGPTRKH YQPYAPPRDF AAYRS             885

SEQ ID NO: 208         moltype = AA  length = 485
FEATURE                Location/Qualifiers
REGION                 1..485
                       note = Anti-mesothelin CAR (M12)
source                 1..485
                       mol_type = protein
                       organism = synthetic construct
SEQUENCE: 208
MALPVTALLL PLALLLHAAR PAIRLTQSPS LLSASVGDRV TVTCRASQGG GNYLAWYQQK  60
PGKAPKLLIY GASKLQSGVP SRFSGSGSGT EFTLTISSLQ PEDFATYYCQ QLNSYPVTFG  120
QGTKVDIKGG GGSGGGGSGG GGSEVQLVES GAEVKKPGAS VKVSCKASGY TFTTYYIHWV  180
RQAPGQGLEW MGIINPSSGS TTYTQKFQGR VTMTRDTSTS TVYIELSGLR SEDTAVYYCA  240
RGETLRGYFD YWQGQTLVTV SSTTTPAPRP PTPAPTIASQ PLSLRPEACR PAAGGAVHTR  300
GLDFACDIYI WAPLAGTCGV LLLSLVITLY CKRGRKKLLY IFKQPFMRPV QTTQEEDGCS  360
CRFPEEEEGG CELRVKFSRS ADAPAYKQGQ NQLYNELNLG RREEYDVLDK RRGRDPEMGG  420
KPRRKNPQEG LYNELQKDKM AEAYSEIGMK GERRRGKGHD GLYQGLSTAT KDTYDALHMQ  480
ALPPR                                                       485

SEQ ID NO: 209         moltype = AA  length = 486
FEATURE                Location/Qualifiers
REGION                 1..486
                       note = Anti-mesothelin CAR (M32)
source                 1..486
                       mol_type = protein
                       organism = synthetic construct
SEQUENCE: 209
MALPVTALLL PLALLLHAAR PDIRMTQSPS SLSASVGDRV TVTCQASEDI NNSLNWYQQK  60
PGKAPQLLIY DASDLETGVP SRFSGRGSGR DFTLTISSLQ PEDFATYYCQ QLNSYPLTFG  120
GGTKLEIKGG GGSGGGGSGG GGSQVQLVQS GAEVKKPGAS VKVSCKASGF TFIGYYLHWV  180
RQAPGQGLEW MGIINPSGGR TSMAQKFQGR VSMTTDTSTG TVYLDLGRLG SDDTAVYYCA  240
RADNWNAGSM DVWGNGTTVT VSSTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                      486

SEQ ID NO: 210         moltype = AA  length = 884
FEATURE                Location/Qualifiers
REGION                 1..884
                       note = Anti-mesothelin CAR+LACO (A40C28+M12)
source                 1..884
                       mol_type = protein
                       organism = synthetic construct
SEQUENCE: 210
MALPVTALLL PLALLLHAAR PQVQLVQSGA EVKKPGASVK VSCTASGFNI KDYYVHWVKQ  60
APGQGLEWMG RIDPEDGDSK YAPKFQGKAT MTADTSTSTV YMELSSLRSE DTAVYYCTTS  120
YYVGTYGYWG QGTLVTVSSG GGGSGGGGSG GGGSDIQMTQ SPSSLSASVG DRVTITCSAS  180
SSVSYMLWFQ QKPGKAPKLL IYSTSNLASG VPSRFSGSGS GTDFTLTISS LQPEDFATYY  240
CQQRTFYPYT FGGGTKVEIK RTASTTTPAP RPPTPAPTIA SQPLSLRPEA CRPAAGGAVH  300
```

```
TRGLDFACDF WVLVVVGGVL ACYSLLVTVA FIIFWVRSKR SRLLHSDYMN MTPRRPGPTR    360
KHYQPYAPPR DFAAYRSVKQ TLNFDLLKLA GDVESNPGPM ALPVTALLLP LALLLHAARP    420
AIRLTQSPSL LSASVGDRVT VTCRASQGGG NYLAWYQQKP GKAPKLLIYG ASKLQSGVPS    480
RFSGSGSGTE FTLTISSLQP EDFATYYCQQ LNSYPVTFGQ GTKVDIKGGG GSGGGGSGGG    540
GSEVQLVESG AEVKKPGASV KVSCKASGYT FTTYYIHWVR QAPGQGLEWM GIINPSSGST    600
TYTQKFQGRV TMTRDTSTST VYIELSGLRS EDTAVYYCAR GETLRGYFDY WGQGTLVTVS    660
STTTPAPRPP TPAPTIASQP LSLRPEACRP AAGGAVHTRG LDFACDIYIW APLAGTCGVL    720
LLSLVITLYC KRGRKKLLYI FKQPFMRPVQ TTQEEDGCSC RFPEEEGGC ELRVKFSRSA     780
DAPAYKQGQN QLYNELNLGR REEYDVLDKR RGRDPEMGGK PRRKNPQEGL YNELQKDKMA    840
EAYSEIGMKG ERRRGKGHDG LYQGLSTATK DTYDALHMQA LPPR                    884

SEQ ID NO: 211           moltype = AA   length = 518
FEATURE                  Location/Qualifiers
REGION                   1..518
                         note = 1412-4D11 (Anti-CD28/anti-CD40 bispecific Ab)
source                   1..518
                         mol_type = protein
                         organism = synthetic construct
SEQUENCE: 211
MALPVTALLL PLALLLHAAR PQVQLVQSGA EVKKPGASVK VSCKASGYTF TSYYIHWVRQ    60
APGQGLEWIG CIYPGNVNTN YNEKFKDRAT LTVDTSISTA YMELSRLRSD DTAVYFCTRS    120
HYGLDWNFDV WGQGTTVTVS SVEGGSGGSG GSGGSGVMD DIQMTQSPSS LSASVGDRVT    180
ITCHASQNIY VWLNWYQQKP GKAPKLLIYK ASNLHTGVPS RFSGSGSGTD FTLTISSLQP    240
EDFATYYCQQ GQTYPYTFGG GTKVEIKGGG GSQLQLQESG PGLLKPSETL SLTCTVSGGS    300
ISSPGYYGGW IRQPPGKGLE WIGSIYKSGS TYHNPSLKSR VTISVDTSKN QFSLKLSSVT    360
AADTAVYYCT RPVVRYFGWF DPWGQGTLVT VSSASGGGGS GGGGSGGGGS AIQLTQSPSS    420
LSASVGDRVT ITCRASQGIS SALAWYQQKP GKAPKLLIYD ASNLESGVPS RFSGSGSGTD    480
FTLTISSLQP EDFATYYCQQ FNSYPTFGQG TKVEIKRT                           518

SEQ ID NO: 212           moltype = AA   length = 491
FEATURE                  Location/Qualifiers
REGION                   1..491
                         note = Anti-CD123 CAR (C5)
source                   1..491
                         mol_type = protein
                         organism = synthetic construct
SEQUENCE: 212
MALPVTALLL PLALLLHAAR PNFMLTQPHS VSESPGKTVT LSCTRSSGSI AGSYVQWYQQ    60
RPGSSPTTVI FQDNQRPSGV PDRFSGSIDK SSNSASLTIS GLKTEDEADY YCQSYDSNNQ    120
VFGGGTKLTV LGGGGSGGGG SGGGGSEVHL VESGGGVVRP GGSLRLSCAA SGFTFGDYGM    180
SWVRQAPGKG LEWVSGINWN GGRTGYADSV KGRFTISRDN AKNSLYLQMN SLRAEDTALY    240
YCARARGSGS YFGYMDVWGK GTTVTVSSTT TPAPRPPTPA PTIASQPLSL RPEACRPAAG    300
GAVHTRGLDF ACDIYIWAPL AGTCGVLLLS LVITLYCKRG RKKLLYIFKQ PFMRPVQTTQ    360
EEDGCSCRFP EEEEGGCELR VKFSRSADAP AYKQGQNQLY NELNLGRREE YDVLDKRRGR    420
DPEMGGKPRR KNPQEGLYNE LQKDKMAEAY SEIGMKGERR RGKGHDGLYQ GLSTATKDTY    480
DALHMQALPP R                                                        491

SEQ ID NO: 213           moltype = AA   length = 495
FEATURE                  Location/Qualifiers
REGION                   1..495
                         note = Anti-CD123 CAR (C7)
source                   1..495
                         mol_type = protein
                         organism = synthetic construct
SEQUENCE: 213
MALPVTALLL PLALLLHAAR PEIVLTQSPG TLSLSPGEKA TLSCRASQSV SSSYLAWYQQ    60
KPGQAPRLLI YGASSRATGI PDRFSGSGSG TDFTLTISRL EPEDFAVYYC QQYGSSPLTF    120
GGGTKLEIKG GGGSGGGGSG GGGSQVQLVQ SGAEVKKPGA SVKVSCKASG YTFTSYGISW    180
VRQAPGQGLE WMGWISAYNG NTNYAQKLQG RVTMTTDTST STAYMELRSL RSDDTAVYYC    240
ARDPYDDYGG NSRDEEDAFD IWGQGTMVTV SSTTTPAPRP PTPAPTIASQ PLSLRPEACR    300
PAAGGAVHTR GLDFACDIYI WAPLAGTCGV LLLSLVITLY CKRGRKKLLY IFKQPFMRPV    360
QTTQEEDGCS CRFPEEEEGG CELRVKFSRS ADAPAYKQGQ NQLYNELNLG RREEYDVLDK    420
RRGRDPEMGG KPRRKNPQEG LYNELQKDKM AEAYSEIGMK GERRRGKGHD GLYQGLSTAT    480
KDTYDALHMQ ALPPR                                                    495

SEQ ID NO: 214           moltype = AA   length = 495
FEATURE                  Location/Qualifiers
REGION                   1..495
                         note = Anti-CD123 CAR (C11)
source                   1..495
                         mol_type = protein
                         organism = synthetic construct
SEQUENCE: 214
MALPVTALLL PLALLLHAAR PQSVVTQPPS ASGTPGQRVT ISCSGSSSNI GSNYVYWYQQ    60
LPGTAPKLLI YRNNQRPSGV PDRFSGSKSG TSASLAISGL RSEDEADYYC AAWDDSLSGY    120
VFGTGTKLTV LGGGGSGGGG SGGGGSEVQL VESGGGLVQP GRSLRLSCTA SGFTFGDYAM    180
SWVRQAPGKG LEWVGFIRSK AYGGTTEYAA SVKGRFTISR DDSKSIAYLQ MNSLKTEDTA    240
VYYCTRDIGY YGSGSYSPFD YWGQGTLVTV SSTTTPAPRP PTPAPTIASQ PLSLRPEACR    300
PAAGGAVHTR GLDFACDIYI WAPLAGTCGV LLLSLVITLY CKRGRKKLLY IFKQPFMRPV    360
```

```
QTTQEEDGCS CRFPEEEEGG CELRVKFSRS ADAPAYKQGQ NQLYNELNLG RREEYDVLDK    420
RRGRDPEMGG KPRRKNPQEG LYNELQKDKM AEAYSEIGMK GERRRGKGHD GLYQGLSTAT    480
KDTYDALHMQ ALPPR                                                    495

SEQ ID NO: 215          moltype = AA  length = 5
FEATURE                 Location/Qualifiers
REPEAT                  1..5
                        note = repeat - (GGGGS)n, n=1, 2, 3, 4, or 5
REGION                  1..5
                        note = Linker
source                  1..5
                        mol_type = protein
                        organism = synthetic construct
SEQUENCE: 215
GGGGS                                                                 5

SEQ ID NO: 216          moltype = AA  length = 5
FEATURE                 Location/Qualifiers
REGION                  1..5
                        note = linker
REPEAT                  1..5
                        note = (EAAAK)n, n=1,2,3, 4,or 5
source                  1..5
                        mol_type = protein
                        organism = synthetic construct
SEQUENCE: 216
EAAAK                                                                 5

SEQ ID NO: 217          moltype =    length =
SEQUENCE: 217
000

SEQ ID NO: 218          moltype = AA  length = 5
FEATURE                 Location/Qualifiers
REGION                  1..5
                        note = Linker
source                  1..5
                        mol_type = protein
                        organism = synthetic construct
SEQUENCE: 218
GGGGS                                                                 5

SEQ ID NO: 219          moltype = AA  length = 17
FEATURE                 Location/Qualifiers
REGION                  1..17
                        note = linker
source                  1..17
                        mol_type = protein
                        organism = synthetic construct
SEQUENCE: 219
GSGGGGSGGG GSGGGGS                                                   17

SEQ ID NO: 220          moltype = AA  length = 20
FEATURE                 Location/Qualifiers
REGION                  1..20
                        note = P2A
source                  1..20
                        mol_type = protein
                        organism = synthetic construct
SEQUENCE: 220
ATNFSLLKQA GDVEENPGPM                                                20

SEQ ID NO: 221          moltype = AA  length = 18
FEATURE                 Location/Qualifiers
REGION                  1..18
                        note = T2A
source                  1..18
                        mol_type = protein
                        organism = synthetic construct
SEQUENCE: 221
EGRGSLLTCG DVEENPGP                                                  18

SEQ ID NO: 222          moltype = AA  length = 20
FEATURE                 Location/Qualifiers
REGION                  1..20
                        note = E2A
source                  1..20
                        mol_type = protein
                        organism = synthetic construct
```

```
SEQUENCE: 222
QCTNYALLKL AGDVESNPGP                                                   20

SEQ ID NO: 223          moltype = AA  length = 22
FEATURE                 Location/Qualifiers
REGION                  1..22
                        note = F2A
source                  1..22
                        mol_type = protein
                        organism = synthetic construct
SEQUENCE: 223
VKQTLNFDLL KLAGDVESNP GP                                                22

SEQ ID NO: 224          moltype = AA  length = 522
FEATURE                 Location/Qualifiers
REGION                  1..522
                        note = 4D5-6.CD3 (HER2 BiTE)
source                  1..522
                        mol_type = protein
                        organism = synthetic construct
SEQUENCE: 224
MDFQVQIFSF LLISASVIMS RGDIQMTQSP SSLSASVGDR VTITCRASQD VNTAVAWYQQ        60
KPGKAPKLLI YSASFLYSGV PSRFSGSRSG TDFTLTISSL QPEDFATYYC QQHYTTPPTF       120
GQGTKVEIKR TGSTSGSGKP GSGEGSEVQL VESGGGLVQP GGSLRLSCAA SGFNIKDTYI       180
HWVRQAPGKG LEWVARIYPT NGYTRYADSV KGRFTISADT SKNTAYLQMN SLRAEDTAVY       240
YCSRWGGDGF YAMDVWGQGT LVTVSSGGGG SDIKLQQSGA ELARPGASVK MSCKTSGYTF       300
TRYTMHWVKQ RPGQGLEWIG YINPSRGYTN YNQKFKDKAT LTTDKSSSTA YMQLSSLTSE       360
DSAVYFCARY YDDHYCLDYW GQGTTLTVSS VEGGSGGSGG SGGSGGVDDA AIQLTQSPAI       420
MSASPGEKVT MTCRASSSVS YMNWYQQKSG TSPKRWIYDT SKVASGVPYR FSGSGSGTSY       480
SLTISSMEAE DAATYYCQQW SSNPLTFGAG TKLELKHHHH HH                          522

SEQ ID NO: 225          moltype = DNA  length = 1569
FEATURE                 Location/Qualifiers
misc_feature            1..1569
                        note = 4D5-6.CD3 (HER2 BiTE)
source                  1..1569
                        mol_type = other DNA
                        organism = synthetic construct
SEQUENCE: 225
atggacttcc aggttcagat cttttcgttc ctgctgatca gcgcctctgt tatcatgtcg        60
cgcggcgaca tccagatgac ccagtcccct tcctccctct ctgcctctgt gggagaccgc       120
gttaccatca catgccgagc ttcccaggac gtgaacacag ccgtggcctg gtaccagcag       180
aagcccggga aggcacccaa actcctcatc tactccgcct ccttcctata cagtggcgtg       240
ccttcccgat tctccggctc caggagtggc acggacttta cgctcaccat tagtagcctg       300
cagcccgaag acttcgcgac ctactattgt cagcaacact acacgacgcc accaactttc       360
ggccagggta ccaaggtcga gattaagcga accggcagta ccagtgggtc tggcaagccc       420
ggcagcggcg agggatccga ggtccagctg gtcgagtccg gcggggggct ggtgcagccg       480
ggcggctcgc tgaggttatc ttgcgccgcc agtggcttca acatcaagga tacttacatc       540
cactgggtga ggcaggctcc gggcaagggc ctggaatggg tggctaggat ctaccctact       600
aacgggtaca cacgctacgc agattcggtg aaaggccgct tcactatctc cgccgacacc       660
tcgaagaaca ctgcttacct gcagatgaac ccctcaggcc gaagatcc tgcagtctac        720
tactgctccc gctggggtgg ggacggcttc gtcgccatag acgtgtgggg tcagggcact       780
ctagttacag tgtcatccgg aggtggtgga tccgatatca aactgcagca gtcaggggct       840
gaactggcaa gacctgggc tcagtgaag atgtcctgca agacttctgg ctacacctt         900
actaggtaca cgatgcactg ggtaaaacag aggcctggac agggtctgga atggattgga       960
tacattaatc ctagccgtgg ttatactaat acaatcaga agttcaagga caaggccaca      1020
ttgactacag acaaatcctc cagcacagcc tacatgcaac tgagcagcct gacatctgag      1080
gactctgcgg tctatttctg tgcaagatat tatgatgatc attactgcct tgactactgg      1140
ggccaaggca ccactctcac agtctcctca gtcgaaggtg gaagtggagg ttctggtgga      1200
agtggaggtt cgggtggagt cgacgacgcc gccattcagc tgacccagtc tccagcaatc      1260
atgtctgcat ctccagggga aaggtcacc atgacctgca gagccagttc aagtgtaagt      1320
tacatgaact ggtaccagca gaagtcaggc acctccccca aaagatggat ttatgacaca      1380
tccaaagtgg cttctggagt cccttatcgc ttcagtggca gtgggtctgg gacctcatac      1440
tctctcacaa tcagcagcat ggaggctgaa gatgctgcca cttattactg ccaacagtgg      1500
agtagtaacc cgctcacgtt cggtgctggg accaagctgg agctgaaaca tcatcaccat      1560
catcattaa                                                              1569
```

LYMPHOCYTES-ANTIGEN PRESENTING CELLS CO-STIMULATORS AND USES THEREOF

This application is a continuation of PCT Patent Application No. PCT/CN2021/112742, filed Aug. 16, 2021, which claims priority to PCT Patent Application No. PCT/CN2020/109484, filed Aug. 17, 2020, each of which is entirely incorporated herein by reference.

1. FIELD

The present invention relates to molecular biology, cell biology, and immuno-oncology.

2. BACKGROUND

T cells can be engineered to express T cell receptors (TCRs) (Morgan R A et al, *Science* (2006) 314(5796):126-129; Robbins P F et al, *J Clin Oncol* (2011) 29(7):917-924; Rapoport A P et al, *Nature Medicine* (2015) 21(8):914-921) or chimeric antigen receptor (CAR) (Kochenderfer J N et al, *Blood* (2010) 116(20):4099-4102; Kalos M et. al., *Science Translational Medicine* (2011) 3(95):95ra73) that recognize tumor antigens to kill tumors for the treatment of cancers and other diseases. Although T cells engineered with CARs specific to the B cell markers, such as CD19, showed dramatic clinical responses in hematological malignancies, effective immunotherapy in solid cancers has proven to be challenging, mainly due to the immune escape caused by complex, dynamic tumor microenvironment (TME) that induces T cell hypofunction and exhaustion and limits the antitumor immune response (Anderson K G et al, *Cancer Cell* (2017) 31(3):311-325). Thus, strategies to circumvent suppressive pathways without causing systemic toxicities represent unmet need. The present disclosures address this need and provide related advantages.

3. SUMMARY

Provided herein are fusion proteins that are referred to as Lymphocytes-Antigen presenting cells Co-stimulators ("LACO-Stims"). Fusion proteins provided herein comprise a first domain that activates an antigen-presenting cell (APC) and a second domain that activates an immune effector cell, wherein (i) the first domain comprises (a) a ligand that binds an activation receptor of the APC, or a receptor-binding fragment thereof, or (b) an antibody that binds an activation receptor of the APC, or an antigen-binding fragment thereof; and (ii) the second domain comprises (a) a co-stimulatory receptor of the immune effector cell, or a functional fragment thereof, (b) a co-stimulatory ligand of the immune effector cell, or a receptor-binding fragment thereof, or (c) an antibody that binds a co-stimulatory receptor of the immune effector cell, or an antigen-binding fragment thereof.

In some embodiments, the APC is selected from the group consisting of a dendritic cell, a macrophage, a myeloid derived suppressor cell, a monocyte, a B cell, a T cell, and a Langerhans cell. In some embodiments, the activation receptor of the APC is selected from the group consisting of CD40, CD80, CD86, CD91, DEC-205 and DC-SIGN.

In some embodiments, the first domain of the fusion proteins provided herein comprises the ligand that binds CD40, CD80, CD86, CD91, DEC-205 or DC-SIGN, or a receptor binding fragment thereof. In some embodiments, the first domain of the fusion proteins provided herein comprises a receptor-binding fragment of CD40 Ligand (CD40L). In some embodiments, the first domain of the fusion proteins provided herein comprises CD40L.

In some embodiments, the first domain of the fusion proteins provided herein comprises an antibody that binds the activation receptor of the APC, or an antigen-binding fragment thereof. In some embodiments, the first domain of the fusion proteins provided herein is an anti-CD40 antibody or an antigen-binding fragment thereof. In some embodiments, the first domain is a monoclonal antibody. In some embodiments, the first domain is a chimeric, humanized, or human antibody. In some embodiments, the first domain is a Fab, Fab', F(ab')2, Fv, scFv, (scFv)2, single chain antibody, dual variable region antibody, diabody, nanobody, or single variable region antibody.

In some embodiments, the first domain of the fusion proteins provided herein is an anti-CD40 antibody or an antigen-binding fragment thereof that comprises a heavy chain variable domain and/or a light chain variable domain, wherein a) the heavy chain variable domain has an amino acid sequence of SEQ ID NO:76, and/or the light chain variable domain has an amino acid sequence of SEQ ID NO:77; b) the heavy chain variable domain has an amino acid sequence of SEQ ID NO:79, and/or the light chain variable domain has an amino acid sequence of SEQ ID NO:80; c) the heavy chain variable domain has an amino acid sequence of SEQ ID NO:82, and/or the light chain variable domain has an amino acid sequence of SEQ ID NO:83; d) the heavy chain variable domain has an amino acid sequence of SEQ ID NO:85, and/or the light chain variable domain has an amino acid sequence of SEQ ID NO:86; e) the heavy chain variable domain has an amino acid sequence of SEQ ID NO:88, and/or the light chain variable domain has an amino acid sequence of SEQ ID NO:89; or f) the heavy chain variable domain has an amino acid sequence of SEQ ID NO:91, and/or the light chain variable domain has an amino acid sequence of SEQ ID NO:92.

In some embodiments, the first domain of the fusion proteins provided herein is an anti-CD40 scFv. In some embodiments, the scFv has an amino acid sequence selected from the group consisting of SEQ ID NOs:75, 78, 81, 84, 87, and 90.

In some embodiments, provided herein are fusion proteins that comprise a first domain that activates an antigen-presenting cell (APC) and a second domain that activates an immune effector cell, wherein the immune effector cell is selected from the group consisting of a T cell, an NK cell, an NKT cell, a macrophage, a neutrophil, and a granulocyte. In some embodiments, the second domain of the fusion proteins provided herein comprises a cytoplasmic domain of the co-stimulatory receptor. In some embodiments, the co-stimulatory receptor is selected from the group consisting of CD28, 4-1BB, ICOS, CD27, OX40, DAP10, 2B4, CD30, CD2, LIGHT, GITR, TLR, DR3, and CD43. In some embodiments, the co-stimulatory receptor is CD28. In some embodiments, the co-stimulatory receptor is 4-1BB. In some embodiments, the second domain further comprises the transmembrane domain of the co-stimulatory receptor.

In some embodiments, the second domain of the fusion proteins provided herein is a co-stimulatory ligand of the immune effector cell, or a receptor-binding fragment thereof. In some embodiments, the co-stimulatory ligand is selected from the group consisting of CD58, CD70, CD83, CD80, CD86, CD137L, CD252, CD275, CD54, CD49a, CD112, CD150, CD155, CD265, CD270, TL1A, CD127, IL-4R, GITR-L, TIM-4, CD153, CD48, CD160, CD200R, and CD44.

In some embodiments, the second domain of the fusion proteins provided herein is an antibody that binds the co-stimulatory receptor, or an antigen-binding fragment thereof. In some embodiments, the co-stimulatory receptor is selected from the group consisting of CD28, 4-1BB, ICOS, CD27, OX40, DAP10, 2B4, CD30, CD2, LIGHT, GITR, TLR, DR3, and CD43. In some embodiments, the co-stimulatory receptor is CD28. In some embodiments, the co-stimulatory receptor is 4-1BB. In some embodiments, the second domain is a monoclonal antibody. In some embodiments, the second domain is a chimeric, humanized, or human antibody. In some embodiments, the second domain is a Fab, Fab', F(ab')2, Fv, scFv, (scFv)2, single chain antibody, dual variable region antibody, diabody, nanobody, or single variable region antibody.

In some embodiments, the second domain of the fusion proteins provided herein is an antibody that binds CD28, or an antigen-binding fragment thereof. In some embodiments, the anti-CD28 antibody or an antigen-binding fragment thereof comprises a heavy chain variable domain having an amino acid sequence of SEQ ID NO:73, and/or a light chain variable domain having an amino acid sequence of SEQ ID NO:74. In some embodiments, the second domain of the fusion proteins provided herein is a scFv that that binds CD28. In some embodiments, the scFv has the amino acid sequence of SEQ ID NO:72.

In some embodiments of the fusion proteins provided herein, the N-terminus of the first domain is linked to the C-terminus of the second domain. In some embodiments, the N-terminus of the second domain is linked to the C-terminus of the first domain. In some embodiments, the first domain and the second domain of the fusion proteins provided herein are linked via a linker. In some embodiments, the linker is a trimerization motif. In some embodiments, the linker is a T4 fibritin trimerization motif.

In some embodiments of the fusion proteins provided herein, the first domain comprises CD40L or a receptor-binding fragment thereof, and the second domain comprises a CD28 cytoplasmic domain. In some embodiments, the first domain comprises a CD40L. In some embodiments, the N-terminus of the first domain is linked to the C-terminus of the second domain.

In some embodiments of the fusion proteins provided herein, the first domain comprises CD40L or a receptor-binding fragment thereof, and the second domain comprises an anti-CD28 antibody or an antigen-binding fragment thereof. In some embodiments, the N-terminus of the first domain is linked to the C-terminus of the second domain. In some embodiments, the two domains are linked via a T4 fibritin trimerization motif.

In some embodiments of the fusion proteins provided herein, the first domain comprises an anti-CD40 antibody or an antigen-binding fragment thereof, and the second domain comprises an anti-CD28 antibody or an antigen-binding fragment thereof. In some embodiments, the N-terminus of the first domain is linked to the C-terminus of the second domain.

In some embodiments of the fusion proteins provided herein, the first domain comprises an anti-CD40 antibody or an antigen-binding fragment thereof, and the second domain comprises a CD28 transmembrane region and a CD28 cytoplasmic domain. In some embodiments, the first and second domains are linked via a CD8 hinge, a CD28 hinge, or an IgG Fc region. In some embodiments, the N-terminus of the second domain is linked to the C-terminus of the first domain.

In some embodiments, the fusion proteins provided herein have an amino acid sequence that is at least 85%, 90%, 95%, 98%, or 99% identical to SEQ ID NO:93. In some embodiments, the fusion proteins provided herein have an amino acid sequence that is at least 85%, 90%, 95%, 98%, or 99% identical to SEQ ID NO:94. In some embodiments, the fusion proteins provided herein have an amino acid sequence that is at least 85%, 90%, 95%, 98%, or 99% identical to SEQ ID NO:95. In some embodiments, the fusion proteins provided herein have an amino acid sequence that is at least 85%, 90%, 95%, 98%, or 99% identical to SEQ ID NO:96. In some embodiments, the fusion proteins provided herein have an amino acid sequence that is at least 85%, 90%, 95%, 98%, or 99% identical to SEQ ID NO:97. In some embodiments, the fusion proteins provided herein have an amino acid sequence that is at least 85%, 90%, 95%, 98%, or 99% identical to SEQ ID NO:98. In some embodiments, the fusion proteins provided herein have an amino acid sequence that is at least 85%, 90%, 95%, 98%, or 99% identical to SEQ ID NO:99. In some embodiments, the fusion proteins provided herein have an amino acid sequence that is at least 85%, 90%, 95%, 98%, or 99% identical to SEQ ID NO:100. In some embodiments, the fusion proteins provided herein have an amino acid sequence that is at least 85%, 90%, 95%, 98%, or 99% identical to SEQ ID NO:101. In some embodiments, the fusion proteins provided herein have an amino acid sequence that is at least 85%, 90%, 95%, 98%, or 99% identical to SEQ ID NO:102. In some embodiments, the fusion proteins provided herein have an amino acid sequence that is at least 85%, 90%, 95%, 98%, or 99% identical to SEQ ID NO:103. In some embodiments, the fusion proteins provided herein have an amino acid sequence that is at least 85%, 90%, 95%, 98%, or 99% identical to SEQ ID NO:104. In some embodiments, the fusion proteins provided herein have an amino acid sequence that is at least 85%, 90%, 95%, 98%, or 99% identical to SEQ ID NO:105. In some embodiments, the fusion proteins provided herein have an amino acid sequence that is at least 85%, 90%, 95%, 98%, or 99% identical to SEQ ID NO:106. In some embodiments, the fusion proteins provided herein have an amino acid sequence that is at least 85%, 90%, 95%, 98%, or 99% identical to SEQ ID NO:199. In some embodiments, the fusion proteins provided herein have an amino acid sequence that is at least 85%, 90%, 95%, 98%, or 99% identical to SEQ ID NO:201. In some embodiments, the fusion proteins provided herein have an amino acid sequence that is at least 85%, 90%, 95%, 98%, or 99% identical to SEQ ID NO:211. In some embodiments, the fusion proteins provided herein have an amino acid sequence selected from the group consisting of SEQ ID NOs:93-106, 199, 201 and 211.

In some embodiments, provided herein are polynucleotides that encode the fusion proteins provided herein. In some embodiments, provided herein are also vectors that comprise the polynucleotides provided herein. In some embodiments, the vector is a viral vector. In some embodiments, the vector is a retroviral vector, a lentiviral vector, an adenoviral vector, or an adeno-associated viral vector.

A genetically engineered immune effector cell that recombinantly expresses the fusion protein provided herein, wherein the immune effector cell is selected from the group consisting of a T cell, an NK cell, an NKT cell, a macrophage, a neutrophil, and a granulocyte.

In some embodiments, provided herein are genetically engineered immune effector cells comprising a polynucleotide disclosed herein or a vector disclosed herein, wherein the immune effector cell is selected from the group consisting of a T cell, an NK cell, an NKT cell, a macrophage, a neutrophil, and a granulocyte. In some embodiments, the immune effector cell is a T cell. In some embodiments, the immune effector cell is a NK cell. In some embodiments, the immune effector cell is a macrophage.

In some embodiments, the genetically engineered immune effector cells provided herein further recombinantly express a chimeric antigen receptor (CAR), a T cell receptor (TCR) or a Bi-specific T-cell engager (BiTE), wherein the CAR, TCR or BiTE binds a tumor antigen or a viral antigen. In some embodiments, the cells provided herein further comprise a polynucleotide that encodes a CAR, a TCR, or BiTE, wherein the CAR, TCR or BiTE binds a tumor antigen or a viral antigen. In some embodiments, the CAR, TCR or BiTE binds a viral antigen selected from the group consisting of HPV, EBV, and HIV. In some embodiments, the CAR, TCR or BiTE binds a tumor antigen selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin. In some embodiments, the CAR has an amino acid sequence selected from the group consisting of SEQ ID NOs:107-121 and 203. In some embodiments, the TCR has an amino acid sequence selected from the group consisting of SEQ ID NOs:122-129. In some embodiments, the BiTE has an amino acid sequence that is SEQ ID NO:130, 131 or 224.

In some embodiments, the genetically engineered immune effector cell provided herein is derived from a cell isolated from peripheral blood or bone marrow. In some embodiments, the cell provided herein is derived from a cell differentiated in vitro from a stem or progenitor cell selected from the group consisting of a T cell progenitor cell, a hematopoietic stem and progenitor cell, a hematopoietic multipotent progenitor cell, an embryonic stem cell, and an induced pluripotent cell.

In some embodiments, the genetically engineered immune effector cell provided herein is a T cell. In some embodiments, the genetically engineered immune effector cell provided herein is a cytotoxic T cell, a helper T cell, or a gamma delta T, a CD4+/CD8+ double positive T cell, a CD4+ T cell, a CD8+ T cell, a CD4/CD8 double negative T cell, a CD3+ T cell, a naive T cell, an effector T cell, a cytotoxic T cell, a helper T cell, a memory T cell, a regulator T cell, a Th0 cell, a Th1 cell, a Th2 cell, a Th3 (Treg) cell, a Th9 cell, a Th17 cell, a Thαβ helper cell, a Tfh cell, a stem memory TSCM cell, a central memory TCM cell, an effector memory TEM cell, an effector memory TEMRA cell, or a gamma delta T cell.

In some embodiments, provided herein is a population of the genetically engineered immune effector cells that are derived from cells isolated from peripheral blood mononuclear cells (PBMC), peripheral blood leukocytes (PBL), tumor infiltrating lymphocytes (TIL), cytokine-induced killer cells (CIK), lymphokine-activated killer cells (LAK), or marrow infiltrate lymphocytes (MILs).

In some embodiments, provided herein is a pharmaceutical composition comprising the fusion protein disclosed herein, and a pharmaceutically acceptable excipient.

In some embodiments, provided herein is a pharmaceutical composition comprising the genetically engineered immune effector cell or population of cells disclosed herein and a pharmaceutically acceptable excipient.

In some embodiments, provided herein are uses of the fusion proteins disclosed herein in cancer treatment. In some embodiments, provided herein are uses of the fusion protein proteins disclosed herein for the preparation of a medicament for the treatment of cancer. In some embodiments, the fusion protein disclosed herein is used in combination with an immune effector cell. In some embodiments, the immune effector cell is selected from the group consisting of a CAR T cell, a TCRT cell, a TIL, a CIK, a LAK, and a MIL.

In some embodiments, provided herein are uses of the cell or population of cells disclosed herein in cancer treatment. In some embodiments, provided herein are uses of the cell or population of cells disclosed herein for the preparation of a medicament for the treatment of cancer. In some embodiments, provided herein are uses of the pharmaceutical composition disclosed herein in cancer treatment. In some embodiments, provided herein are uses of the pharmaceutical composition disclosed herein for the preparation of a medicament for the treatment of cancer.

In some embodiments, the fusion protein, the cell, population of cells, or pharmaceutical composition provided herein is used in combination with an additional therapy.

In some embodiments, provided herein are methods of treating cancer in a subject in need thereof comprising administering a therapeutically effective amount of the fusion protein disclosed herein to the subject. In some embodiments, the methods provided herein further comprise administering a cell therapy to the subject. In some embodiments, the cell therapy is selected from the group consisting of a CAR T therapy, a TCRT therapy, a TIL therapy, a CIK therapy, a LAK therapy, and a MIL therapy.

In some embodiments, provided herein are methods of treating cancer in a subject in need thereof comprising administering a therapeutically effective amount of the cell or population of cells disclosed herein to the subject. In some embodiments, provided herein are methods of treating cancer in a subject in need thereof comprising administering a therapeutically effective amount of the pharmaceutical composition disclosed herein to the subject. In some embodiments, the methods provided herein further comprise administering an additional therapy to the subject.

In some embodiments, the subject is a human.

In some embodiments of the uses or methods provided herein, the fusion protein, the cell, population of cells, or pharmaceutical composition reduces cancer-induced immunosuppression.

In some embodiments, provided herein are uses in cancer treatment or methods of treating cancer, wherein the cancer is a hematological cancer. In some embodiments, the cancer is a solid tumor.

In some embodiments, provided herein are methods of genetically engineering an immune effector cell comprising transferring the polynucleotide disclosed herein into the cell. In some embodiments, the polynucleotide is transferred via electroporation. In some embodiments, the polynucleotide is transferred via viral transduction. In some embodiments, the polynucleotide is transferred via viral transduction using a lentivirus, a retrovirus, an adenovirus, or an adeno-associated virus. In some embodiments, the polynucleotide is transferred using a transposon system. In some embodiments, the transposon system is Sleeping Beauty or PiggyBac. In some embodiments, the polynucleotide is transferred using gene-editing. In some embodiments, the polynucleotide is transferred using gene-editing via a CRISPR-Cas system, a ZFN system, or a TALEN system. In some embodiments, provided herein are methods of genetically engineering an immune effector cell comprising transferring the polynucleotide disclosed herein into the cell, wherein the immune effector cell is selected from the group consisting of a T cell, an NK cell, an NKT cell, a macrophage, a neutrophil, and a granulocyte cell.

4. BRIEF DESCRIPTION OF DRAWINGS

Figure 3:
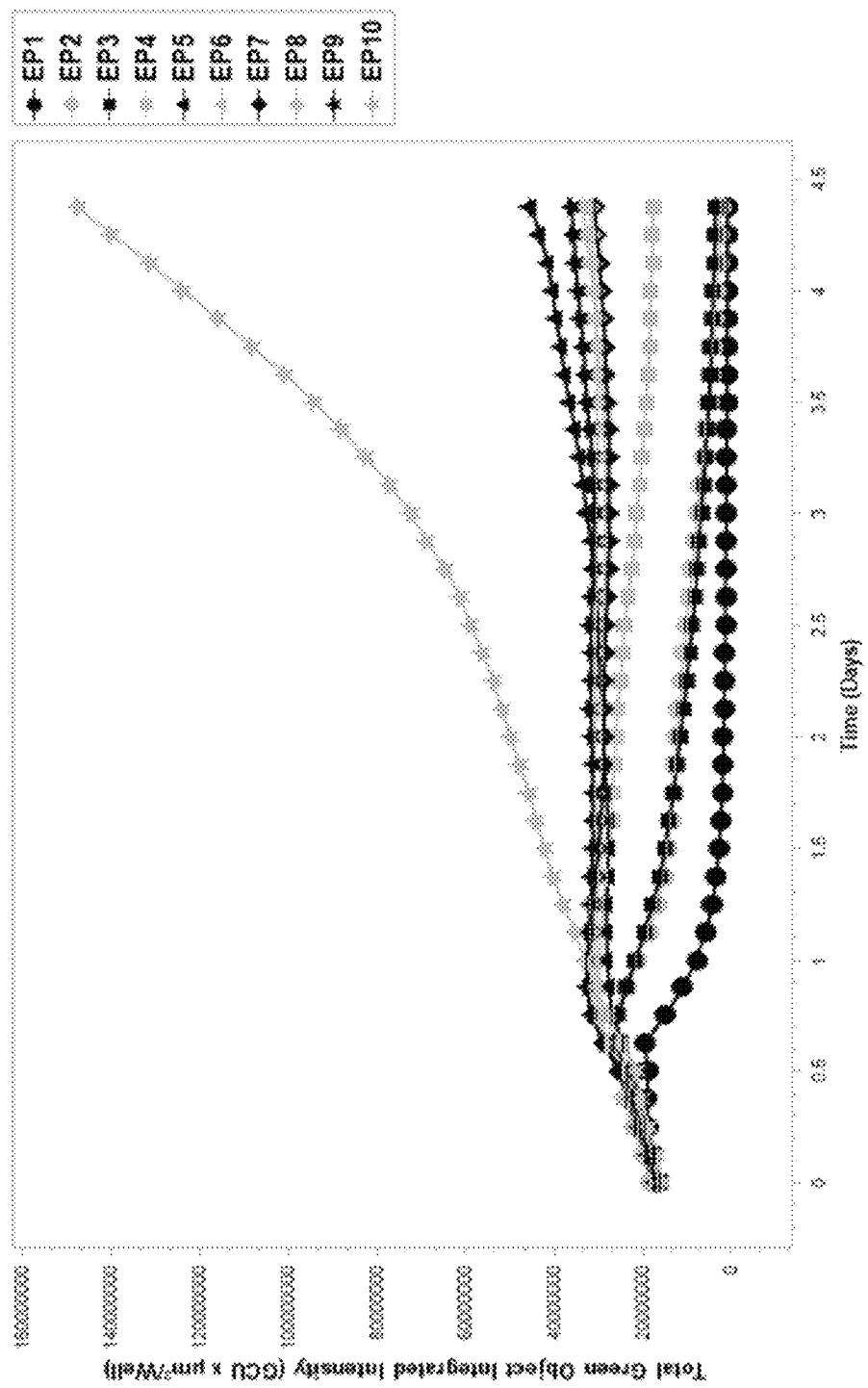

FIG. 3 shows tumor growth after being co-cultured with T cells co-expressing a CAR and LACO-Stim as listed in Table 1. E:T ratio was 30:1. E: Effector cells (T cells); T: Target cells (A549-ESO cells).

Figure 4:
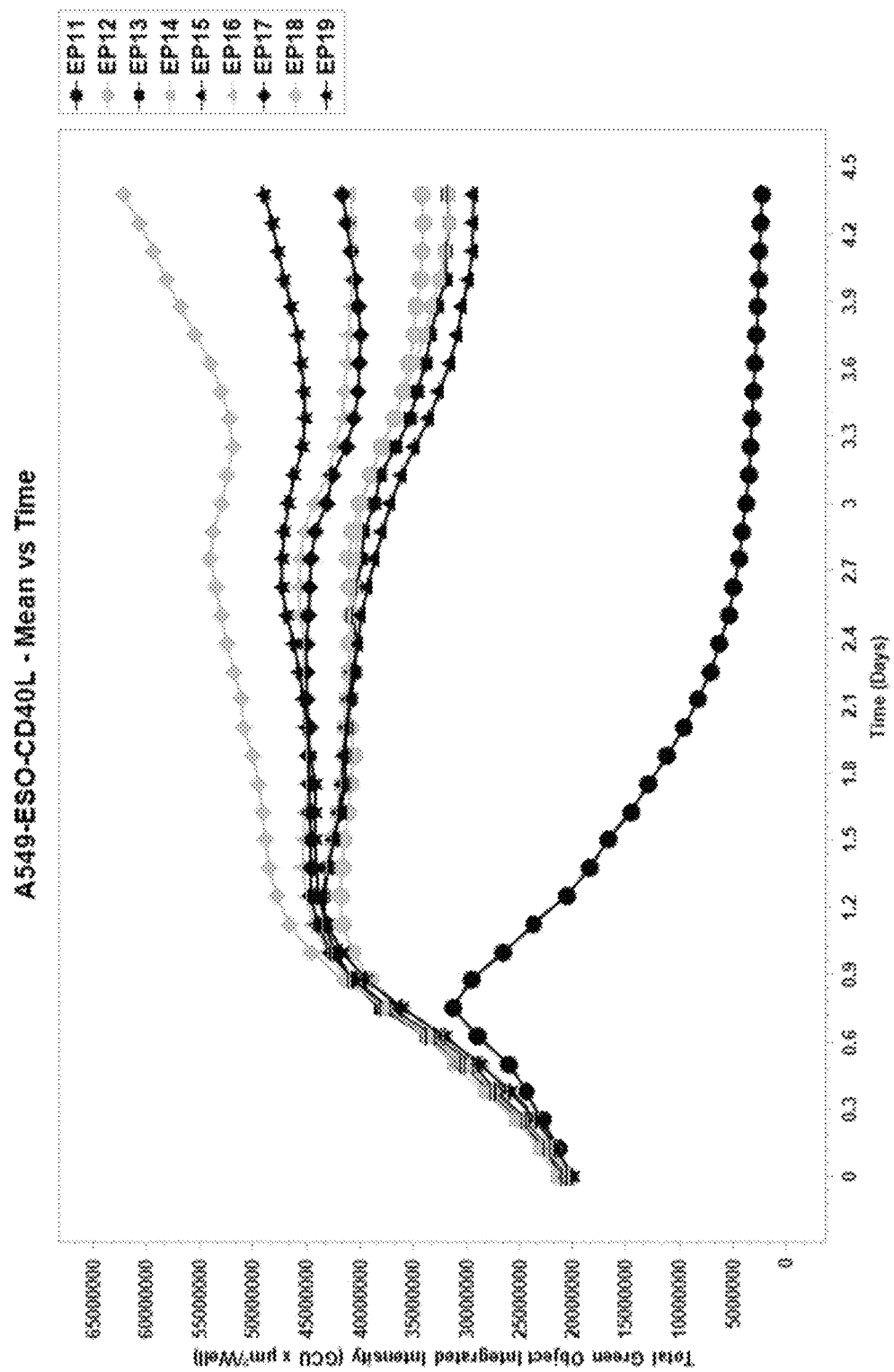

FIG. 4 shows tumor growth after being co-cultured with T cells co-expressing a TCR and LACO-Stim as listed in Table 1. E:T ratio was 30:1.

Figure 5:
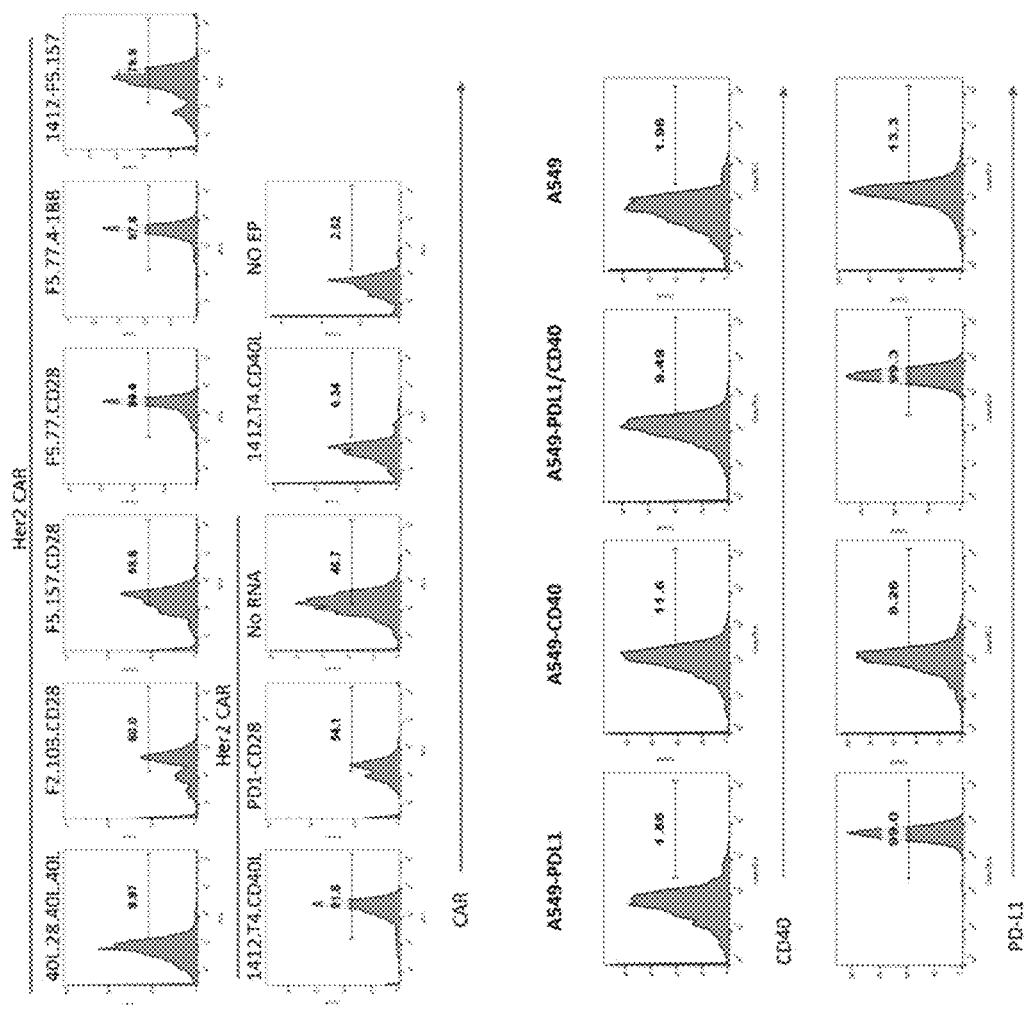

FIG. 5 shows CAR expression of transferred T cells and CD40 or PD-L1 expression on A549 tumor line. Upper panel: Flow cytometry detecting CAR expression of T cells electroporated (EP) with RNA for a Her2 CAR and other constructs for different fusion proteins as indicated. Lower panel: Flow cytometry detecting CD40 or PD-L1 expression of A549 electroporated (EP) with RNA for CD40 and/or PD-L1.

Figure 6:
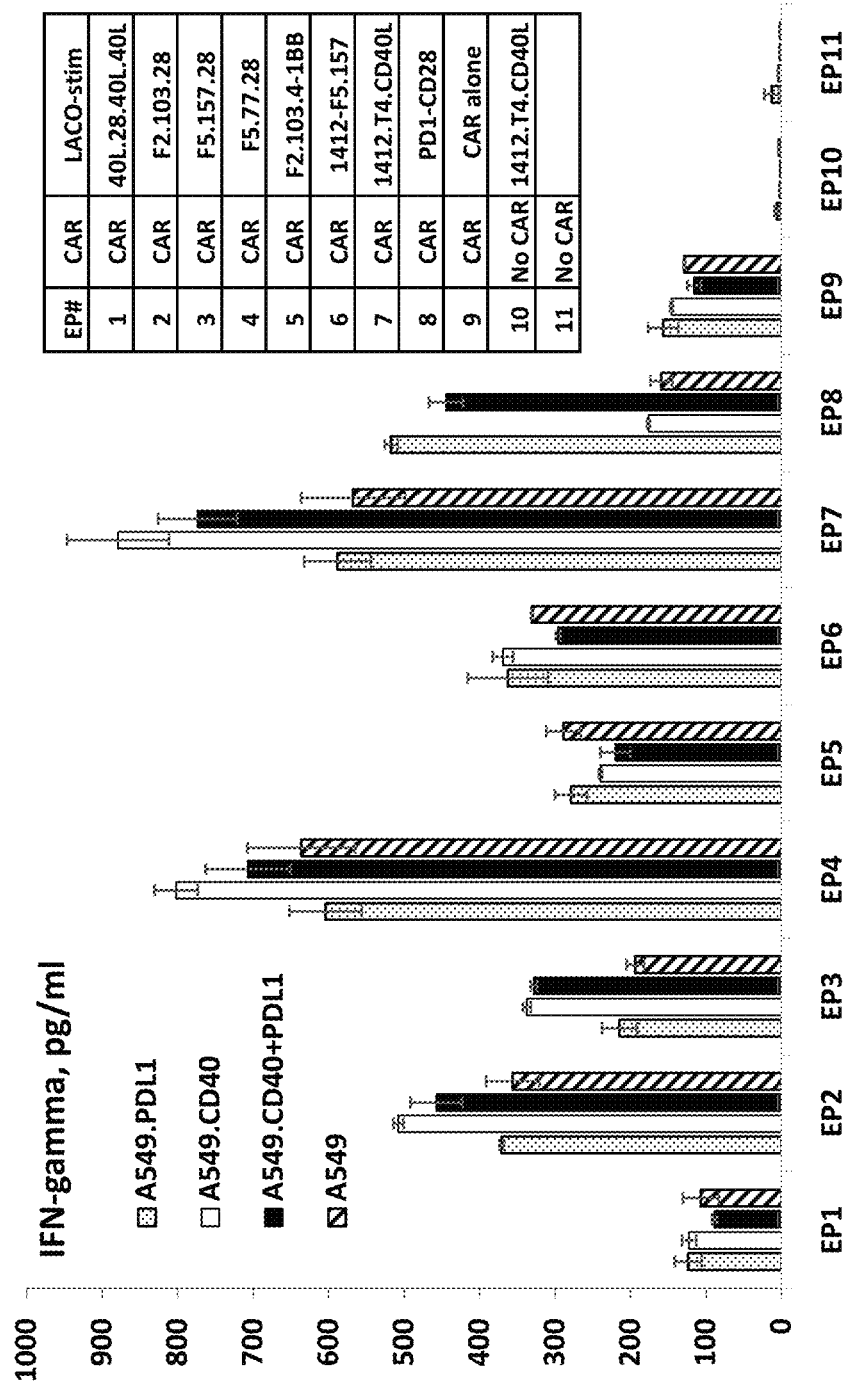

FIG. 6 shows IFN-gamma production of T cells. T cells were electroporated (EP) with RNA for a Her2 CAR and other constructs for different fusion proteins as indicated and stimulated with A549 tumor lines that were transferred with either CD40, PD-L1 or both as indicated for 24 h. IFN-gamma secretion was detected by ELISA.

Figure 7:
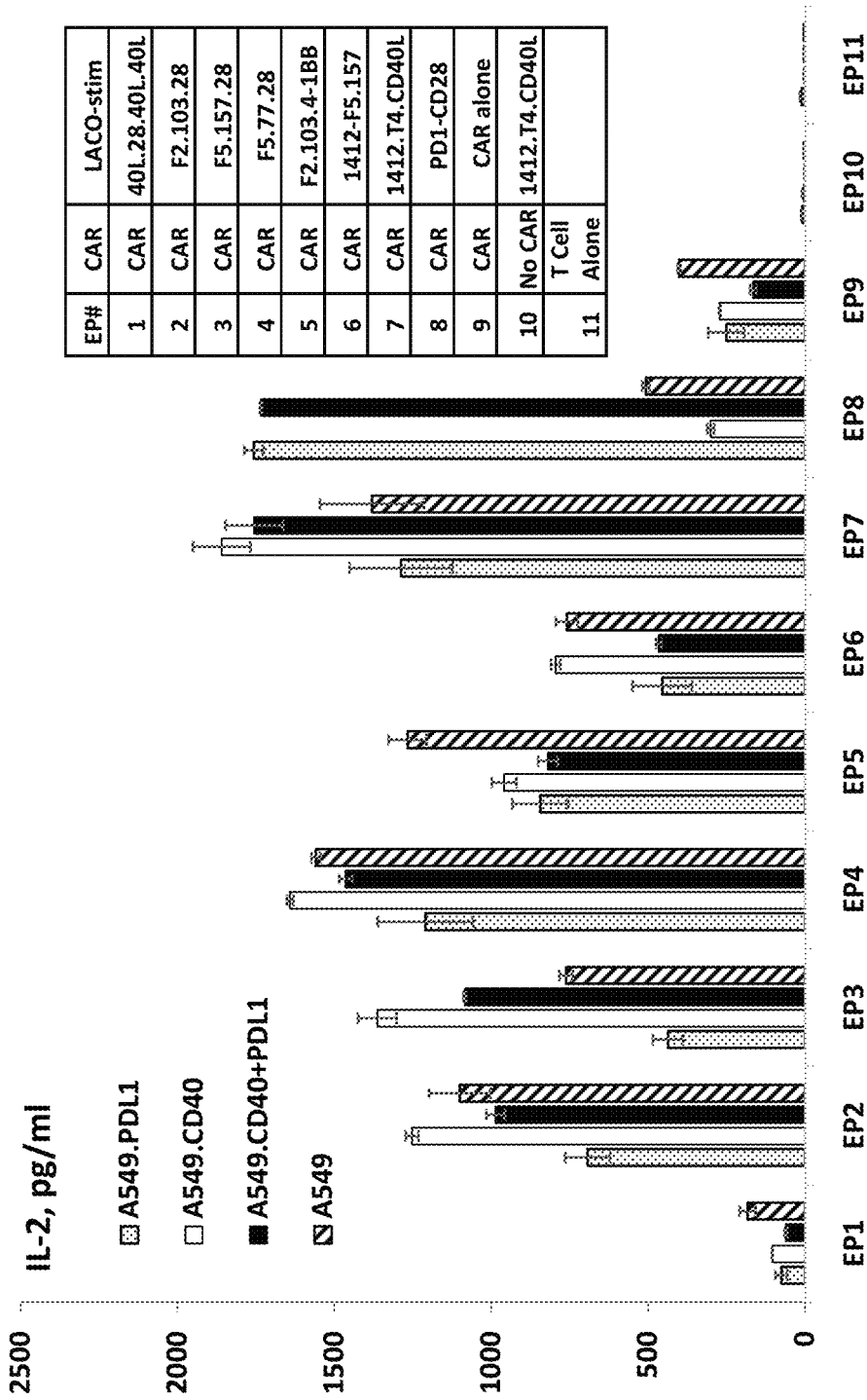

FIG. 7 shows IL-2 production of T cells. T cells were electroporated (EP) with RNA for a Her2 CAR and other constructs for different fusion proteins as indicated and stimulated with A549 tumor lines that were transferred with either with CD40, or PD-L1 or both as indicated for 24 h. IL-2 secretion was detected by ELISA.

Figure 8:
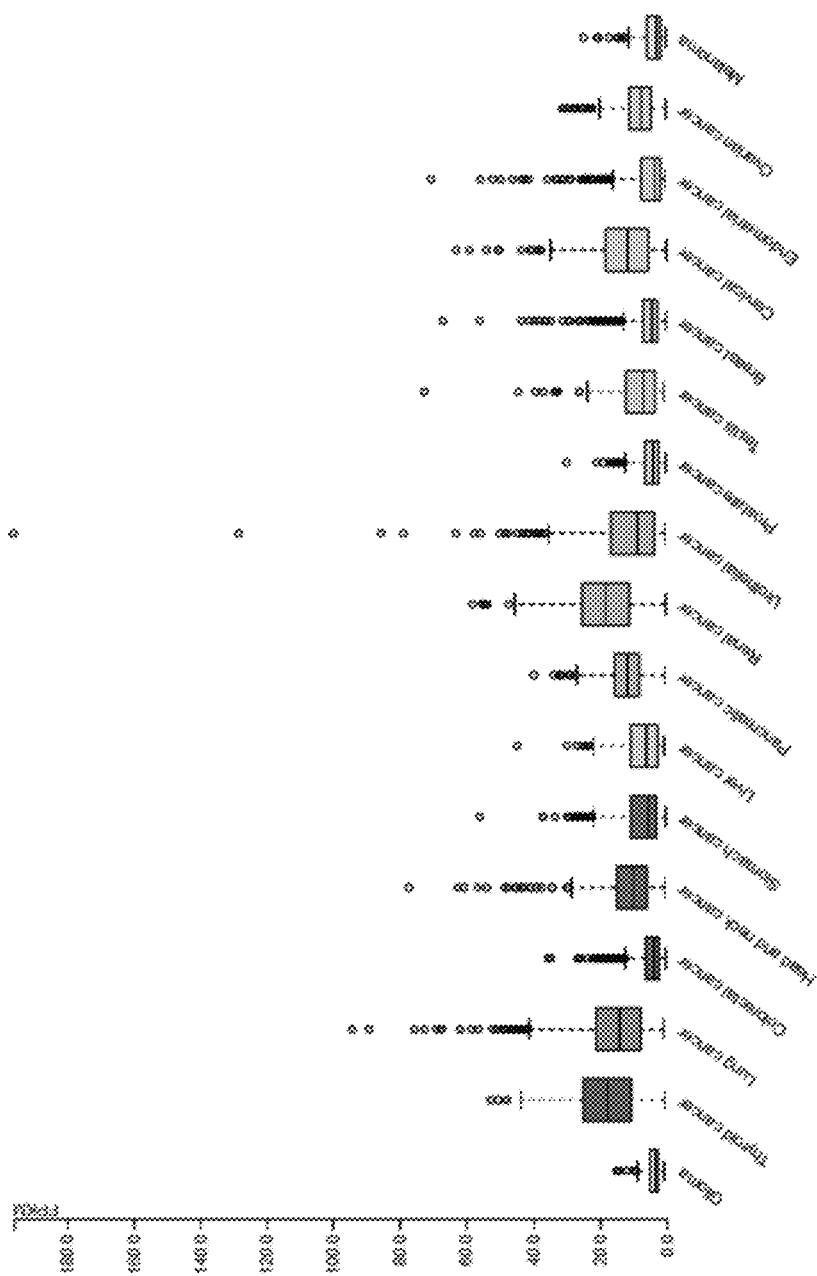

FIG. 8 shows RNA expression of CD40 in different cancers from TCGA dataset.

Figure 9:
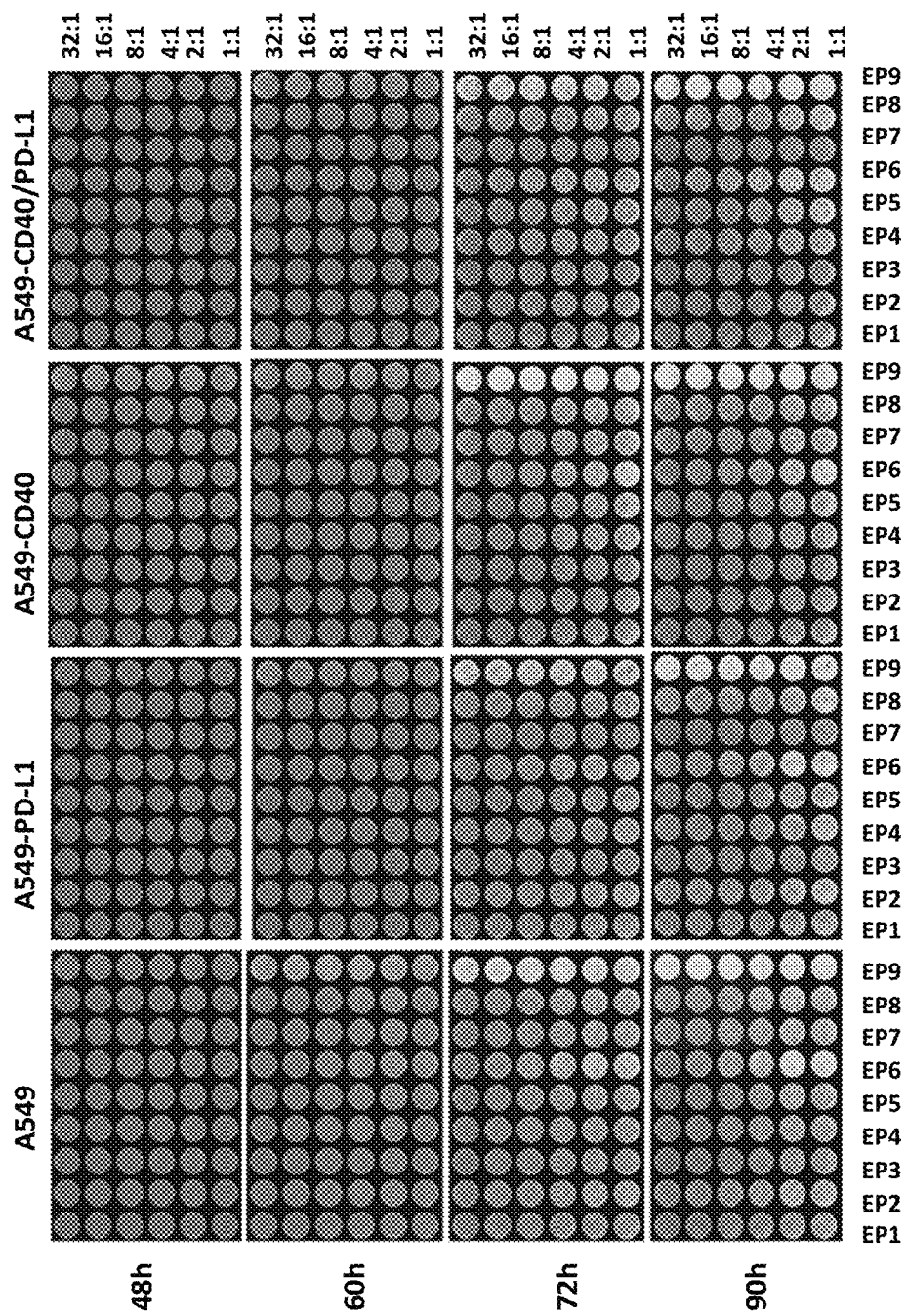

FIG. 9 shows real time image of different tumor targets (as indicated on the top, all expressing GFP) that were co-cultured with different T cells (as indicated on the bottom and Table 2) at different E:T ratios (as indicated on the right) at different time points (as indicated on the left).

Figure 10:
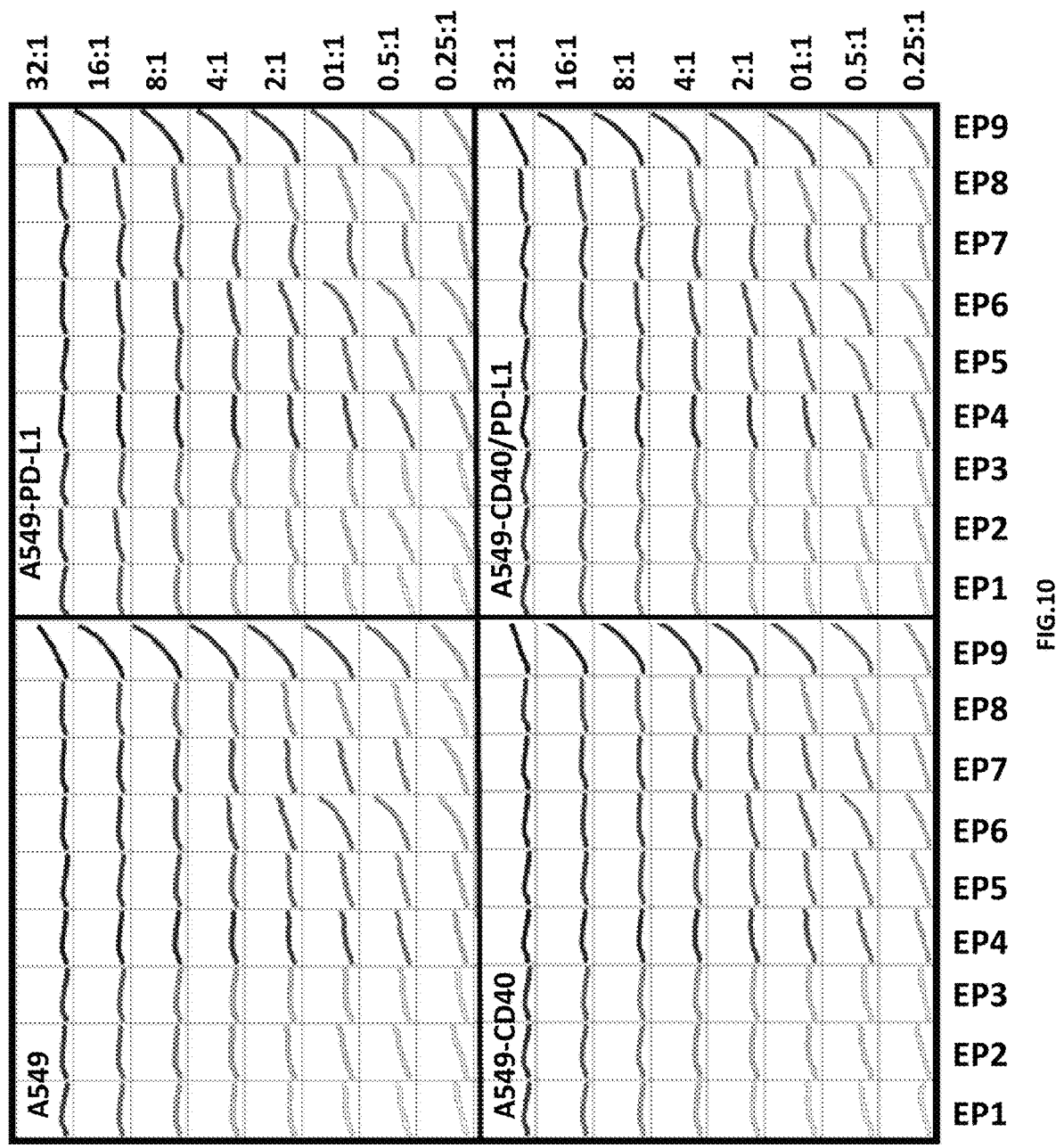

FIG. 10 shows real time growth curves of different tumor targets that were co-cultured with different T cells (as indicated on the bottom and Table 2) at different E:T ratios (as indicated on the right).

Figure 11A:
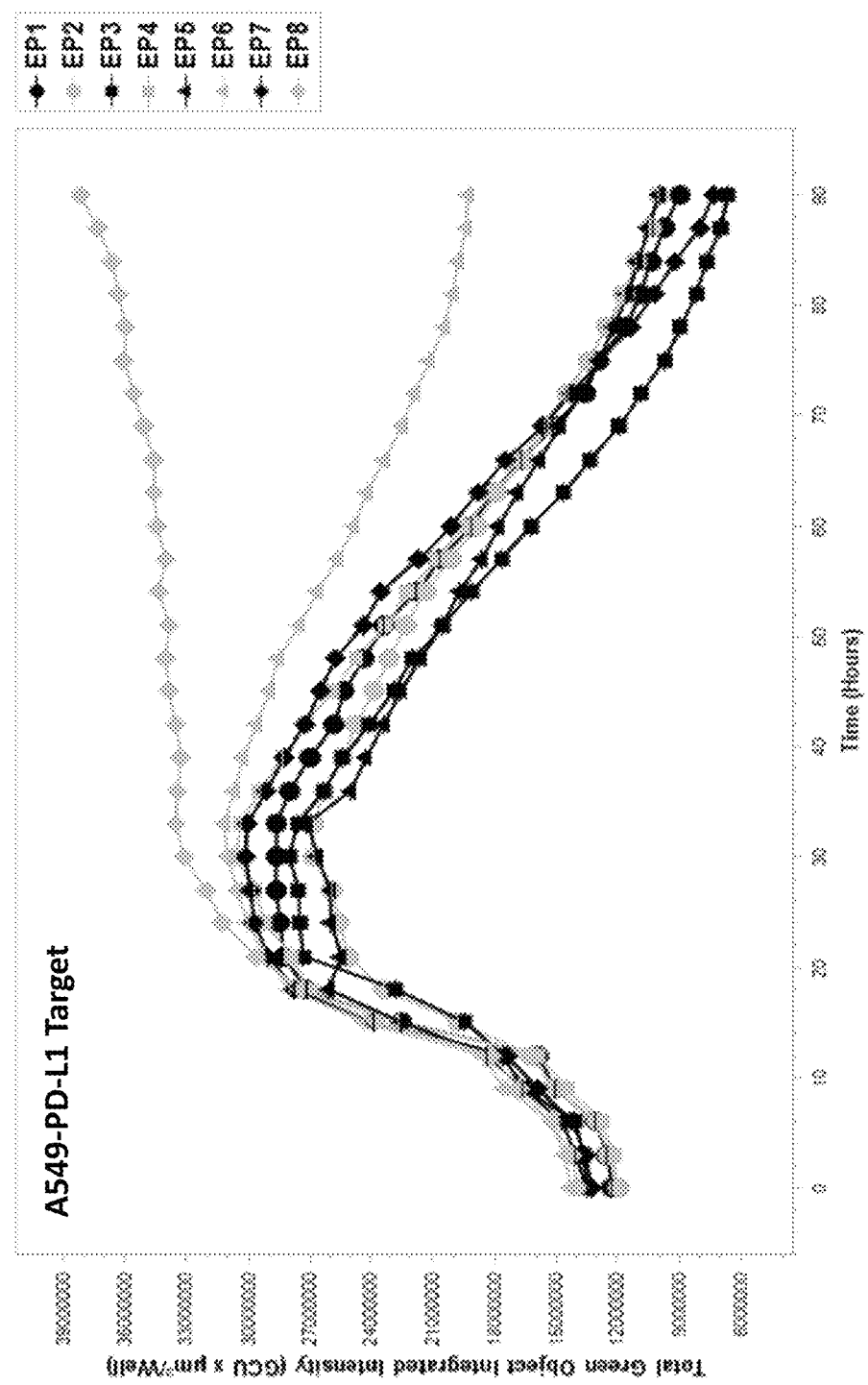
Figure 11B:
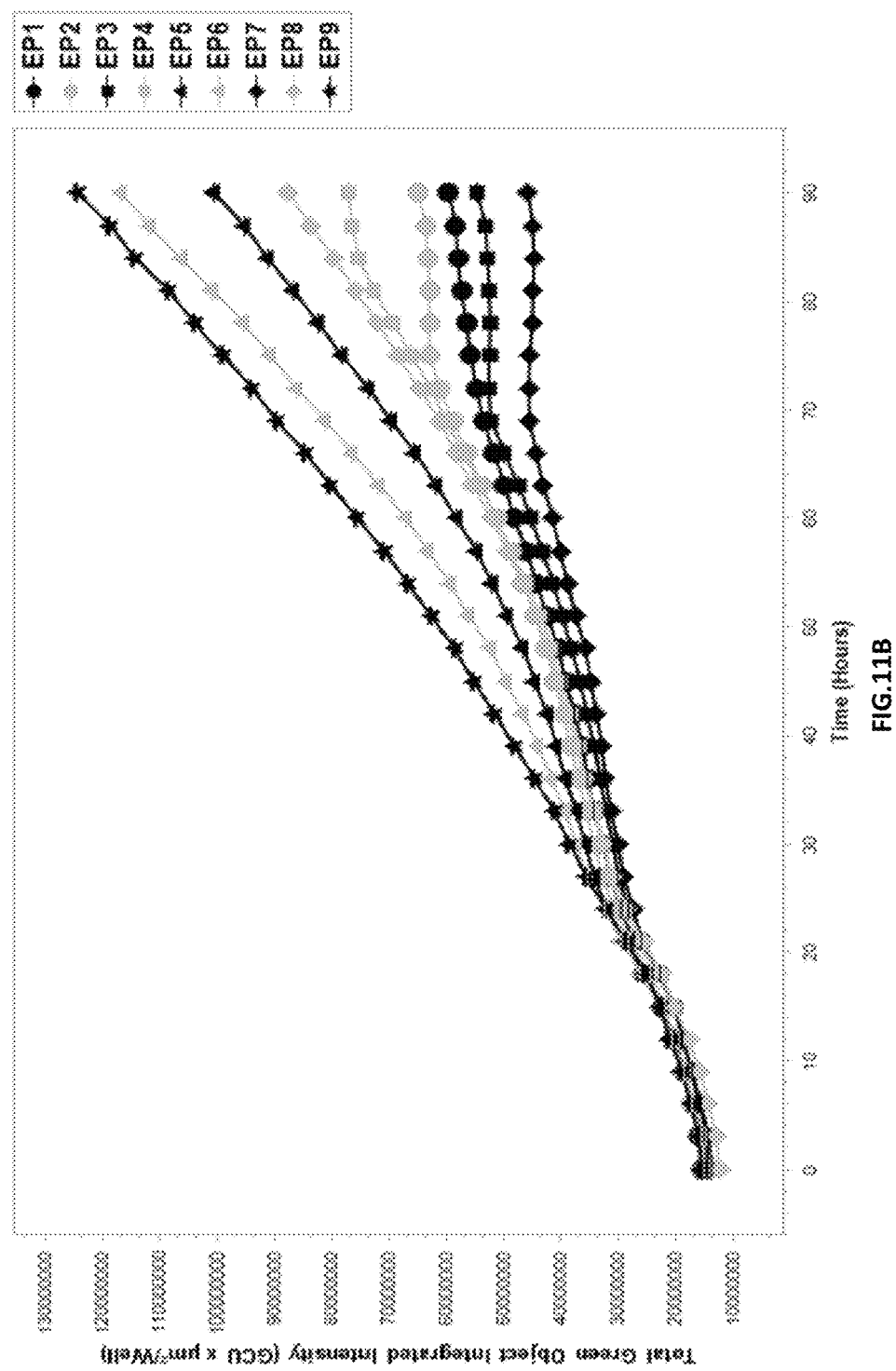

FIGS. 11A-11B FIG. 11A shows real time growth curves of A549 transferred with PD-L1 (expressing GFP) in the presence of different T cells as listed in Table 2 at E:T ratio of 32:1. FIG. 11B shows real time growth curves of A549 transferred with PD-L1 (expressing GFP) in the presence of different T cells as listed in Table 2 at E:T ratio of 0.25:1.

Figure 12A:
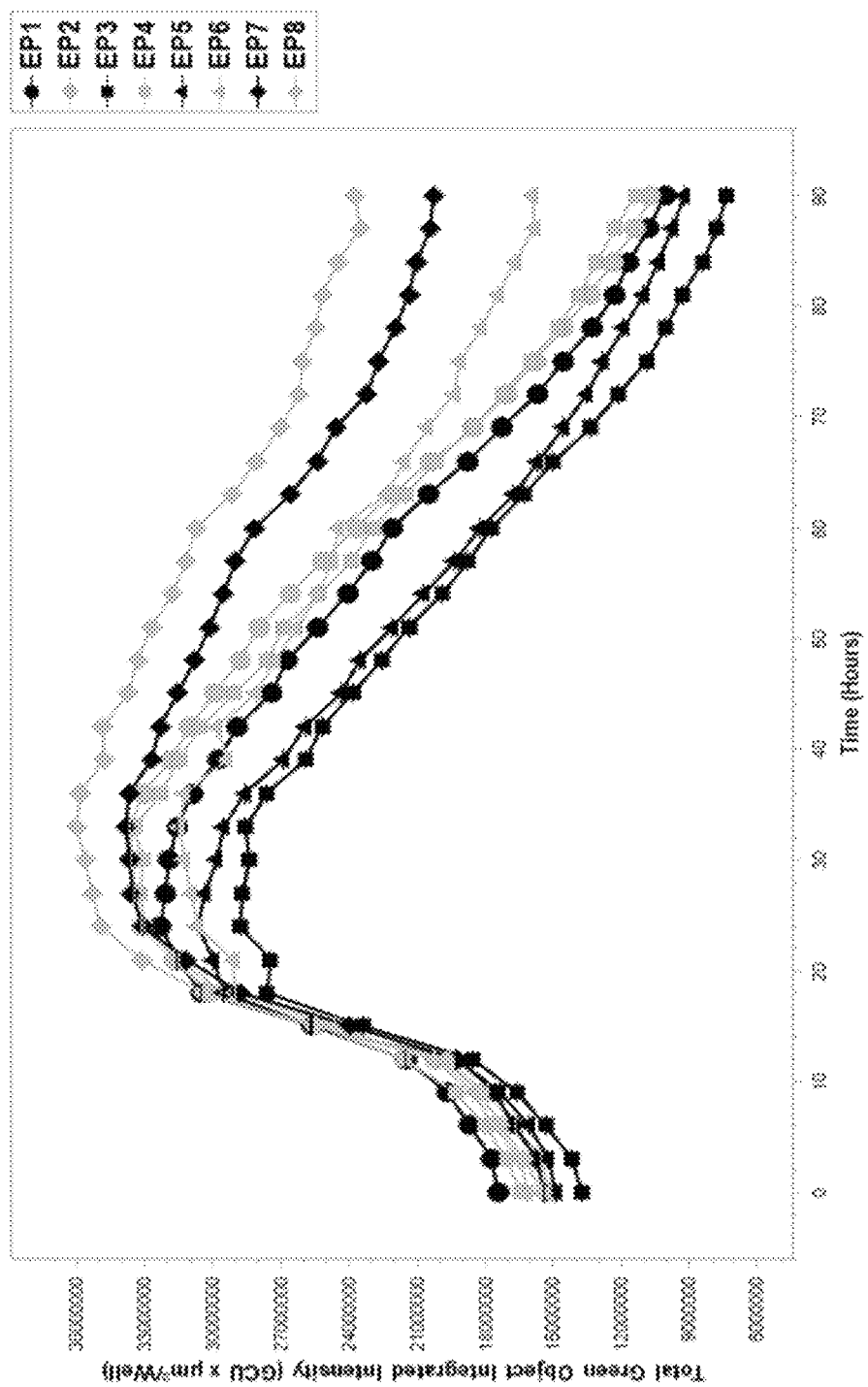
Figure 12B:
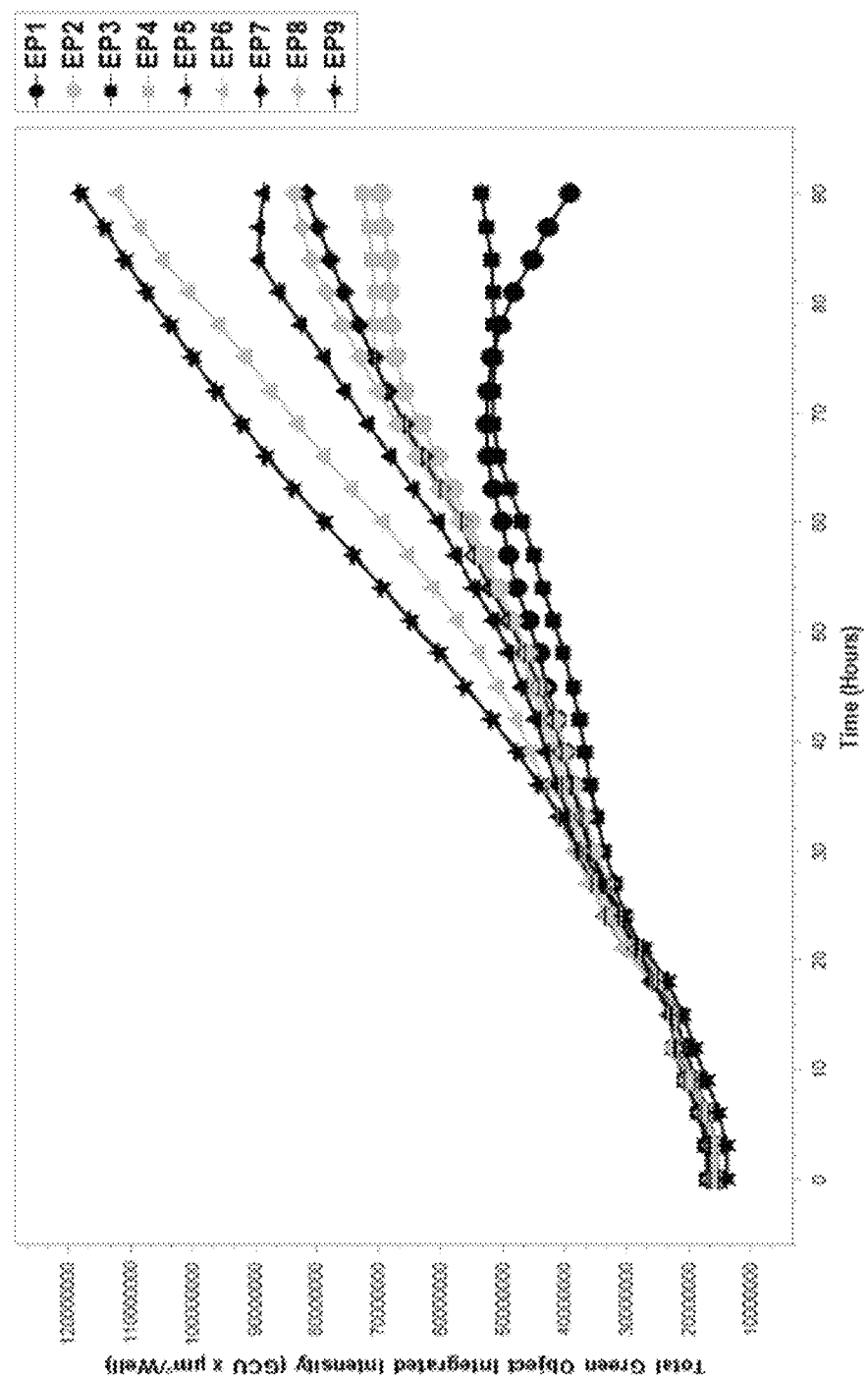

FIGS. 12A-12B FIG. 12A shows real time growth curves of A549 transferred with CD40 (expressing GFP) in the presence of different T cells as listed in Table 2 at E:T ratio of 32:1. FIG. 12B shows real time growth curves of A549 transferred with CD40 (expressing GFP) in the presence of different T cells as listed in Table 2 at E:T ratio of 0.25:1.

Figure 13A:
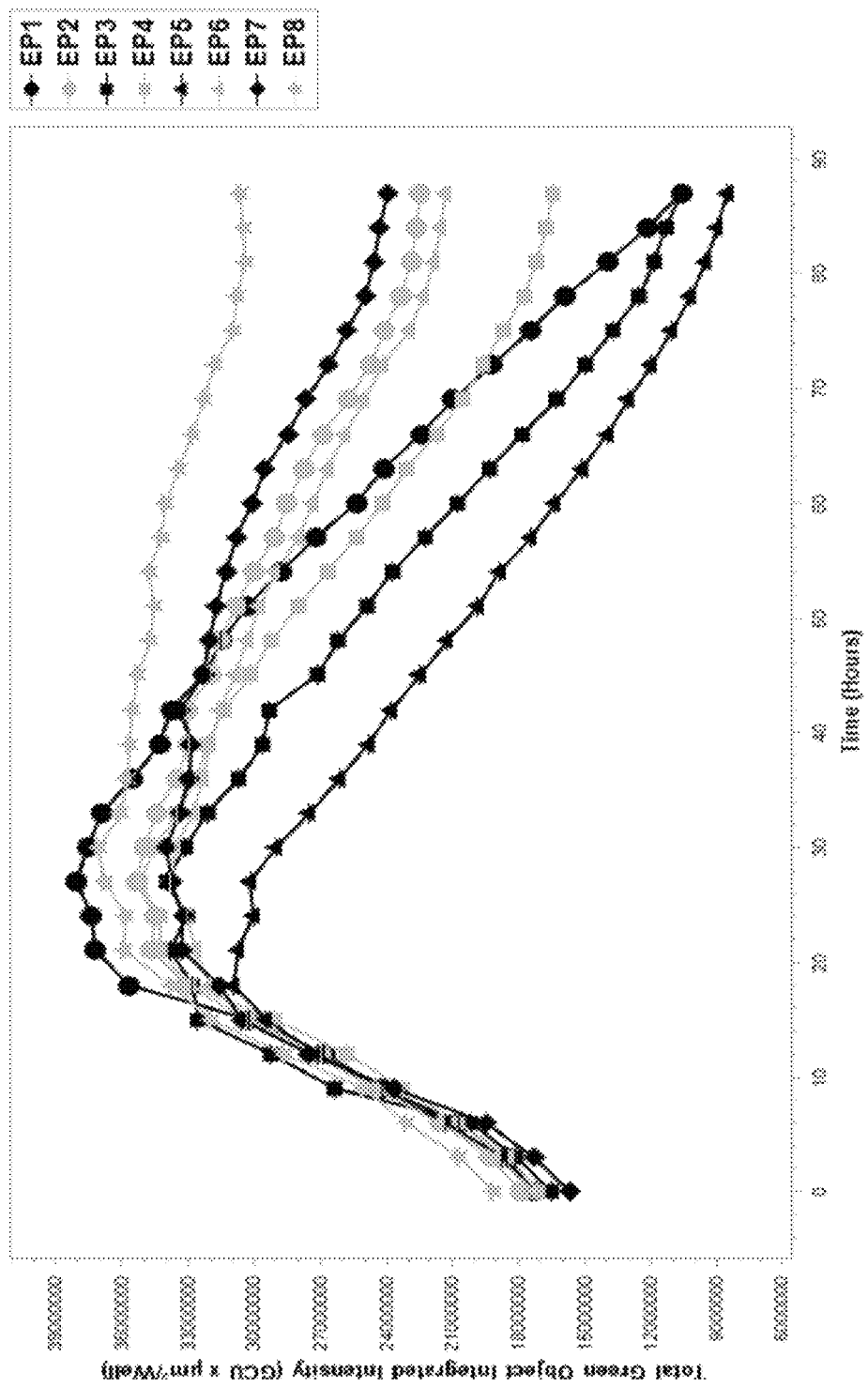
Figure 13B:
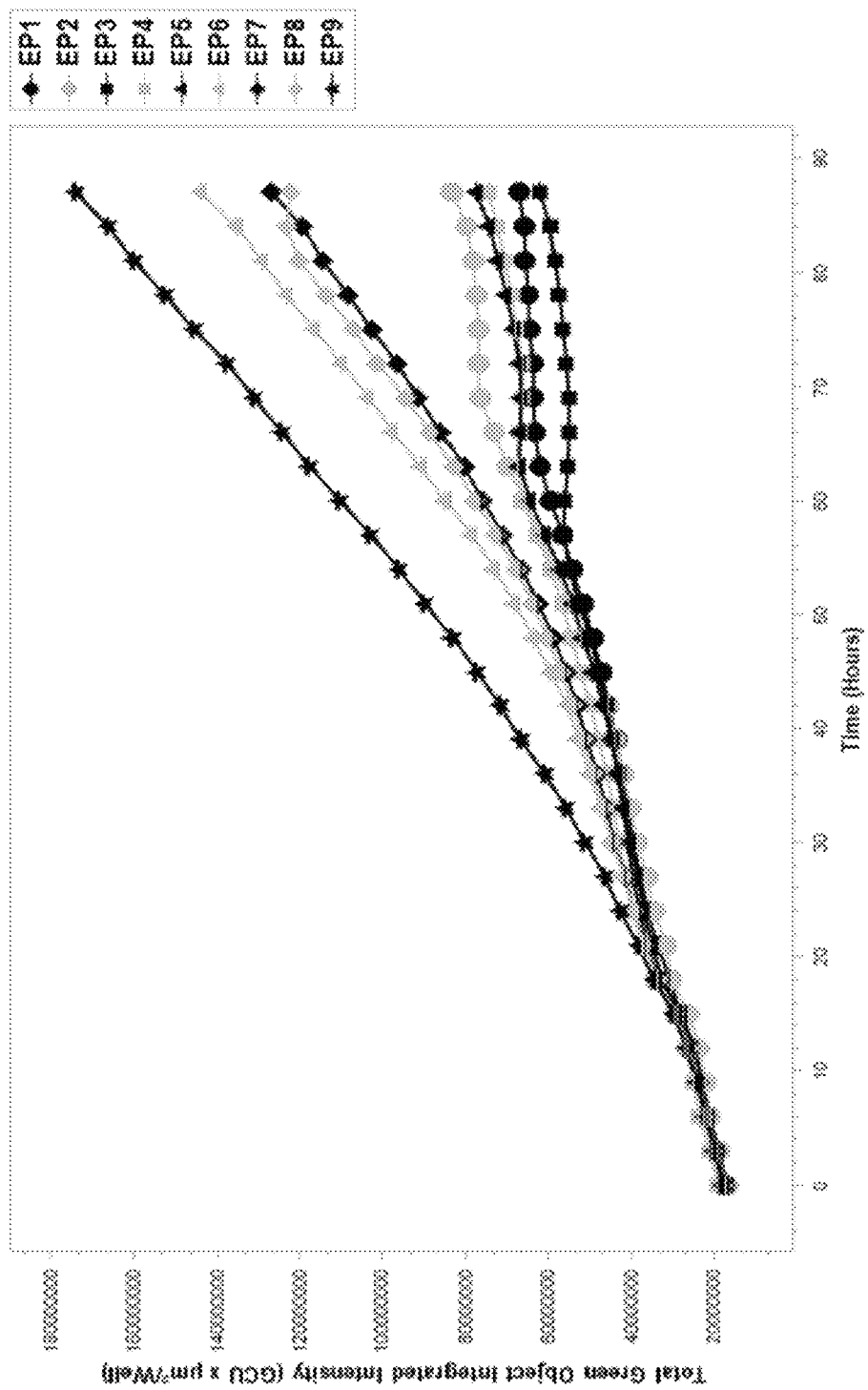

FIGS. 13A-13B FIG. 13A shows real time growth curves of A549 (expressing GFP) in the presence of different T cells as listed in Table 2 at E:T ratio of 32:1. FIG. 13B shows real time growth curves of A549 (expressing GFP) in the presence of different T cells as listed in Table 2 at E:T ratio of 0.25:1.

Figure 14:
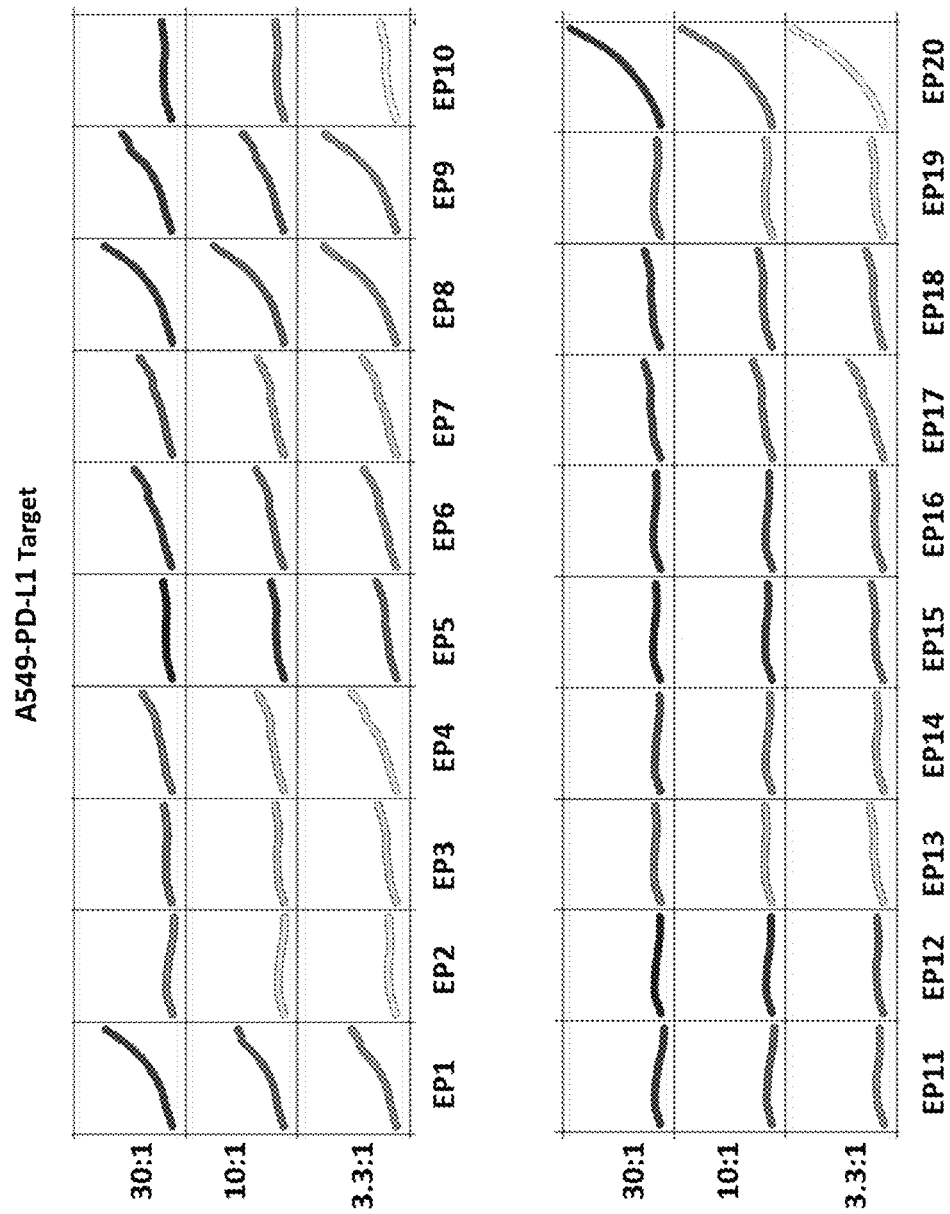

FIG. 14 shows real time growth curves of A549 transferred with PD-L1 (expressing GFP) in the presence of different T cells (as indicated at the bottom and Table 3) at different E:T ratio (as indicated on the left).

Figure 15:
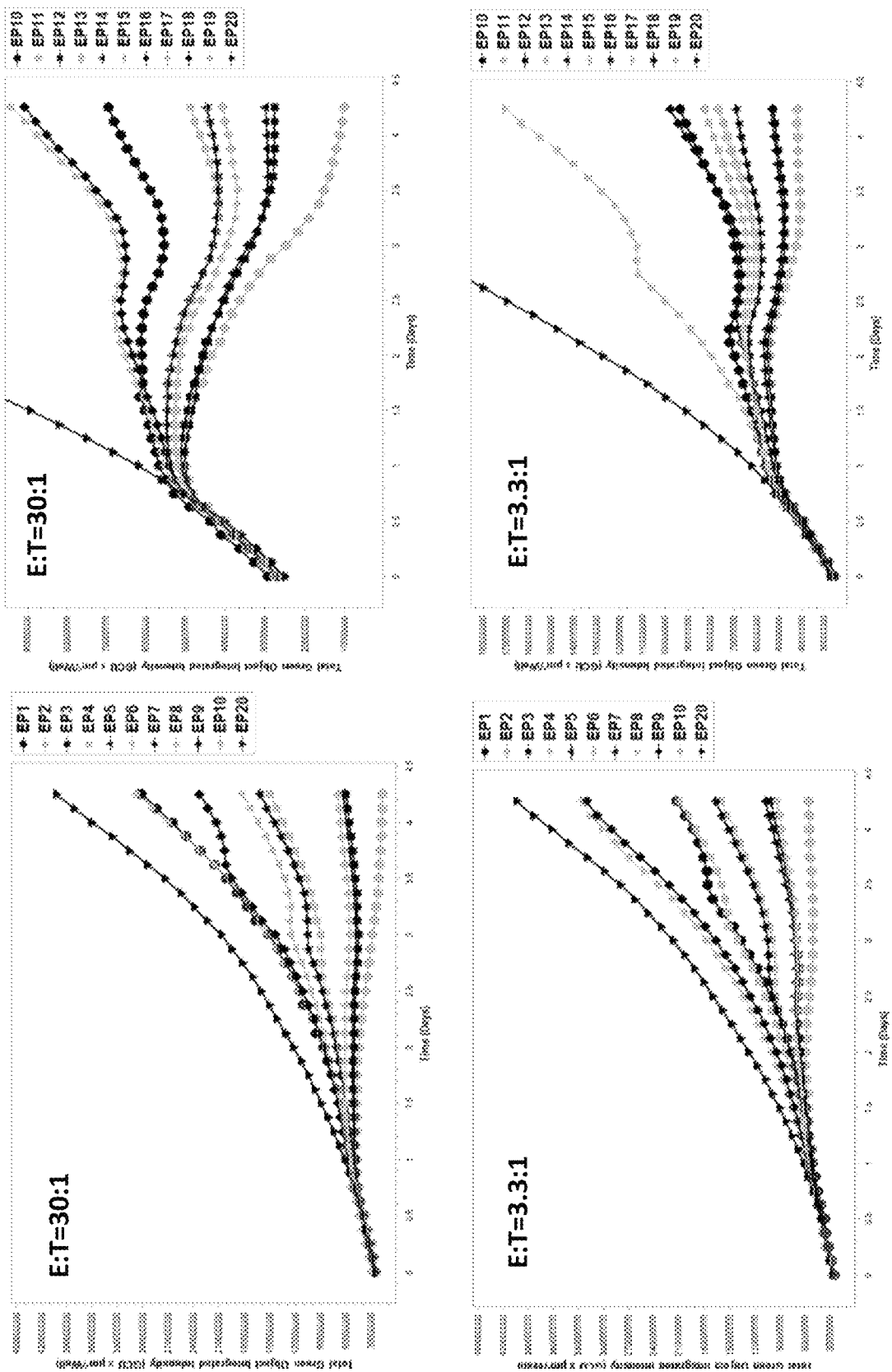

FIG. 15 shows real time growth curves of A549-PD-L1 (expressing GFP) in the presence of T cells as listed in Table 3 at E:T ratio of 30:1 (upper panel) or 3.3:1 (lower panel).

Figure 16:
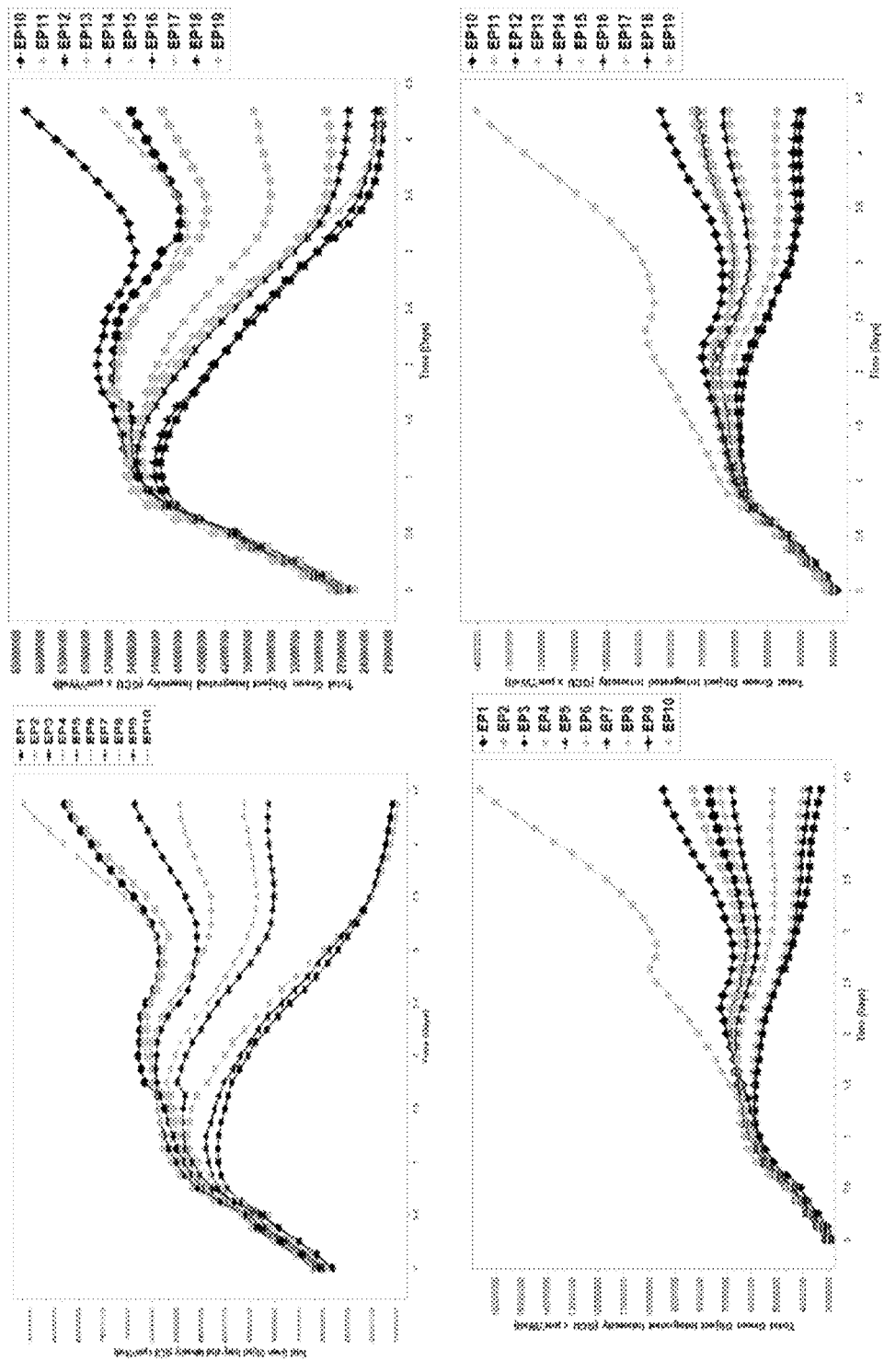

FIG. 16 shows real time growth curves of A549-CD40 (expressing GFP) in the presence of T cells as listed in Table 3 at E:T ratio of 30:1 (upper panel) or 3.3:1 (lower panel).

Figure 17:
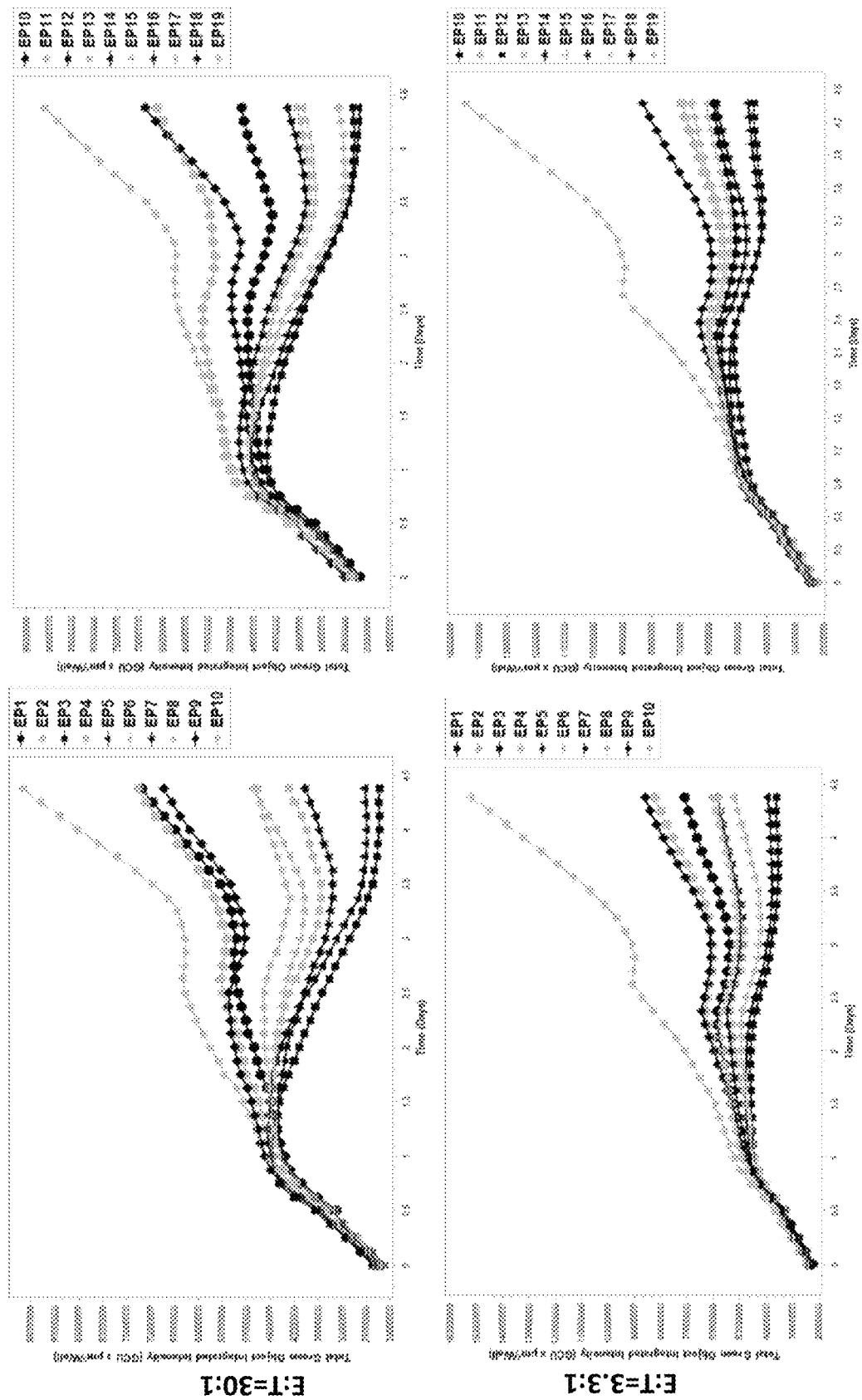

FIG. 17 shows real time growth curves of A549 (expressing GFP) in the presence of T cells as listed in Table 3 at E:T ratio of 30:1 (upper panel) or 3.3:1 (lower panel).

Figure 18:
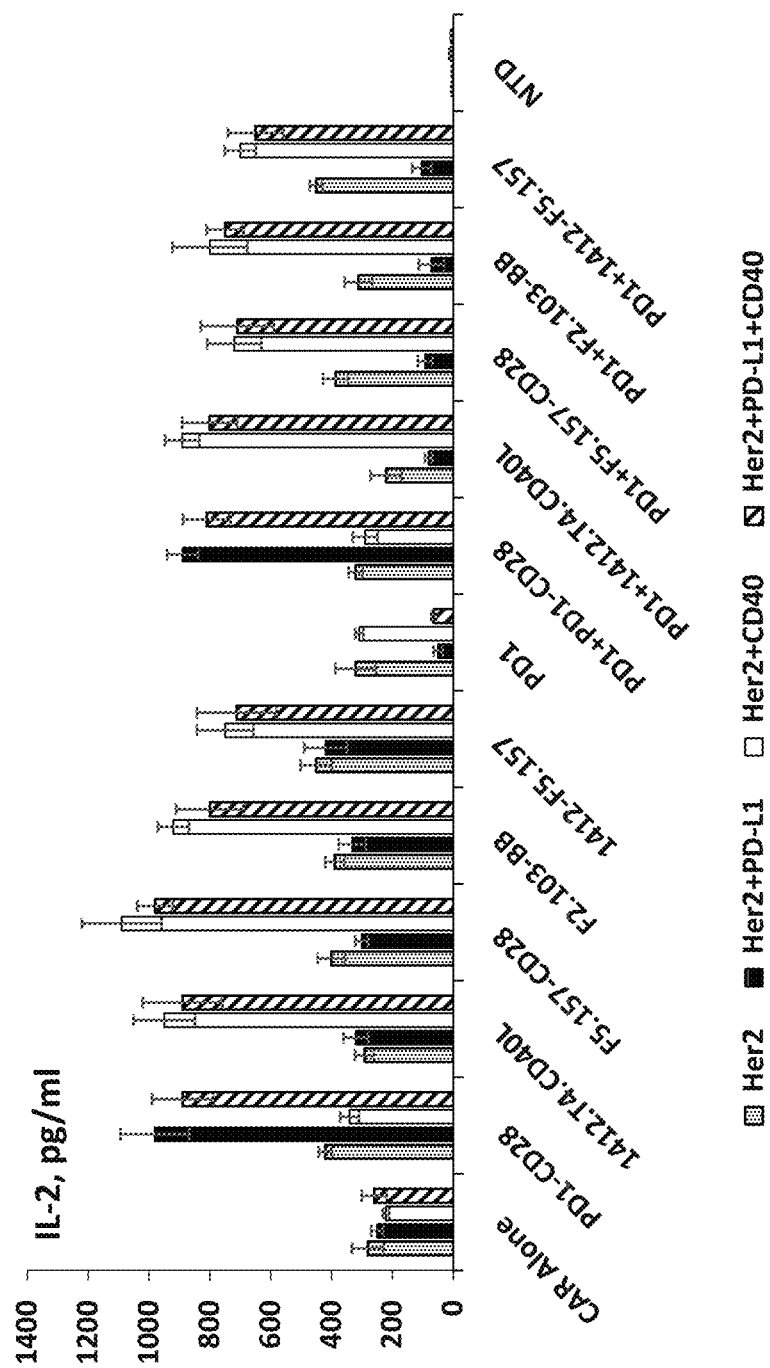

FIG. 18 shows IL-2 secretion of T cells transferred with a Her2 CAR alone, or in combination with a LACO-Stim and/or PD1 as indicated after being added to Her2-Fc, PD-L1-Fc and/or CD40-Fc proteins coated plates and cultured for 24 h.

Figure 19:
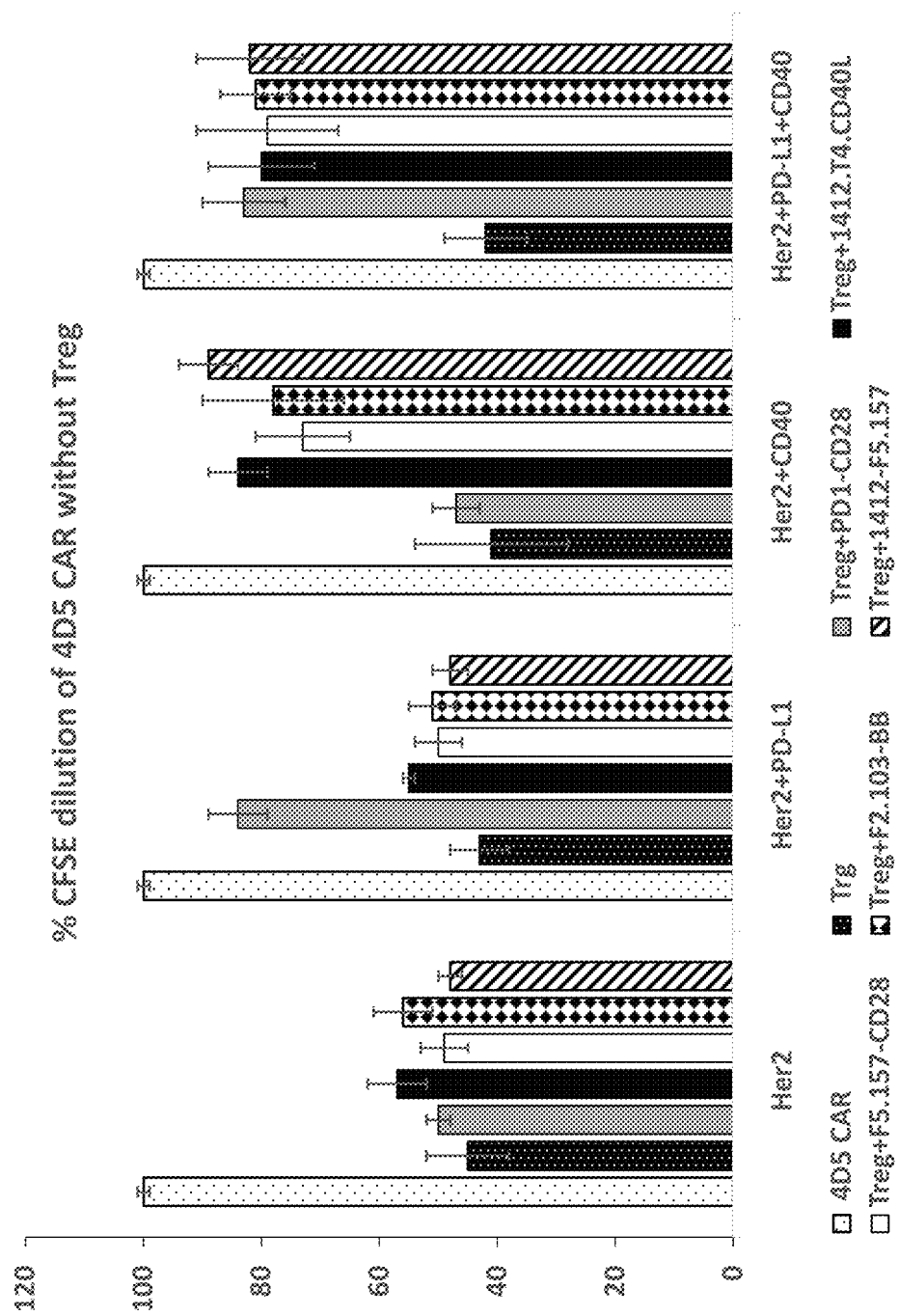

FIG. 19 shows CFSE dilution of CFSE labeled T cells transferred with a Her2 CAR alone or in combination with a LACO-Stim. $CD4^+/CD25^+$ Treg cells were added to the T cells as indicated at Effector:Treg ratio of 4:1. The T cells were added to Her2-Fc, PD-L1-Fc and/or CD40-Fc proteins coated plates and cultured for 3 days. CFSE dilution was detected by flow cytometry.

Figure 20:
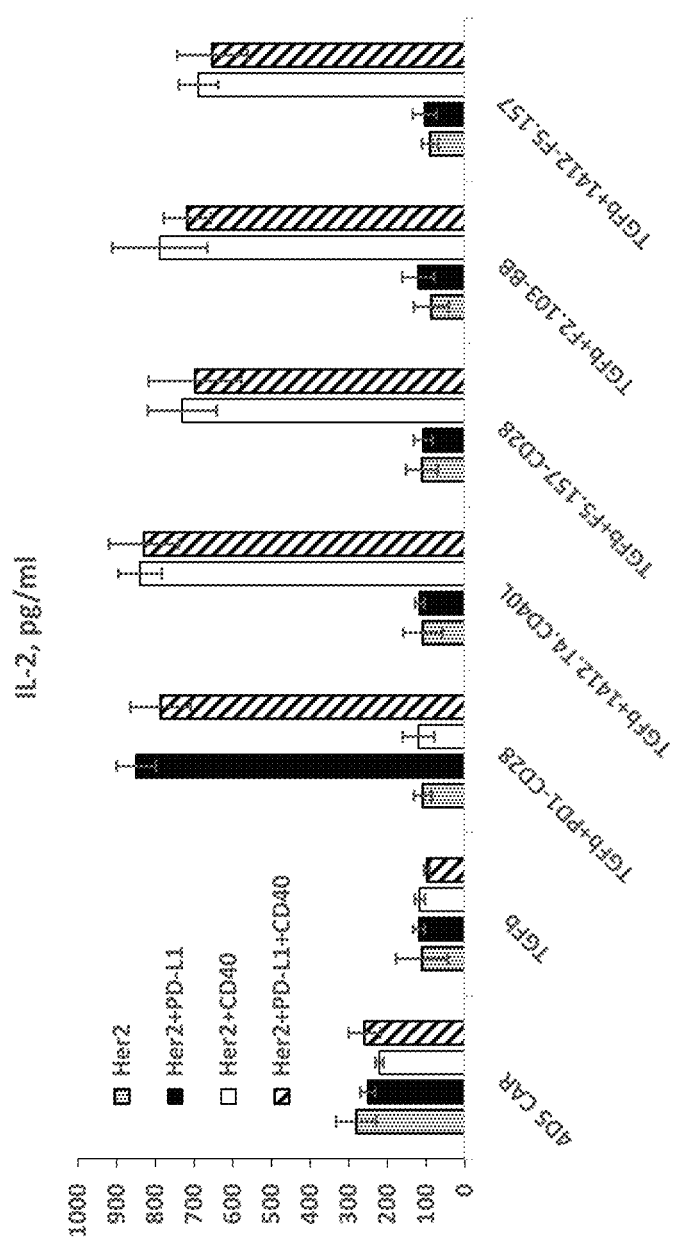

FIG. 20 shows IL-2 secretion of T cells transferred with a Her2 CAR that were co-transferred with a LACO-Stim. TGF-beta was added to the T cells as indicated. The T cells were added to Her2-Fc, PD-L1-Fc and/or CD40-Fc proteins coated plates and cultured for 24 h. IL-2 production was detected by ELISA.

Figure 21A:
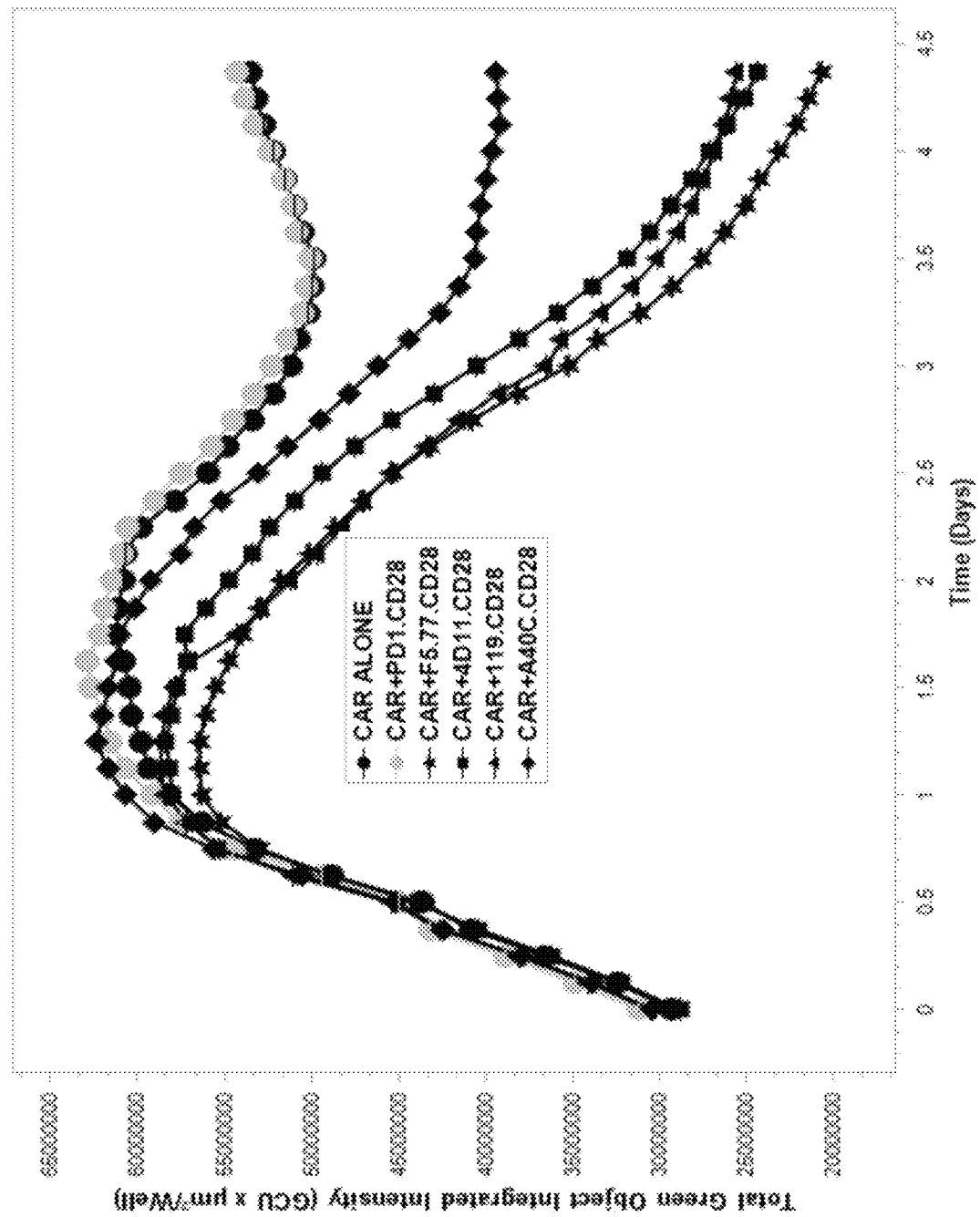
Figure 21B:
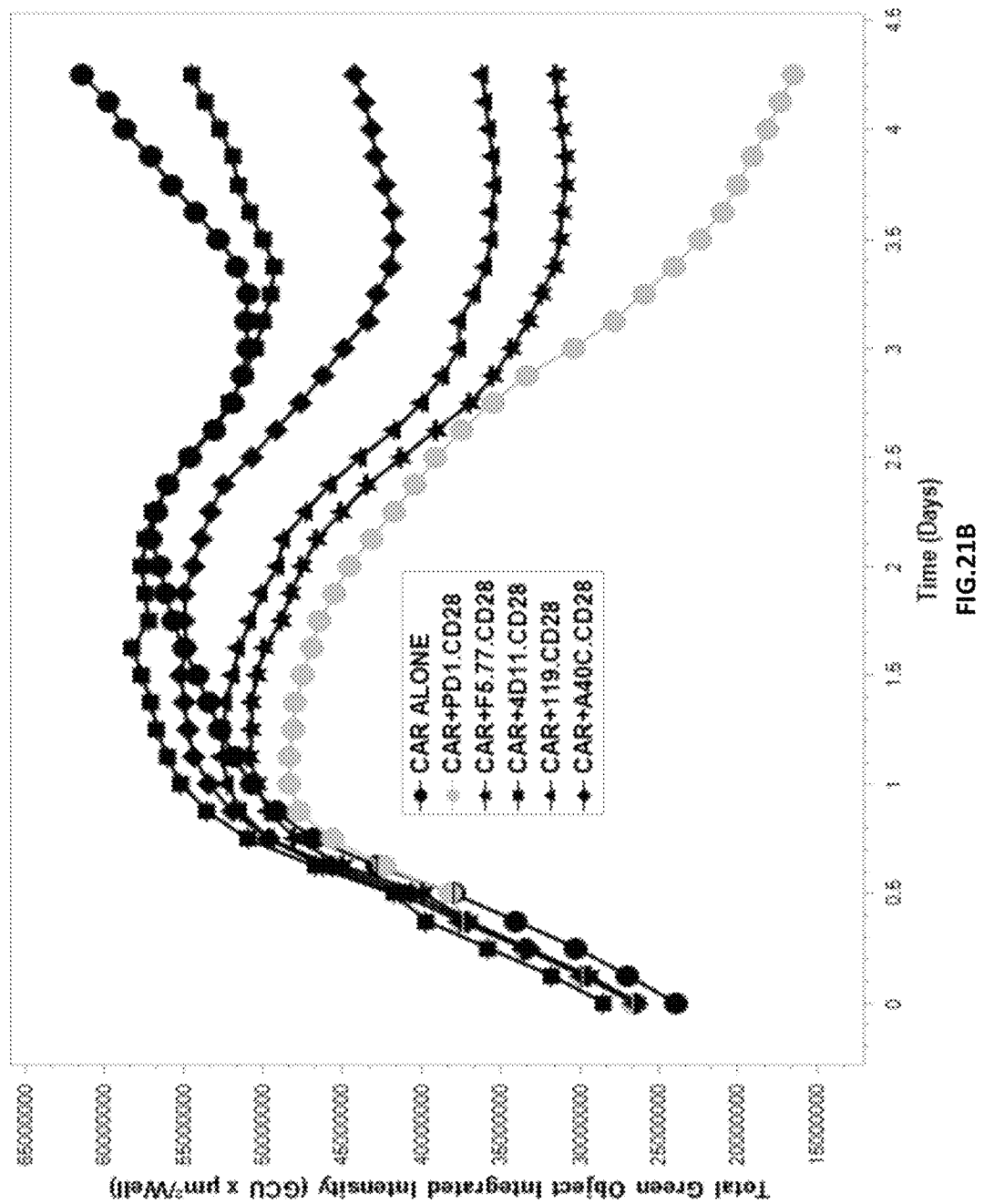

FIGS. 21A-21B. FIG. 21A shows real time growth curves of A549-CD40 (expressing GFP) in the presence of T cells as indicated at E:T ratio of 10:1. FIG. 21B shows real time growth curves of A549-PD-L1 (expressing GFP) in the presence of T cells as indicated at E:T ratio of 10:1.

Figure 22A:
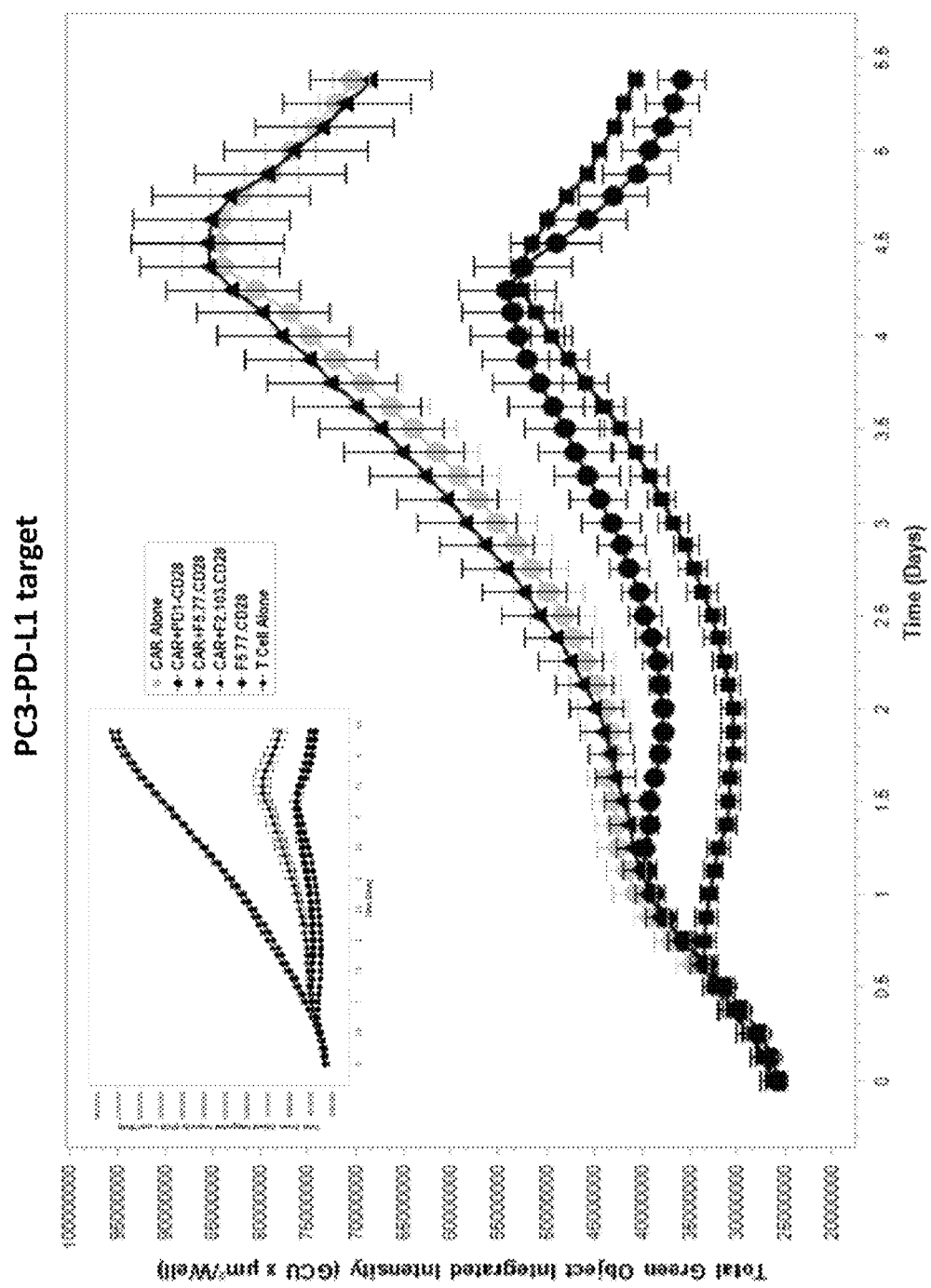
Figure 22B:
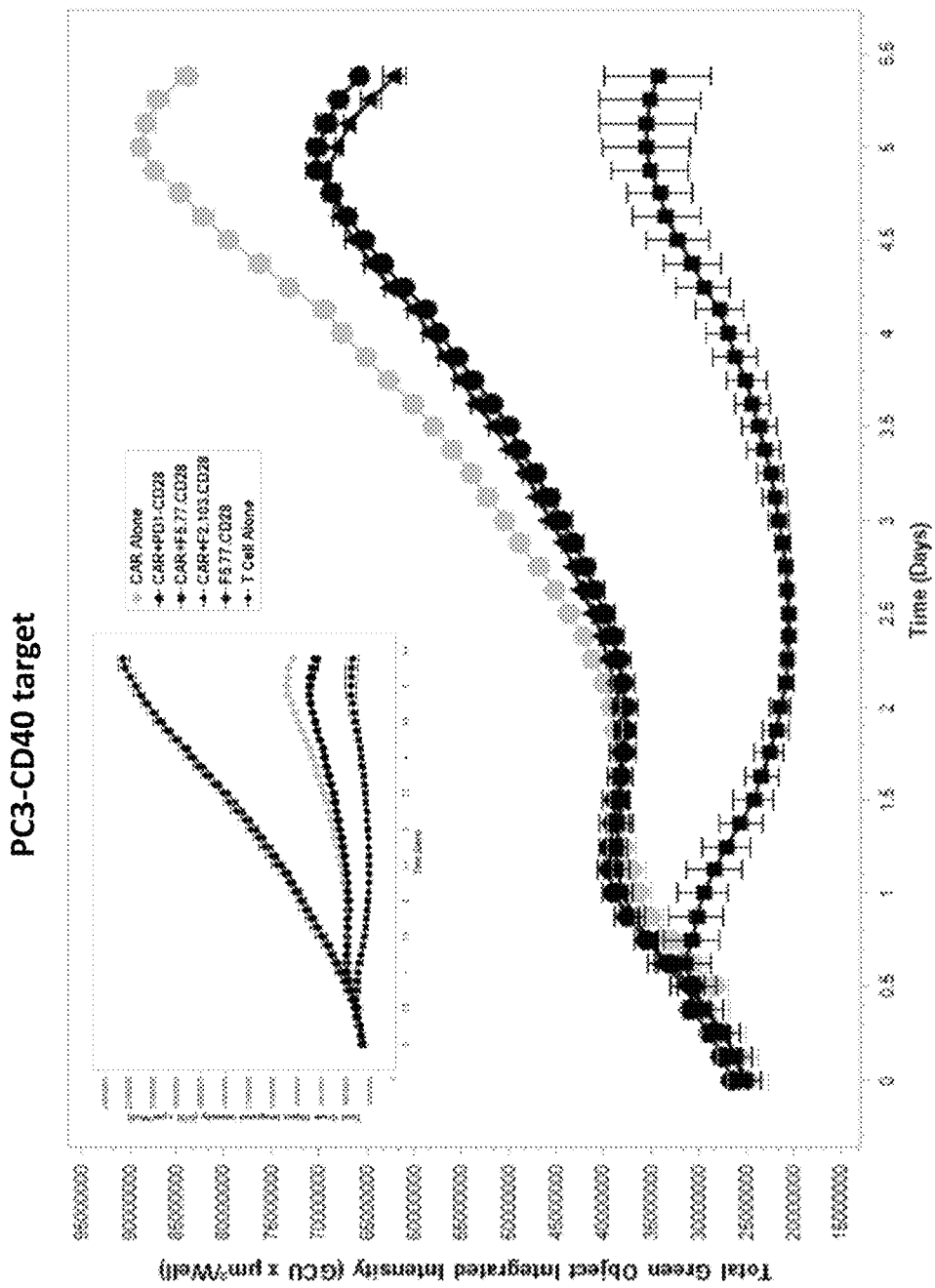
Figure 22C:
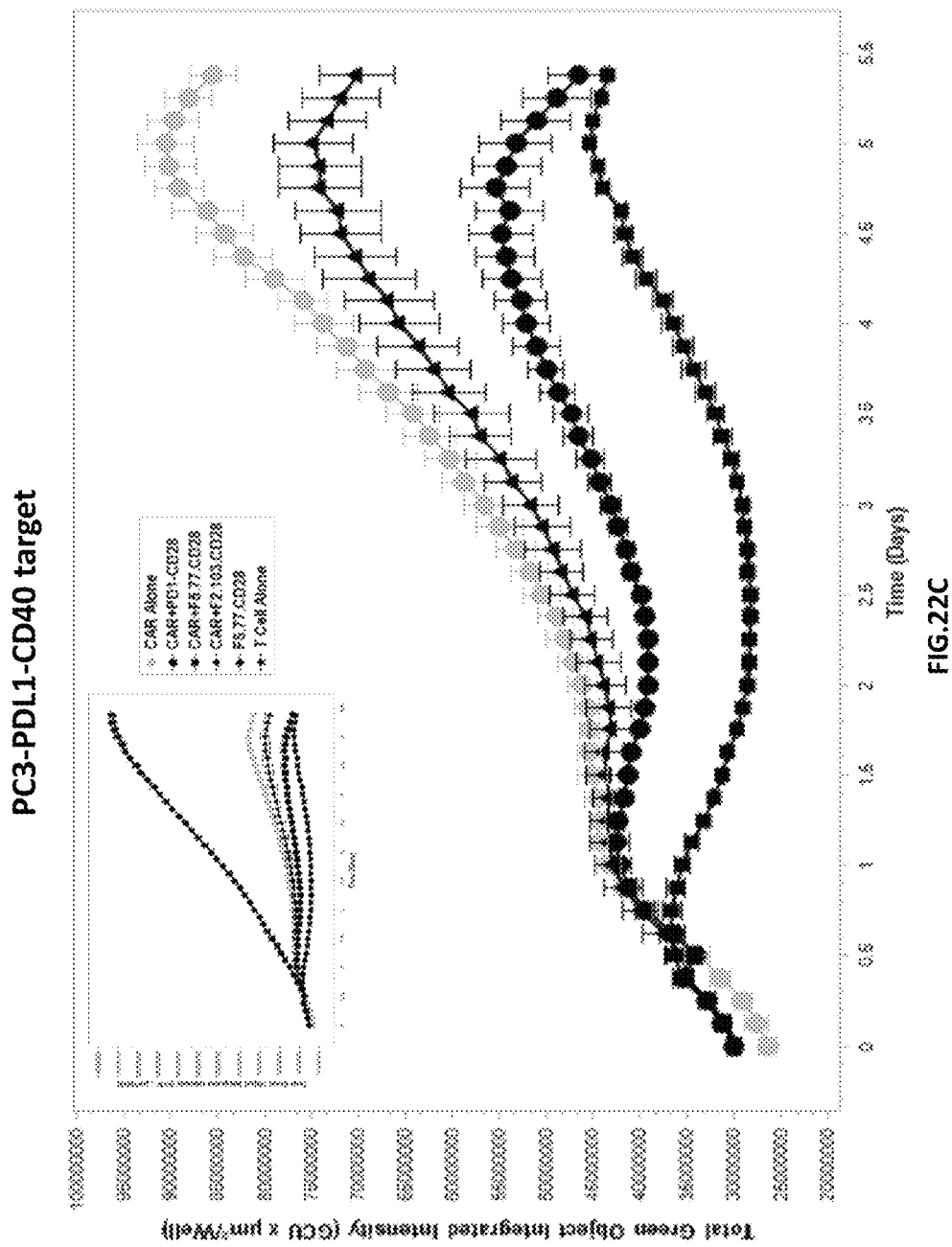
Figure 22D:
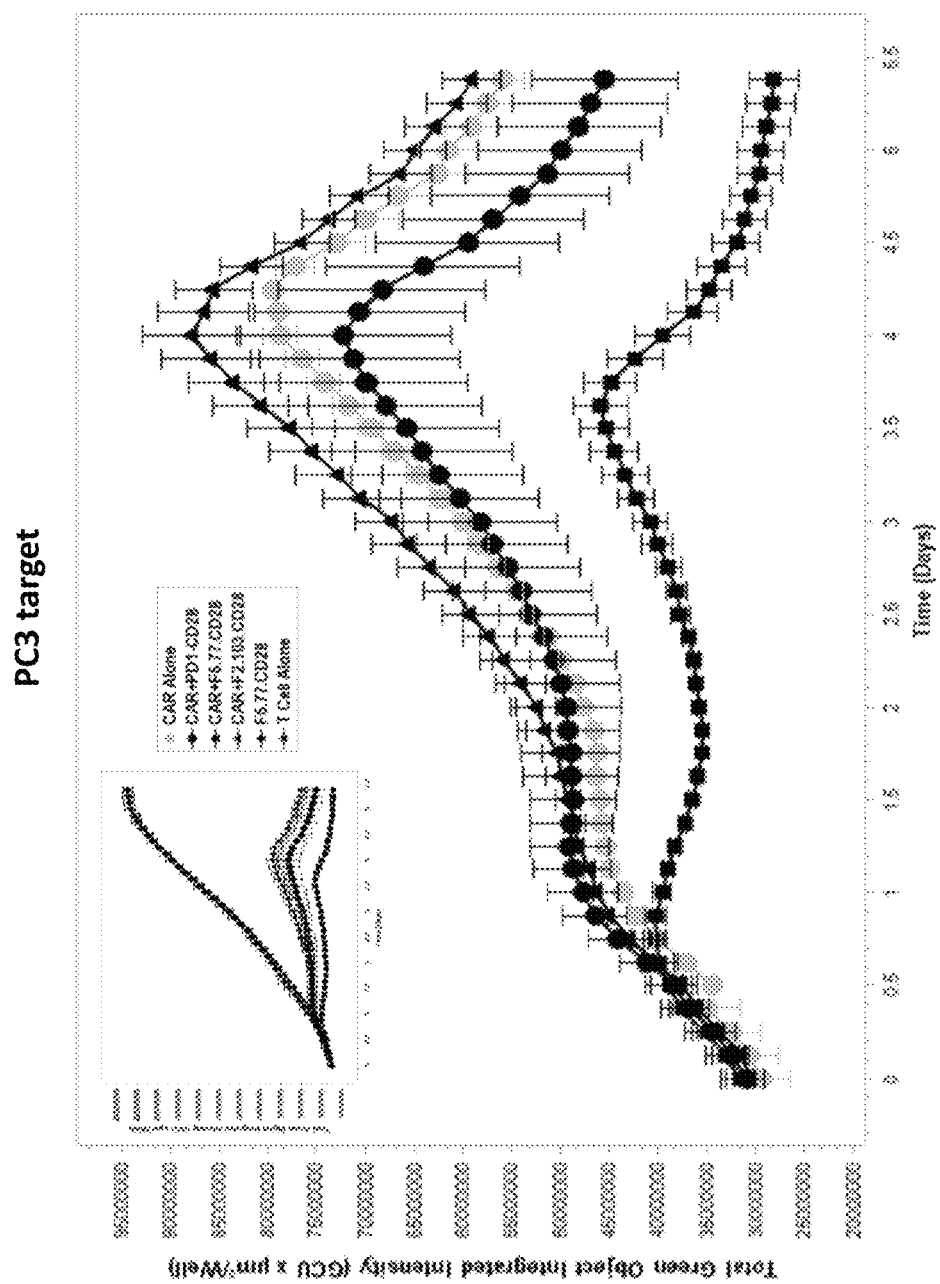

FIGS. 22A-22D FIG. 22A shows real time growth curves of PC3-PD-L1 (expressing GFP) in the presence of T cells as indicated at E:T ratio of 1:1. FIG. 22B shows real time growth curves of PC3-CD40 (expressing GFP) in the presence of T cells as indicated at E:T ratio of 1:1. FIG. 22C shows real time growth curves of PC3-PD-L1-CD40 (expressing GFP) in the presence of T cells as indicated at E:T ratio of 1:1. FIG. 22D shows real time growth curves of PC3 (expressing GFP) in the presence of T cells as indicated at E:T ratio of 1:1. Complete data sets with negative control groups (T Cell Alone and F5.77.CD28 (without a CAR)) are shown in the upper left quadrants.

Figure 23:
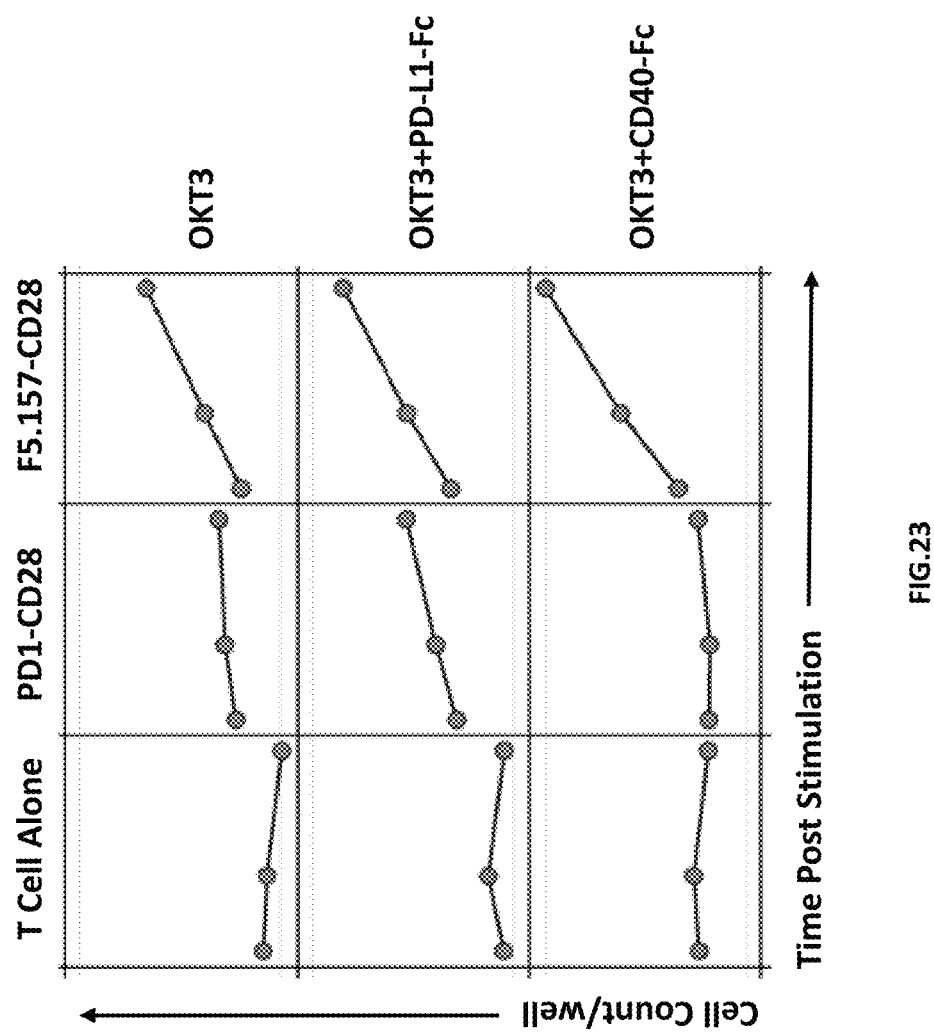

FIG. 23 shows proliferation of different T cells under different stimuli as indicated, at 70 h, 80 h and 100 h post stimulation.

Figure 24:
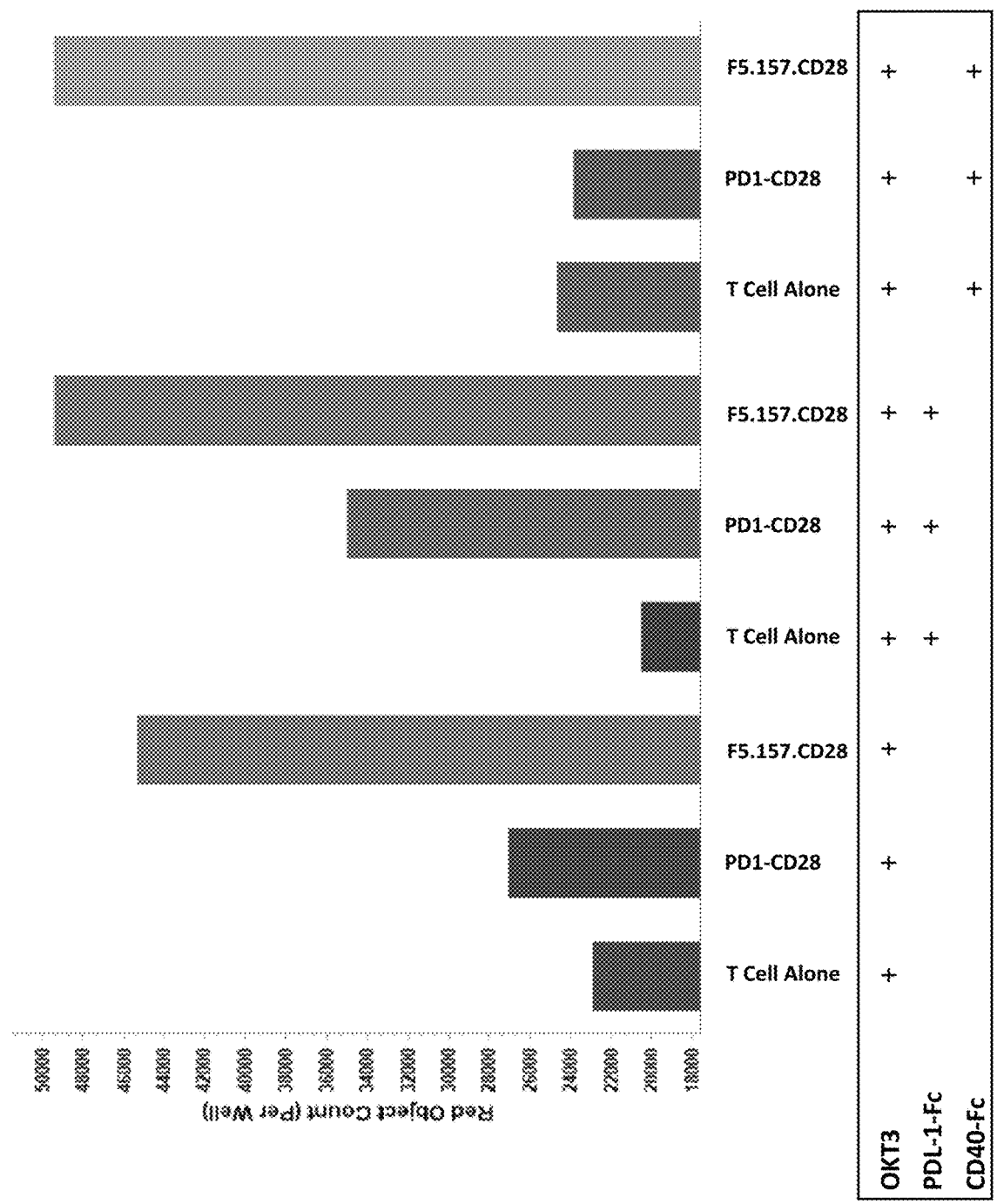

FIG. 24 shows proliferation of different T cells under different stimuli as indicated, 2 days post stimulation.

Figure 25:
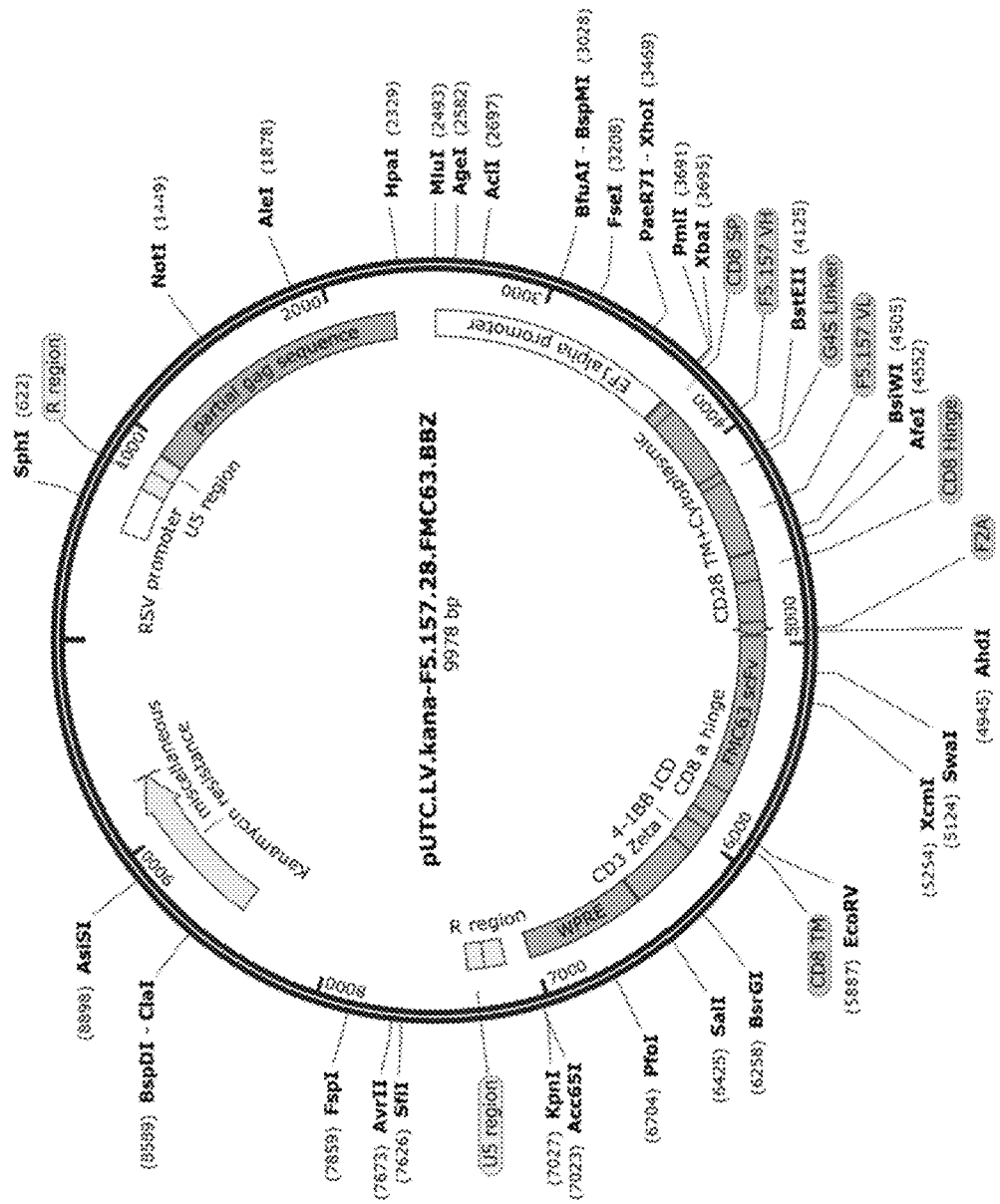

FIG. 25 shows the lentiviral vector map of CD19 CAR and a LACO-Stim (F5.157.CD28).

Figure 26:
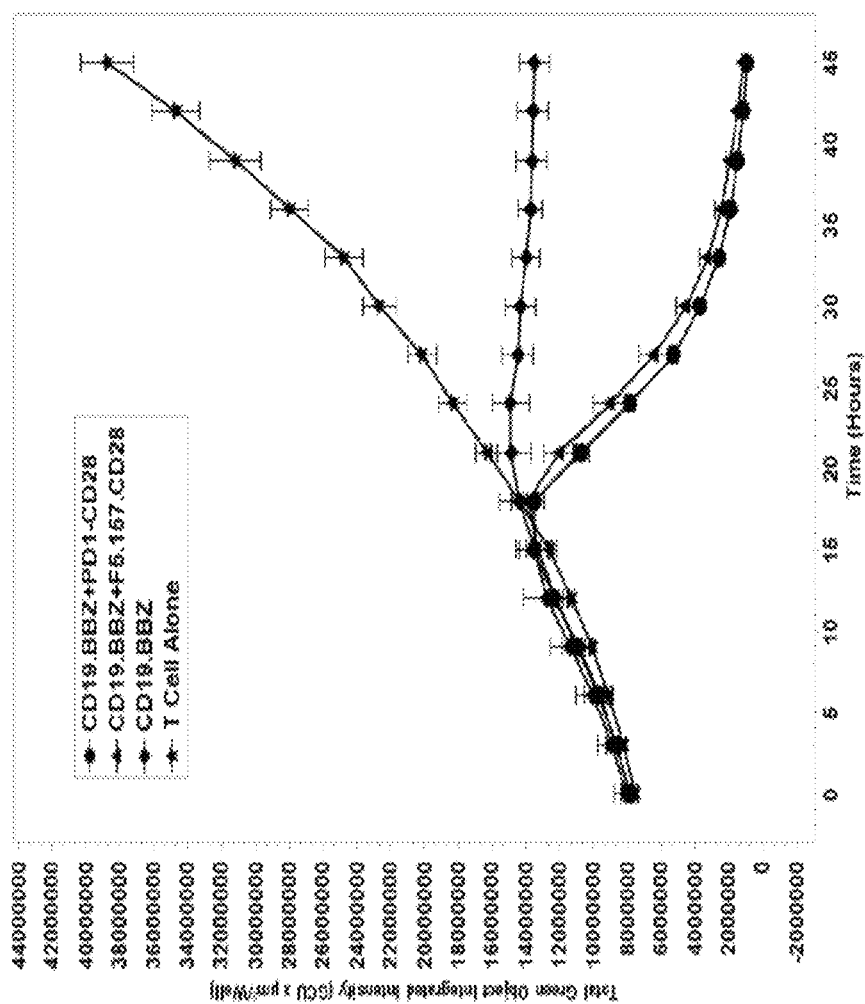

FIG. 26 shows tumor growth suppression by T cells transduced with lentiviral vectors carrying different genes as indicated.

Figure 27:
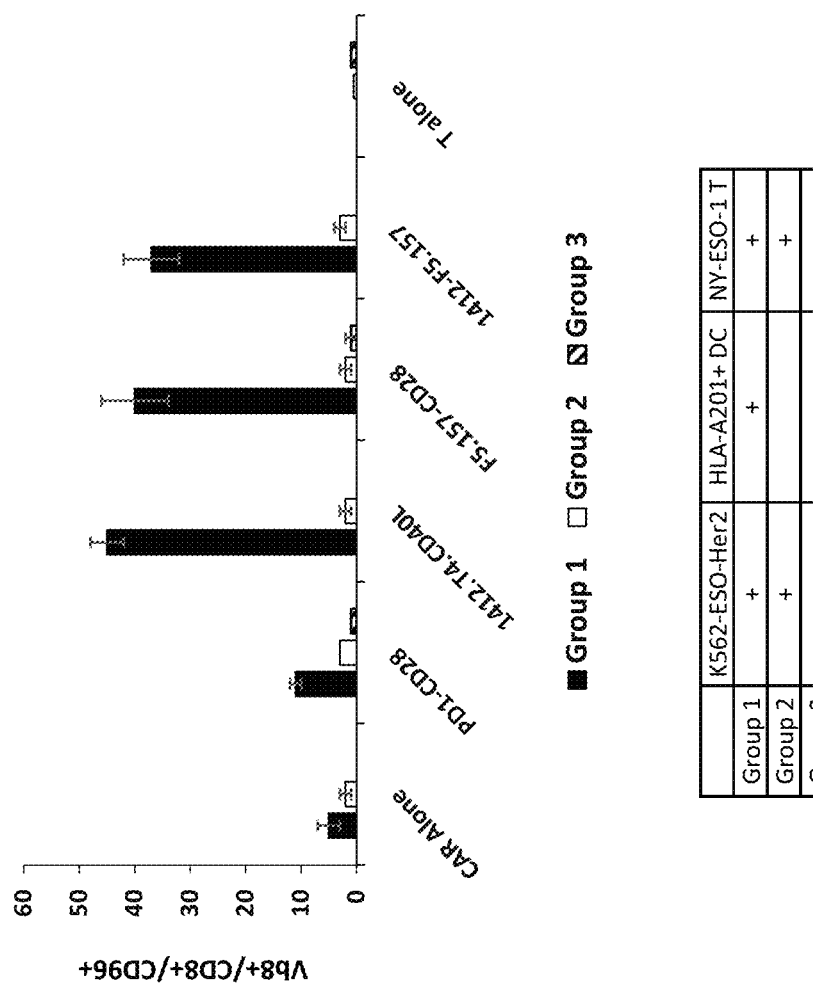

FIG. 27 shows that LACO-Stims promoted dendritic cells epitope spreading through engagement of CD40 on the dendritic cells.

Figure 28:
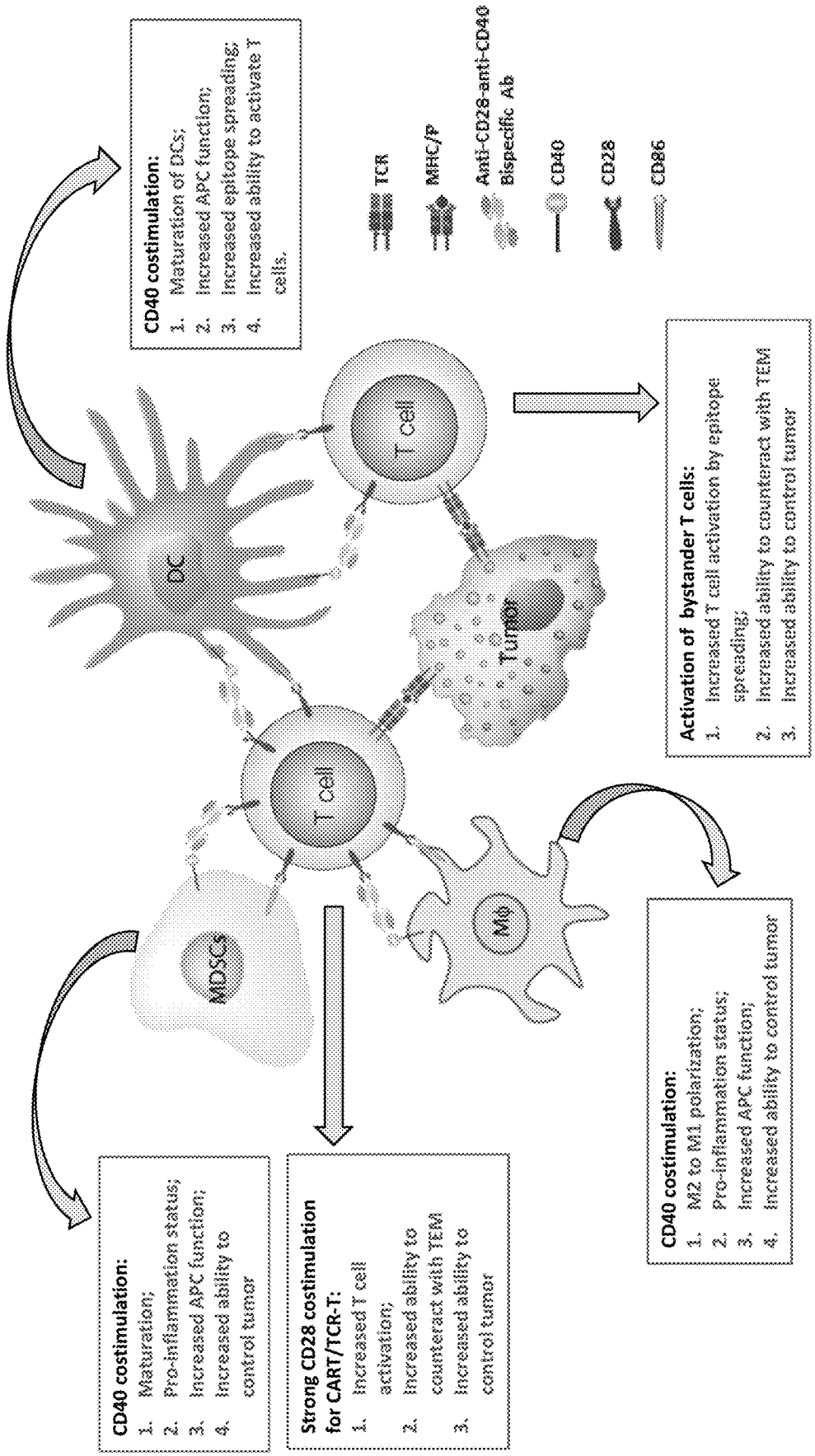

FIG. 28 shows mechanism of LACO-Stims (e.g., CD28-CD40 bispecific antibody) in orchestrating T cells and APC anti-tumor activities.

Figure 29:
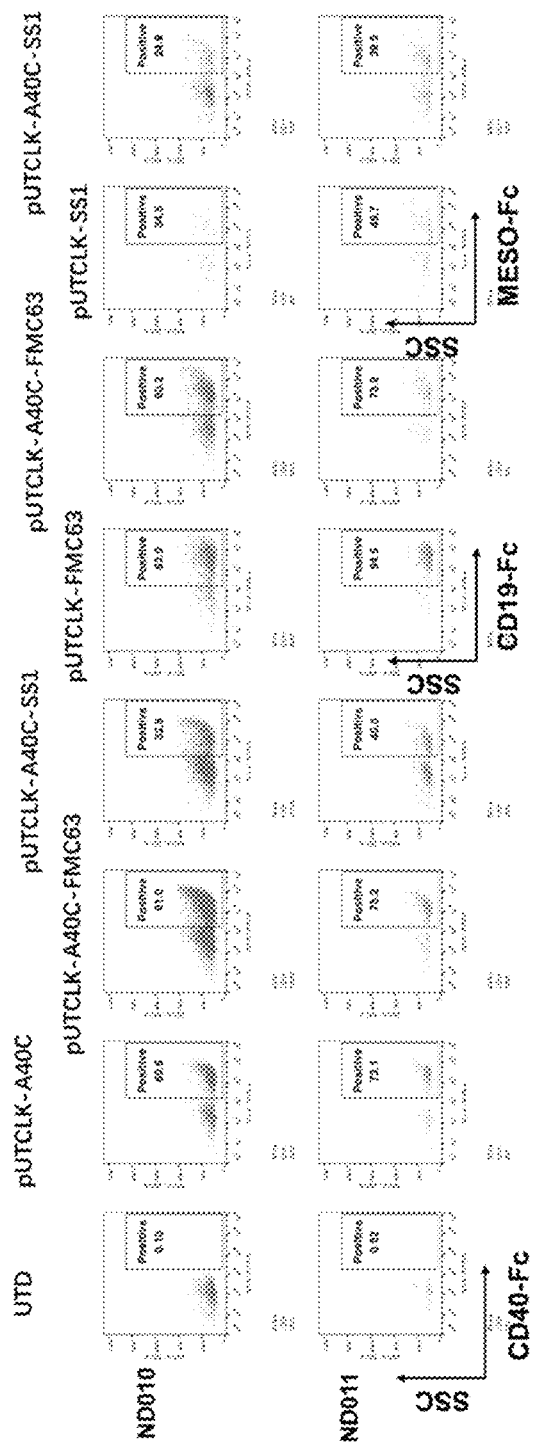

FIG. 29 shows expression of LACO-stim A40C.CD28 (A40C) CD19 CAR (FMC63.BBZ (FMC63)), MSLN CAR (ss1.BBZ (ss1)) of lentiviral vectors transduced T cells.

Figure 30:
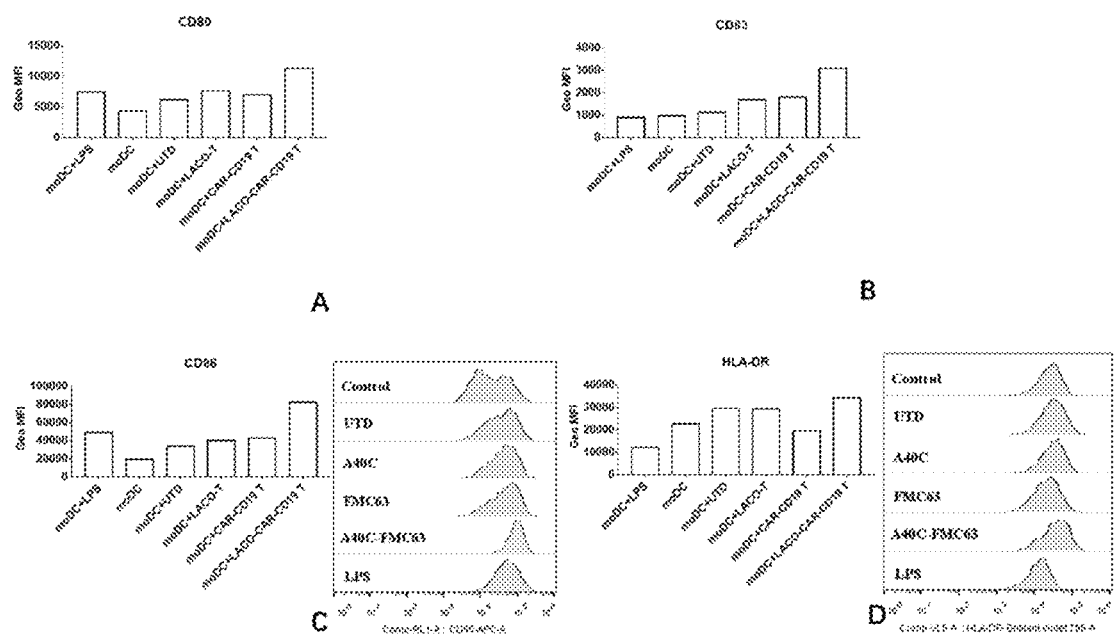

FIG. 30 shows staining results of moDCs co-cultured with LPS (10 ng/mL), or UTD, LACO-stim T, CAR-CD19 T, or LACO-stim-CAR-CD19 using mouse anti-human CD11b, CD80(A), CD83(B), CD86(C), and HLA-DR(D).

Figure 31:
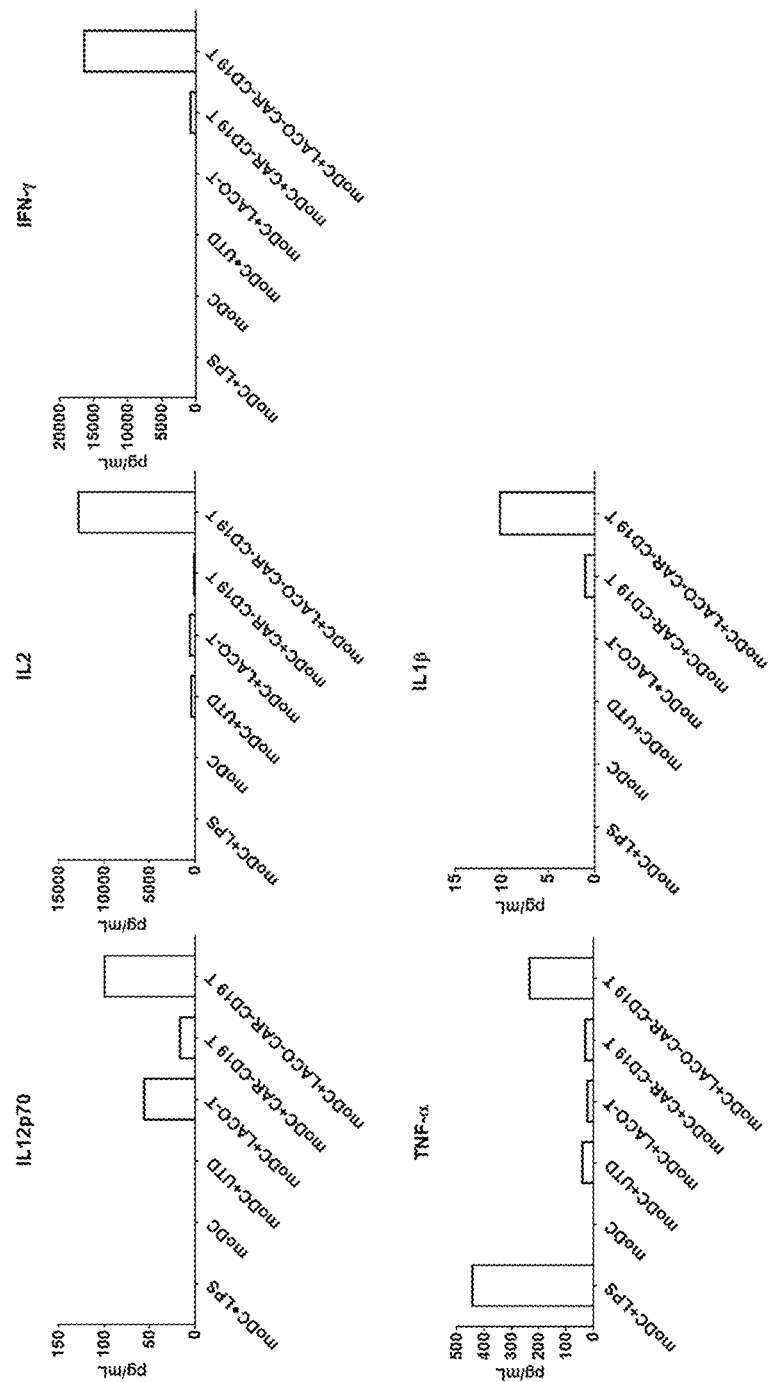

FIG. 31 shows ELISA results measuring cytokine secretion, including IL12p70, IL2, IFNγ, TNF-α, IL1β from autologous moDCs co-cultured with LACO-stim T or LACO-stim-CAR-CD19.

Figure 32:
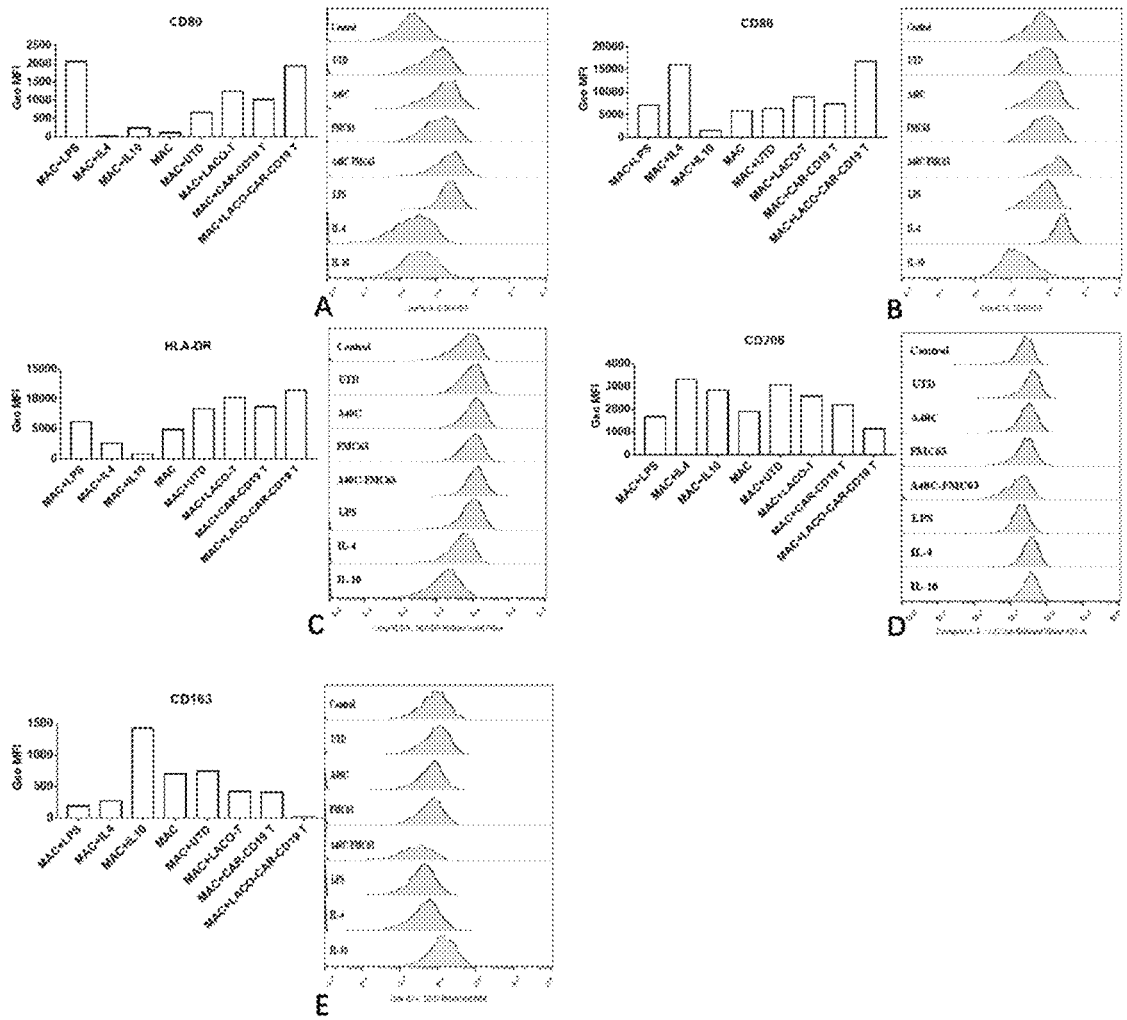

FIG. 32 shows staining results of M0 macrophages co-cultured with LPS (10 ng/mL), IL-4 (20 ng/mL), IL-10 (20 ng/mL), UTD, LACO-stim T, CAR-CD19 T, or LACO-stim-CAR-CD19 T, demonstrating the phonotypic change of M0 macrophages induced by LACO-stim T and LACO-stim-CAR-CD19.

Figure 33:
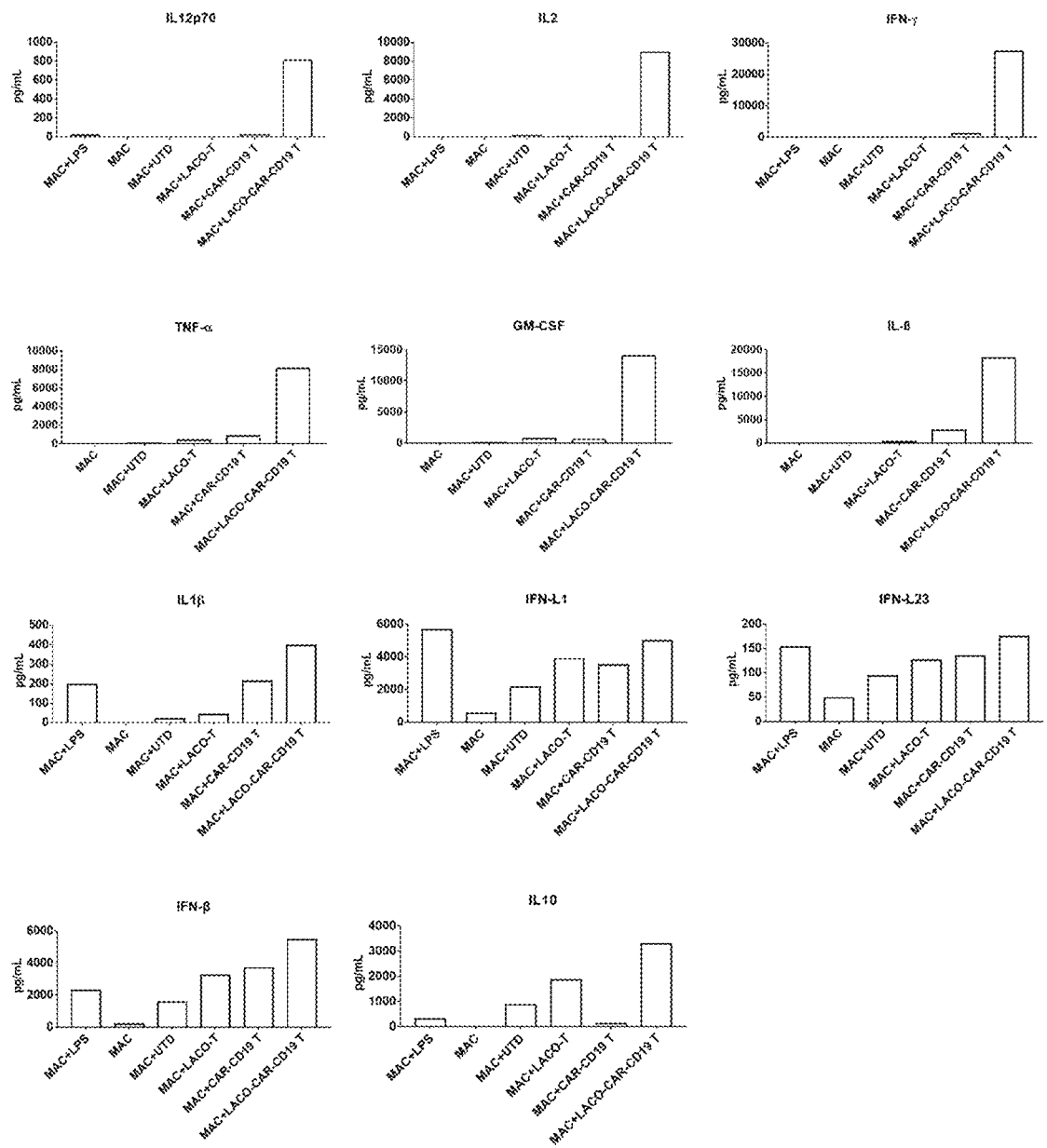

FIG. 33 shows results from ELISA or LEGENDplex multiplex assay (BioLegend) measuring cytokine secretion, including IL1β, IFN-L1, IFN-L23, IFNβ, and IL-10, from autologous macrophages co-cultured with LACO-stim-CAR-CD19.

Figure 34:
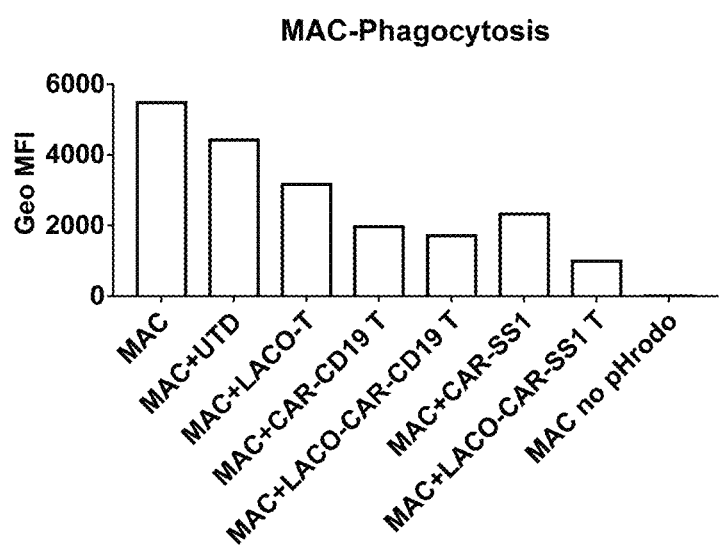

FIG. 34 shows flow cytometry results measuring the phagocytotic function of macrophages co-cultured with UTD, LACO-stim T, CAR-CD19 T, LACO-stim-CAR-CD19 T, or LACO-stim-CAR-MESO.

Figure 35:
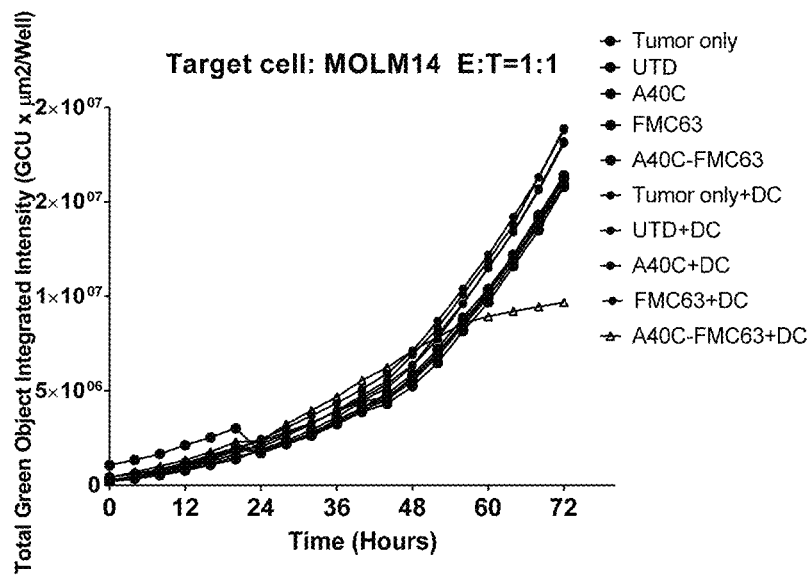

FIG. 35 shows non-CD19 specific tumor killing by autologous moDC co-cultured with UTD, LACO-stim T, CAR-CD19 T, or LACO-stim-CAR-CD19 T.

Figure 36:
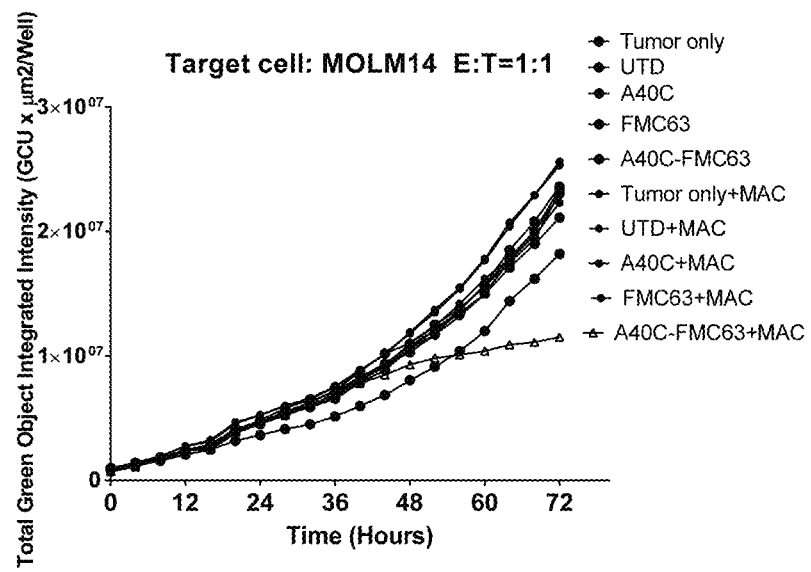

FIG. 36 shows non-CD19 specific tumor killing by autologous macrophages co-cultured with UTD, LACO-stim T, CAR-CD19 T, or LACO-stim-CAR-CD19 T.

Figure 37:
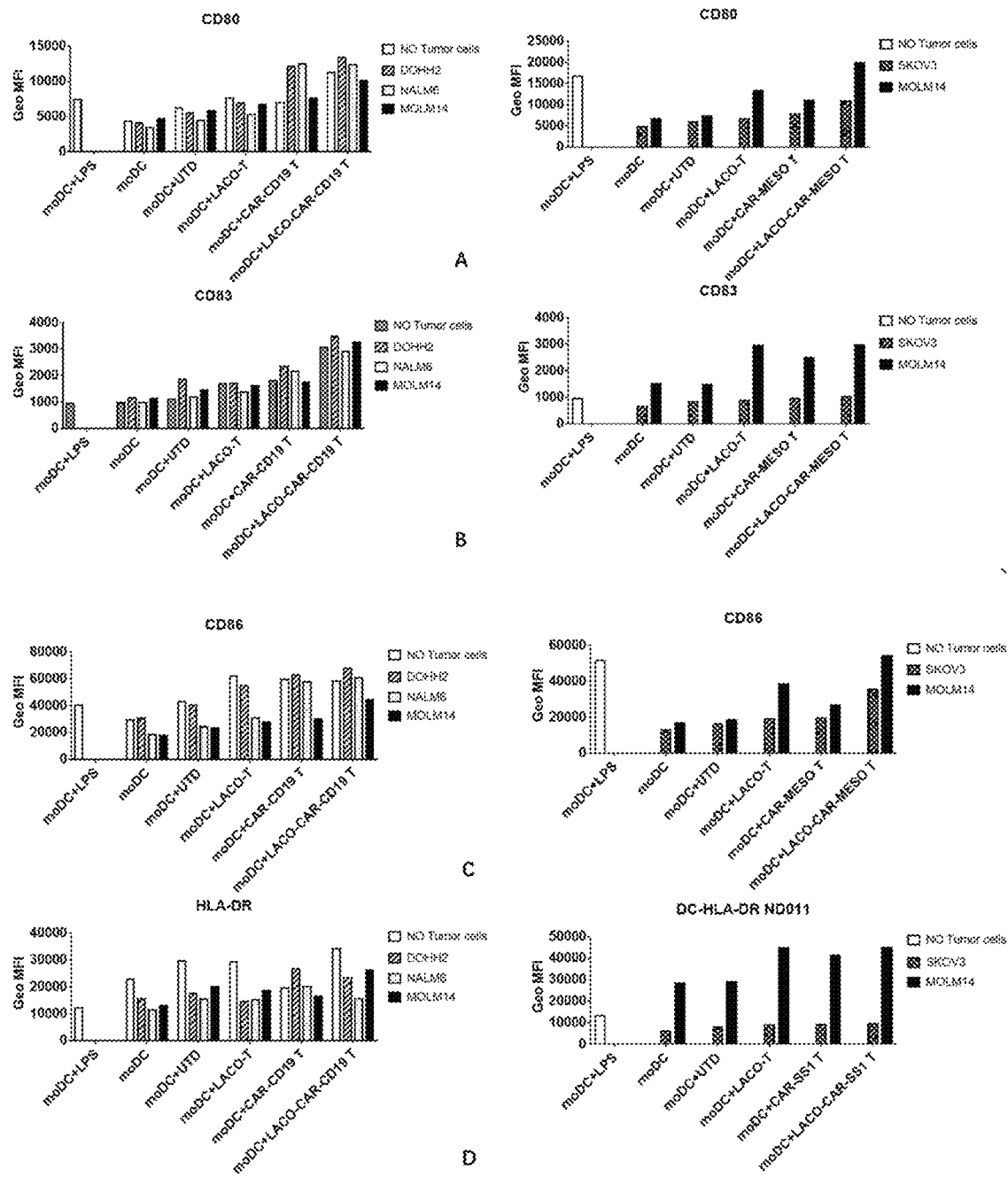

FIG. 37 shows maturation of moDCs co-cultured with tumor cell line 24 h, and supplemented with LPS (10 ng/mL), UTD, LACO-stim T, CAR-CD19 T, LACO-stim-CAR-CD19 T, CAR-MESO, or LACO-stim-CAR-MESO T, measured by staining with mouse anti-human CD11b, CD80, CD83, CD86, and HLA-DR.

Figure 38A:
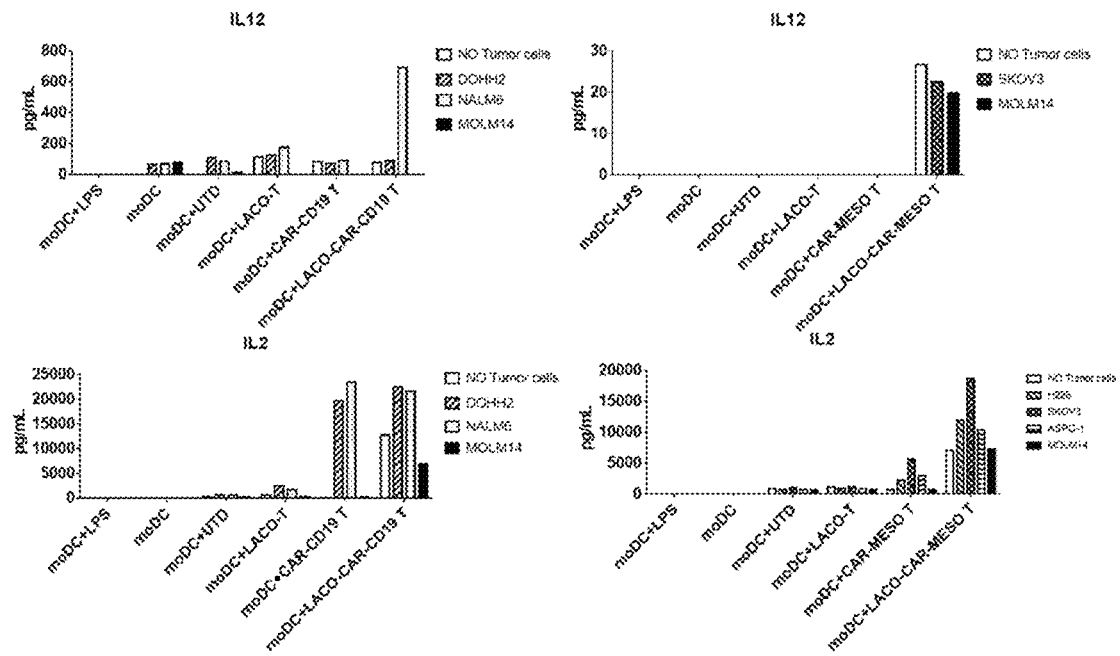
Figure 38B:
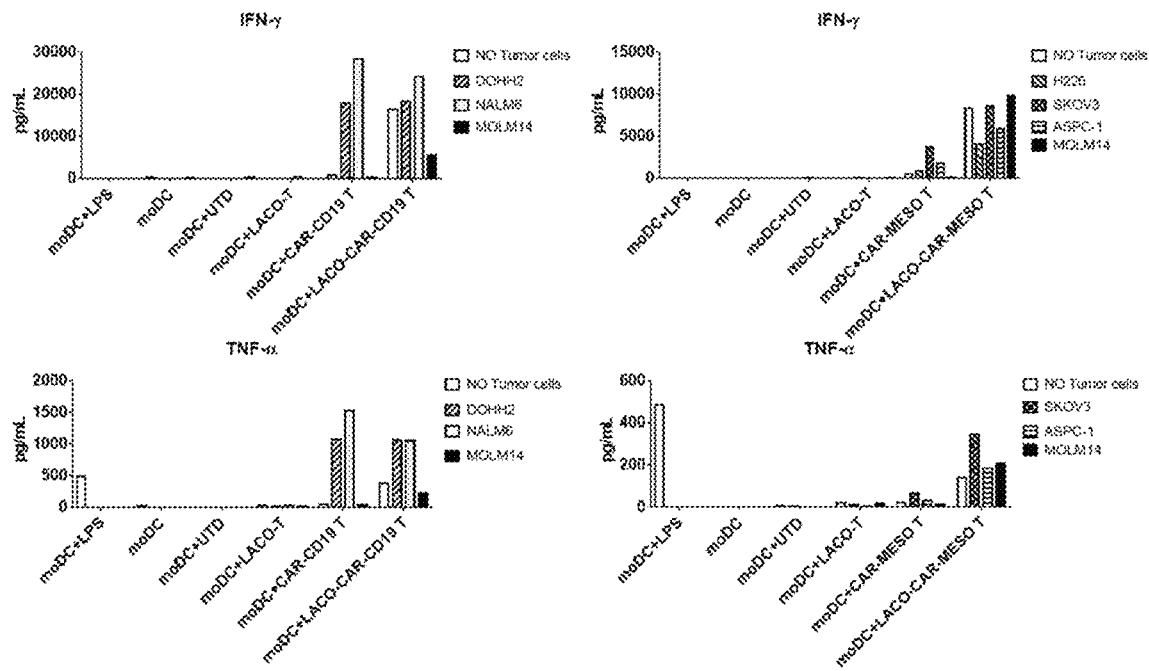
Figure 38C:
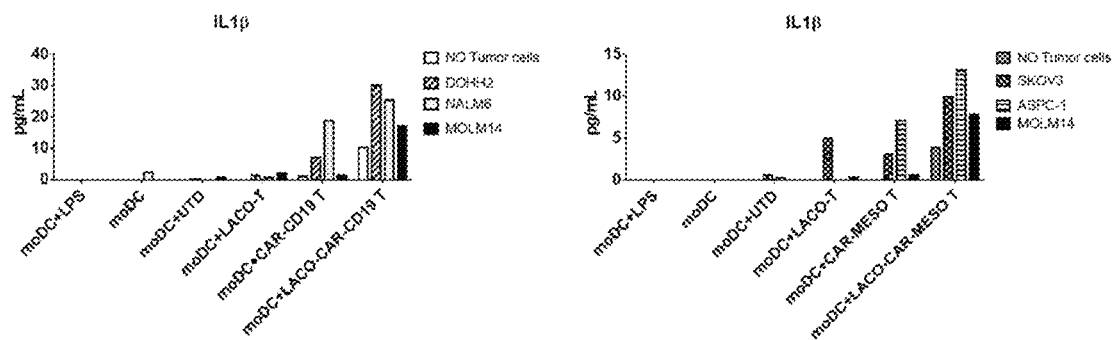

FIGS. 38A-38C show ELISA results measuring cytokine secretion, including IL12 (FIG. 38A), IL2 (FIG. 38A), IFN-γ (FIG. 38B), TNF-α (FIG. 38B), and IL1β (FIG. 38C) from moDCs co-cultured with tumor cell lines and LACO-stim T, LACO-stim-CAR-CD19 and LACO-stim-CAR-MESO.

Figure 39A:
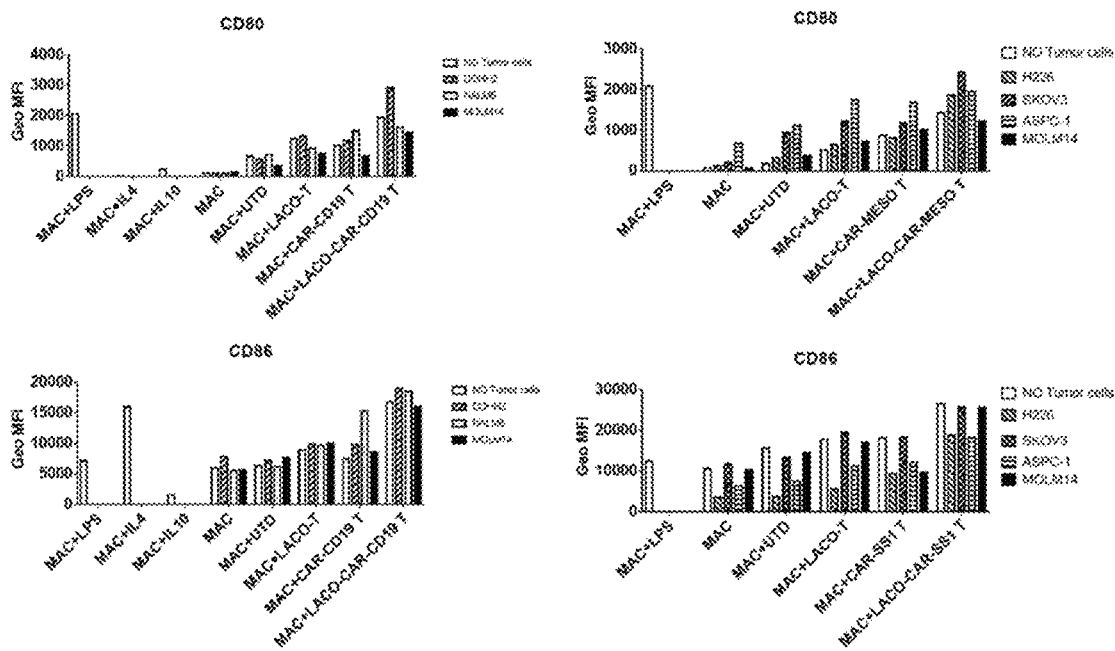
Figure 39B:
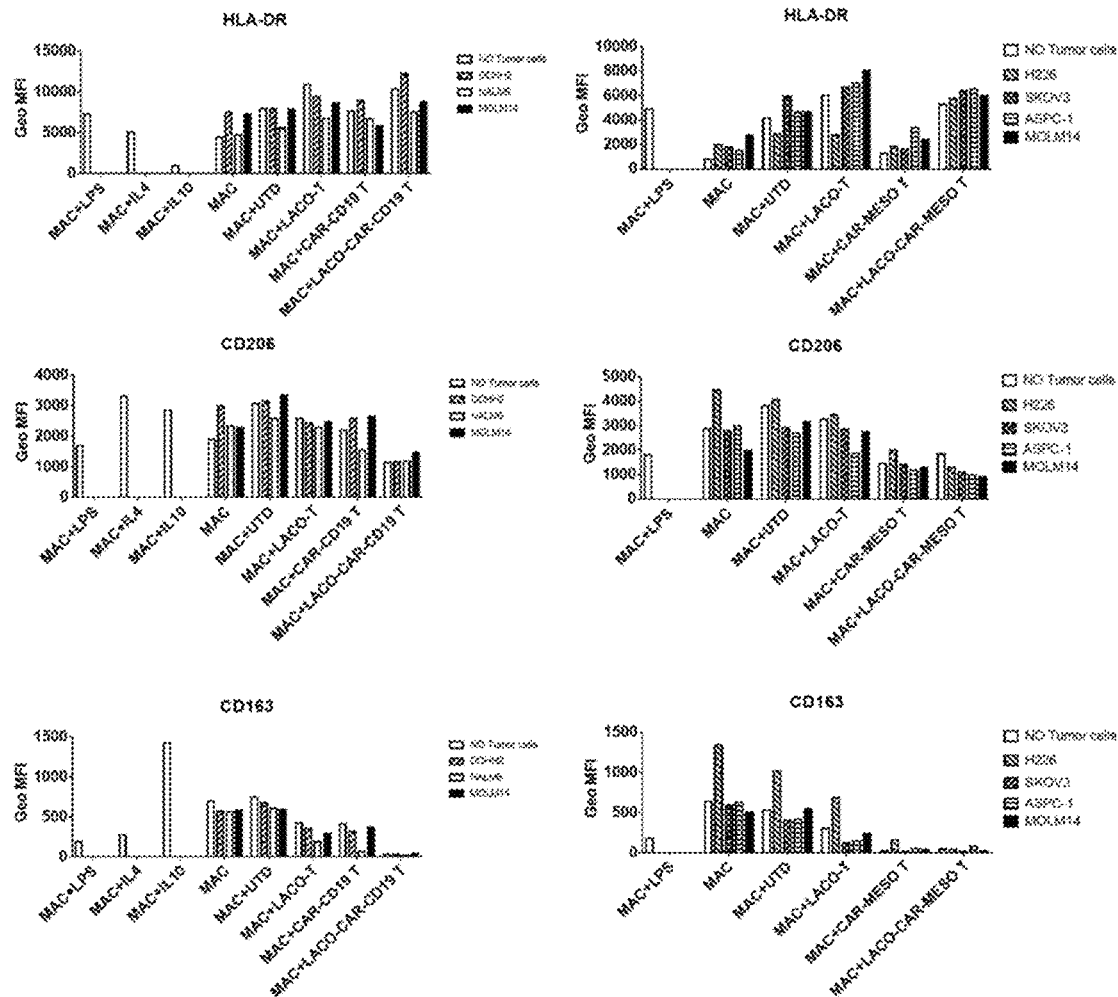

FIGS. 39A-39B show staining results of macrophages co-cultured with tumor cell line, and supplemented with LPS (10 ng/mL), IL-4 (20 ng/mL), IL-10 (20 ng/mL), UTD, LACO-stim T, CAR-CD19 T, LACO-stim-CAR-CD19, CAR-MESO or LACO-stim-CAR-MESO with anti-CD80 (FIG. 39A), anti-CD86 (FIG. 39A), anti-HLA-DR (FIG. 39B), anti-CD206 (FIG. 39B), and anti-CD163 (FIG. 39B).

Figure 40A:
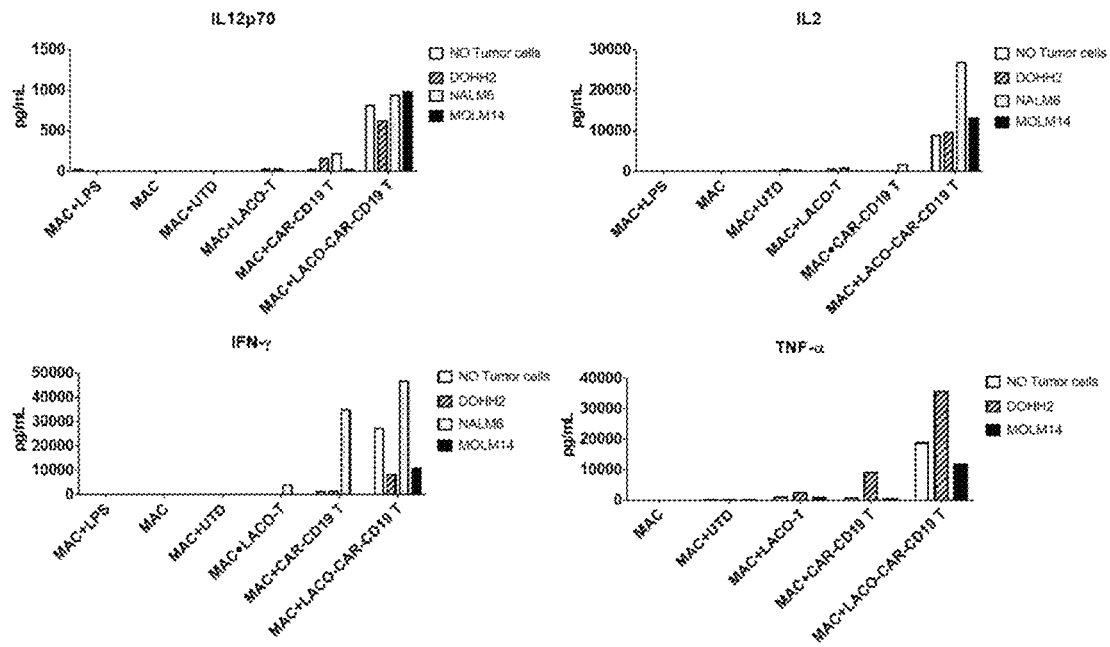
Figure 40B:
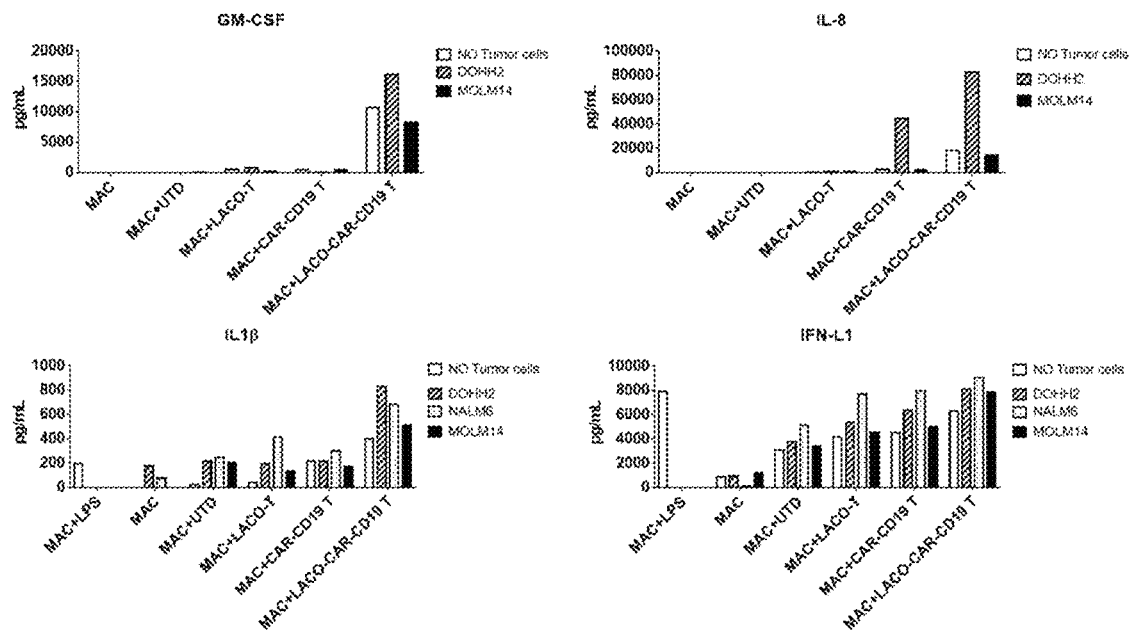
Figure 40C:
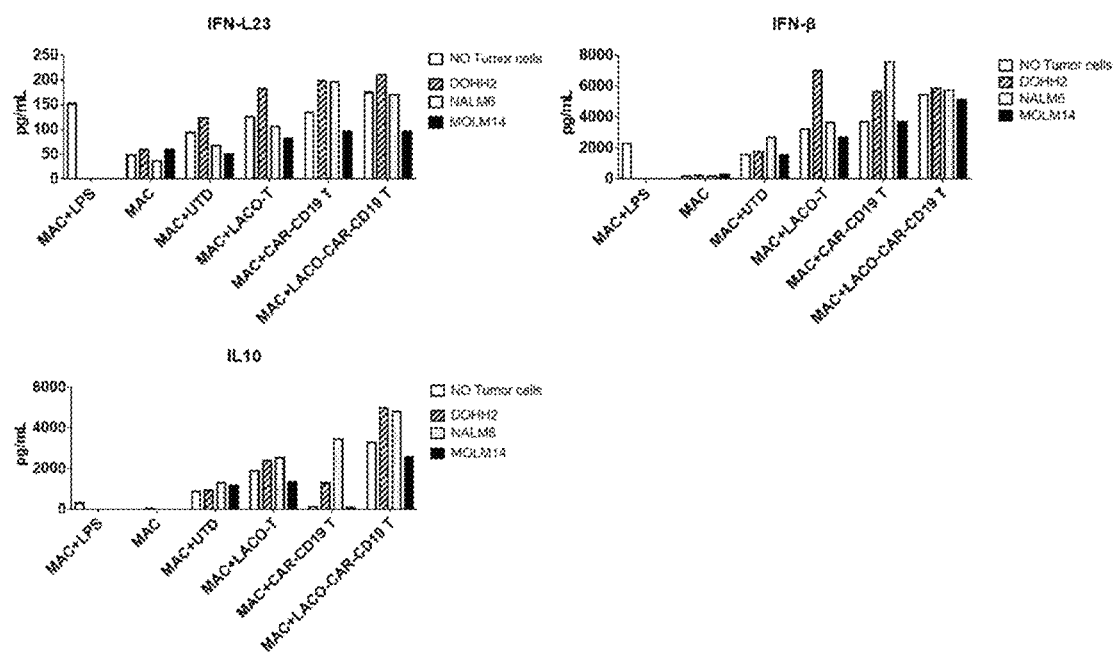

FIGS. 40A-40C shows results from ELISA or LEGENDplex multiplex assay (BioLegend) measuring cytokine secretion, including IL12p70 (FIG. 40A), IL2 (FIG. 40A), IFNγ (FIG. 40A), TNF-α (FIG. 40A), GM-CSF (FIG. 40B), IL8 (FIG. 40B), IL1β (FIG. 40B), IFN-L1 (FIG. 40B), IFN-L23 (FIG. 40C), IFNβ (FIG. 40C), and IL-10 (FIG. 40C), from autologous MAC co-cultured with tumor cell lines, and supplemented with LPS (10 ng/mL), UTD, LACO-stim T, CAR-CD19 T, or LACO-stim-CAR-CD19 T.

Figure 41:
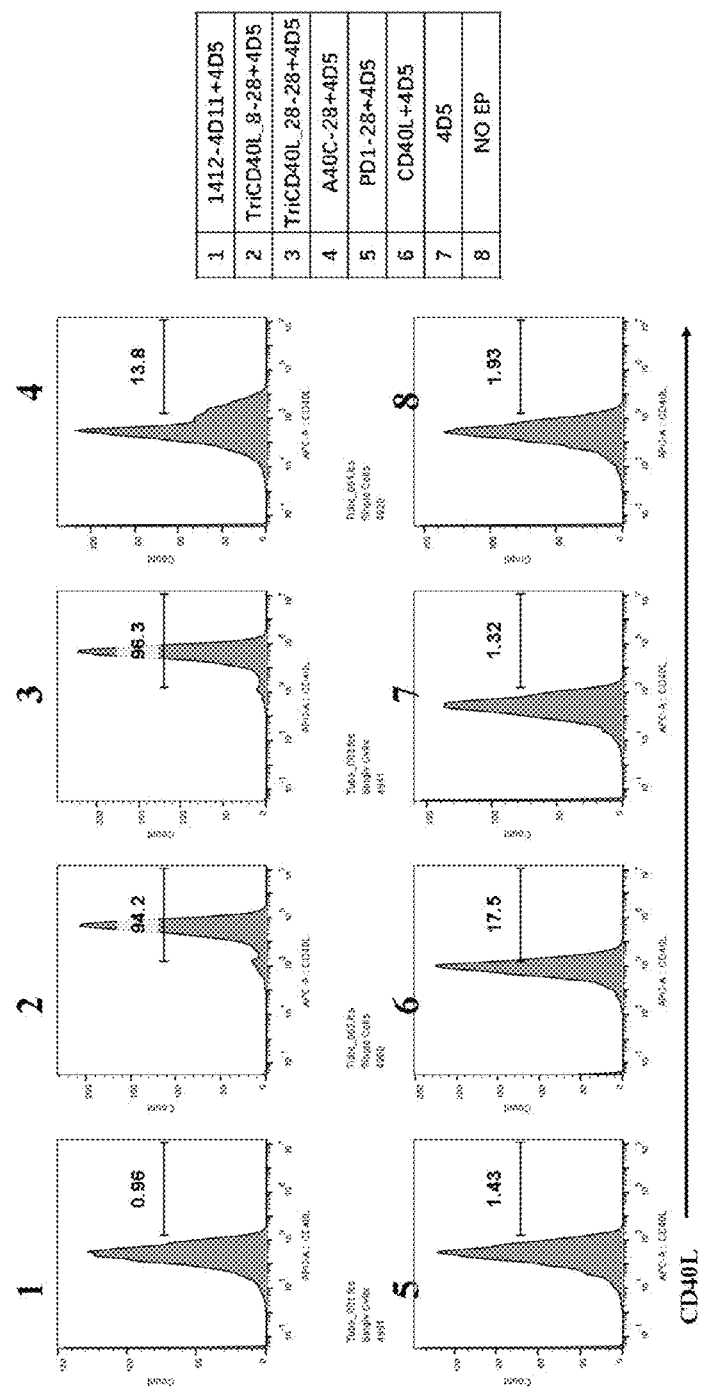

FIG. 41 provides flow cytometry data showing the CD40L expression of T cells co-electroporated with various CARs or LACO-stim-CARs.

Figure 42:
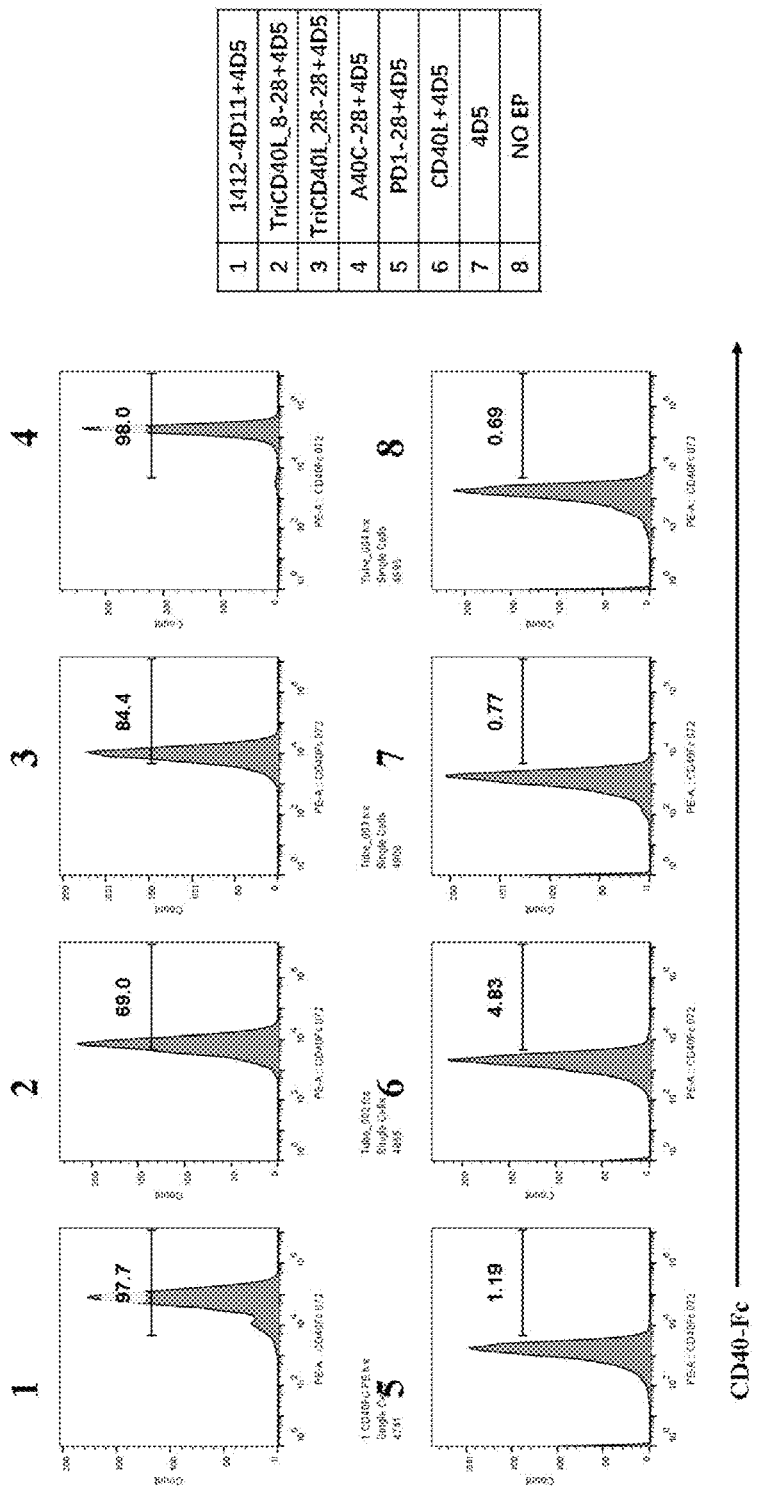

FIG. 42 provides flow cytometry data showing the detection of CD40-Fc of T cells co-electroporated with various CARs or LACO-stim-CARs.

Figure 43:
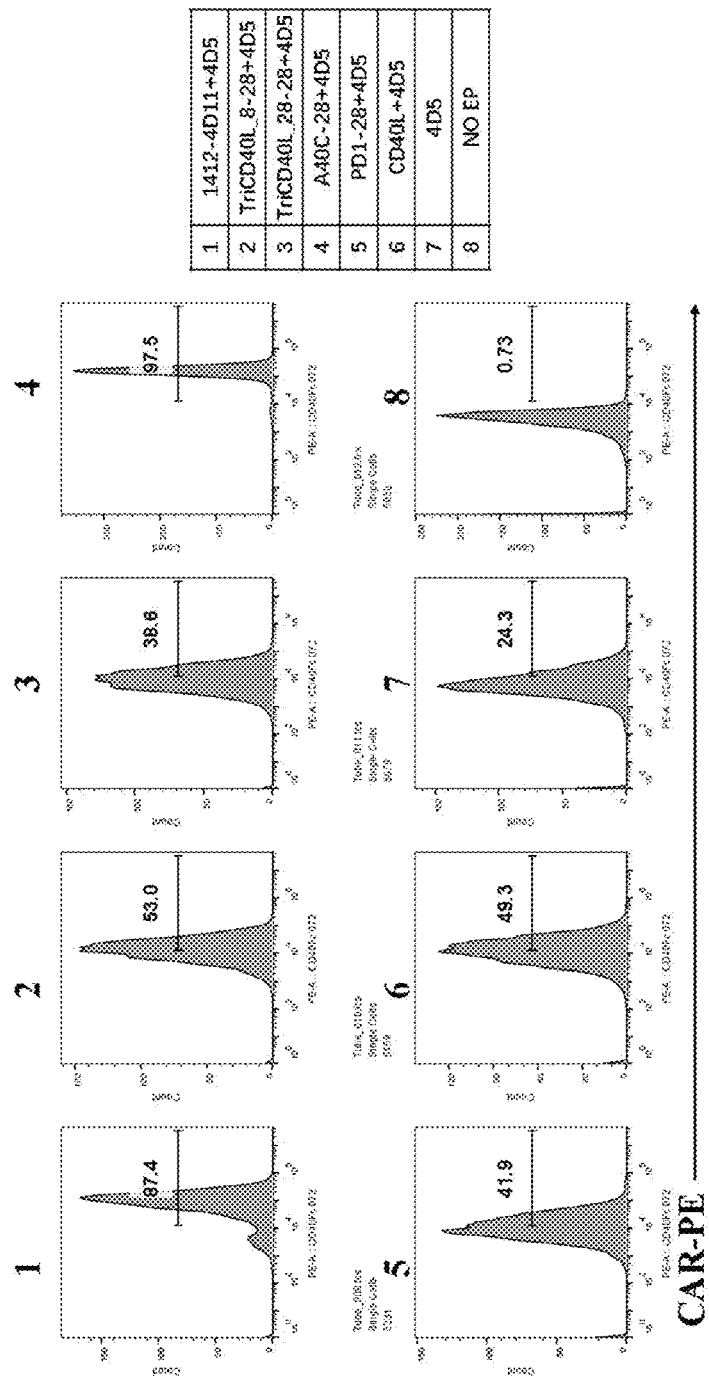

FIG. 43 provides flow cytometry data showing the CAR expression of T cells co-electroporated with various CARs or LACO-stim-CARs.

Figure 44:
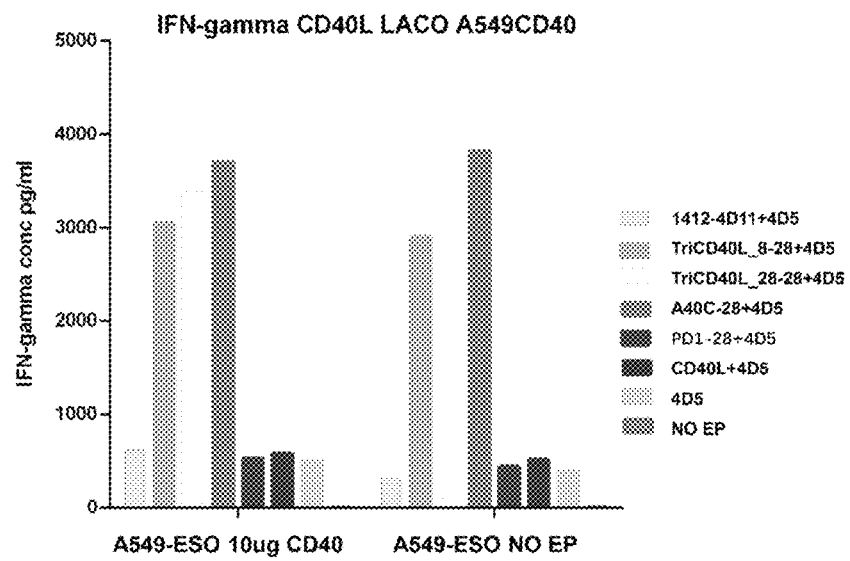

FIG. 44 provides ELISA data showing the IFN-gamma secretion of T cells co-electroporated with various CARs or LACO-stim-CARs and stimulated by tumor cells with or without CD40 expression.

Figure 45:
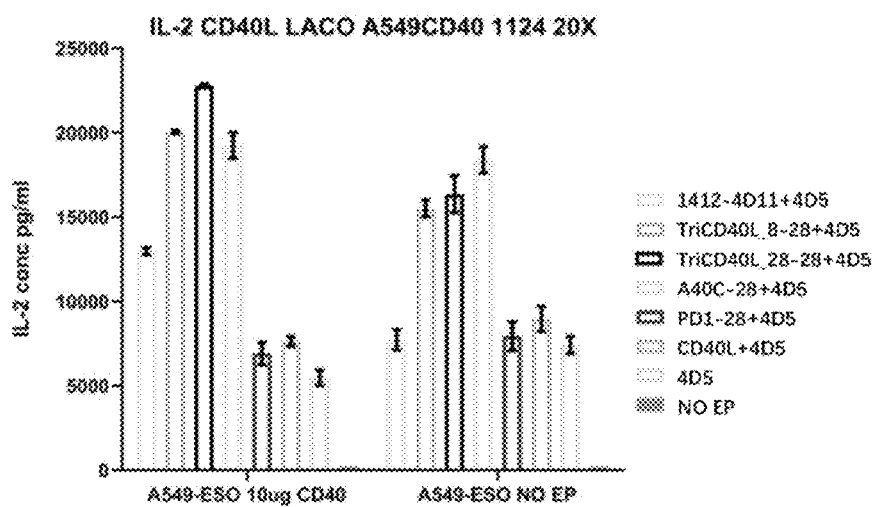

FIG. 45 provides ELISA data showing the IL-2 secretion of T cells co-electroporated with various CARs or LACO-stim-CARs and stimulated by tumor cells with or without CD40 expression.

Figure 46:
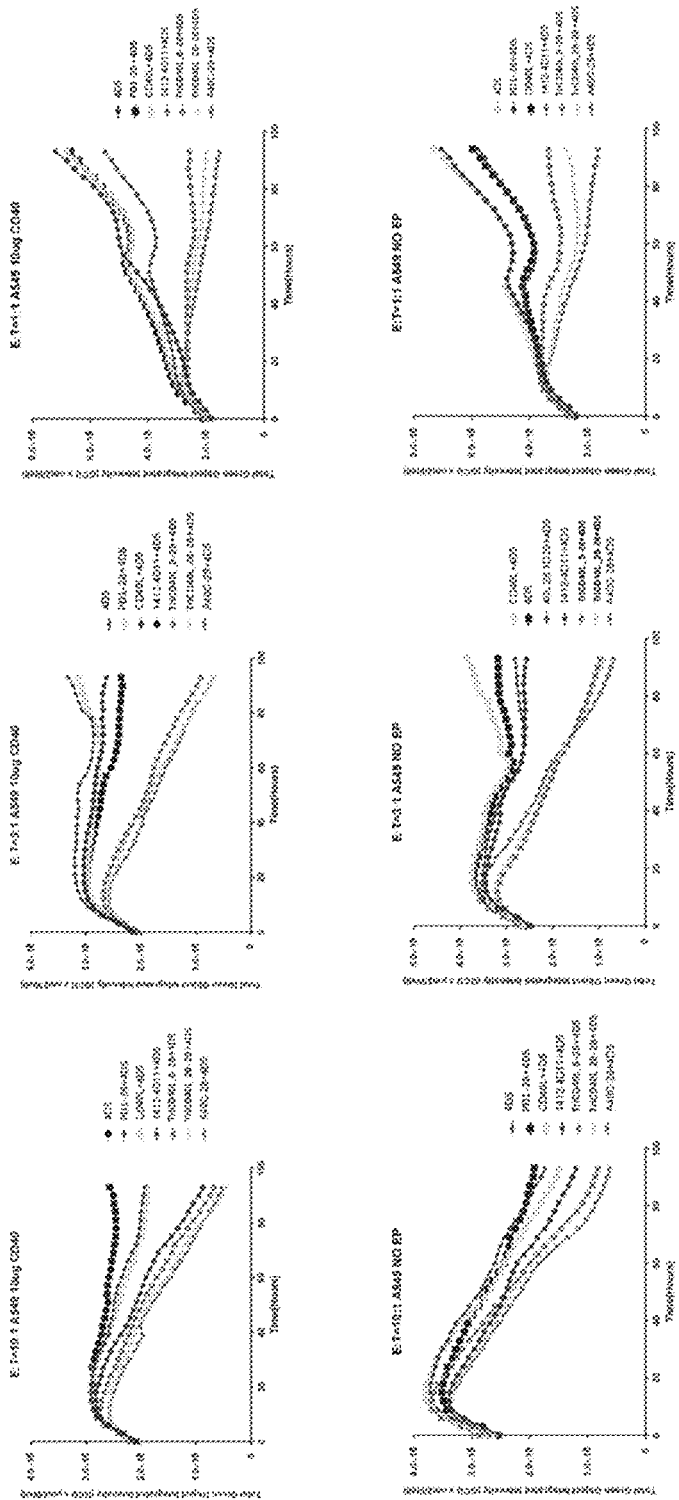

FIG. 46 shows killing effects of T cells co-electroporated with various CARs or LACO-stim-CARs against tumor cells with or without CD40 expression.

Figure 47:
Figure 47:
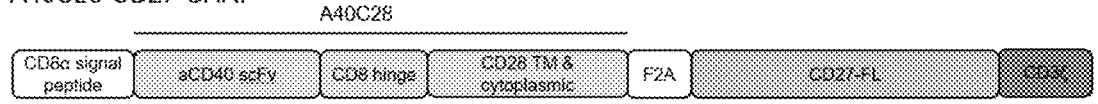

FIG. 47 shows the schematic structures of CD27-CAR and A40C28-CD27-CAR.

Figure 48A:
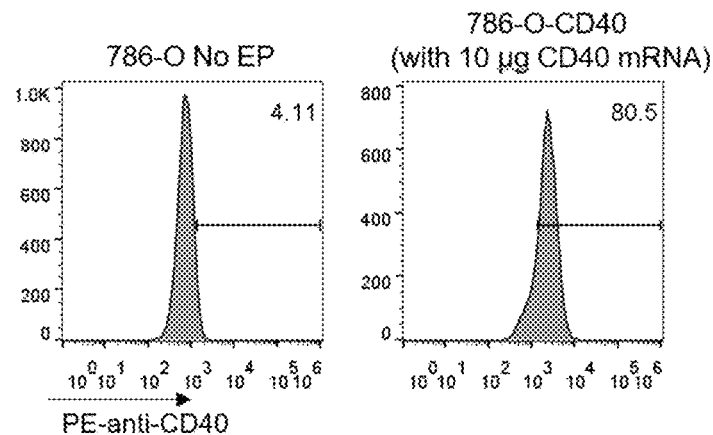
Figure 48B:
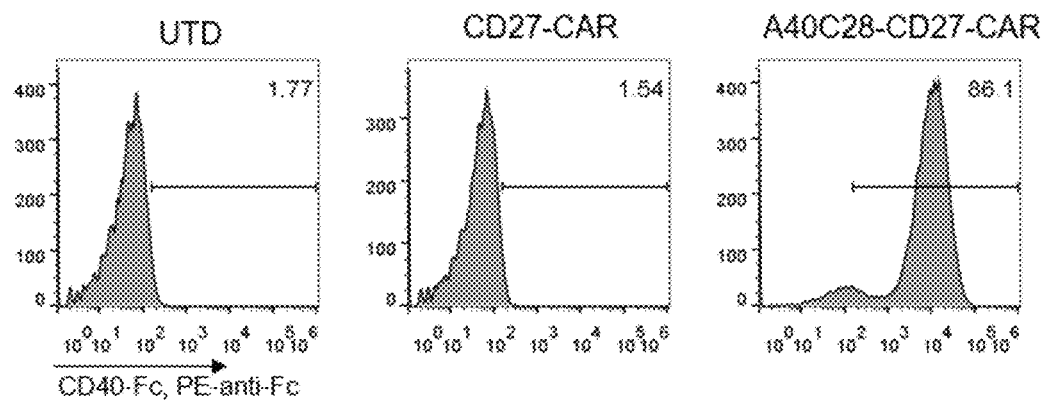
Figure 48B:
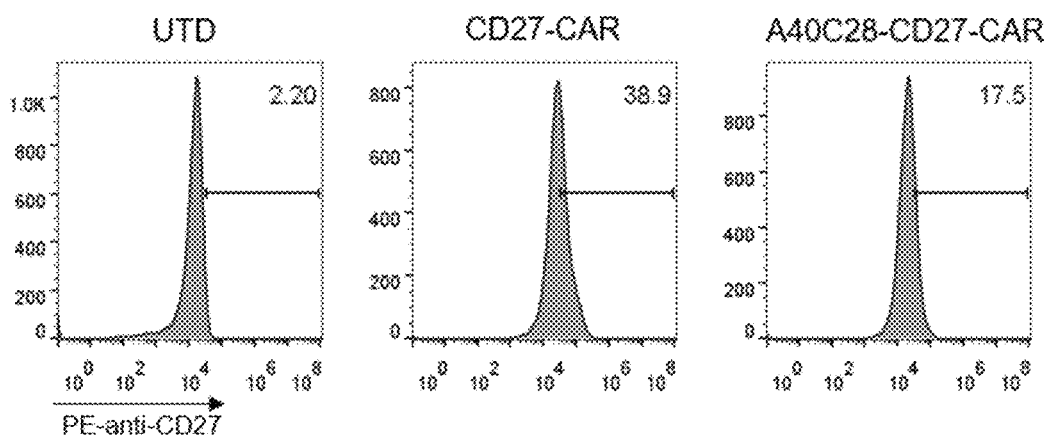

FIGS. 48A-48B provide flow cytometry data showing CD40 expression in target cells electroporated with CD40mRNA (FIG. 48A), and A40C28 & CD27-CAR expression in designated CAR-T cells (FIG. 48B).

Figure 49:
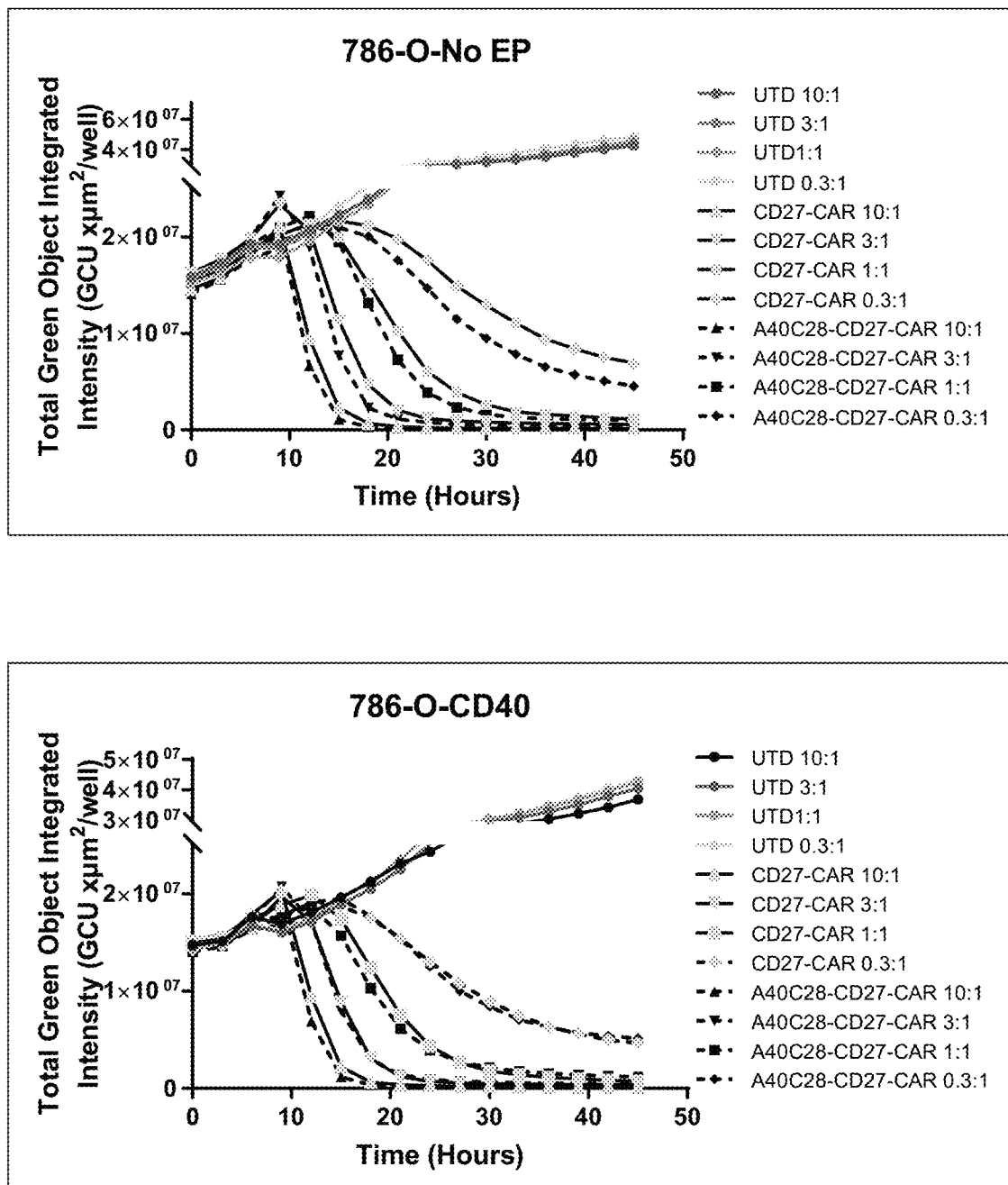

FIG. 49 provides tumor killing curves by CD27-CAR T cells and A40C28-CD27-CAR T cells at the indicated E:T ratios. Upper panel: 786-O-CBG cells; lower panel: 786-O-CBG cells electroporated with 10 μg CD40 mRNA (786-O-CD40).

Figure 50:
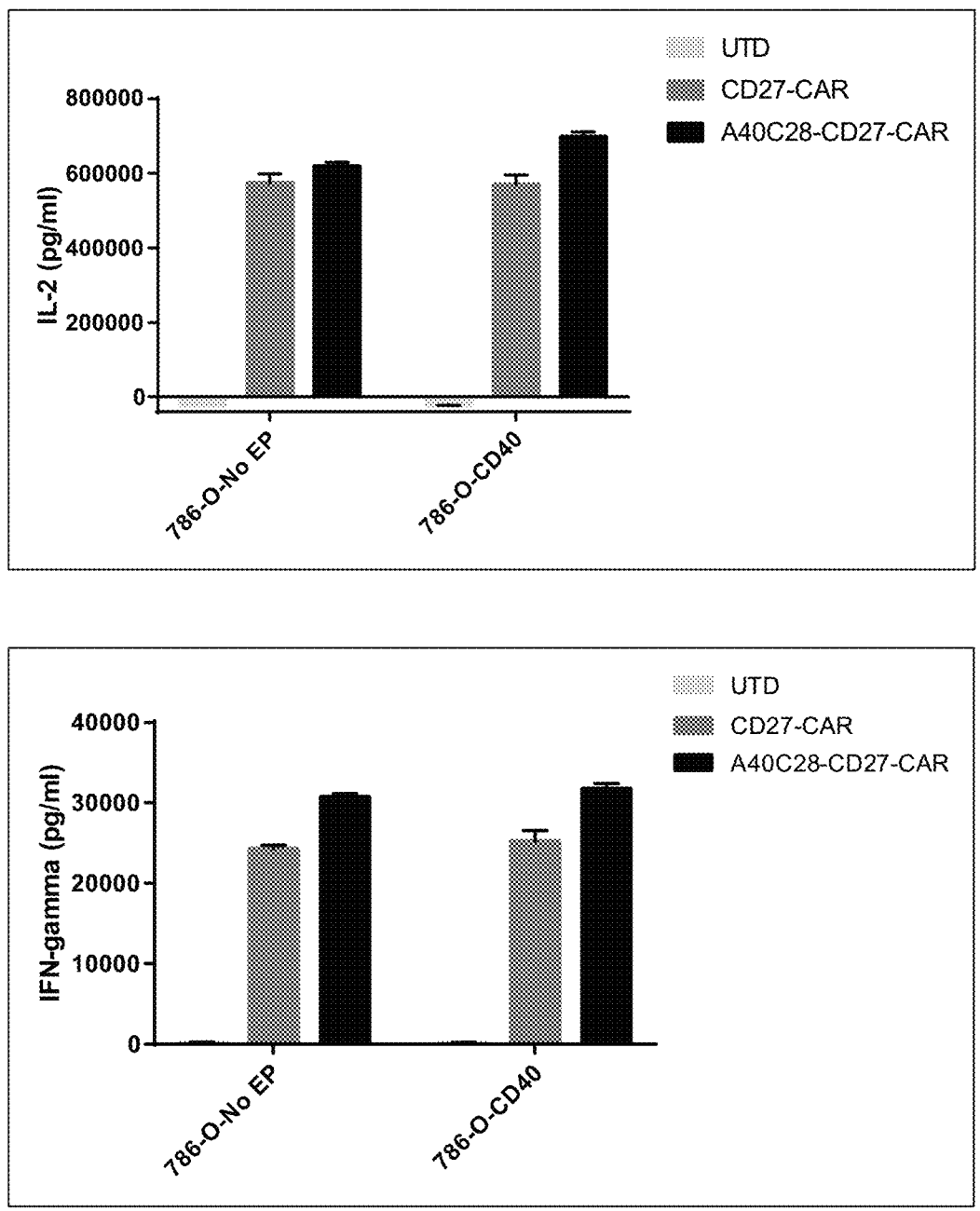

FIG. 50 provides ELISA data showing IL-2 & IFN-gamma release by indicated CAR T cells incubated with 786-O-CBG cells with E:T=1:1 for 24 h.

Figure 51A:
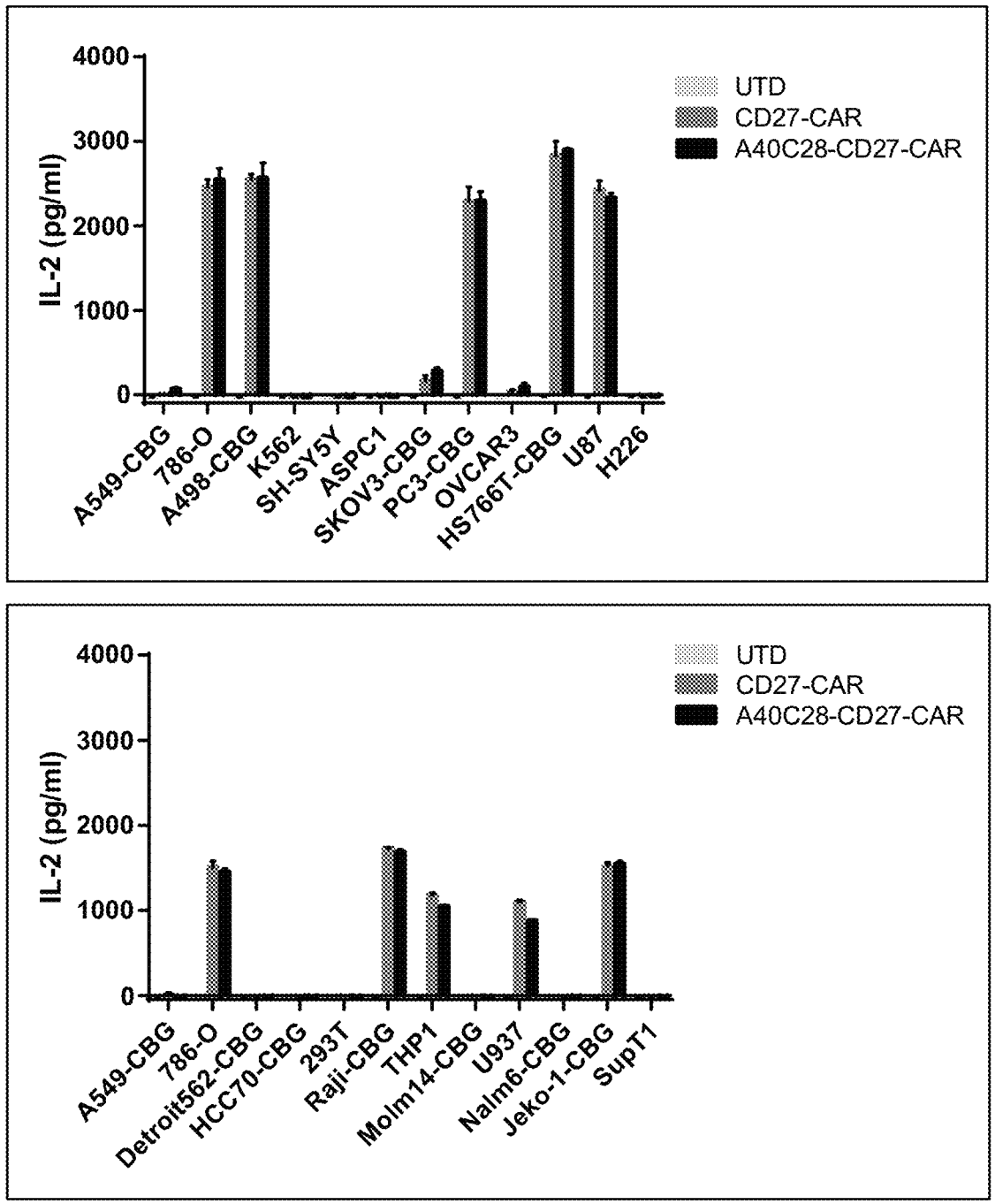
Figure 51B:
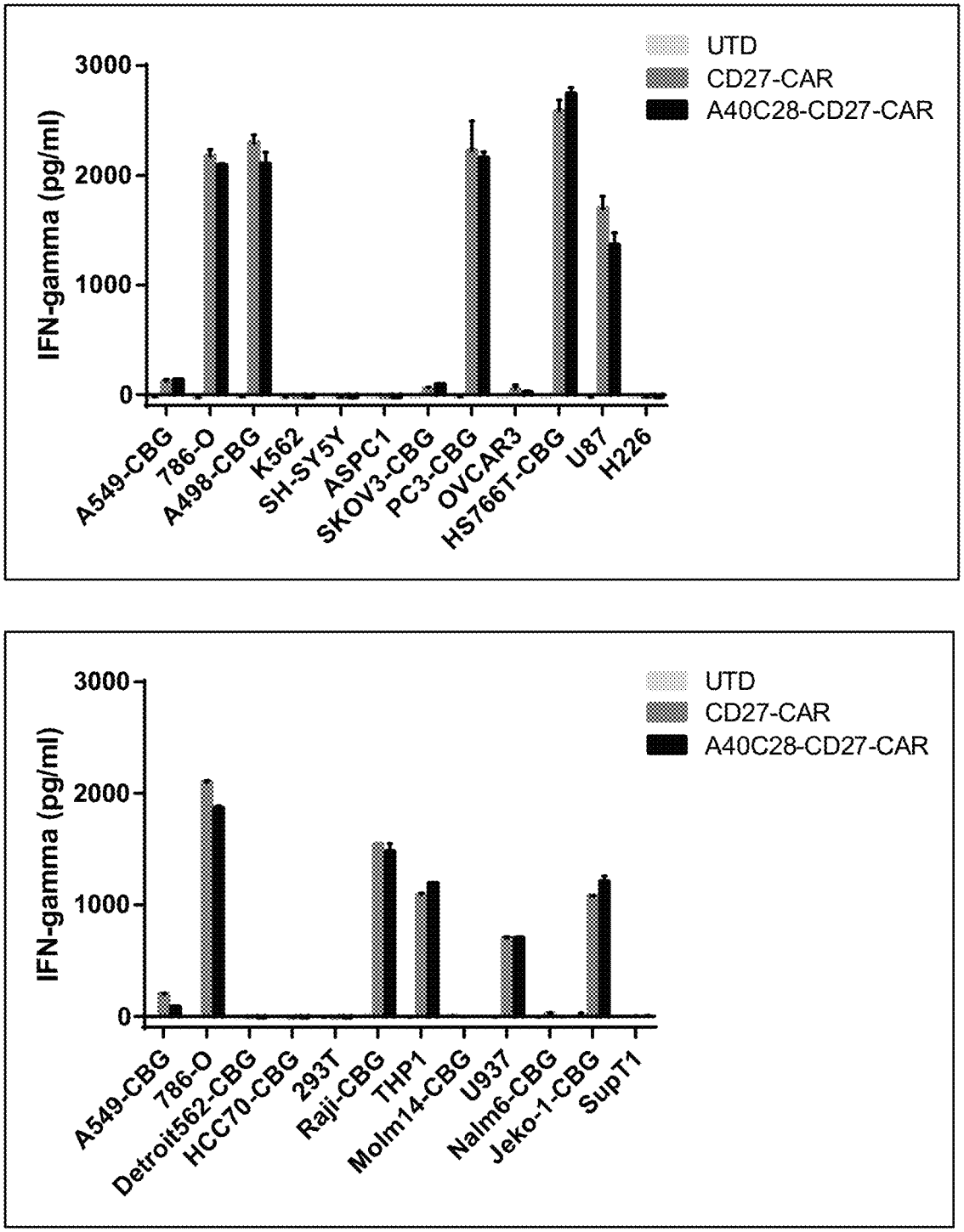

FIGS. 51A-51B provides ELISA data showing IL-2 (FIG. 51A) & IFN-gamma (FIG. 51B) release by indicated CAR T cells incubated with different types of tumor cells with E:T=1:1 for 24 h.

Figure 52:
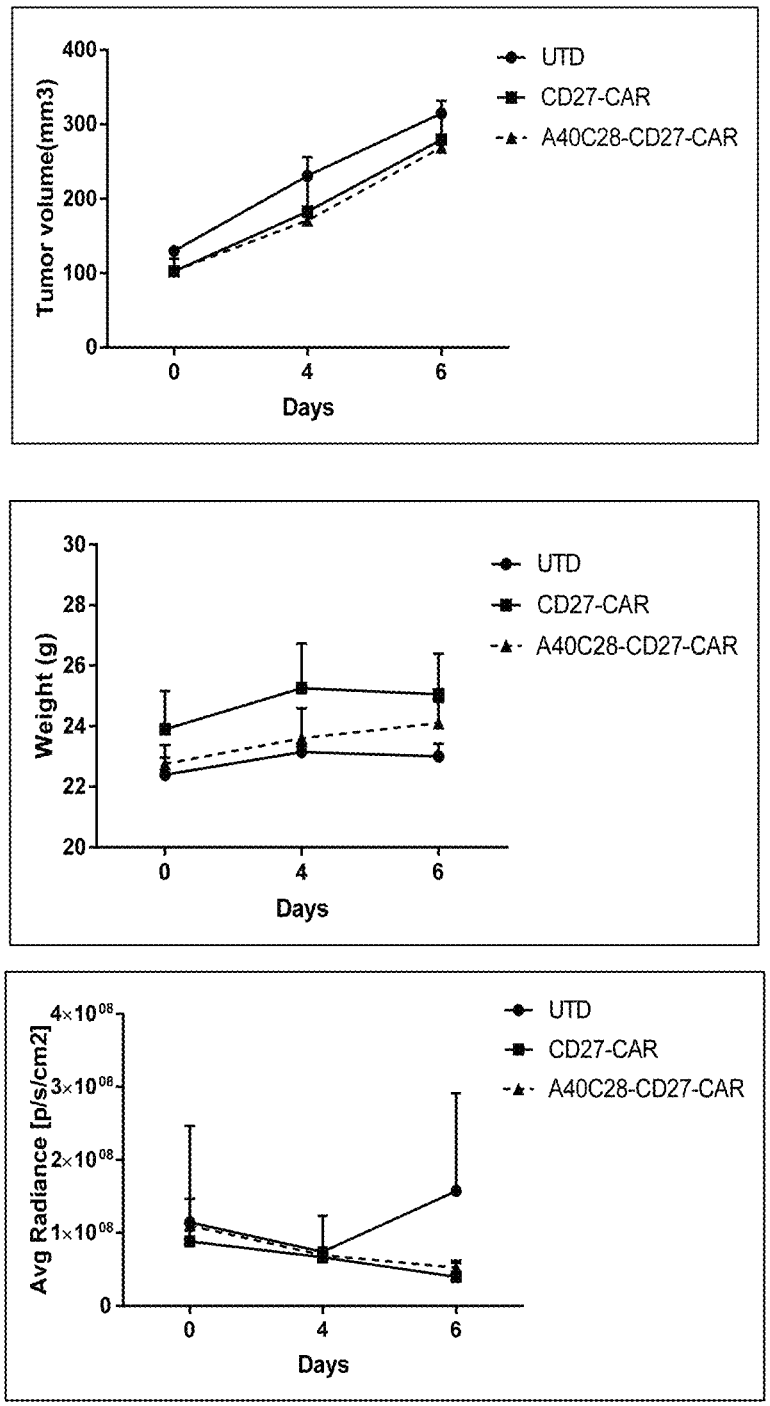

FIG. 52 provides mouse model data showing the anti-tumor activities of CD27-CAR T cells and A40C28-CD27-CAR T cells.

Figure 53:
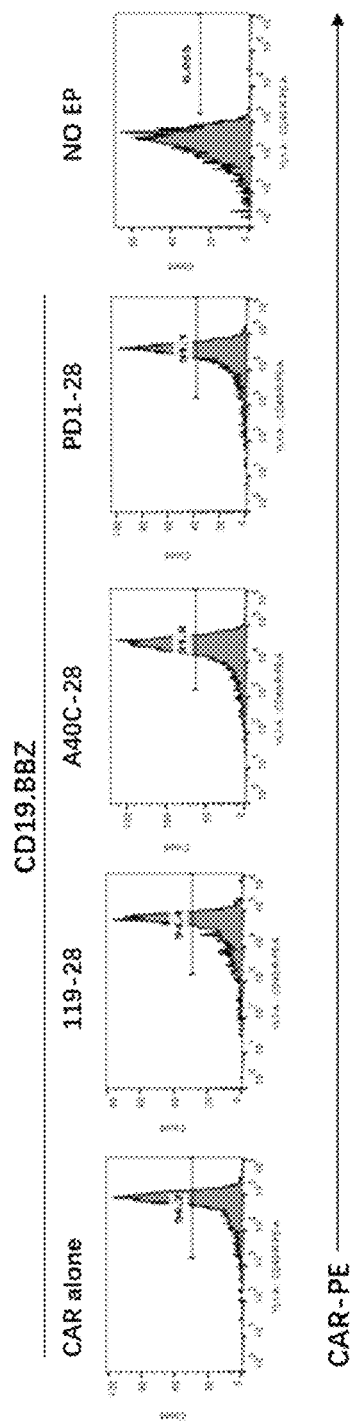

FIG. 53 provides flow cytometry data showing the CAR expression in T cells electroporated with indicated CD19 CAR (FMC63.BBz) mRNA, alone or with LACO molecule 119-28 or A40C-28, or PD1-28.

Figure 54:
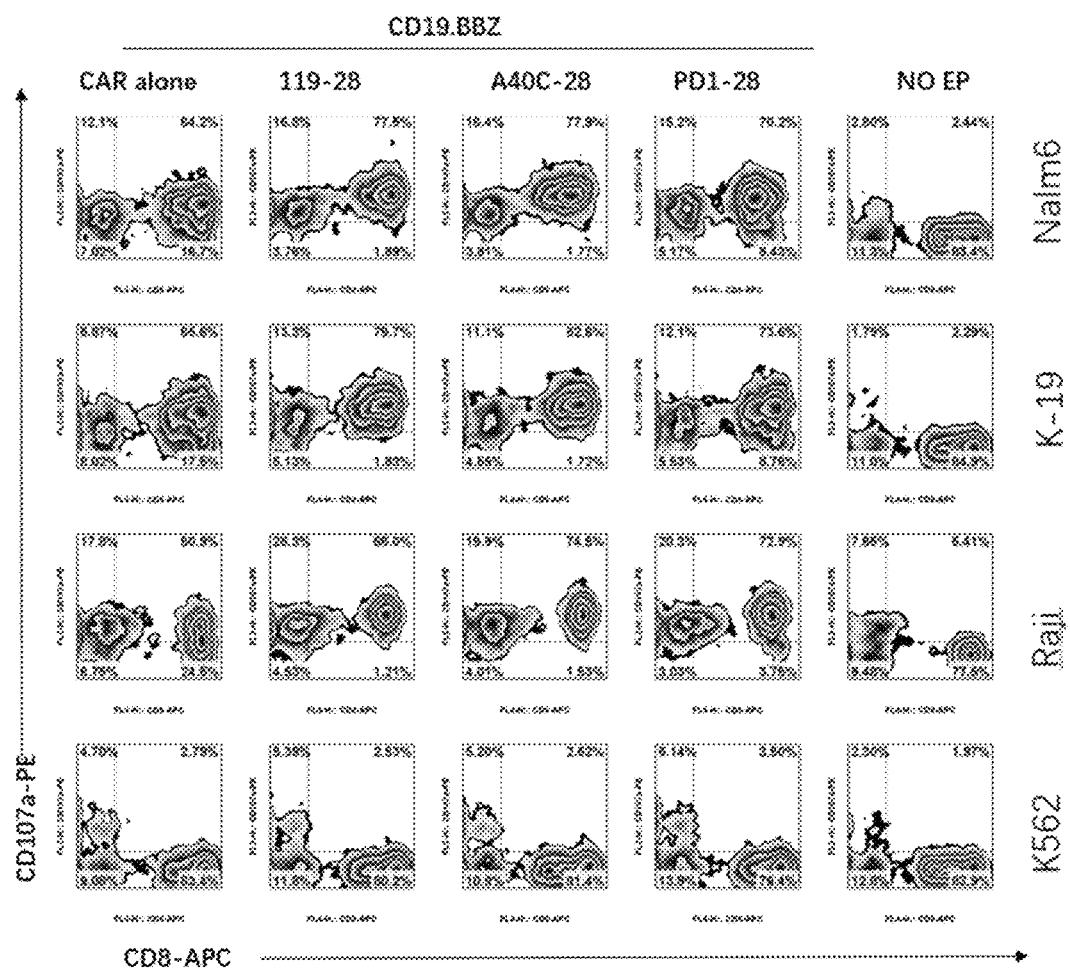

FIG. 54 shows the CD107a expression in T cell expressing CD19 CAR FMC63.BBz, alone or with LACO molecule 119-28 or A40C-28, or PD1-28 and cultured with tumor cells Nalm6, K-19, Raji, or K562.

Figure 55A:
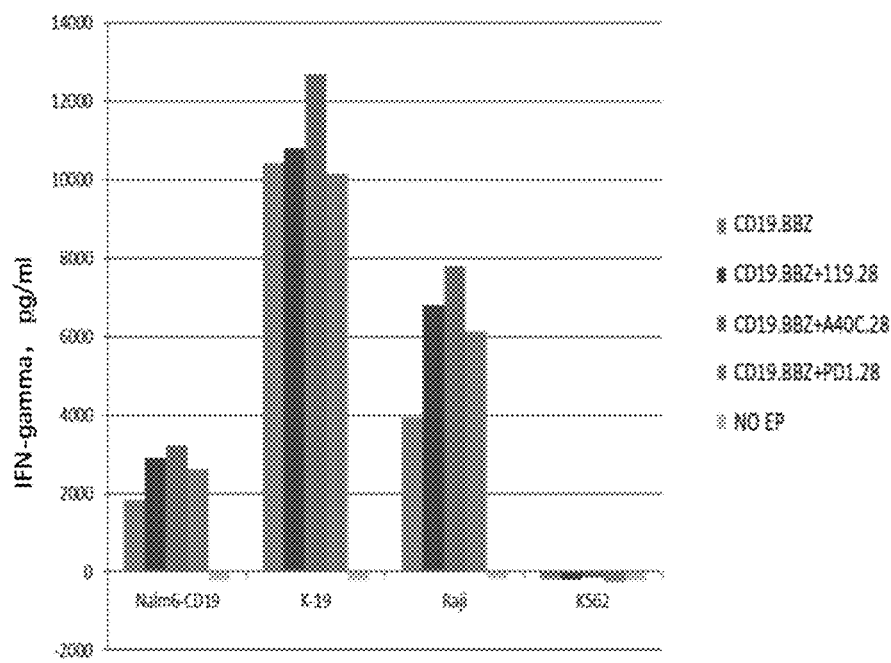
Figure 55B:
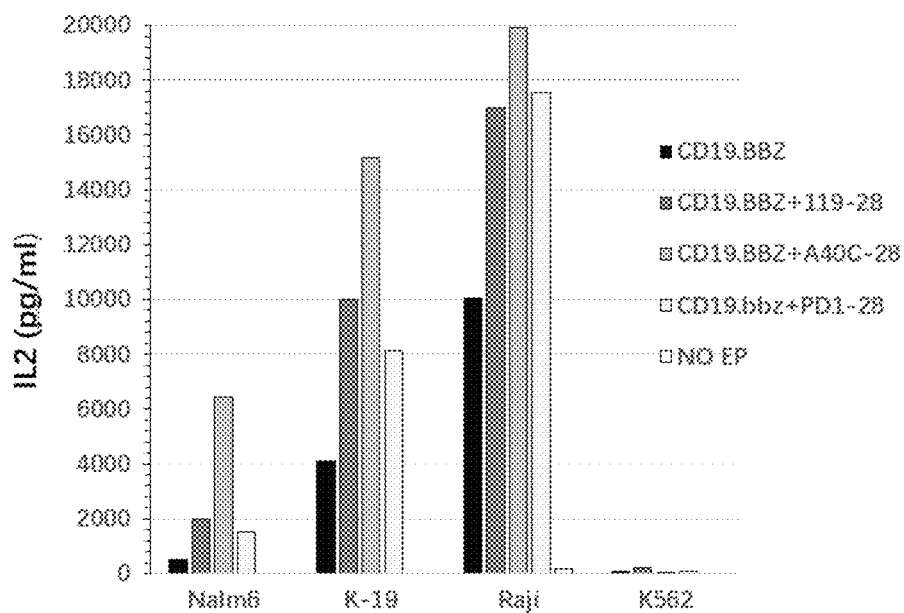

FIGS. 55A-55B provide ELISA data showing the cytokine secretion of T cells electroporated with CD19 (FMC63.BBz) mRNA, alone or with LACO molecule 119-28 or A40C-28, or PD1-28, and stimulated by tumor cells Nalm6, K-19, Raji, or K562. FIG. 55A shows IFN-gamma secretion. FIG. 55B shows IL-2 secretion.

Figure 56:
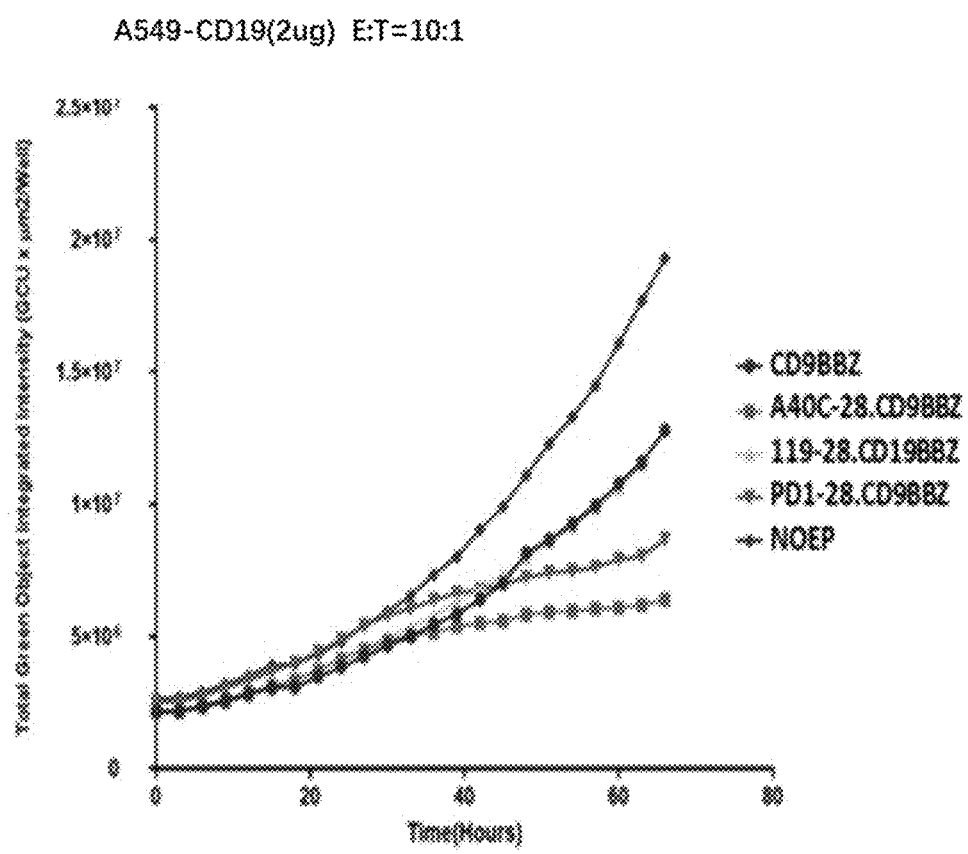

FIG. 56 provides results of a real-time, impedance-based cytotoxicity assay evaluating the cytolytic activities of the indicated CD19 CAR (FMC63.BBz) T cells, expressing CAR alone or with 119-28, A40C-28, or PD1-28A against CD19-expressing A549 tumor cells.

Figure 57:
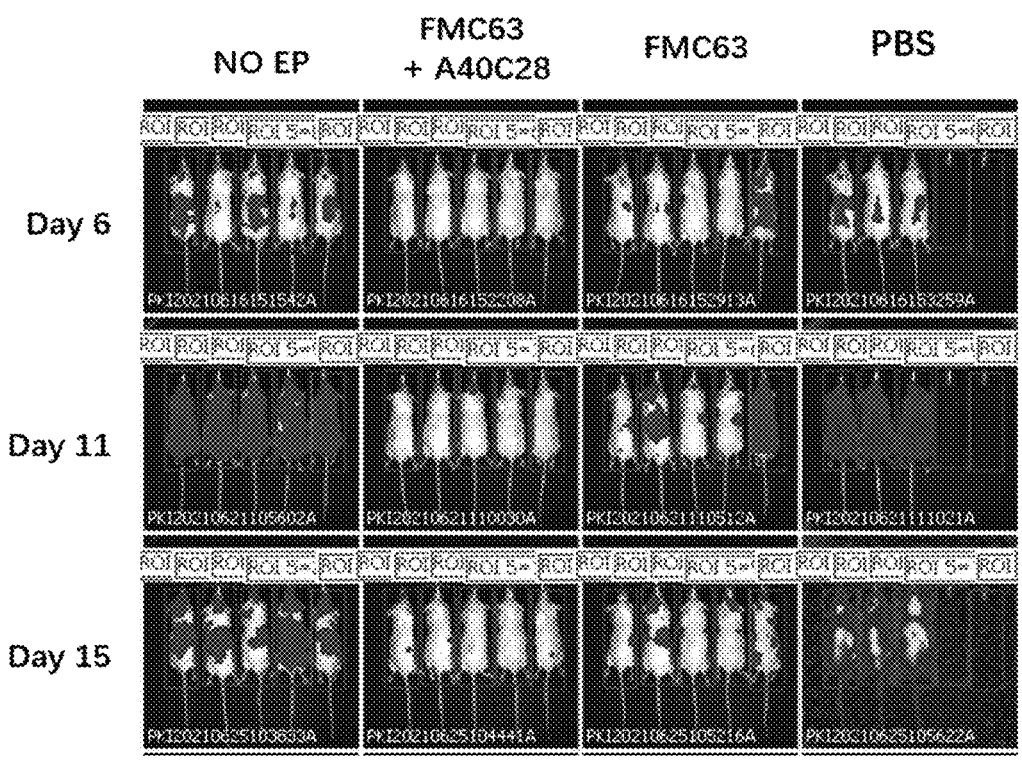

FIG. 57 provides mouse model data showing induced regression of advanced tumors in Raji-CBG engrafted NSG mice resulted from treatment of CD19 CAR (FMC63.BBz) T cells, expressing CAR alone or with LACO-stim A40C-28.

Figure 58:
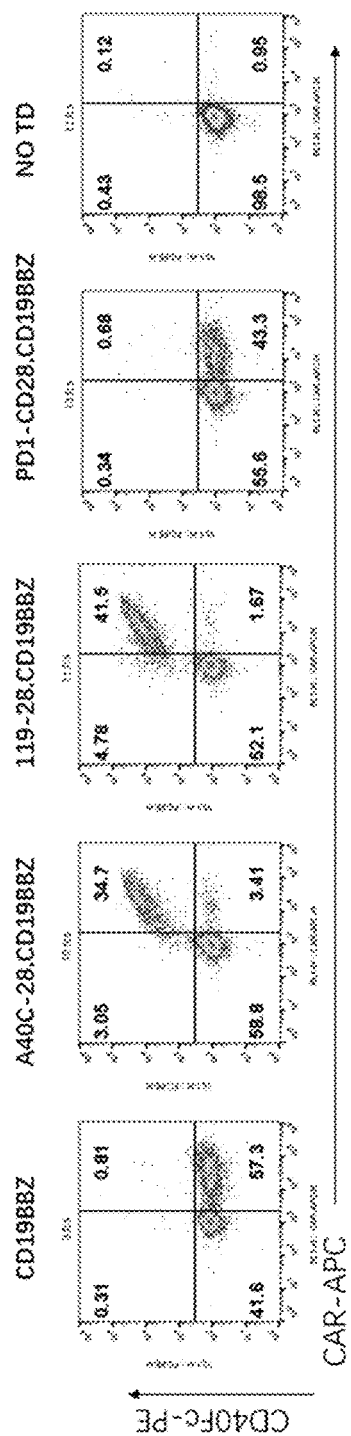

FIG. 58 provides flow cytometry data showing the expression of CAR and LACO-stim transduced to T cells using lentiviral vectors.

Figure 59A:
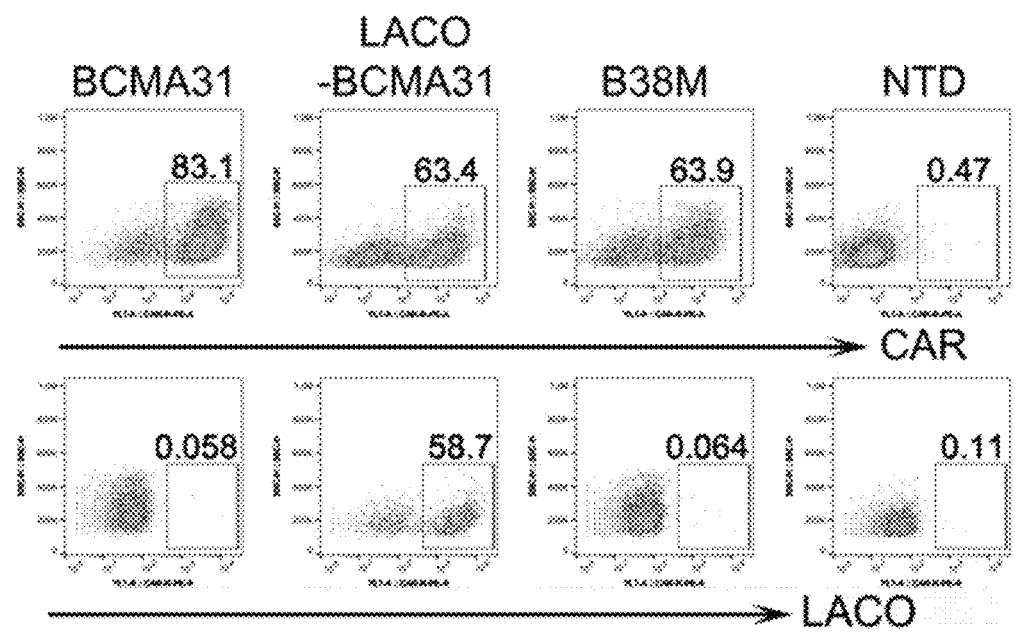
Figure 59B:
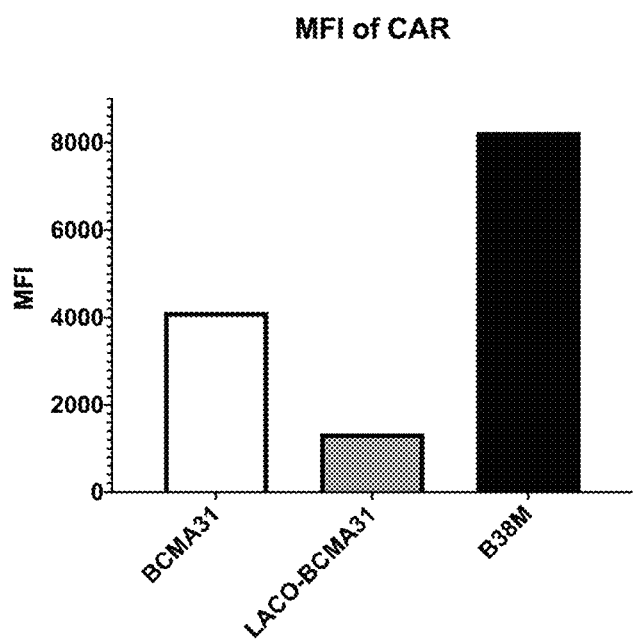

FIGS. 59A-59B provide the FACS results showing the expression levels of CAR and LACO in the T cells (FIG. 59A) and the MFI of CAR (FIG. 59B).

Figure 60A:
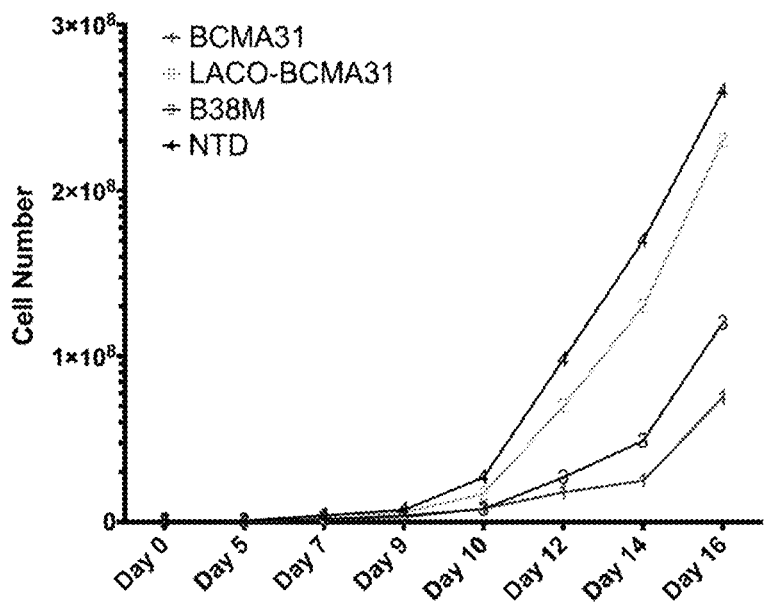
Figure 60B:
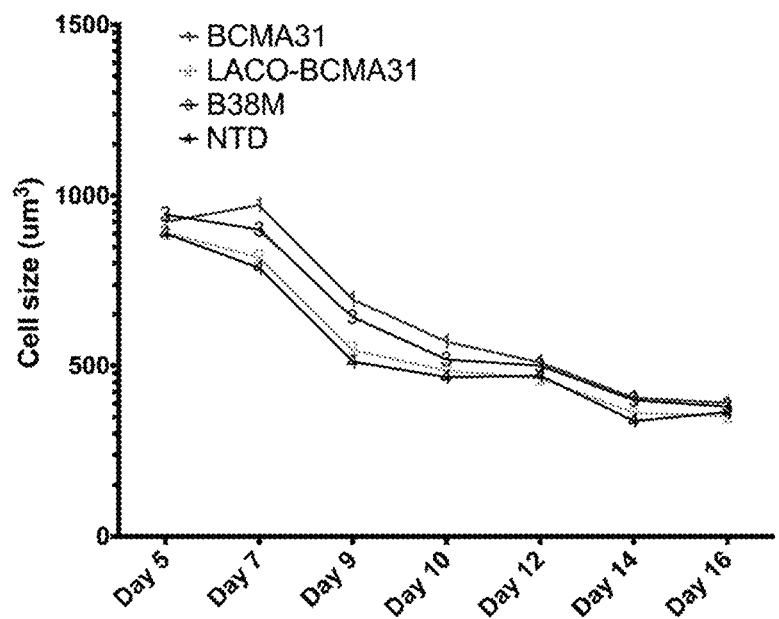

FIGS. 60A-60B provide results showing the numbers (FIG. 60A) and the sizes of designated CART cells (FIG. 60B) during culture.

Figure 61A:
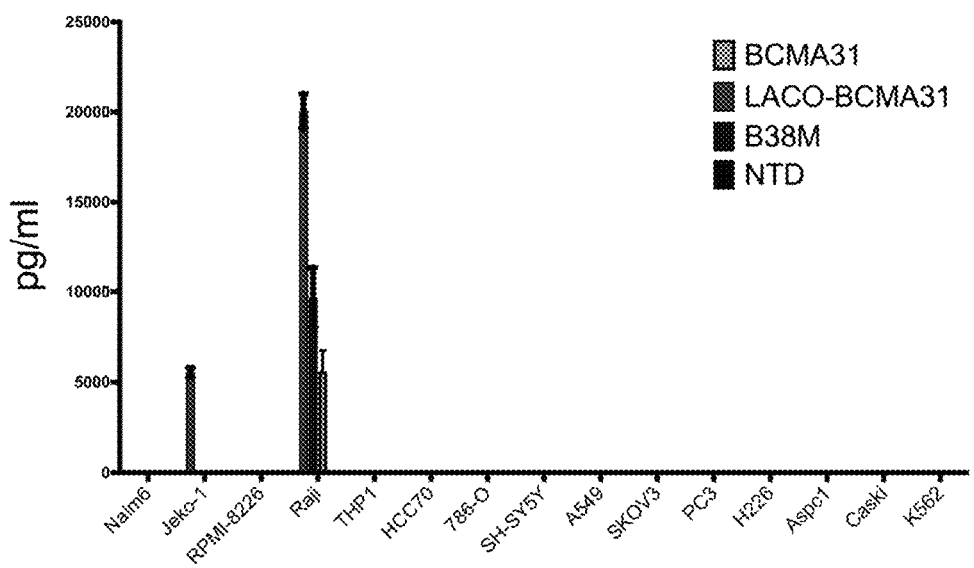
Figure 61B:
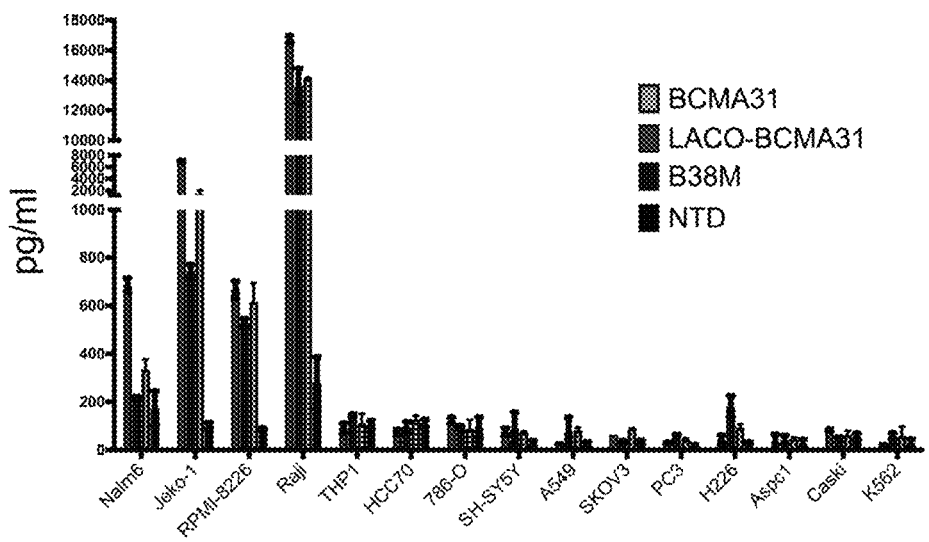

FIGS. 61A-61B provide ELISA results showing cytokine production by T cells after coculture with a panel of tumor cells. FIG. 61A shows IL-2 production. FIG. 61B shows INF-γ production.

Figure 62A:
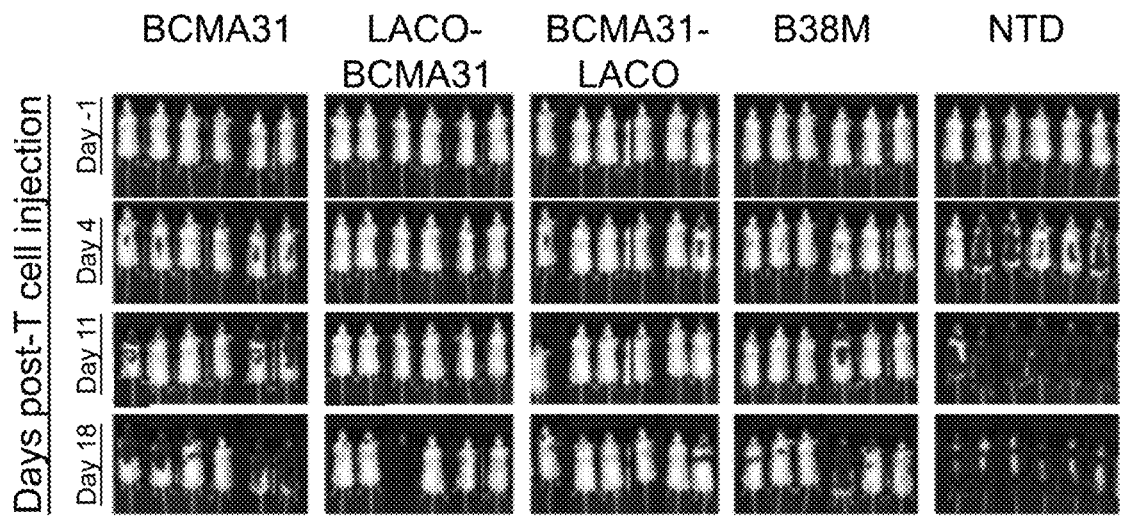
Figure 62B:
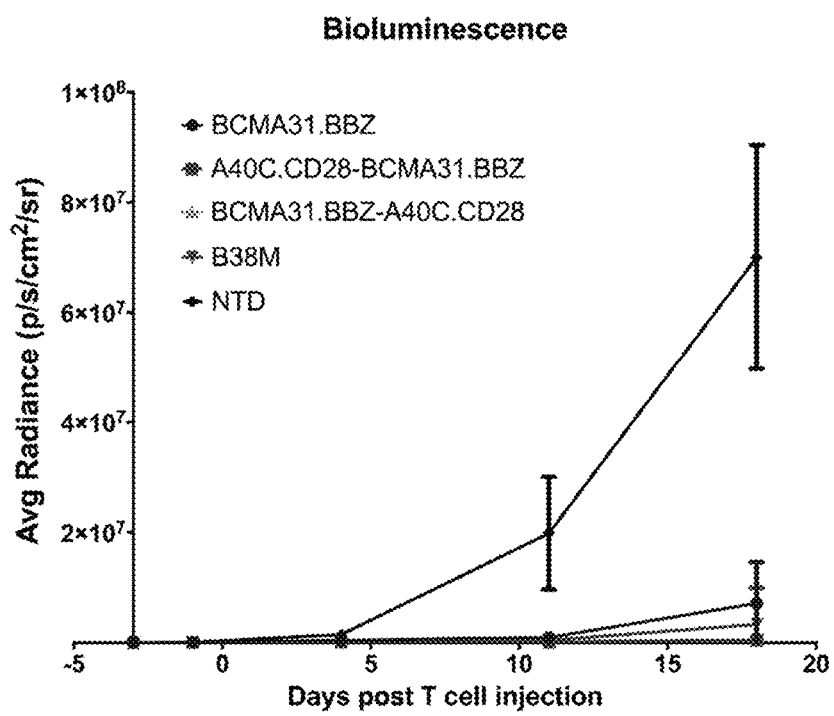

FIGS. 62A-62B provides results of in vivo animal experiment comparing the killing effects of BCMA31, LACO-BCMA31, BCMA31-LACO, and B38M CART cells against Jeko-1 tumor cells. FIG. 62A shows the bioluminescence imaging of Jeko-1 tumors. FIG. 62B shows the average Radiance of bioluminescence.

Figure 63:
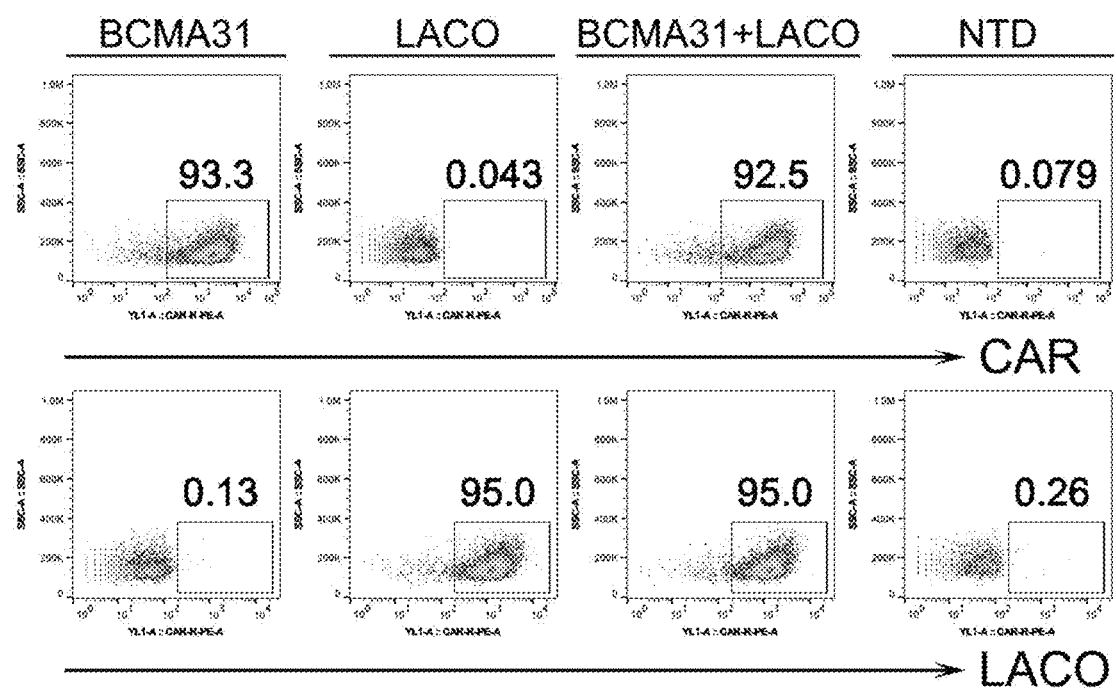

FIG. 63 provides FACS results showing the expression levels of CAR and LACO in the T cells after mRNA electroporation.

Figure 64:

FIG. 64 provides the expression of CD107a in designated CART cells after coculture with different tumor cells.

Figure 65A:
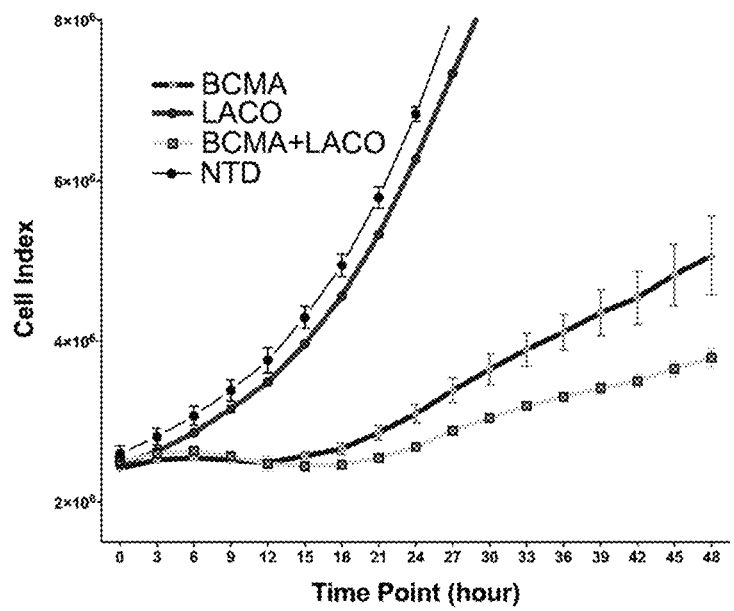
Figure 65B:
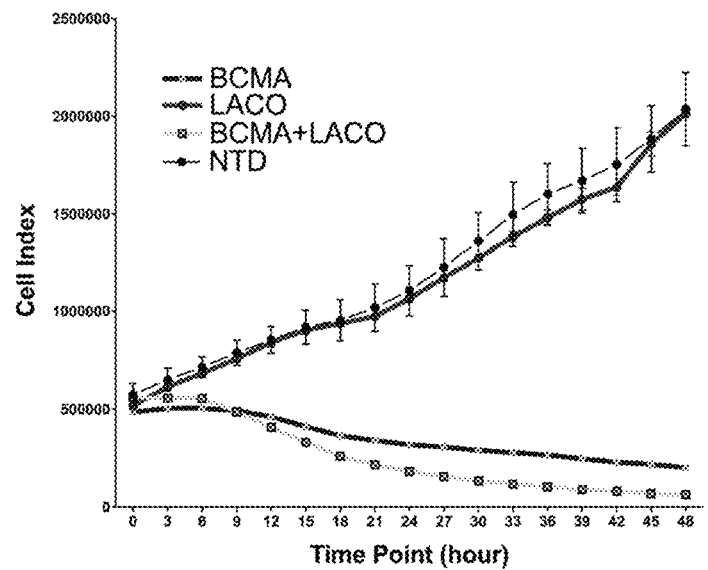
Figure 65C:
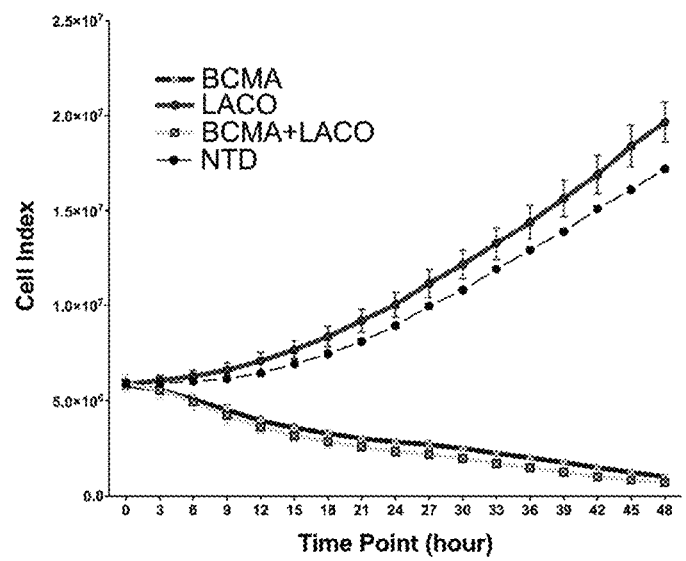
Figure 65D:
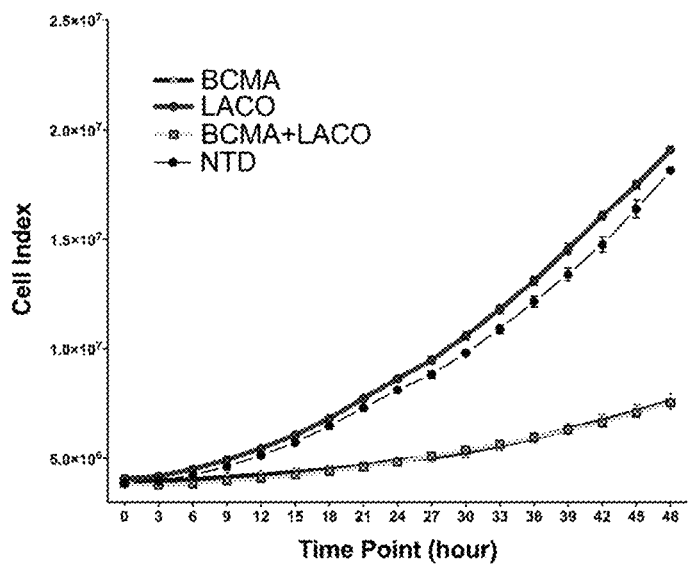

FIGS. 65A-65D provide results of Incucyte Live-Cell Analysis of the cytotoxic T cell activities of designated CART cells against different tumor cells. FIG. 65A: Nalm6 cells; FIG. 65B: Jeko-1 cells; FIG. 65C: RPMI-8226 cells; FIG. 65D: Raji cells.

Figure 66:
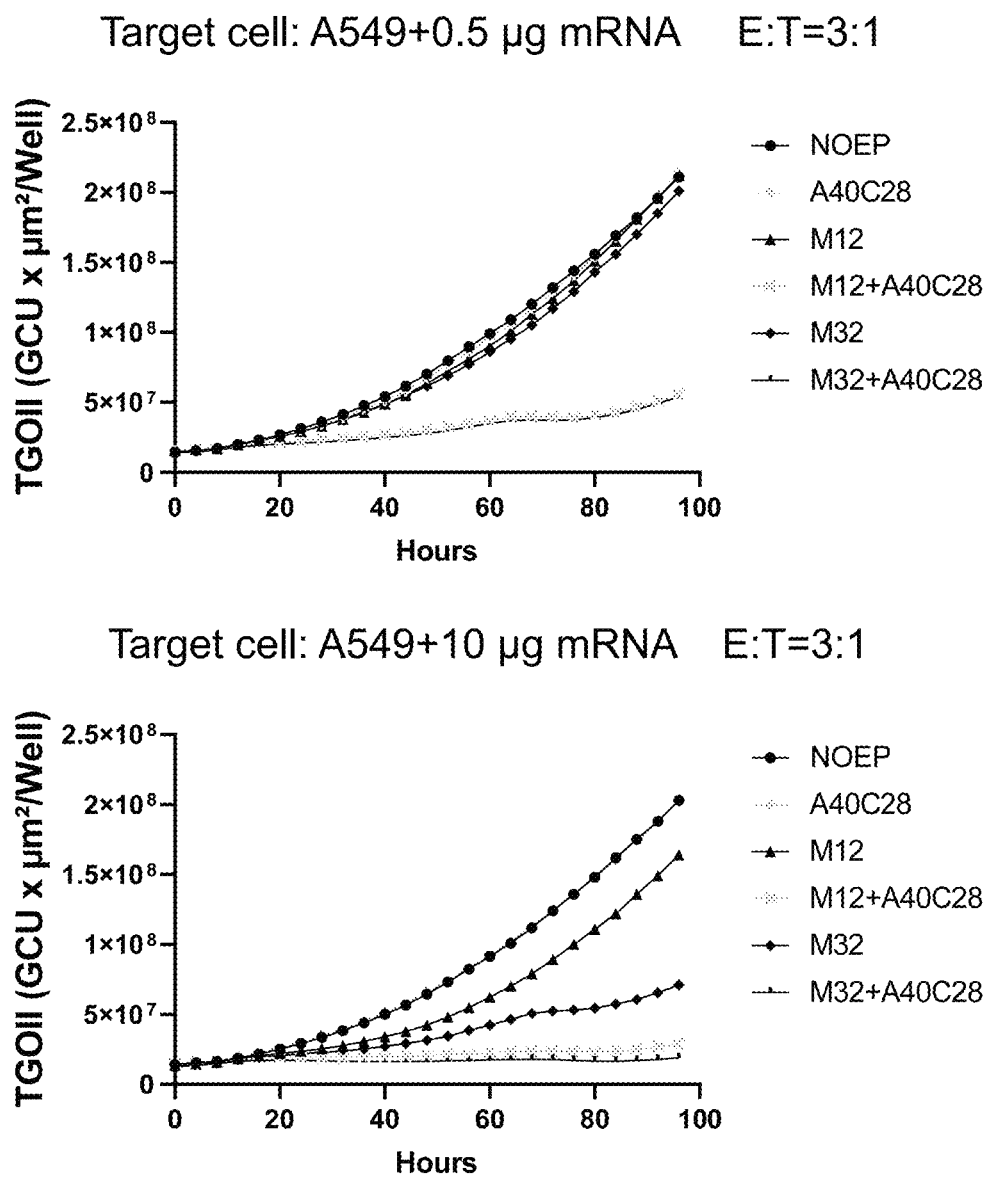

FIG. 66 provides the killing curves of different mRNA-based anti-mesothelin CAR-T cells, including mock T cells (NO EP), T cells with A40C28, anti-mesothelin M12+/−A40C28 CAR-T cells and M32+/−A40C28 CAR-T cells, to A549-GFP tumor cells that were electroporated with 0, 0.5 mg or 10 mg mesothelin mRNA at E/T ratio=3:1.

Figure 67:
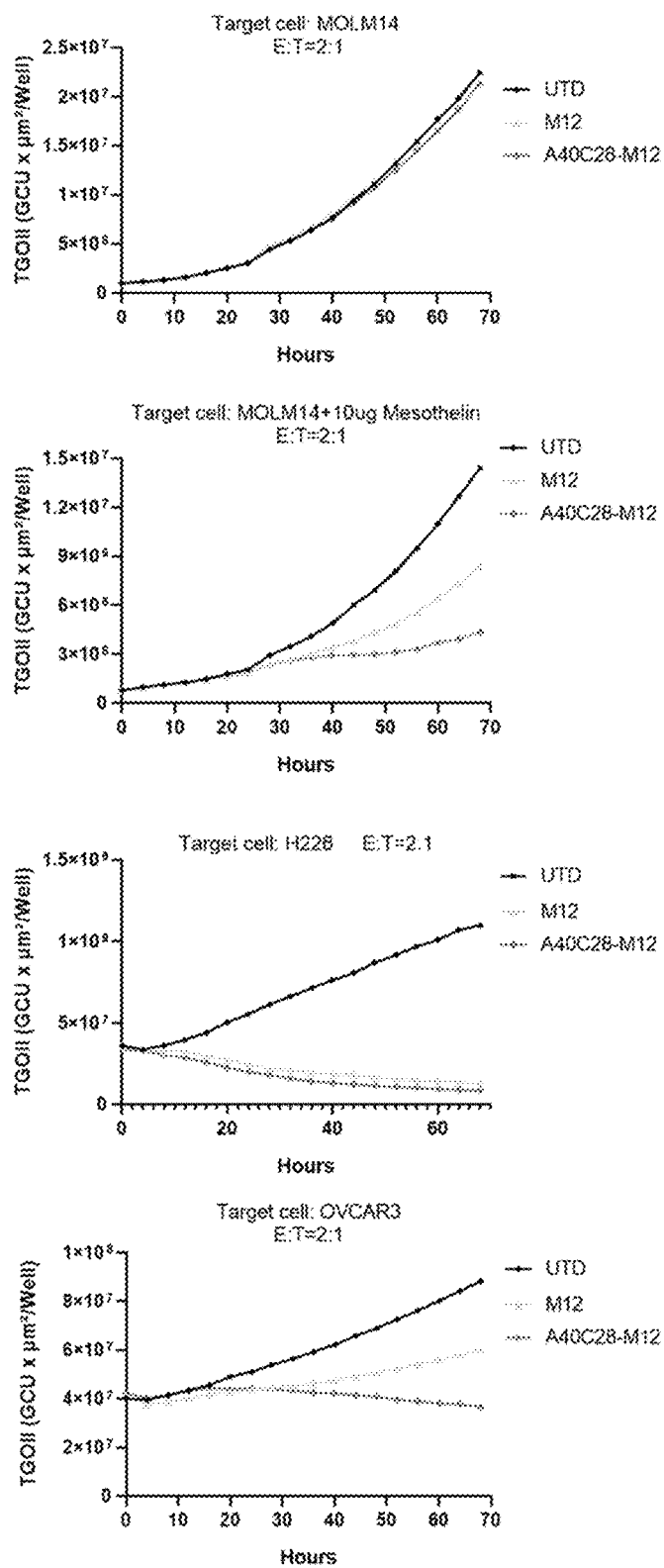

FIG. 67 provides the killing curves of lentivirus-based anti-mesothelin CAR-T cells, including mock T cells (UTD) and anti-mesothelin M12+/−A40C28 CAR-T cells, to 11226, OVCAR3 and MOLM14 cells that were electroporated with 0 or 10 mg mesothelin mRNA at E/T ratio=2:1.

Figure 68:
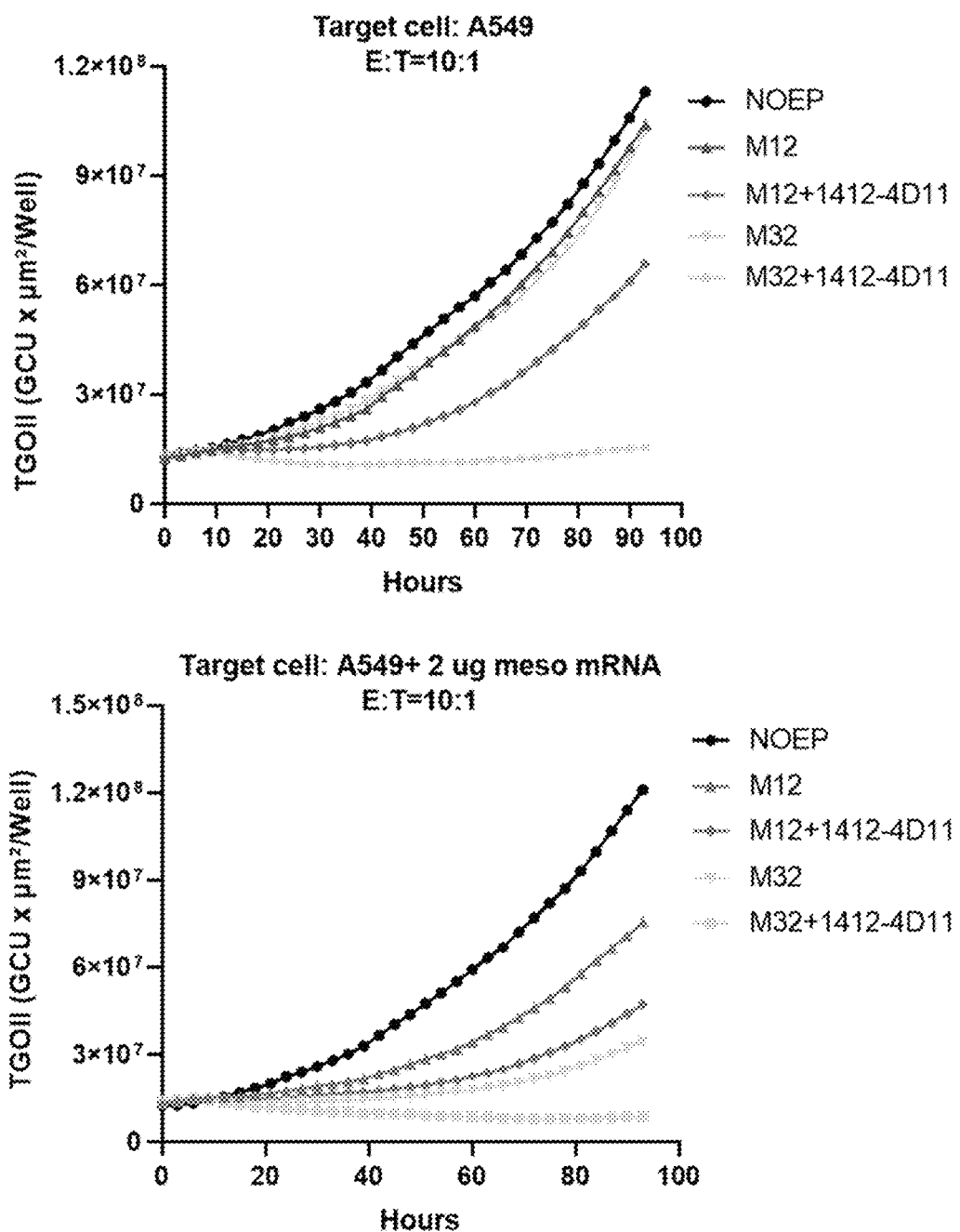

FIG. 68 provides the killing curves of different mRNA-based anti-mesothelin CAR-T cells, including mock T cells (NO EP), anti-mesothelin M12+/−1412-4D11 CAR-T cells and M32+/−1412-4D11 CAR-T cells, to A549-GFP tumor cells that were electroporated with 0 or 2 mg mesothelin mRNA at E/T ratio=10:1.

Figure 69:
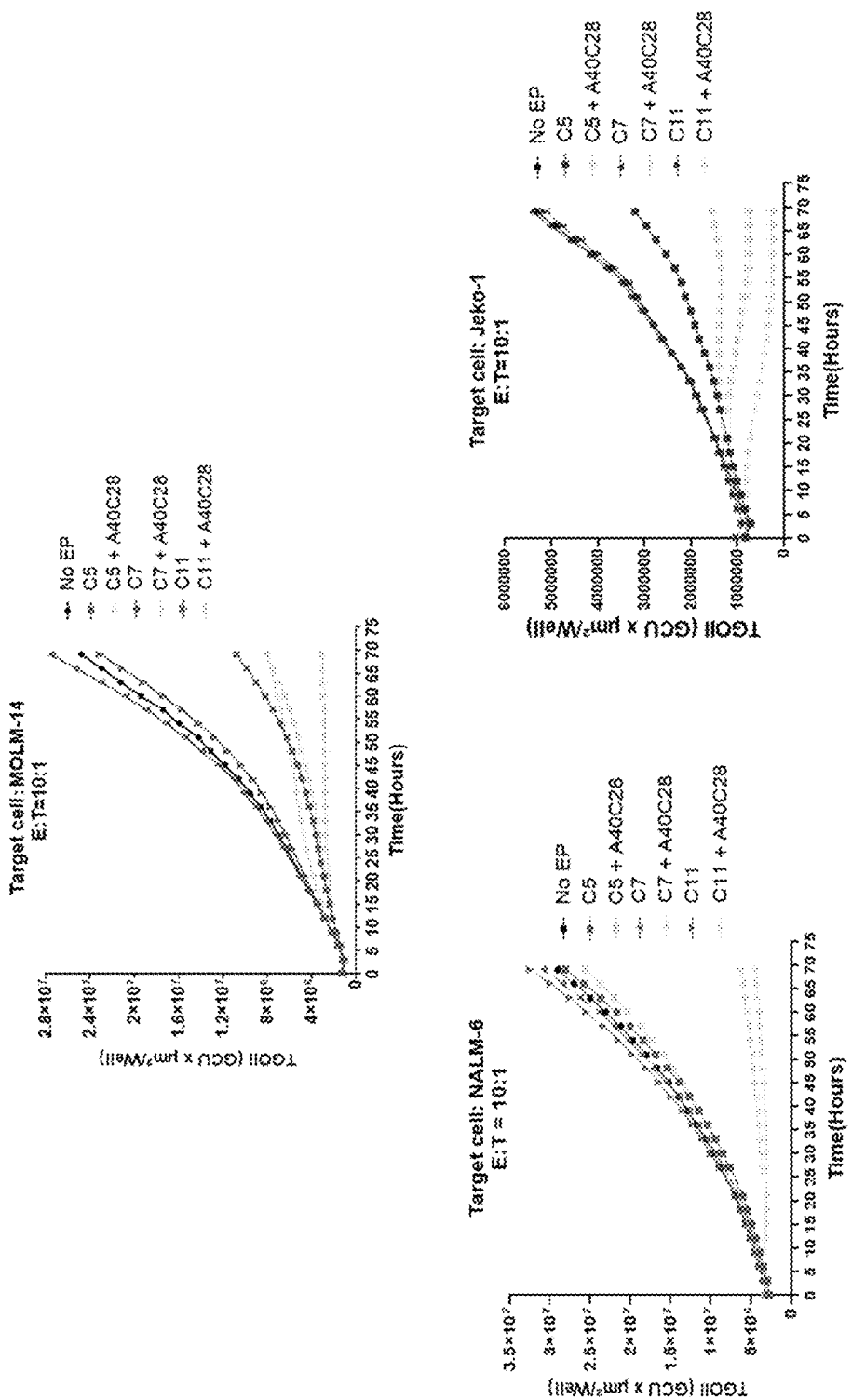

FIG. 69 provides the killing curves of different mRNA-based anti-CD123 CART cells with or without LACO (A40C.CD28) against MOLM-14, NALM6 or JEKO-1 tumor cells at E/T ratio=10:1.

Figure 70:
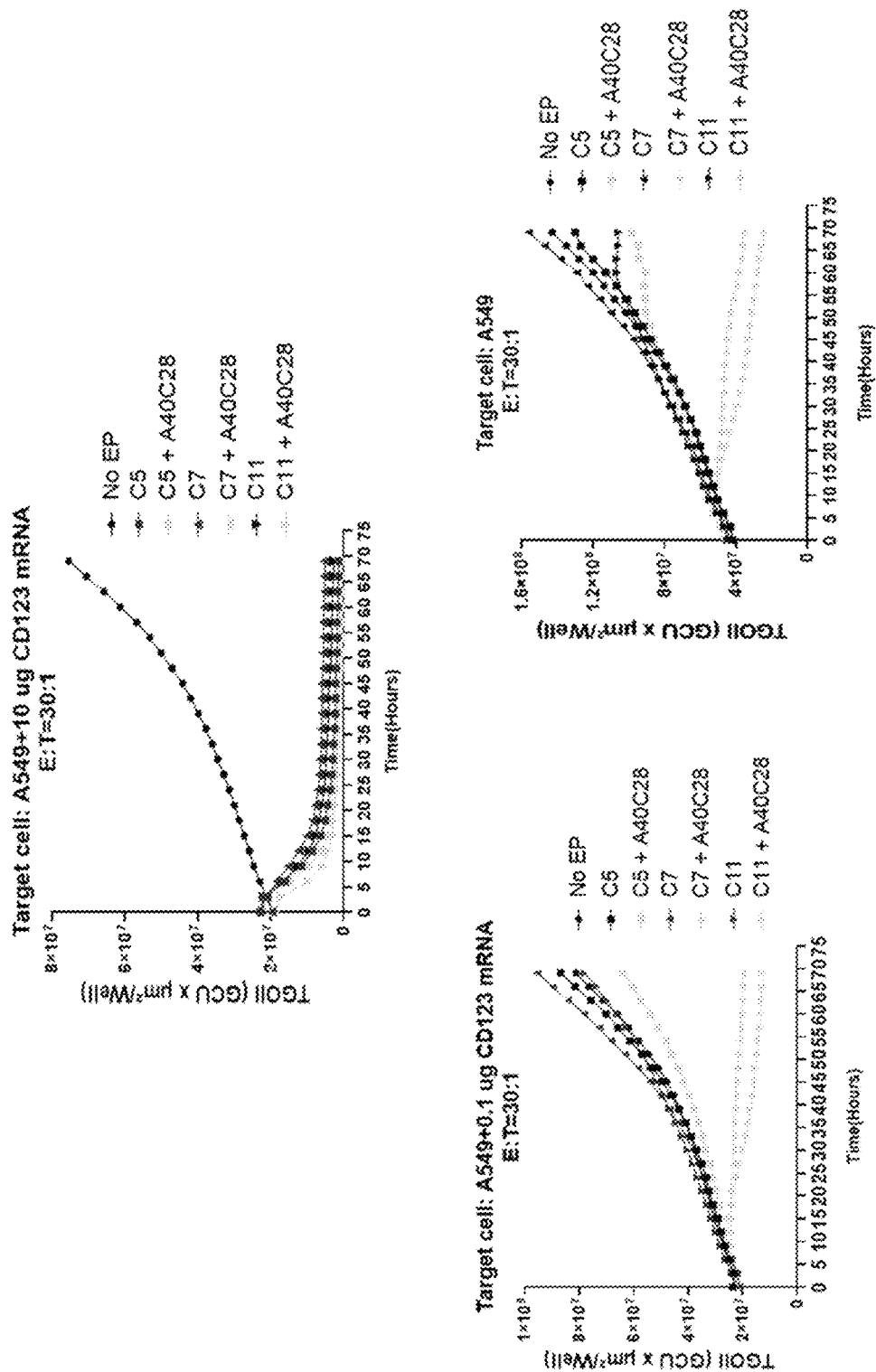

FIG. 70 provides the killing curves of different mRNA-based anti-CD123 CART cells with or without LACO (A40C.CD28) against A549 tumor cells that were electroporated with 10 μg, 0.1 μg or 0 CD123 mRNA at E/T ratio=30:1.

Figure 71:
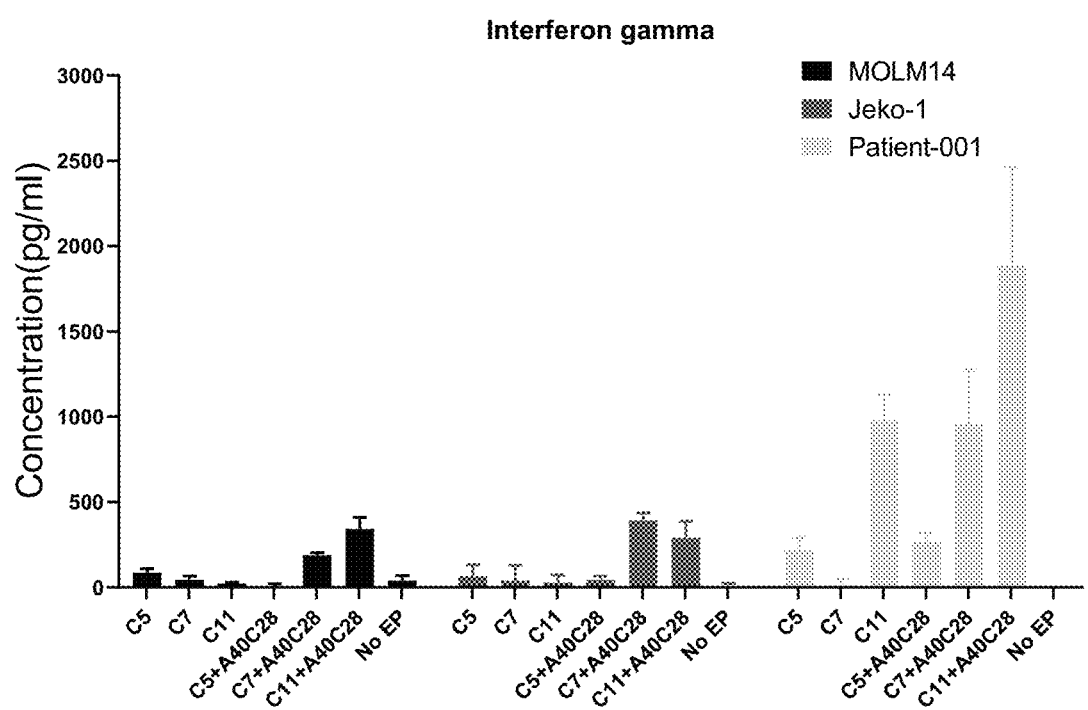

FIG. 71 provides ELISA results showing the IFN-gamma secretion of the T cells electroporated with different CD123 CAR with or without LACO.

Figure 72:
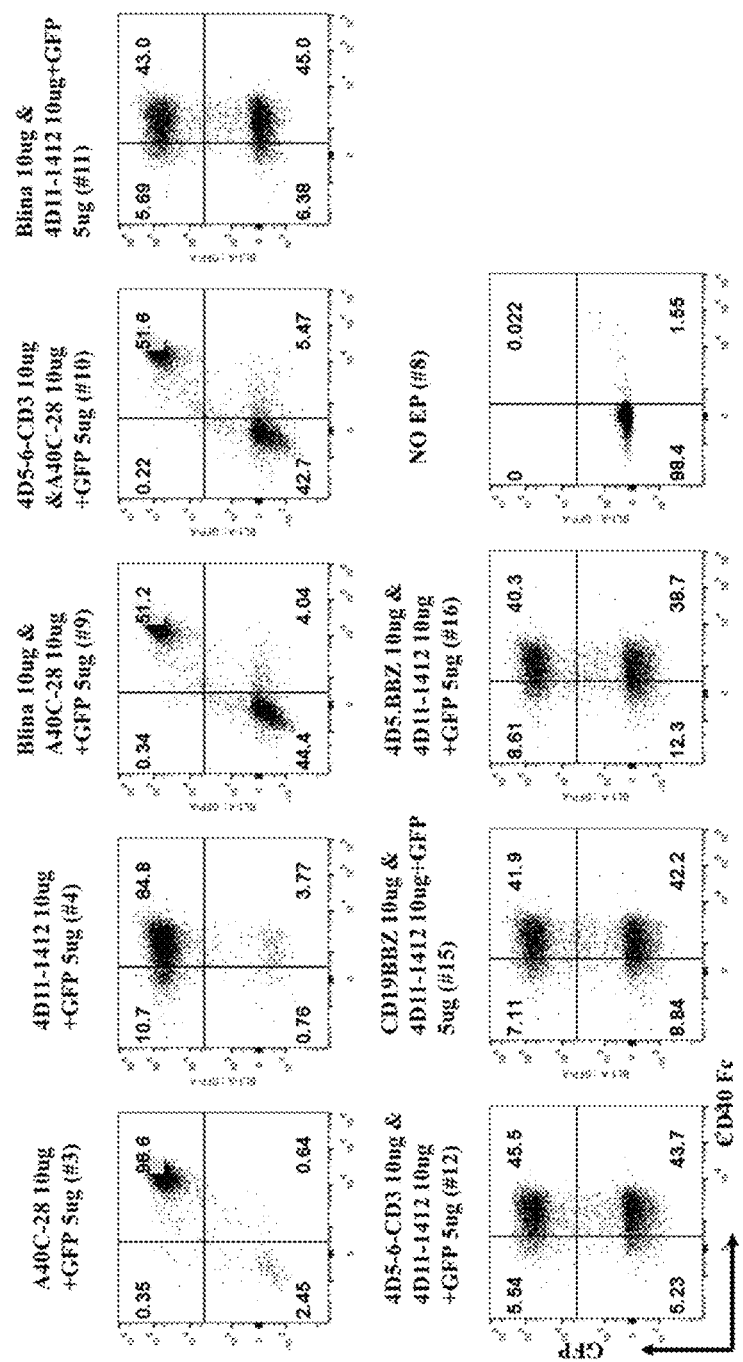

FIG. 72 provides flow cytometry data detecting GFP and LACO-stim (CD40 Fc) in T cells expressing LACO (A40C-28 or 4D11-1412), BITE (aCD19/CD3: "Blina" or aHer2/CD3: "4D5-6-CD3") and/or CAR (anti-Her2, 4D5.BBz).

Figure 73:
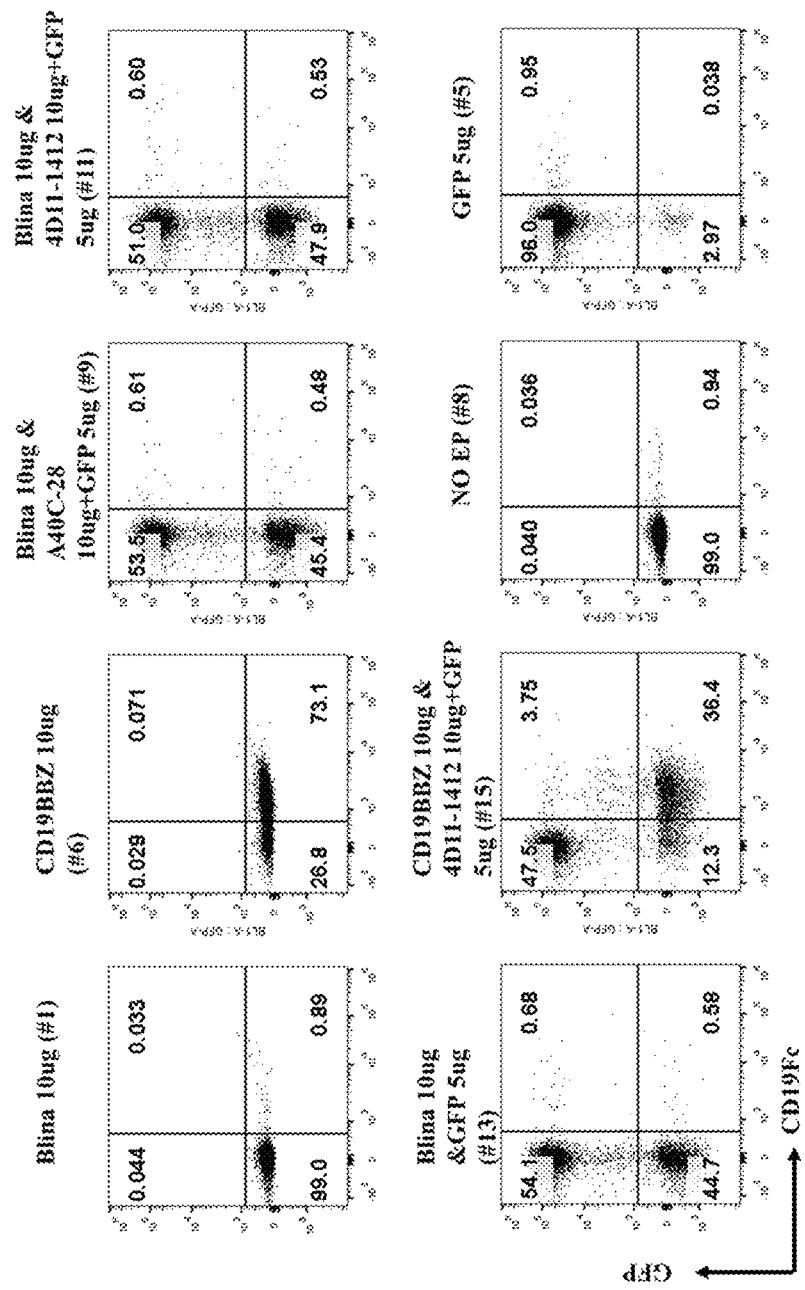

FIG. 73 provides flow cytometry data detecting GFP and CD19 CAR (CD19-Fc) in T cells.

Figure 74:
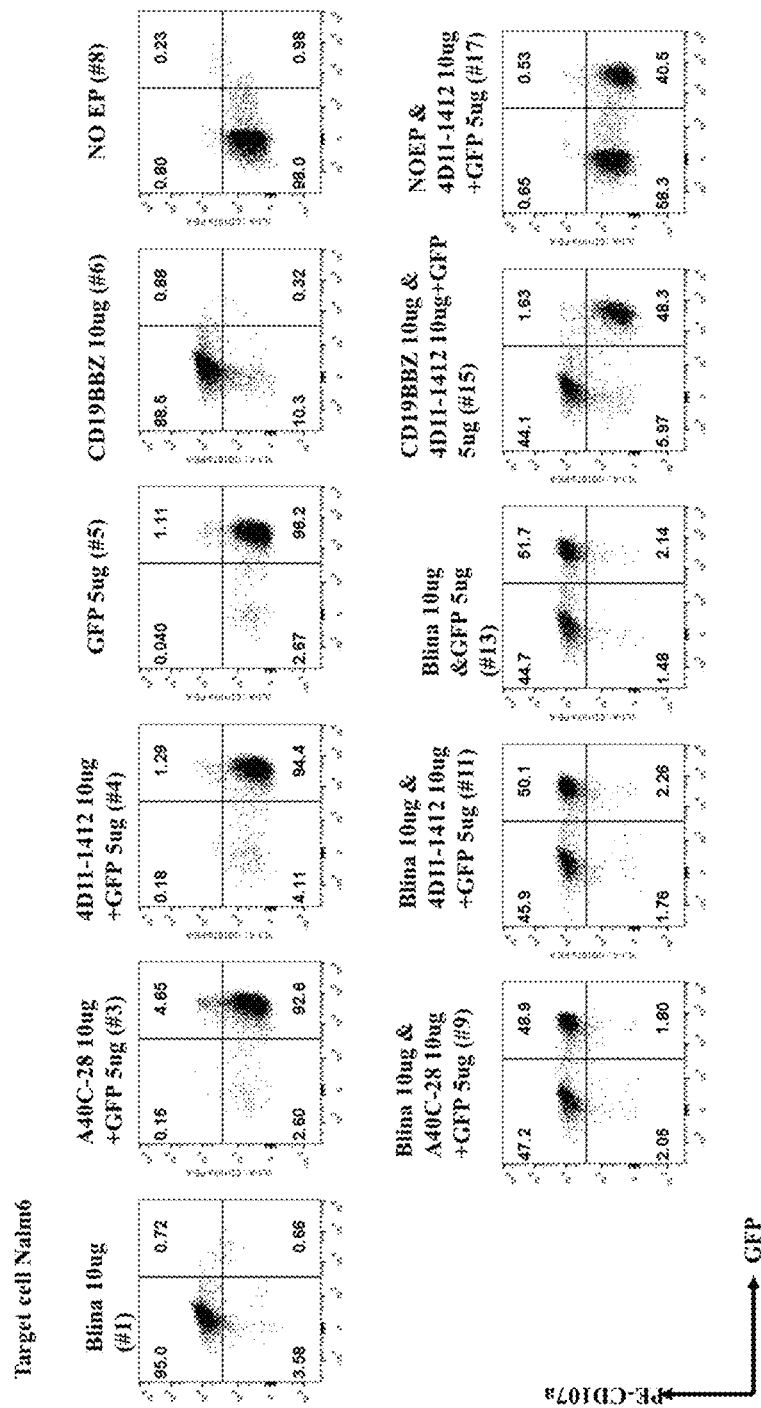

FIG. 74 provides flow cytometry data detecting GFP and CD107a of the T cells stimulated with a CD19 positive tumor line Nalm6.

Figure 75:
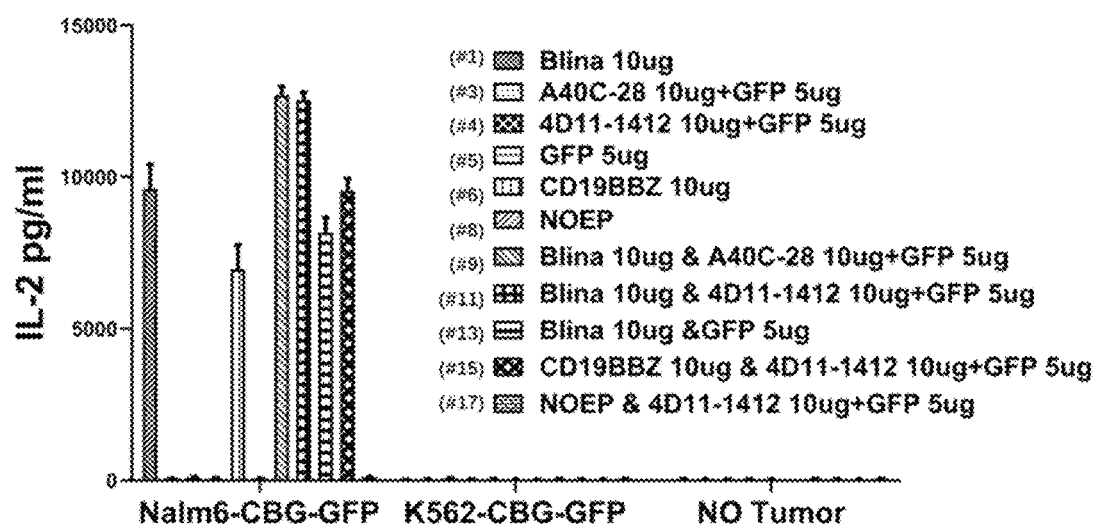

FIG. 75 provides ELISA data showing IL-2 secretion by T cells stimulated with a CD19 positive tumor line Nalm6.

Figure 76:
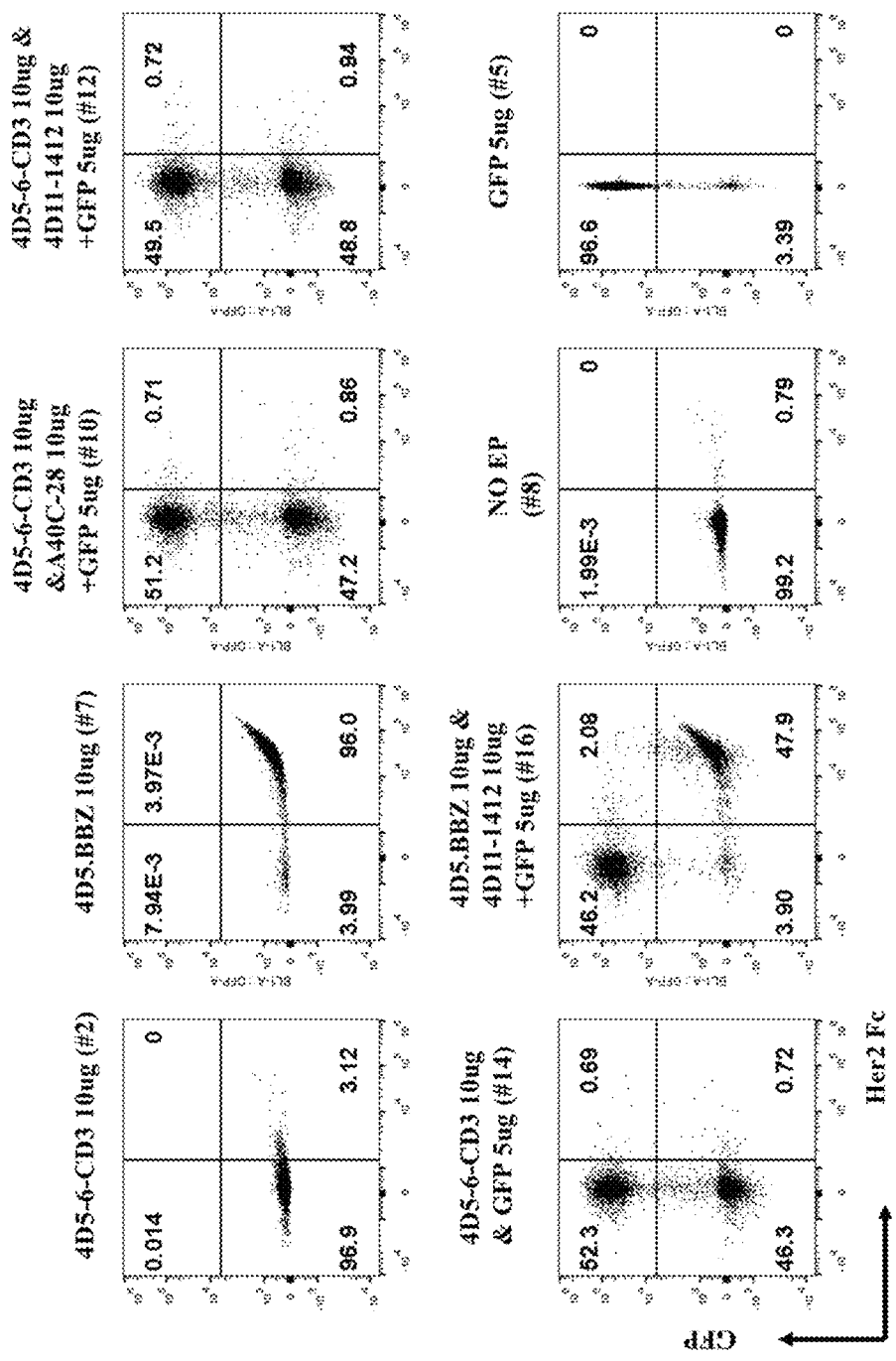

FIG. 76 provides flow cytometry data detecting GFP and Her2 BiTE (4D5-6-CD3) or CAR (4D5.BBZ) (Her2-FC) of the T cells.

Figure 77:
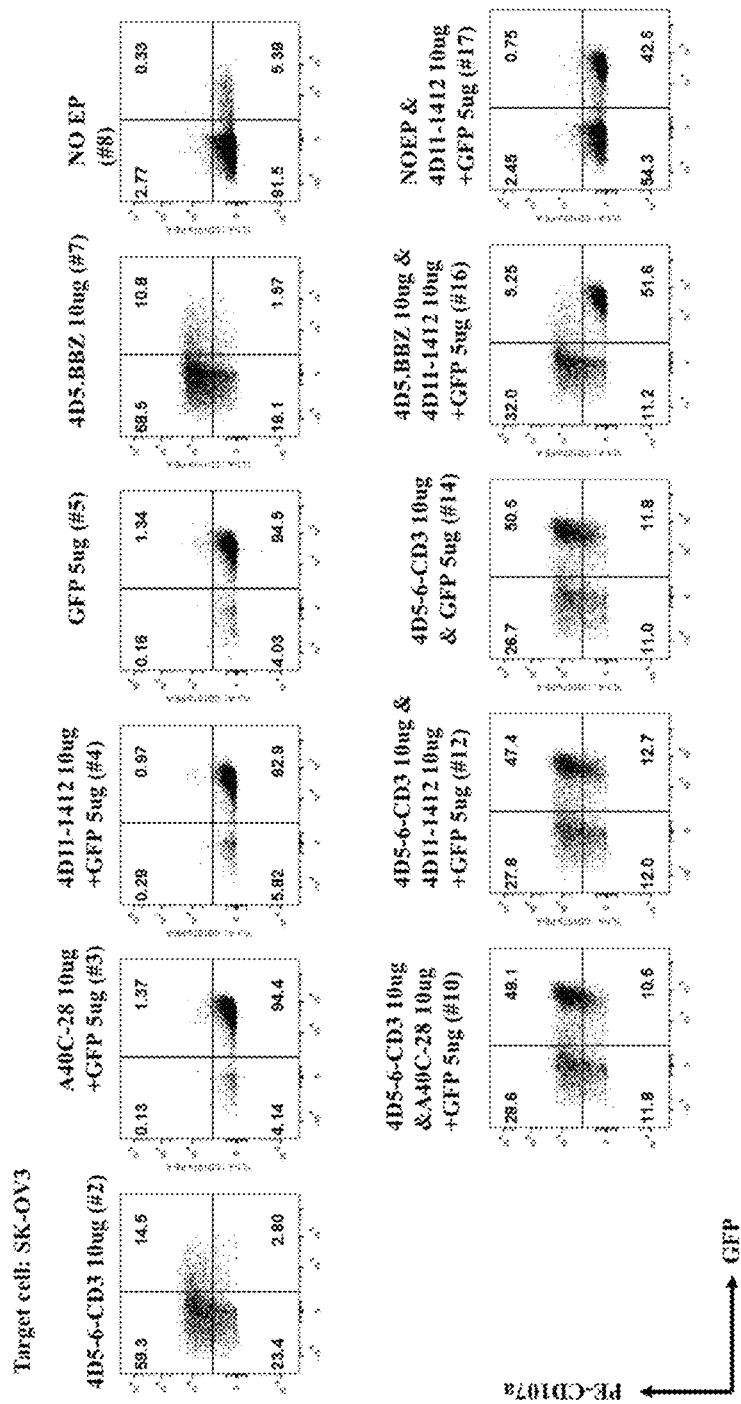

FIG. 77 provides flow cytometry data detecting GFP and CD107a of the T cells stimulated with a Her2 positive tumor line SK-OV3.

Figure 78:
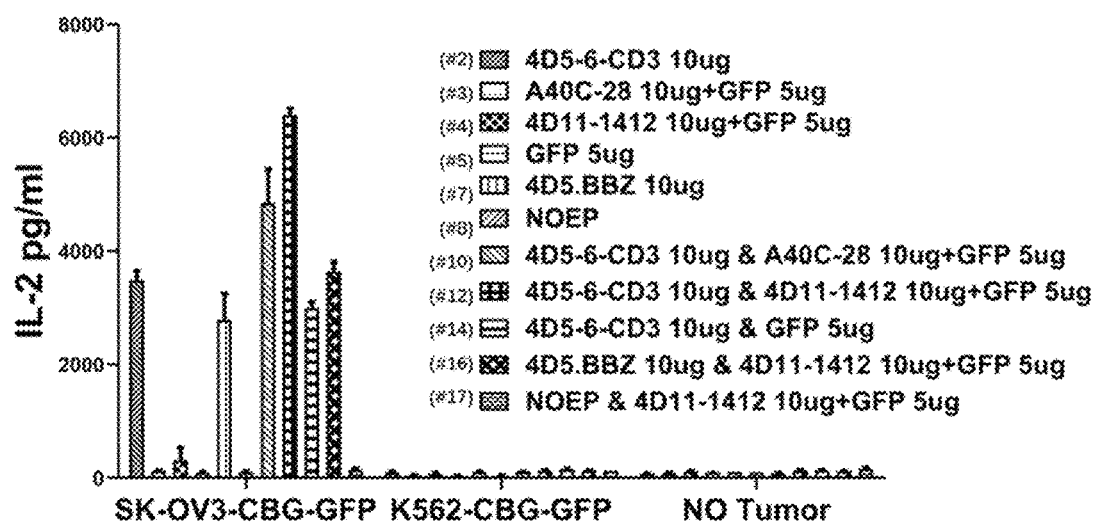

FIG. 78 provides ELISA data showing IL-2 secretion by T cells stimulated with a Her2 positive tumor line SK-OV3.

5. DETAILED DESCRIPTION

Before the present disclosure is further described, it is to be understood that the disclosure is not limited to the particular embodiments set forth herein, and it is also to be understood that the terminology used herein is for the purpose of describing particular embodiments, and is not intended to be limiting.

The present disclosures relate to fusion proteins that comprise two functional domains, wherein the first domain can activate an antigen-presenting cell, and the second domain can activate an immune effector cell. The fusion proteins of the present disclosure are also referred to as Lymphocytes-Antigen presenting cells Co-stimulators ("LACO-Stims"). Expression of the fusion proteins disclosed herein can not only promote the proliferation and activation of immune effector cells (e.g., T cells), but also stimulate the maturation and epitope spreading activities of antigen-presenting cells. In some embodiments, expression of the fusion proteins in genetically engineered T cell disclosed herein helps them overcome immunosuppression in tumor microenvironment mediated by such as the PD1/PD-L1 signaling, regulatory T cells (Tregs) and TGF-beta signaling, and enhances their anti-tumor activities.

5.1 Definitions

Unless otherwise defined herein, scientific and technical terms used in the present disclosures shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The terms "polypeptide," "peptide," "protein," and their grammatical equivalents as used interchangeably herein refer to polymers of amino acids of any length, which can be linear or branched. It can include unnatural or modified amino acids or be interrupted by non-amino acids. A polypeptide, peptide, or protein can also be modified with, for example, disulfide bond formation, glycosylation, lipidation, acetylation, phosphorylation, or any other manipulation or modification.

The term "fusion protein" as used herein refers to a protein, peptide or polypeptide that has an amino acid sequence derived from two or more separate proteins, peptides or polypeptides. The fusion protein also includes a linking region of amino acids between amino acid portions derived from separate proteins, peptides, or polypeptides. Such linking region of amino acids is referred herein as a "linker."

The term "variant" as used herein in relation to a protein or a polypeptide with particular sequence features (the "reference protein" or "reference polypeptide") refers to a different protein or polypeptide comprising one or more (such as, for example, about 1 to about 25, about 1 to about 20, about 1 to about 15, about 1 to about 10, or about 1 to about 5) amino acid substitutions, deletions, and/or additions as compared to the reference protein or reference polypeptide. The changes to an amino acid sequence can be amino acid substitutions. The changes to an amino acid sequence can be conservative amino acid substitutions. A functional fragment or a functional variant of a protein or polypeptide maintains the basic structural and functional properties of the reference protein or polypeptide.

The terms "polynucleotide," "nucleic acid," and their grammatical equivalents as used interchangeably herein mean polymers of nucleotides of any length and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical," percent "identity," and their grammatical equivalents as used herein in the context of two or more polynucleotides or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, Megalign, BestFit, GCG Wisconsin Package, and variants thereof. In some embodiments, two polynucleotides or polypeptides provided herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-1000 bases or more, and in some embodiments the sequences are substantially identical over the full length of the sequences being compared, such as a nucleotide sequence encoding a protein of interest.

The term "antibody," and its grammatical equivalents as used herein refer to an immunoglobulin molecule that recognizes and specifically binds a target, such as a protein, polypeptide, peptide, carbohydrate, polynucleotide, lipid, or a combination of any of the foregoing, through at least one antigen-binding site wherein the antigen-binding site is usually within the variable region of the immunoglobulin molecule. As used herein, the term encompasses intact polyclonal antibodies, intact monoclonal antibodies, single-domain antibodies (sdAbs; e.g., camelid antibodies, alpaca antibodies), single-chain Fv (scFv) antibodies, heavy chain antibodies (HCAbs), light chain antibodies (LCAbs), multispecific antibodies, bispecific antibodies, monospecific antibodies, monovalent antibodies, and any other modified immunoglobulin molecule comprising an antigen-binding site (e.g., dual variable domain immunoglobulin molecules) as long as the antibodies exhibit the desired biological activity. Antibodies also include, but are not limited to, mouse antibodies, camel antibodies, chimeric antibodies, humanized antibodies, and human antibodies. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. Unless expressly indicated otherwise, the term "antibody" as used herein include "antigen-binding fragment" of intact antibodies. The term "antigen-binding fragment" as used herein refers to a portion or fragment of an intact antibody that is the antigenic determining variable region of an intact antibody. Examples of antigen-binding fragments include, but are not limited to, Fab, Fab', F(ab')2, Fv, linear antibodies, single chain antibody molecules (e.g., scFv), heavy chain antibodies (HCAbs), light chain antibodies (LCAbs), disulfide-linked scFv (dsscFv), diabodies, tribodies, tetrabodies, minibodies, dual variable domain antibodies (DVD), single variable domain antibodies (sdAbs; e.g., camelid antibodies, alpaca antibodies), and single variable domain of heavy chain antibodies (VHH).

The term "vector," and its grammatical equivalents as used herein refer to a vehicle that is used to carry genetic material (e.g., a polynucleotide sequences), which can be introduced into a host cell, where it can be replicated and/or expressed. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more polynucleotides are to be co-expressed, both polynucleotides can be inserted, for example, into a single expression vector or in separate expression vectors. For single vector expression, the encoding polynucleotides can be operationally linked to one common expression control sequence or linked to different expression control sequences, such as one inducible promoter and one constitutive promoter. The introduction of polynucleotides into a host cell can be confirmed using methods well known in the art. It is understood by those skilled in the art that the polynucleotides are expressed in a sufficient amount to produce a desired product (e.g., a fusion protein as described herein), and it is further understood that expression levels can be optimized to obtain sufficient expression using methods well known in the art.

The term "genetic engineering" or its grammatical equivalents when used in reference to a cell is intended to mean alteration of the genetic materials of the cell that is not normally found in a naturally occurring cell. Genetic alterations include, for example, modifications introducing expressible polynucleotides, other additions, mutations/alterations, deletions and/or other functional disruption of the cell's genes. Such modifications can be done in, for example, coding regions and functional fragments thereof of a gene. Additional modifications can be done in, for example, non-coding regulatory regions in which the modifications alter expression of a gene.

The term "transfer," "transduce," "transfect," and their grammatical equivalents as used herein refer to a process by which an exogenous polynucleotide is introduced into the host cell. A "transferred," "transfected," or "transduced" cell is one which has been transferred, transduced, or transfected with an exogenous polynucleotide. The cell includes the primary subject cell and its progeny. As is understood in the art, a polynucleotide can be "transfer" into a host cell using any type of approaches, including e.g., a chemical method, a physical method, or a biological method. A polynucleotide is commonly "transduced" into a host cell using a virus. By contrast, a polynucleotide is commonly "transfected" into a host cell using a non-viral approach. These terms are used interchangeable at times, and a person of ordinary skill in the art would readily understand their meanings when used in context.

As used herein, the term "encode" and its grammatical equivalents refer to the inherent property of specific sequences of nucleotides in a polynucleotide or a nucleic acid, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein. Unless otherwise specified, a "nucleotide sequence encoding an amino acid sequence" includes all nucleotide sequences that are degenerate versions of each other and that encode the same amino acid sequence. Nucleotide sequences that encode proteins and RNA can include introns.

A polypeptide, peptide, protein, antibody, polynucleotide, vector, cell, or composition which is "isolated" is a polypeptide, peptide, protein, antibody, polynucleotide, vector, cell, or composition which is in a form not found in nature. Isolated polypeptides, peptides, proteins, antibodies, polynucleotides, vectors, cells, or compositions include those which have been purified to a degree that they are no longer in a form in which they are found in nature. In some embodiments, a polypeptide, peptide, protein, antibody, polynucleotide, vector, cell, or composition which is isolated is substantially pure.

The term "treat" and its grammatical equivalents as used herein in connection with a disease or a condition, or a subject having a disease or a condition refer to an action that suppresses, eliminates, reduces, and/or ameliorates a symptom, the severity of the symptom, and/or the frequency of the symptom associated with the disease or disorder being treated. For example, when used in reference to a cancer or tumor, the term "treat" and its grammatical equivalents refer to an action that reduces the severity of the cancer or tumor, or retards or slows the progression of the cancer or tumor, including (a) inhibiting the growth, or arresting development of the cancer or tumor, (b) causing regression of the cancer or tumor, or (c) delaying, ameliorating or minimizing one or more symptoms associated with the presence of the cancer or tumor.

The term "administer" and its grammatical equivalents as used herein refer to the act of delivering, or causing to be delivered, a therapeutic or a pharmaceutical composition to the body of a subject by a method described herein or otherwise known in the art. The therapeutic can be a compound, a polypeptide, a cell, or a population of cells. Administering a therapeutic or a pharmaceutical composition includes prescribing a therapeutic or a pharmaceutical composition to be delivered into the body of a subject. Exemplary forms of administration include oral dosage forms, such as tablets, capsules, syrups, suspensions; injectable dosage forms, such as intravenous (IV), intramuscular (IM), or intraperitoneal (IP); transdermal dosage forms, including creams, jellies, powders, or patches; buccal dosage forms; inhalation powders, sprays, suspensions, and rectal suppositories.

The terms "effective amount," "therapeutically effective amount," and their grammatical equivalents as used herein refer to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to the subject. The therapeutically effective amount can be ascertained by measuring relevant physiological effects. The exact amount required vary from subject to subject, depending on the age, weight, and general condition of the subject, the severity of the condition being treated, the judgment of the clinician, and the like. An appropriate "effective amount" in any individual case can be determined by one of ordinary skill in the art using routine experimentation.

The term "pharmaceutically acceptable excipient" refers to a material that is suitable for drug administration to an individual along with an active agent without causing any undesirable biological effects or interacting in a deleterious manner with any of the other components of the pharmaceutical composition.

The term "subject" as used herein refers to any animal (e.g., a mammal), including, but not limited to, humans, non-human primates, canines, felines, rodents, and the like, which is to be the recipient of a particular treatment. A subject can be a human. A subject can be a patient with a particular disease or condition.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Exemplary genes and polypeptides are described herein with reference to GenBank numbers, GI numbers and/or SEQ ID NOS. It is understood that one skilled in the art can readily identify homologous sequences by reference to sequence sources, including but not limited to GenBank (ncbi.nlm.nih.gov/genbank/) and EMBL (embl.org/).

5.2 LACO-Stim Fusion Proteins

In some embodiments, provided herein are fusion proteins comprising a first domain that activates an antigen-presenting cell ("APC"; e.g., a dendritic cell) and a second domain that activates an immune effector cell (e.g., a T cell), wherein the first domain comprises (a) a ligand that binds an activation receptor of the APC, or a receptor-binding fragment thereof, or (b) an antibody that binds an activation receptor of the antigen-presenting cell, or an antigen-binding fragment thereof; and wherein the second domain comprises (a) a co-stimulatory receptor of the immune effector cell, or a functional fragment thereof, (b) a co-stimulatory ligand of the immune effector cell, or a receptor-binding fragment thereof, or (c) an antibody that binds a co-stimulatory receptor of the immune effector cell, or an antigen-binding fragment thereof.

In some embodiments, the fusion protein is a membrane protein. In some embodiments, the fusion protein is a soluble protein. In some embodiments, the fusion protein is a bispecific antibody. In some embodiments, the C-terminus of the first domain is linked to the N-terminus of the second domain. In some embodiments, the N-terminus of the first domain is linked to the C-terminus of the second domain.

In some embodiments, the first domain and the second domain are linked via a linker. The linker can be a flexible linker or a rigid linker. In some embodiments, the linker has the amino acid sequence of (GGGGS)n, n=1, 2, 3, 4, or 5 (SEQ ID NO:215). In some embodiments, the linker has the amino acid sequence of (EAAAK)n, n=1, 2, 3, 4, or 5 (SEQ ID NO:216). In some embodiments, the linker has the amino acid sequence of (PA)nP, n=1, 2, 3, 4, or 5 (SEQ ID NO:217). In some embodiments, the linker has the amino acid sequence of GSGGGGSGGGGSGGGGS (SEQ ID NO:219). In some embodiments, the linker has the amino acid sequence of GGGGS (SEQ ID NO:218). In some embodiments, the linker is a CD8 hinge (SEQ ID NO:69). In some embodiments, the linker is a CD28 hinge (SEQ ID NO:70). In some embodiments, the linker is an IgG Fc hinge (SEQ ID NO:71). In some embodiments, the linker can be a trimerization motif selected from the group consisting of a T4 fibritin trimerization motif (SEQ ID NO:1), an isoleucine zipper (SEQ ID NO:2 or 3), a GCN4II motif (SEQ ID NO:4 or 5), a Matrilin-1 motif (SEQ ID NO:6 or 7), and a collagen XV trimerization motif (SEQ ID NO:8).

5.2.1 APC Activators

Fusion proteins provided herein comprise a first domain that activates an antigen presenting cell (APC), wherein the first domain comprises (a) a ligand that binds an activation receptor of the APC, or a receptor-binding fragment thereof, or (b) an antibody that binds an activation receptor of the APC, or an antigen-binding fragment thereof. An APC refers to any cell that displays one or more antigens on its surface, for example, in combination with one or more major histocompatibility complex (MHC) proteins. The MHC/antigen complex can be recognized by T-cells using their T-cell receptors (TCRs) and elicit an immune response.

5.2.1.1 Antigen-Presenting Cells (APCs)

APCs include, for example, dendritic cells (DCs), macrophages, monocytes, myeloid derived suppressor cells, certain B cells, T cells and Langerhans cells.

Dendritic Cells: Dendritic cells (DCs) are bone marrow-derived cells that function as professional antigen presenting cells. Immature DCs are characterized by a high capacity for antigen capture and processing, but low T cell stimulatory capability. Inflammatory mediators promote DC maturation. Once DCs have reached the mature stage, they have undergone a dramatic change in their properties. Specifically, they have substantially lost the ability to capture antigen and have acquired an increased capacity to stimulate T cells. Typically, mature DCs present antigen that has been captured at the level of peripheral tissues to naive T cells.

Macrophages: Macrophages are immune cells that are specialized for detection, phagocytosis, and destruction of target cells including pathogens and tumor cells. As such, macrophages are potent effectors of the innate immune system and are capable of at least three distinct anti-tumor functions: phagocytosis of dead and dying cells, cytotoxicity against tumor cells themselves, and presentation of tumor antigens to orchestrate an adaptive anti-tumor immune responses. In adult humans, unpolarized, uncommitted, or resting macrophages (M0) differentiate from bone marrow-derived monocyte precursors and express the common markers of the lineage, including CD 14, CD 16, CD64, CD68, CD71, and CCR5. Exposure to various stimuli can induce M0 macrophages to polarize into several distinct populations identified by surface marker and cytokine/chemokine secretion.

Monocytes: Monocytes are multipotent cells that circulate in the blood, bone marrow, and spleen, and generally do not proliferate when in a steady state. Typically, they comprise chemokine receptors and pathogen recognition receptors that mediate migration from blood to tissues, for example, during an infection. Monocytes can produce inflammatory cytokines and/or take up cells and toxic molecules and can also differentiate into inflammatory DCs or macrophages.

Myeloid derived suppressor cells: Myeloid-derived suppressor cells (MDSCs) are a heterogeneous population of cells that expand in cancer, inflammation, infection and transplantation. MDSCs have a remarkable ability to regulate adaptive and innate immune responses. Despite the widely accepted immunosuppressive capacities of MDSC, a new function has emerged which is immune stimulation and antitumor activity. MDSCs consist of myeloid progenitor cells and immature myeloid cells, which can propagate continuously in pathological conditions, and are the main source of APCs. (Li A et al, *Int J Clin Exp Med* 2017; 10(8):12217-12222)

B Cells: B cells account for up to 25% of all cells in some tumors and that 40% of tumor-infiltrating lymphocytes in some breast cancer subjects are B cells (Yuen et al. *Trends Cancer,* 2016, 2(12): 747-757). Additionally, therapeutic immune checkpoint blockade may also target activated B cells, in additional to activated T cells, since PD-1, PD-L1, CTLA-4, and the B7 molecules are expressed on B cells. In addition to the immune-regulatory function of producing antibodies and antibody-antigen complexes, B cells can affect the functions of other immune cells by presenting antigens, providing co-stimulation and secreting cytokines. Membrane-bound immunoglobulin on the B cell surface serves as the cell's receptor for antigen and is known as a B cell receptor (BCR). Activation of BCRs on the surface of a B cell leads to clonal expansion of that B cell and specific antibody production. Additionally, B cells can internalize an antigen that binds to a BCR and present it to helper (CD4+) T cells. Unlike T cells, B cells can recognize soluble antigen for which their BCR is specific.

T cells: T cells are immune effector cells that play important roles in the induction and maintenance of an effective immune response, such as an antiviral response or antitumor response. It has been recognized in the art that T cells can also present peptide epitopes from both viral antigens and tumor antigens. See e.g., Atanackovic et al., *Journal of immunological methods* 278.1-2 (2003): 57-66.

Langerhans cells: Langerhans cells constitute the first line of immunologic defense in the skin. These cells are derived from the bone marrow and can normally be found scattered among the keratinocytes of the stratum spinosum. Langerhans cells are APCs derived from the monocyte lineage and function in the afferent limb of the immune response. They take up foreign invaders and process them to present to T cells. Once they present antigens, they migrate to lymph nodes to activate T cells. These cells are essential for the induction of delayed-type hypersensitivity reactions.

5.2.1.2 Activation Receptor of APCs

As understood in the art, a molecule can activate an APC by promoting its maturation, pro-inflammatory status, cytotoxicity, antigen-presentation, epitope-spreading, cytokine production, co-stimulation of immune effector cells (e.g., T cells), or any combination thereof. In some embodiments, the first domains of fusion proteins provided herein activate an APC by promoting the maturation and activation of the APC (e.g., a DC). In some embodiments, the first domains of fusion proteins provided herein activate an APC by promoting epitope spreading among the APCs and other immune effector cells (e.g., T cells). In some embodiments, the first domains of fusion proteins provided herein activate an APC by promoting antigen-presentation of the APC. In some embodiments, the first domains of fusion proteins provided herein activate an APC by promoting its cytotoxicity against the foreign substance (e.g., the cancer cell).

In some embodiments, fusion proteins provided herein comprise a first domain that activates an APC, which comprises a ligand that binds an activation receptor of the APC, or a receptor-binding fragment thereof. An "activation receptor" refers to a membrane protein expressed on the APC that can elicit signaling to promote the mobilization, differentiation, proliferation, and/or activation of the APC upon binding with a ligand or an antibody. APC activation receptors include, for example, CD40, CD80, CD86, CD91, DEC-205, and DC-SIGN.

A "ligand" of a receptor refers to a molecule that can selectively bind the receptor. In some embodiments, the ligand is a polypeptide. A "receptor-binding fragment" of a ligand refers to a fragment of the ligand that retains its capacity to bind its receptor. Various ligands can stimulate the growth, differentiation, migration, and/or activation of dendritic cells or other APCs by binding to an activation receptor on the APCs. (See, e.g., Banchereau J et al., *Nature* (1998) 392: 245-52; Young J W et al., *Stem Cells* (1996) 14:376-387; Cella M et al., *Curr Opin Immunol.* (1997) 9:10-16; Curti A et al., *J. Biol. Regul. Homeost. Agents* (2001) 15:49-52). Examples of ligands that can modulate differentiation, maturation, expansion and/or activation of dendritic cells or other APCs include, for example, CD40 ligand (CD40L), CD80 ligand, CD86 ligand, CD91 ligand (RAP1), DEC-205 ligand, and DC-SIGN ligand. In some embodiments, fusion proteins provided herein include a first domain that comprises a ligand disclosed herein that binds an activation receptor of APCs, or a receptor-binding fragment thereof.

In some embodiments, the first domain of the fusion proteins provided herein comprises an antibody that binds an activation receptor of an APC, or an antigen-binding fragment thereof. In some embodiments, the first domain of the fusion proteins provided herein comprises an antibody or an antigen-binding fragment that binds CD40, CD80, CD86, CD91, DEC-205, or DC-SIGN. CD40/CD40L: CD40 is a 48 kD transmembrane glycoprotein surface receptor that is a member of the Tumor Necrosis Factor Receptor superfamily (TNFRSF). Exemplary amino acid sequences of human CD40 are described (see, e.g., Accession: ALQ33424.1 GI: 957949089; SEQ ID NO:166), CD40 was initially characterized as a co-stimulatory receptor expressed on APCs that played a central role in B and T cell activation. The ligand for CD40, CD154 (also known as TRAP, T-BAM, CD40 Ligand or CD40L) is a type II integral membrane protein. CD40L has been reported to promote induction of dendritic cells and facilitate development of immunogenic responses. See, e.g., Elgueta R et. al., *Immunol Rev.* (2009) 229(1): 10.1111; Ma D & Clark E A, *Semin Immunol.* 2009 21(5): 265-272; Borges L et al., *J Immunol.* (1999) 163:1289-1297; Grewal I, *Immunol Res.* (1997) 16:59-70. Exemplary polynucleotides that encode CD40 ligand and equivalents are described (see, e.g., Genbank Accession Nos. X65453 and L07414), as are preparations, compositions, and methods of use (U.S. Pat. No. 6,290,972). An exemplary amino acid sequence for human CD40L is provided below. The extracellular domain (SEQ ID NO:12) is underlined.

```
                                       (SEQ ID NO: 9)
MIETYNQTSPRSAATGLPISMKIFMYLLTVFLITQ

MIGSALFAVYLHRRLDKIEDERNLHEDFVFMKTIQ

RCNTGERSLSLLNCEEIKSQFEGFVKDIMLNKEET

KKENSFEMQKGDQNPQIAAHVISEASSKTTSVLQW

AEKGYYTMSNNLVTLENGKQLTVKRQGLYYIYAQV

TFCSNREASSQAPFIASLCLKSPGRFERILLRAAN

THSSAKPCGQQSIHLGGVFELQPGASVFVNVTDPS

QVSHGTGFTSFGLLKL
```

In some embodiments, the first domain of the fusion proteins provided herein comprises CD40L or a receptor-binding fragment of CD40L. In some embodiments, the receptor-binding fragment of CD40L comprises amino acids 119-261 of CD40L (SEQ ID NO:9). In some embodiments, the receptor-binding fragment of CD40L comprises the extracellular domain of CD40L. In some embodiments, the first domain of the fusion proteins provided herein comprises three copies of CD40L or a receptor-binding fragment of CD40L. In some embodiments, the first domain of the fusion proteins provided herein comprises three copies of amino acids 119-261 of CD40L (SEQ ID NO:9). In some embodiments, the first domain of the fusion proteins provided herein comprises an antibody that binds CD40, or an antigen-binding fragment thereof.

CD80 and CD86: CD80 (B7.1) and CD86 (B7.2) expressed on antigen presenting cells play important roles of costimulatory molecules necessary for a sustained immune response. Exemplary amino acid sequences of human CD80 are described (see, e.g., Accession: EAW79565.1 GI: 119599971; SEQ ID NO:54). Exemplary amino acid sequences of human CD86 are described (see, e.g., Accession: NP_787058.5 GI: 1519311816; SEQ ID NO:57). CD80 and CD86 can bind to either CD28 or CTLA-4 (ligands for CD80/CD86, also referred to as their counter receptors on T cells), although with different affinity. CD80 is expressed on activated B cells and interferon induced monocytes, but not resting B cells. CD86 is constitutively expressed at very low levels on resting monocytes, dendritic cells and B cells, and its expression is enhanced on activated T cells, NK cells and B lymphocytes. Both CD80 and CD86 contain extracellular immunoglobulin superfamily V and C-like domains, a hydrophobic transmembrane region and a cytoplasmic tail. Both CD80 and CD86 are heavily glycosylated. CD80 is a 44-54 kD glycoprotein comprised of a 223 amino acid extracellular domain, a 23 amino acid transmembrane domain, and a 61 amino acid cytoplasmic tail. CD80 contains 3 potential protein kinase phosphorylation sites. CD86 is a 306 amino acid membrane glycoprotein. It consists of a 220 amino acid extracellular region, a 23 amino acid hydrophobic transmembrane domain and a 60 amino acid cytoplasmic tail.

In some embodiments, the first domain of the fusion proteins provided herein comprises a CD80 ligand or a receptor-binding fragment of the CD80 ligand. In some embodiments, the first domain of the fusion proteins provided herein comprises a CD86 ligand or a receptor-binding fragment of the CD86 ligand. In some embodiments, the CD80/CD86 ligand is CD28. In some embodiments, the receptor-binding fragment of the CD80/CD86 ligand comprises the extracellular domain of CD28. In some embodiments, the CD80/CD86 ligand is CTLA-4. In some embodiments, the receptor-binding fragment of the CD80/CD86 ligand comprises the extracellular domain of CTLA-4. In some embodiments, the CD80 ligand is PD-L1. In some embodiments, the receptor-binding fragment of the CD80 ligand comprises the extracellular domain of PD-L1. In some embodiments, the first domain of the fusion proteins provided herein comprises an antibody that binds CD80, or an antigen-binding fragment thereof. In some embodiments, the first domain of the fusion proteins provided herein comprises an antibody that binds CD86, or an antigen-binding fragment thereof.

CD91/RAP1: CD91 is a receptor on APCs that influences response to nascent tumors. (Sedlacek A L et al., *JCI Insight*. 2019; 4(7): e127239). Exemplary amino acid sequences of human CD91 are described (see, e.g., Accession: NP_002323.2 GI: 126012562; SEQ ID NO:60). CD91 provides an essential and highly efficient conduit for cross-presentation of tumor antigens to T cells, and this pathway is necessary for mounting successful immune responses for surveillance of tumors. CD91 is also involved in activating NK cell responses, activating DCs to produce costimulation, and priming T cells. Receptor-associated protein (RAP1) with a molecular weight of 39 kDa is an ER resident protein and molecular chaperone for LDL receptor-related protein that has a high binding affinity to CD91 (Kd: about 3 nM) and capable of activating the CD91 signaling in APCs. Exemplary polynucleotides that encode RAP1 and equivalents are described (see, e.g., Genbank Accession Nos. AAI12068.1, AAI05075.1, and P30533.1). An exemplary amino acid sequence for human RAP1 is provided below. Domain 3 of RAP1 (amino acid resides 219-323 of RAP1, SEQ ID NO:168), which binds CD91, is underlined.

```
                                         (SEQ ID NO: 167)
MAPRRVRSFLRGLPALLLLLLFLGPWPAASHGGKY

SREKNQPKPSPKRESGEEFRMEKLNQLWEKAQRLH

LPPVRLAELHADLKIQERDELAWKKLKLDGLDEDG

EKEARLIRNLNVILAKYGLDGKKDARQVTSNSLSG

TQEDGLDDPRLEKLWHKAKTSGKFSGEELDKLWRE

FLHHKEKVHEYNVLLETLSRTEEIHENVISPSDLS
```

-continued
```
DIKGSVLHSRHTELKEKLRSINQGLDRLRRVSHQG

YSTEAEFEEPRVIDLWDLAQSANLTDKELEAFREE

LKHFEAKIEKHNHYQKQLEIAHEKLRHAESVGDGE

RVSRSREKHALLEGRTKELGYTVKKHLQDLSGRIS

RARHNEL
```

In some embodiments, the first domain of the fusion proteins provided herein comprises RAP1 or a receptor-binding fragment of RAP1. In some embodiments, the receptor-binding fragment of RAP1 comprises domain 3 of RAP1. In some embodiments, the first domain of the fusion proteins provided herein comprises an antibody that binds CD91, or an antigen-binding fragment thereof.

DEC-205: The function of an APC has been connected to high levels in the expression of the DEC-205 receptor, also called CD205 or lymphocytic antigen 75, especially in dendritic cells located in areas of T cells of peripheral or secondary lymph organs. Exemplary amino acid sequences of human DEC-205 are described (see, e.g., Accession: NP_002340.2 GI: 144446030; SEQ ID NO:63). The DEC-205 receptor is an endocytic receptor with a broad extracellular domain that contains various subdomains: a cysteine-rich (CR) domain, a fibronectin type II (FN) domain and 10 contiguous carbohydrate recognition domains (CRDs). These multi-lectin domains affect the efficiency of the processing and presentation of antigens in vivo. The pioneering experiments that described the cellular processes of directing an antigen were carried out using the DEC-205 human receptor, where the T-cell-mediated response changes dramatically when the maturation stimulus of the dendritic cells is added at the same time as the directing of the antigen using an antibody directed against the DEC-205 receptor. The proliferation of T cells increases by various orders of magnitude when compared to a classic immunization protocol. When the antigens are directed at the dendritic cells via DEC-205, there is an increase in the stimulation of the cooperating T cells (Th); this triggers or promotes the humoral immune response or antibody production.

In some embodiments, the first domain of the fusion proteins provided herein comprises a DEC-205 ligand or a receptor-binding fragment of a DEC-205 ligand. Keratins are natural ligands for DEC-205. In some embodiments, the first domain of the fusion proteins provided herein comprises a keratin or a receptor-binding fragment of a keratin. In some embodiments, the first domain of the fusion proteins provided herein comprises an antibody that binds DEC-205, or an antigen-binding fragment thereof.

DC-SIGN: DC specific ICAM-3 grabbing non-integrin (DC-SIGN) receptor is a C-type lectin containing an external calcium-dependent mannose binding lectin domain. DC-SIGN interacts with a variety of compounds such as the envelope glycoprotein gp120 of human immunodeficiency virus type 1 (HIV-1), HIV-2 and simian immunodeficiency virus (SIV) as well as other pathogens such as hepatitis C, Ebola, cytomegalovirus, Dengue virus, *Mycobacterium, Leishmania, Candida albicans* and *Helicobacter pylori*. DC-SIGN plays an important role in pathogen transmission and the establishment of infection. Exemplary amino acid sequences of human DC-SIGN are described (see, e.g., Accession: AAK20997.1 GI: 13383468; SEQ ID NO:66).

The DC-SIGN receptor is also capable of binding ICAM2 and ICAM3. ICAM2 is expressed on endothelial cells and ICAM3 is expressed on T cells. DC-SIGN furthermore interacts with β2-integrin Mac-1 (CD11b/CD18), which is expressed on neutrophils and promotes the interaction with DC cells, therefore controlling the immune responses mounted. As another example, CEACAM1, which is expressed on neutrophils is also capable of interacting with DC-SIGN.

In some embodiments, the first domain of the fusion proteins provided herein comprises a DC-SIGN ligand or a receptor-binding fragment of the DC-SIGN ligand. In some embodiments, the DC-SIGN ligand is ICAM2, ICAM3, CD18, or CEACAM1, or a receptor-binding fragment thereof. In some embodiments, the DC-SIGN ligand is ICAM2 or a receptor-binding fragment thereof. Exemplary amino acid sequences of human ICAM2 are described (see, e.g., Accession: CAG46611.1 GI: 49456581; SEQ ID NO:169). In some embodiments, the DC-SIGN ligand is ICAM3 or a receptor-binding fragment thereof. Exemplary amino acid sequences of human ICAM3 are described (see, e.g., Accession: P32942.2 GI: 206729872; SEQ ID NO:170). In some embodiments, the DC-SIGN ligand is CD18 or a receptor-binding fragment thereof. Exemplary amino acid sequences of human CD18 are described (see, e.g., Accession: P05107.2 GI: 124056465; SEQ ID NO:171). In some embodiments, the DC-SIGN ligand is CEACAM1 or a receptor-binding fragment thereof. Exemplary amino acid sequences of human CEACAM1 are described (see, e.g., Accession: AAH14473.1 GI: 15680237; SEQ ID NO:172). In some embodiments, the first domain of the fusion proteins provided herein comprises an antibody that binds DC-SIGN, or an antigen-binding fragment thereof.

5.2.2 Co-Stimulatory Receptors of Immune Effector Cells

In some embodiments, provided herein are fusion proteins comprising a first domain that activates an antigen-presenting cell (e.g., a dendritic cell) and a second domain that activates an immune effector cell (e.g., a T cell), wherein the second domain comprises (a) a co-stimulatory receptor of the immune effector cell, or a functional fragment thereof, (b) a co-stimulatory ligand of the immune effector cell, or a receptor-binding fragment thereof, or (c) an antibody that binds a co-stimulatory receptor of the immune effector cell, or an antigen-binding fragment thereof.

"Immune effector cells" as used herein and understood in the art refer to cells that are of hematopoietic origin and play a direct role in the immune response against a target, such as a pathogen, a cancer cell, or a foreign substance. Immune effector cells include T cells, B cell, natural killer (NK) cells, NKT cells, macrophages, granulocytes, neutrophils, eosinophils, mast cells, and basophils. In some embodiments, the second domain of the fusion proteins provided herein that activates an immune effector cell comprises a co-stimulatory receptor of the immune effector cell. In some embodiments, the immune effector cell is a T cell, an NK cell, an NKT cell, a macrophage, a neutrophil, or a granulocyte. In some embodiments, the immune effector cell is a T cell. In some embodiments, the immune effector cell is a NK cell. In some embodiments, the immune effector cell is a macrophage.

"Stimulation" of an immune effector cell means a primary response induced by binding of a stimulatory molecule with its cognate ligand thereby mediating a signal transduction event in the immune effector cell which can alter expression of certain genes and/or reorganization of cytoskeletal structures, and the like. A "stimulatory molecule" of an immune effector cell refers to a molecule on the immune effector cell that, upon binding with its cognate ligand, which is commonly present on an APC, can mediate signal transduction to promote the maturation, differentiation, proliferation, and/or activation of the immune effector cell. For example, a stimulatory molecule of the T cells, the TCR/CD3 complex triggers the activation of the T cells. The ligand for a stimulatory molecule, or "stimulatory ligand," means a ligand that is commonly present on an APC and can bind with a stimulatory molecule on the immune effector cell to mediate a primary response by the immune effector cell, including, but not limited to, maturation, differentiation, activation, initiation of an immune response, proliferation, and the like. Stimulatory ligands are well-known in the art and encompass, for example, an MHC Class I molecule loaded with a peptide, an anti-CD3 antibody, a superagonist anti-CD28 antibody, and a superagonist anti-CD2 antibody.

A "co-stimulatory signal," as used herein and understood in the art, refers to a signal from a co-stimulatory receptor (e.g., CD28 or 4-1BB), which in combination with a primary signal (e.g., TCR/CD3) promotes optimal clonal expansion, differentiation and effector functions of immune effector cells (e.g., T cells). A "co-stimulatory receptor" of an immune effector cell, s used herein and understood in the art, refers to a molecule on the immune effector cell that specifically binds with a "co-stimulatory ligand" to mediate a co-stimulatory response by the immune effector cell, such as heightened activation or proliferation of the immune effector cell. Co-stimulatory receptors for immune effector cells include, but are not limited to, CD28, 4-1BB, ICOS, CD27, OX40, DAP10, CD30, 2B4, CD2, LIGHT, GITR, TLR, DR3, and CD43. A "functional fragment" of a co-stimulatory receptor is a fragment of the co-stimulatory receptor that retains its function to mediate a co-stimulatory signal and stimulate the immune effector cell. In some embodiments, a functional fragment of a co-stimulatory receptor retains the co-stimulatory domain of the co-stimulatory receptor. In some embodiments, the co-stimulatory domain is the cytoplasmic domain of the co-stimulatory receptor. In some embodiments, signals from co-stimulatory receptors of immune effector cells (e.g., T cells) lower the activation threshold for the immune effector cells. In some embodiments, signals from co-stimulatory receptors of T cells lead to the augmentation of TCR signaling events necessary for efficient cytokine production (via augmented transcriptional activity and messenger RNA stabilization), cell cycle progression, survival, regulation of metabolism and T cell responses.

A "co-stimulatory ligand," as used herein and understood in the art, refers to a molecule that specifically binds a cognate co-stimulatory receptor on an immune effector cell, thereby providing a signal which, in addition to the primary signal provided by the stimulatory molecule, mediates a response in the immune effector cell, including, but not limited to, proliferation, activation, differentiation, and the like. The co-stimulatory ligand can be present on an APC (e.g., a dendritic cell). Co-stimulatory ligands include, but are not limited to, CD58, CD70, CD83, CD80, CD86, CD137L (4-1BBL), CD252 (OX40L), CD275 (ICOS-L), CD54 (ICAM-1), CD49a, CD112 (PVRL2), CD150 (SLAM), CD155 (PVR), CD265 (RANK), CD270 (HVEM), TL1A, CD127, IL-4R, GITR-L, TIM-4, CD153 (CD30L), CD48, CD160, CD200R (OX2R), and CD44. A "receptor-binding fragment" of a co-stimulatory ligand refers to a fragment of the ligand that retains its capacity to bind its receptor.

Some co-stimulatory receptors and co-stimulatory ligands are exemplified below. It is understood that any co-stimulatory receptors and/or co-stimulatory ligands provided herein or otherwise known in the art can be used as part of the fusion proteins provided herein.

CD28: Cluster of Differentiation 28 (CD28) is a protein expressed on T cells that provides co-stimulatory signals for T cell activation and survival. CD28 is the receptor for CD80 (B7.1) and CD86 (B7.2) proteins. CD28 is a co-stimulatory receptor for optimal T cell clonal expansion, differentiation and effector functions. CD28 engagement lowers the T cell activation threshold and leads to the augmentation of TCR signaling events necessary for efficient cytokine production (via augmented transcriptional activity and messenger RNA stabilization), cell cycle progression, survival, regulation of metabolism and T cell responses. CD28 is a crucial player for immunological synapse (IS) organization, where it enhances close contact between T cells and APCs.

In some embodiments, provided herein are fusion proteins comprising a first domain that activates an APC and a second domain that activates an immune effector cell, wherein the second domain comprises a CD28 polypeptide, or a functional fragment thereof. In some embodiments, the second domain comprises the cytoplasmic domain of CD28. In some embodiments, provided herein are fusion proteins comprising a first domain that activates an APC and a second domain that activates an immune effector cell, wherein the second domain comprises a ligand or a receptor-binding fragment thereof that binds CD28. In some embodiments, provided herein are fusion proteins comprising a first domain that activates an APC and a second domain that activates an immune effector cell, wherein the second domain comprises an antibody that binds CD28, or an antigen-binding fragment thereof. In some embodiments, the second domain of fusion proteins provided herein comprises a functional fragment of CD28, which comprises a portion of an intracellular/cytoplasmic domain of CD28 that can function as a co-stimulatory signaling domain. A CD28 can have an amino acid sequence corresponding to the sequence having GenBank No. P10747 (P10747.1, GI:115973) or NP_006130 (NP_006130.1, GI:5453611), as provided below, or functional fragments thereof. In one embodiment, a fusion protein disclosed herein can have an amino acid sequence comprising the cytoplasmic domain of CD28 corresponding to amino acids 180 to 220 of CD28 (underlined part of the sequence below, SEQ ID NO:14) or a fragment thereof. In another embodiment, a fusion protein disclosed herein can have an amino acid sequence further comprising the transmembrane domain of CD28 corresponding to amino acids 153 to 179, or a functional fragment thereof. It is understood that sequences of CD28 that are shorter or longer than a specific delineated domain can be included in a fusion protein disclosed herein, if desired.

```
  1  MLRLLLALNL FPSIQVTGNK ILVKQSPMLV AYDNAVNLSC

KYSYNLFSRE FRASLHKGLD

61  SAVEVCVVYG NYSQQLQVYS KTGFNCDGKL GNESVTFYLQ

NLYVNQTDIY FCKIEVMYPP

121  PYLDNEKSNG TIIHVKGKHL CPSPLFPGPS KPFWVLVVVG

GVLACYSLLV TVAFIIFWVR

181  SKRSRLLHSD YMNMTPRRPG PTRKHYQPYA PPRDFAAYRS (NP_006130; SEQ ID NO: 13)
```

4-1BB. 4-1BB, also referred to as tumor necrosis factor receptor superfamily member 9, can act as a tumor necrosis factor (TNF) ligand and have stimulatory activity (Stephan M T et al., Nat Med (2007) 13(12):1440-1449). In some embodiments, provided herein are fusion proteins comprising a first domain that activates an APC and a second domain that activates an immune effector cell, wherein the second domain comprises a 4-1BB polypeptide, or a functional fragment thereof. In some embodiments, the second domain comprises the cytoplasmic domain of 4-1BB. In some embodiments, provided herein are fusion proteins comprising a first domain that activates an APC and a second domain that activates an immune effector cell, wherein the second domain comprises a ligand or a receptor-binding fragment thereof that binds 4-1BB. In some embodiments, provided herein are fusion proteins comprising a first domain that activates an APC and a second domain that activates an immune effector cell, wherein the second domain comprises an antibody that binds 4-1BB, or an antigen-binding fragment thereof. In one embodiment, the second domain of fusion proteins provided herein can comprise a co-stimulatory signaling domain derived from 4-1BB. A 4-1BB polypeptide can have an amino acid sequence corresponding to the sequence having GenBank No. P41273 (P41273.1, GI:728739) or NP_001552 (NP_001552.2, GI:5730095) or fragments thereof. In one embodiment, the second domain of fusion proteins provided herein can have a co-stimulatory domain comprising the cytoplasmic domain of 4-1BB corresponding to amino acids 214 to 255 (underlined part of the sequence below, SEQ ID NO:17), or a functional fragment thereof. It is understood that sequences of 4-1BB that are shorter or longer than a specific delineated domain can be included in a fusion protein disclosed herein, if desired.

```
  1  MGNSCYNIVA TLLLVLNFER TRSLQDPCSN CPAGTFCDNN

RNQICSPCPP NSFSSAGGQR

61  TCDICRQCKG VFRTRKECSS TSNAECDCTP GFHCLGAGCS

MCEQDCKQGQ ELTKKGCKDC

121  CFGTFNDQKR GICRPWTNCS LDGKSVLVNG TKERDVVCGP

SPADLSPGAS SVTPPAPARE

181  PGHSPQIISF FLALTSTALL FLLFFLTLRF SVVKRGRKKL

LYIFKQPFMR PVQTTQEEDG

241  CSCRFPEEEE GGCEL (NP_001552; SEQ ID NO: 16)
```

OX40. OX40, also referred to as tumor necrosis factor receptor superfamily member 4 precursor or CD134, is a member of the TNFR-superfamily of receptors. In some embodiments, provided herein are fusion proteins comprising a first domain that activates an APC and a second domain that activates an immune effector cell, wherein the second domain comprises an OX40 polypeptide, or a functional fragment thereof. In some embodiments, the second domain comprises the cytoplasmic domain of OX40. In some embodiments, provided herein are fusion proteins comprising a first domain that activates an APC and a second domain that activates an immune effector cell, wherein the second domain comprises a ligand or a receptor-binding fragment thereof that binds OX40. In some embodiments, provided herein are fusion proteins comprising a first domain that activates an APC and a second domain that activates an immune effector cell, wherein the second domain comprises an antibody that binds OX40, or an antigen-binding fragment thereof. In one embodiment, the second domain of fusion proteins provided herein can comprise a co-stimulatory signaling domain derived from OX40. An OX40 polypeptide can have an amino acid sequence corresponding to the sequence having GenBank No. P43489 (P43489.1, GI:1171933) or NP_003318 (NP_003318.1, GI:4507579), provided below, or fragments thereof. In one embodiment, fusion proteins provided herein can have a co-stimulatory domain comprising the cytoplasmic domain of OX40 corresponding to amino acids 236 to 277 (underlined part of the sequence below, SEQ ID NO:26), or a functional fragment thereof. It is understood that sequences of OX40 that are shorter or longer than a specific delineated domain can be included in a fusion protein, if desired.

```
  1  MCVGARRLGR GPCAALLLLG LGLSTVTGLH CVGDTYPSND
     RCCHECRPGN GMVSRCSRSQ
 61  NTVCRPCGPG FYNDVVSSKP CKPCTWCNLR SGSERKQLCT
     ATQDTVCRCR AGTQPLDSYK
121  PGVDCAPCPP GHFSPGDNQA CKPWTNCTLA GKHTLQPASN
     SSDAICEDRD PPATQPQETQ
181  GPPARPITVQ PTEAWPRTSQ GPSTRPVEVP GGRAVAAILG
     LGLVLGLLGP LAILLALYLL
241  RRDQRLPPDA HKPPGGGSFR TPIQEEQADA HSTLAKI
     (NP_003318; SEQ ID NO: 25)
```

DAP10, also referred to as hematopoietic cell signal transducer, is a signaling subunit that associates with a large family of receptors in hematopoietic cells. In some embodiments, the second domain of fusion proteins provided herein comprises a DAP10 polypeptide, or a functional fragment thereof. A DAP10 polypeptide can have the amino acid sequence of GenBank No. NP_055081.1 (GI:15826850), or fragments thereof. A DAP10 polypeptide can have the amino acid sequence of SEQ ID NO:28 In some embodiments, the second domain comprises the cytoplasmic domain of DAP10. In some embodiments, the second domain comprises a ligand or a receptor-binding fragment thereof that binds DAP10. In some embodiments, the second domain comprises an antibody that binds DAP10, or an antigen-binding fragment thereof. In some embodiments, the second domain can comprise a co-stimulatory signaling domain derived from DAP10. A DAP10 co-stimulatory signaling domain can have the cytoplasmic domain of DAP10 corresponding to amino acids 70 to 93 of SEQ ID NO:28, or a functional fragment thereof. It is understood that sequences of DAP10 that are shorter or longer than a specific delineated domain can be included in a fusion protein, if desired.

```
                                           (SEQ ID NO: 28)
  1  MIHLGHILFL LLLPVAAAQT TPGERSSLPA FYPGTSGSCS
     GCGSLSLPLL AGLVAADAVA
 61  SLLIVGAVFL CARPRRSPAQ EDGKVYINMP GRG
```

ICOS. Inducible T-cell co-stimulator precursor (ICOS), also referred to as CD278, is a CD28-superfamily co-stimulatory receptor that is expressed on activated T cells. In some embodiments, provided herein are fusion proteins comprising a first domain that activates an APC and a second domain that activates an immune effector cell, wherein the second domain comprises an ICOS polypeptide, or a functional fragment thereof. In some embodiments, provided herein are fusion proteins comprising a first domain that activates an APC and a second domain that activates an immune effector cell, wherein the second domain comprises a ligand or a receptor-binding fragment thereof that binds ICOS. In some embodiments, the second domain comprises the cytoplasmic domain of ICOS. In some embodiments, provided herein are fusion proteins comprising a first domain that activates an APC and a second domain that activates an immune effector cell, wherein the second domain comprises an antibody that binds ICOS, or an antigen-binding fragment thereof. In one embodiment, the second domain of fusion proteins provided herein can comprise a co-stimulatory signaling domain derived from ICOS. An ICOS polypeptide can have an amino acid sequence corresponding to the sequence having GenBank No. NP_036224 (NP_036224.1, GI:15029518), provided below, or fragments thereof. In one embodiment, the second domain of fusion proteins provided herein can have a co-stimulatory domain comprising the cytoplasmic domain of ICOS corresponding to amino acids 162 to 199 of ICOS (underlined part of the sequence below, SEQ ID NO:20), or a functional fragment thereof. It is understood that sequences of ICOS that are shorter or longer than a specific delineated domain can be included in a fusion protein, if desired.

```
                                      (NP_036224; SEQ ID NO: 19)
  1  MKSGLWYFFL FCLRIKVLTG EINGSANYEM FIFHNGGVQI LCKYPDIVQQ FKMQLLKGGQ
 61  ILCDLTKTKG SGNTVSIKSL KFCHSQLSNN SVSFFLYNLD HSHANYYFCN LSIFDPPPFK
121  VTLTGGYLHI YESQLCCQLK FWLPIGCAAF VVVCILGCIL ICWLTKKKYS SSVHDPNGEY
181  MFMRAVNTAK KSRLTDVTL
```

CD27: CD27 (TNFRSF7) is a transmembrane receptor expressed on subsets of human CD8+ and CD4+ T-cells, NKT cells, NK cell subsets and hematopoietic progenitors and induced in FOXP3+ CD4 T-cells and B cell subsets. Previous studies have found that CD27 can provide costimulatory signals that improve human T-cell survival and anti-tumor activity in vivo. (See Song and Powell; *Oncoimmunology* 1(4):547-549 (2012)). In some embodiments, provided herein are fusion proteins comprising a first domain that activates an APC and a second domain that activates an immune effector cell, wherein the second domain comprises a CD27 polypeptide, or a functional fragment thereof. In some embodiments, the second domain comprises the cytoplasmic domain of CD27. In some embodiments, provided herein are fusion proteins comprising a first domain that activates an APC and a second domain that activates an immune effector cell, wherein the second domain comprises a ligand or a receptor-binding fragment thereof that binds CD27. In some embodiments, provided herein are fusion proteins comprising a first domain that activates an APC and a second domain that activates an immune effector cell, wherein the second domain comprises an antibody that binds CD27, or an antigen-binding fragment thereof. In one embodiment, the second domain of fusion proteins provided herein can comprise a co-stimulatory domain derived from CD27. A CD27 polypeptide can have an amino acid sequence corresponding to the sequence having UniProtKB/Swiss-Prot No.: P26842.2 (GI: 269849546), provided below, or fragments thereof. In one embodiment, the second domain of fusion proteins provided herein can comprise a co-stimulatory domain comprising the cytoplasmic domain of CD27 corresponding to amino acids 213 to 260 (underlined part of the sequence below, SEQ ID NO:23), or a functional fragment thereof. It is understood that sequences of CD27 that are shorter or longer than a specific delineated domain can be included in a fusion protein, if desired.

```
                                            (SEQ ID NO: 22)
  1  MARPHPWWLC VLGTLVGLSA TPAPKSCPER HYWAQGKLCC

QMCEPGTFLV KDCDQHRKAA

61  QCDPCIPGVS FSPDHHTRPH CESCRHCNSG LLVRNCTITA

NAECACRNGW QCRDKECTEC

121  DPLPNPSLTA RSSQALSPHP QPTHLPYVSE MLEARTAGHM

QTLADFRQLP ARTLSTHWPP

181  QRSLCSSDFI RILVIFSGMF LVFTLAGALF LHQRRKYRSN

KGESPVEPAE PCHYSCPREE

241  EGSTIPIQED YRKPEPACSP
```

CD30: CD30 and its ligand (CD30L) are members of the tumor necrosis factor receptor (TNFR) and tumor necrosis factor (TNF) superfamilies, respectively. CD30, in many respects, behaves similarly to Ox40 and enhances proliferation and cytokine production induced by TCR stimulation. (Goronzy and Weyand, *Arthritis research & therapy* 10, no. S1 (2008): S3.) In some embodiments, provided herein are fusion proteins comprising a first domain that activates an APC and a second domain that activates an immune effector cell, wherein the second domain comprises a CD30 polypeptide, or a functional fragment thereof. In some embodiments, the second domain comprises the cytoplasmic domain of CD30. In some embodiments, provided herein are fusion proteins comprising a first domain that activates an APC and a second domain that activates an immune effector cell, wherein the second domain comprises a ligand or a receptor-binding fragment thereof that binds CD30. In some embodiments, provided herein are fusion proteins comprising a first domain that activates an APC and a second domain that activates an immune effector cell, wherein the second domain comprises an antibody that binds CD30, or an antigen-binding fragment thereof. In one embodiment, the second domain of fusion proteins provided herein can comprise a co-stimulatory domain derived from CD30. A CD30 polypeptide can have an amino acid sequence corresponding to the sequence having GenBank No.: AAA51947.1 (GI: 180096), provided below, or fragments thereof. In one embodiment, the second domain of fusion proteins provided herein can comprise a co-stimulatory domain comprising the cytoplasmic domain of CD30 corresponding to amino acids 407 to 595 (underlined part of the sequence below, SEQ ID NO:32), or a functional fragment thereof. It is understood that sequences of CD30 that are shorter or longer than a specific delineated domain can be included in a fusion protein, if desired.

```
                                            (SEQ ID NO: 31)
  1  MRVLLAALGL LFLGALRAFP QDRPFEDTCH GNPSHYYDKA

VRRCCYRCPM GLFPTQQCPQ

61  RPTDCRKQCE PDYYLDEADR CTACVTCSRD DLVEKTPCAW

NSSRVCECRP GMFCSTSAVN

121  SCARCFFHSV CPAGMIVKFP GTAQKNTVCE PASPGVSPAC

ASPENCKEPS SGTIPQAKPT

181  PVSPATSSAS TMPVRGGTRL AQEAASKLTR APDSPSSVGR

PSSDPGLSPT QPCPEGSGDC

241  RKQCEPDYYL DEAGRCTACV SCSRDDLVEK TPCAWNSSRT

CECRPGMICA TSATNSCARC

301  VPYPICAAET VTKPQDMAEK DTTFEAPPLG TQPDCNPTPE

NGEAPASTSP TQSLLVDSQA

361  SKTLPIPTSA PVALSSTGKP VLDAGPVLFW VILVLVVVVG

SSAFLLCHRR ACRKRIRQKL

421  HLCYPVQTSQ PKLELVDSRP RRSSTQLRSG ASVTEPVAEE

RGLMSQPLME TCHSVGAAYL

481  ESLPLQDASP AGGPSSPRDL PEPRVSTEHT NNKIEKIYIM

KADTVIVGTV KAELPEGRGL

541  AGPAEPELEE ELEADHTPHY PEQETEPPLG SCSDVMLSVE

EEGKEDPLPT AASGK
```

2B4 2B4 (CD244) is a co-stimulatory receptor expressed on both NK cells and CD8+ T cells. It targets a non-MHC like molecule (CD48) expressed on hematopoietic cells, including B and T cells, as well as on activated monocytes and granulocytes. Activation of 2B4 by binding of its ligand on target cells leads to NK (or T cell) activation, and target killing. In some embodiments, provided herein are fusion proteins comprising a first domain that activates an APC and a second domain that activates an immune effector cell, wherein the second domain comprises a 2B4 polypeptide, or a functional fragment thereof. In some embodiments, the second domain comprises the cytoplasmic domain of 2B4. In some embodiments, provided herein are fusion proteins comprising a first domain that activates an APC and a second domain that activates an immune effector cell, wherein the second domain comprises a ligand or a receptor-binding fragment thereof that binds 2B4. In some embodiments, provided herein are fusion proteins comprising a first domain that activates an APC and a second domain that activates an immune effector cell, wherein the second domain comprises an antibody that binds 2B4, or an antigen-binding fragment thereof. In one embodiment, the second domain of fusion proteins provided herein can comprise a co-stimulatory domain derived from 2B4. A 2B4 polypeptide can have an amino acid sequence corresponding to the sequence having Accession No: Q9BZW8.2 (GI: 47605541), provided below, or fragments thereof. In one embodiment, the second domain of fusion proteins provided herein can comprise a co-stimulatory domain comprising the cytoplasmic domain of 2B4 corresponding to amino acids 251 to 370 (underlined part of the sequence below, SEQ ID NO:35), or a functional fragment thereof. It is understood that sequences of 2B4 that are shorter or longer than a specific delineated domain can be included in a fusion protein, if desired.

(SEQ ID NO: 34)
MLGQVVTLILLLLLKVYQGKGCQGSADHVVSISGVPLQLQPNSIQTKVDS

IAWKKLLPSQNGFHHILKWENGSLPSNTSNDRFSFIVKNLSLLIKAAQQQ

DSGLYCLEVTSISGKVQTATFQVFVFESLLPDKVEKPRLQGQGKILDRGR

CQVALSCLVSRDGNVSYAWYRGSKLIQTAGNLTYLDEEVDINGTHTYTCN

VSNPVSWESHTLNLTQDCQNAHQEFRFWPFLVIIVILSALFLGTLACFCV

WRRKRKEKQSETSPKEFLTIYEDVKDLKTRRNHEQEQTFPGGGSTIYSMI

QSQSSAPTSQEPAYTLYSLIQPSRKSGSRKRNHSPSFNSTIYEVIGKSQP

KAQNPARLSRKELENFDVYS

CD2 The engagement of the CD2 molecule by its ligand CD58 co-stimulates proliferation, cytokine production, and effector function in this T cells, especially the CD28-deficient T cells subset. CD58 is broadly expressed on APCs including dendritic cells. Engagement of CD2 amplifies TCR signals in CD28⁻CD8⁺ T cells, demonstrating that the CD2-CD58 interaction has a genuine costimulatory effect. CD2 signals could promote the control of viral infection by CD28⁻CD8⁺ T cells, but they could also contribute to the continuous expansion of CD28⁻CD8⁺ T cells during chronic stimulation by persistent Ag. (Judith Leitner J et. al., *Immunol*, 2015, 195 (2) 477-487). In some embodiments, provided herein are fusion proteins comprising a first domain that activates an APC and a second domain that activates an immune effector cell, wherein the second domain comprises a CD2 polypeptide, or a functional fragment thereof. In some embodiments, the second domain comprises the cytoplasmic domain of CD2. In some embodiments, provided herein are fusion proteins comprising a first domain that activates an APC and a second domain that activates an immune effector cell, wherein the second domain comprises a ligand or a receptor-binding fragment thereof that binds CD2. In some embodiments, provided herein are fusion proteins comprising a first domain that activates an APC and a second domain that activates an immune effector cell, wherein the second domain comprises an antibody that binds CD2, or an antigen-binding fragment thereof. In one embodiment, the second domain of fusion proteins provided herein can comprise a co-stimulatory domain derived from CD2. A CD2 polypeptide can have an amino acid sequence corresponding to the sequence having Accession: NP_001758.2 GI: 156071472, provided below, or fragments thereof. In one embodiment, the second domain of fusion proteins provided herein can comprise a co-stimulatory domain comprising the cytoplasmic domain of CD2 corresponding to amino acids 236 to 351 (underlined part of the sequence below, SEQ ID NO:38), or a functional fragment thereof. It is understood that sequences of CD2 that are shorter or longer than a specific delineated domain can be included in a fusion protein, if desired.

(SEQ ID NO: 37)
MSFPCKFVASFLLIFNVSSKGAVSKEITNALETWGALGQDINLDIPSFQM

SDDIDDIKWEKTSDKKKIAQFRKEKETFKEKDTYKLFKNGTLKIKHLKTD

DQDIYKVSIYDTKGKNVLEKIFDLKIQERVSKPKISWTCINTTLTCEVMN

GTDPELNLYQDGKHLKLSQRVITHKWTTSLSAKFKCTAGNKVSKESSVEP

VSCPEKGLDIYLIIGICGGGSLLMVFVALLVFYIT<u>KRKKQRSRRNDEELE

TRAHRVATEERGRKPHQIPASTPQNPATSQHPPPPPGHRSQAPSHRPPPP

GHRVQHQPQKRPPAPSGTQVHQQKGPPLPRPRVQPKPPHGAAENSLSPSS

N</u>

LIGHT TNF superfamily member 14 (also known as LTg, CD258, HVEML, LIGHT) is a co-stimulatory receptor involved in cellular immune responses. LIGHT can function as a costimulatory factor for the activation of lymphoid cells and as a deterrent to infection by herpesvirus. LIGHT has been shown to stimulate the proliferation of T cells, and trigger apoptosis of various tumor cells. LIGHT is found in T cells and stromal cells. LIGHT is expressed on immature dendritic cells (DCs) generated from human PBMCs. Engagement of LIGHT co-stimulates human T cell proliferation, amplifies the NF-κB signaling pathway, and preferentially induces the production of IFN-γ, but not IL-4, in the presence of an antigenic signal. (Tamada K et al., *J Immunol*, 2000, 164 (8) 4105-4110). In some embodiments, provided herein are fusion proteins comprising a first domain that activates an APC and a second domain that activates an immune effector cell, wherein the second domain comprises a LIGHT polypeptide, or a functional fragment thereof. In some embodiments, the second domain comprises the cytoplasmic domain of LIGHT. In some embodiments, provided herein are fusion proteins comprising a first domain that activates an APC and a second domain that activates an immune effector cell, wherein the second domain comprises a ligand or a receptor-binding fragment thereof that binds LIGHT. In some embodiments, provided herein are fusion proteins comprising a first domain that activates an APC and a second domain that activates an immune effector cell, wherein the second domain comprises an antibody that binds LIGHT, or an antigen-binding fragment thereof. In one embodiment, the second domain of fusion proteins provided herein can comprise a co-stimulatory domain derived from LIGHT. A LIGHT polypeptide can have an amino acid sequence corresponding to the sequence provided below (Accession: NP_001363816.1 GI: 1777376047), or fragments thereof. In one embodiment, the second domain of fusion proteins provided herein can comprise a co-stimulatory domain comprising the cytoplasmic domain of LIGHT corresponding to amino acids 1 to 37 (underlined part of the sequence below, SEQ ID NO:41), or a functional fragment thereof. It is understood that sequences of LIGHT that are shorter or longer than a specific delineated domain can be included in a fusion protein, if desired.

(SEQ ID NO: 40)
<u>MEESVVRPSVFVVDGQTDIPFTRLGRSHRRQSCSVAR</u>VGLGLLLLLMGAG

LAVQGWFLLQLHWRLGEMVTRLPDGPAGSWEQLIQERRSHEVNPAAHLTG

-continued

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGEKVVVRVLDERLVRLRDGTRSYFGAFMV

GITR TNF receptor superfamily member 18 (also known as TNFRSF18, AITR, GITR; CD357; GITR-D; ENERGEN) has been shown to have increased expression upon T-cell activation. Stimulation of T cells through GITR has been shown to enhance immunity to tumors and viral pathogens, and to exacerbate autoimmune disease. The effects of stimulation through GITR are generally thought to be caused by attenuation of the effector activity of immunosuppressive CD4+CD25+ regulatory T (TReg) cells. (Shevach, E. and Stephens, G. Nat Rev Immunol 6, 613-618 (2006)). In some embodiments, provided herein are fusion proteins comprising a first domain that activates an APC and a second domain that activates an immune effector cell, wherein the second domain comprises a GITR polypeptide, or a functional fragment thereof. In some embodiments, the second domain comprises the cytoplasmic domain of GITR. In some embodiments, provided herein are fusion proteins comprising a first domain that activates an APC and a second domain that activates an immune effector cell, wherein the second domain comprises a ligand or a receptor-binding fragment thereof that binds GITR. In some embodiments, provided herein are fusion proteins comprising a first domain that activates an APC and a second domain that activates an immune effector cell, wherein the second domain comprises an antibody that binds GITR, or an antigen-binding fragment thereof. In one embodiment, the second domain of fusion proteins provided herein can comprise a co-stimulatory domain derived from GITR. A GITR polypeptide can have an amino acid sequence corresponding to the sequence provided below (Accession: AAI52382.1 GI: 158931986), or fragments thereof. In one embodiment, the second domain of fusion proteins provided herein can comprise a co-stimulatory domain comprising the cytoplasmic domain of GITR corresponding to amino acids 184 to 241 (underlined part of the sequence below, SEQ ID NO:44), or a functional fragment thereof. It is understood that sequences of GITR that are shorter or longer than a specific delineated domain can be included in a fusion protein, if desired.

(SEQ ID NO: 43)
MAQHGAMGAFRALCGLALLCALSLGQRPTGGPGCGPGRLLLGTGTDARCC

RVHTTRCCRDYPGEECCSEWDCMCVQPEFHCGDPCCTTCRHHPCPPGQGV

QSQGKFSFGFQCIDCASGTFSGGHEGHCKPWTDCTQFGFLTVFPGNKTHN

AVCVPGSPPAEPLGWLTVVLLAVAACVLLLTSAQLGLHIWQLRSQCMWPR

ETQLLLEVPPSTEDARSCQFPEEERGERSAEEKGRLGDLWV

DR3 TNF receptor superfamily member 25 (also known as DR3, TR3, DDR3, LARD, APO-3, TRAMP, WSL-1, GEF720, WSL-LR, PLEKHG5, or TNFRSF12) is expressed preferentially in the tissues enriched in lymphocytes, and it plays a role in regulating lymphocyte homeostasis. This receptor has been shown to stimulate NF-kappa B activity and regulate cell apoptosis. The signal transduction of this receptor is mediated by various death domain containing adaptor proteins. Multiple alternatively spliced transcript variants of this gene encoding distinct isoforms have been reported, most of which are potentially secreted molecules. The alternative splicing of this gene in B and T cells encounters a programmed change upon T-cell activation, which predominantly produces full-length, membrane bound isoforms, and is involved in controlling lymphocyte proliferation induced by T-cell activation. In some embodiments, provided herein are fusion proteins comprising a first domain that activates an APC and a second domain that activates an immune effector cell, wherein the second domain comprises a DR3 polypeptide, or a functional fragment thereof. In some embodiments, the second domain comprises the cytoplasmic domain of DR3. In some embodiments, provided herein are fusion proteins comprising a first domain that activates an APC and a second domain that activates an immune effector cell, wherein the second domain comprises a ligand or a receptor-binding fragment thereof that binds DR3. In some embodiments, provided herein are fusion proteins comprising a first domain that activates an APC and a second domain that activates an immune effector cell, wherein the second domain comprises an antibody that binds DR3, or an antigen-binding fragment thereof. In one embodiment, the second domain of fusion proteins provided herein can comprise a co-stimulatory domain derived from DR3. A DR3 polypeptide can have an amino acid sequence corresponding to the sequence provided below (Accession: AAI17190.1 GI: 109658976), or fragments thereof. In one embodiment, the second domain of fusion proteins provided herein can comprise a co-stimulatory domain comprising the cytoplasmic domain of DR3 corresponding to amino acids 221 to 417 (underlined part of the sequence below, SEQ ID NO:47), or a functional fragment thereof. It is understood that sequences of DR3 that are shorter or longer than a specific delineated domain can be included in a fusion protein, if desired.

(SEQ ID NO: 46)
MEQRPRGCAAVAAALLLVLLGARAQGGTRSPRCDCAGDFHKKIGLFCCRG

CPAGHYLKAPCTEPCGNSTCLVCPQDTFLAWENHHNSECARCQACDEQAS

QVALENCSAVADTRCGCKPGWFVECQVSQCVSSSPFYCQPCLDCGALHRH

TRLLCSRRDTDCGTCLPGFYEHGDGCVSCPTSTLGSCPERCAAVCGWRQM

FWVQVLLAGLVVPLLLGATLTYTYRHCWPHKPLVTADEAGMEALTPPPAT

HLSPLDSAHTLLAPPDSSEKICTVQLVGNSWTPGYPETQEALCPQVTWSW

DQLPSRALGPAAAPTLSPESPAGSPAMMLQPGPQLYDVMDAVPARRWKEF

VRTLGLREAEIEAVEVEIGRFRDQQYEMLKRWRQQQPAGLGAVYAALERM

GLDGCVEDLRSRLQRGP

CD43 CD43 (also known as SPN sialophorin, LSN, GALGP, GPL115) is a highly sialylated glycoprotein that functions in antigen-specific activation of T cells, and is found on the surface of thymocytes, T lymphocytes, monocytes, granulocytes, and some B lymphocytes. It contains a mucin-like extracellular domain, a transmembrane region and a carboxy-terminal intracellular region. In stimulated immune effector cells, proteolytic cleavage of the extracellular domain occurs in some cell types, releasing a soluble extracellular fragment. In some embodiments, provided herein are fusion proteins comprising a first domain that activates an APC and a second domain that activates an immune effector cell, wherein the second domain comprises a CD43 polypeptide, or a functional fragment thereof. In some embodiments, the second domain comprises the cytoplasmic domain of CD43. In some embodiments, provided herein are fusion proteins comprising a first domain that activates an APC and a second domain that activates an immune effector cell, wherein the second domain comprises a ligand or a receptor-binding fragment thereof that binds CD43. In some embodiments, provided herein are fusion proteins comprising a first domain that activates an APC and a second domain that activates an immune effector cell, wherein the second domain comprises an antibody that binds CD43, or an antigen-binding fragment thereof. In one embodiment, the second domain of fusion proteins provided herein can comprise a co-stimulatory domain derived from CD43. A CD43 polypeptide can have an amino acid sequence corresponding to the sequence provided below (Accession: EAW80016.1 GI: 119600422; Accession: EAW80015.1 GI: 119600421), or fragments thereof. In one embodiment, the second domain of fusion proteins provided herein can comprise a co-stimulatory domain comprising the cytoplasmic domain of CD43 corresponding to amino acids 277 to 400 (underlined part of the sequence below, SEQ ID NO:51), or a functional fragment thereof. It is understood that sequences of CD43 that are shorter or longer than a specific delineated domain can be included in a fusion protein, if desired.

(SEQ ID NO: 50)
MATLLLLLGVLVVSPDALGSTTAVQTPTSGEPLVSTSEPLSSKMYTTSIT

SDPKADSTGDQTSALPPSTSINEGSPLWTSIGASTGSPLPEPTTYQEVSI

KMSSVPQETPHATSHPAVPITANSLGSHTVTGGTITTNSPETSSRTSGAP

VTTAASSLETSRGTSGPPLTMATVSLETSKGTSGPPVTMATDSLETSTGT

TGPPVTMTTGSLEPSSGASGPQVSSVKLSTMMSPTTSTNASTVPFRNPDE

NSRGMLPVAVLVALLAVIVLVALLLL<u>WRRRQKRRTGALVLSRGGKRNGVV

DAWAGPAQVPEEGAVTVTVGGSGGDKGSGFPDGEGSSRRPTLTTFFGRRK

SRQGSLAMEELKSGSGPSLKGEEEPLVASEDGAVDAPAPDEPEGGDGAAP</u>

CD58 (also known as AG3; LFA3; LFA-3) is a member of the immunoglobulin superfamily and a ligand of the T lymphocyte CD2 protein. CD58 is localized to the plasma membrane and functions in adhesion and activation of T lymphocytes. (See e.g Abdul Razak F R, et al. *Genes Immun,* 2016 September PMID 27467287; Schneider M, et al. Genes Chromosomes Cancer, 2015 October PMID 26194173.) A polypeptide can have an amino acid sequence corresponding to the sequence provided below (e.g., Accession NP_001770; NP_001138294). In some embodiments, provided herein are fusion proteins comprising a first domain that activates an APC and a second domain that activates an immune effector cell, wherein the second domain comprises CD58, or a receptor-binding fragment thereof. In some embodiments, the second domain of the fusion proteins provided herein comprises the extracellular domain of CD58 corresponding to amino acids 29-215 (underlined below). It is understood that sequences of CD58 that are shorter or longer than a specific delineated domain can be included in a fusion protein, if desired.

(SEQ ID NO: 178)
MVAGSDAGRA LGVLSVVCLL HCFGFISC<u>FS QQIYGVVYGN

VTFHVPSNVP LKEVLWKKQK DKVAELENSE FRAFSSFKNR

VYLDTVSGSL TIYNLTSSDE DEYEMESPNI TDTMKFFLYV

LESLPSPTLT CALTNGSIEV QCMIPEHYNS HRGLIMYSWD

CPMEQCKRNS TSIYFKMEND LPQKIQCTLS NPLFNTTSSI

ILTTCIPSSG HSRHRYALIP IPLAVITTCI VLYMNGILKC

DRKPDRTNSN</u>

CD70 (also known as Ki-24, CD27L, TNFSF7) is known to enhance the generation of cytotoxic T-cells and contribute to T-cell activation. CD70 is a cytokine that belongs to the tumor necrosis factor (TNF) ligand family, which is a ligand for TNFRSF27/CD27. It is a surface antigen on activated T and B lymphocytes. It induces proliferation of costimulated T cells, enhances the generation of cytolytic T cells, and contributes to T cell activation. This cytokine is also reported to play a role in regulating B-cell activation, cytotoxic function of natural killer cells, and immunoglobulin synthesis. (See e.g., Masamoto I, et al. Leuk Lymphoma, 2016; Jacobs J, et al. Pharmacol Ther, 2015 November). A CD70 polypeptide can have an amino acid sequence corresponding to the sequence provided below (e.g., Accession: NP_001243; NP_001317261; XP 016883012). In some embodiments, provided herein are fusion proteins comprising a first domain that activates an APC and a second domain that activates an immune effector cell, wherein the second domain comprises CD70, or a receptor-binding fragment thereof. In some embodiments, the second domain of the fusion proteins provided herein comprises the extracellular domain of CD70 corresponding to amino acids 39-193 (underlined below). It is understood that sequences of CD70 that are shorter or longer than a specific delineated domain can be included in a fusion protein, if desired.

(SEQ ID NO: 179)
MPEEGSGCSVRRRPYGCVLRAALVPLVAGLVICLVVC<u>IQRFAQAQQQLPL

ESLGWDVAELQLNHTGPQQDPRLYWQGGPALGRSFLHGPELDKGQLRIHR

DGIYMVHIQVTLAICSSTTASRHHPTTLAVGICSPASRSISLLRLSFHQG

CTIASQRLTPLARGDTLCTNLTGTLLPSRNTDETFFGVQWVRP</u>

CD83 (also known as BL11, HB15) is a single-pass type I membrane protein and member of the immunoglobulin superfamily of receptors. CD83 can bind CD83L and is involved in the regulation of antigen presentation. (Li Z, et al. Haematologica, 2018 April; Ju X, et al. J Immunol, 2016 Dec. 15. PMID 29351987; Horvatinovich J M, et al. J Immunol, 2017 Mar. 15. PMID 28193829.) A CD83 polypeptide can have an amino acid sequence corresponding to the sequence provided below (e.g., NP_001035370, NP_001238830, NP_004224). In some embodiments, provided herein are fusion proteins comprising a first domain that activates an APC and a second domain that activates an immune effector cell, wherein the second domain comprises CD83, or a receptor-binding fragment thereof. In some embodiments, the second domain comprises the extracellular domain of CD83 corresponding to amino acids 20-144 (underlined below). It is understood that sequences of CD83 that are shorter or longer than a specific delineated domain can be included in a fusion protein, if desired.

(SEQ ID NO: 180)
MSRGLQLLLL SCAYSLAPA<u>T PEVKVACSED VDLPCTAPWD

PQVPYTVSWV KLLEGGEERM ETPQEDHLRG QHYHQKGQNG

```
                                                    -continued
SFDAPNERPY SLKIRNTTSC NSGTYRCTLQ DPDGORNLSG

KVILRVTGCP AQRKEETFKK YRAEIVLLLA LVIFYLTLII

FTCKFARLQS IFPDFSKAGM ERAFLPVTSP NKHLGLVTPH

KTELV
```

CD80 (also known as B7, B7-1, B7.1, BB1, CD28LG, CD28LG1, LAB7) is a single-pass type I membrane protein and member of the immunoglobulin superfamily of receptors. CD80's function involves antigen presentation regulation and immune stimulation. CD80 binds CD28 or CTLA-4, which induces T-cell proliferation and cytokine production. (See e.g., Feng X Y, et al. Future Oncol, 2019 February PMID 30628844). A CD80 polypeptide can have an amino acid sequence corresponding to the sequence provided below (e.g., EAW79565.1; NP_005182). In some embodiments, provided herein are fusion proteins comprising a first domain that activates an APC and a second domain that activates an immune effector cell, wherein the second domain comprises CD80, or a receptor-binding fragment thereof. In some embodiments, the second domain comprises the extracellular domain of CD80 corresponding to amino acids 35-242 (underlined below). It is understood that sequences of CD80 that are shorter or longer than a specific delineated domain can be included in a fusion protein, if desired.

```
                                           (SEQ ID NO: 54)
MGHTRRQGTS PSKCPYLNFF QLLVLAGLSH FCSGVIHVTK

EVKEVATLSC GHNVSVEELA QTRIYWQKEK KMVLTMMSGD

MNIWPEYKNR TIFDITNNLS IVILALRPSD EGTYECVVLK

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP

DNLLPSWAIT LISVNGIFVI CCLTYCFAPR CRERRRNERL

RRESVRPV
```

CD86 (also known as B70, B7-2, CD28LG2) is an integrin alpha X chain protein which can bind CD28 and CD152. This protein combines with the beta 2 chain (ITGB2) to form a leukocyte-specific integrin referred to as inactivated-C3b (iC3b) receptor 4 (CR4). The alpha X beta 2 complex overlap the properties of the alpha M beta 2 integrin in the adherence of neutrophils and monocytes to stimulated endothelium cells, and in the phagocytosis of complement coated particles. (See e.g., Takacs F, et al. Pathol Oncol Res, 2019 PMID 30406401; Schutz C et al. Leukemia. 2017; 31(4):829-836. doi:10.1038/leu.2017.9.) A CD86 polypeptide can have an amino acid sequence corresponding to the sequence provided below (e.g., Accession: NP_787058.5 NP_001193853). In some embodiments, provided herein are fusion proteins comprising a first domain that activates an APC and a second domain that activates an immune effector cell, wherein the second domain comprises CD86, or a receptor-binding fragment thereof. In some embodiments, the second domain comprises the extracellular domain of CD86 corresponding to amino acids 24-247 (underlined below). It is understood that sequences of CD86 that are shorter or longer than a specific delineated domain can be included in a fusion protein, if desired.

```
                                           (SEQ ID NO: 57)
MDPQCTMGLSNILFVMAFLLSGAAPLKIQAYFNETADLPCQFANSQNQS

LSELVVFWQDQENLVLNEVYLGKEKFDSVHSKYMGRTSFDSDSWTLRLH

NLQIKDKGLYQCIIHHKKPTGMIRIHQMNSELSVLANFSQPEIVPISNI

TENVYINLTCSSIHGYPEPKKMSVLLRTKNSTIEYDGVMQKSQDNVTEL

YDVSISLSVSFPDVTSNMTIFCILETDKTRLLSSPFSIELEDPQPPPDH

IPWITAVLPTVIICVMVFCLILWKWKKKKRPRNSYKCGTNTMEREESEQ

TKKREKIHIPERSDEAQRVFKSSKTSSCDKSDTCF
```

CD137L (also known as 4-1BBL, TNFSF9, CDw137, ILA) is a member of the tumor necrosis factor (TNF) receptor family. This transmembrane cytokine is a bidirectional signal transducer that acts as a ligand for TNFRSF9/4-1BB, which is a costimulatory receptor molecule in T lymphocytes. This cytokine and its receptor are involved in the antigen presentation process and in the generation of cytotoxic T cells. 4-1BBL has been shown to reactivate anergic T lymphocytes in addition to promoting T lymphocyte proliferation. This cytokine has also been shown to be required for the optimal CD8 responses in CD8 T cells. This cytokine is expressed in carcinoma cell lines and is thought to be involved in T cell-tumor cell interaction. (See e.g., Shen Y L, et al. J Dig Dis, 2017 July PMID 28547807; Qian Y, et al. Med Oncol, 2015 March PMID 25631633.) A CD137L polypeptide can have an amino acid sequence corresponding to the sequence provided below (e.g., NP_003802.1). In some embodiments, provided herein are fusion proteins comprising a first domain that activates an APC and a second domain that activates an immune effector cell, wherein the second domain comprises CD137L, or a receptor-binding fragment thereof. In some embodiments, the second domain comprises the extracellular domain of CD137L corresponding to amino acids 50-254 (underlined below). It is understood that sequences of CD137L that are shorter or longer than a specific delineated domain can be included in a fusion protein, if desired.

```
                                          (SEQ ID NO: 181)
MEYASDASLD PEAPWPPAPR ARACRVLPWA LVAGLLLLLL

LAAACAVFLA CPWAVSGARA SPGSAASPRL REGPELSPDD

PAGLLDLRQG MFAQLVAQNV LLIDGPLSWY SDPGLAGVSL

TGGLSYKEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE
```

CD252 (also known as OX40L, gp34) an integrin beta chain, which combines with different alpha chains to form integrin heterodimers. CD252 is the ligand for receptor TNFRSF4 (OX40). CD252 co-stimulates T-cell proliferation and cytokine production. CD252 also functions in T cell APC interactions and mediates adhesion of activated T cells to endothelial cells. (See e.g., Roszik J, et al. Cancer Immunol Immunother, 2019 September PMID 31501955)

A CD252 polypeptide can have an amino acid sequence corresponding to the sequence provided below (e.g., NP_001284491 XP 005245532; NP_003317). In some embodiments, provided herein are fusion proteins comprising a first domain that activates an APC and a second domain that activates an immune effector cell, wherein the second domain comprises CD252, or a receptor-binding fragment thereof. In some embodiments, the second domain comprises the extracellular domain of CD252 corresponding to amino acids 51-183 (underlined below). It is understood that sequences of CD252 that are shorter or longer than a specific delineated domain can be included in a fusion protein, if desired.

(SEQ ID NO: 182)
MERVQPLEEN VGNAARPRFE RNKLLLVASV IQGLGLLLCF

TYICLHFSAL QVSHRYPRIQ SIKVQFTEYK KEKGFILTSQ

KEDEIMKVQN NSVIINCDGF YLISLKGYFS QEVNISLHYQ

KDEEPLFQLK KVRSVNSLMV ASLTYKDKVY LNVTTDNTSL

DDFHVNGGEL ILIHQNPGEF CVL

CD275 (also known as ICOS-L, B7-H2, B7-RP1, GL50). CD275 is a ligand for ICOS/CD278, which is a costimulatory receptor that promotes T-cell proliferation and cytokine secretion. CD275 can also induce B-cell proliferation and differentiation. (See e.g., Han Y, et al. *Front Immunol,* 2018. PMID 30319662; Cao Y, et al. *Int Immunopharmacol,* 2018 March PMID 29414642.) A CD275 polypeptide can have an amino acid sequence corresponding to the sequence provided below (e.g., NP_001269979, NP_001269980, NP_001269981, NP_056074, NP_001352688 XP 016883799). In some embodiments, provided herein are fusion proteins comprising a first domain that activates an APC and a second domain that activates an immune effector cell, wherein the second domain comprises CD275, or a receptor-binding fragment thereof. In some embodiments, the second domain comprises the extracellular domain of CD275 corresponding to amino acids 19-256 (underlined below). It is understood that sequences of CD275 that are shorter or longer than a specific delineated domain can be included in a fusion protein, if desired.

(SEQ ID NO: 183)
MRLGSPGLLF LLFSSLRADT QEKEVRAMVG SDVELSCACP

EGSRFDLNDV YVYWQTSESK TVVTYHIPQN SSLENVDSRY

RNRALMSPAG MLRGDFSLRL FNVTPQDEQK FHCLVLSQSL

GFQEVLSVEV TLHVAANFSV PVVSAPHSPS QDELTFTCTS

INGYPRPNVY WINKTDNSLL DQALQNDTVF LNMRGLYDVV

SVLRIARTPS VNIGCCIENV LLQQNLTVGS QTGNDIGERD

KITENPVSTG EKNAATWSIL AVLCLLVVVA VAIGWVCRDR

CLQHSYAGAW AVSPETELTG HV

CD54 (also known as ICAM-1) is a cell surface glycoprotein which is typically expressed on endothelial cells and cells of the immune system. It binds to integrins of type CD11a/CD18, or CD11b/CD18. The function of CD54 includes cell adhesion, lymphocyte activation, and migration. (See e.g., Reyes-Botella, C., et at *Journal Periodontology* 71.4 (2000): 614-617; Schildberg, Frank A., et al. *Hepatology* 54.1 (2011): 262-272.) A CD54 polypeptide can have an amino acid sequence corresponding to the sequence provided below (e.g., NP_000192). In some embodiments, provided herein are fusion proteins comprising a first domain that activates an APC and a second domain that activates an immune effector cell, wherein the second domain comprises CD54, or a receptor-binding fragment thereof. In some embodiments, the second domain comprises the extracellular domain of CD54 corresponding to amino acids 28-480 (underlined below). It is understood that sequences of CD54 that are shorter or longer than a specific delineated domain can be included in a fusion protein, if desired.

(SEQ ID NO: 184)
MAPSSPRPAL PALLVLLGAL FPGPGNAQTS VSPSKVILPR

GGSVLVTCST SCDQPKLLGI ETPLPKKELL LPGNNRKVYE

LSNVQEDSQP MCYSNCPDGQ STAKTFLTVY WTPERVELAP

LPSWQPVGKN LTLRCQVEGG APRANLTVVL LRGEKELKRE

PAVGEPAEVT TTVLVRRDHH GANFSCRTEL DLRPQGLELF

ENTSAPYQLQ TFVLPATPPQ LVSPRVLEVD TQGTVVCSLD

GLFPVSEAQV HLALGDQRLN PTVTYGNDSF SAKASVSVTA

EDEGTQRLTC AVILGNQSQE TLQTVTIYSF PAPNVILTKP

EVSEGTEVTV KCEAHPRAKV TLNGVPAQPL GPRAQLLLKA

TPEDNGRSFS CSATLEVAGQ LIHKNQTREL RVLYGPRLDE

RDCPGNWTWP ENSQQTPMCQ AWGNPLPELK CLKDGTFPLP

IGESVTVTRD LEGTYLCRAR STQGEVTRKV TVNVLSPRYE

IVIITVVAAA VIMGTAGLST YLYNRQRKIK KYRLQQAQKG

TPMKPNTQAT PP

CD49a (also known as VLA1, or ITGA1) is an alpha 1 subunit of integrin receptor. CD49a is known to mediate memory CD8+ T cell persistence and response and NK cell activity. CD49a is found to be expressed on macrophages. (See e.g., Bromley et al., *Am Assoc Immunol* (2020): 81-10; Li et al. *American Journal of Reproductive immunology* 81.4 (2019): e13101; Sun el al. *Cancer immunology research* (2019).)

A CD49a polypeptide can have an amino acid sequence corresponding to the sequence provided below (e.g., NP_852478). In some embodiments, provided herein are fusion proteins comprising a first domain that activates an APC and a second domain that activates an immune effector cell, wherein the second domain comprises CD49a, or a receptor-binding fragment thereof. In some embodiments, the second domain comprises the extracellular domain of CD49a corresponding to amino acids 29-1141 (underlined below). It is understood that sequences of CD49a that are shorter or longer than a specific delineated domain can be included in a fusion protein, if desired.

(SEQ ID NO: 185)
MAPRPRARPG VAVACCWLLT VVLRCCVSFN VDVKNSMTFS

GPVEDMFGYT VQQYENEEGK WVLIGSPLVG QPKNRTGDVY

KCPVGRGESL PCVKLDLPVN TSIPNVTEVK ENMTFGSTLV

TNPNGGFLAC GPLYAYRCGH LHYTTGICSD VSPTFQVVNS

IAPVQECSTQ LDIVIVLDGS NSIYPWDSVT AFLNDLLERM

DIGPKQTQVG IVQYGENVTH EFNLNKYSST EEVLVAAKKI

VQRGGRQTMT ALGIDTARKE AFTEARGARR GVKKVMVIVT

DGESHDNHRL KKVIQDCEDE NIQRFSIAIL GSYNRGNLST

EKFVEEIKSI ASEPTEKHFF NVSDELALVT IVKTLGERIF

ALEATADQSA ASFEMEMSQT GFSAHYSQDW VMLGAVGAYD

WNGTVVMQKA SQIIIPRNTT FNVESTKKNE PLASYLGYTV

NSATASSGDV LYIAGQPRYN HTGQVIIYRM EDGNIKILQT

LSGEQIGSYF GSILTTTDID KDSNTDILLV GAPMYMGTEK

EEQGKVYVYA LNQTRFEYQM SLEPIKQTCC SSRQHNSCTT

ENKNEPCGAR FGTAIAAVKD LNLDGFNDIV IGAPLEDDHG

GAVYIYHGSG KTIRKEYAQR IPSGGDGKTL KFFGQSIHGE

MDLNGDGLTD VTIGGLGGAA LFWSRDVAVV KVTMNFEPNK

VNIQKKNCHM EGKETVCINA TVCFDVKLKS KEDTIYEADL

QYRVTLDSLR QISRSFFSGT QERKVQRNIT VRKSECTKHS

FYMLDKHDFQ DSVRITLDFN LTDPENGPVL DDSLPNSVHE

YIPFAKDCGN KEKCISDLSL HVATTEKDLL IVRSQNDKFN

VSLTVKNTKD SAYNTRTIVH YSPNLVFSGI EAIQKDSCES

NHNITCKVGY PFLRRGEMVT FKILFQFNTS YLMENVTIYL

SATSDSEEPP ETLSDNVVNI SIPVKYEVGL QFYSSASEYH

ISIAANETVP EVINSTEDIG NEINIFYLIR KSGSFPMPEL

KLSISFPNMT SNGYPVLYPT GLSSSENANC RPHIFEDPFS

INSGKKMTTS TDHLKRGTIL DCNTCKFATI TCNLTSSDIS

QVNVSLILWK PTFIKSYFSS LNLTIRGELR SENASLVLSS

SNQKRELAIQ ISKDGLPGRV PLWVILLSAF AGLLLLMLLI

LALWKIGFFK RPLKKKMEK

CD112 (also known as PVRL2, PRR2, Nectin-2, HVEB) is a human plasma membrane glycoprotein. It can bind, for example, CD226, Nectin-3, DNAM-1, and Afadin. Among other things, CD112 is found to bind to DNAM-1 on NK cells to induce its cytolytic activity. (See e.g., Bekes I, et al. *Cancer Sci*, 2019 June PMID 30843637; Fujimoto Y, et al. *Acta Virol*, 2016 March PMID 26982466; *J Exp Med* (2003) 198 (4): 557-567).

A CD112 polypeptide can have an amino acid sequence corresponding to the sequence provided below (e.g., Accession NO: NP_001036189, NP_002847). In some embodiments, provided herein are fusion proteins comprising a first domain that activates an APC and a second domain that activates an immune effector cell, wherein the second domain comprises CD112, or a receptor-binding fragment thereof. In some embodiments, the second domain comprises the extracellular domain of CD112 corresponding to amino acids 32-360 (underlined below). It is understood that sequences of CD112 that are shorter or longer than a specific delineated domain can be included in a fusion protein, if desired.

(SEQ ID NO: 186)
MARAAALLPSRSPPTPLLWPLLLLLLLETGA<u>QDVRVQVLPEVRGQLGGT

VELPCHLLPPVPGLYISLVTWQRPDAPANHQNVAAFHPKMGPSFPSPKP

GSERLSFVSAKQSTGQDTEAELQDATLALHGLTVEDEGNYTCEFATFPK

GSVRGMTWLRVIAKPKNQAEAQKVTFSQDPTTVALCISKEGRPPARISW

LSSLDWEAKETQVSGTLAGTVTVTSRFTLVPSGRADGVTVTCKVEHESF

EEPALIPVTLSVRYPPEVSISGYDDNWYLGRTDATLSCDVRSNPEPTGY

DWSTTSGTFPTSAVAQGSQLVIHAVDSLFNTTFVCTVTNAVGMGRAEQV

IFVRETPNTAGAGATGGIIGGIIAAIIATAVAATGILICRQQRKEQTLQ

GAEEDEDLEGPPSYKPPTPKAKLEAQEMPSQLFTLGASEHSPLKTPYFD

AGASCTEQEMPRYHELPTLEERSGPLHPGATSLGSPIPVPPGPPAVEDV

SLDLEDEEGEEEEEYLDKINPIYDALSYSSPSDSYQGKGFVMSRAMYV</u>

CD150 (also known as SLAM, SLAMF1, IPO-3) belongs to the signaling lymphocytic activation molecule family. CD150 can bind CD45. The function of CD150 includes co-stimulation of T-cells and B-cells. (See e.g., Sidorenko and Clark, *Nature immunology* 4.1 (2003): 19-24. Yusuf et al. *The Journal of Immunology* 185.1 (2010): 190-202; De Salort et al. *Immunology letters* 134.2 (2011): 129-136.)

A CD150 polypeptide can have an amino acid sequence corresponding to the sequence provided below (e.g., Accession NO: NP_001317683, XP 016857618, NP_003028). In some embodiments, provided herein are fusion proteins comprising a first domain that activates an APC and a second domain that activates an immune effector cell, wherein the second domain comprises CD150, or a receptor-binding fragment thereof. In some embodiments, the second domain comprises the extracellular domain of CD150 corresponding to amino acids 21-237 (underlined below). It is understood that sequences of CD150 that are shorter or longer than a specific delineated domain can be included in a fusion protein, if desired.

(SEQ ID NO: 187)
MDPKGLLSLTFVLFLSLAFG<u>ASYGTGGRMMNCPKILRQLGSKVLLPLTY

ERINKSMNKSIHIVVTMAKSLENSVENKIVSLDPSEAGPPRYLGDRYKF

YLENLTLGIRESRKEDEGWYLMTLEKNVSVQRFCLQLRLYEQVSTPEIK

VLNKTQENGTCTLILGCTVEKGDHVAYSWSEKAGTHPLNPANSSHLLSL

TLGPQHADNIYICTVSNPISNNSQTFSPWPGCRTDPSETKPWAVYAGLL

GGVIMILIMVVILQLRRRGKTNHYQTTVEKKSLTIYAQVQKPGPLQKKL

DSFPAQDPCTTIYVAATEPVPESVQETNSITVYASVTLPES</u>

CD155 (also known as PVR, NECL-5) is a transmembrane glycoprotein belonging to the immunoglobulin superfamily. The external domain mediates cell attachment to the extracellular matrix molecule vitronectin, while its intracellular domain interacts with the dynein light chain Tctex-1/DYNLT1. CD155 serves as a cellular receptor for poliovirus in the first step of poliovirus replication. CD155 can bind poliovirus, vitronectin, CD226, CD96, αVβ3, CD111, CD112. CD155 is known to mediate NK cell adhesion and trigger their effector functions. (See e.g., Chan et al. *The journal of immunology* 184.2 (2010): 902-911.) A CD155 polypeptide can have an amino acid sequence corresponding to the sequence provided below (e.g., NP_001129240; NP_001129241; NP_001129242; NP_006496). In some embodiments, provided herein are fusion proteins comprising a first domain that activates an APC and a second domain that activates an immune effector cell, wherein the second domain comprises CD155, or a receptor-binding fragment thereof. In some embodiments, the second domain comprises the extracellular domain of CD155 corresponding to amino acids 21-343 (underlined below). It is understood that sequences of CD155 that are shorter or longer than a specific delineated domain can be included in a fusion protein, if desired.

```
                                        (SEQ ID NO: 188)
MARAMAAAWP  LLLVALLVLS  WPPPGTGDVV  VQAPTQVPGF

LGDSVTLPCY  LQVPNMEVTH  VSQLTWARHG  ESGSMAVFHQ

TQGPSYSESK  RLEFVAARLG  AELRNASLRM  FGLRVEDEGN

YTCLFVTFPQ  GSRSVDIWLR  VLAKPQNTAE  VQKVQLTGEP

VPMARCVSTG  GRPPAQITWH  SDLGGMPNTS  QVPGFLSGTV

TVTSLWILVP  SSQVDGKNVT  CKVEHESFEK  PQLLTVNLTV

YYPPEVSISG  YDNNWYLGQN  EATLTCDARS  NPEPTGYNWS

TTMGPLPPFA  VAQGAQLLIR  PVDKPINTTL  ICNVTNALGA

RQAELTVQVK  EGPPSEHSGM  SRNAIIFLVL  GILVFLILLG

IGIYFYWSKC  SREVLWHCHL  CPSSTEHASA  SANGHVSYSA

VSRENSSSQD  PQTEGTR
```

CD265 (also known as RANK, TRANCE-R, ODFR, TNFRSF11A) is a member of the TNF-receptor superfamily. CD265 induces the activation of NF-kappa B and MAPK8/JNK and plays important role in regulating interaction between T cells and dendritic cells. CD265 can bind TRANCE. CD265 enhances T-cell growth and dendritic cell function, and regulates in lymph node organogenesis. (See e.g., Hanada et al., *Journal of Molecular Medicine* 89.7 (2011): 647-656.) A CD265 polypeptide can have an amino acid sequence corresponding to the sequence provided below (e.g., NP_001257878, NP_001257879, NP_003830). In some embodiments, provided herein are fusion proteins comprising a first domain that activates an APC and a second domain that activates an immune effector cell, wherein the second domain comprises CD265, or a receptor-binding fragment thereof. In some embodiments, the second domain comprises the extracellular domain of CD265 corresponding to amino acids 30-212 (underlined below). It is understood that sequences of CD265 that are shorter or longer than a specific delineated domain can be included in a fusion protein, if desired.

```
                                        (SEQ ID NO: 189)
MAPRARRRRP  LFALLLLCAL  LARLQVALQI  APPCTSEKHY

EHLGRCCNKC  EPGKYMSSKC  TTTSDSVCLP  CGPDEYLDSW

NEEDKCLLHK  VCDTGKALVA  VVAGNSTTPR  RCACTAGYHW

SQDCECCRRN  TECAPGLGAQ  HPLQLNKDTV  CKPCLAGYFS

DAFSSTDKCR  PWTNCTFLGK  RVEHHGTEKS  DAVCSSSLPA

RKPPNEPHVY  LPGLIILLLF  ASVALVAAII  FGVCYRKKGK

ALTANLWHWI  NEACGRLSGD  KESSGDSCVS  THTANFGQQG

ACEGVLLLTL  EEKTFPEDMC  YPDQGGVCQG  TCVGGGPYAQ

GEDARMLSLV  SKTEIEEDSF  RQMPTEDEYM  DRPSQPTDQL

LFLTEPGSKS  TPPFSEPLEV  GENDSLSQCF  TGTQSTVGSE
```

```
                        -continued
SCNCTEPLCR  TDWTPMSSEN  YLQKEVDSGH  CPHWAASPSP

NWADVCTGCR  NPPGEDCEPL  VGSPKRGPLP  QCAYGMGLPP

EEEASRTEAR  DQPEDGADGR  LPSSARAGAG  SGSSPGGQSP

ASGNVTGNSN  STFISSGQVM  NFKGDIIVVY  VSQTSQEGAA

AAAEPMGRPV  QEETLARRDS  FAGNGPRFPD  PCGGPEGLRE

PEKASRPVQE  QGGAKA
```

CD270 (also known as HVEM, HveA, TR2, TNFRSF14) is a member of the TNF receptor superfamily. CD270 can bind CD258 and CD272. It functions in signal transduction pathways that activate inflammatory and inhibitory T-cell immune response. It binds herpes simplex virus (HSV) viral envelope glycoprotein D (gD), mediating its entry into cells. (See e.g., Meng Q, et al. *J Immunol*, 2019 Apr. 1. PMID 30770415) A CD270 polypeptide can have an amino acid sequence corresponding to the sequence provided below (e.g., NP_001284534; NP_003811). In some embodiments, provided herein are fusion proteins comprising a first domain that activates an APC and a second domain that activates an immune effector cell, wherein the second domain comprises CD270, or a receptor-binding fragment thereof. In some embodiments, the second domain comprises the extracellular domain of CD270 corresponding to amino acids 39-202 (underlined below). It is understood that sequences of CD270 that are shorter or longer than a specific delineated domain can be included in a fusion protein, if desired.

```
                                        (SEQ ID NO: 190)
MEPPGDWGPP  PWRSTPKTDV  LRLVLYLTFL  GAPCYAPALP

SCKEDEYPVG  SECCPKCSPG  YRVKEACGEL  TGTVCEPCPP

GTYIAHLNGL  SKCLQCQMCD  PAMGLRASRN  CSRTENAVCG

CSPGHFCIVQ  DGDHCAACRA  YATSSPGQRV  QKGGTESQDT

LCQNCPPGTF  SPNGTLEECQ  HQTKCSWLVT  KAGAGTSSSH

WVWWFLSGSL  VIVIVCSTVG  LIICVKRRKP  RGDVVKVIVS

VQRKRQEAEG  EATVIEALQA  PPDVTTVAVE  ETIPSFTGRS

PNH
```

TL1A (also known as TL1; TL1A; VEGI; TNFSF15, TNLG1B; VEGI192A) is a cytokine that belongs to the TNF ligand family. This cytokine is a ligand for receptor TNFRSF25 and decoy receptor TNFRSF21/DR6. TL1A can activate NF-kappaB and MAP kinases, and acts as an autocrine factor to induce apoptosis in endothelial cells. This cytokine is also found to stimulate enhance IFN-γ production in human T cells and NK cells. (See e.g., Papadakis et al., *The Journal of Immunology* 172.11 (2004): 7002-7007.) A TL1A polypeptide can have an amino acid sequence corresponding to the sequence provided below (e.g., Accession No. NP_005109; NP_001191273). In some embodiments, provided herein are fusion proteins comprising a first domain that activates an APC and a second domain that activates an immune effector cell, wherein the second domain comprises TL1A, or a receptor-binding fragment thereof. In some embodiments, the second domain comprises the extracellular domain of TL1A corresponding to amino acids 57-251 (underlined below). It is understood that sequences of TL1A that are shorter or longer than a specific delineated domain can be included in a fusion protein, if desired.

(SEQ ID NO: 191)
```
MAEDLGLSFG ETASVEMLPE HGSCRPKARS SSARWALTCC

LVLLPFLAGL TTYLLVSQLR AQGEACVQFQ ALKGQEFAPS

HQQVYAPLRA DGDKPRAHLT VVRQTPTQHF KNQFPALHWE

HELGLAFTKN RMNYTNKFLL IPESGDYFIY SQVTFRGMTS

ECSEIRQAGR PNKPDSITVV ITKVTDSYPE PTQLLMGTKS

VCEVGSNWFQ PIYLGAMFSL QEGDKLMVNV SDISLVDYTK

EDKTFFGAFL L
```

CD127 (also known as ILRA; CD127; IL7RA; CDW127; IL-7R-alpha) is an s a receptor for interleukin 7 (IL7). This protein has been shown to play a critical role in V(D)J recombination during lymphocyte development. Defects in this gene may be associated with severe combined immunodeficiency (SCID). (See e.g., Carrette et al. *Seminars in immunology*. 24 (3) Academic Press, 2012.) A CD127 polypeptide can have an amino acid sequence corresponding to the sequence provided below (e.g., Accession No: NP_002176, XP_942460). In some embodiments, provided herein are fusion proteins comprising a first domain that activates an APC and a second domain that activates an immune effector cell, wherein the second domain comprises CD127, or a receptor-binding fragment thereof. In some embodiments, the second domain comprises the extracellular domain of CD127 corresponding to amino acids 21-239 (underlined below). It is understood that sequences of CD127 that are shorter or longer than a specific delineated domain can be included in a fusion protein, if desired.

(SEQ ID NO: 192)
```
MTILGTTFGM VFSLLQVVSG ESGYAQNGDL EDAELDDYSF

SCYSQLEVNG SQHSLTCAFE DPDVNITNLE FEICGALVEV

KCLNFRKLQE IYFIETKKFL LIGKSNICVK VGEKSLTCKK

IDLTTIVKPE APFDLSVVYR EGANDFVVTF NTSHLQKKYV

KVLMHDVAYR QEKDENKWTH VNLSSTKLTL LQRKLQPAAM

YEIKVRSIPD HYFKGFWSEW SPSYYFRTPE INNSSGEMDP

ILLTISILSF FSVALLVILA CVLWKKRIKP IVWPSLPDHK

KTLEHLCKKP RKNLNVSFNP ESFLDCQIHR VDDIQARDEV

EGFLQDTFPQ QLEESEKQRL GGDVQSPNCP SEDVVITPES

FGRDSSLTCL AGNVSACDAP ILSSSRSLDC RESGKNGPHV

YQDLLLSLGT TNSTLPPPFS LQSGILTLNP VAQGQPILTS

LGSNQEEAYV TMSSFYQNQ
```

IL-4R (also known as CD124; IL4RA; IL-4RA) is a type I transmembrane protein that can bind interleukin 4 and interleukin 13 to regulate IgE production. It can promote differentiation of Th2 cells. It is also found to activate macrophage during allergy and parasitic infections. (See e.g., Maldonado et al. *Journal of Experimental Medicine* 206.4 (2009): 877-892.) An IL-4R polypeptide can have an amino acid sequence corresponding to the sequence provided below (e.g., Accession No.: NP_000409, NP_001244335, NP_001244336, NP_001244926). In some embodiments, provided herein are fusion proteins comprising a first domain that activates an APC and a second domain that activates an immune effector cell, wherein the second domain comprises IL-4R, or a receptor-binding fragment thereof. In some embodiments, the second domain comprises the extracellular domain of IL-4R corresponding to amino acids 26-232 (underlined below). It is understood that sequences of IL-4R that are shorter or longer than a specific delineated domain can be included in a fusion protein, if desired.

(SEQ ID NO: 193)
```
MGWLCSGLLF PVSCLVLLQV ASSGNMKVLQ EPTCVSDYMS

ISTCEWKMNG PTNCSTELRL LYQLVFLLSE AHTCIPENNG

GAGCVCHLLM DDVVSADNYT LDLWAGQQLL WKGSFKPSEH

VKPRAPGNLT VHTNVSDTLL LTWSNPYPPD NYLYNHLTYA

VNIWSENDPA DFRIYNVTYL EPSLRIAAST LKSGISYRAR

VRAWAQCYNT TWSEWSPSTK WHNSYREPFE QHLLLGVSVS

CIVILAVCLL CYVSITKIKK EWWDQIPNPA RSRLVAIIIQ

DAQGSQWEKR SRGQEPAKCP HWKNCLTKLL PCFLEHNMKR

DEDPHKAAKE MPFQGSGKSA WCPVEISKTV LWPESISVVR

CVELFEAPVE CEEEEEVEEE KGSFCASPES SRDDFQEGRE

GIVARLTESL FLDLLGEENG GFCQQDMGES CLLPPSGSTS

AHMPWDEFPS AGPKEAPPWG KEQPLHLEPS PPASPTQSPD

NLTCTETPLV IAGNPAYRSF SNSLSQSPCP RELGPDPLLA

RHLEEVEPEM PCVPQLSEPT TVPQPEPETW EQILRRNVLQ

HGAAAAPVSA PTSGYQEFVH AVEQGGTQAS AVVGLGPPGE

AGYKAFSSLL ASSAVSPEKC GFGASSGEEG YKPFQDLIPG

CPGDPAPVPV PLFTFGLDRE PPRSPQSSHL PSSSPEHLGL

EPGEKVEDMP KPPLPQEQAT DPLVDSLGSG IVYSALTCHL

CGHLKQCHGQ EDGGQTPVMA SPCCGCCCGD RSSPPTTPLR

APDPSPGGVP LEASLCPASL APSGISEKSK SSSSFHPAPG

NAQSSSQTPK IVNFVSVGPT YMRVS
```

GITR-L (also known as AITRL, GITRL, TL6, TNF18, TNLG2A, hGITRL) is a cytokine that belongs to the TNF ligand family. This cytokine is a ligand for receptor NFRSF18/AITR/GITR. It has been shown to modulate T lymphocyte survival in peripheral tissues. This cytokine is also found to be expressed in endothelial cells and is thought to be important for interaction between T lymphocytes and endothelial cells. (See e.g., Tang X, et al. Oncotarget, 2016 Feb. 23. MED 26657118; Placke T, et al. J Immunol, 2012 Jul. 1. PMID 22649191) A GITR-L polypeptide can have an amino acid sequence corresponding to the sequence provided below (e.g., NP_005083). In some embodiments, provided herein are fusion proteins comprising a first domain that activates an APC and a second domain that activates an immune effector cell, wherein the second domain comprises GITR-L, or a receptor-binding fragment thereof. In some embodiments, the second domain comprises the extracellular domain of GITR-L corresponding to amino acids 72-199 (underlined below). It is understood that sequences of GITR-L that are shorter or longer than a specific delineated domain can be included in a fusion protein, if desired.

```
                                          (SEQ ID NO: 194)
MTLHPSPITCEFLFSTALISPKMCLSHLENMPLSHSRTQGAQRSSWKLWL

FCSIVMLLFLCSFSWLIFIFLQLETAKEPCMAKFGPLPSKWQMASSEPPC

VNKVSDWKLEILQNGLYLIYGQVAPNANYNDVAPFEVRLYKNKDMIQTLT

NKSKIQNVGGTYELHVGDTIDLIFNSEHQVLKNNTYWGIILLANPQFIS
```

TIM-4 (also known as SMUCKLER, TIMD4) TIM-4 is expressed on APC and can deliver co-stimulating signals to T cells by binding to TIM-1. It has been found to induce T cell differentiation, expansion and survival. (See e.g., Rodriguez-Manzanet et al. *The Journal of Immunology* 180.7 (2008): 4706-4713; Nurtanio and Yang. *North American journal of medical sciences* 3.5 (2011): 217.) A TIM-4 polypeptide can have an amino acid sequence corresponding to the sequence provided below (e.g., Accession: NP_001140198.1; NP_612388.2; Q96H15.2). In some embodiments, provided herein are fusion proteins comprising a first domain that activates an APC and a second domain that activates an immune effector cell, wherein the second domain comprises TIM-4, or a receptor-binding fragment thereof. In some embodiments, the second domain comprises the extracellular domain of TIM-4 corresponding to amino acids 25-314 (underlined below). It is understood that sequences of TIM-4 that are shorter or longer than a specific delineated domain can be included in a fusion protein, if desired.

```
                                          (SEQ ID NO: 195)
MSKEPLILWL  MIEFWWLYLT  PVTSETVVTE  VLGHRVTLPC

LYSSWSHNSN  SMCWGKDQCP  YSGCKEALIR  TDGMRVTSRK

SAKYRLQGTI  PRGDVSLTIL  NPSESDSGVY  CCRIEVPGWF

NDVKINVRLN  LQRASTTTHR  TATTTTRRTT  TTSPTTTRQM

TTTPAALPTT  VVTTPDLTTG  TPLQMTTIAV  FTTANTCLSL

TPSTLPEEAT  GLLTPEPSKE  GPILTAESET  VLPSDSWSSV

ESTSADTVLL  TSKESKVWDL  PSTSHVSMWK  TSDSVSSPQP

GASDTAVPEQ  NKTTKTGQMD  GIPMSMKNEM  PISQLLMIIA

PSLGFVLFAL  FVAFLLRGKL  METYCSQKHT  RLDYIGDSKN

VLNDVQHGRE  DEDGLFTL
```

CD153 (CD30L, TNFSF8), cytokine that belongs to the tumor necrosis factor (TNF) ligand family. This cytokine is a ligand for TNFRSF8/CD30, which is a cell surface antigen and a marker for Hodgkin lymphoma and related hematologic malignancies. CD153 binds to CD30 and induces proliferation and activation of T-cells (See e.g., Shimozato, et al. *Biochemical and biophysical research communications* 256, 3 (1999): 519-526; Croft, *Nature Reviews Immunology*, 3.8 (2003): 609-620. Marín and Luis, *Tuberculosis* 102 (2017): 8-15.) A CD153 polypeptide can have an amino acid sequence corresponding to the sequence provided below (e.g., Accession NO: NP_001235, NP_001239219). In some embodiments, provided herein are fusion proteins comprising a first domain that activates an APC and a second domain that activates an immune effector cell, wherein the second domain comprises CD153, or a receptor-binding fragment thereof. In some embodiments, the second domain comprises the extracellular domain of CD153 corresponding to amino acids 63-234 (underlined below). It is understood that sequences of CD153 that are shorter or longer than a specific delineated domain can be included in a fusion protein, if desired.

```
                                          (SEQ ID NO: 196)
MDPGLQQALN  GMAPPGDTAM  HVPAGSVASH  LGTTSRSYFY

LTTATLALCL  VFTVATIMVL  VVQRTDSIPN  SPDNVPLKGG

NCSEDLLCIL  KRAPFKKSWA  YLQVAKHLNK  TKLSWNKDGI

LHGVRYQDGN  LVIQFPGLYF  IICQLQFLVQ  CPNNSVDLKL

ELLINKHIKK  QALVTVCESG  MQTKHVYQNL  SQFLLDYLQV

NTTISVNVDT  FQYIDTSTFP  LENVLSIFLY  SNSD
```

CD48 (also known as BCM1, BLAST, BLAST1, MEM-102, or SLAMF2) is a member of the CD2 subfamily of immunoglobulin-like receptors which includes SLAM (signaling lymphocyte activation molecules) proteins. CD48 can bind to CD2 and deliver a co-stimulatory signal to T cells. CD48 is found on the surface of lymphocytes and other immune cells, dendritic cells, and endothelial cells, and participates in activation and differentiation pathways in these cells. A CD48 polypeptide can have an amino acid sequence corresponding to the sequence provided below (Accession: EAW52705.1 GI: 119573090; Accession: CAG33293.1 GI: 48146141), or fragments thereof. In some embodiments, provided herein are fusion proteins comprising a first domain that activates an APC and a second domain that activates an immune effector cell, wherein the second domain comprises CD48, or a receptor-binding fragment thereof. In some embodiments, the second domain comprises the mature form of CD48 corresponding to amino acids 27-220 (underlined below). It is understood that sequences of CD48 that are shorter or longer than a specific delineated domain can be included in a fusion protein, if desired.

```
                                          (SEQ ID NO: 53)
MCSRGWDSCLALELLLLPLSLLVTSIQGHLVHMTVVSGSNVTLNISESLP

ENYKQLTWFYTFDQKIVEWDSRKSKYFESKFKGRVRLDPQSGALYISKVQ

KEDNSTYIMRVLKKTGNEQEWKIKLQVLDPVPKPVIKIEKIEDMDDNCYL

KLSCVIPGESVNYTWYGDKRPFPKELQNSVLETTLMPHNYSRCYTCQVSN

SVSSKNGTVCLSPPCTLARSFGVEWIASWLVVTVPTILGLLLT
```

CD160 (also known as NK1, BY55, or NK28) is a 27 kDa glycoprotein. The expression of CD160 is tightly associated with peripheral blood NK cells and CD8 T lymphocytes with cytolytic effector activity. A CD160 polypeptide can have an amino acid sequence corresponding to the sequence provided below (e.g., Accession: EAW71440.1 GI: 119591846; Accession: CAI13713.1 GI: 55959477), or fragments thereof. In some embodiments, provided herein are fusion proteins comprising a first domain that activates an APC and a second domain that activates an immune effector cell, wherein the second domain comprises CD160, or a receptor-binding fragment thereof. In some embodiments, the second domain comprises the mature form of CD160 corresponding to amino acids 25-159 (underlined below). It is understood that sequences of CD160 that are shorter or longer than a specific delineated domain can be included in a fusion protein, if desired.

(SEQ ID NO: 49)
MLLEPGRGCCALAILLAIVDIQSG<u>GCINITSSASQEGTRLNLICTVWHKK

EEAEGFVVFLCKDRSGDCSPETSLKQLRLKRDPGIDGVGEISSQLMFTIS

QVTPLHSGTYQCCARSQKSGIRLQGHFFSILFTETGNYTVTGLKQRQHLE

FSHNEGTLSSGFLQEKVWVMLVTSLVALQAL</u>

CD200R (also known as HCRTR2, MOX2R, OX2R) can bind the OX-2 membrane glycoprotein. CD200R is a cell surface glycoprotein containing two immunoglobulin-like domains. It is reported to control myeloid function in a tissue-specific manner. It is also reported to regulate activity of an immune cell by recruiting accessory molecules (e.g., DAP12) to cell surface (See e.g., Gorczynski, *International Scholarly Research Notices* 2012 (2.012).9 A CD200R polypeptide can have an amino acid sequence corresponding to the sequence provided below (e.g., Accession NO: NP_620161; NP_620385). In some embodiments, provided herein are fusion proteins comprising a first domain that activates an APC and a second domain that activates an immune effector cell, wherein the second domain comprises CD200R, or a receptor-binding fragment thereof. In some embodiments, the second domain comprises the extracellular domain of CD200R corresponding to amino acids 29-243 (underlined below). It is understood that sequences of CD200R that are shorter or longer than a specific delineated domain can be included in a fusion protein, if desired.

(SEQ ID NO: 197)
MLCPWRTANLGLLLILTIFLVAASSSLC<u>MDEKQITQNYSKVLAEVNTSWP

VKMATNAVLCCPPIALRNLIIITWEIILRGQPSCTKAYRKETNETKETNC

TDERITWVSRPDQNSDLQIRPVAITHDGYYRCIMVTPDGNFHRGYHLQVL

VTPEVTLFQNRNRTAVCKAVAGKPAAQISWIPEGDCATKQEYWSNGTVTV

KSTCHWEVHNVSTVTCHVSHLTGNKSLYIELLPVPGAKKSAKL</u>YIPYIIL

TIIILTIVGFIWLLKVNGCRKYKLNKTESTPVVEEDEMQPYASYTEKNNP

LYDTTNKVKASEALQSEVDTDLHTL

CD44 (also known as H-CAM, Pgp-1, Epican, HUTCH-I, LHR, ECMR-III) is a cell-surface glycoprotein involved in cell-cell interactions, cell adhesion and migration. It is a receptor for hyaluronic acid (HA) and can also interact with other ligands, such as osteopontin, collagens, and matrix metalloproteinases (MMPs). This protein participates in a wide variety of cellular functions including lymphocyte activation, recirculation and homing, hematopoiesis, and tumor metastasis. (See e.g., Huet et al. *The Journal of Immunology* 143.3 (1989): 798-801.) A CD44 polypeptide can have an amino acid sequence corresponding to the sequence provided below (e.g., Accession No. NP_000601, NP_001001389). In some embodiments, provided herein are fusion proteins comprising a first domain that activates an APC and a second domain that activates an immune effector cell, wherein the second domain comprises CD44, or a receptor-binding fragment thereof. In some embodiments, the second domain comprises the extracellular domain of CD44 corresponding to amino acids 21-649 (underlined below). It is understood that sequences of CD44 that are shorter or longer than a specific delineated domain can be included in a fusion protein, if desired.

(SEQ ID NO: 198)
MDKFWWHAAW GLCLVPLSLA <u>QIDLNITCRF AGVFHVEKNG

RYSISRTEAA DLCKAFNSTL PTMAQMEKAL SIGFETCRYG

FIEGHVVIPR IHPNSICAAN NTGVYILTSN TSQYDTYCFN

ASAPPEEDCT SVTDLPNAFD GPITITIVNR DGTRYVQKGE

YRTNPEDIYP SNPTDDDVSS GSSSERSSTS GGYIFYTFST

VHPIPDEDSP WITDSTDRIP ATTLMSTSAT ATETATKRQE

TWDWFSWLFL PSESKNHLHT TTQMAGTSSN TISAGWEPNE

ENEDERDRHL SFSGSGIDDD EDFISSTIST TPRAFDHTKQ

NQDWTQWNPS HSNPEVLLQT TTRMTDVDRN GTTAYEGNWN

PEAHPPLIHH EHHEEEETPH STSTIQATPS STTEETATQK

EQWFGNRWHE GYRQTPKEDS HSTTGTAAAS AHTSHPMQGR

TTPSPEDSSW TDFFNPISHP MGRGHQAGRR MDMDSSHSIT

LQPTANPNTG LVEDLDRTGP LSMTTQQSNS QSFSTSHEGL

EEDKDHPTTS TLTSSNRNDV TGGRRDPNHS EGSTTLLEGY

TSHYPHTKES RTFIPVTSAK TGSFGVTAVT VGDSNSNVNR

SLSGDQDTFH PSGGSHTTHG SESDGHSHGS QEGGANTTSG

PIRTPQIPEW LIILASLLAL</u> ALILAVCIAV NSRRRCGQKK

KLVINSGNGA VEDRKPSGLN GEASKSQEMV HLVNKESSET

PDQFMTADET RNLQNVDMKI GV

5.2.3 Exemplary LACO-Stim Fusion Proteins

Accordingly, provided herein are fusion proteins comprising a first domain that activates an antigen-presenting cell (APC) and a second domain that activates an immune effector cell, wherein the first domain comprises (a) a ligand that binds an activation receptor of the APC, or a receptor-binding fragment thereof, or (b) an antibody that binds an activation receptor of the APC, or an antigen-binding fragment thereof; and wherein the second domain comprises (a) a co-stimulatory receptor of the immune effector cell, or a functional fragment thereof, (b) a ligand that binds a co-stimulatory receptor of the immune effector cell, or a receptor-binding fragment thereof, or (c) an antibody that binds a co-stimulatory receptor of the immune effector cell, or an antigen-binding fragment thereof. In some embodiments, the APC is selected from the group consisting of a dendritic cell, a macrophage, a myeloid derived suppressor cell, a monocyte, a B cell, a T cell, and a Langerhans cell. In some embodiments, the immune effector cell is selected from the group consisting of a T cell, an NK cell, an NKT cell, a macrophage, a neutrophil, and a granulocyte.

In some embodiments, the first domain comprises (a) a ligand that binds an activation receptor of the APC, or a receptor-binding fragment thereof, or (b) an antibody that binds an activation receptor of the APC, or an antigen-binding fragment thereof, wherein the activation receptor of the APC is selected from the group consisting of CD40, CD80, CD86, CD91, DEC-205 and DC-SIGN. In some embodiments, the first domain comprises a ligand that binds an activation receptor of the APC, or a receptor-binding fragment thereof. In some embodiments, the first domain comprises a ligand that binds CD40, or a receptor-binding fragment thereof. In some embodiments, the first domain comprises CD40L. In some embodiments, the receptor-binding fragment of CD40L comprises amino acids 119-261 of CD40L (SEQ ID NO:9). In some embodiments, the receptor-binding fragment of CD40L comprises the extracellular domain of CD40L. In some embodiments, the first domain of the fusion proteins provided herein comprises three copies of CD40L or a receptor-binding fragment of CD40L. In some embodiments, the first domain of the fusion proteins provided herein comprises three copies of amino acids 119-261 of CD40L (SEQ ID NO:9). In some embodiments, the first domain comprises a ligand that binds CD80, or a receptor-binding fragment thereof. In some embodiments, the first domain comprises a ligand that binds CD86, or a receptor-binding fragment thereof. In some embodiments, the first domain comprises the extracellular domain of CD28. In some embodiments, the first domain comprises CD28. In some embodiments, the first domain comprises the extracellular domain of CTLA-4. In some embodiments, the first domain comprises CTLA-4. In some embodiments, the first domain comprises a ligand that binds CD91, or a receptor-binding fragment thereof. In some embodiments, the first domain comprises domain 3 of RAP1. In some embodiments, the first domain comprises RAP1. In some embodiments, the first domain comprises a ligand that binds DEC-205, or a receptor-binding fragment thereof. In some embodiments, the first domain comprises a ligand that binds DC-SIGN, or a receptor-binding fragment thereof. In some embodiments, the first domain comprises ICAM2, ICAM3, CD18, or CEACAM1, or a receptor-binding fragment of. In some embodiments, the first domain comprises ICAM2, or a receptor-binding fragment of. In some embodiments, the first domain comprises ICAM3, or a receptor-binding fragment of. In some embodiments, the first domain comprises CD18, or a receptor-binding fragment of. In some embodiments, the first domain comprises CEACAM1, or a receptor-binding fragment of.

In some embodiments, the first domain comprises an antibody that binds an activation receptor of the APC, or an antigen-binding fragment thereof. In some embodiments, the activation receptor of the APC is selected from the group consisting of CD40, CD80, CD86, CD91, DEC-205 and DC-SIGN. In some embodiments, the first domain comprises an antibody that binds CD40, or an antigen-binding fragment thereof. In some embodiments, the first domain comprises an antibody that binds CD80, or an antigen-binding fragment thereof. In some embodiments, the first domain comprises an antibody that binds CD86, or an antigen-binding fragment thereof. In some embodiments, the first domain comprises an antibody that binds CD91, or an antigen-binding fragment thereof. In some embodiments, the first domain comprises an antibody that binds DEC-205, or an antigen-binding fragment thereof. In some embodiments, the first domain comprises an antibody that binds DC-SIGN, or an antigen-binding fragment thereof. In some embodiments, the first domain comprises a monoclonal antibody. In some embodiments the first domain comprises a chimeric antibody. In some embodiments the first domain comprises a humanized antibody. In some embodiments the first domain comprises a human antibody. In some embodiments, the first domain comprises a Fab, Fab', F(ab')2, Fv, scFv, (scFv)2, single chain antibody, dual variable region antibody, diabody, nanobody, or single variable region antibody. In some embodiments the first domain comprises a human antibody. In some embodiments, the first domain comprises a scFv.

In some embodiments, the first domain of the fusion proteins provided herein comprise an anti-CD40 antibody or antigen-binding fragment thereof. In some embodiments, the first domain of the fusion proteins provided herein comprise an anti-CD40 scFv. In some embodiments, the anti-CD40 antibody or antigen-binding fragment thereof comprises the antibody designated as F2.103, F5.157, F5.77, 4D11, A40C, or 119 as provided below in Table A.

TABLE A

Anti-CD40 Antibodies

| Antibody | Heavy chain variable domain (VH) | Light chain variable domain (VL) |
|---|---|---|
| F2.103 | EVQLVESGGGLVQPGGSLRLSCAVSGFTFS TYWMHWVRQAPGKGLVWVSRINSDGSST TYADSVKGRFTISRDNAKNTLYLQMNSLR AEDTAVYYCARDRVLWIGELSYYGMDVW GQGTTVTVSS (SEQ ID NO: 76) | DIQMTQSPSTLSASVGDRVTITCRASQSISN WLAWYQQKPGKAPKLLLYKASGLESGVPS RFSGSGSGTEFTLTINSLQPDDFATYYCQQS NSYSWTFGHGTKVEIKRT (SEQ ID NO: 77) |
| F5.157 | EVQLLESGGGLVQPGGSLRLSCAASGFAFS SYAMSWVRQAPGKGLEWVSAISGSGGSTY YADSVKGRFTISRDNSKNTLYLQMNSLRPR TRPYITVRKMGGTMVRGVMGTLTTGAREP WSPSPQ (SEQ ID NO: 79) | IQMTQSPSSVSASAGDRVTITCRASQGISSW LAWYQQKPGKAPKLLIYAGSSLQSGVPSRF SGSGFGTDFTLTIGSLQPEDFATYYCQQASS FPRTFGQGTKVEIKRTVLHHLSSSRHLMS (SEQ ID NO: 80) |
| F5.77 | EVQLLESGGGLVQPGGSLRLSCAASGFTFS SYAMSWVRQAPGKGLEWVSAISGSGGSTY YADSVKGRFTISRDNSKNTLYLQMNSLRA EDTAVYYCAKDGGYYGSGSYGYFDYWGQ GTLVTVSS (SEQ ID NO: 82) | DIQMTQSPSSVSGSVGDRVTITCRASQGISS WLAWYQQKPGKAPKLLIYAGSSLQSGVPS RFSGSGFGTDFTLTISSLQPEDFATYYCQQA SSFPRTFGQGTKVEIKRT (SEQ ID NO: 83) |
| 4D11 | QLQLQESGPGLLKPSETLSLTCTVSGGSISS PGYYGGWIRQPPGKGLEWIGSIYKSGSTYH NPSLKSRVTISVDTSKNQFSLKLSSVTAADT AVYYCTRPVVRYFGWFDPWGQGTLVTVS S (SEQ ID NO: 85) | AIQLTQSPSSLSASVGDRVTITCRASQGISSA LAWYQQKPGKAPKLLIYDASNLESGVPSRF SGSGSGTDFTLTISSLQPEDFATYYCQQFNS YPTFGQGTKVEIKRT (SEQ ID NO: 86) |
| A40C | QVQLVQSGAEVKKPGASVKVSCTASGFNI KDYYVHWVKQAPGQGLEWMGRIDPEDGD SKYAPKFQGKATMTADTSTSTVYMELSSL RSEDTAVYYCTTSYYVGTYGYWGQGTLV TVSS (SEQ ID NO: 88) | DIQMTQSPSSLSASVGDRVTITCSASSSVSY MLWQQKPGKAPKLLIYSTSNLASGVPSRF SGSGSGTDFTLTISSLQPEDFATYYCQQRTF YPYTFGGGTKVEIKRT (SEQ ID NO: 89) |

TABLE A-continued

Anti-CD40 Antibodies

| 119 | QVQLQQSGPGLVKPSQTLSLTCAISGDSVS<br>SNSATWNWIRQSPSRDLEWLGRTYYRSKW<br>YRDYVGSVKSRIIINPDTSNNQFSLQLNSVT<br>PEDTAIYYCTRAQWLGGDYPYYYSMDVW<br>GQGTTVTVSS (SEQ ID NO: 91) | EIVLTQSPATLSLSPGERATLSCRASQSVSS<br>YLAWYQQKPGQAPRLLIYDASNRATGIPA<br>RFSGSGSGTDFTLTISSLEPEDFAVYYCQQR<br>SNTFGPGTKVDIKRT (SEQ ID NO: 92) |

| Antibody | scFv |
|---|---|
| F2.103 | EVQLVESGGGLVQPGGSLRLSCAVSGFTFSTYWMHWVRQAPGKGLVWVSRINSDGSSTTY<br>ADSVKGRFTISRDNAKNTLYLQMNSLRAEDTAVYYCARDRVLWIGELSYYGMDVWGQGT<br>TVTVSSGGGGSGGGGSGGGGSDIQMTQSPSTLSASVGDRVTITCRASQSISNWLAWYQQKP<br>GKAPKLLLYKASGLESGVPSRFSGSGSGTEFTLTINSLQPDDFATYYCQQSNSYSWTFGHGT<br>KVEIKRT (SEQ ID NO: 75) |
| F5.157 | EVQLLESGGGLVQPGGSLRLSCAASGFAFSSYAMSWVRQAPGKGLEWVSAISGSGGSTYYA<br>DSVKGRFTISRDNSKNTLYLQMNSLRPRTRPYITVRKMGGTMVRGVMGTLTTGAREPWSPS<br>PQGGGGSGGGGSGGGGSIQMTQSPSSVSASAGDRVTITCRASQGISSWLAWYQQKPGKAPK<br>LLIYAGSSLQSGVPSRFSGSGFGTDFTLTIGSLQPEDFATYYCQQASSFPRTFGQGTKVEIKRT<br>VLHHLSSSSRHLMS (SEQ ID NO: 78) |
| F5.77 | EVQLLESGGGLVQPGGSLRLSCAASGFTFSSYAMSWVRQAPGKGLEWVSAISGSGGSTYYA<br>DSVKGRFTISRDNSKNTLYLQMNSLRAEDTAVYYCAKDGGYYGSGSYGYFDYWGQGTLV<br>TVSSGGGGSGGGGSGGGGSDIQMTQSPSSVSGSVGDRVTITCRASQGISSWLAWYQQKPGK<br>APKLLIYAGSSLQSGVPSRFSGSGFGTDFTLTISSLQPEDFATYYCQQASSFPRTFGQGTKVEI<br>KRT (SEQ ID NO: 81) |
| 4D11 | QLQLQESGPGLLKPSETLSLTCTVSGGSISSPGYYGGWIRQPPGKGLEWIGSIYKSGSTYHNP<br>SLKSRVTISVDTSKNQFSLKLSSVTAADTAVYYCTRPVVRYFGWFDPWGQGTLVTVSSASG<br>GGGSGGGGSGGGGSAIQLTQSPSSLSASVGDRVTITCRASQGISSALAWYQQKPGKAPKLLI<br>YDASNLESGVPSRFSGSGSGTDFTLTISSLQPEDFATYYCQQFNSYPTFGQGTKVEIKRT<br>(SEQ ID NO: 84) |
| A40C | QVQLVQSGAEVKKPGASVKVSCTASGFNIKDYYVHWVKQAPGQGLEWMGRIDPEDGDSK<br>YAPKFQGKATMTADTSTSTVYMELSSLRSEDTAVYYCTTSYYVGTYGYWGQGTLVTVSSG<br>GGGSGGGGSGGGGSDIQMTQSPSSLSASVGDRVTITCSASSSVSYMLWFQQKPGKAPKLLIY<br>STSNLASGVPSRFSGSGSGTDFTLTISSLQPEDFATYYCQQRTFYPYTFGGGTKVEIKRT<br>(SEQ ID NO: 87) |
| 119 | QVQLQQSGPGLVKPSQTLSLTCAISGDSVSSNSATWNWIRQSPSRDLEWLGRTYYRSKWYR<br>DYVGSVKSRIIINPDTSNNQFSLQLNSVTPEDTAIYYCTRAQWLGGDYPYYYSMDVWGQGT<br>TVTVSSGGGGSGGGGSGGGGSEIVLTQSPATLSLSPGERATLSCRASQSVSSYLAWYQQKPG<br>QAPRLLIYDASNRATGIPARFSGSGSGTDFTLTISSLEPEDFAVYYCQQRSNTFG<br>PGTKVDIKRT<br>(SEQ ID NO: 90) |

In some embodiments, the first domain of the fusion proteins provided herein comprises an anti-CD40 antibody or antigen-binding fragment thereof, wherein the antibody or antigen-binding fragment has (a) a heavy chain variable domain (VH) having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:76, 79, 82, 85, 88, or 91; and/or (b) a light chain variable domain (VL) having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:77, 80, 83, 86, 89, or 92. In some embodiments, the first domain of the fusion proteins provided herein comprises an anti-CD40 antibody or antigen-binding fragment thereof, wherein the antibody or antigen-binding fragment has (a) a VH having an amino acid sequence that is SEQ ID NO:76, 79, 82, 85, 88, or 91; and/or (b) a VL having an amino acid sequence that is SEQ ID NO:77, 80, 83, 86, 89, or 92. In some embodiments, the first domain of the fusion proteins provided herein comprises an anti-CD40 antibody or antigen-binding fragment thereof, wherein the antibody or antigen-binding fragment has a VH and a VL having the amino acid sequences of (1) SEQ ID NOs: 76 and 77, respectively; (2) SEQ ID NOs: 79 and 80, respectively; (3) SEQ ID NOs: 82 and 83, respectively; (4) SEQ ID NOs: 85 and 86, respectively; (5) SEQ ID NOs: 88 and 89, respectively; or (6) SEQ ID NOs: 91 and 92, respectively.

In some embodiments, the first domain of the fusion proteins provided herein comprise an anti-CD40 scFv. In some embodiments, the first domain of the fusion proteins provided herein comprise an anti-CD40 scFv having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:75, 78, 81, 84, 87, or 90. In some embodiments, the first domain of the fusion proteins provided herein comprise an anti-CD40 scFv having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:75. In some embodiments, the first domain of the fusion proteins provided herein comprise an anti-CD40 scFv having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:78. In some embodiments, the first domain of the fusion proteins provided herein comprise an anti-CD40 scFv having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:81. In some embodiments, the first domain of the fusion proteins provided herein comprise an anti-CD40 scFv having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:84. In some embodiments, the first domain of the fusion proteins provided herein comprise an anti-CD40 scFv having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:87. In some embodiments, the first domain of the fusion proteins provided herein comprise an anti-CD40 scFv having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:90. In some embodiments, the first domain of the fusion proteins provided herein comprise an anti-CD40 scFv having the amino acid sequence of SEQ ID NO:75. In some embodiments, the first domain of the fusion proteins provided herein comprise an anti-CD40 scFv having the amino acid sequence of SEQ ID NO:78. In some embodiments, the first domain of the fusion proteins provided herein comprise an anti-CD40 scFv having the amino acid sequence of SEQ ID NO:81. In some embodiments, the first domain of the fusion proteins provided herein comprise an anti-CD40 scFv having the amino acid sequence of SEQ ID NO:84. In some embodiments, the first domain of the fusion proteins provided herein comprise an anti-CD40 scFv having the amino acid sequence of SEQ ID NO:87. In some embodiments, the first domain of the fusion proteins provided herein comprise an anti-CD40 scFv having the amino acid sequence of SEQ ID NO:90.

In some embodiments, the second domain of fusion proteins provided herein comprises (a) a co-stimulatory receptor of the immune effector cell, or a functional fragment thereof, or (b) an antibody that binds a co-stimulatory receptor of the immune effector cell, or an antigen-binding fragment thereof. The immune effector cell can be selected from the group consisting of a T cell, an NK cell, an NKT cell, a macrophage, a neutrophil, and a granulocyte. In some embodiments, the second domain of fusion proteins provided herein comprises a co-stimulatory receptor of the immune effector cell, or a functional fragment thereof, wherein the immune cell is a T cell, an NK cell, an NKT cell, a macrophage, a neutrophil, or a granulocyte. In some embodiments, the co-stimulatory receptor of the immune effector cell is selected from the group consisting of CD28, 4-1BB, ICOS, CD27, OX40, DAP10, 2B4, CD30, CD2, LIGHT, GITR, DR3, and CD43. In some embodiments, the second domain of fusion proteins provided herein comprises a functional fragment of a co-stimulatory receptor selected from the group consisting of CD28, 4-1BB, ICOS, CD27, OX40, DAP10, 2B4, CD30, CD2, LIGHT, GITR, DR3, and CD43. In some embodiments, the functional fragment comprises the cytoplasmic domain of the co-stimulatory receptor. In some embodiments, the second domain of fusion proteins provided herein further comprises the transmembrane domain of the co-stimulatory receptor. In some embodiments, the second domain of fusion proteins provided herein comprises a functional fragment of CD28. In some embodiments, the second domain of fusion proteins provided herein comprises the cytoplasmic domain of CD28. In some embodiments, the second domain of fusion proteins provided herein comprises a functional fragment of 4-1BB. In some embodiments, the second domain of fusion proteins provided herein comprises the cytoplasmic domain of 4-1BB. In some embodiments, the second domain of fusion proteins provided herein comprises a functional fragment of ICOS. In some embodiments, the second domain of fusion proteins provided herein comprises the cytoplasmic domain of ICOS. In some embodiments, the second domain of fusion proteins provided herein comprises a functional fragment of CD27. In some embodiments, the second domain of fusion proteins provided herein comprises the cytoplasmic domain of CD27. In some embodiments, the second domain of fusion proteins provided herein comprises a functional fragment of OX40. In some embodiments, the second domain of fusion proteins provided herein comprises the cytoplasmic domain of OX40. In some embodiments, the second domain of fusion proteins provided herein comprises a functional fragment of DAP10. In some embodiments, the second domain of fusion proteins provided herein comprises the cytoplasmic domain of DAP10. In some embodiments, the second domain of fusion proteins provided herein comprises a functional fragment of 2B4. In some embodiments, the second domain of fusion proteins provided herein comprises the cytoplasmic domain of 2B4. In some embodiments, the second domain of fusion proteins provided herein comprises a functional fragment of CD30. In some embodiments, the second domain of fusion proteins provided herein comprises the cytoplasmic domain of CD30. In some embodiments, the second domain of fusion proteins provided herein comprises a functional fragment of CD2. In some embodiments, the second domain of fusion proteins provided herein the cytoplasmic domain of CD2. In some embodiments, the second domain of fusion proteins provided herein comprises a functional fragment of LIGHT. In some embodiments, the second domain of fusion proteins provided herein comprises the cytoplasmic domain of LIGHT. In some embodiments, the second domain of fusion proteins provided herein comprises a functional fragment of GITR. In some embodiments, the second domain of fusion proteins provided herein comprises the cytoplasmic domain of GITR. In some embodiments, the second domain of fusion proteins provided herein comprises a functional fragment of DR3. In some embodiments, the second domain of fusion proteins provided herein comprises the cytoplasmic domain of DR3. In some embodiments, the second domain of fusion proteins provided herein comprises a functional fragment of CD43. In some embodiments, the second domain of fusion proteins provided herein comprises the cytoplasmic domain of CD43.

In some embodiments, the second domain of fusion proteins provided herein comprises an antibody that binds a co-stimulatory receptor of the immune effector cell, or an antigen-binding fragment thereof. The immune effector cell can be selected from the group consisting of a T cell, an NK cell, an NKT cell, a macrophage, a neutrophil, and a granulocyte. In some embodiments, the co-stimulatory receptor of the immune effector cell is selected from the group consisting of CD28, 4-1BB, ICOS, CD27, OX40, DAP10, 2B4, CD30, CD2, LIGHT, GITR, DR3, and CD43. In some embodiments, the second domain of fusion proteins provided herein comprises an antibody that binds CD28, or an antigen-binding fragment thereof. In some embodiments, the second domain of fusion proteins provided herein comprises an antibody that binds 4-1BB, or an antigen-binding fragment thereof. In some embodiments, the second domain the second domain of the fusion proteins provided herein comprise an anti-CD28 scFv. In some embodiments, the anti-CD28 antibody or antigen-binding fragment thereof comprises the antibody that is designated 1412.

TABLE B

Exemplary Anti-CD28 Antibody

| Antibody | Heavy chain variable domain (VH) | Light chain variable domain (VL) |
|---|---|---|
| 1412 | QVQLVQSGAEVKKPGASVKVSCKASGYTF TSYYIHWVRQAPGQGLEWIGCIYPGNVNT NYNEKFKDRATLTVDTSISTAYMELSRLRS DDTAVYFCTRSHYGLDWNFDVWGQGTTV TVSS (SEQ ID NO: 73) | VMDDIQMTQSPSSLSASVGDRVTITCHASQ NIYVWLNWYQQKPGKAPKLLIYKASNLHT GVPSRFSGSGSGTDFTLTISSLQPEDFATYY CQQGQTYPYTFGGGTKVEIK (SEQ ID NO: 74) |

| Antibody | ScFv |
|---|---|
| 1412 | ALPVTALLLPLALLLHAARPQVQLVQSGAEVKKPGASVKVSCKASGYTFTSYYIHWVRQAP GQGLEWIGCIYPGNVNTNYNEKFKDRATLTVDTSISTAYMELSRLRSDDTAVYFCTRSHYG LDWNFDVWGQGTTVTVSSVEGGSGGSGGSGGSGGVMDDIQMTQSPSSLSASVGDRVTITC HASQNIYVWLNWYQQKPGKAPKLLIYKASNLHTGVPSRFSGSGSGTDFTLTISSLQPEDFAT YYCQQGQTYPYTFGGGTKVEIK (SEQ ID NO: 72) | of fusion proteins provided herein comprises an antibody that binds ICOS, or an antigen-binding fragment thereof. In some embodiments, the second domain of fusion proteins provided herein comprises an antibody that binds CD27, or an antigen-binding fragment thereof. In some embodiments, the second domain of fusion proteins provided herein comprises an antibody that binds OX40, or an antigen-binding fragment thereof. In some embodiments, the second domain of fusion proteins provided herein comprises an antibody that binds DAP10, or an antigen-binding fragment thereof. In some embodiments, the second domain of fusion proteins provided herein comprises an antibody that binds 2B4, or an antigen-binding fragment thereof. In some embodiments, the second domain of fusion proteins provided herein comprises an antibody that binds CD30, or an antigen-binding fragment thereof. In some embodiments, the second domain of fusion proteins provided herein comprises an antibody that binds CD2, or an antigen-binding fragment thereof. In some embodiments, the second domain of fusion proteins provided herein comprises an antibody that binds LIGHT, or an antigen-binding fragment thereof. In some embodiments, the second domain of fusion proteins provided herein comprises an antibody that binds GITR, or an antigen-binding fragment thereof. In some embodiments, the second domain of fusion proteins provided herein comprises an antibody that binds DR3, or an antigen-binding fragment thereof. In some embodiments, the second domain of fusion proteins provided herein comprises an antibody that binds CD43, or an antigen-binding fragment thereof.

In some embodiments, the second domain comprises a monoclonal antibody. In some embodiments the second domain comprises a chimeric antibody. In some embodiments the second domain comprises a humanized antibody. In some embodiments the second domain comprises a human antibody. In some embodiments, the second domain comprises a Fab, Fab', F(ab')2, Fv, scFv, (scFv)2, single chain antibody, dual variable region antibody, diabody, nanobody, or single variable region antibody. In some embodiments the second domain comprises a human antibody. In some embodiments, the second domain comprises a scFv.

In some embodiments, the second domain of the fusion proteins provided herein comprise an anti-CD28 antibody or antigen-binding fragment thereof. In some embodiments, In some embodiments, the second domain of the fusion proteins provided herein comprises an anti-CD28 antibody or antigen-binding fragment thereof, wherein the antibody or antigen-binding fragment has (a) a VH having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:73; and/or (b) a VL having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:74. In some embodiments, the second domain of the fusion proteins provided herein comprises an anti-CD28 antibody or antigen-binding fragment thereof, wherein the antibody or antigen-binding fragment has (a) a VH having an amino acid sequence that is SEQ ID NO:73; and/or (b) a VL having an amino acid sequence that is SEQ ID NO:74. In some embodiments, the second domain of the fusion proteins provided herein comprise an anti-CD28 scFv having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:72. In some embodiments, the second domain of the fusion proteins provided herein comprise an anti-CD28 scFv having the amino acid sequence of SEQ ID NO:72.

The fusion proteins described herein (i.e. the LACO-Stim molecules) can include any combinations of APC activators (ligands or antibodies that bind activation receptors) and immune effector cell activators (co-stimulatory receptors or antibodies that bind co-stimulatory receptors) disclosed herein or otherwise known in the art. For illustration purposes, provided below are various forms of the CD40-C28 LACO-Stim fusion proteins that activates APCs (e.g., the dendritic cells) via the CD40/CD40L signaling and activates immune effector cells (e.g., the T cells) via the CD28 signaling.

5.2.3.1 Exemplary LACO-Stim (1): Ligand for APC Activation Receptor+Co-Stimulatory Receptor (e.g., CD40L-CD28)

In some embodiments, fusion proteins provided herein comprise a first domain that activates APC and a second domain that activates an immune effector cell, wherein the first domain comprises a ligand that binds an activation receptor of the APC, or a receptor-binding fragment thereof, and the second domain comprises a co-stimulatory receptor of the immune effector cell, or a functional fragment thereof. In some embodiments, the second domain comprises the cytoplasmic domain of a co-stimulatory receptor of the immune effector cell. In some embodiments, the C-terminus of the first domain is linked to the N-terminus of the second domain. In some embodiments, the N-terminus of the first domain is linked to the C-terminus of the second domain. In some embodiments, provided herein are fusion proteins that are membrane fusion proteins. In some embodiments, the first domain and the second domain are linked via a linker. The linker can be a flexible linker or a rigid linker. In some embodiments, the linker has the amino acid sequence of (GGGGS)n, n=1, 2, 3, 4, or 5 (SEQ ID NO:215). In some embodiments, the linker has the amino acid sequence of (EAAAK)n, n=1, 2, 3, 4, or 5 (SEQ ID NO:216). In some embodiments, the linker has the amino acid sequence of (PA)nP, n=1, 2, 3, 4, or 5 (SEQ ID NO:217). In some embodiments, the linker has the amino acid sequence of GSGGGGSGGGGSGGGS (SEQ ID NO:219). In some embodiments, the linker has the amino acid sequence of GGGGS (SEQ ID NO:218).

In some embodiments, the first domain comprises a ligand that binds an APC activation receptor selected from the group consisting of CD40, CD80, CD86, CD91, DEC-205, and DC-SIGN, or a receptor-binding fragment thereof. In some embodiments, the first domain of the fusion proteins provided herein comprises full length CD40L. In some embodiments, the first domain of the fusion proteins provided herein can have an amino acid sequence that is at least 85%, at least 88%, at least 90%, at least 95%, at least 98%, or 100% identical to SEQ ID NO:9. In some embodiments, the first domain of the fusion proteins provided herein has the amino acid sequence of SEQ ID NO:9. In some embodiments, the first domain of the fusion proteins provided herein comprises the extracellular domain of CD40L (e.g., SEQ ID NO:12). In some embodiments, the first domain of the fusion proteins provided herein can have an amino acid sequence that is at least 85%, at least 88%, at least 90%, at least 95%, at least 98%, or 100% identical to SEQ ID NO:12. In some embodiments, the first domain of the fusion proteins provided herein has the amino acid sequence of SEQ ID NO:12. In some embodiments, the first domain of the fusion proteins provided herein can have amino acids 119-261 of CD40L (SEQ ID NO:9). In some embodiments, the first domain of the fusion proteins provided herein comprises three copies of the CD40L, or a functional fragment thereof. In some embodiments, the first domain of the fusion proteins provided herein comprises three copies of the extracellular domain of the CD40L. In some embodiments, the first domain of the fusion proteins provided herein comprises three copies of amino acids 119-261 of CD40L (SEQ ID NO:9).

In some embodiments, the second domain comprises a co-stimulatory receptor selected from the group consisting of CD28, 4-1BB, ICOS, CD27, OX40, DAP10, 2B4, CD30, CD2, LIGHT, GITR, TLR, DR3, and CD43, or a functional fragment thereof. In some embodiments, the second domain comprises the cytoplasmic domain of a co-stimulatory receptor selected from the group consisting of CD28, 4-1BB, ICOS, CD27, OX40, DAP10, 2B4, CD30, CD2, LIGHT, GITR, TLR, DR3, and CD43. In some embodiments, the second domain of the fusion proteins provided herein comprises a CD28 cytoplasmic domain (e.g., SEQ ID NO:14). In some embodiments, the second domain of the fusion proteins provided herein can have an amino acid sequence that is at least 85%, at least 88%, at least 90%, at least 95%, at least 98%, or 100% identical to SEQ ID NO:14. In some embodiments, the second domain of the fusion proteins provided herein has the amino acid sequence of SEQ ID NO:14. In some embodiments, the second domain of the fusion proteins provided herein further comprises a CD28 transmembrane domain (e.g., SEQ ID NO:15). In some embodiments, the second domain of the fusion proteins provided herein comprises a 4-1BB cytoplasmic domain (e.g., SEQ ID NO:17). In some embodiments, the second domain of the fusion proteins provided herein can have an amino acid sequence that is at least 85%, at least 88%, at least 90%, at least 95%, at least 98%, or 100% identical to SEQ ID NO:17. In some embodiments, the second domain of the fusion proteins provided herein has the amino acid sequence of SEQ ID NO:17. In some embodiments, the second domain of the fusion proteins provided herein further comprises a 4-1BB transmembrane domain (e.g., SEQ ID NO:18).

In some embodiments, fusion proteins provided herein have a first domain that comprises CD40L or a receptor-binding fragment thereof, and a second domain that comprises a CD28 cytoplasmic domain. In some embodiments, fusion proteins provided herein have a first domain that comprises CD40L or a receptor-binding fragment thereof, and a second domain that comprises a 4-1BB cytoplasmic domain. In some embodiments, fusion proteins provided herein have a first domain that comprises CD40L or a receptor-binding fragment thereof, and a second domain that comprises an ICOS cytoplasmic domain. In some embodiments, fusion proteins provided herein have a first domain that comprises CD40L or a receptor-binding fragment thereof, and a second domain that comprises a CD27 cytoplasmic domain. In some embodiments, fusion proteins provided herein have a first domain that comprises CD40L or a receptor-binding fragment thereof, and a second domain that comprises an OX40 cytoplasmic domain. In some embodiments, fusion proteins provided herein have a first domain that comprises CD40L or a receptor-binding fragment thereof, and a second domain that comprises a DAP10 cytoplasmic domain. In some embodiments, fusion proteins provided herein have a first domain that comprises CD40L or a receptor-binding fragment thereof, and a second domain that comprises a 2B4 cytoplasmic domain. In some embodiments, fusion proteins provided herein have a first domain that comprises CD40L or a receptor-binding fragment thereof, and a second domain that comprises a CD30 cytoplasmic domain. In some embodiments, fusion proteins provided herein have a first domain that comprises CD40L or a receptor-binding fragment thereof, and a second domain that comprises a CD2 cytoplasmic domain. In some embodiments, fusion proteins provided herein have a first domain that comprises CD40L or a receptor-binding fragment thereof, and a second domain that comprises a LIGHT cytoplasmic domain. In some embodiments, fusion proteins provided herein have a first domain that comprises CD40L or a receptor-binding fragment thereof, and a second domain that comprises a GITR cytoplasmic domain. In some embodiments, fusion proteins provided herein have a first domain that comprises CD40L or a receptor-binding fragment thereof, and a second domain that comprises a TLR cytoplasmic domain. In some embodiments, fusion proteins provided herein have a first domain that comprises CD40L or a receptor-binding fragment thereof, and a second domain that comprises a DR3 cytoplasmic domain. In some embodiments, fusion proteins provided herein have a first domain that comprises CD40L or a receptor-binding fragment thereof, and a second domain that comprises a CD43 cytoplasmic domain. The receptor-binding fragment of CD40L can be amino acids 119-261 of CD40L (SEQ ID NO:9). In some embodiments, the first domain comprises full length CD40L.

embodiments, fusion proteins provided herein have an amino acid sequence that is at least 85% identical to SEQ ID NO:199. In some embodiments, fusion proteins provided herein have an amino acid sequence that is at least 90% identical to SEQ ID NO:199. In some embodiments, fusion proteins provided herein have an amino acid sequence that is at least 95% identical to SEQ ID NO:199. In some

| Exemplary LACO-Stim Fusion Protein | Sequence |
|---|---|
| (CD40L cytoplasmic domain -CD28 cytoplasmic domain- CD40L transmembrane region - CD40L extracellular domain) | MIETYNQTSPRSAATGLPISMKRSKRSRLLHSDYMNMTPRRPGPTRKHYQPYAP PRDFAAYRSIFMYLLTVFLITQMIGSALFAVYLHRRLDKIEDERNLHEDFVFMKT IQRCNTGERSLSLLNCEEIKSQFEGFVKDIMLNKEETKKENSFEMQKGDQNPQIA AHVISEASSKTTSVLQWAEKGYYTMSNNLVTLENGKQLTVKRQGLYYIYAQVT FCSNREASSQAPFIASLCLKSPGRFERILLRAANTHSSAKPCGQQSIHLGGVFELQ PGASVFVNVTDPSQVSHGTGFTSFGLLKL (SEQ ID NO: 93) |
| TriCD40L_8-28 (Trimer of a CD40L extracellular domain, CD8 transmembrane domain and CD28 cytoplasmic domain) | MALPVTALLLPLALLLHAARPNPQIAAHVISEASSKTTSVLQWAEKGYYTMSNN LVTLENGKQLTVKRQGLYYIYAQVTFCSNREASSQAPFIASLCLKSPGRFERILL RAANTHSSAKPCGQQSIHLGGVFELQPGASVFVNVTDPSQVSHGTGFTSFGLLK LGGGGSGGGSNPQIAAHVISEASSKTTSVLQWAEKGYYTMSNNLVTLENGKQL TVKRQGLYYIYAQVTFCSNREASSQAPFIASLCLKSPGRFERILLRAANTHSSAK PCGQQSIHLGGVFELQPGASVFVNVTDPSQVSHGTGFTSFGLLKLGGGGSGGGS NPQIAAHVISEASSKTTSVLQWAEKGYYTMSNNLVTLENGKQLTVKRQGLYYI YAQVTFCSNREASSQAPFIASLCLKSPGRFERILLRAANTHSSAKPCGQQSIHLGG VFELQPGASVFVNVTDPSQVSHGTGFTSFGLLKLGSGGGGSGGGGSGGGGSTTT PAPRPPTPAPTIASQPLSLRPEACRPAAGGAVHTRGLDFACDIYIWAPLAGTCGV LLLSLVITLYCRSKRSRLLHSDYMNMTPRRPGPTRKHYQPYAPPRDFAAYRS (SEQ ID NO: 199) |
| TriCD40L_28-28 (Trimer of a CD40L extracellular domain, CD28 transmembrane domain and CD28 cytoplasmic domain) | MALPVTALLLPLALLLHAARPNPQIAAHVISEASSKTTSVLQWAEKGYYTMSNN LVTLENGKQLTVKRQGLYYIYAQVTFCSNREASSQAPFIASLCLKSPGRFERILL RAANTHSSAKPCGQQSIHLGGVFELQPGASVFVNVTDPSQVSHGTGFTSFGLLK LGGGGSGGGSNPQIAAHVISEASSKTTSVLQWAEKGYYTMSNNLVTLENGKQL TVKRQGLYYIYAQVTFCSNREASSQAPFIASLCLKSPGRFERILLRAANTHSSAK PCGQQSIHLGGVFELQPGASVFVNVTDPSQVSHGTGFTSFGLLKLGGGGSGGGS NPQIAAHVISEASSKTTSVLQWAEKGYYTMSNNLVTLENGKQLTVKRQGLYYI YAQVTFCSNREASSQAPFIASLCLKSPGRFERILLRAANTHSSAKPCGQQSIHLGG VFELQPGASVFVNVTDPSQVSHGTGFTSFGLLKLGSGGGGSGGGGSGGGGSIEV MYPPPYLDNEKSNGTIIHVKGKHLCPSPLFPGPSKPFWVLVVVGGVLACYSLLV TVAFIIFWVRSKRSRLLHSDYMNMTPRRPGPTRKHYQPYAPPRDFAAYRS (SEQIDNO: 201) |

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as 40L.28.40L.40L (SEQ ID NO:93). In some embodiments, fusion proteins provided herein have an amino acid sequence that is at least 85% identical to SEQ ID NO:93. In some embodiments, fusion proteins provided herein have an amino acid sequence that is at least 90% identical to SEQ ID NO:93. In some embodiments, fusion proteins provided herein have an amino acid sequence that is at least 95% identical to SEQ ID NO:93. In some embodiments, fusion proteins provided herein have an amino acid sequence that is at least 98% identical to SEQ ID NO:93. In some embodiments, fusion proteins provided herein have an amino acid sequence that is at least 99% identical to SEQ ID NO:93. In some embodiments, fusion proteins provided herein have an amino acid sequence that is identical to SEQ ID NO:93.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as TriCD40L_8-28 (SEQ ID NO:199). In some embodiments, fusion proteins provided herein have an amino acid sequence that is at least 98% identical to SEQ ID NO:199. In some embodiments, fusion proteins provided herein have an amino acid sequence that is at least 99% identical to SEQ ID NO:199. In some embodiments, fusion proteins provided herein have an amino acid sequence that is identical to SEQ ID NO:199.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as TriCD40L_28-28 (SEQ ID NO:201). In some embodiments, fusion proteins provided herein have an amino acid sequence that is at least 85% identical to SEQ ID NO:201. In some embodiments, fusion proteins provided herein have an amino acid sequence that is at least 90% identical to SEQ ID NO:201. In some embodiments, fusion proteins provided herein have an amino acid sequence that is at least 95% identical to SEQ ID NO:201. In some embodiments, fusion proteins provided herein have an amino acid sequence that is at least 98% identical to SEQ ID NO:201. In some embodiments, fusion proteins provided herein have an amino acid sequence that is at least 99% identical to SEQ ID NO:201. In some embodiments, fusion proteins provided herein have an amino acid sequence that is identical to SEQ ID NO:201.

As a person of ordinary skill in the art would understand, the functional fragment of CD40L or full length CD40L in the fusion proteins exemplified herein can be replaced with another ligand for an activation receptor for APC that is disclosed herein or otherwise known in the art, including, for example, the extracellular domain or the full length of a CD80 ligand (e.g., CD28 or CTLA-4), a CD86 ligand (e.g., CD28 or CTLA-4), a CD91 ligand (e.g., RAP1), a DEC-205 ligand or a DC-SIGN ligand (e.g., ICAM2, ICAM3, CD18, or CEACAM1). As a person of ordinary skill in the art would understand, the CD28 cytoplasmic domain in the fusion proteins exemplified herein can be replaced with the cytoplasmic domain of another co-stimulator for immune effector cells that is disclosed herein or otherwise known in the art, including, for example, the cytoplasmic domain of 4-1BB, ICOS, CD27, OX40, DAP10, 2B4, CD30, CD2, LIGHT, GITR, TLR, DR3, or CD43; or a different functional fragment of 4-1BB, ICOS, CD27, OX40, DAP10, 2B4, CD30, CD2, LIGHT, GITR, TLR, DR3, or CD43, that retains the function of the full-length protein to activate the immune effector cell.

5.2.3.2 Exemplary LACO-Stim (2): Ligand for APC Activation Receptor+Antibody Binding Co-Stimulatory Receptor (e.g., aCD28-CD40L)

In some embodiments, fusion proteins provided herein comprise a first domain that activates an APC and a second domain that activates an immune effector cell, wherein the first domain comprises an antibody that binds an activation receptor of the APC, or an antigen-binding fragment thereof, and wherein the second domain comprises an antibody that binds a co-stimulatory receptor of the immune effector cell, or an antigen-binding fragment thereof. In some embodiments, the C-terminus of the first domain is linked to the N-terminus of the second domain. In some embodiments, the N-terminus of the first domain is linked to the C-terminus of the second domain. In some embodiments, fusion proteins provided herein are antibody-based soluble proteins.

In some embodiments, the two domains of the fusion proteins disclosed herein are linked via a trimerization motif. In some embodiments, the linker is a trimerization motif selected from the group consisting of a T4 fibritin trimerization motif, an isoleucine zipper, a GCN4II motif, a Matrilin-1 motif, and a collagen XV trimerization motif. In some embodiments, the linker is a T4 fibritin trimerization motif (e.g., SEQ ID NO:1). In some embodiments, the linker has the amino acid sequence of SEQ ID NO:1. In some embodiments, the linker is an isoleucine zipper (e.g., SEQ ID NO:2 or 3). In some embodiments, the linker has the amino acid sequence of SEQ ID NO:2. In some embodiments, the linker has the amino acid sequence of SEQ ID NO:3. In some embodiments, the linker is a GCN4II motif (e.g., SEQ ID NO:4 or 5). In some embodiments, the linker has the amino acid sequence of SEQ ID NO:4. In some embodiments, the linker has the amino acid sequence of SEQ ID NO:5. In some embodiments, the linker is a Matrilin-1 motif (e.g., SEQ ID NO:6 or 7). In some embodiments, the linker has the amino acid sequence of SEQ ID NO:6. In some embodiments, the linker has the amino acid sequence of SEQ ID NO:7. In some embodiments, the linker is a collagen XV trimerization motif (e.g., SEQ ID NO:8). In some embodiments, the linker has the amino acid sequence of SEQ ID NO:8.

In some embodiments, the first domain comprises a ligand that binds an APC activation receptor selected from the group consisting of CD40, CD80, CD86, CD91, DEC-205, and DC-SIGN, or a receptor-binding fragment thereof. In some embodiments, the first domain of the fusion proteins provided herein comprises the extracellular domain of CD40L (e.g., SEQ ID NO:12). In some embodiments, the first domain of the fusion proteins provided herein can have an amino acid sequence that is at least 85%, at least 88%, at least 90%, at least 95%, at least 98%, or 100% identical to SEQ ID NO:12. In some embodiments, the first domain of the fusion proteins provided herein has the amino acid sequence of SEQ ID NO:12. In some embodiments, the first domain of the fusion proteins provided herein comprises full length CD40L. In some embodiments, the first domain of the fusion proteins provided herein can have an amino acid sequence that is at least 85%, at least 88%, at least 90%, at least 95%, at least 98%, or 100% identical to SEQ ID NO:9. In some embodiments, the first domain of the fusion proteins provided herein has the amino acid sequence of SEQ ID NO:9. In some embodiments, the first domain of the fusion proteins provided herein can have amino acids 119-261 of CD40L (SEQ ID NO:9). In some embodiments, the first domain of the fusion proteins provided herein comprises three copies of the CD40L, or a functional fragment thereof. In some embodiments, the first domain of the fusion proteins provided herein comprises three copies of the extracellular domain of the CD40L. In some embodiments, the first domain of the fusion proteins provided herein comprises three copies of amino acids 119-261 of CD40L (SEQ ID NO:9).

In some embodiments, the second domain comprises an antibody that binds a co-stimulatory receptor of the immune effector cell, or an antigen-binding fragment thereof, wherein the co-stimulatory receptor is selected from the group consisting of CD28, 4-1BB, ICOS, CD27, OX40, DAP10, 2B4, CD30, CD2, LIGHT, GITR, TLR, DR3, and CD43. In some embodiments, provided herein are fusion proteins having a first domain that comprises CD40L or a receptor-binding fragment thereof and a second domain that comprises an anti-CD28 antibody or an antigen-binding fragment thereof. In some embodiments, provided herein are fusion proteins having a first domain that comprises CD40L or a receptor-binding fragment thereof and a second domain that comprises an anti-4-1BB antibody or an antigen-binding fragment thereof. In some embodiments, provided herein are fusion proteins having a first domain that comprises CD40L or a receptor-binding fragment thereof and a second domain that comprises an anti-ICOS antibody or an antigen-binding fragment thereof. In some embodiments, provided herein are fusion proteins having a first domain that comprises CD40L or a receptor-binding fragment thereof and a second domain that comprises an anti-CD27 antibody or an antigen-binding fragment thereof. In some embodiments, provided herein are fusion proteins having a first domain that comprises CD40L or a receptor-binding fragment thereof and a second domain that comprises an anti-OX40 antibody or an antigen-binding fragment thereof. In some embodiments, provided herein are fusion proteins having a first domain that comprises CD40L or a receptor-binding fragment thereof and a second domain that comprises an anti-DAP10 antibody or an antigen-binding fragment thereof. In some embodiments, provided herein are fusion proteins having a first domain that comprises CD40L or a receptor-binding fragment thereof and a second domain that comprises an anti-2B4 antibody or an antigen-binding fragment thereof. In some embodiments, provided herein are fusion proteins having a first domain that comprises CD40L or a receptor-binding fragment thereof and a second domain that comprises an anti-CD30 antibody or an antigen-binding fragment thereof. In some embodiments, provided herein are fusion proteins having a first domain that comprises CD40L or a receptor-binding fragment thereof and a second domain that comprises an anti-CD2 antibody or an antigen-binding fragment thereof. In some embodiments, provided herein are fusion proteins having a first domain that comprises CD40L or a receptor-binding fragment thereof and a second domain that comprises an anti-LIGHT antibody or an antigen-binding fragment thereof. In some embodiments, provided herein are fusion proteins having a first domain that comprises CD40L or a receptor-binding fragment thereof and a second domain that comprises an anti-GITR antibody or an antigen-binding fragment thereof. In some embodiments, provided herein are fusion proteins having a first domain that comprises CD40L or a receptor-binding fragment thereof and a second domain that comprises an anti-TLR antibody or an antigen-binding fragment thereof. In some embodiments, provided herein are fusion proteins having a first domain that comprises CD40L or a receptor-binding fragment thereof and a second domain that comprises an anti-DR3 antibody or an antigen-binding fragment thereof. In some embodiments, provided herein are fusion proteins having a first domain that comprises CD40L or a receptor-binding fragment thereof and a second domain that comprises an anti-CD43 antibody or an antigen-binding fragment thereof. In some embodiments, the receptor-binding fragment of CD40L can have amino acids 119-261 of CD40L (SEQ ID NO:9).

In some embodiments, provided herein are fusion proteins having a first domain that comprises CD40L or a receptor-binding fragment thereof and a second domain that comprises an anti-CD28 antibody or an antigen-binding fragment thereof. The anti-CD28 antibody or antigen-binding fragment can be any anti-CD28 antibody or antigen-binding fragment disclosed herein or otherwise known in the art that can activate CD28 signaling. In some embodiments, the anti-CD28 antibody or antigen-binding fragment is the antibody designated 1412. In some embodiments, the anti-CD28 antibody or antigen-binding fragment thereof has (a) a VH having an amino acid sequence that is SEQ ID NO:73; and/or (b) a VL having an amino acid sequence that is SEQ ID NO:74. In some embodiments, the anti-CD28 antibody or antigen-binding fragment thereof comprises an anti-CD28 scFv having the amino acid sequence of SEQ ID NO:72.

| Exemplary LACO-Stim Fusion Protein | Sequence |
|---|---|
| 1412-T4-CD40L (anti-CD28 scFv (1412) - T4 fibritin trimerization motif-CD40L extracellular region | MALPVTALLLPLALLLHAARPQVQLVQSGAEVKK PGASVKVSCKASGYTFTSYYIHWVRQAPGQGLEW IGCIYPGNVNTNYNEKFKDRATLTVDTSISTAYM ELSRLRSDDTAVYFCTRSHYGLDWNFDVWGQGTT VTVSSVEGGSGGSGGSGGSGGVMDDIQMTQSPSS LSASVGDRVTITCHASQNIYVWLNWYQQKPGKAP KLLIYKASNLHTGVPSRFSGSGSGTDFTLTISSL PEDFATYYCQQGQTYPYTFGGGTKVEIKGYIPEA PRDGQAYVRKDGEWVLLSTFLGDQNPQIAAHVIS EASSKTTSVLQWAEKGYYTMSNNLVTLENGKQLT VKRQGLYYIYAQVTFCSNREASSQAPFIASLCLK SPGRFERILLRAANTHSSAKPCGQQSIHLGGVFE LQPGASVFVNVTDPSQVSHGTGFTSFGLLKL (SEQ ID NO: 94) |

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as 1412-T4-CD40L (SEQ ID NO:94). In some embodiments, fusion proteins provided herein have an amino acid sequence that is at least 85% identical to SEQ ID NO:94. In some embodiments, fusion proteins provided herein have an amino acid sequence that is at least 90% identical to SEQ ID NO:94. In some embodiments, fusion proteins provided herein have an amino acid sequence that is at least 95% identical to SEQ ID NO:94. In some embodiments, fusion proteins provided herein have an amino acid sequence that is at least 98% identical to SEQ ID NO:94. In some embodiments, fusion proteins provided herein have an amino acid sequence that is at least 99% identical to SEQ ID NO:94. In some embodiments, fusion proteins provided herein have an amino acid sequence that is identical to SEQ ID NO:94.

As a person of ordinary skill in the art would understand, the extracellular domain of CD40L in the fusion proteins exemplified herein can be replaced with the extracellular domain or a receptor-binding fragment of another ligand for an activation receptor for APC that is disclosed herein or otherwise known in the art, including, for example, the extracellular domain or the receptor-binding domain of a CD80 ligand (e.g., CD28 or CTLA-4), a CD86 ligand (e.g., CD28 or CTLA-4), a CD91 ligand (e.g., RAP1), a DEC-205 ligand or a DC-SIGN ligand (e.g., ICAM2, ICAM3, CD18, or CEACAM1). As a person of ordinary skill in the art would understand, the anti-CD28 antibody or antigen-binding fragment in the fusion proteins exemplified herein can be replaced with an antibody or antigen-binding fragment that binds and activates another co-stimulator for immune effector cells that is disclosed herein or otherwise known in the art, including, for example, an antibody or antigen-binding fragment that binds 4-1BB, ICOS, CD27, OX40, DAP10, 2B4, CD30, CD2, LIGHT, GITR, TLR, DR3, or CD43.

5.2.3.3 Exemplary LACO-Stim (3): Antibody for APC Activation Receptor+Antibody for Co-Stimulatory Receptor (e.g., aCD40/aCD28 Bispecific Ab)

In some embodiments, provided herein are bispecific antibodies. A "bispecific antibody," as used herein and understood in the art, refers to an antibody having binding specificities for at least two different antigenic epitopes. The epitopes can be from the same antigen or two different antigens. In some embodiments, provided herein are fusion proteins comprising a first domain that activates an APC and a second domain that activates an immune effector cell, wherein the first domain comprises an antibody that binds an activation receptor of the APC, or an antigen-binding fragment thereof, and wherein the second domain comprises an antibody that binds a co-stimulatory receptor of the immune effector cell, or an antigen-binding fragment thereof. Accordingly, bispecific antibodies disclosed herein have binding specificities for (1) an activation receptor for an APC (e.g., a dendritic cell) and (2) a co-stimulatory receptor for an immune effector cell (e.g., a T cell). In some embodiments, the C-terminus of the first domain is linked to the N-terminus of the second domain. In some embodiments, the N-terminus of the first domain is linked to the C-terminus of the second domain.

In some embodiments, the first domain and the second domain are linked via a linker. The linker can be a flexible linker or a rigid linker. In some embodiments, the linker has the amino acid sequence of (GGGGS)n, n=1, 2, 3, 4, or 5 (SEQ ID NO:215). In some embodiments, the linker has the amino acid sequence of (EAAAK)n, n=1, 2, 3, 4, or 5 (SEQ ID NO:216). In some embodiments, the linker has the amino acid sequence of (PA)nP, n=1, 2, 3, 4, or 5 (SEQ ID NO:217). In some embodiments, the linker has the amino acid sequence of GSGGGGSGGGGSGGGGS (SEQ ID NO:219). In some embodiments, the linker has the amino acid sequence of GGGGS (SEQ ID NO:218).

In some embodiments, provided herein are fusion proteins are bispecific antibodies comprising a first domain that binds an activation receptor of the APC, or an antigen-binding fragment thereof, and a second domain comprises an antibody that binds a co-stimulatory receptor of the immune effector cell, or an antigen-binding fragment thereof. In some embodiments, the first domain comprises an antibody or antigen-binding fragment thereof that binds CD40, CD80, CD86, CD91, DEC-205 or DC-SIGN. In some embodiments, the second domain comprise an antibody or antigen-binding fragment thereof that binds CD28, 4-1BB, ICOS, CD27, OX40, DAP10, 2B4, CD30, CD2, LIGHT, GITR, TLR, DR3, or CD43.

In some embodiments, provided herein are bispecific antibodies comprising a first domain that is an anti-CD40 antibody or an antigen-binding fragment thereof, and a second domain comprises an anti-CD28 antibody or an antigen-binding fragment thereof. In some embodiments, provided herein are bispecific antibodies comprising a first domain that is an anti-CD40 antibody or an antigen-binding fragment thereof, and a second domain comprises an anti-4-1BB antibody or an antigen-binding fragment thereof. In some embodiments, provided herein are bispecific antibodies comprising a first domain that is an anti-CD40 antibody or an antigen-binding fragment thereof, and a second domain comprises an anti-ICOS antibody or an antigen-binding fragment thereof. In some embodiments, provided herein are bispecific antibodies comprising a first domain that is an anti-CD40 antibody or an antigen-binding fragment thereof, and a second domain comprises an anti-CD27 antibody or an antigen-binding fragment thereof. In some embodiments, provided herein are bispecific antibodies comprising a first domain that is an anti-CD40 antibody or an antigen-binding fragment thereof, and a second domain comprises an anti-OX40 antibody or an antigen-binding fragment thereof. In some embodiments, provided herein are bispecific antibodies comprising a first domain that is an anti-CD40 antibody or an antigen-binding fragment thereof, and a second domain comprises an anti-DAP10 antibody or an antigen-binding fragment thereof. In some embodiments, provided herein are bispecific antibodies comprising a first domain that is an anti-CD40 antibody or an antigen-binding fragment thereof, and a second domain comprises an anti-2B4 antibody or an antigen-binding fragment thereof. In some embodiments, provided herein are bispecific antibodies comprising a first domain that is an anti-CD40 antibody or an antigen-binding fragment thereof, and a second domain comprises an anti-CD30 antibody or an antigen-binding fragment thereof. In some embodiments, provided herein are bispecific antibodies comprising a first domain that is an anti-CD40 antibody or an antigen-binding fragment thereof, and a second domain comprises an anti-CD2 antibody or an antigen-binding fragment thereof. In some embodiments, provided herein are bispecific antibodies comprising a first domain that is an anti-CD40 antibody or an antigen-binding fragment thereof, and a second domain comprises an anti-LIGHT antibody or an antigen-binding fragment thereof. In some embodiments, provided herein are bispecific antibodies comprising a first domain that is an anti-CD40 antibody or an antigen-binding fragment thereof, and a second domain comprises an anti-GITR antibody or an antigen-binding fragment thereof. In some embodiments, provided herein are bispecific antibodies comprising a first domain that is an anti-CD40 antibody or an antigen-binding fragment thereof, and a second domain comprises an anti-TLR antibody or an antigen-binding fragment thereof. In some embodiments, provided herein are bispecific antibodies comprising a first domain that is an anti-CD40 antibody or an antigen-binding fragment thereof, and a second domain comprises an anti-DR3 antibody or an antigen-binding fragment thereof. In some embodiments, provided herein are bispecific antibodies comprising a first domain that is an anti-CD40 antibody or an antigen-binding fragment thereof, and a second domain comprises an anti-CD43 antibody or an antigen-binding fragment thereof.

Methods for making bispecific antibodies are known in the art. For example, bispecific antibodies can be produced recombinantly using the co-expression of two immunoglobulin heavy chain/light chain pairs. See, e.g., Milstein et al. (1983) Nature 305: 537-39. Alternatively, bispecific antibodies can be prepared using chemical linkage. See, e.g., Brennan et al. (1985) Science 229:81. Bispecific antibodies include bispecific antigen-binding fragments. See, e.g., Holliger et al. (1993) Proc. Natl. Acad. Sci. U.S.A. 90:6444-48; Gruber et al. (1994) J. Immunol. 152:5368. Techniques for making bispecific antibodies include, but are not limited to, recombinant co-expression of two immunoglobulin heavy chain-light chain pairs having different specificities (see Milstein and Cuello, Nature 305: 537 (1983), WO 93/08829, and Traunecker et al, EMBO J. 10: 3655 (1991)), and "knob-in-hole" engineering (see, e.g., U.S. Pat. No. 5,731,168). Multi-specific antibodies can also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science 229:81 (1985)); using leucine zippers to produce bispecific antibodies (see, e.g., Kostelny et al., J. Immunol. 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g., Gruber et al., J. Immunol., 152:5368 (1994)); and preparing trispecific antibodies as described, e.g., in Tutt et al. J. Immunol. 147: 60 (1991). Engineered antibodies with three or more functional antigen binding sites, including "Octopus antibodies," are also included herein (see, e.g., US 2006/0025576A1). Bispecific antibodies can be constructed by linking two different antibodies, or portions thereof. For example, a bispecific antibody can comprise Fab, F(ab')$_2$, Fab', scFv, and sdAb from two different antibodies.

In some embodiments, the first domain of the fusion proteins provided herein comprises an anti-CD40 antibody or an antigen-binding fragment thereof. The anti-CD40 antibody or antigen-binding fragment can be any anti-CD40 antibody or antigen-binding fragment disclosed herein or otherwise known in the art that can activate CD40 signaling. In some embodiments, the anti-CD40 antibody or antigen-binding fragment thereof comprises the antibody designated as F2.103, F5.157, F5.77, 4D11, A40C, or 119 as provided above in Table A. In some embodiments, the anti-CD40 antibody or antigen-binding fragment thereof has a VH and a VL having the amino acid sequences of (1) SEQ ID NOs: 76 and 77, respectively; (2) SEQ ID NOs: 79 and 80, respectively; (3) SEQ ID NOs: 82 and 83, respectively; (4) SEQ ID NOs: 85 and 86, respectively; (5) SEQ ID NOs: 88 and 89, respectively; or (6) SEQ ID NOs: 91 and 92, respectively. In some embodiments, the anti-CD40 antibody or antigen-binding fragment thereof comprises an anti-CD40 scFv having the amino acid sequence of SEQ ID NO:78. In some embodiments, the anti-CD40 antibody or antigen-binding fragment thereof comprises an anti-CD40 scFv having the amino acid sequence of SEQ ID NO:81. In thereof has (a) a VH having an amino acid sequence that is SEQ ID NO:73; and/or (b) a VL having an amino acid sequence that is SEQ ID NO:74. In some embodiments, the anti-CD28 antibody or antigen-binding fragment thereof comprises an anti-CD28 scFv having the amino acid sequence of SEQ ID NO:72.

| Exemplary LACO-Stim Fusion Protein Sequence | |
|---|---|
| 1412-F2.103 (Anti-CD28/anti-CD40 bispecific Ab) | MALPVTALLLPLALLLHAARPQVQLVQSGAEVKKPGASVKVSCKASGYTFTSY YIHWVRQAPGQGLEWIGCIYPGNVNTNYNEKFKDRATLTVDTSISTAYMELSRL RSDDTAVYFCTRSHYGLDWNFDVWGQGTTVTVSSVEGGSGGSGGSGGSGGVM DDIQMTQSPSSLSASVGDRVTITCHASQNIYVWLNWYQQKPGKAPKLLIYKASN LHTGVPSRFSGSGSGTDFTLTISSLQPEDFATYYCQQGQTYPYTFGGGTKVEIKG GGGSEVQLVESGGGLVQPGGSLRLSCAVSGFTFSTYWMHWVRQAPGKGLVWV SRINSDGSSTTYADSVKGRFTISRDNAKNTLYLQMNSLRAEDTAVYYCARDRVL WIGELSYYGMDVWGQGTTVTVSSGGGGSGGGGSGGGGSDIQMTQSPSTLSASV GDRVTITCRASQSISNWLAWYQQKPGKAPKLLLYKASGLESGVPSRFSGSGSGT EFTLTINSLQPDDFATYYCQQSNSYSWTFGHGTKVEIKRT (SEQ ID NO: 95) |
| 1412-F5.157 (Anti-CD28/anti-CD40 bispecific Ab) | MALPVTALLLPLALLLHAARPQVQLVQSGAEVKKPGASVKVSCKASGYTFTSY YIHWVRQAPGQGLEWIGCIYPGNVNTNYNEKFKDRATLTVDTSISTAYMELSRL RSDDTAVYFCTRSHYGLDWNFDVWGQGTTVTVSSVEGGSGGSGGSGGSGGVM DDIQMTQSPSSLSASVGDRVTITCHASQNIYVWLNWYQQKPGKAPKLLIYKASN LHTGVPSRFSGSGSGTDFTLTISSLQPEDFATYYCQQGQTYPYTFGGGTKVEIKG GGGSEVQLLESGGGLVQPGGSLRLSCAASGFAFSSYAMSWVRQAPGKGLEWVS AISGSGGSTYYADSVKGRFTISRDNSKNTLYLQMNSLRPRTRPYITVRKMGGTM VRGVMGTLTTGAREPWSPSPQGGGGSGGGGSGGGGSIQMTQSPSSVSASAGDR VTITCRASQGISSWLAWYQQKPGKAPKLLIYAGSSLQSGVPSRFSGSGFGTDFTL TIGSLQPEDFATYYCQQASSFPRTFGQGTKVEIKRTVLHHLSSSSRHLMS (SEQ ID NO: 96) |
| 1412-F5.77 (Anti-CD28/anti-CD40 bispecific Ab) | MALPVTALLLPLALLLHAARPQVQLVQSGAEVKKPGASVKVSCKASGYTFTSY YIHWVRQAPGQGLEWIGCIYPGNVNTNYNEKFKDRATLTVDTSISTAYMELSRL RSDDTAVYFCTRSHYGLDWNFDVWGQGTTVTVSSVEGGSGGSGGSGGSGGVM DDIQMTQSPSSLSASVGDRVTITCHASQNIYVWLNWYQQKPGKAPKLLIYKASN LHTGVPSRFSGSGSGTDFTLTISSLQPEDFATYYCQQGQTYPYTFGGGTKVEIKG GGGSEVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCAKDGGY YGSGSYGYFDYWGQGTLVTVSSGGGGSGGGGSGGGGSDIQMTQSPSSVSGSVG DRVTITCRASQGISSWLAWYQQKPGKAPKLLIYAGSSLQSGVPSRFSGSGFGTDF TLTISSLQPEDFATYYCQQASSFPRTFGQGTKVEIKRT (SEQ ID NO: 97) |
| 1412-4D11 (Anti-CD28/anti-CD40 bispecific Ab) | MALPVTALLLPLALLLHAARPQVQLVQSGAEVKKPGASVKVSCKASGYTFTSY YIHWVRQAPGQGLEWIGCIYPGNVNTNYNEKFKDRATLTVDTSISTAYMELSRL RSDDTAVYFCTRSHYGLDWNFDVWGQGTTVTVSSVEGGSGGSGGSGGSGGVM DDIQMTQSPSSLSASVGDRVTITCHASQNIYVWLNWYQQKPGKAPKLLIYKASN LHTGVPSRFSGSGSGTDFTLTISSLQPEDFATYYCQQGQTYPYTFGGGTKVEIKG GGGSQLQLQESGPGLLKPSETLSLTCTVSGGSISSPGYYGGWIRQPPGKGLEWIG SIYKSGSTYHNPSLKSRVTISVDTSKNQFSLKLSSVTAADTAVYYCTRPVVRYFG WFDPWGQGTLVTVSSASGGGGSGGGGSGGGGSAIQLTQSPSSLSASVGDRVTIT CRASQGISSALAWYQQKPGKAPKLLIYDASNLESGVPSRFSGSGSGTDFTLTISSL QPEDFATYYCQQFNSYPTFGQGTKVEIKRT (SEQ ID NO: 211) | some embodiments, the anti-CD40 antibody or antigen-binding fragment thereof comprises an anti-CD40 scFv having the amino acid sequence of SEQ ID NO:84. In some embodiments, the anti-CD40 antibody or antigen-binding fragment thereof comprises an anti-CD40 scFv having the amino acid sequence of SEQ ID NO:87. In some embodiments, the anti-CD40 antibody or antigen-binding fragment thereof comprises an anti-CD40 scFv having the amino acid sequence of SEQ ID NO:90.

In some embodiments, the anti-CD28 antibody or antigen-binding fragment can be any anti-CD28 antibody or antigen-binding fragment disclosed herein or otherwise known in the art that activate CD28 signaling. In some embodiments, the anti-CD28 antibody or antigen-binding fragment is the antibody designated 1412. In some embodiments, the anti-CD28 antibody or antigen-binding fragment In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as 1412-F2.103 (SEQ ID NO:95). In some embodiments, fusion proteins provided herein have an amino acid sequence that is at least 85% identical to SEQ ID NO:95. In some embodiments, fusion proteins provided herein have an amino acid sequence that is at least 90% identical to SEQ ID NO:95. In some embodiments, fusion proteins provided herein have an amino acid sequence that is at least 95% identical to SEQ ID NO:95. In some embodiments, fusion proteins provided herein have an amino acid sequence that is at least 98% identical to SEQ ID NO:95. In some embodiments, fusion proteins provided herein have an amino acid sequence that is at least 99% identical to SEQ ID NO:95. In some embodiments, fusion proteins provided herein have an amino acid sequence that is identical to SEQ ID NO:95.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as 1412-F5.157 (SEQ ID NO:96). In some embodiments, fusion proteins provided herein have an amino acid sequence that is at least 85% identical to SEQ ID NO:96. In some embodiments, fusion proteins provided herein have an amino acid sequence that is at least 90% identical to SEQ ID NO:96. In some embodiments, fusion proteins provided herein have an amino acid sequence that is at least 95% identical to SEQ ID NO:96. In some embodiments, fusion proteins provided herein have an amino acid sequence that is at least 98% identical to SEQ ID NO:96. In some embodiments, fusion proteins provided herein have an amino acid sequence that is at least 99% identical to SEQ ID NO:96. In some embodiments, fusion proteins provided herein have an amino acid sequence that is identical to SEQ ID NO:96.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as 1412-F5.77 (SEQ ID NO:97). In some embodiments, fusion proteins provided herein have an amino acid sequence that is at least 85% identical to SEQ ID NO:97. In some embodiments, fusion proteins provided herein have an amino acid sequence that is at least 90% identical to SEQ ID NO:97. In some embodiments, fusion proteins provided herein have an amino acid sequence that is at least 95% identical to SEQ ID NO:97. In some embodiments, fusion proteins provided herein have an amino acid sequence that is at least 98% identical to SEQ ID NO:97. In some embodiments, fusion proteins provided herein have an amino acid sequence that is at least 99% identical to SEQ ID NO:97. In some embodiments, fusion proteins provided herein have an amino acid sequence that is identical to SEQ ID NO:97.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as 1412-4D11 (SEQ ID NO:211). In some embodiments, fusion proteins provided herein have an amino acid sequence that is at least 85% identical to SEQ ID NO:211. In some embodiments, fusion proteins provided herein have an amino acid sequence that is at least 90% identical to SEQ ID NO:211. In some embodiments, fusion proteins provided herein have an amino acid sequence that is at least 95% identical to SEQ ID NO:211. In some embodiments, fusion proteins provided herein have an amino acid sequence that is at least 98% identical to SEQ ID NO:211. In some embodiments, fusion proteins provided herein have an amino acid sequence that is at least 99% identical to SEQ ID NO:211. In some embodiments, fusion proteins provided herein have an amino acid sequence that is identical to SEQ ID NO:211.

As a person of ordinary skill in the art would understand, the anti-CD40 antibody or antigen-binding fragment thereof in the fusion proteins exemplified herein can be replaced with an antibody or antigen-binding fragment that binds another activation receptor for APC that is disclosed herein or otherwise known in the art, including, for example, CD80, CD86, CD91, DEC-205 or DC-SIGN. As a person of ordinary skill in the art would understand, the anti-CD28 antibody or antigen-binding fragment in the fusion proteins exemplified herein can be replaced with an antibody or antigen-binding fragment that binds another co-stimulator for immune effector cells that is disclosed herein or otherwise known in the art, including, for example, an antibody or antigen-binding fragment that binds 4-1BB, ICOS, CD27, OX40, DAP10, 2B4, CD30, CD2, LIGHT, GITR, TLR, DR3, or CD43.

5.2.3.4 Exemplary LACO-Stim (4): Antibody for Activation Receptor+Co-Stimulatory Receptor (e.g., aCD40-CD28; aCD40-4-1BB)

In some embodiments, provided herein are fusion proteins comprising a first domain that activates an APC and a second domain that activates an immune effector cell, wherein the first domain comprises an antibody that binds an activation receptor of the APC, or an antigen-binding fragment thereof, and wherein the second domain comprises a co-stimulatory receptor of the immune effector cell, or a functional fragment thereof. In some embodiments, the C-terminus of the first domain is linked to the N-terminus of the second domain. In some embodiments, the N-terminus of the first domain is linked to the C-terminus of the second domain. In some embodiments, provided herein are antibody-based membrane fusion protein.

In some embodiments, the first and second domains are linked via a CD8 hinge, a CD28 hinge, or an IgG Fc region. In some embodiments, the first and second domains are linked via a CD8 hinge. In some embodiments, the CD8 hinge has the amino acid sequence of SEQ ID NO:69. In some embodiments, the first and second domains are linked via a CD28 hinge. In some embodiments, the CD28 hinge has the amino acid sequence of SEQ ID NO:70. In some embodiments, the first and second domains are linked via an IgG Fc region. In some embodiments, the IgG Fc region has the amino acid sequence of SEQ ID NO:71.

In some embodiments, provided herein are fusion proteins comprising a first domain comprising an antibody that binds an activation receptor of the APC, or an antigen-binding fragment thereof, and a second domain comprising an antibody that binds a co-stimulatory receptor of the immune effector cell, or an antigen-binding fragment thereof. In some embodiments, the first domain comprises an antibody or antigen-binding fragment thereof that binds CD40, CD80, CD86, CD91, DEC-205 or DC-SIGN. In some embodiments, the first domain of the fusion proteins provided herein comprises an anti-CD40 antibody or an antigen-binding fragment thereof. The anti-CD40 antibody or antigen-binding fragment can be any anti-CD40 antibody or antigen-binding fragment disclosed herein or otherwise known in the art that activate CD40 signaling. In some embodiments, the anti-CD40 antibody or antigen-binding fragment thereof comprises the antibody designated as F2.103, F5.157, F5.77, 4D11, A40C, or 119 as provided above in Table A. In some embodiments, the anti-CD40 antibody or antigen-binding fragment thereof has a VH and a VL that have the amino acid sequences of (1) SEQ ID NOs: 76 and 77, respectively; (2) SEQ ID NOs: 79 and 80, respectively; (3) SEQ ID NOs: 82 and 83, respectively; (4) SEQ ID NOs: 85 and 86, respectively; (5) SEQ ID NOs: 88 and 89, respectively; or (6) SEQ ID NOs: 91 and 92, respectively. In some embodiments, the anti-CD40 antibody or antigen-binding fragment thereof comprises an anti-CD40 scFv having the amino acid sequence of SEQ ID NO:75. In some embodiments, the anti-CD40 antibody or antigen-binding fragment thereof comprises an anti-CD40 scFv having the amino acid sequence of SEQ ID NO:78. In some embodiments, the anti-D40 antibody or antigen-binding fragment thereof comprises an anti-CD40 scFv having the amino acid sequence of SEQ ID NO:81. In some embodiments, the anti-CD40 antibody or antigen-binding fragment thereof comprises an anti-CD40 scFv having the amino acid sequence of SEQ ID NO:84. In some embodiments, the anti-CD40 antibody or antigen-binding fragment thereof comprises an anti-CD40 scFv having the amino acid sequence of SEQ ID NO:87. In some embodiments, the anti-CD40 antibody or antigen-binding fragment thereof comprises an anti-CD40 scFv having the amino acid sequence of SEQ ID NO:90.

In some embodiments, the second domain comprises a co-stimulatory receptor selected from the group consisting of CD28, 4-1BB, ICOS, CD27, OX40, DAP10, 2B4, CD30, CD2, LIGHT, GITR, TLR, DR3, and CD43, or a functional fragment thereof. In some embodiments, the second domain comprises the cytoplasmic domain of a co-stimulatory receptor selected from the group consisting of CD28, 4-1BB, ICOS, CD27, OX40, DAP10, 2B4, CD30, CD2, LIGHT, GITR, TLR, DR3, and CD43. In some embodiments, the second domain of the fusion proteins provided herein comprises a CD28 cytoplasmic domain (e.g., SEQ ID NO:14). In some embodiments, the second domain of the fusion proteins provided herein can have an amino acid sequence that is at least 85%, at least 88%, at least 90%, at least 95%, at least 98%, or 100% identical to SEQ ID NO:14. In some embodiments, the second domain of the fusion proteins provided herein has the amino acid sequence of SEQ ID NO:14. In some embodiments, the second domain of the fusion proteins provided herein further comprises a CD28 transmembrane domain (e.g., SEQ ID NO:15). In some embodiments, the second domain of the fusion proteins provided herein comprises a 4-1BB cytoplasmic domain (e.g., SEQ ID NO:17). In some embodiments, the second domain of the fusion proteins provided herein can have an amino acid sequence that is at least 85%, at least 88%, at least 90%, at least 95%, at least 98%, or 100% identical to SEQ ID NO:17. In some embodiments, the second domain of the fusion proteins provided herein has the amino acid sequence of SEQ ID NO:17. In some embodiments, the second domain of the fusion proteins provided herein further comprises a 4-1BB transmembrane domain (e.g., SEQ ID NO:18).

In some embodiments, fusion proteins provided herein have a first domain that comprises an anti-CD40 antibody or an antigen-binding fragment thereof, and a second domain that comprises a CD28 cytoplasmic domain. In some embodiments, fusion proteins provided herein have a first domain that comprises an anti-CD40 antibody or an antigen-binding fragment thereof, and a second domain that comprises a 4-1BB cytoplasmic domain. In some embodiments, fusion proteins provided herein have a first domain that comprises an anti-CD40 antibody or an antigen-binding fragment thereof, and a second domain that comprises an ICOS cytoplasmic domain. In some embodiments, fusion proteins provided herein have a first domain that comprises an anti-CD40 antibody or an antigen-binding fragment thereof, and a second domain that comprises a CD27 cytoplasmic domain. In some embodiments, fusion proteins provided herein have a first domain that comprises an anti-CD40 antibody or an antigen-binding fragment thereof, and a second domain that comprises an OX40 cytoplasmic domain. In some embodiments, fusion proteins provided herein have a first domain that comprises an anti-CD40 antibody or an antigen-binding fragment thereof, and a second domain that comprises a DAP10 cytoplasmic domain. In some embodiments, fusion proteins provided herein have a first domain that comprises an anti-CD40 antibody or an antigen-binding fragment thereof, and a second domain that comprises a 2B4 cytoplasmic domain. In some embodiments, fusion proteins provided herein have a first domain that comprises an anti-CD40 antibody or an antigen-binding fragment thereof, and a second domain that comprises a CD30 cytoplasmic domain. In some embodiments, fusion proteins provided herein have a first domain that comprises an anti-CD40 antibody or an antigen-binding fragment thereof, and a second domain that comprises a CD2 cytoplasmic domain. In some embodiments, fusion proteins provided herein have a first domain that comprises an anti-CD40 antibody or an antigen-binding fragment thereof, and a second domain that comprises a LIGHT cytoplasmic domain. In some embodiments, fusion proteins provided herein have a first domain that comprises an anti-CD40 antibody or an antigen-binding fragment thereof, and a second domain that comprises a GITR cytoplasmic domain. In some embodiments, fusion proteins provided herein have a first domain that comprises an anti-CD40 antibody or an antigen-binding fragment thereof, and a second domain that comprises a TLR cytoplasmic domain. In some embodiments, fusion proteins provided herein have a first domain that comprises an anti-CD40 antibody or an antigen-binding fragment thereof, and a second domain that comprises a DR3 cytoplasmic domain. In some embodiments, fusion proteins provided herein have a first domain that comprises an anti-CD40 antibody or an antigen-binding fragment thereof, and a second domain that comprises a CD43 cytoplasmic domain. In some embodiments, the first domain comprises full length CD40L.

In some embodiments, fusion proteins provided herein further comprise a transmembrane region. In some embodiments, the transmembrane region is derived from the same co-stimulatory receptor. In some embodiments, the transmembrane region is derived from a different co-stimulatory receptor. In some embodiments, fusion proteins provided herein have a first domain that comprises an anti-CD40 antibody or an antigen-binding fragment thereof, and a second domain that comprises a CD28 transmembrane region and a CD28 cytoplasmic domain. In some embodiments, provided herein are fusion proteins having a first domain that comprises an anti-CD40 antibody or an antigen-binding fragment thereof, and a second domain that comprises a 4-1BB transmembrane region and a 4-1BB cytoplasmic domain.

| Exemplary LACO-Stim Fusion Protein | Sequence |
|---|---|
| F2.103.CD28: (Anti-CD40 scFv-CD28 membrane chimeric fusion protein) | MALPVTALLLPLALLLHAARPEVQLVESGGGLVQPGGSLRLSCAVSGFTFSTYW MHWVRQAPGKGLVWVSRfNSDGSSTTYADSVKGRFTISRDNAKNTLYLQMNS LRAEDTAVYYCARDRVLWIGELSYYGMDVWGQTTVTVSSGGGGSGGGGSG GGGSDIQMTQSPSTLSASVGDRVTITCRASQGISNWLAWYQQKPGKAPKLLLYK ASGLESGVPSRFSGSGSGTEFTLTINSLQPDDFATYYCQQSNSYSWTFGHGTKVE KRTASTTTPAPRPPTPAPTIASQPLSLRPEACRPAAGGAVHTRGLDFACDFWVL VVVGGVLACYSLLVTVAFIIFWVRSKRSRLLHSDYMNMTPRRPGPTRKHYQPY APPRDFAAYRS (SEQ ID NO: 98) |
| F5.157.CD28: (Anti-CD40 scFv-CD28 membrane chimeric fusion protein) | MALPVTALLLPLALLLHAARPEVQLLESGGGLVQPGGSLRLSCAASGFAFSSYA MSWVRQAPGKGLEWVSAISGSGGSTYYADSVKGRFTISRDNSKNTLYLQMNSL RPRTRPYITVRKMGGTMVRGVMGTLTTGAREPWSPSPQGGGGSGGGGSGGGG SIQMTQSPSSVSASAGDRVTITCRASQGISSWLAWYQQKPGKAPKLLIYAGSSLQ SGVPSRFSGSGFGTDFTLTIGSLQPEDFATYYCQQASSFPRTFGQGTKVEIKRTVL HHLSSSSRHLMSASTTTPAPRPPTPAPTIASQPLSLRPEACRPAAGGAVHTRGLDF ACDFWVLVVVGGVLACYSLLVTVAFIIFWVRSKRSRLLHSDYMNMTPRRPGPT RKHYQPY APPRDFAAYRS (SEQ ID NO: 99) |
| F5.77.CD28 (Anti-CD40 scFv-CD28 membrane chimeric fusion protein): | MALPVTALLLPLALLLHAARPEVQLLESGGGLVQPGGSLRLSCAASGFTFSSYA MSWVRQAPGKGLEWVSAISGSGGSTYYADSVKGRFTISRDNSKNTLYLQMNSL RAEDTAVYYCAKDGGYYGSGSYGYFDYWGQGTLVTVSSGGGGSGGGGSGGG GSDIQMTQSPSSVSGSVGDRVTITCRASQGISSWLAWYQQKPGKAPKLLIYAGS SLQSGVPSRFSGSGFGTDFTLTISSLQPEDFATYYCQQASSFPRTFGQGTKVEIKR TASTTTPAPRPPTPAPTIASQPLSLRPEACRPAAGGAVHTRGLDFACDFWVLVVV GGVLACYSLLVTVAFIIFWVRSKRSRLLHSDYMNMTPRRPGPTRKHYQPYAPPR DFAAYRS (SEQ ID NO: 100) |
| F2.103.BB (Anti-CD40 scFv-4-1BB membrane chimeric fusion protein): | MALPVTALLLPLALLLHAARPEVQLVESGGGLVQPGGSLRLSCAVSGFTFSTYW MHWVRQAPGKGLVWVSR3NSDGSSTTYADSVKGRFT3SRDNAKNTLYLQMNS LRAEDTAVYYCARDRVLW3GELSYYGMDVWGQTTVTVSSGGGGSGGGGSG GGGSD3QMTQSPSTLSASVGDRVT3TCRASQS3SNWLAWYQQKPGKAPKLLLYK ASGLESGVPSRFSGSGSGTEFTLT3NSLQPDDFATYYCQQSNSYSWTFGHGTKVE jKRTTTTPAPRPPTPAPTfASQPLSLRPEACRPAAGGAVHTRGLDFACDfYfWAPL AGTCGVLLLSLV3TLYCRGRKKLLY3FKQPFMRPVQTTQEEDGCSCRFPEEEEGG CE (SEQ ID NO: 101) |
| F5.157.BB (Anti-CD40 ScFv-4-1BB membrane chimeric fusion protein): | MALPVTALLLPLALLLHAARPEVQLLESGGGLVQPGGSLRLSCAASGFAFSSYA MSWVRQAPGKGLEWVSAISGSGGSTYYADSVKGRFTISRDNSKNTLYLQMNSL RPRTRPYITVRKMGGTMVRGVMGTLTTGAREPWSPSPQGGGGSGGGGSGGGG SIQMTQSPSSVSASAGDRVTITCRASQGISSWLAWYQQKPGKAPKLLIYAGSSLQ SGVPSRFSGSGFGTDFTLTIGSLQPEDFATYYCQQASSFPRTFGQGTKVEIKRTVL HHLSSSSRHLMSTTTPAPRPPTPAPTIASQPLSLRPEACRPAAGGAVHTRGLDFA CDIYIWAPLAGTCGVLLLSLVITLYCRGRKKLLYIFKQPFMRPVQTTQEEDGCSC RFPEEEEGGCE (SEQ ID NO: 102) |
| F5.77.BB (Anti-CD40 scFv-4-1BB membrane chimeric fusion protein) | MALPVTALLLPLALLLHAARPEVQLLESGGGLVQPGGSLRLSCAASGFTFSSYA MSWVRQAPGKGLEWVSAISGSGGSTYYADSVKGRFTISRDNSKNTLYLQMNSL RAEDTAVYYCAKDGGYYGSGSYGYFDYWGQGTLVTVSSGGGGSGGGGSGGG GSDIQMTQSPSSVSGSVGDRVTITCRASQGISSWLAWYQQKPGKAPKLLIYAGS SLQSGVPSRFSGSGFGTDFTLTISSLQPEDFATYYCQQASSFPRTFGQGTKVEIKR TTTTPAPRPPTPAPTIASQPLSLRPEACRPAAGGAVHTRGLDFACDIYIWAPLAGT CGVLLLSLVITLYCRGRKKLLYIFKQPFMRPVQTTQEEDGCSCRFPEEEEGGCE (SEQ ID NO: 103) |
| 4D11.CD28 (Anti-CD40 scFv-CD28 membrane chimeric fusion protein) | MALPVTALLLPLALLLHAARPQLQLQESGPGLLKPSETLSLTCTVSGGSISSPGY YGGWIRQPPGKGLEWIGSIYKSGSTYHNPSLKSRVTISVDTSKNQFSLKLSSVTA ADTAVYYCTRPVVRYFGWFDPWGQGTLVTVSSASGGGGSGGGGSGGGGSAIQ LTQSPSSLSASVGDRVTITCRASQGISSALAWYQQKPGKAPKLLIYDASNLESGV PSRFSGSGSGTDFTLTISSLQPEDFATYYCQQFNSYPTFGQGTKVEIKRTASTTTP APRPPTPAPTIASQPLSLRPEACRPAAGGAVHTRGLDFACDFWVLVVVGGVLAC YSLLVTVAFIIFWVRSKRSRLLHSDYMNMTPRRPGPTRKHYQPYAPPRDFAAYR S (SEQ ID NO: 104) |
| A40C.CD28 (Anti-CD40 scFv-CD28 membrane chimeric fusion protein) | MALPVTALLLPLALLLHAARPQVQLVQSGAEVKKPGASVKVSCTASGFNIKDY YVHWVKQAPGQGLEWMGRIDPEDGDSKYAPKFQGKATMTADTSTSTVYMEL SSLRSEDTAVYYCTTSYYVGTYGYWGQGTLVTVSSGGGGSGGGGSGGGGSDIQ MTQSPSSLSASVGDRVTITCSASSSVSYMLWFQQKPGKAPKLLIYSTNLASGVP SRFSGSGSGTDFTLTISSLQPEDFATYYCQQRTFYPYTFGGGTKVEIKRTASTTTP APRPPTPAPTIASQPLSLRPEACRPAAGGAVHTRGLDFACDFWVLVVVGGVLAC YSLLVTVAFIIFWVRSKRSRLLHSDYMNMTPRRPGPTRKHYQPYAPPRDFAAYR S (SEQ ID NO: 105) |
| 119.CD28 (Anti-CD40 scFv-CD28 membrane chimeric fusion protein) | MALPVTALLLPLALLLHAARPQVQLQQSGPGLVKPSQTLSLTCAISGDSVSSNSA TWNWIRQSPSRDLEWLGRTYYRSKWYRDYVGSVKSRIIINPDTSNNQFSLQLNS VTPEDTAIYYCTRAQWLGGDYPYYYSMDVWGQGTTVTVSSGGGGSGGGGSG GGGSEIVLTQSPATLSLSPGERATLSCRASQSVSSYLAWYQQKPGQAPRLLIYDA SNRATGIPARFSGSGSGTDFTLTISSLEPEDFAVYYCQQRSNTFGPGTKVDIKRTA |

| Exemplary LACO-Stim Fusion Protein | Sequence |
|---|---|
| | STTTPAPRPPTPAPTIASQPLSLRPEACRPAAGGAVHTRGLDFACDFWVLVVVG GVLACYSLLVTVAFIIFWVRSKRSRLLHSDYMNMTPRRPGPTRKHYQPYAPPRD FAAYRS (SEQ fD NO: 106) |

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as F2.103.CD28 (SEQ ID NO:98). In some embodiments, fusion proteins provided herein have an amino acid sequence that is at least 85% identical to SEQ ID NO:98. In some embodiments, fusion proteins provided herein have an amino acid sequence that is at least 90% identical to SEQ ID NO:98. In some embodiments, fusion proteins provided herein have an amino acid sequence that is at least 95% identical to SEQ ID NO:98. In some embodiments, fusion proteins provided herein have an amino acid sequence that is at least 98% identical to SEQ ID NO:98. In some embodiments, fusion proteins provided herein have an amino acid sequence that is at least 99% identical to SEQ ID NO:98. In some embodiments, fusion proteins provided herein have an amino acid sequence that is identical to SEQ ID NO:98.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as F5.157.CD28 (SEQ ID NO:99). In some embodiments, fusion proteins provided herein have an amino acid sequence that is at least 85% identical to SEQ ID NO:99. In some embodiments, fusion proteins provided herein have an amino acid sequence that is at least 90% identical to SEQ ID NO:99. In some embodiments, fusion proteins provided herein have an amino acid sequence that is at least 95% identical to SEQ ID NO:99. In some embodiments, fusion proteins provided herein have an amino acid sequence that is at least 98% identical to SEQ ID NO:99. In some embodiments, fusion proteins provided herein have an amino acid sequence that is at least 99% identical to SEQ ID NO:99. In some embodiments, fusion proteins provided herein have an amino acid sequence that is identical to SEQ ID NO:99.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as F5.77.CD28 (SEQ ID NO:100). In some embodiments, fusion proteins provided herein have an amino acid sequence that is at least 85% identical to SEQ ID NO:100. In some embodiments, fusion proteins provided herein have an amino acid sequence that is at least 90% identical to SEQ ID NO:100. In some embodiments, fusion proteins provided herein have an amino acid sequence that is at least 95% identical to SEQ ID NO:100. In some embodiments, fusion proteins provided herein have an amino acid sequence that is at least 98% identical to SEQ ID NO:100. In some embodiments, fusion proteins provided herein have an amino acid sequence that is at least 99% identical to SEQ ID NO:100. In some embodiments, fusion proteins provided herein have an amino acid sequence that is identical to SEQ ID NO:100.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as F2.103.BB (SEQ ID NO:101). In some embodiments, fusion proteins provided herein have an amino acid sequence that is at least 85% identical to SEQ ID NO:101. In some embodiments, fusion proteins provided herein have an amino acid sequence that is at least 90% identical to SEQ ID NO:101. In some embodiments, fusion proteins provided herein have an amino acid sequence that is at least 95% identical to SEQ ID NO:101. In some embodiments, fusion proteins provided herein have an amino acid sequence that is at least 98% identical to SEQ ID NO:101. In some embodiments, fusion proteins provided herein have an amino acid sequence that is at least 99% identical to SEQ ID NO:101. In some embodiments, fusion proteins provided herein have an amino acid sequence that is identical to SEQ ID NO:101.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as F5.157.BB (SEQ ID NO:102). In some embodiments, fusion proteins provided herein have an amino acid sequence that is at least 85% identical to SEQ ID NO:102. In some embodiments, fusion proteins provided herein have an amino acid sequence that is at least 90% identical to SEQ ID NO:102. In some embodiments, fusion proteins provided herein have an amino acid sequence that is at least 95% identical to SEQ ID NO:102. In some embodiments, fusion proteins provided herein have an amino acid sequence that is at least 98% identical to SEQ ID NO:102. In some embodiments, fusion proteins provided herein have an amino acid sequence that is at least 99% identical to SEQ ID NO:102. In some embodiments, fusion proteins provided herein have an amino acid sequence that is identical to SEQ ID NO:102.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as F5.77.BB (SEQ ID NO:103). In some embodiments, fusion proteins provided herein have an amino acid sequence that is at least 85% identical to SEQ ID NO:103.

In some embodiments, fusion proteins provided herein have an amino acid sequence that is at least 90% identical to SEQ ID NO:103. In some embodiments, fusion proteins provided herein have an amino acid sequence that is at least 95% identical to SEQ ID NO:103. In some embodiments, fusion proteins provided herein have an amino acid sequence that is at least 98% identical to SEQ ID NO:103. In some embodiments, fusion proteins provided herein have an amino acid sequence that is at least 99% identical to SEQ ID NO:103. In some embodiments, fusion proteins provided herein have an amino acid sequence that is identical to SEQ ID NO:103.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as 4D11.CD28 (SEQ ID NO:104). In some embodiments, fusion proteins provided herein have an amino acid sequence that is at least 85% identical to SEQ ID NO:104. In some embodiments, fusion proteins provided herein have an amino acid sequence that is at least 90% identical to SEQ ID NO:104. In some embodiments, fusion proteins provided herein have an amino acid sequence that is at least 95% identical to SEQ ID NO:104. In some embodiments, fusion proteins provided herein have an amino acid sequence that is at least 98% identical to SEQ ID NO:104. In some embodiments, fusion proteins provided herein have an amino acid sequence that is at least 99% identical to SEQ ID NO:104. In some embodiments, fusion proteins provided herein have an amino acid sequence that is identical to SEQ ID NO:104.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as A40C.CD28 (SEQ ID NO:105). In some embodiments, fusion proteins provided herein have an amino acid sequence that is at least 85% identical to SEQ ID NO:105. In some embodiments, fusion proteins provided herein have an amino acid sequence that is at least 90% identical to SEQ ID NO:105. In some embodiments, fusion proteins provided herein have an amino acid sequence that is at least 95% identical to SEQ ID NO:105. In some embodiments, fusion proteins provided herein have an amino acid sequence that is at least 98% identical to SEQ ID NO:105. In some embodiments, fusion proteins provided herein have an amino acid sequence that is at least 99% identical to SEQ ID NO:105. In some embodiments, fusion proteins provided herein have an amino acid sequence that is identical to SEQ ID NO:105.

In some embodiments, fusion proteins provided herein have an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence of the fusion protein designated as 119.CD28 (SEQ ID NO:106). In some embodiments, fusion proteins provided herein have an amino acid sequence that is at least 85% identical to SEQ ID NO:106. In some embodiments, fusion proteins provided herein have an amino acid sequence that is at least 90% identical to SEQ ID NO:106. In some embodiments, fusion proteins provided herein have an amino acid sequence that is at least 95% identical to SEQ ID NO:106. In some embodiments, fusion proteins provided herein have an amino acid sequence that is at least 98% identical to SEQ ID NO:106. In some embodiments, fusion proteins provided herein have an amino acid sequence that is at least 99% identical to SEQ ID NO:106. In some embodiments, fusion proteins provided herein have an amino acid sequence that is identical to SEQ ID NO:106.

As a person of ordinary skill in the art would understand, the anti-CD40 antibody or antigen-binding fragment thereof in the fusion proteins exemplified herein can be replaced with an antibody or antigen-binding fragment that binds and activates another activation receptor for APC that is disclosed herein or otherwise known in the art, including, for example, CD80, CD86, CD91, DEC-205 or DC-SIGN. As a person of ordinary skill in the art would understand, the CD28 cytoplasmic domain or 4-1BB cytoplasmic domain in the fusion proteins exemplified herein can be replaced with the cytoplasmic domain of another co-stimulator for immune effector cells that is disclosed herein or otherwise known in the art, including, for example, the cytoplasmic domain of ICOS, CD27, OX40, DAP10, 2B4, CD30, CD2, LIGHT, GITR, TLR, DR3, or CD43; or a different functional fragment of 4-1BB, ICOS, CD27, OX40, DAP10, 2B4, CD30, CD2, LIGHT, GITR, TLR, DR3, or CD43 that retains the function of the full-length protein to activate the immune effector cell.

5.2.3.5 Exemplary LACO-Stim (5): Antibody for APC Activation Receptor+Ligand for Co-Stimulatory Receptor (e.g., aCD40-CD80; aCD40-CD86)

In some embodiments, provided herein are fusion proteins comprising a first domain that activates an APC and a second domain that activates an immune effector cell, wherein the first domain comprises an antibody that binds an activation receptor of the antigen-presenting cell, or an antigen-binding fragment thereof; and wherein the second domain comprises a co-stimulatory ligand of the immune effector cell, or a receptor-binding fragment thereof. In some embodiments, the C-terminus of the first domain is linked to the N-terminus of the second domain. In some embodiments, the N-terminus of the first domain is linked to the C-terminus of the second domain. In some embodiments, provided herein are antibody-based soluble fusion protein. In some embodiments, provided herein are antibody-based soluble fusion protein.

In some embodiments, the first domain comprises an antibody or antigen-binding fragment thereof that binds CD40, CD80, CD86, CD91, DEC-205 and DC-SIGN. In some embodiments, the first domain comprises an antibody or antigen-binding fragment thereof that binds CD40. In some embodiments, the first domain comprises an antibody or antigen-binding fragment thereof that binds CD80. In some embodiments, the first domain comprises an antibody or antigen-binding fragment thereof that binds CD86. In some embodiments, the first domain comprises an antibody or antigen-binding fragment thereof that binds CD91. In some embodiments, the first domain comprises an antibody or antigen-binding fragment thereof that binds DEC-205. In some embodiments, the first domain comprises an antibody or antigen-binding fragment thereof that binds DC-SIGN. The antibodies and antigen-binding fragments can be any antibody or antigen-binding fragment disclosed herein or otherwise known in the art.

In some embodiments, provided herein are fusion proteins comprising a first domain comprising an antibody that binds an activation receptor of the APC, or an antigen-binding fragment thereof, and a second domain comprising a co-stimulatory ligand of the immune effector cell, or a receptor-binding fragment thereof. In some embodiments, the first domain comprises an antibody or antigen-binding fragment thereof that binds CD40, CD80, CD86, CD91, DEC-205 or DC-SIGN. In some embodiments, the second domain comprises a ligand selected from the group consisting of CD58, CD70, CD83, CD80, CD86, CD137L, CD252, CD275, CD54, CD49a, CD112, CD150, CD155, CD265, CD270, TL1A, CD127, IL-4R, GITR-L, TIM-4, CD153, CD48, CD160, CD200R, and CD44, or a receptor-binding fragments thereof.

In some embodiments, the first domain of the fusion proteins provided herein comprises an anti-CD40 antibody or an antigen-binding fragment thereof. The anti-CD40 antibody or antigen-binding fragment can be any anti-CD40 antibody or antigen-binding fragment disclosed herein or otherwise known in the art that activate CD40 signaling. In some embodiments, the anti-CD40 antibody or antigen-binding fragment thereof comprises the antibody designated as F2.103, F5.157, F5.77, 4D11, A40C, or 119 as provided above in Table A. In some embodiments, the anti-CD40 antibody or antigen-binding fragment thereof has a VH and a VL that have the amino acid sequences of (1) SEQ ID NOs: 76 and 77, respectively; (2) SEQ ID NOs: 79 and 80, respectively; (3) SEQ ID NOs: 82 and 83, respectively; (4) SEQ ID NOs: 85 and 86, respectively; (5) SEQ ID NOs: 88 and 89, respectively; or (6) SEQ ID NOs: 91 and 92, respectively. In some embodiments, the anti-CD40 antibody or antigen-binding fragment thereof comprises an anti-CD40 scFv having the amino acid sequence of SEQ ID NO:75. In some embodiments, the anti-CD40 antibody or antigen-binding fragment thereof comprises an anti-CD40 scFv having the amino acid sequence of SEQ ID NO:78. In some embodiments, the anti-CD40 antibody or antigen-binding fragment thereof comprises an anti-CD40 scFv having the amino acid sequence of SEQ ID NO:81. In some embodiments, the anti-CD40 antibody or antigen-binding fragment thereof comprises an anti-CD40 scFv having the amino acid sequence of SEQ ID NO:84. In some embodiments, the anti-CD40 antibody or antigen-binding fragment thereof comprises an anti-CD40 scFv having the amino acid sequence of SEQ ID NO:87. In some embodiments, the anti-CD40 antibody or antigen-binding fragment thereof comprises an anti-CD40 scFv having the amino acid sequence of SEQ ID NO:90.

In some embodiments, the fusion protein comprises a first domain that comprises an antibody or antigen-binding fragment thereof that binds CD40, and a second domain comprises the ligand selected from the group consisting of CD58, CD70, CD83, CD80, CD86, CD137L, CD252, CD275, CD54, CD49a, CD112, CD150, CD155, CD265, CD270, TL1A, CD127, IL-4R, GITR-L, TIM-4, CD153, CD48, CD160, CD200R, CD44, and receptor-binding fragments thereof. In some embodiments, the fusion protein comprises a first domain that comprises an antibody or antigen-binding fragment thereof that binds CD40, and a second domain comprises CD58 (e.g., SEQ ID NO:178) or a receptor-binding fragment thereof. In some embodiments, the fusion protein comprises a first domain that comprises an antibody or antigen-binding fragment thereof that binds CD40, and a second domain comprises CD70 (e.g., SEQ ID NO:179) or a receptor-binding fragment thereof. In some embodiments, the fusion protein comprises a first domain that comprises an antibody or antigen-binding fragment thereof that binds CD40, and a second domain comprises CD83 (e.g., SEQ ID NO:180) or a receptor-binding fragment thereof. In some embodiments, the fusion protein comprises a first domain that comprises an antibody or antigen-binding fragment thereof that binds CD40, and a second domain comprises CD80 (e.g., SEQ ID NO:54) or a receptor-binding fragment thereof. In some embodiments, the fusion protein comprises a first domain that comprises an antibody or antigen-binding fragment thereof that binds CD40, and a second domain comprises CD86 (e.g., SEQ ID NO:57) or a receptor-binding fragment thereof. In some embodiments, the fusion protein comprises a first domain that comprises an antibody or antigen-binding fragment thereof that binds CD40, and a second domain comprises CD137L (e.g., SEQ ID NO:181) or a receptor-binding fragment thereof. In some embodiments, the fusion protein comprises a first domain that comprises an antibody or antigen-binding fragment thereof that binds CD40, and a second domain comprises CD252 (e.g., SEQ ID NO:182) or a receptor-binding fragment thereof. In some embodiments, the fusion protein comprises a first domain that comprises an antibody or antigen-binding fragment thereof that binds CD40, and a second domain comprises CD275 (e.g., SEQ ID NO:183) or a receptor-binding fragment thereof. In some embodiments, the fusion protein comprises a first domain that comprises an antibody or antigen-binding fragment thereof that binds CD40, and a second domain comprises CD54 (e.g., SEQ ID NO:184) or a receptor-binding fragment thereof. In some embodiments, the fusion protein comprises a first domain that comprises an antibody or antigen-binding fragment thereof that binds CD40, and a second domain comprises CD49a (e.g., SEQ ID NO:185) or a receptor-binding fragment thereof. In some embodiments, the fusion protein comprises a first domain that comprises an antibody or antigen-binding fragment thereof that binds CD40, and a second domain comprises CD112 (e.g., SEQ ID NO:186) or a receptor-binding fragment thereof. In some embodiments, the fusion protein comprises a first domain that comprises an antibody or antigen-binding fragment thereof that binds CD40, and a second domain comprises CD150 (e.g., SEQ ID NO:187) or a receptor-binding fragment thereof. In some embodiments, the fusion protein comprises a first domain that comprises an antibody or antigen-binding fragment thereof that binds CD40, and a second domain comprises CD155 (e.g., SEQ ID NO:188) or a receptor-binding fragment thereof. In some embodiments, the fusion protein comprises a first domain that comprises an antibody or antigen-binding fragment thereof that binds CD40, and a second domain comprises CD265 (e.g., SEQ ID NO:189) or a receptor-binding fragment thereof. In some embodiments, the fusion protein comprises a first domain that comprises an antibody or antigen-binding fragment thereof that binds CD40, and a second domain comprises CD270 (e.g., SEQ ID NO:190) or a receptor-binding fragment thereof. In some embodiments, the fusion protein comprises a first domain that comprises an antibody or antigen-binding fragment thereof that binds CD40, and a second domain comprises TL1A (e.g., SEQ ID NO:191) or a receptor-binding fragment thereof. In some embodiments, the fusion protein comprises a first domain that comprises an antibody or antigen-binding fragment thereof that binds CD40, and a second domain comprises CD127 (e.g., SEQ ID NO:192) or a receptor-binding fragment thereof. In some embodiments, the fusion protein comprises a first domain that comprises an antibody or antigen-binding fragment thereof that binds CD40, and a second domain comprises IL-4R (e.g., SEQ ID NO:193) or a receptor-binding fragment thereof. In some embodiments, the fusion protein comprises a first domain that comprises an antibody or antigen-binding fragment thereof that binds CD40, and a second domain comprises GITR-L (e.g., SEQ ID NO:194) or a receptor-binding fragment thereof. In some embodiments, the fusion protein comprises a first domain that comprises an antibody or antigen-binding fragment thereof that binds CD40, and a second domain comprises TIM-4 (e.g., SEQ ID NO:195) or a receptor-binding fragment thereof. In some embodiments, the fusion protein comprises a first domain that comprises an antibody or antigen-binding fragment thereof that binds CD40, and a second domain comprises CD153 (e.g., SEQ ID NO:196) or a receptor-binding fragment thereof. In some embodiments, the fusion protein comprises a first domain that comprises an antibody or antigen-binding fragment thereof that binds CD40, and a second domain comprises CD48 (e.g., SEQ ID NO:53) or a receptor-binding fragment thereof. In some embodiments, the fusion protein comprises a first domain that comprises an antibody or antigen-binding fragment thereof that binds CD40, and a second domain comprises CD160 (e.g., SEQ ID NO:49) or a receptor-binding fragment thereof. In some embodiments, the fusion protein comprises a first domain that comprises an antibody or antigen-binding fragment thereof that binds CD40, and a second domain comprises CD200R (e.g., SEQ ID NO:197) or a receptor-binding fragment thereof. In some embodiments, the fusion protein comprises a first domain that comprises an antibody or antigen-binding fragment thereof that binds CD40, and a second domain comprises CD44 (e.g., SEQ ID NO:198) or a receptor-binding fragment thereof. A person of ordinary skill in the art can readily determine a proper receptor-binding fragment of a ligand that retains its binding affinity toward its receptor and function to activate the receptor.

As a person of ordinary skill in the art would understand, the anti-CD40 antibody or antigen-binding fragment thereof in the fusion proteins exemplified herein can be replaced with an antibody or antigen-binding fragment that binds another activation receptor for APC that is disclosed herein or otherwise known in the art, including, for example, CD80, CD86, CD91, DEC-205 or DC-SIGN.

5.2.3.6 Exemplary LACO-Stim (6): Ligand for APC Activation Receptor+Co-Stimulatory Ligand (e.g., CD40L-CD86; CD40L-CD80)

In some embodiments, provided herein are fusion proteins comprising a first domain that activates an APC and a second domain that activates an immune effector cell, wherein the first domain comprises a ligand that binds an activation receptor of the APC, or a receptor-binding fragment thereof, and wherein the second domain comprises a co-stimulatory ligand of the immune effector cell, or a receptor-binding fragment thereof. In some embodiments, the C-terminus of the first domain is linked to the N-terminus of the second domain. In some embodiments, the N-terminus of the first domain is linked to the C-terminus of the second domain.

In some embodiments, fusion proteins provided herein comprise a first domain comprising a ligand that binds an activation receptor selected from the group consisting of CD40, CD80, CD86, CD91, DEC-205, and DC-SIGN, or a functional-fragment thereof, and a second domain comprising a co-stimulatory ligand selected from the group consisting of CD58, CD70, CD83, CD80, CD86, CD137L, CD252, CD275, CD54, CD49a, CD112, CD150, CD155, CD265, CD270, TL1A, CD127, IL-4R, GITR-L, TIM-4, CD153, CD48, CD160, CD200R, CD44 or a receptor-binding fragment thereof.

In some embodiments, the first domain of the fusion proteins provided herein comprises the extracellular domain of CD40L (e.g., SEQ ID NO:12). In some embodiments, the first domain of the fusion proteins provided herein can have an amino acid sequence that is at least 85%, at least 88%, at least 90%, at least 95%, at least 98%, or 100% identical to SEQ ID NO:12. In some embodiments, the first domain of the fusion proteins provided herein has the amino acid sequence of SEQ ID NO:12. In some embodiments, the first domain of the fusion proteins provided herein comprises full length CD40L. In some embodiments, the first domain of the fusion proteins provided herein can have an amino acid sequence that is at least 85%, at least 88%, at least 90%, at least 95%, at least 98%, or 100% identical to SEQ ID NO:9. In some embodiments, the first domain of the fusion proteins provided herein has the amino acid sequence of SEQ ID NO:9. In some embodiments, the first domain of the fusion proteins provided herein can have amino acids 119-261 of CD40L (SEQ ID NO:9). In some embodiments, the first domain of the fusion proteins provided herein comprises three copies of the CD40L, or a functional fragment thereof. In some embodiments, the first domain of the fusion proteins provided herein comprises three copies of the extracellular domain of the CD40L. In some embodiments, the first domain of the fusion proteins provided herein comprises three copies of amino acids 119-261 of CD40L (SEQ ID NO:9).

In some embodiments, the fusion protein comprises a first domain that comprises CD40L or a receptor-binding fragment thereof, and a second domain comprises a ligand selected from the group consisting of CD58, CD70, CD83, CD80, CD86, CD137L, CD252, CD275, CD54, CD49a, CD112, CD150, CD155, CD265, CD270, TL1A, CD127, IL-4R, GITR-L, TIM-4, CD153, CD48, CD160, CD200R, CD44, or receptor-binding fragments thereof. In some embodiments, the fusion protein comprises a first domain that comprises CD40L or a receptor-binding fragment thereof, and a second domain comprises CD58 (e.g., SEQ ID NO:178) or a receptor-binding fragment thereof. In some embodiments, the fusion protein comprises a first domain that comprises CD40L or a receptor-binding fragment thereof, and a second domain comprises CD70 (e.g., SEQ ID NO:179) or a receptor-binding fragment thereof. In some embodiments, the fusion protein comprises a first domain that comprises CD40L or a receptor-binding fragment thereof, and a second domain comprises CD83 (e.g., SEQ ID NO:180) or a receptor-binding fragment thereof. In some embodiments, the fusion protein comprises a first domain that comprises CD40L or a receptor-binding fragment thereof, and a second domain comprises CD80 (e.g., SEQ ID NO:54) or a receptor-binding fragment thereof. In some embodiments, the fusion protein comprises a first domain that comprises CD40L or a receptor-binding fragment thereof, and a second domain comprises CD86 (e.g., SEQ ID NO:57) or a receptor-binding fragment thereof. In some embodiments, the fusion protein comprises a first domain that comprises CD40L or a receptor-binding fragment thereof, and a second domain comprises CD137L (e.g., SEQ ID NO:181) or a receptor-binding fragment thereof. In some embodiments, the fusion protein comprises a first domain that comprises CD40L or a receptor-binding fragment thereof, and a second domain comprises CD252 (e.g., SEQ ID NO:182) or a receptor-binding fragment thereof. In some embodiments, the fusion protein comprises a first domain that comprises CD40L or a receptor-binding fragment thereof, and a second domain comprises CD275 (e.g., SEQ ID NO:183) or a receptor-binding fragment thereof. In some embodiments, the fusion protein comprises a first domain that comprises CD40L or a receptor-binding fragment thereof, and a second domain comprises CD54 (e.g., SEQ ID NO:184) or a receptor-binding fragment thereof. In some embodiments, the fusion protein comprises a first domain that comprises CD40L or a receptor-binding fragment thereof, and a second domain comprises CD49a (e.g., SEQ ID NO:185) or a receptor-binding fragment thereof. In some embodiments, the fusion protein comprises a first domain that comprises CD40L or a receptor-binding fragment thereof, and a second domain comprises CD112 (e.g., SEQ ID NO:186) or a receptor-binding fragment thereof. In some embodiments, the fusion protein comprises a first domain that comprises CD40L or a receptor-binding fragment thereof, and a second domain comprises CD150 (e.g., SEQ ID NO:187) or a receptor-binding fragment thereof. In some embodiments, the fusion protein comprises a first domain that comprises CD40L or a receptor-binding fragment thereof, and a second domain comprises CD155 (e.g., SEQ ID NO:188) or a receptor-binding fragment thereof. In some embodiments, the fusion protein comprises a first domain that comprises CD40L or a receptor-binding fragment thereof, and a second domain comprises CD265 (e.g., SEQ ID NO:189) or a receptor-binding fragment thereof. In some embodiments, the fusion protein comprises a first domain that comprises CD40L or a receptor-binding fragment thereof, and a second domain comprises CD270 (e.g., SEQ ID NO:190) or a receptor-binding fragment thereof. In some embodiments, the fusion protein comprises a first domain that comprises CD40L or a receptor-binding fragment thereof, and a second domain comprises TL1A (e.g., SEQ ID NO:191) or a receptor-binding fragment thereof. In some embodiments, the fusion protein comprises a first domain that comprises CD40L or a receptor-binding fragment thereof, and a second domain comprises CD127 (e.g., SEQ ID NO:192) or a receptor-binding fragment thereof. In some embodiments, the fusion protein comprises a first domain that comprises CD40L or a receptor-binding fragment thereof, and a second domain comprises IL-4R (e.g., SEQ ID NO:193) or a receptor-binding fragment thereof. In some embodiments, the fusion protein comprises a first domain that comprises CD40L or a receptor-binding fragment thereof, and a second domain comprises GITR-L (e.g., SEQ ID NO:194) or a receptor-binding fragment thereof. In some embodiments, the fusion protein comprises a first domain that comprises CD40L or a receptor-binding fragment thereof, and a second domain comprises TIM-4 (e.g., SEQ ID NO:195) or a receptor-binding fragment thereof. In some embodiments, the fusion protein comprises a first domain that comprises CD40L or a receptor-binding fragment thereof, and a second domain comprises CD153 (e.g., SEQ ID NO:196) or a receptor-binding fragment thereof. In some embodiments, the fusion protein comprises a first domain that comprises CD40L or a receptor-binding fragment thereof, and a second domain comprises CD48 (e.g., SEQ ID NO:53) or a receptor-binding fragment thereof. In some embodiments, the fusion protein comprises a first domain that comprises CD40L or a receptor-binding fragment thereof, and a second domain comprises CD160 (e.g., SEQ ID NO:49) or a receptor-binding fragment thereof. In some embodiments, the fusion protein comprises a first domain that comprises CD40L or a receptor-binding fragment thereof, and a second domain comprises CD200R (e.g., SEQ ID NO:197) or a receptor-binding fragment thereof. In some embodiments, the fusion protein comprises a first domain that comprises CD40L or a receptor-binding fragment thereof, and a second domain comprises CD44 (e.g., SEQ ID NO:198) or a receptor-binding fragment thereof. A person of ordinary skill in the art can readily determine a proper receptor-binding fragment of a ligand that retains its binding affinity toward its receptor and function to activate the receptor.

As a person of ordinary skill in the art would understand, CD40L or receptor-binding fragment thereof in the fusion proteins exemplified herein can be replaced with another ligand for an activation receptor for APC that is disclosed herein or otherwise known in the art, including, for example, the extracellular domain or the full length of a CD80 ligand (e.g., CD28 or CTLA-4), a CD86 ligand (e.g., CD28 or CTLA-4), a CD91 ligand (e.g., RAP1), a DEC-205 ligand or a DC-SIGN ligand (e.g., ICAM2, ICAM3, CD18, or CEACAM1).

5.3 Polynucleotides and Vectors

In some embodiments, provided herein are polynucleotides that encode a fusion protein described herein. The term "polynucleotide that encode a polypeptide" encompasses a polynucleotide which includes only coding sequences for the polypeptide as well as a polynucleotide which includes additional coding and/or non-coding sequences. The polynucleotides of the disclosure can be in the form of RNA or in the form of DNA. RNA can be messenger RNA (mRNA). DNA includes cDNA, genomic DNA, and synthetic DNA; and can be double-stranded or single-stranded, and if single stranded can be the coding strand or non-coding (anti-sense) strand.

In some embodiments, provided herein are polynucleotides encoding a polypeptide having an amino acid sequence selected from SEQ ID NOs:93-106. Also provided is a polynucleotide that hybridizes to a polynucleotide encoding an amino acid sequence selected from SEQ ID NOs:93-106. In some embodiments, the hybridization is under conditions of high stringency as is known to those skilled in the art. In some embodiments, provided herein are polynucleotides encoding a polypeptide having the amino acid sequence of SEQ ID NO:93. In some embodiments, provided herein are polynucleotides encoding a polypeptide having the amino acid sequence of SEQ ID NO:94. In some embodiments, provided herein are polynucleotides encoding a polypeptide having the amino acid sequence of SEQ ID NO:95. In some embodiments, provided herein are polynucleotides encoding a polypeptide the amino acid sequence of SEQ ID NO:96. In some embodiments, provided herein are polynucleotides encoding a polypeptide having the amino acid sequence of SEQ ID NO:97. In some embodiments, provided herein are polynucleotides encoding a polypeptide having the amino acid sequence of SEQ ID NO:211. In some embodiments, provided herein are polynucleotides encoding a polypeptide having the amino acid sequence of SEQ ID NO:98. In some embodiments, provided herein are polynucleotides encoding a polypeptide having the amino acid sequence of SEQ ID NO:99. In some embodiments, provided herein are polynucleotides encoding a polypeptide having the amino acid sequence of SEQ ID NO:100. In some embodiments, provided herein are polynucleotides encoding a polypeptide having the amino acid sequence of SEQ ID NO:101. In some embodiments, provided herein are polynucleotides encoding a polypeptide having the amino acid sequence of SEQ ID NO:102. In some embodiments, provided herein are polynucleotides encoding a polypeptide having the amino acid sequence of SEQ ID NO:103. In some embodiments, provided herein are polynucleotides encoding a polypeptide having the amino acid sequence of SEQ ID NO:104. In some embodiments, provided herein are polynucleotides encoding a polypeptide having the amino acid sequence of SEQ ID NO:105. In some embodiments, provided herein are polynucleotides encoding a polypeptide having the amino acid sequence of SEQ ID NO:106.

The present disclosure also provides variants of the polynucleotides described herein, wherein the variant encodes, for example, fragments, analogs, and/or derivatives of a fusion protein described herein. In some embodiments, the present disclosure provides a polynucleotide encoding a polypeptide that is at least 80% identical, at least 85% identical, at least 90% identical, at least 95% identical, at least 96% identical, at least 97% identical, at least 98% identical, or at least 99% identical to a fusion protein described herein. In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated 40L.28.40L.40L (SEQ ID NO:93). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated 1412-T4-CD40L (SEQ ID NO:94). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated 1412-F2.103 (SEQ ID NO:95). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated 1412-F5.157 (SEQ ID NO:96). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated 1412-4D11 (SEQ ID NO:211). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated 1412-F5.77 (SEQ ID NO:97). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated F2.103.CD28 (SEQ ID NO:98). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated F5.157.CD28 (SEQ ID NO:99). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated F5.77.CD28 (SEQ ID NO:100). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated F2.103.BB (SEQ ID NO:101). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated F5.157.BB (SEQ ID NO:102). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated F5.77.BB (SEQ ID NO:103). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated 4D11.CD28 (SEQ ID NO:104). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated A40C.CD28 (SEQ ID NO:105). In some embodiments, provided herein are polynucleotides encoding a polypeptide that is at least 80% identical, at least 85% identical, at least 90% identical, at least 95% identical, at least 96% identical, at least 97% identical, at least 98% identical, or at least 99% identical to the fusion protein designated 119.CD28 (SEQ ID NO:106).

As used herein, the phrase "a polynucleotide having a nucleotide sequence at least 95% identical to a polynucleotide" means that the nucleotide sequence of the polynucleotide is identical to a reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (e.g., change codons in the human mRNA to those preferred by a bacterial host such as *E. coli*). In some embodiments, a polynucleotide variant comprises at least one silent mutation in a non-coding or a coding region of the sequence.

If desired, polynucleotides provided herein can be codon optimized to increase efficiency of expression of the fusion protein in a given cell. Codon optimization can be used to achieve higher levels of expression in a given cell. Factors that are involved in different stages of protein expression include codon adaptability, mRNA structure, and various cis-elements in transcription and translation. Any suitable codon optimization methods or technologies that are known to one skilled in the art can be used to modify the polynucleotides provided herein. Such codon optimization methods are well known, including commercially available codon optimization services, for example, OptimumGene™ (GenScript; Piscataway, N.J.), Encor optimization (EnCor Biotechnology; Gainseville Fla.), Blue Heron (Blue Heron Biotech; Bothell, Wash.), and the like. Optionally, multiple codon optimizations can be performed based on different algorithms, and the optimization results blended to generate a codon optimized polynucleotide encoding a polypeptide.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, provided herein are polynucleotides having a nucleotide sequence selected from the group consisting of SEQ ID NOs:132-145. In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to a nucleotide sequence selected from the group consisting of SEQ ID NOs:132-145. Also provided is a polynucleotide that hybridizes to a polynucleotide having a nucleotide sequence selected from the group consisting of SEQ ID NOs:132-145. In some embodiments, the hybridization is under conditions of high stringency as is known to those skilled in the art.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:132. In some embodiments, provided herein are polynucleotides that hybridizes to a polynucleotide having the nucleotide sequence SEQ ID NO:132. In some embodiments, provided herein are polynucleotides having the nucleotide sequence of SEQ ID NO:132.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:133. In some embodiments, provided herein are polynucleotides that hybridizes to a polynucleotide having the nucleotide sequence SEQ ID NO:133. In some embodiments, provided herein are polynucleotides having the nucleotide sequence of SEQ ID NO:133.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:134. In some embodiments, provided herein are polynucleotides that hybridizes to a polynucleotide having the nucleotide sequence SEQ ID NO:134. In some embodiments, provided herein are polynucleotides having the nucleotide sequence of SEQ ID NO:134.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:135. In some embodiments, provided herein are polynucleotides that hybridizes to a polynucleotide having the nucleotide sequence SEQ ID NO:135. In some embodiments, provided herein are polynucleotides having the nucleotide sequence of SEQ ID NO:135.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:136. In some embodiments, provided herein are polynucleotides that hybridizes to a polynucleotide having the nucleotide sequence SEQ ID NO:136. In some embodiments, provided herein are polynucleotides having the nucleotide sequence of SEQ ID NO:136.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:137. In some embodiments, provided herein are polynucleotides that hybridizes to a polynucleotide having the nucleotide sequence SEQ ID NO:137. In some embodiments, provided herein are polynucleotides having the nucleotide sequence of SEQ ID NO:137.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:138. In some embodiments, provided herein are polynucleotides that hybridizes to a polynucleotide having the nucleotide sequence SEQ ID NO:138. In some embodiments, provided herein are polynucleotides having the nucleotide sequence of SEQ ID NO:138.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:139. In some embodiments, provided herein are polynucleotides that hybridizes to a polynucleotide having the nucleotide sequence SEQ ID NO:139. In some embodiments, provided herein are polynucleotides having the nucleotide sequence of SEQ ID NO:139.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:140. In some embodiments, provided herein are polynucleotides that hybridizes to a polynucleotide having the nucleotide sequence SEQ ID NO:140. In some embodiments, provided herein are polynucleotides having the nucleotide sequence of SEQ ID NO:140.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:141. In some embodiments, provided herein are polynucleotides that hybridizes to a polynucleotide having the nucleotide sequence SEQ ID NO:141. In some embodiments, provided herein are polynucleotides having the nucleotide sequence of SEQ ID NO:141.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:142. In some embodiments, provided herein are polynucleotides that hybridizes to a polynucleotide having the nucleotide sequence SEQ ID NO:142. In some embodiments, provided herein are polynucleotides having the nucleotide sequence of SEQ ID NO:142.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:143. In some embodiments, provided herein are polynucleotides that hybridizes to a polynucleotide having the nucleotide sequence SEQ ID NO:143. In some embodiments, provided herein are polynucleotides having the nucleotide sequence of SEQ ID NO:143.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:144. In some embodiments, provided herein are polynucleotides that hybridizes to a polynucleotide having the nucleotide sequence SEQ ID NO:144. In some embodiments, provided herein are polynucleotides having the nucleotide sequence of SEQ ID NO:144.

In some embodiments, provided herein are polynucleotides having a nucleotide sequence at least 80% identical, at least 85% identical, at least 90% identical, at least 95% identical, at least 96% identical, at least 97% identical, at least 98% identical, or at least 99% identical to SEQ ID NO:145. In some embodiments, provided herein are polynucleotides that hybridizes to a polynucleotide having the nucleotide sequence SEQ ID NO:145. In some embodiments, provided herein are polynucleotides having the nucleotide sequence of SEQ ID NO:145.

In some embodiments, a polynucleotide comprises the coding sequence for a fusion protein fused in the same reading frame to a polynucleotide which aids in expression and secretion of a polypeptide from a host cell (e.g., a leader sequence which functions as a secretory sequence for controlling transport of a polypeptide). The polypeptide can have the leader sequence cleaved by the host cell to form a "mature" form of the polypeptide.

In some embodiments, a polynucleotide comprises the coding sequence for a fusion protein fused in the same reading frame to a marker or tag sequence. For example, in some embodiments, a marker sequence is a hexa-histidine tag (HIS-tag) that allows for efficient purification of the polypeptide fused to the marker. In some embodiments, a marker sequence is a hemagglutinin (HA) tag derived from the influenza hemagglutinin protein when a mammalian host (e.g., COS-7 cells) is used. In some embodiments, the marker sequence is a FLAG™ tag. In some embodiments, a marker may be used in conjunction with other markers or tags.

In some embodiments, a polynucleotide is isolated. In some embodiments, a polynucleotide is substantially pure.

Vectors and cells comprising the polynucleotides described herein are also provided. In some embodiments, an expression vector comprises a polynucleotide encoding a fusion protein described herein. In some embodiments, a host cell comprises a polynucleotide encoding a fusion protein described herein. In some embodiments, a host cell comprises an expression vector comprising a polynucleotide encoding a fusion protein described herein. The vector can be a viral vector. In one embodiment, the vector is a retroviral vector, for example, a gamma retroviral vector, which is employed for the introduction of the polynucleotides described herein into a target cell. The vector can be a lentiviral vector. The vector can be an adenoviral vector. The vector can be an adeno-associated viral vector. In some embodiments, the vectors and constructs can optionally be designed to include a reporter.

Provided herein are cells comprising the fusion proteins described herein. Provided herein are also cells comprising the polynucleotides encoding the fusion proteins described herein. In some embodiments, the cells produce the fusion proteins described herein.

5.4 Genetically Engineered Immune Effector Cells

Provided herein are genetically engineered immune effector cells recombinantly expressing the fusion proteins disclosed herein. Provided herein are also genetically engineered cells comprising the polynucleotides disclosed herein. In some embodiments, provided herein are also genetically engineered cells comprising the vectors disclosed herein.

In some embodiments, the genetically engineered immune effector cell provided herein is selected from the group consisting of a T cell, an NK cell, an NKT cell, a macrophage, a neutrophil, and a granulocyte. In some embodiments, the cell provided herein is a T cell. In some embodiments, the cell provided herein is an NK cell. In some embodiments, the cell provided herein is an NKT cell. In some embodiments, the cell provided herein is a macrophage. In some embodiments, the cell provided herein is a neutrophil. In some embodiments, the cell provided herein is a granulocyte. In some embodiments, the genetically engineered immune effector cells provided herein are isolated. In some embodiments, the genetically engineered immune effector cells provided herein are substantially pure.

In some embodiments, the immune effector cell provided herein is a T cell. The T cell can be a cytotoxic T cell, a helper T cell, or a gamma delta T, a CD4+/CD8+ double positive T cell, a CD4+ T cell, a CD8+ T cell, a CD4/CD8 double negative T cell, a CD3+ T cell, a naive T cell, an effector T cell, a cytotoxic T cell, a helper T cell, a memory T cell, a regulator T cell, a Th0 cell, a Th1 cell, a Th2 cell, a Th3 (Treg) cell, a Th9 cell, a Th17 cell, a Thαβ helper cell, a Tfh cell, a stem memory TSCM cell, a central memory TCM cell, an effector memory TEM cell, an effector memory TEMRA cell, or a gamma delta T cell. In some embodiments, the T cell is a cytotoxic T cell. In some embodiments, the genetically engineered T cells provided herein are isolated. In some embodiments, the genetically engineered T cells provided herein are substantially pure.

In some embodiments, genetically engineered cells provided herein are derived from cells isolated from a subject. As used herein, a genetically engineered cell that is "derived from" a source cell means that the genetically engineered cell is obtained by taking the source cell and genetically manipulating the source cell. The source cell can be from a natural source. For example, the source cell can be a primary cell isolated from a subject. The subject can be an animal or a human. The source cell can also be a cell that has undergone passages or genetically manipulation in vitro.

In some embodiments, genetically engineered cells provided herein are derived from cells isolated from a human. Immune effector cells (e.g., T cells) can be obtained from many sources, including peripheral blood mononuclear cells, bone marrow, lymph node tissue, cord blood, thymus tissue, tissue from a site of infection, ascites, pleural effusion, spleen tissue, and tumors. In certain embodiments, T cell lines available in the art can be used. In some embodiments, genetically engineered cells provided herein are derived from cells isolated from peripheral blood. In some embodiments, genetically engineered cells provided herein are derived from cells isolated from bone marrow. In some embodiments, genetically engineered cells provided herein are derived from cells isolated from peripheral blood mononuclear cells (PBMC).

In some embodiments, genetically engineered cells provided herein are derived from cells differentiated in vitro from a stem or progenitor cell. In some embodiments, the stem or progenitor cell is selected from the group consisting of a T cell progenitor cell, a hematopoietic stem and progenitor cell, a hematopoietic multipotent progenitor cell, an embryonic stem cell, and an induced pluripotent cell. In some embodiments, genetically engineered cells provided herein are derived from cells differentiated in vitro from a T cell progenitor cell. In some embodiments, genetically engineered cells provided herein are derived from cells differentiated in vitro from a hematopoietic stem and progenitor cell. In some embodiments, genetically engineered cells provided herein are derived from cells differentiated in vitro from a hematopoietic multipotent progenitor cell. In some embodiments, genetically engineered cells provided herein are derived from cells differentiated in vitro from an embryonic stem cell. In some embodiments, genetically engineered cells provided herein are derived from cells differentiated in vitro from an induced pluripotent cell.

In some embodiments, provided herein are a population of the genetically engineered cells disclosed herein. The population of cells can be a homogenous population of cells. The population of cells can be a heterogeneous population of cells. In some embodiments, the population of cells can be a heterogeneous population of cells comprising any combination of the cells disclosed herein. In some embodiments, the population of genetically engineered cells provided herein are derived from tumor-infiltrating lymphocytes (TIL). In some embodiments, the population of genetically engineered cells provided herein are derived from peripheral blood mononuclear cells (PBMC). In some embodiments, the population of genetically engineered cells provided herein are derived from peripheral blood leukocytes (PBL). In some embodiments, the population of genetically engineered cells provided herein are derived from tumor infiltrating lymphocytes (TIL). In some embodiments, the population of genetically engineered cells provided herein are derived from marrow infiltrate lymphocytes (MILs). In some embodiments, the population of genetically engineered cells provided herein are derived from cytokine-induced killer cells (CIK). In some embodiments, the population of genetically engineered cells provided herein are derived from lymphokine-activated killer cells (LAK).

In some embodiments, the genetically engineered immune effector cells provided herein further recombinantly express a chimeric antigen receptor (CAR), a T cell receptor (TCR) or a Bi-specific T-cell engager (BiTE). In some embodiments, the genetically engineered cells disclosed herein further express a CAR. In some embodiments, the genetically engineered cells disclosed herein further express a TCR. In some embodiments, the genetically engineered cells disclosed herein further express a BiTE. In some embodiments, the genetically engineered immune effector cells provided herein further comprise a polynucleotide that encodes a CAR, a TCR or a BiTE (CAR/TCR/BiTE). In some embodiments, the genetically engineered immune effector cells provided herein further comprise a polynucleotide that encodes a CAR. In some embodiments, the genetically engineered immune effector cells provided herein further comprise a polynucleotide that encodes a TCR. In some embodiments, the genetically engineered immune effector cells provided herein further comprise a polynucleotide that encodes a BiTE. In some embodiments, the CAR, TCR or BiTE binds a tumor antigen or a viral antigen.

In some embodiments, the genetically engineered immune effector cells provided herein comprise a first polynucleotide that encodes a fusion protein disclosed herein and a second polynucleotide that encodes a CAR, a TCR or a BiTE (CAR/TCR/BiTE). In some embodiments, the genetically engineered immune effector cells provided herein comprise a polynucleotide having a first fragment encoding a fusion protein disclosed herein and a second fragment that encodes a CAR, a TCR or a BiTE (CAR/TCR/BiTE). The first fragment and the second fragment can be linked by a nucleotide sequence encoding a linker. The linker can be a self-cleaving linker. In some embodiments, the first and second fragment are linked by a nucleotide sequence encoding a 2A peptide. In some embodiments, the 2A linker is a P2A peptide (SEQ ID NO:220). In some embodiments, the linker is a T2A peptide (SEQ ID NO:221). In some embodiments, the linker is an E2A peptide (SEQ ID NO:222). In some embodiments, the linker is an F2A peptide (SEQ ID NO:223). In some embodiments, provided herein are polynucleotides comprising a first fragment encoding a fusion protein provided herein and a second fragment encoding a CAR/TCR/BiTE, wherein the first and second fragments are linked by a nucleotide sequence encoding a F2A peptide (SEQ ID NO:223). In some embodiments, the first fragment (fusion protein-encoding) is located at the 5' end of the second fragment (CAR/TCR/BiTE encoding). In some embodiments, the first fragment (fusion protein-encoding) is located at the 3' end of the second fragment (CAR/TCR/BiTE encoding).

In some embodiments, the genetically engineered immune effector cells provided herein further expresses a CAR or comprises a polynucleotide that encodes a CAR. The CAR can be any CAR disclosed herein or otherwise known in the art. In some embodiments, the CAR comprises an antigen-binding domain that specifically binds a tumor antigen. As such, in some embodiments, provided herein are also genetically engineered cells expressing a fusion protein disclosed herein and a CAR. In some embodiments, genetically engineered cells provided herein comprise a polynucleotide that comprises a first fragment encoding a fusion protein, and a second fragment encoding a CAR. In some embodiments, genetically engineered cells provided herein comprise a first polynucleotide encoding a fusion protein provided herein, and a second polynucleotide encoding a CAR In some embodiments, the genetically engineered immune effector cells provided herein further expresses a TCR or comprises a polynucleotide that encodes a TCR. The TCR can be any TCR disclosed herein or otherwise known in the art. In some embodiments, the TCR comprises an antigen-binding domain that specifically binds a tumor antigen. As such, in some embodiments, provided herein are also genetically engineered cells expressing a fusion protein disclosed herein and a TCR. In some embodiments, genetically engineered cells provided herein comprise a polynucleotide that comprises a first fragment encoding a fusion protein, and a second fragment encoding a TCR. In some embodiments, genetically engineered cells provided herein comprise a first polynucleotide encoding a fusion protein and a second polynucleotide encoding a TCR.

In some embodiments, the genetically engineered immune effector cells provided herein further expresses a BiTE or comprises a polynucleotide that encodes a BiTE. The BiTE can be any BiTE disclosed herein or otherwise known in the art. In some embodiments, the BiTE comprises an antigen-binding domain that specifically binds a tumor antigen. As such, in some embodiments, provided herein are also genetically engineered cells expressing a fusion protein disclosed herein and a BiTE. In some embodiments, genetically engineered cells provided herein comprise a polynucleotide that comprises a first fragment encoding a fusion protein, and a second fragment encoding a BiTE. In some embodiments, genetically engineered cells provided herein comprise a first polynucleotide encoding a fusion protein and a second polynucleotide encoding a BiTE.

In some embodiments, the CAR, TCR, or BiTE provided herein include a target-binding domain that binds an antigen. In some embodiments, the antigen is a viral antigen. In some embodiments, the viral antigen is EBV. In some embodiments, the viral antigen is HPV. In some embodiments, the viral antigen is HIV. It is understood that these or other viral antigens can be utilized for targeting by a CAR, TCR, or BiTE disclosed herein.

In some embodiments, the CAR, TCR, or BiTE provided herein include a target-binding domain that binds a cancer antigen or a tumor antigen. Any suitable cancer antigen or tumor antigen can be chosen based on the type of cancer exhibited by a subject (cancer patient) to be treated. It is understood that the selected cancer antigen is expressed in a manner such that the cancer antigen is accessible for binding. Generally, the cancer antigen to be targeted by a cell expressing a CAR, TCR, or BiTE is expressed on the cell surface of a cancer cell. However, it is understood that any cancer antigen that is accessible for binding is suitable for targeting.

Suitable antigens include, but are not limited to, B-cell maturation antigen (BCMA), mesothelin (MSLN), prostate specific membrane antigen (PSMA), prostate stem cell antigen (PSCA), carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD70, CD74, CD123, CD133, CD138, CD33, CD200R, alpha-fetoprotein (AFP), B7H3, B7H4, IL3Ra2, CS1, C-Met, Ber-EP4 (EpCAM-1,) epithelial glycoprotein2 (EGP 2), epithelial glycoprotein-40 (EGP-40), epithelial cell adhesion molecule (EpCAM), folate-binding protein (FBP), fetal acetylcholine receptor (AChR), folate receptor-α and β (FRα and β), Ganglioside G2 (GD2), Ganglioside G3 (GD3), human Epidermal Growth Factor Receptor 2 (HER-2/ERB2), Epidermal Growth Factor Receptor (EGFR), Epidermal Growth Factor Receptor vIII (EGFRvIII), ERB3, ERB4, GDNF family receptor alpha 4 (GFRa4), Histone 3 variant (H3.3), human telomerase reverse transcriptase (hTERT), Interleukin-13 receptor subunit alpha-2 (IL13Rα2), κ-light chain, kinase insert domain receptor (KDR), Lewis A (CA19.9), Lewis Y (LeY), L1 cell adhesion molecule (L1CAM), melanoma-associated antigen 1 (melanoma antigen family A1, MAGE-A1), MAGE-A3, Mucin 16 (Muc-16), Mucin 1 (Muc-1), Tn-MUC1, NKG2D ligands, cancer-testis antigen NY-ESO-1, oncofetal antigen (h5T4), tumor-associated glycoprotein 72 (TAG-72), vascular endothelial growth factor R (VEGF-R), Wilms tumor protein (WT-1), type 1 tyrosine-protein kinase transmembrane receptor (ROR1), B7-H3 (CD276), B7-H6 (Nkp30), Chondroitin sulfate proteoglycan-4 (CSPG4), DNAX Accessory Molecule (DNAM-1), Ephrin type A Receptor 2 (EpHA2), Fibroblast Associated Protein (FAP), Gp100/ HLA-A2, Glypican 3 (GPC3), HA-1H, HERK-V, IL-11Rα, Latent Membrane Protein 1 (LMP1), MAG3, Neural cell-adhesion molecule (N-CAM/CD56), NY-ESO-1, Melan-A (MART1), PD-L1, WT1 transcription factor (WT1), P53, KRAS, TCRB1, TCRB2, and Trail Receptor (TRAIL R). It is understood that these or other cancer antigens can be utilized for targeting by a CAR, TCR, or BiTE disclosed herein.

Additionally, it is recognized in the art that the cell-based immune system frequently responds to the neoantigens that arise as a consequence of DNA damage that can lead to malignant transformation, and recognition of neoantigens can be an important driver of the clinical activity of cell therapies, such as adoptive T cell therapies. (E.g., Schumacher, *Science* 348.6230 (2015): 69-74. Schumacher et al., *Annual review of immunology* 37 (2019): 173-200.) Neoantigens can be identified using classical approaches focusing on common shared mutations (e.g., mutated BRAF, KRAS, and p53), or using next-generation sequencing techniques. (e.g., Lu, Yong-Chen, and Paul F. Robbins. *Seminars in immunology*. Vol. 28. No. L Academic Press, 2016.) In some embodiments, the CAR, TCR, or BiTE provided herein include a target-binding domain that binds a cancer neoantigen or a tumor neoantigen.

In some embodiments, the genetically engineered immune effector cells provided herein further comprise a polynucleotide that encodes a CAR, TCR, or BiTE that binds a cancer antigen or tumor antigen. In some embodiments, the genetically engineered immune effector cells provided herein further recombinantly express a CAR, TCR, or BiTE that binds a cancer antigen or tumor antigen. In some embodiments, the cancer antigen or tumor antigen is selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin. In some embodiments, the cancer antigen or tumor antigen is Her2. In some embodiments, the cancer antigen or tumor antigen is NY-ESO-1. In some embodiments, the cancer antigen or tumor antigen is CD19. In some embodiments, the cancer antigen or tumor antigen is CD20. In some embodiments, the cancer antigen or tumor antigen is CD22. In some embodiments, the cancer antigen or tumor antigen is PSMA. In some embodiments, the cancer antigen or tumor antigen is c-Met. In some embodiments, the cancer antigen or tumor antigen is GPC3. In some embodiments, the cancer antigen or tumor antigen is IL13ra2. In some embodiments, the cancer antigen or tumor antigen is EGFR. In some embodiments, the cancer antigen or tumor antigen is CD123. In some embodiments, the cancer antigen or tumor antigen is CD7. In some embodiments, the cancer antigen or tumor antigen is GD2. In some embodiments, the cancer antigen or tumor antigen is PSCA. In some embodiments, the cancer antigen or tumor antigen is EBV16-E7. In some embodiments, the cancer antigen or tumor antigen is H3.3. In some embodiments, the cancer antigen or tumor antigen is EGFRvIII. In some embodiments, the cancer antigen or tumor antigen is BCMA. In some embodiments, the cancer antigen or tumor antigen is Mesothelin.

5.4.1 CARs

The genetically engineered immune effector cells (e.g., T cells) provided herein can be used in cancer treatment. In some embodiments, provided herein is a genetically engineered T cell that expresses the fusion protein disclosed herein. In some embodiments, provided herein is a genetically engineered T cell that comprises the polynucleotide disclosed herein. In some embodiments, provided herein is a CAR-T cell.

In some embodiments, the fusion proteins provided herein can be co-expressed with a CAR in an immune effector cell. In some embodiments, a fusion protein provided herein can be conjugated to a CAR. CARs retarget immune effector cells (e.g., T cells) to tumor surface antigens (Sadelain et al., *Nat. Rev. Cancer.* 3(1):35-45 (2003); Sadelain et al, *Cancer Discovery* 3(4):388-398 (2013)). CARs are engineered receptors that provide both antigen binding and immune effector cell activation functions. CARs can be used to graft the specificity of an antibody, such as a monoclonal antibody, onto an immune effector cell such as a T cell, a NK cell, or a macrophage. First-generation receptors link an antibody-derived tumor-binding element, such as an scFv, that is responsible for antigen recognition to either CD3zeta or Fc receptor signaling domains, which trigger T-cell activation. The advent of second-generation CARs, which combine activating and costimulatory signaling domains, has led to encouraging results in patients with chemorefractory B-cell malignancies (Brentjens et al., *Science Translational Medicine* 5(177):177ra38 (2013); Brentjens et al., *Blood* 118(18):4817-4828 (2011); Davila et al, *Science Translational Medicine* 6(224):224ra25 (2014); Grupp et al, *N. Engl. J. Med.* 368(16):1509-1518 (2013); Kalos et al., *Science Translational Medicine* 3(95):95ra73 (2011)). The extracellular antigen-binding domain of a CAR is usually derived from a monoclonal antibody (mAb) or from receptors or their ligands. Antigen binding by the CARs triggers phosphorylation of immunoreceptor tyrosine-based activation motifs (ITAMs) in the intracellular domain, initiating a signaling cascade required for cytolysis induction, cytokine secretion, and proliferation.

In some embodiments, a fusion protein provided herein can be conjugated to CAR that has an antigen binding domain that binds to a cancer antigen. In some embodiments, the CAR can be a "first generation," "second generation" or "third generation" CAR (see, for example, Sadelain et al., *Cancer Discov.* 3(4):388-398 (2013); Jensen et al, *Immunol. Rev.* 257:127-133 (2014); Sharpe et al, *Dis. Model Mech.* 8(4):337-350 (2015); Brentjens et al, *Clin. Cancer Res.* 13:5426-5435 (2007); Gade et al., *Cancer Res.* 65:9080-9088 (2005); Maher et al., *Nat. Biotechnol.* 20:70-75 (2002); Kershaw et al., *J. Immunol.* 173:2143-2150 (2004); Sadelain et al, *Curr. Opin. Immunol.* 21(2):215-223 (2009); Hollyman et al., *J. Immunother.* 32:169-180 (2009)).

"First generation" CARs are typically composed of an extracellular antigen binding domain, for example, a single-chain variable fragment (scFv), fused to a transmembrane domain, which is fused to a cytoplasmic/intracellular domain of the T cell receptor chain. "First generation" CARs typically have the intracellular domain from the CD3ζ-chain, which is the primary transmitter of signals from endogenous T cell receptors (TCRs). "First generation" CARs can provide de novo antigen recognition and cause activation of both $CD4^+$ and $CD8^+$ T cells through their CD3ζ chain signaling domain in a single fusion molecule, independent of HLA-mediated antigen presentation. "Second-generation" CARs comprises a cancer antigen-binding domain fused to an intracellular signaling domain capable of activating immune effector cells such as T cells and a co-stimulatory domain designed to augment immune effector cell, such as T cell, potency and persistence (Sadelain et al., *Cancer Discov.* 3:388-398 (2013)). CAR design can therefore combine antigen recognition with signal transduction, two functions that are physiologically borne by two separate complexes, the TCR heterodimer and the CD3 complex. "Second generation" CARs include an intracellular domain from various co-stimulatory receptors, for example, CD28, 4-1BB, ICOS, OX40, and the like, in the cytoplasmic tail of the CAR to provide additional signals to the cell. "Second generation" CARs provide both co-stimulation, for example, by CD28 or 4-1BB domains, and activation, for example, by a CD3ζ signaling domain. Studies have indicated that "Second Generation" CARs can improve the anti-tumor activity of T cells. "Third generation" CARs provide multiple co-stimulation, for example, by comprising both CD28 and 4-1BB domains, and activation, for example, by comprising a CD3ζ activation domain.

As described above, a CAR also contains a signaling domain that functions in the immune effector cell expressing the CAR. Such a signaling domain can be, for example, derived from CDζ, Fc receptor γ, FcγRIIa, FcRβ (FcεR1b), CD3γ, CD3δ, CD3ε, CD79a, CD79b, DAP10, or DAP12. In general, the signaling domain will induce persistence, trafficking and/or effector functions in the transduced immune effector cells such as T cells (Sharpe et al., *Dis. Model Mech.* 8:337-350 (2015); Finney et al, *J. Immunol.* 161:2791-2797 (1998); Krause et al., *J. Exp. Med.* 188:619-626 (1998)). In the case of CDζ or Fc receptor γ, the signaling domain corresponds to the intracellular domain of the respective polypeptides, or a fragment of the intracellular domain that is sufficient for signaling. Exemplary signaling domains are described below in more detail.

In certain non-limiting embodiments, an intracellular domain of a CAR can further comprise at least one co-stimulatory signaling domain. In some embodiments, an intracellular domain of a CAR can comprise two co-stimulatory signaling domains. Such a co-stimulatory signaling domain can provide increased activation of an immune effector cell. A co-stimulatory signaling domain can be derived from a CD28 polypeptide, a 4-1BB polypeptide, an OX40 polypeptide, an ICOS polypeptide, a DAP10 polypeptide, a 2B4 polypeptide, a CD27 polypeptide, a CD30 polypeptide, a CD40 polypeptide and the like. CARs comprising an intracellular domain that comprises a co-stimulatory signaling region comprising 4-1BB, ICOS or DAP-10 have been described previously (see U.S. Pat. No. 7,446,190, which is incorporated herein by reference, which also describes representative sequences for 4-1BB, ICOS and DAP-10). In some embodiments, the intracellular domain of a CAR can comprise a co-stimulatory signaling region that comprises two co-stimulatory receptors, such as CD28 and 4-1BB (see Sadelain et al., *Cancer Discov.* 3(4):388-398 (2013)), or CD28 and OX40, or other combinations of co-stimulatory ligands, as disclosed herein.

The extracellular domain of a CAR can be fused to a leader or a signal peptide that directs the nascent protein into the endoplasmic reticulum and subsequent translocation to the cell surface. It is understood that, once a polypeptide containing a signal peptide is expressed at the cell surface, the signal peptide has generally been proteolytically removed during processing of the polypeptide in the endoplasmic reticulum and translocation to the cell surface. Thus, a polypeptide such as a CAR is generally expressed at the cell surface as a mature protein lacking the signal peptide, whereas the precursor form of the polypeptide includes the signal peptide. A signal peptide or leader can be essential if a CAR is to be glycosylated and/or anchored in the cell membrane. The signal sequence or leader is a peptide sequence generally present at the N-terminus of newly synthesized proteins that directs their entry into the secretory pathway. The signal peptide is covalently joined to the N-terminus of the extracellular antigen-binding domain of a CAR as a fusion protein. Any suitable signal peptide, as are well known in the art, can be applied to a CAR to provide cell surface expression in an immune cell (see Gierasch *Biochem.* 28:923-930 (1989); von Heijne, *J. Mol. Biol.* 184 (1):99-105 (1985)). Particularly useful signal peptides can be derived from cell surface proteins naturally expressed in the immune cell provided herein, including any of the signal peptides of the polypeptides disclosed herein. Thus, any suitable signal peptide can be utilized to direct a CAR to be expressed at the cell surface of an immune effector cell provided herein.

In certain non-limiting embodiments, a CAR can also comprise a spacer region or sequence that links the domains of the CAR to each other. For example, a spacer can be included between a signal peptide and an antigen binding domain, between the antigen binding domain and the transmembrane domain, between the transmembrane domain and the intracellular domain, and/or between domains within the intracellular domain, for example, between a stimulatory domain and a co-stimulatory domain. The spacer region can be flexible enough to allow interactions of various domains with other polypeptides, for example, to allow the antigen binding domain to have flexibility in orientation in order to facilitate antigen recognition. The spacer region can be, for example, the hinge region from an IgG, the $CH_2CH_3$ (constant) region of an immunoglobulin, and/or portions of CD3 (cluster of differentiation 3) or some other sequence suitable as a spacer.

The transmembrane domain of a CAR generally comprises a hydrophobic alpha helix that spans at least a portion of the membrane. Different transmembrane domains result in different receptor stability. After antigen recognition, receptors cluster and a signal is transmitted to the cell. In an embodiment, the transmembrane domain of a CAR can be derived from another polypeptide that is naturally expressed in the immune effector cell. In one embodiment, a CAR can have a transmembrane domain derived from CD8, CD28, CD3ζ, CD4, 4-1BB, OX40, ICOS, CTLA-4, PD-1, LAG-3, 2B4, BTLA, T-cell receptor (TCR) α chain, TCR β chain, or TCR ζ chain, CD28, CD3 ε, CD45, CD5, CD8, CD9, CD16, CD22, CD33, CD37, CD64, CD80, CD86, CD134, CD137, CD154, or other polypeptides expressed in the immune effector cell. Alternatively, the transmembrane domain can be synthetic, in which case it comprises predominantly hydrophobic residues such as leucine and valine. Optionally, the transmembrane domain can be derived from a polypeptide that is not naturally expressed in the immune effector cell, so long as the transmembrane domain can function in transducing signal from antigen bound to the CAR to the intracellular signaling and/or co-stimulatory domains. In some embodiments, the transmembrane domain can comprise a triplet of phenylalanine, tryptophan and valine at each end. Optionally, a short oligo- or polypeptide linker, preferably between 2 and 10 amino acids in length can form the linkage between the transmembrane domain and the cytoplasmic signaling domain of the CAR. A glycine-serine doublet provides a particularly suitable linker.

CD3ζ. In a non-limiting embodiment, a CAR can comprise a signaling domain derived from a CD3ζ polypeptide, for example, a signaling domain derived from the intracellular domain of CD3ζ, which can activate or stimulate an immune effector cell, for example, a T cell. CD3ζ comprises 3 Immune-receptor-Tyrosine-based-Activation-Motifs (ITAMs), and transmits an activation signal to the cell, for example, a cell of the lymphoid lineage such as a T cell, after antigen is bound. A CD3ζ polypeptide can have an amino acid sequence corresponding to the sequence having Gen-Bank No. NP_932170 (NP_932170.1, GI:37595565; see below), or fragments thereof. In one embodiment, the CD3ζ polypeptide has an amino acid sequence of amino acids 52 to 164 of the CD3ζ polypeptide sequence provided below, or a fragment thereof that is sufficient for signaling activity. An exemplary CAR has an intracellular domain comprising a CD3ζ polypeptide comprising amino acids 52 to 164 of the CD3ζ polypeptide sequence provided below. Another exemplary CAR has an intracellular domain comprising a CD3ζ polypeptide comprising amino acids 52 to 164 of the CD3ζ polypeptide provided below. Still another exemplary CAR has an intracellular domain comprising a CD3ζ polypeptide comprising amino acids 52 to 164 of the CD3ζ polypeptide provided below. See GenBank NP_932170 for reference to domains within CD3ζ, for example, signal peptide, amino acids 1 to 21; extracellular domain, amino acids 22 to 30; transmembrane domain, amino acids 31 to 51; intracellular domain, amino acids 52 to 164.

```
                                      (NP_932170; SEQ ID NO: 173)
  1  MKWKALFTAA ILQAQLPITE AQSFGLLDPK LCYLLDGILF

IYGVILTALF LRVKFSRSAD

61  APAYQQGQNQ LYNELNLGRR EEYDVLDKRR GRDPEMGGKP

QRRKNPQEGL YNELQKDKMA

121  EAYSEIGMKG ERRRGKGHDG LYQGLSTATK DTYDALHMQA

LPPR
```

FcRγ Activating types of IgG receptor FcγRs form multimeric complexes including the Fc receptor common γ chain (FcRγ) that contains an intracellular tyrosine-based activating motif (ITAM), whose activation triggers oxidative bursts, cytokine release, phagocytosis, antibody-dependent cell-mediated cytotoxicity, and degranulation. In one embodiment, a CAR can comprise a transmembrane domain derived from FcRγ. In one embodiment, a CAR can comprise a co-stimulatory domain derived from FcRγ. An FcRγ polypeptide can have an amino acid sequence corresponding to the sequence having NCBI Reference Sequence: NP_004097.1 (GI: 4758344), provided below, or fragments thereof. In one embodiment, a CAR can have a co-stimulatory domain comprising the intracellular domain of FcRγ, or a fragment thereof. In another embodiment, a CAR can have a transmembrane domain of FcRγ, or a fragment thereof. It is understood that an "FcRγ polynucleotide" refers to a polynucleotide encoding an FcRγ polypeptide.

```
                                              (SEQ ID NO: 174)
  1  MIPAVVLLLL LLVEQAAALG EPQLCYILDA ILFLYGIVLT

LLYCRLKIQV RKAAITSYEK

61  SDGVYTGLST RNQETYETLK HEKPPQ
```

DAP10. DAP10, also referred to as hematopoietic cell signal transducer, is a signaling subunit that associates with a large family of receptors in hematopoietic cells. In some embodiments, provided herein are fusion proteins comprising a first domain that activates an APC and a second domain that activates an immune effector cell, wherein the second domain comprises a DAP10 polypeptide, or a functional fragment thereof. In some embodiments, the second domain comprises the cytoplasmic domain of DAP10. In some embodiments, provided herein are fusion proteins comprising a first domain that activates an APC and a second domain that activates an immune effector cell, wherein the second domain comprises an antibody that binds DAP10, or an antigen-binding fragment thereof. In one embodiment, the second domain of fusion proteins provided herein can comprise a co-stimulatory domain derived from DAP10. A DAP10 polypeptide can have an amino acid sequence corresponding to the sequence having GenBank No. NP_055081.1 (GI:15826850), provided below, or fragments thereof. In one embodiment, the second domain of fusion proteins provided herein can comprise a co-stimulatory domain comprising the cytoplasmic domain of DAP10 corresponding to amino acids 70 to 93 (underlined part of the sequence below, SEQ ID NO:29), or a functional fragment thereof. It is understood that sequences of DAP10 that are shorter or longer than a specific delineated domain can be included in a fusion protein, if desired.

(SEQ ID NO: 28)
```
  1 MIHLGHILFL LLLPVAAAQT TPGERSSLPA FYPGTSGSCS GCGSLSLPLL AGLVAADAVA

61 SLLIVGAVFL CARPRRSPAQ EDGKVYINMP GRG
```

DAP12. DAP12 is found in cells of the myeloid lineage, such as macrophages and granulocytes, where it associates, for instance, with the triggering receptor expressed on myeloid cell members (TREM) and MDL1 (myeloid DAP12-associating lectin 1/CLEC5A), both involved in inflammatory responses against pathogens like viruses and bacteria. In the lymphoid lineage, DAP12 is expressed in NK cells and associates with activating receptors such as the C-type lectin receptor NKG2C, the natural cytotoxicity receptor NKp44, and the short-tailed KIR3DS1 and KIR2DS1/2/5, respectively. In particular, NGK2C is the dominant activating NK cell receptor for controlling CMV infection in both humans and mice. It was found that a DAP12-containing CAR generated sufficient activating signals in NK cells upon cross-linking with its Ag. Töpfer et al., *J Immunol* 194:3201-12 (2015). In one embodiment, a CAR can comprise a co-stimulatory domain derived from DAP12. A DAP12 polypeptide can have an amino acid sequence corresponding to the sequence having GenBank No. AAD09437.1 (GI: 2905996), provided below, or fragments thereof. In one embodiment, a CAR can have a signaling domain comprising the intracellular domain of DAP12, or a fragment thereof. In another embodiment, a CAR can have a transmembrane domain of DAP12, or a fragment thereof. It is understood that a "DAP12 polynucleotide" refers to a polynucleotide encoding a DAP12 polypeptide.

(SEQ ID NO: 175)
```
  1 MGGLEPCSRL LLLPLLLAVS GLRPVQAQAQ SDCSCSTVSP GVLAGIVMGD LVLTVLIALA

61 VYFLGRLVPR GRGAAEAATR KQRITETESP YQELQGQRSD VYSDLNTQRP YYK
```

CD28. Cluster of Differentiation 28 (CD28) is a protein expressed on T cells that provides co-stimulatory signals for T cell activation and survival. CD28 is the receptor for CD80 (B7.1) and CD86 (B7.2) proteins. In one embodiment, a CAR can comprise a co-stimulatory signaling domain derived from CD28. For example, as disclosed herein, a CAR can include at least a portion of an intracellular/cytoplasmic domain of CD28, for example an intracellular/cytoplasmic domain that can function as a co-stimulatory signaling domain. A CD28 polypeptide can have an amino acid sequence corresponding to the sequence having GenBank No. P10747 (P10747.1, GI:115973) or NP_006130 (NP_006130.1, GI:5453611), as provided below, or fragments thereof. If desired, CD28 sequences additional to the intracellular domain can be included in a CAR of the invention. For example, a CAR can comprise the transmembrane of a CD28 polypeptide. In one embodiment, a CAR can have an amino acid sequence comprising the intracellular domain of CD28 corresponding to amino acids 180 to 220 of CD28, or a fragment thereof (SEQ ID NO:14). In another embodiment, a CAR can have an amino acid sequence comprising the transmembrane domain of CD28 corresponding to amino acids 153 to 179, or a fragment embodiment, a CAR can comprise a co-stimulatory signaling domain derived from 4-1BB. A 4-1BB polypeptide can have an amino acid sequence corresponding to the sequence having GenBank No. P41273 (P41273.1, GI:728739) or NP_001552 (NP_001552.2, GI:5730095) or fragments thereof. In one embodiment, a CAR can have a co-stimulatory domain comprising the intracellular domain of 4-1BB corresponding to amino acids 214 to 255, or a fragment thereof. In another embodiment, a CAR can have a transmembrane domain of 4-1BB corresponding to amino acids 187 to 213, or a fragment thereof. An exemplary CAR is MBBz, which has an intracellular domain comprising a 4-1BB polypeptide (for example, amino acids 214 to 255 of NP_001552, SEQ ID NO:17). See GenBank NP_001552 for reference to domains within 4-1BB, for example, signal peptide, amino acids 1 to 17; extracellular domain, amino acids 18 to 186; transmembrane domain, amino acids 187 to 213 (SEQ ID NO:18); intracellular domain, amino acids 214 to 255 (SEQ ID NO:17). It is understood that sequences of 4-1BB that are shorter or longer than a specific delineated domain can be included in a CAR, if desired. It is also understood that a "4-1BB polynucleotide" refers to a polynucleotide encoding a 4-1BB polypeptide.

```
                                                       (NP_001552; SEQ ID NO: 16)
  1 MGNSCYNIVA TLLLVLNFER TRSLQDPCSN CPAGTFCDNN RNQICSPCPP NSFSSAGGQR

61 TCDICRQCKG VFRTRKECSS TSNAECDCTP GFHCLGAGCS MCEQDCKQGQ ELTKKGCKDC

121 CFGTFNDQKR GICRPWTNCS LDGKSVLVNG TKERDVVCGP SPADLSPGAS SVTPPAPARE

181 PGHSPQIISF FLALTSTALL FLLFFLTLRF SVVKRGRKKL LYIFKQPFMR PVQTTQEEDG

241 CSCRFPEEEE GGCEL
``` thereof. An exemplary CAR can comprise a co-stimulatory signaling domain corresponding to an intracellular domain of CD28. An exemplary CAR can also comprise a transmembrane domain derived from CD28. Thus, an exemplary CAR can comprise two domains from CD28, a co-stimulatory signaling domain and a transmembrane domain. In one embodiment, a CAR has an amino acid sequence comprising the transmembrane domain and the intracellular domain of CD28 and comprises amino acids 153 to 220 of CD28. In another embodiment, a CAR comprises amino acids 117 to 220 of CD28. Another exemplary CAR having a transmembrane domain and intracellular domain of CD28 is P28z. In one embodiment, a CAR can comprise a transmembrane domain derived from a CD28 polypeptide comprising amino acids 153 to 179 of the CD28 polypeptide provided below (SEQ ID NO:15). See GenBank NP_006130 for reference to domains within CD28, for example, signal peptide, amino acids 1 to 18; extracellular domain, amino acids 19 to 152; transmembrane domain, amino acids 153 to 179; intracellular domain, amino acids 180 to 220. It is understood that sequences of CD28 that are shorter or longer than a specific delineated domain can be included in a CAR, if desired.

OX40. OX40, also referred to as tumor necrosis factor receptor superfamily member 4 precursor or CD134, is a member of the TNFR-superfamily of receptors. In one embodiment, a CAR can comprise a co-stimulatory signaling domain derived from OX40. An OX40 polypeptide can have an amino acid sequence corresponding to the sequence having GenBank No. P43489 (P43489.1, GI:1171933) or NP_003318 (NP_003318.1, GI:4507579), provided below, or fragments thereof. In one embodiment, a CAR can have a co-stimulatory domain comprising the intracellular domain of OX40 corresponding to amino acids 236 to 277 (SEQ ID NO:26), or a fragment thereof. In another embodiment, a CAR can have an amino acid sequence comprising the transmembrane domain of OX40 corresponding to amino acids 215 to 235 of OX40 (SEQ ID NO:27), or a fragment thereof. See GenBank NP_003318 for reference to domains within OX40, for example, signal peptide, amino acids 1 to 28; extracellular domain, amino acids 29 to 214; transmembrane domain, amino acids 215 to 235 (SEQ ID NO:27); intracellular domain, amino acids 236 to 277 (SEQ ID NO:26). It is understood that sequences of OX40 that are shorter or longer than a specific delineated domain can be

```
                                                       (NP_006130; SEQ ID NO: 13)
  1 MLRLLLALNL FPSIQVTGNK ILVKQSPMLV AYDNAVNLSC KYSYNLFSRE FRASLHKGLD

61 SAVEVCVVYG NYSQQLQVYS KTGFNCDGKL GNESVTFYLQ NLYVNQTDIY FCKIEVMYPP

121 PYLDNEKSNG TIIHVKGKHL CPSPLFPGPS KPFWVLVVVG GVLACYSLLV TVAFIIFWVR

181 SKRSRLLHSD YMNMTPRRPG PTRKHYQPYA PPRDFAAYRS
```

4-1BB. 4-1BB, also referred to as tumor necrosis factor receptor superfamily member 9, can act as a tumor necrosis factor (TNF) ligand and have stimulatory activity. In one included in a CAR, if desired. It is also understood that an "OX40 polynucleotide" refers to a polynucleotide encoding an OX40 polypeptide.

```
                                                (NP_003318; SEQ ID NO: 25)
  1 MCVGARRLGR GPCAALLLLG LGLSTVTGLH CVGDTYPSND RCCHECRPGN GMVSRCSRSQ

61 NTVCRPCGPG FYNDVVSSKP CKPCTWCNLR SGSERKQLCT ATQDTVCRCR AGTQPLDSYK

121 PGVDCAPCPP GHFSPGDNQA CKPWTNCTLA GKHTLQPASN SSDAICEDRD PPATQPQETQ

181 GPPARPITVQ PTEAWPRTSQ GPSTRPVEVP GGRAVAAILG LGLVLGLLGP LAILLALYLL

241 RRDQRLPPDA HKPPGGGSFR TPIQEEQADA HSTLAKI
```

ICOS. Inducible T-cell co-stimulator precursor (ICOS), also referred to as CD278, is a CD28-superfamily co-stimulatory receptor that is expressed on activated T cells. In one embodiment, a CAR can comprise a co-stimulatory signaling domain derived from ICOS. An ICOS polypeptide can have an amino acid sequence corresponding to the sequence having GenBank No. NP_036224 (NP_036224.1, GI:15029518), provided below, or fragments thereof. In one embodiment, a CAR can have a co-stimulatory domain comprising the intracellular domain of ICOS corresponding to amino acids 162 to 199 of ICOS (SEQ ID NO:20). In another embodiment, a CAR can have an amino acid sequence comprising the transmembrane domain of ICOS corresponding to amino acids 141 to 161 of ICOS (SEQ ID NO:21), or a fragment thereof. See GenBank NP_036224 for reference to domains within ICOS, for example, signal peptide, amino acids 1 to 20; extracellular domain, amino acids 21 to 140; transmembrane domain, amino acids 141 to 161 (SEQ ID NO:21); intracellular domain, amino acids 162 to 199 (SEQ ID NO:20). It is understood that sequences of ICOS that are shorter or longer than a specific delineated domain can be included in a CAR, if desired. It is also understood that an "ICOS polynucleotide" refers to a polynucleotide encoding an ICOS polypeptide.

(SEQ ID NO:29), or a fragment thereof. In another embodiment, a CAR can have a transmembrane domain of DAP10 corresponding to amino acids 49 to 69 (SEQ ID NO:30), or a fragment thereof. See GenBank NP_055081.1 for reference to domains within DAP10, for example, signal peptide, amino acids 1 to 19; extracellular domain, amino acids 20 to 48; transmembrane domain, amino acids 49 to 69 (SEQ ID NO:30); intracellular domain, amino acids 70 to 93 (SEQ ID NO:29). It is understood that sequences of DAP10 that are shorter or longer than a specific delineated domain can be included in a CAR, if desired. It is also understood that a "DAP10 polynucleotide" refers to a polynucleotide encoding a DAP10 polypeptide.

```
                                                           (SEQ ID NO: 28)
  1 MIHLGHILFL LLLPVAAAQT TPGERSSLPA FYPGTSGSCS GCGSLSLPLL AGLVAADAVA

61 SLLIVGAVFL CARPRRSPAQ EDGKVYINMP GRG
```

CD27: CD27 (TNFRSF7) is a transmembrane receptor expressed on subsets of human CD8+ and CD4+ T-cells, NKT cells, NK cell subsets and hematopoietic progenitors and induced in FOXP3+CD4 T-cells and B cell subsets. Previously studies have found that CD27 can either actively provide costimulatory signals that improve human T-cell survival and anti-tumor activity in vivo. (See Song and Powell; *Oncoimmunology* 1, no. 4 (2012): 547-549). In one embodiment, a CAR can comprise a co-stimulatory domain derived from CD27. In one embodiment, a CAR can have a

```
                                                (NP_036224; SEQ ID NO: 19)
  1 MKSGLWYFFL FCLRIKVLTG EINGSANYEM FIFHNGGVQI LCKYPDIVQQ FKMQLLKGGQ

61 ILCDLTKTKG SGNTVSIKSL KFCHSQLSNN SVSFFLYNLD HSHANYYFCN LSIFDPPPFK

121 VTLTGGYLHI YESQLCCQLK FWLPIGCAAF VVVCILGCIL ICWLTKKKYS SSVHDPNGEY

181 MFMRAVNTAK KSRLTDVTL
```

DAP10. DAP10, also referred to as hematopoietic cell signal transducer, is a signaling subunit that associates with a large family of receptors in hematopoietic cells. In one embodiment, a CAR can comprise a co-stimulatory domain derived from DAP10. A DAP10 polypeptide can have an amino acid sequence corresponding to the sequence having GenBank No. NP_055081.1 (GI:15826850), provided below, or fragments thereof. In one embodiment, a CAR can have a co-stimulatory domain comprising the intracellular domain of DAP10 corresponding to amino acids 70 to 93 co-stimulatory domain comprising the intracellular domain of CD27 corresponding to amino acids 213 to 260 (SEQ ID NO:23), or a fragment thereof. In another embodiment, a CAR can have a transmembrane domain of CD27 corresponding to amino acids 192 to 212 (SEQ ID NO:24), or a fragment thereof. A CD27 polypeptide can have an amino acid sequence corresponding to the sequence having UniProtKB/Swiss-Prot No.: P26842.2 (GI: 269849546), provided below, or fragments thereof.

```
                                                           (SEQ ID NO: 22)
  1 MARPHPWWLC VLGTLVGLSA TPAPKSCPER HYWAQGKLCC QMCEPGTFLV KDCDQHRKAA

61 QCDPCIPGVS FSPDHHTRPH CESCRHCNSG LLVRNCTITA NAECACRNGW QCRDKECTEC
```

```
121 DPLPNPSLTA RSSQALSPHP QPTHLPYVSE MLEARTAGHM QTLADFRQLP ARTLSTHWPP

181 QRSLCSSDFI RILVIFSGMF LVFTLAGALF LHQRRKYRSN KGESPVEPAE PCHYSCPREE

241 EGSTIPIQED YRKPEPACSP
```

In one embodiment, a CAR can have a co-stimulatory domain comprising the intracellular domain of CD27 or a fragment thereof. In another embodiment, a CAR can have a transmembrane domain of CD27 or a fragment thereof. It is understood that sequences of CD27 that are shorter or longer than a specific delineated domain can be included in a CAR, if desired. It is also understood that a "CD27 polynucleotide" refers to a polynucleotide encoding an CD27 polypeptide.

CD30: CD30 and its ligand (CD30L) are members of the tumor necrosis factor receptor (TNFR) and tumor necrosis factor (TNF) superfamilies, respectively. CD30, in many respects, behaves similarly to Ox40 and enhances proliferation and cytokine production induced by TCR stimulation. (Goronzy and Weyand, *Arthritis research & therapy* 10, no. S1 (2008): S3.) In one embodiment, a CAR can comprise a co-stimulatory domain derived from CD30. In one embodiment, a CAR can comprise a co-stimulatory domain derived from CD30. In one embodiment, a CAR can have a co-stimulatory domain comprising the intracellular domain of CD30 corresponding to amino acids 407 to 595 (SEQ ID NO:32), or a fragment thereof. In another embodiment, a CAR can have a transmembrane domain of CD30 corresponding to amino acids 386 to 406 (SEQ ID NO:33), or a fragment thereof. A CD30 polypeptide can have an amino acid sequence corresponding to the sequence having GenBank No.: AAA51947.1 (GI: 180096), provided below, or fragments thereof.

CD8. Cluster of differentiation 8 (CD8) is a transmembrane glycoprotein that serves as a co-receptor for the T cell receptor (TCR). CD8 binds to a major histocompatibility complex (MHC) molecule and is specific for the class I MHC protein. In one embodiment, a CAR can comprise a transmembrane domain derived from CD8. A CD8 polypeptide can have an amino acid sequence corresponding to the sequence having GenBank No. NP_001139345.1 (GI: 225007536), as provided below, or fragments thereof. In one embodiment, a CAR can have an amino acid sequence comprising the transmembrane domain of CD8 corresponding to amino acids 183 to 203, or fragments thereof. In one embodiment, an exemplary CAR has a transmembrane domain derived from a CD8 polypeptide. In one non-limiting embodiment, a CAR can comprise a transmembrane domain derived from a CD8 polypeptide comprising amino acids 183 to 203. In addition, a CAR can comprise a hinge domain comprising amino acids 137-182 of the CD8 polypeptide provided below. In another embodiment, a CAR can comprise amino acids 137-203 of the CD8 polypeptide provided below. In yet another embodiment, a CAR can comprise amino acids 137 to 209 of the CD8 polypeptide provided below. See GenBank NP_001139345.1 for reference to domains within CD8, for example, signal peptide, amino acids 1 to 21; extracellular domain, amino acids 22 to 182; transmembrane domain amino acids, 183 to 203; intra-

```
                                                          (SEQ ID NO: 31)
  1 MRVLLAALGL LFLGALRAFP QDRPFEDTCH GNPSHYYDKA VRRCCYRCPM GLFPTQQCPQ

61 RPTDCRKQCE PDYYLDEADR CTACVTCSRD DLVEKTPCAW NSSRVCECRP GMFCSTSAVN

121 SCARCFFHSV CPAGMIVKFP GTAQKNTVCE PASPGVSPAC ASPENCKEPS SGTIPQAKPT

181 PVSPATSSAS TMPVRGGTRL AQEAASKLTR APDSPSSVGR PSSDPGLSPT QPCPEGSGDC

241 RKQCEPDYYL DEAGRCTACV SCSRDDLVEK TPCAWNSSRT CECRPGMICA TSATNSCARC

301 VPYPICAAET VTKPQDMAEK DTTFEAPPLG TQPDCNPTPE NGEAPASTSP TQSLLVDSQA

361 SKTLPIPTSA PVALSSTGKP VLDAGPVLFW VILVLVVVG SSAFLLCHRR ACRKRIRQKL

421 HLCYPVQTSQ PKLELVDSRP RRSSTQLRSG ASVTEPVAEE RGLMSQPLME TCHSVGAAYL

481 ESLPLQDASP AGGPSSPRDL PEPRVSTEHT NNKIEKIYIM KADTVIVGTV KAELPEGRGL

541 AGPAEPELEE ELEADHTPHY PEQETEPPLG SCSDVMLSVE EEGKEDPLPT AASGK
```

In one embodiment, a CAR can have a co-stimulatory domain comprising the intracellular domain of CD30 or a fragment thereof. In another embodiment, a CAR can have a transmembrane domain of CD30 or a fragment thereof. It is understood that sequences of CD30 that are shorter or longer than a specific delineated domain can be included in a CAR, if desired. It is also understood that a "CD30 polynucleotide" refers to a polynucleotide encoding an CD30 polypeptide.

cellular domain, amino acids 204 to 235. It is understood that additional sequence of CD8 beyond the transmembrane domain of amino acids 183 to 203 can be included in a CAR, if desired. It is further understood that sequences of CD8 that are shorter or longer than a specific delineated domain can be included in a CAR, if desired. It also is understood that a "CD8 polynucleotide" refers to a polynucleotide encoding a CD8 polypeptide.

```
                                                   (NP_001139345.1; SEQ ID NO: 176)
  1 MALPVTALLL PLALLLHAAR PSQFRVSPLD RTWNLGETVE LKCQVLLSNP TSGCSWLFQP

61 RGAAASPTFL LYLSQNKPKA AEGLDTQRFS GKRLGDTFVL TLSDFRRENE GYYFCSALSN

121 SIMYFSHFVP VFLPAKPTTT PAPRPPTPAP TIASQPLSLR PEACRPAAGG AVHTRGLDFA

181 CDIYIWAPLA GTCGVLLLSL VITLYCNHRN RRRVCKCPRP WKSGDKPSL SARYV
```

CD4. Cluster of differentiation 4 (CD4), also referred to as T-cell surface glycoprotein CD4, is a glycoprotein found on the surface of immune cells such as T helper cells, monocytes, macrophages, and dendritic cells. In one embodiment, a CAR can comprise a transmembrane domain derived from CD4. CD4 exists in various isoforms. It is understood that any isoform can be selected to achieve a desired function. Exemplary isoforms include isoform 1 (NP_000607.1, GI:10835167), isoform 2 (NP_001181943.1, GI:303522479), isoform 3 (NP_001181944.1, GI:303522485; or NP_001181945.1, GI:303522491; or NP_001181946.1, GI:303522569), and the like. One exemplary isoform sequence, isoform 1, is provided below. In one embodiment, a CAR can have an amino acid sequence comprising the transmembrane domain of CD4 corresponding to amino acids 397 to 418, or fragments thereof. See GenBank NP_000607.1 for reference to domains within CD4, for example, signal peptide, amino acids 1 to 25; extracellular domain, amino acids 26 to 396; transmembrane domain amino acids, 397 to 418; intracellular domain, amino acids 419 to 458. It is understood that additional sequence of CD4 beyond the transmembrane domain of amino acids 397 to 418 can be included in a CAR, if desired. It is further understood that sequences of CD4 that are shorter or longer than a specific delineated domain can be included in a CAR, if desired. It also is understood that a "CD4 polynucleotide" refers to a polynucleotide encoding a CD4 polypeptide.

of NK cells. For example, DNAX-activation protein 12 (DAP12) is known to activate signaling for NK cells.

CARs provided herein can include a target-binding domain as disclosed above. In some embodiments, fusion proteins disclosed herein can be co-expressed with a CAR targeting a tumor antigen selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin in a cell. In some embodiments, fusion proteins disclosed herein is conjugated to a CAR targeting a tumor antigen selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin. In some embodiments, genetically engineered immune effector cells provided herein further comprise a polynucleotide encoding a CAR targeting a tumor antigen selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin. In some embodiments, genetically engineered immune effector cells provided herein further recombinantly express a CAR targeting a tumor antigen selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin.

```
                                                   (NP_000607.1; SEQ ID NO: 177)
  1 MNRGVPFRHL LLVLQLALLP AATQGKKVVL GKKGDTVELT CTASQKKSIQ FHWKNSNQIK

61 ILGNQGSFLT KGPSKLNDRA DSRRSLWDQG NFPLIIKNLK IEDSDTYICE VEDQKEEVQL

121 LVFGLTANSD THLLQGQSLT LTLESPPGSS PSVQCRSPRG KNIQGGKTLS VSQLELQDSG

181 TWTCTVLQNQ KKVEFKIDIV VLAFQKASSI VYKKEGEQVE FSFPLAFTVE KLTGSGELWW

241 QAERASSSKS WITFDLKNKE VSVKRVTQDP KLQMGKKLPL HLTLPQALPQ YAGSGNLTLA

301 LEAKTGKLHQ EVNLVVMRAT QLQKNLTCEV WGPTSPKLML SLKLENKEAK VSKREKAVWV

361 LNPEAGMWQC LLSDSGQVLL ESNIKVLPTW STPVQPMALI VLGGVAGLLL FIGLGIFFCV

421 RCRHRRRQAE RMSQIKRLLS EKKTCQCPHR FQKTCSPI
```

In addition to T cells, CAR can be engineered into other types of immune effector cells, such as NK cells, NKT cells, macrophages, or granulocytes. In some embodiments, the engineered cell is a NK cell. CARs provided herein can retarget NK cells to tumor surface antigens (see e.g., Hu et al. *Acta Pharmacol Sin* 39, 167-176 (2018)). CAR-NK cells can use the first generation of CAR constructs that contain CD3 as an intracellular signaling domain or the second generation of CAR constructs that express a second signaling domain (e.g., CD28, 4-1BB) in conjunction with CD3ζ. In general, the second generation of CARs in NK cells is more active than first-generation CARs. In some embodiments, CAR constructs are based on the activating features In some embodiments, the CAR targets Her2. In some embodiments, the CAR targeting Her2 has the amino acid sequence of SEQ ID NO:107, which can be encoded by, for example, the nucleotide sequence of SEQ ID NO:146. In some embodiments, the CAR targets CD19. In some embodiments, the CAR targeting CD19 has the amino acid sequence of SEQ ID NO:108, which can be encoded by, for example, the nucleotide sequence of SEQ ID NO:147. In some embodiments, the CAR targets Mesothelin. In some embodiments, the CAR targeting mesothelin has the amino acid sequence of SEQ ID NO:109, which can be encoded by, for example, the nucleotide sequence of SEQ ID NO:148. In some embodiments, the CAR targets PSMA. In some embodiments, the CAR targeting PSMA has the amino acid sequence of SEQ ID NO:110, which can be encoded by, for example, the nucleotide sequence of SEQ ID NO:149. In some embodiments, the CAR targets c-Met. In some embodiments, the CAR targeting c-Met has the amino acid sequence of SEQ ID NO:111, which can be encoded by, for example, the nucleotide sequence of SEQ ID NO:150. In some embodiments, the CAR targets BCMA. In some embodiments, the CAR targeting BCMA has the amino acid sequence of SEQ ID NO:112, which can be encoded by, for example, the nucleotide sequence of SEQ ID NO:151. In some embodiments, the CAR targeting BCMA has the amino acid sequence of SEQ ID NO:113, which can be encoded by, for example, the nucleotide sequence of SEQ ID NO:152. In some embodiments, the CAR targeting BCMA has the amino acid sequence of SEQ ID NO:114, which can be encoded by, for example, the nucleotide sequence of SEQ ID NO:153. In some embodiments, the CAR targets GPC3. In some embodiments, the CAR targeting GPC3 has the amino acid sequence of SEQ ID NO:115, which can be encoded by, for example, the nucleotide sequence of SEQ ID NO:154. In some embodiments, the CAR targets IL13ra2. In some embodiments, the CAR targeting IL13ra2 has the amino acid sequence of SEQ ID NO:116. In some embodiments, the CAR targets EGFR. In some embodiments, the CAR targeting EGFR has the amino acid sequence of SEQ ID NO:117, which can be encoded by, for example, the nucleotide sequence of SEQ ID NO:155. In some embodiments, the CAR targets CD123. In some embodiments, the CAR targeting CD123 has the amino acid sequence of SEQ ID NO:118, which can be encoded by, for example, the nucleotide sequence of SEQ ID NO:157. In some embodiments, the CAR targets CD7. In some embodiments, the CAR targeting CD7 has the amino acid sequence of SEQ ID NO:119, which can be encoded by, for example, the nucleotide sequence of SEQ ID NO:159. In some embodiments, the CAR targets GD2. In some embodiments, the CAR targeting GD2 has the amino acid sequence of SEQ ID NO:120, which can be encoded by, for example, the nucleotide sequence of SEQ ID NO:158. In some embodiments, the CAR targets PSCA. In some embodiments, the CAR targeting PSCA has the amino acid sequence of SEQ ID NO:121, which can be encoded by, for example, the nucleotide sequence of SEQ ID NO:156. In some embodiments, the CAR targets CD70. In some embodiments, the CAR targeting CD70 has the amino acid sequence of SEQ ID NO:203.

In some embodiments, the CAR provided herein include a target-binding domain that binds a viral antigen. In some embodiments, the viral antigen is EBV. In some embodiments, the viral antigen is HPV. In some embodiments, the viral antigen is HIV.

| CAR | Amino Acid Sequences |
|---|---|
| 4D5.BBZ (Her2 CAR) | MDFQVQIFSFLLISASVIMSRGDIQMTQSPSSLSASVGDRVTITCRASQDVNTAVAWY QQKPGKAPKLLIYSASFLYSGVPSRFSGSRSGTDFTLTISSLQPEDFATYYCQQHYTTP PTFGQGTKVEIKRTGSTSGSGKPGSGEGSEVQLVESGGGLVQPGGSLRLSCAASGFNI KDTYIHWVRQAPGKGLEWVARIYPTNGYTRYADSVKGRFTISADTSKNTAYLQMNS LRAEDTAVYYCSRWGGDGFYAMDVWGQGTLVTVSSTTTPAPRPPTPAPTIASQPLSL RPEACRPAAGGAVHTRGLDFACDIYIWAPLAGTCGVLLLSLVITLYCKRGRKKLLYIF KQPFMRPVQTTQEEDGCSCRFPEEEEGGCELRVKFSRSADAPAYKQGQNQLYNELNL GRREEYDVLDKRRGRDPEMGGKPRRKNPQEGLYNELQKDKMAEAYSEIGMKGERR RGKGHDGLYQGLSTATKDTYDALHMQALPPR (SEQ ID NO: 107) |
| FMC63.BBZ (CD19 CAR) | MALPVTALLLPLALLLHAARPDIQMTQTTSSLSASLGDRVTISCRASQDISKYLNWYQ QKPDGTVKLLIYHTSRLHSGVPSRFSGSGSGTDYSLTISNLEQEDIATYFCQQGNTLPY TFGGGTKLEITGGGGSGGGGSGGGGSEVKLQESGPGLVAPSQSLSVTCTVSGVSLPDY GVSWIRQPPRKGLEWLGVIWGSETTYYNSALKSRLTIIKDNSKSQVFLKMNSLQTDD TAIYYCAKHYYYGGSYAMDYWGQGTSVTVSSTTTPAPRPPTPAPTIASQPLSLRPEAC RPAAGGAVHTRGLDFACDIYIWAPLAGTCGVLLLSLVITLYCKRGRKKLLYIFKQPFM RPVQTTQEEDGCSCRFPEEEEGGCELRVKFSRSADAPAYKQGQNQLYNELNLGRREE YDVLDKRRGRDPEMGGKPRRKNPQEGLYNELQKDKMAEAYSEIGMKGERRRGKGH DGLYQGLSTATKDTYDALHMQALPPR (SEQ ID NO: 108) |
| ss1.BBZ (Mesothelin CAR) | MALPVTALLLPLALLLHAARPGSQVQLQQSGPELEKPGASVKISCKASGYSFTGYTM NWVKQSHGKSLEWIGLITPYNGASSYNQKFRGKATLTVDKSSSTAYMDLLSLTSEDS AVYFCARGGYDGRGFDYWGQGTTVTVSSGGGGSGGGGSSGGGSDIELTQSPAIMSA SPGEKVTMTCSASSSVSYMHWYQQKSGTSPKRWIYDTSKLASGVPGRFSGSGSGNSY SLTISSVEAEDDATYYCQQWSKHPLTYGAGTKLEIKASTTTPAPRPPTPAPTIASQPLS LRPEACRPAAGGAVHTRGLDFACDIYIWAPLAGTCGVLLLSLVITLYCKRGRKKLLYI FKQPFMRPVQTTQEEDGCSCRFPEEEEGGCELRVKFSRSADAPAYKQGQNQLYNELN LGRREEYDVLDKRRGRDPEMGGKPRRKNPQEGLYNELQKDKMAEAYSEIGMKGER RRGKGHDGLYQGLSTATKDTYDALHMQALPPR (SEQ ID NO: 109) |
| J591.BBZ (PSMA CAR) | MTQSHKFMSTSVGDRVSIICKASQDVGTAVDWYQQKPGQSPKLLIYWASTRHTGVP DRFTGSGSGTDFTLTITNVQSEDLADYFCQQYNSYPLTFGAGTMLDLKGGGGSGGGG SSGGGSEVQLQQSGPELVKPGTSVRISCKTSGYTFTEYTIHWVKQSHGKSLEWIGNIN PNNGGTTYNQKFEDKATLTVDKSSSTAYMELRSLTSEDSAVYYCAAGWNFDYWGQ GTTLTVSSASSGTTTPAPRPPTPAPTIASQPLSLRPEACRPAAGGAVHTRGLDFACDIYI WAPLAGTCGVLLLSLVITLYCKRGRKKLLYIFKQPFMRPVQTTQEEDGCSCRFPEEEE GGCELRVKFSRSADAPAYKQGQNQLYNELNLGRREEYDVLDKRRGRDPEMGGKPR RKNPQEGLYNELQKDKMAEAYSEIGMKGERRRGKGHDGLYQGLSTATKDTYDALH MQALPPR (SEQ ID NO: 110) |
| c-Met CAR | MALPVTALLLPLALLLHAARPGSDIQMTQSPSSVSASVGDRVTITCRASQGINTWLA WYQQKPGKAPKLLIYAASSLKSGVPSRFSGSGSGADFTLTISSLQPEDFATYYCQQAN SFPLTFGGGTKVEIKGSTSGSGKPGSGEGSTKGQVQLVQSGAEVKKPGASVKVSCEAS GYTFTSYGFSWVRQAPGQGLEWMGWISASNGNTYYAQKLQGRVTMTTDTSTSSAY MELRSLRSDDTAVYYCARVYADYADYWGQGTLVTVASTTTPAPRPPTPAPTIASQPL SLRPEACRPAAGGAVHTRGLDFACDFWVLVVVGGVLACYSLLVTVAFIIFWVRSKRS |

-continued

| CAR | Amino Acid Sequences |
|---|---|
| | RLLHSDYMNMTPRRPGPTRKHYQPYAPPRDFAAYRSKRGRKKLLYIFKQPFMRPVQT<br>TQEEDGCSCRFPEEEEGGCELRVKFSRSADAPAYKQGQNQLYNELNLGRREEYDVLD<br>KRRGRDPEMGGKPRRKNPQEGLYNELQKDKMAEAYSEIGMKGERRRGKHDGLYQ<br>GLSTATKDTYDALHMQALPPR (SEQ ID NO: 111) |
| BCMA CAR | MALPVTALLLPLALLLHAARPEVQLVESGGGLVQPGGSLRLSCAVSGFALSNHGMS<br>WVRRAPGKGLEWVSGIVYSGSTYYAASVKGRFTISRDNSRNTLYLQMNSLRPEDTAI<br>YYCSAHGGESDVWGQGTTVTVSSASGGGGSGGRASGGGGSDIQLTQSPSSLSASVGD<br>RVTITCRASQSISSYLNWYQQKPGKAPKLLIYAASSLQSGVPSRFSGSGSGTDFTLTISS<br>LQPEDFATYYCQQSYSTPYTFGQGTKVEIKTTTPAPRPPTPAPTIASQPLSLRPEACRPA<br>AGGAVHTRGLDFACDIYIWAPLAGTCGVLLLSLVITLYCKRGRKKLLYIFKQPFMRPV<br>QTTQEEDGCSCRFPEEEEGGCELRVKFSRSADAPAYKQGQNQLYNELNLGRREEYDV<br>LDKRRGRDPEMGGKPRRKNPQEGLYNELQKDKMAEAYSEIGMKGERRRGKHDGL<br>YQGLSTATKDTYDALHMQALPPR (SEQ ID NO: 112) |
| FHVH33.BBZ<br>(BCMA<br>CAR) | MALPVTALLLPLALLLHAARPEVQLLESGGGLVQPGGSLRLSCAASGFTFSSYAMSW<br>VRQAPGKGLEWVSSISGSGDYIYYADSVKGRFTISRDISKNTLYLQMNSLRAEDTAVY<br>YCAKEGTGANSSLADYRGQGTLVTVSSTTTPAPRPPTPAPTIASQPLSLRPEACRPAAG<br>GAVHTRGLDFACDIYIWAPLAGTCGVLLLSLVITLYCRGRKKLLYIFKQPFMRPVQTT<br>QEEDGCSCRFPEEEEGGCELRVKFSRSADAPAYKQGQNQLYNELNLGRREEYDVLD<br>KRRGRDPEMGGKPRRKNPQEGLYNELQKDKMAEAYSEIGMKGERRRGKHDGLYQ<br>GLSTATKDTYDALHMQALPPR (SEQ ID NO: 113) |
| BCMA338.BBZ<br>(BCMA<br>CAR) | MALPVTALLLPLALLLHAARPQVKLEESGGGLVQAGRSLRLSCAASEHTFSSHVMG<br>WFRQAPGKERESVAVIGWRDISTSYADSVKGRFTISRDNAKKTLYLQMNSLKPEDTA<br>VYYCAARRIDAADFDSWGQGTQVTVSSGGGGSEVQLVESGGGLVQAGGSLRLSCAA<br>SGRTFTMGWFRQAPGKEREFVAAISLSPTLAYYAESVKGRFTISRDNAKNTVVLQMN<br>SLKPEDTALYYCAADRKSVMSIRPDYWGQGTQVTVSSTSTTTPAPRPPTPAPTIASQP<br>LSLRPEACRPAAGGAVHTRGLDFACDIYIWAPLAGTCGVLLLSLVITLYCKRGRKKLL<br>YIFKQPFMRPVQTTQEEDGCSCRFPEEEEGGCELRVKFSRSADAPAYQGGQNQLYNE<br>LNLGRREEYDVLDKRRGRDPEMGGKPRRKNPQEGLYNELQKDKMAEAYSEIGMKG<br>ERRRGKHDGLYQGLSTATKDTYDALHMQALPPR (SEQ ID NO: 114) |
| G33.BBZ<br>(GPC3 CAR) | MALPVTALLLPLALLLHAARPQVQLQQSGAELVRPGASVKLSCKASGYTFTDYEMH<br>WVKQTPVHGLKWIGALDPKTGDTAYSQKFKGKATLTADKSSSTAYMELRSLTSEDS<br>AVYYCTRFYSYTYWGQGTLVTVSAGGGGSGGGGSGGGGSDVVMTQTPLSLPVSLG<br>DQASISCRSSQSLVHSNGNTYLHWYLQKPGQSPKLLIYKVSNRFSGVPDRFSGSGSGT<br>DFTLKISRVEAEDLGVYFCSQNTHVPPTFGSGTKLEIKTTTPAPRPPTPAPTIASQPLSL<br>RPEACRPAAGGAVHTRGLDFACDIYIWAPLAGTCGVLLLSLVITLYCKRGRKKLLYIF<br>KQPFMRPVQTTQEEDGCSCRFPEEEEGGCELRVKFSRSADAPAYKQGQNQLYNELNL<br>GRREEYDVLDKRRGRDPEMGGKPRRKNPQEGLYNELQKDKMAEAYSEIGMKGERR<br>RGKGHDGLYQGLSTATKDTYDALHMQALPPR (SEQ ID NO: 115) |
| IL13(EQ).BBZ<br>(IL13ra2<br>CAR) | MLLLVTSLLLCELPHPAFLLIPGPVPPSTALRYLIEELVNITQNQKAPLCNGSMVWSIN<br>LTAGMYCAALESLINVSGCSAIEKTQRMLSGFCPHKVSAGQFSSLHVRDTKIEVAQFV<br>KDLLLHLKKLFREGRFNESKYGPPCPPCPAPEFEGGPSVFLFPPKPKDTLMISRTPEVT<br>CVVVDVSQEDPEVQFNWYVDGVEVHNAKTKPREEQFQSTYRVVSVLTVLHQDWLN<br>GKEYKCKVSNKGLPSSIEKTISKAKGQPREPQVYTLPPSQEEMTKNQVSLTCLVKGFY<br>PSDIAVEWESNGQPENNYKTTPPVLDSDGSFFLYSRLTVDKSRWQEGNVFSCSVMHE<br>ALHNHYTQKSLSLSLGKMALIVLGGVAGLLLFIGLGIFFKRGRKKLLYIFKQPFMRPV<br>QTTQEEDGCSCRFPEEEEGGCELGGGRVKFSRSADAPAYQQGQNQLYNELNLGRREE<br>YDVLDKRRGRDPEMGGKPRRKNPQEGLYNELQKDKMAEAYSEIGMKGERRRGKGH<br>DGLYQGLSTATKDTYDALHMQALPPRLEGGGEGRGSLLTCGDVEENPGPRMPPPRLL<br>FFLLFLTPMEVRPEEPLVVKVEEGDNAVLQCLKGTSDGPTQQLTWSRESPLKPFLKLS<br>LGLPGLGIHMRPLAIWLFIFNVSQMGGFYLCQPGPPSEKAWQPGWTVNVEGSGELF<br>RWNVSDLGGLGCGLKNRSSEGPSSPSGKLMSPKLYVWAKDRPEIWEGEPPCVPPRDS<br>LNQSLSQDLTMAPGSTLWLSCGVPPDSVSRGPLSWTHVHPKGPKSLLSLELKDDRPA<br>RDMWVMETGLLLPRATAQDAGKYYCHRGNLTMSFHLEITARPVLWHWLLRTGGW<br>KVSAVTLAYLIFCLCSLVGILHLQRALVLRRKR (SEQ ID NO: 116) |
| C10.BBZ<br>(EGFR CAR) | MGWSCIILFLVATATGVHSDYKDDDDKEVQLVQSGAEVKKPGSSVKVSCKASGGTF<br>SSYAISWVRQAPGQGLEWMGGIIPIFGTANYAQKFQGRVTITADESTSTAYMELSSLR<br>SEDTAVYYCAREEGPYCSSTSCYGAFDIWGQGTLVTVSSGGGGSGGGGSGGGGSQS<br>VLTQDPAVSVALGQTVKITCQGDSLRSYFASWYQQKPGQAPTLVMYARNDRPAGVP<br>DRFSGSKSGTSASLAISGLQSEDEADYYCAAWDDSLNGYLFGAGTKLTVLGRVTVSS<br>AEPKSCDKTHTCPPCPGSIYIWAPLAGTCGVLLLSLVITLYCKRGRKKLLYIFKQPFMR<br>PVQTTQEEDGCSCRFPEEEEGGCELRVKFSRSADAPAYQQGQNQLYNELNLGRREEY<br>DVLDKRRGRDPEMGGKPRRKNPQEGLYNELQKDKMAEAYSEIGMKGERRRGKHD<br>GLYQGLSTATKDTYDALHMQALPPR (SEQ ID NO: 117) |
| 7G3L.BBZ<br>(CD123<br>CAR) | MTQSPDSLAVSLGERATINCKSSQSLLNSGNQKNYLTWYLQKPGQPPKLLIYWASTR<br>ESGVPDRFSGSGSGTDFTLTISSLQAEDVAVYYCQNDYSYPYTFGQGTKLEIKRTTTP<br>APRPPTPAPTIASQPLSLRPEACRPAAGGAVHTRGLDFACDIYIWAPLAGTCGVLLLSL<br>VITLYCRGRKKLLYIFKQPFMRPVQTTQEEDGCSCRFPEEEEGGCELRVKFSRSADAP<br>AYKQGQNQLYNELNLGRREEYDVLDKRRGRDPEMGGKPRRKNPQEGLYNELQKDK<br>MAEAYSEIGMKGERRRGKHDGLYQGLSTATKDTYDALHMQALPPR (SEQ ID<br>NO: 118) |

-continued

| CAR | Amino Acid Sequences |
|---|---|
| 3A1e.BBZ (CD7 CAR) | MLEVKQTLNFDLLKLAGDVESNPGPMALPVTALLLPLALLLHAARPQVKLQESGGG<br>LVKPGGSLKLSCAASGFTFSSYAMSWVRQTPEKRLEWVATISSGGSYTYYPDSVKGR<br>FTISRDNAKNTLYLQMSSLRSEDTAMYYCARQDGYYPGWFANWGQGTTVTVSSGG<br>GGSGGGGSGGGGSDIELTQSPAIMSASLGEEITLTCSASSSVSYMHWYQQKSGTSPKL<br>LIYSTSNLASGVPSRFSGSGSGTFYSLTISSVEAEDAADYYCHQWSSYTFGGGTKLEIK<br>RTTTPAPRPPTPAPTIASQPLSLRPEACRPAAGGAVHTRGLDFACDIYIWAPLAGTCGV<br>LLLSLVITLYCRGRKKLLYIFKQPFMRPVQTTQEEDGCSCRFPEEEEGGCELRVKFSRS<br>ADAPAYKQGQNQLYNELNLGRREEYDVLDKRRGRDPEMGGKPRRKNPQEGLYNEL<br>QKDKMAEAYSEIGMKGERRRGKGHDGLYQGLSTATKDTYDALHMQALPPR<br>(SEQ ID NO: 119) |
| 14.g2a.BBZ (GD2 CAR) | MEFGLSWLFLVAILKGVQCSRDILLTQTPLSLPVSLGDQASISCRSSQSLVHRNGNTYL<br>HWYLQKPGQSPKLLIHKVSNRFSGVPDRFSGSGSGTDFTLKISRVEAEDLGVYFCSQS<br>THVPPLTFGAGTKLELKRADAAPTVSIFPGSGGGGSGGEVKLQQSGPSLVEPGASVMI<br>SCKASGSSFTGYNMNWVRQNIGKSLEWIGAIDPYYGGTSYNQKFKGRATLTVDKSSS<br>TAYMHLKSLTSEDSAVYYCVSGMEYWGQGTSVTVSSAKTTPPSVYGRVTVSSTTTP<br>APRPPTPAPTIASQPLSLRPEACRPAAGGAVHTRGLDFACDIYIWAPLAGTCGVLLLSL<br>VITLYCKRGRKKLLYIFKQPFMRPVQTTQEEDGCSCRFPEEEEGGCELRVKFSRSADA<br>PAYKQGQNQLYNELNLGRREEYDVLDKRRGRDPEMGGKPRRKNPQEGLYNELQKD<br>KMAEAYSEIGMKGERRRGKGHDGLYQGLSTATKDTYDALHMQALPPR (SEQ ID<br>NO: 120) |
| 2B3.BBZ (PSCA CAR) | MALPVTALLLPLALLLHAARPDIQLTQSPSSLSASVGDRVTITCSASSSVRFIHWYQQK<br>PGKAPKRLIYDTSKLASGVPSRFSGSGSGTDFTLTISSLQPEDFATYYCQQWSSSPFTF<br>GQGTKVEIKGSTSGGGSGGGSGGGGSSEVQLVESGGGLVQPGGSLRLSCAASGFNIK<br>DYYIHWVRQAPGKGLEWVAWIDPENGDTEFVPKFQGRATISADTSKNTAYLQMNSL<br>RAEDTAVYYCKTGGFWGQGTLVTVSSAAGTTTPAPRPPTPAPTIASQPLSLRPEACRP<br>AAGGAVHTRGLDFACDIYIWAPLAGTCGVLLLSLVITLYCKRGRKKLLYIFKQPFMRP<br>VQTTQEEDGCSCRFPEEEEGGCELRVKFSRSADAPAYKQGQNQLYNELNLGRREEYD<br>VLDKRRGRDPEMGGKPRRKNPQEGLYNELQKDKMAEAYSEIGMKGERRRGKGHDG<br>LYQGLSTATKDTYDALHMQALPPR (SEQ ID NO: 121) |
| CD27.Z (CD70 CAR) | MARPHPWWLCVLGTLVGLSATPAPKSCPERHYWAQGKLCCQMCEPGTFLVKDCDQ<br>HRKAAQCDPCIPGVSFSPDHHTRPHCESCRHCNSGLLVRNCTITANAECACRNGWQC<br>RDKECTECDPLPNPSLTARSSQALSPHPQPTHLPYVSEMLEARTAGHMQTLADFRQLP<br>ARTLSTHWPPQRSLCSSDFIRILVIFSGMFLVFTLAGALFLHQRRKYRSNKGESPVEPA<br>EPCRYSCPREEEGSTIPIQEDYRKPEPACSPRVKFSRSADAPAYQQGQNQLYNELNLG<br>RREEYDVLDKRRGRDPEMGGKPRRKNPQEGLYNELQKDKMAEAYSEIGMKGERRR<br>GKGHDGLYQGLSTATKDTYDALHMQALPPR (SEQ ID NO:203) |

5.4.2 TCRs

Fusion proteins provided herein can be co-expressed with a TCR in a genetically engineered cells provided herein or conjugated to a TCR. In some embodiments, provided herein are genetically engineered immune effector cells recombinantly expressing a fusion protein disclosed herein, further recombinantly expressing a TCR. In some embodiments, provided herein are genetically engineered immune effector cells comprising a polynucleotide encoding a fusion protein disclosed herein, further comprising a polynucleotide encoding a TCR.

T cell receptors (TCRs) are antigen-specific molecules that are responsible for recognizing antigenic peptides presented in the context of a product of the MHC on the surface of APCs or any nucleated cells. This system endows T cells, via their TCRs, with the potential ability to recognize the entire array of intracellular antigens expressed by a cell (including virus proteins) that are processed into short peptides, bound to an intracellular MHC molecule, and delivered to the surface as a peptide-MHC complex. This system allows foreign protein (e.g., mutated cancer antigen or virus protein) or aberrantly expressed protein to serve a target for T cells (e.g., Davis and Bjorkman (1988) *Nature*, 334, 395-402; Davis et al. (1998) *Annu Rev Immunol*, 16, 523-544).

The interaction of a TCR and a peptide-MHC complex can drive the T cell into various states of activation, depending on the affinity (or dissociation rate) of binding. The TCR recognition process allows a T cell to discriminate between a normal, healthy cell and, for example, one that has become transformed via a virus or malignancy, by providing a diverse repertoire of TCRs, wherein there is a high probability that one or more TCRs will be present with a binding affinity for the foreign peptide bound to an MHC molecule that is above the threshold for stimulating T cell activity (Manning and Kranz (1999) *Immunology Today*, 20, 417-422).

Wild type TCRs isolated from either human or mouse T cell clones that were identified by in vitro culturing have been shown to have relatively low binding affinities ($K_D$=1-300 µM) (Davis et al. (1998) *Annu Rev Immunol*, 16, 523-544). This is partly because that T cells that develop in the thymus are negatively selected (tolerance induction) on self-peptide-MHC ligands, such that T cells with too high of an affinity are deleted (Starr et al. (2003) *Annu Rev Immunol*, 21, 139-76). To compensate for these relatively low affinities, T cells have evolved a co-receptor system in which the cell surface molecules CD4 and CD8 bind to the MHC molecules (class II and class I, respectively) and synergize with the TCR in mediating signaling activity. CD8 is particularly effective in this process, allowing TCRs with very low affinity (e.g., $K_D$=300 µM) to mediate potent antigen-specific activity.

Directed evolution can be used to generate TCRs with higher affinity for a specific peptide-MHC complex. Methods that can be used include yeast display (Holler et al. (2003) *Nat Immunol*, 4, 55-62; Holler et al. (2000) *Proc Natl*

*Acad Sci USA,* 97, 5387-92), phage display (Li et al (2005) *Nat Biotechnol,* 23, 349-54), and T cell display (Chervin et al. (2008) *J Immunol Methods,* 339, 175-84). All three approaches involve engineering, or modifying, a TCR that exhibits the normal, low affinity of the wild-type TCR, to increase the affinity for the cognate peptide-MHC complex (the original antigen that the T cells were specific for).

As such, in some embodiments, the fusion proteins provided herein can be co-expressed with a TCR in a cell. In some embodiments, a fusion protein provided herein can be conjugated to a TCR. In some embodiments, the TCR comprises an alpha (α) chain and a beta (β) chain. In some embodiments, the TCR comprises a gamma chain (γ) and a delta (δ) chain. The extracellular regions of the αβ chains (or the γδ chains) are responsible for antigen recognition and engagement. Antigen binding stimulates downstream signaling through the multimeric CD3 complex that associates with the intracellular domains of the αβ (or γδ) chains as three dimers (εγ, εδ, ζζ).

TCRs provided herein can be genetically engineered to bind specific antigens. In some embodiments, fusion protein disclosed herein can be co-expressed with a TCR targeting a tumor antigen in a cell. In some embodiments, fusion protein disclosed herein can be conjugated with a TCR targeting a tumor antigen. In some embodiments, provided herein are genetically engineered cells recombinantly expressing a fusion protein and a TCR targeting a tumor antigen. In some embodiments, provided herein are genetically engineered cells comprising a polynucleotide encoding a fusion protein and a polynucleotide encoding a TCR targeting a tumor antigen. In some embodiments, the tumor antigen is selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin.

In some embodiments, the TCR comprises a TCR α chain targeting NY-ESO-1. The TCR α chain targeting NY-ESO-1 can have the amino acid sequence of SEQ ID NO:122, which can be encoded by, for example, the nucleotide sequence of SEQ ID NO:160. In some embodiments, the TCR comprises a TCR β chain targeting NY-ESO-1. The TCR β chain targeting NY-ESO-1 can have the amino acid sequence of SEQ ID NO:123, which can be encoded by, for example, the nucleotide sequence of SEQ ID NO:161. In some embodiments, the TCR targeting NY-ESO-1 comprises a TCR α chain and a TCR β chain.

In some embodiments, the TCR comprises a TCR α chain targeting EBV16-E7. The TCR α chain targeting EBV16-E7 can have the amino acid sequence of SEQ ID NO:125. In some embodiments, the TCR comprises a TCR β chain targeting EBV16-E7. The TCR β chain targeting EBV16-E7 can have the amino acid sequence of SEQ ID NO:126. In some embodiments, the TCR targeting EBV16-E7 comprises a TCR α chain and a TCR β chain. The TCR targeting EBV16-E7 can have the amino acid sequence of SEQ ID NO:124, which can be encoded by, for example, the nucleotide sequence of SEQ ID NO:162.

In some embodiments, the TCR comprises a TCR α chain targeting H3.3. The TCR α chain targeting H3.3 can have the amino acid sequence of SEQ ID NO:128. In some embodiments, the TCR comprises a TCR β chain targeting H3.3. The TCR β chain targeting H3.3 can have the amino acid sequence of SEQ ID NO:129. In some embodiments, the TCR targeting H3.3 comprises a TCR α chain and a TCR β chain. The TCR targeting H3.3 can have the amino acid sequence of SEQ ID NO:127, which can be encoded by, for example, the nucleotide sequence of SEQ ID NO:163.

In some embodiments, the TCR provided herein include a target-binding domain that binds a viral antigen. In some embodiments, the viral antigen is EBV. In some embodiments, the viral antigen is HPV. In some embodiments, the viral antigen is HIV.

| TCR | Amino Acid Sequences |
|---|---|
| NY-ESO-1 TCR α chain | METLLGVSLVILWLQLARVNSQQGEEDPQALSIQEGENATMNCSYKTSINNLQWYRQN SGRGLVHLILIRSNEREKHSGRLRVTLDTSKKSSSLLITASRAADTASYFCATDGAGKST FGDGTTLTVKPNIQKPDPAVYQLRDSKSSDKSVCLFTDFDSQTNVSQSKDSDVYITDKT VLDMRSMDFKSNSAVAWSNKSDFACANAFNNSIIPADTFFPSPESSCDVKLVEKSFETD TNLNFQNLSVIGFRILLLKVAGFNLLMTLRLWSS (SEQ ID NO: 122) |
| NY-ESO-1 β chain | MDSWTLCCVSLCILVAKHTDAGVIQSPRHEVTEMGQEVTLRCKPISGHDYLFWYRQTM MRGLELLIYFNNNVPIDDSGMPEDRFSAKMPNASFSTLKIQPSEPRDSAVYFCASTIGAQ PQHFGDGTRLSILEDLNKVFPPEVAVFEPSEAEISHTQKATLVCLATGFFPDHVELSWW VNGKEVHSGVSTDPQPLKEQPALNDSRYCLSSRLRVSATFWQNPRNHFRCQVQFYGLS ENDEWTQDRAKPVTQIVSAEAWGRADCGFTSVSYQQGVLSATILYEILLGKATLYAVL VSALVLMAMVKRKDF (SEQ ID NO: 123) |
| EBV16-E7 TCR | MWGVFLLYVSMKMGGTTGQNIDQPTEMTATEGAIVQINCTYQTSGFNGLFWYQQHA GEAPTFLSYNVLDGLEEKGRFSSFLSRSKGYSYLLLKELQMKDSASYLCASVDGNNRL AFGKGNQVVVIPNIQNPDPAVYQLRDSKSSDKSVCLFTDFDSQTNVSQSKDSDVYITDK CVLDMRSMDFKSNSAVAWSNKSDFACANAFNNSIIPEDTFFPSPESSCDVKLVEKSFET DTNLNFQNLSVIGFRILLLKVAGFNLLMTLRLWSSRAKREGRGSLLTCGDVEENPGPMG PGLLCWALLCLLGAGLVDAGVTQSPTHLIKTRGQQVTLRCSPKSGHDTVSWYQQALG QGPQFIFQYYEEEERQRGNFPDRFSGHQFPNYSSELNVNALLLGDSALYLCASSLGWRG GRYNEQFFGPGTRLTVLEDLKNVFPPEVAVFEPSEAEISHTQKATLVCLATGFYPDHVE LSWWVNGKEVHSGVCTDPQPLKEQPALNDSRYCLSSRLRVSATFWQNPRNHFRCQVQ FYGLSENDEWTQDRAKPVTQIVSAEAWGRADCGFTSESYQQGVLSATILYEILLGKATL YAVLVSALVLMAMVKRKDSRG (SEQ ID NO: 124) |
| EBV16-E7 TCR α chain | MWGVFLLYVSMKMGGTTGQNIDQPTEMTATEGAIVQINCTYQTSGFNGLFWYQQHA GEAPTFLSYNVLDGLEEKGRFSSFLSRSKGYSYLLLKELQMKDSASYLCASVDGNNRL AFGKGNQVVVIPNIQNPDPAVYQLRDSKSSDKSVCLFTDFDSQTNVSQSKDSDVYITDK CVLDMRSMDFKSNSAVAWSNKSDFACANAFNNSIIPEDTFFPSPESSCDVKLVEKSFET DTNLNFQNLSVIGFRILLLKVAGFNLLMTLRLWSS (SEQ ID NO: 125) |

| TCR | Amino Acid Sequences |
|---|---|
| H3.3K27M TCR β chain | MGPGLLCWALLCLLGAGLVDAGVTQSPTHLIKTRGQQVTLRCSPKSGHDTVSWYQQA LGQGPQPIFQYYEEEERQRGNFPDRFSGHQFPNYSSELNVNALLLGDSALYLCASSLGW RGGRYNEQFFGPGTRLTVLEDLKNVFPPEVAVFEPSEAEISHTQKATLVCLATGFYPDH VELSWWVNGKEVHSGVCTDPQPLKEQPALNDSRYCLSSRLRVSATFWQNPRNHFRCQ VQFYGLSENDEWTQDRAKPVTQIVSAEAWGRADCGFTSESYQQGVLSATILYEILLGK ATLYAVLVSALVLMAMVKRKDSRG (SEQ ID NO: 126) |
| H3.3K27M TCR | MLTASLLRAVIASICVVSSMAQKVTQAQTEISVVEKEDVTLDCVYETRDTTYYLFWYK QPPSGELVFLIRRNSFDEQNEISGRYSWNFQKSTSSFNFTITASQVVDSAVYFCALSEEND MRFGAGTRLTVKPNIQNPDPAVYQLRDSKSSDKSVCLFTDFDSQTNVSQSKDSDVYITD KTVLDMRSMDFKSNSAVAWSNKSDFACANAFNNSIIPEDTFFPSPESSCDVKLVEKSFE TDTNLNFQNLSVIGFRILLLLKVAGFNLLMTLRLWSSVKQTLNFDLLKLAGDVESNPGPM GPQLLGYVVLCLLGAGPLEAQVTQNPRYLITVTGKKLTVTCSQNMNHEYMSWYRQDP GLGLRQIYYSMNVEVTDKGDVPEGYKVSRKEKRNFPLILESPNPNQTSLYFCASGWGG PFYEQYFGPGTRLTVTEDLKNVFPPEVAVFEPSEAEISHTQKATLVCLATGFYPDHVELS WWVNGKEVHSGVSTDPQPLKEQPALNDSRYCLSSRLRVSATFWQNPRNHFRCQVQFY GLSENDEWTQDRAKPVTQIVSAEAWGRADCGFTSESYQQGVLSATILYEILLGKATLY AVLVSALVLMAMVKRKDSRG (SEQ ID NO: 127) |
| H3.3K27M TCR α chain | MLTASLLRAVIASICVVSSMAQKVTQAQTEISVVEKEDVTLDCVYETRDTTYYLFWYK QPPSGELVFLIRRNSFDEQNEISGRYSWNFQKSTSSFNFTITASQVVDSAVYFCALSEEND MRFGAGTRLTVKPNIQNPDPAVYQLRDSKSSDKSVCLFTDFDSQTNVSQSKDSDVYITD KTVLDMRSMDFKSNSAVAWSNKSDFACANAFNNSIIPEDTFFPSPESSCDVKLVEKSFE TDTNLNFQNLSVIGFRILLLLKVAGFNLLMTLRLWSS (SEQ ID NO: 128) |
| H3.3K27M TCR β chain | MGPQLLGYVVLCLLGAGPLEAQVTQNPRYLITVTGKKLTVTCSQNMNHEYMSWYRQ DPGLGLRQIYYSMNVEVTDKGDVPEGYKVSRKEKRNFPLILESPNPNQTSLYFCASGW GGPFYEQYFGPGTRLTVTEDLKNVFPPEVAVFEPSEAEISHTQKATLVCLATGFYPDHV ELSWWVNGKEVHSGVSTDPQPLKEQPALNDSRYCLSSRLRVSATFWQNPRNHFRCQV QFYGLSENDEWTQDRAKPVTQIVSAEAWGRADCGFTSESYQQGVLSATILYEILLGKA TLYAVLVSALVLMAMVKRKDSRG (SEQ ID NO: 129) |

5.4.3 BiTEs

Bispecific T-cell engagers (BiTEs) are bispecific antibodies that bind to a T cell antigen (e.g., CD3) and a tumor antigen. BiTEs have been shown to induce directed lysis of target tumor cells and thus provide great potential therapies for cancers and other disorders. Fusion proteins provided herein can be co-expressed with a BiTE in a genetically engineered cells provided herein or conjugated to a BiTE. In some embodiments, provided herein are genetically engineered immune effector cells recombinantly expressing a fusion protein disclosed herein, further recombinantly expressing a BiTE. In some embodiments, provided herein are genetically engineered immune effector cells comprising a polynucleotide encoding a fusion protein disclosed herein, further comprising a polynucleotide encoding a BiTE.

BiTEs are bispecific antibodies that bind to a T cell antigen (e.g., CD3) and a tumor antigen. In some embodiments, the BiTEs bind CD3. In some embodiments, the tumor antigen is selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin.

In some embodiments, the BiTEs comprise a bispecific antibody that binds CD3 and CD19. The BiTEs that bind CD3 and CD19 can have the amino acid sequence of SEQ ID NO:130, which can be encoded by, for example, the nucleotide sequence of SEQ ID NO:164. In some embodiments, the BiTEs comprise a bispecific antibody that binds CD3 and CD19. In some embodiments, the BiTEs comprise a bispecific antibody that binds CD3 and Her2. The BiTEs that bind CD3 and Her2 can have the amino acid sequence of SEQ ID NO:224, which can be encoded by, for example, the nucleotide sequence of SEQ ID NO:225. In some embodiments, the BiTEs comprise a bispecific antibody that binds CD3 and EGFRvIII. The BiTEs that bind CD3 and EGFRvIII can have the amino acid sequence of SEQ ID NO:131, which can be encoded by, for example, the nucleotide sequence of SEQ ID NO:165. In some embodiments, the BiTEs comprise a bispecific antibody that binds CD3 and Mesothelin. In some embodiments, the BiTEs comprise a bispecific antibody that binds CD3 and BCMA.

In some embodiments, the BiTE provided herein include a target-binding domain that binds a viral antigen. In some embodiments, the viral antigen is EBV. In some embodiments, the viral antigen is HPV. In some embodiments, the viral antigen is HIV.

| BiTE | Amino Acid Sequences |
|---|---|
| CD19-CD3 BiTE | MGWSCIILFLVATATGVHSDYKDDDDKDIQLTQSPASLAVSLGQRATISCKASQSVDYD GDSYLNWYQQIPGQPPKLLIYDASNLVSGIPPRFSGSGSGTDFTLNIHPVEKVDAATYHC QQSTEDPWTFGGGTKLEIKGGGGSGGGGSGGGGSQVQLQQSGAELVRPGSSVKISCKA SGYAFSSYWMNWVKQRPGQGLEWIGQIWPGDGDTNYNGKFKGKATLTADESSSTAY MQLSSLASEDSAVYFCARRETTTVGRYYYAMDYWGQGTTVTVSSGGGGSDIKLQQSG AELARPGASVKMSCKTSGYTFTRYTMHWVKQRPGQGLEWIGYINPSRGYTNYNQKFK |

-continued

| BiTE | Amino Acid Sequences |
|---|---|
| | DKATLTTDKSSSTAYMQLSSLTSEDSAVYFCARYYDDHYCLDYWGQGTTLTVSSVEG<br>GSGGGSGGSGGSGGVDDAAIQLTQSPAIMSASPGEKVTMTCRASSSVSYMNWYQQKSG<br>TSPKRWIYDTSKVASGVPYRFSGSGSGTSYSLTISSMEAEDAATYYCQQWSSNPLTFGA<br>GTKLELKHHHHHH (SEQ ID NO: 130) |
| 139-CD3<br>(EGFRvIII<br>BiTE) | MGWSCIILFLVATATGVHSDYKDDDDKDIQMTQSPSSLSASVGDRVTITCRASQGIRNN<br>LAWYQQKPGKAPKRLIYAASNLQSGVPSRFTGSGSGTEFTLIVSSLQPEDFATYYCLQH<br>HSYPLTSGGGTKVEIKGGGGSGGGGSGGGGSEVQVLESGGGLVQPGGSLRLSCAASGF<br>TFSSYAMSWVRQAPGKGLEWVSAISGSGGSTNYADSVKGRFTISRDNSKNTLYLQMNS<br>LRAEDTAVYYCAGSSGWSEYWGQGTLVTVSSGGGGSDIKLQQSGAELARPGASVKMS<br>CKTSGYTFTRYTMHWVKQRPGQGLEWIGYINPSRGYTNYNQKFKDKATLTTDKSSSTA<br>YMQLSSLTSEDSAVYYCARYYDDHYCLDYWGQGTTLTVSSVEGGSGGSGGSGGSGGV<br>DDAAIQLTQSPAIMSASPGEKVTMTCRASSSVSYMNWYQQKSGTSPKRWIYDTSKVAS<br>GVPYRFSGSGSGTSYSLTISSMEAEDAATYYCQQWSSNPLTFGAGTKLELKHHHHHH<br>(SEQ ID NO: 132) |
| 4D5-6.CD3<br>(HIR2<br>BiTE) | MDFQVQIFSFLLISASVIMSRGDIQMTQSPSSLSASVGDRVTITCRASQDVNTAVAWYQ<br>QKPGKAPKLLIYSASFLYSGVPSRFSGSRSGTDFTLTISSLQPEDFATYYCQQHYTTPPTF<br>GQGTKVEIKRTGSTSGSGKPGSGEGSEVQLVESGGGLVQPGGSLRLSCAASGFNIKDTYI<br>HWVRQAPGKGLEWVARIYPTNGYTRYADSVKGRFTISADTSKNTAYLQMNSLRAEDT<br>AVYYCSRWGGDGFVAMDVWGQGTLVTVSSGGGGSDIKLQQSGAELARPGASVKMSC<br>KTSGYTFTRYTMHWVKQRPGQGLEWIGYINPSRGYTNYNQKFKDKATLTTDKSSSTA<br>YMQLSSLTSEDSAVYFCARYYDDHYCLDYWGQGTTLTVSSVEGGSGGSGGSGGSGGV<br>DDAAIQLTQSPAIMSASPGEKVTMTCRASSSVSYMNWYQQKSGTSPKRWIYDTSKVAS<br>GVPYRFSGSGSGTSYSLTISSMEAEDAATYYCQQWSSNPLTFGAGTKLELKHHHHHH<br>(SEQ ID NO:224) |

5.5 Methods of Production 5.5.1 Polynucleotides and Fusion Proteins

Polynucleotides provided herein can be prepared, manipulated, and/or expressed using any of a variety of well-established techniques known and available in the art. Many vectors can be used. Examples of vectors are plasmid, autonomously replicating sequences, and transposable elements. Exemplary transposon systems such as Sleeping Beauty and PiggyBac can be used, which can be stably integrated into the genome (e.g., Ivics et al., *Cell*, 91 (4): 501-510 (1997); Cadiñanos et al., (2007) *Nucleic Acids Research*. 35 (12): e87). Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells.

In some embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. In some embodiments, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus. Typically, the host cell comprises the viral replication transactivator protein that activates the replication.

"Expression control sequences," "control elements," or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements can vary in their strength and specificity. Depending on the vector system and host utilized, any number of suitable transcription and translation elements, including ubiquitous promoters and inducible promoters can be used.

Illustrative ubiquitous expression control sequences that can be used in present disclosure include, but are not limited to, a cytomegalovirus (CMV) immediate early promoter, a viral simian virus 40 (SV40) promoter (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc. The fusion proteins described herein can be produced by any method known in the art, including chemical synthesis and recombinant expression techniques. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) MOLECULAR CLONING: A LABORATORY MANUAL, Cold Spring Harbor Laboratory Press; Sambrook et al. (1989), MOLECULAR CLONING: A LABORATORY MANUAL, Second Edition, Cold Spring Harbor Laboratory Press; Sambrook et al. (2001) MOLECULAR CLONING: A LABORATORY MANUAL, Cold Spring Harbor Laboratory Press, Cold Spring Harbor, N.Y.; Ausubel et al., CURRENT PROTOCOLS IN MOLECULAR BIOLOGY, John Wiley & Sons (1987 and annual updates); CURRENT PROTOCOLS IN IMMUNOLOGY, John Wiley & Sons (1987 and annual updates) Gait (ed.) (1984) OLIGONUCLEOTIDE SYNTHESIS: A PRACTICAL APPROACH, IRL Press; Eckstein (ed.) (1991) OLIGONUCLEOTIDES AND ANALOGUES: A PRACTICAL APPROACH, IRL Press; Birren et al. (eds.) (1999) GENOME ANALYSIS: A LABORATORY MANUAL, Cold Spring Harbor Laboratory Press; Borrebaeck (ed.) (1995) ANTIBODY ENGINEERING, Second Edition, Oxford University Press; Lo (ed.) (2006) ANTIBODY ENGINEERING: METHODS AND PROTOCOLS (METHODS IN MOLECULAR BIOLOGY); Vol. 248, Humana Press, Inc; each of which is incorporated herein by reference in its entirety.

The fusion proteins described herein can be produced and isolated using methods known in the art. Peptides can be synthesized, in whole or in part, using chemical methods (see, e.g., Caruthers (1980). Nucleic Acids Res. Symp. Ser. 215; Horn (1980); and Banga, A. K., Therapeutic Peptides and Proteins, Formulation, Processing and Delivery Systems (1995) Technomic Publishing Co., Lancaster, Pa.). Peptide synthesis can be performed using various solid phase techniques (see, e.g., Roberge Science 269:202 (1995); Merrifield, Methods. Enzymol. 289:3 (1997)) and automated synthesis may be achieved, e.g., using the ABI 431A Peptide Synthesizer (Perkin Elmer) in accordance with the manufacturer's instructions. Peptides can also be synthesized using combinatorial methodologies. Synthetic residues and polypeptides can be synthesized using a variety of procedures and methodologies known in the art (see, e.g., Organic Syntheses Collective Volumes, Gilman, et al. (Eds) John Wiley & Sons, Inc., NY). Modified peptides can be produced by chemical modification methods (see, for example, Belousov, *Nucleic Acids Res.* 25:3440 (1997); Frenkel, *Free Radic. Biol. Med.* 19:373 (1995); and Blommers, *Biochemistry* 33:7886 (1994)). Peptide sequence variations, derivatives, substitutions and modifications can also be made using methods such as oligonucleotide-mediated (site-directed) mutagenesis, alanine scanning, and PCR based mutagenesis. Site-directed mutagenesis (Carter et al., *Nucl. Acids Res.*, 13:4331 (1986); Zoller et al., *Nucl. Acids Res.* 10:6487 (1987)), cassette mutagenesis (Wells et al., *Gene* 34:315 (1985)), restriction selection mutagenesis (Wells et al., *Philos. Trans. R. Soc. London SerA* 317:415 (1986)) and other techniques can be performed on cloned DNA to produce invention peptide sequences, variants, fusions and chimeras, and variations, derivatives, substitutions and modifications thereof.

The fusion proteins described herein can be prepared using a wide variety of techniques known in the art including the use of hybridoma and recombinant technologies, or a combination thereof. In some embodiments, a recombinant expression vector is used to express a polynucleotide encoding a fusion protein described herein. For example, a recombinant expression vector can be a replicable DNA construct that includes synthetic or cDNA-derived DNA fragments encoding a fusion protein operatively linked to suitable transcriptional and/or translational regulatory elements derived from mammalian, microbial, viral or insect genes. In some embodiments, coding sequences of fusion proteins disclosed herein can be ligated into such expression vectors for their expression in mammalian cells. In some embodiments, a viral vector is used. DNA regions are "operatively linked" when they are functionally related to each other. For example, a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide can include an N-terminal methionine residue.

A wide variety of expression host/vector combinations can be employed. Suitable host cells for expression include prokaryotes, yeast cells, insect cells, or higher eukaryotic cells under the control of appropriate promoters. Appropriate cloning and expression vectors for use with bacterial, fungal, yeast, and mammalian cellular hosts, as well as methods of protein production, including antibody production are well-known in the art. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Useful expression vectors for eukaryotic hosts include, for example, vectors comprising expression control sequences from SV40, bovine papilloma virus, adenovirus, and cytomegalovirus. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

5.5.2 Antibodies and Antigen-Binding Fragments

Provided herein are antibodies and antigen-binding fragments thereof that include but are not limited to monoclonal antibodies, polyclonal antibodies, synthetic antibodies, human antibodies, humanized antibodies, and antigen-binding fragments thereof.

Methods of antibody production are well-known in the art. See for example, in Harlow et al., Antibodies: A Laboratory Manual, (Cold Spring Harbor Laboratory Press, 2nd ed. 1988); Hammerling et at, in: Monoclonal Antibodies and T-Cell Hybridomas 563 681 (Elsevier, N.Y., 1981), each of which is incorporated herein by reference in its entirety. For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. For example, anti-CD19 antibodies directed against the human CD19 antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (*Int. Rev. Immunol.*, 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., *Proc. Natl. Acad. Sci. USA*, 90:2551 (1993); Jakobovits et al., *Nature*, 362:255-258 (1993); Bruggermann et al., *Year in Immunol.*, 7:33 (1993); and Duchosal et al., *Nature*, 355:258 (1992).

Human antibodies can also be derived from phage-display libraries (Hoogenboom et al., *J. Mol. Biol.*, 227:381 (1991); Marks et al. *J. Mol. Biol.*, 222:581-597 (1991); Vaughan et al., *Nature Biotech.*, 14:309 (1996)). Phage display technology (McCafferty et al., *Nature*, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson and Chiswell, *Current Opinion in Structural Biology* 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., *J. Mol. Biol.*, 222:581-597 (1991), or Griffith et al., *EMBO J.*, 12:725-734 (1993). See, also, U.S. Pat. Nos. 5,565,332 and 5,573,905, each of which is incorporated herein by reference in its entirety.

Human antibodies can also be generated by in vitro activated B cells (see, U.S. Pat. Nos. 5,567,610 and 5,229,275, each of which is incorporated herein by reference in its entirety). Human antibodies can also be generated in vitro using hybridoma techniques such as, but not limited to, that described by Roder et al. (*Methods Enzymol.*, 121:140-167 (1986)).

Alternatively, in some embodiments, a non-human antibody is humanized, where specific sequences or regions of the antibody are modified to increase similarity to an antibody naturally produced in a human. In some embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, *Molecular Immunology*, 28(4/5): 489-498; Studnicka et al., 1994, *Protein Engineering*, 7(6):

805-814; and Roguska et al., 1994, *PNAS,* 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., *J. Immunol.,* 169:1119-25 (2002), Caldas et al., *Protein Eng.,* 13(5):353-60 (2000), Morea et al., *Methods,* 20(3):267-79 (2000), Baca et al., *J. Biol. Chem.,* 272(16):10678-84 (1997), Roguska et al., *Protein Eng.,* 9(10):895-904 (1996), Couto et al., *Cancer Res.,* 55 (23 Supp):5973s-5977s (1995), Couto et al., *Cancer Res.,* 55(8):1717-22 (1995), Sandhu J S, *Gene,* 150(2):409-10 (1994), and Pedersen et al., *J. Mol. Biol.,* 235(3):959-73 (1994), each of which is incorporated herein in its entirety by reference. Often, framework residues in the framework regions can be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, *Nature,* 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., *Nature,* 321:522-525 (1986); Riechmann et al., *Nature,* 332:323-327 (1988); Verhoeyen et al, *Science,* 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FR residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., *Protein Engineering,* 7(6):805-814 (1994); and Roguska et al., *PNAS,* 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.,* 151:2296 (1993); Chothia et al, *J. Mol. Biol.,* 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993), the contents of which are incorporated herein by reference herein in their entirety).

Antibodies can be humanized with retention of high affinity for the target antigen and other favorable biological properties. For example, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A "humanized" antibody retains a similar antigenic specificity as the original antibody, for example, the ability to bind human CD40 antigen. However, using certain methods of humanization, the affinity and/or specificity of binding of the antibody for a particular antigen can be increased using methods of "directed evolution," as described by Wu et al., *J. Mol. Biol.,* 294:151 (1999), the contents of which are incorporated herein by reference herein in their entirety.

5.5.3 Genetically Engineered Immune Effector Cells

In some embodiments, provided herein is a genetically engineered immune effector cell that recombinantly expresses a fusion protein disclosed herein. In some embodiments, provided herein is a genetically engineered immune effector cell that comprises a polynucleotide encoding a fusion protein disclosed herein. In some embodiments, provided herein is a genetically engineered immune effector cell that comprises a vector comprising a polynucleotide encoding a fusion protein disclosed herein. In some embodiments, provided herein is a genetically engineered immune effector cell that recombinantly expresses a fusion protein disclosed herein and a CAR, TCR, or BiTE (CAR/TCR/BiTE). In some embodiments, provided herein is a genetically engineered immune effector cell that comprises a polynucleotide encoding a fusion protein disclosed herein and a CAR/TCR/BiTE.

5.5.3.1 Methods of Genetic Engineering

With respect to generating cells recombinantly expressing a fusion protein disclosed herein, one or more polynucleotides encoding the fusion protein is introduced into the target cell using a suitable expression vector. The target immune effector cells (e.g., T cells) are transferred with one or more polynucleotides encoding a fusion protein, or a CAR/TCR/BiTE and a fusion protein. The CAR/TCR/BiTE and fusion protein encoding polynucleotides can be on separate vectors or on the same vector, as desired. For example, a polynucleotide encoding a CAR or a fusion protein disclosed herein can be cloned into a suitable vector, such as a viral vector, and introduced into the target cell using well known molecular biology techniques (see Ausubel et al., *Current Protocols in Molecular Biology*, John Wiley and Sons, Baltimore, Md. (1999)). Any vector suitable for expression in a cell, particularly a human cell, can be used. The vectors contain suitable expression elements such as promoters that provide for expression of the encoded nucleic acids in the target cell. In the case of a retroviral vector, cells can optionally be activated to increase transduction efficiency (see Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al., *Mol. Ther.* 8:29-41 (2003); Agarwal et al, *J. Virol.* 72:3720-3728 (1998); Pollok et al., *Hum. Gene Ther.* 10:2221-2236 (1998); Quinn et al., *Hum. Gene Ther.* 9:1457-1467 (1998); see also commercially available methods such as Dynabeads™ human T cell activator products, Thermo Fisher Scientific, Waltham, Mass.).

In one embodiment, the vector is a retroviral vector, for example, a gamma retroviral or lentiviral vector, which is employed for the introduction of a fusion protein and/or a CAR, TCR, or BiTE into the target cell. For genetic modification of the cells to express a fusion protein and/or a CAR, TCR, or BiTE, a retroviral vector can be employed for transduction. However, it is understood that any suitable viral vector or non-viral delivery system can be used. Combinations of a retroviral vector and an appropriate packaging line are also suitable, where the capsid proteins will be functional for infecting human cells. Various amphotropic virus-producing cell lines are known, including, but not limited to, PA12 (Miller et al., *Mol. Cell. Biol.* 5:431-437 (1985)); PA317 (Miller et al., *Mol. Cell. Biol.* 6:2895-2902 (1986)); and CRIP (Dams et al, *Proc. Natl. Acad. Sci. USA* 85:6460-6464 (1988)). Non-amphotropic particles are suitable too, for example, particles pseudotyped with VSVG, RD114 or GALV envelope and any other known in the art (Relander et al., *Mol. Therap.* 11:452-459 (2005)). Possible methods of transduction also include direct co-culture of the cells with producer cells (for example, Bregni et al., *Blood* 80:1418-1422 (1992)), or culturing with viral supernatant alone or concentrated vector stocks with or without appropriate growth factors and polycations (see, for example, Xu et al., *Exp. Hemat.* 22:223-230 (1994); Hughes, et al. *J. Clin. Invest.* 89:1817-1824 (1992)).

Other viral vectors that can be used include, for example, adenoviral, lentiviral, and adeno-associated viral vectors, vaccinia virus, a bovine papilloma virus derived vector, or a herpes virus, such as Epstein-Barr Virus (see, for example, Miller, *Hum. Gene Ther.* 1(1):5-14 (1990); Friedman, *Science* 244:1275-1281 (1989); Eglitis et al., *BioTechniques* 6:608-614 (1988); Tolstoshev et al., *Current Opin. Biotechnol.* 1:55-61 (1990); Sharp, *Lancet* 337:1277-1278 (1991); Cornetta et al., *Prog. Nucleic Acid Res. Mol. Biol.* 36:311-322 (1989); Anderson, *Science* 226:401-409 (1984); Moen, *Blood Cells* 17:407-416 (1991); Miller et al., *Biotechnology* 7:980-990 (1989); Le Gal La Salle et al., *Science* 259:988-990 (1993); and Johnson, *Chest* 107:77S-83S (1995)). Retroviral vectors are particularly well developed and have been used in clinical settings (Rosenberg et al., *N. Engl. J. Med.* 323:370 (1990); Anderson et al., U.S. Pat. No. 5,399,346). Generally, the chosen vector exhibits high efficiency of infection and stable integration and expression (see, for example, Cayouette et al., *Human Gene Therapy* 8:423-430 (1997); Kido et al., *Current Eye Research* 15:833-844 (1996); Bloomer et al., *J. Virol.* 71:6641-6649 (1997); Naldini et al., *Science* 272:263-267 (1996); and Miyoshi et al., *Proc. Natl. Acad. Sci. U.S.A.* 94:10319-10323 (1997)).

Particularly useful vectors for expressing a fusion protein disclosed herein and/or CAR/TCR/BiTE include vectors that have been used in human gene therapy. In one non-limiting embodiment, a vector is a retroviral vector. The use of retroviral vectors for expression in T cells or other immune effector cells, including engineered T cells, has been described (see Scholler et al., *Sci. Transl. Med.* 4:132-153 (2012; Parente-Pereira et al., *J. Biol. Methods* 1(2):e7 (1-9)(2014); Lamers et al., *Blood* 117(1):72-82 (2011); Reviere et al., *Proc. Natl. Acad. Sci. USA* 92:6733-6737 (1995)). In one embodiment, the vector is an SGF retroviral vector such as an SGF γ-retroviral vector, which is Moloney murine leukemia-based retroviral vector. SGF vectors have been described previously (see, for example, Wang et at, *Gene Therapy* 15:1454-1459 (2008)).

The vectors used herein employ suitable promoters for expression in a particular host cell. The promoter can be an inducible promoter or a constitutive promoter. In some embodiments, the promoter of an expression vector provides expression in a stem cell, such as a hematopoietic stem cell. In some embodiments, the promoter of an expression vector provides expression in an immune effector cell, such as a T cell. Non-viral vectors can be used as well, so long as the vector contains suitable expression elements for expression in the target cell. Some vectors, such as retroviral vectors, can integrate into the host genome.

In some embodiments, provided herein are methods of genetically engineering an immune effector cell by transferring a polynucleotide provided herein into the cell using a non-viral delivery system. For example, physical methods for introducing a polynucleotide into a host cell include calcium phosphate precipitation, lipofection, particle bombardment, microinjection, electroporation, and the like. In some embodiments, RNA electroporation can be used (Van Driessche et al. *Folia histochemica et cytobiologica* 43:4 213-216 (2005)). In some embodiments, DNA transfection and transposon can be used. In some embodiments, the Sleeping Beauty system or PiggyBac system is used (e.g., Ivics et at, *Cell,* 91 (4): 501-510 (1997); Cadiñanos et al. (2007) *Nucleic Acids Research.* 35 (12): e87). Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and Liposomes. An exemplary colloidal system for use as a delivery vehicle in vitro and in vivo is a liposome (e.g., an artificial membrane vesicle).

In some embodiments, provided herein are methods of genetically engineering an immune effector cell by transferring a polynucleotide provided herein into the cell using gene-editing. If desired, targeted integration can be implemented using technologies such as a nuclease, transcription activator-like effector nucleases (TALENs), Zinc-finger nucleases (ZFNs), clustered regularly interspaced short palindromic repeats (CRISPRs), homologous recombination, non-homologous end joining, microhomology-mediated end joining, homology-mediated end joining and the like (Gersbach et al., *Nucl. Acids Res.* 39:7868-7878 (2011); Vasileva, et al. *Cell Death Dis.* 6:e1831. (Jul. 23 2015); Sontheimer, *Hum. Gene Ther.* 26(7):413-424 (2015); Yao et al. Cell Research volume 27, 801-814(2017)). In some embodiments, methods provided herein use a ZFN system. A zinc-finger nuclease consists of a DNA recognition domain and a non-specific endonuclease. The DNA recognition domain consists of a series of Cys2-His2 zinc-finger proteins linked in series, and each zinc-finger unit includes about 30 amino acids for specifically binding to DNA. The non-specific endonuclease is a FokI endonuclease which forms a dimer to cleave the DNA. In some embodiments, methods provided herein use a TALEN system. TALEN is a transcription activator-like effector nuclease. The TALE protein is a core component of a DNA binding domain, and generally consists of a plurality of basic repeat units linked in series. The designed and combined series of units can specifically recognize a DNA sequence and cleave a specific DNA sequence by coupling the FokI endonuclease.

In some embodiments, methods provided herein use a CRISPR-Cas system. The CRISPR-Cas system can be a CRISPR-Cas9 system. CRISPR/Cas system is a nuclease system consisting of clustered regularly interspaced short palindromic repeats (CRISPR) and CRISPR binding proteins (i.e., Cas proteins), which can cleave nearly all genomic sequences adjacent to protospacer-adjacent motifs (PAM) in eukaryocytes (Cong et al. *Science* 2013. 339: 819-823). The "CRISPR/Cas system" is used to refer collectively to transcripts involving CRISPR-related ("Cas") genes, as well as other elements involving the expression thereof or directing the activity thereof, including sequences encoding a Cas gene, tracr (trans-activated CRISPR) sequences (for example, tracrRNA or active partial tracrRNA), tracr pairing sequences (in the background of an endogenous CRISPR system, cover "direct repeats" and processed partial direct repeats), guide sequences, or other sequences from the CRISPR locus and transcripts. In general, the CRISPR system is characterized as an element that facilitates the formation of a CRISPR complex at a site of a target sequence (also called a protospacer in the endogenous CRISPR system). Unrestricted examples of the Cas protein include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 homologues, or modified forms thereof. In some embodiments, the Cas protein is a Cas9 protein (Gasiunas, Barrangou et al. 2012; Jinek, Chylinski et al. 2012; Deltcheva, Chylinski et al. 2011; Makarova, Grishin et al. (2006)). Amino acid sequences of the Cas9 protein are known in the art. Exemplary sequences can be found, for example, in the SwissProt database under the accession number Q99ZW2, in the UniProt database under the number A1IQ68, Q03LF7, or J7RUA5.

The vectors and constructs can optionally be designed to include a reporter. For example, the vector can be designed to express a reporter protein, which can be useful to identify cells comprising the vector or polynucleotides provided on the vector, such as polynucleotides that have integrated into the host chromosome. In one embodiment, the reporter can be expressed as a bicistronic or multicistronic expression construct with the fusion protein or the CAR/TCR/BiTE. Exemplary reporter proteins include, but are not limited to, fluorescent proteins, such as mCherry, green fluorescent protein (GFP), blue fluorescent protein, for example, EBFP, EBFP2, Azurite, and mKalama1, cyan fluorescent protein, for example, ECFP, Cerulean, and CyPet, and yellow fluorescent protein, for example, YFP, Citrine, Venus, and YPet.

Assays can be used to determine the transduction efficiency of a fusion protein disclosed herein or a CAR/TCR/BiTE using routine molecular biology techniques. If a marker has been included in the construct, such as a fluorescent protein, gene transfer efficiency can be monitored by FACS analysis to quantify the fraction of transduced (for example, GFP$^+$) immune effector cells, such as T cells, and/or by quantitative PCR. Using a well-established cocultivation system (Gade et al., *Cancer Res.* 65:9080-9088 (2005); Gong et al., *Neoplasia* 1:123-127 (1999); Latouche et al., *Nat. Biotechnol.* 18:405-409 (2000)) it can be determined whether fibroblast AAPCs expressing cancer antigen (vs. controls) direct cytokine release from transduced immune effector cells, such as T cells, expressing a CAR (cell supernatant LUMINEX (Austin Tex.) assay for IL-2, IL-4, IL-10, IFN-γ, TNF-α, and GM-CSF), T cell proliferation (by carboxyfluorescein succinimidyl ester (CFSE) labeling), and T cell survival (by Annexin V staining). The influence of CD80 and/or 4-1BBL on T cell survival, proliferation, and efficacy can be evaluated. T cells can be exposed to repeated stimulation by cancer antigen positive target cells, and it can be determined whether T cell proliferation and cytokine response remain similar or diminished with repeated stimulation. The cancer antigen CAR constructs can be compared side by side under equivalent assay conditions. Cytotoxicity assays with multiple E:T ratios can be conducted using chromium-release assays.

Combinations and permutations of various methods described herein or otherwise known in the art are expressly contemplated to prepare the genetically engineered cells disclosed herein.

5.5.3.2 Sources of Immune Effector Cells

Immune effector cells provided herein can be obtained from a subject. Sources for the immune effector cells provided herein include, but are not limited to, peripheral blood, umbilical cord blood, bone marrow, or other sources of hematopoietic cells. Immune effector cells (e.g., T cells) can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments, cell lines available in the art can be used. Immune effector cells provided herein can be isolated by methods well known in the art, including commercially available isolation methods (see, for example, Rowland-Jones et al., LYMPHOCYTES: A PRACTICAL APPROACH, Oxford University Press, New York (1999)). Various methods for isolating immune effector cells have been described previously, and can be used, including but not limited to, using peripheral donor lymphocytes (Sadelain et al., *Nat. Rev. Cancer* 3:35-45 (2003); Morgan et al., *Science* 314: 126-129 (2006), and using selectively in vitro-expanded antigen-specific peripheral blood leukocytes employing artificial antigen-presenting cells (AAPCs) or dendritic cells (Dupont et al., *Cancer Res.* 65:5417-5427 (2005); Papanicolaou et al., *Blood* 102:2498-2505 (2003)).

In certain embodiments, immune effector cells (e.g., T cells) disclosed herein can be obtained from a unit of blood collected from a subject using any techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis can be washed to remove the plasma fraction and to place the cells in an appropriate buffer or media for subsequent processing steps. In some embodiments, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step can be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells can be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample can be removed, and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention.

Various techniques can be employed to separate the cells to enrich for desired immune effector cells. For instance, negative selection methods can be used to remove cells that are not the desired immune effector cells. Additionally, positive selection methods can be used to isolate or enrich for desired immune effector cells or precursor cells thereof, or a combination of positive and negative selection methods can be employed. Monoclonal antibodies (MAbs) are particularly useful for identifying markers associated with particular cell lineages and/or stages of differentiation for both positive and negative selections. If a particular type of cell is to be isolated, for example, a particular type of T cell, various cell surface markers or combinations of markers, including but not limited to, CD3, CD4, CD8, CD34 (for hematopoietic stem and progenitor cells) and the like, can be used to separate the cells, as is well known in the art (see Kearse, T CELL PROTOCOLS: DEVELOPMENT AND ACTIVATION, Humana Press, Totowa N.J. (2000); De Libero, T CELL PROTOCOLS, Vol. 514 of Methods in Molecular Biology, Humana Press, Totowa N.J. (2009)). In some embodiments, enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

Procedures for separation of immune effector cells include, but are not limited to, density gradient centrifugation, coupling to particles that modify cell density, magnetic separation with antibody-coated magnetic beads, affinity chromatography; cytotoxic agents joined to or used in conjunction with a monoclonal antibody (mAb), including, but not limited to, complement and cytotoxins, and panning with an antibody attached to a solid matrix, for example, a plate or chip, elutriation, flow cytometry, or any other convenient technique (see, for example, Recktenwald et al., CELL SEPARATION METHODS AND APPLICATIONS, Marcel Dekker, Inc., New York (1998)). It is understood that the immune effector cells used in methods provided herein can be substantially pure cells or can be a polyclonal population. In some embodiments, a polyclonal population can be enriched for a desired immune effector cell. Such an enrichment can take place prior to or after genetically engineering the cells to express a fusion protein provided herein, as desired.

The immune effector cells can be autologous or non-autologous to the subject to which they are administered in the methods of treatment disclosed herein. Autologous cells are isolated from the subject to which the engineered cells are to be administered. Optionally, the cells can be obtained by leukapheresis, where leukocytes are selectively removed from withdrawn blood, made recombinant, and then retransfused into the donor. Alternatively, allogeneic cells from a non-autologous donor that is not the subject can be used. In the case of a non-autologous donor, the cells are typed and matched for human leukocyte antigen (HLA) to determine an appropriate level of compatibility, as is well known in the art. The cells can optionally be cryopreserved after isolation and/or genetic engineering, and/or expansion of genetically engineered cells (see Kaiser et al., supra, 2015)). Methods for cyropreserving cells are well known in the art (see, for example, Freshney, CULTURE OF ANIMAL CELLS: A MANUAL OF BASIC TECHNIQUES, 4th ed., Wiley-Liss, New York (2000); Harrison and Rae, GENERAL TECHNIQUES OF CELL CULTURE, Cambridge University Press (1997)).

In some embodiments, isolated immune effector cells are genetically engineered ex vivo for recombinant expression of a fusion protein. In some embodiments, isolated immune effector cells are genetically engineered ex vivo for recombinant expression of a fusion protein and a CAR/TCR/BiTE. In some embodiments, immune effector cells provided herein are obtained by in vitro sensitization, wherein the sensitization can occur before or after the immune effector cells are genetically engineered to recombinantly express the fusion protein disclosed herein. In an embodiment where the sensitized immune effector cells, such T cells, are isolated from in vivo sources, it will be self-evident that genetic engineering occurs of the already-sensitized immune effector cells.

Also contemplated in the present disclosure is the collection of blood samples or apheresis product from a subject at a time period prior to when the genetically engineered cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment, a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporine, azathioprine, methotrexate, mycophenolate, and FK506, antibodies, or other immunoablative agents such as CAMPATH, anti-CD3 antibodies, cytoxan, fludarabine, cyclosporine, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., *Cell* 66:807-815, 1991; Henderson et al., *Immun* 73:316-321, 1991; Bierer et al., *Curr. Opin. Immun.* 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained can be optimal or improved for their ability to expand ex vivo. Likewise, following ex vivo manipulation using the methods described herein, these cells may be in a preferred state for enhanced engraftment and in vivo expansion. Thus, it is contemplated to collect blood cells, including T cells, NK cells, or other immune effector cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

The immune effector cells disclosed herein can be subjected to conditions that favor maintenance or expansion of cells as well known in the art. (De Libero, *T Cell Protocols*, Vol. 514 of *Methods in Molecular Biology*, Humana Press, Totowa N.J. (2009); Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al, *Mol. Ther.* 8:29-41 (2003); Agarwal et al., *J. Virol* 72:3720-3728 (1998); Pollok et al., *Hum. Gene Ther.* 10:2221-2236 (1999); Quinn et al, *Hum. Gene Ther.* 9:1457-1467 (1998); see also commercially available methods such as Dynabeads™ human T cell activator products, Thermo Fisher Scientific, Waltham, Mass.)). The immune effector cells disclosed herein (e.g., T cells) can optionally be expanded prior to or after ex vivo genetic engineering. Expansion of the cells is particularly useful to increase the number of cells for administration to a subject. Such methods for expansion of cells are well known in the art (see e.g., Kaiser et al., *Cancer Gene Therapy* 22:72-78 (2015); Wolfl et al., *Nat. Protocols* 9:950-966 (2014)). Furthermore, the cells can optionally be cryopreserved after isolation and/or genetic engineering, and/or expansion of genetically engineered cells (see Kaiser et al., supra, 2015)). Methods for cyropreserving cells are well known in the art (see, for example, Freshney, *Culture of Animal Cells: A Manual of Basic Techniques*, 4th ed., Wiley-Liss, New York (2000); Harrison and Rae, *General Techniques of Cell Culture*, Cambridge University Press (1997)).

In some embodiments, provided herein are immune effector cells, such as T cells, that recognize and are sensitized to a viral antigen or a tumor antigen, and also recombinantly express a fusion protein provided herein. Such immune effector cells, such as T cells, can but need not express a CAR that binds to a viral antigen or a tumor antigen, since the cells already are antigen-specific so that their immune response (for example, cytotoxicity) is stimulated specifically by such antigen. Such immune effector cells, such as T cells, that recognize and are sensitized to a viral antigen or a tumor antigen can be obtained by known methods, by way of example, in vitro sensitization methods using naive T cells (see, for example, Wolfl et al., *Nat. Protocols* 9:950-966 (2014)) or hematopoietic progenitor cells (see van Lent et al., *J. Immunol.* 179:4959-4968 (2007)); or obtained from a subject that has been exposed to and is mounting an immune response against the antigen, such as a subject having a viral infection or a tumor antigen (i.e., in vivo sensitized immune effector cells). Methods for isolating an antigen-specific T cell from a subject are well known in the art. Such methods include, but are not limited to, a cytokine capture system or cytokine secretion assay, which is based on the secretion of cytokines from antigen stimulated T cells that can be used to identify and isolate antigen-specific, and expansion of cells in vitro (see Assenmacher et al., Cytometric Cytokine Secretion Assay, in *Analyzing T Cell Responses: How to Analyze Cellular Immune Responses Against Tumor Associated Antigens*, Nagorsen et al., eds., Chapter 10, pp. 183-195, Springer, The Netherlands (2005);

Haney et al., *J. Immunol. Methods* 369:33-41 (2011); Bunos et al., Vox Sanguinis DOI: 10.1 I ll/vox.12291 (2015); Montes et al., *Clin. Exp. Immunol.* 1 42:292-302 (2005); Adusumilli et al., *Sci TranslMed* 6:261ra151 (2014)). Such cytokines include, but are not limited to interferon-γ and tumor necrosis factor-a. The antigen-specific T cells can be isolated using well known techniques as described above for isolating immune effector cells, which include, but are not limited to, flow cytometry, magnetic beads, panning on a solid phase, and so forth. Antigen-specific T cell isolation techniques are also commercially available, which can be used or adapted for clinical applications (see, for example, Miltenyi Biotec, Cambridge, Mass.; Proimmune, Oxford, UK; and the like). Methods for T cell activation and expansion are described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041.

Generally, the T cells provided herein can be expanded by contact with a surface having attached thereto an agent that stimulates a CD3/TCR complex associated signal and a ligand that stimulates a co-stimulatory receptor on the surface of the T cells. In particular, T cell populations can be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, 1998; Haanen et al, *J. Exp. Med.* 190(9):13191328, 1999; Garland et al, *J. Immunol Meth.* 227(1-2):53-63, 1999).

5.6 Pharmaceutical Compositions

Provided herein are also pharmaceutical compositions comprising soluble fusion proteins disclosed herein. Provided herein are also pharmaceutical compositions comprising the genetically engineered immune effector cells disclosed herein. In some embodiments, the pharmaceutical composition comprises an effective amount of the fusion proteins disclosed herein and a pharmaceutically acceptable carrier. In some embodiments, the pharmaceutical composition comprises an effective amount of genetically engineered cells disclosed herein and a pharmaceutically acceptable carrier. In some embodiments, the pharmaceutical compositions are useful in immunotherapy. In some embodiments, the pharmaceutical compositions are useful in immuno-oncology. In some embodiments, the pharmaceutical compositions are useful in inhibiting tumor growth in a subject (e.g., a human patient). In some embodiments, the pharmaceutical compositions are useful in treating cancer in a subject (e.g., a human patient). In some embodiments, the pharmaceutical compositions are useful in treating viral infection.

In some embodiments, the pharmaceutical compositions provided herein comprise soluble fusion proteins provided herein. The fusion protein can be present at various concentrations. In some embodiments, the pharmaceutical compositions provided herein comprise soluble fusion proteins provided herein at 1-1000 mg/ml. In some embodiments, the pharmaceutical compositions comprise soluble fusion proteins provided herein at 10-500 mg/ml, 10-400 mg/ml, 10-300 mg/ml, 10-200 mg/ml, 10-100 mg/ml, 20-100 mg/ml, or 50-100 mg/ml. In some embodiments, the pharmaceutical compositions comprise soluble fusion proteins provided herein at 1-1000 mg/ml. In some embodiments, the pharmaceutical compositions provided herein comprise soluble fusion proteins provided herein at about 10 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 120 mg/ml, about 150 mg/ml, about 180 mg/ml, about 200 mg/ml, about 300 mg/ml, about 500 mg/ml, about 800 mg/ml, or about 1000 mg/ml.

The pharmaceutical compositions comprising genetically engineered cells disclosed herein can comprise a purified population of cells. Those skilled in the art can readily determine the percentage of cells in a cell population using various well-known methods, as described herein. The ranges of purity in cell populations comprising genetically modified cells provided herein can be from about 20% to about 25%, from about 25% to about 30%, from about 30% to about 35%, from about 35% to about 40%, from about 40% to about 45%, from about 45% to about 50%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. In some embodiments, the ranges of purity in cell populations comprising genetically modified cells provided herein can be from about 20% to about 30%, from about 20% to about 50%, from about 20% to about 80%, from about 20% to about 100%, from about 50% to about 80%, or from about 50% to about 100%. Dosages can be readily adjusted by those skilled in the art; for example, a decrease in purity may require an increase in dosage.

Provided herein are also kits for preparation of pharmaceutical compositions having the fusion protein disclosed herein. In some embodiments, the kit comprises the fusion protein disclosed herein and a pharmaceutically acceptable excipient in one or more containers. In another embodiment, the kits can comprise fusion proteins disclosed herein for administration to a subject. In specific embodiments, the kits comprise instructions regarding the preparation and/or administration of the fusion protein.

Provided herein are also kits for preparation of cells disclosed herein. In one embodiment, the kit comprises one or more vectors for generating a genetically engineered cell, such as a T cell, that expresses a fusion protein disclosed herein. The kits can be used to generate genetically engineered cells from autologous or non-autologous cells to be administered to a compatible subject. In another embodiment, the kits can comprise cells disclosed herein for administration to a subject. In specific embodiments, the kits comprise the cells disclosed herein in one or more containers. In specific embodiments, the kits comprise instructions regarding the preparation and/or administration of the genetically engineered cells.

In some embodiments, provided herein is a pharmaceutical composition comprising fusion proteins or cells provided herein wherein the composition is suitable for local administration. In some aspects, local administration comprises intratumoral injection, peritumoral injection, juxtatumoral injection, intralesional injection and/or injection into a tumor draining lymph node, or essentially any tumor-targeted injection where the antitumor agent is expected to leak into primary lymph nodes adjacent to targeted solid tumor.

Pharmaceutically acceptable carriers that can be used in compositions or formulations provided herein include any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). Depending on the route of administration, the active ingredient, i.e., genetically engineered fusion proteins or cells, can be coated in a material to protect the active ingredient from the action of acids and other natural conditions that can inactivate the active ingredient.

Provided herein are also pharmaceutical compositions or formulations that improve the stability of the fusion proteins or cells to allows for their long-term storage. In some embodiments, the pharmaceutical composition or formulation disclosed herein comprises: (a) fusion proteins or cells disclosed herein; (b) a buffering agent; (c) a stabilizing agent; (d) a salt; (e) a bulking agent; and/or (f) a surfactant. In some embodiments, the pharmaceutical composition or formulation is stable for at least 1 month, at least 2 months, at least 3 months, at least 6 months, at least 1 year, at least 2 years, at least 3 years, at least 5 years or more. In some embodiments, the pharmaceutical composition or formulation is stable when stored at 4° C., 25° C., or 40° C.

Buffering agents useful in the pharmaceutical compositions or formulations disclosed herein can be a weak acid or base used to maintain the acidity (pH) of a solution near a chosen value after the addition of another acid or base. Suitable buffering agents can maximize the stability of the pharmaceutical formulations by maintaining pH control of the formulation. Suitable buffering agents can also ensure physiological compatibility or optimize solubility. Rheology, viscosity and other properties can also dependent on the pH of the formulation. Common buffering agents include, but are not limited to, histidine, citrate, succinate, acetate and phosphate. In some embodiments, a buffering agent comprises histidine (e.g., L-histidine) with isotonicity agents and potentially pH adjustment with an acid or a base known in the art. In certain embodiments, the buffering agent is L-histidine. In certain embodiments, the pH of the formulation is maintained between about 2 and about 10, or between about 4 and about 8.

Stabilizing agents are added to a pharmaceutical product in order to stabilize that product. Such agents can stabilize proteins in a number of different ways. Common stabilizing agents include, but are not limited to, amino acids such as glycine, alanine, lysine, arginine, or threonine, carbohydrates such as glucose, sucrose, trehalose, raffinose, or maltose, polyols such as glycerol, mannitol, sorbitol, cyclodextrins or dextrans of any kind and molecular weight, or PEG. In one aspect of the invention, the stabilizing agent is chosen in order to maximize the stability of FIX polypeptide in lyophilized preparations. In certain embodiments, the stabilizing agent is sucrose and/or arginine.

Bulking agents can be added to a pharmaceutical composition or formulation in order to add volume and mass to the product, thereby facilitating precise metering and handling thereof. Common bulking agents include, but are not limited to, lactose, sucrose, glucose, mannitol, sorbitol, calcium carbonate, or magnesium stearate.

Surfactants are amphipathic substances with lyophilic and lyophobic groups. A surfactant can be anionic, cationic, zwitterionic, or nonionic. Examples of nonionic surfactants include, but are not limited to, alkyl ethoxylate, nonylphenol ethoxylate, amine ethoxylate, polyethylene oxide, polypropylene oxide, fatty alcohols such as cetyl alcohol or oleyl alcohol, cocamide MEA, cocamide DEA, polysorbates, or dodecyl dimethylamine oxide. In some embodiments, the surfactant is polysorbate 20 or polysorbate 80.

The pharmaceutical compositions or formulations disclosed herein can further comprise one or more of a buffer system, a preservative, a tonicity agent, a chelating agent, a stabilizer and/or a surfactant, as well as various combinations thereof. The use of preservatives, isotonic agents, chelating agents, stabilizers and surfactants in pharmaceutical compositions or formulations is well-known to the skilled person. Reference may be made to *Remington: The Science and Practice of Pharmacy*, 19$^{th}$ edition, 1995.

In some embodiments, the pharmaceutical composition or formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In some embodiments, the pharmaceutical composition or formulation disclosed herein is freeze-dried, to which the physician or the patient adds solvents and/or diluents prior to use.

Pharmaceutical compositions or formulations disclosed herein can also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that can be employed in the pharmaceutical compositions or formulations described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition or formulation can comprise a preservative or can be devoid of a preservative. Supplementary active compounds can be incorporated into the compositions.

Pharmaceutical compositions or formulations typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, the compositions can include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

The amount of active ingredient which can be combined with a carrier material in the pharmaceutical compositions or formulations disclosed herein can vary. In some embodiments, the amount of active ingredient which can be combined with a carrier material is the amount that produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

The pharmaceutical composition or formulation disclosed herein can be prepared with carriers that protect the active ingredient against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and poly lactic acid. Many methods for the preparation of such formulations are patented or generally known to those skilled in the art. See. e.g., *Sustained and Controlled Release Drug Delivery Systems*, J. R. Robinson, ed., Marcel Dekker, Inc., New York, 1978.

In some embodiments, the fusion proteins or cells described herein can be formulated to ensure proper distribution in vivo. For example, the blood-brain barrier (BBB) excludes many highly hydrophilic compounds. To ensure that the activate ingredient described herein cross the BBB (if desired, e.g., for brain cancers), they can be formulated, for example, in liposomes. For methods of manufacturing liposomes, see, e.g., U.S. Pat. Nos. 4,522,811; 5,374,548; and 5,399,331. The liposomes can comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al) mannosides (Umezawa et al, (1988) *Biochem. Biophys. Res. Commun.* 153: 1038); antibodies (P. G. Bloeman et al. (1995) *FEBS Lett.* 357: 140; M. Owais et al. (1995) *Antimicrob. Agents Chemother.* 39: 180); surfactant protein A receptor (Briscoe et al. (1995) *Am. J. Physiol.* 1233: 134); p120 (Schreier et al. (1994) *J. Biol. Chem.* 269:9090); see also K. Keinanen; M. L. Laukkanen (1994) *FEBS Lett.* 346: 123; J. J. Killion; I. J. Fidler (1994) *Immunomethods* 4:273.

5.7 Methods and Uses

The fusion proteins provided herein can overcome immunosuppressive microenvironment in, for example, tumor or cancer tissues and potentiate a cell-mediated immune response. As disclosed herein, fusion proteins provided herein can be administered to a subject to elicit or enhance an immune response against cancer tissue or viral infection.

In some embodiments, the fusion proteins provided herein can be administered as a single therapy. In some embodiments, the fusion proteins provided herein can be administered in combination with a second therapy to enhance to efficacy of the therapy. The second therapy can be an immune therapy, wherein the administration of the fusion proteins provided herein enhance the efficacy of the immune therapy. In some embodiments, the second therapy is a cell therapy wherein an immune effector cell or cell population is administered into a subject to activate the immune system in the subject against a pathogen (e.g., a virus) or a disease (e.g., a cancer), and the administration of the fusion proteins provided herein enhance the efficacy of the cell therapy. In some embodiments, fusion proteins provided herein can be administered to enhance the proliferation and activation of immune effector cells (e.g., T cells). In some embodiments, fusion proteins provided herein can be administered to stimulate the maturation and epitope spreading activities of antigen-presenting cells. In some embodiments, fusion proteins provided herein can be administered to enable immune effector cells to overcome immunosuppression in tumor microenvironment. The immunosuppression in tumor microenvironment can be mediated by such as the PD1/PD-L1 signaling, regulatory T cells (Tregs) or TGF-beta signaling.

For example, in some embodiments, the fusion proteins can be administered in combination with activated immune effector cells. The activated immune effector cells can be, for example, activated T cells, activated NK cells, activated NKT cells, activated macrophages, activated neutrophils, or activated granulocytes. In some embodiments, the fusion proteins provided herein can be administered with peripheral blood leukocytes (PBL), infiltrating lymphocytes (TIL), cytokine-induced killer cells (CIK), lymphokine-activated killer cells (LAK), or marrow infiltrate lymphocytes (MILs). In some other embodiments, the fusion proteins provided herein can be administered with CART cells, TCRT cells, or BiTE. As a person of ordinary skill in the art would understand, the immune therapy (e.g., cell therapy) to be administered in combination with the fusion protein disclosed herein can be any immune therapy disclosed herein or otherwise known in the art. When the fusion protein is administered in combination with a second therapy, it can be administered prior to, concurrently with, or subsequence to the second therapy. A person of ordinary skill in the art would be able to determine the actual timing of administration to ensure that a synergistic therapeutic effect is achieved.

Additionally, as disclosed herein, immune effector cells can be genetically engineered to express the fusion proteins provided herein to acquire the capacity to overcome immunosuppressive microenvironment in tumor or cancer tissues, and to generate an enhanced immune response in a subject against a disease or a pathogen. Accordingly, the present disclosure also provides methods of using the fusion proteins, genetically engineered cells or cell populations, or pharmaceutical compositions disclosed herein in the treatment of cancer or tumor, or of viral infection.

In some embodiments, provided herein are methods of treating tumor or cancer in a subject in need thereof, comprising administering to the subject a therapeutically effective amount of the fusion proteins disclosed herein. In some embodiments, provided herein are uses of the fusion proteins disclosed herein in treatment of tumor or cancer. In some embodiments, provided herein are uses of the fusion proteins provided herein for the preparation of a medicament for the treatment of tumor or cancer.

In some embodiments, provided herein are methods of treating tumor or cancer in a subject in need thereof, comprising administering to the subject a therapeutically effective amount of the genetically engineered cells disclosed herein. In some embodiments, provided herein are uses of the genetically engineered cells disclosed herein in treatment of tumor or cancer. In some embodiments, provided herein are uses of the genetically engineered cells provided herein for the preparation of a medicament for the treatment of tumor or cancer. In some embodiments, a population of cells comprising the genetically engineered cells is used in the treatment. The population of cells can be homogenous. The population of cells can be heterogenous.

In some embodiments, provided herein are methods of treating tumor or cancer in a subject in need thereof, comprising administering to the subject a therapeutically effective amount of the pharmaceutical composition disclosed herein. In some embodiments, provided herein are uses of the pharmaceutical composition disclosed herein in treatment of tumor or cancer. In some embodiments, provided herein are uses of the pharmaceutical composition provided herein for the preparation of a medicament for the treatment of tumor or cancer.

In another embodiment, the methods and uses provided herein include administering cancer antigen-specific immune effector cells to a subject in need thereof, wherein the cells recombinantly express a CAR/TCR/BiTE comprising an antigen binding domain that specifically binds the cancer antigen. In some embodiments, a fusion protein provided herein is administered in combination with the cancer antigen-specific immune effector cell. In some embodiments, the cancer antigen-specific immune effector cell also expresses a fusion protein provided herein. The cancer antigen can be any cancer antigen disclosed herein or otherwise known in the art. In some embodiments, the cancer antigen is selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin.

The present disclosure also provides methods of using the fusion proteins, the genetically engineered cells or pharmaceutical compositions disclosed herein in treating viral infection. In some embodiments, provided herein are methods of treating viral infection in a subject in need thereof, comprising administering to the subject a therapeutically effective amount of the fusion proteins, the genetically engineered cells or the pharmaceutical compositions disclosed herein. In some embodiments, provided herein are uses of the fusion proteins, the genetically engineered cells, or the pharmaceutical compositions disclosed herein in treatment of viral infection. In some embodiments, provided herein are uses of the fusion proteins, the genetically engineered cells, or the pharmaceutical compositions provided herein for the preparation of a medicament for the treatment of viral infection.

Actual dosage levels of the active ingredients (i.e. the fusion proteins or the genetically engineered immune effector cells provided herein) in the pharmaceutical compositions described herein can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts.

In some embodiments, the fusion protein disclosed herein is administered to a subject in need thereof. The fusion protein can be administered at a flat dose (flat dose regimen). In certain embodiments, the fusion protein disclosed herein is administered at a dose based on body weight. For administration of a fusion protein disclosed herein, the dosage can range from about 0.0001 to 100 mg/kg, 0.01 to 50 mg/kg, 0.01 to 10 mg/kg, 0.01 to 5 mg/kg, 1-10 mg/kg, or 1-5 mg/kg of the host body weight. For example, dosages can be 0.3 mg/kg body weight, 1 mg/kg body weight, 3 mg/kg body weight, 5 mg/kg body weight, or 10 mg/kg body weight.

Fusion proteins provided herein can be administered on multiple occasions. Intervals between single dosages can be, for example, weekly, monthly, every three months, every six months, or yearly. Intervals can also be irregular as indicated by measuring blood levels of fusion protein in the subject. In some methods, dosage is adjusted to achieve a plasma concentration of about 1-1000 pg/ml and in some methods about 25-300 pg/ml. An exemplary treatment regime entails administration once per week, once every two weeks, once every three weeks, once every four weeks, once a month, once every 3 months or once every three to 6 months. Exemplary dosage regimens for a fusion protein described herein include 1 mg/kg body weight or 3 mg/kg body weight via intravenous administration, with the fusion protein being given using one of the following dosing schedules: (i) every four weeks for six dosages, then every three months; (ii) every three weeks; (iii) 3 mg/kg body weight once followed by 1 mg/kg body weight every three weeks.

A fusion protein can be administered as a sustained release formulation, in which case less frequent administration is required. Dosage and frequency vary depending on the half-life of the fusion protein in the patient. In therapeutic applications, a relatively high dosage at relatively short intervals is sometimes required until progression of the disease is reduced or terminated, and until the patient shows partial or complete amelioration of symptoms of disease.

As disclosed herein, the fusion proteins disclosed herein can be used in combination with a cell therapy that involves activated immune effector cells to enhance the efficacy of the cell therapy. In some embodiments, immune effector cells genetically engineered to express the fusion protein disclosed herein can be used in the therapeutic methods disclosed herein. When a cell therapy is adopted, the cells provided herein can be administered as a dose based on cells per kilogram (cells/kg) of body weight of the subject to which the cells are administered. Generally the cell doses are in the range of about $10^4$ to about $10^{10}$ cells/kg of body weight, for example, about $10^5$ to about $10^9$, about $10^5$ to about $10^8$, about $10^5$ to about $10^7$, or about $10^5$ to $10^6$, depending on the mode and location of administration. In general, in the case of systemic administration, a higher dose is used than in regional administration, where the immune are administered in the region of a tumor. Exemplary dose ranges include, but are not limited to, $1\times10^4$ to $1\times10^8$, $2\times10^4$ to $1\times10^8$, $3\times10^4$ to $1\times10^8$, $4\times10^4$ to $1\times10^8$, $5\times10^4$ to $1\times10^8$, $6\times10^4$, to $1\times10^8$, $7\times10^4$ to $1\times10^8$, $8\times10^4$ to $1\times10^8$, $9\times10^4$ to $1\times10^8$, $1\times10^5$ to $1\times10^8$, for example, $1\times10^5$ to $9\times10^7$, $1\times10^5$ to $8\times10^7$, $1\times10^5$ to $7\times10^7$, $1\times10^5$ to $6\times10^7$, $1\times10^5$ to $5\times10^7$, $1\times10^5$ to $4\times10^7$, $1\times10^5$ to $3\times10^7$, $1\times10^5$ to $2\times10^7$, $1\times10^5$ to $1\times10^7$, $1\times10^5$ to $9\times10^6$, $1\times10^5$ to $8\times10^6$, $1\times10^5$ to $7\times10^6$, $1\times10^5$ to $6\times10^6$, $1\times10^5$ to $5\times10^6$, $1\times10^5$ to $4\times10^6$, $1\times10^5$ to $3\times10^6$, $1\times10^5$ to $2\times10^6$, $1\times10^5$ to $1\times10^6$, $2\times10^5$ to $9\times10^7$, $2\times10^5$ to $8\times10^7$, $2\times10^5$ to $7\times10^7$, $2\times10^5$ to $6\times10^7$, $2\times10^5$ to $5\times10^7$, $2\times10^5$ to $4\times10^7$, $2\times10^5$ to $3\times10^7$, $2\times10^5$ to $2\times10^7$, $2\times10^5$ to $1\times10^7$, $2\times10^5$ to $9\times10^6$, $2\times10^5$ to $8\times10^6$, $2\times10^5$ to $7\times10^6$, $2\times10^5$ to $6\times10^6$, $2\times10^5$ to $5\times10^6$, $2\times10^5$ to $4\times10^6$, $3\times10^5$ to $3\times10^6$ cells/kg, and the like. Such dose ranges can be particularly useful for regional administration. In a particular embodiment, cells are provided in a dose of $1\times10^5$ to $1\times10^8$, for example $1\times10^5$ to $1\times10^7$, $1\times10^5$ to $1\times10^6$, $1\times10^6$ to $1\times10^8$, $1\times10^6$ to $1\times10^7$, $1\times10^7$ to $1\times10^8$, $1\times10^5$ to $5\times10^6$, in particular $1\times10^5$ to $3\times10^6$ or $3\times10^5$ to $3\times10^6$ cells/kg for regional administration, for example, intrapleural administration. Exemplary dose ranges also can include, but are not limited to, $5\times10^5$ to $1\times10^8$, for example, $6\times10^5$ to $1\times10^8$ $7\times10^5$ to $1\times10^8$ $8\times10^5$ to $1\times10^8$ $9\times10^5$ to $1\times10^8$ $1\times10^6$ to $1\times10^8$ $1\times10^6$ to $9\times10^7$ $1\times10^6$ to $8\times10^7$, $1\times10^6$ to $7\times10^7$, $1\times10^6$ to $6\times10^7$, $1\times10^6$ to $5\times10^7$, $1\times10^6$ to $4\times10^7$, $1\times10^6$ to $3\times10^7$ cells/kg, and the like. Such does can be particularly useful for systemic administration. In a particular embodiment, cells are provided in a dose of $1\times10^6$ to $3\times10^7$ cells/kg for systemic administration. Exemplary cell doses include, but are not limited to, a dose of $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$ and so forth in the range of about $10^4$ to about $10^{10}$ cells/kg. In addition, the dose can also be adjusted to account for whether a single dose is being administered or whether multiple doses are being administered. The precise determination of what would be considered an effective dose can be based on factors individual to each subject, including their size, age, sex, weight, and condition of the particular subject, as described above. Dosages can be readily determined by those skilled in the art based on the disclosure herein and knowledge in the art.

The fusion proteins, immune effector cells, and pharmaceutical compositions provided herein can be administered to a subject by any methods known in the art, including, but not limited to, pleural administration, intravenous administration, subcutaneous administration, intranodal administration, intratumoral administration, intramuscular administration, intradermal administration, intrathecal administration, intrapleural administration, intraperitoneal administration, intracranial administration, spinal or other parenteral routes of administration, for example by injection or infusion, or direct administration to the thymus. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In some embodiments, subcutaneous administration is adopted. In some embodiments, intravenous administration is adopted. In some embodiments, oral administration is adopted. In one embodiment, the cells provided herein can be delivered regionally to a tumor using well known methods, including but not limited to, hepatic or aortic pump; limb, lung or liver perfusion; in the portal vein; through a venous shunt; in a cavity or in a vein that is nearby a tumor, and the like. In another embodiment, the cells provided herein can be administered systemically. In a preferred embodiment, the cells are administered regionally at the site of a tumor. The cells can also be administered intratumorally, for example, by direct injection of the cells at the site of a tumor and/or into the tumor vasculature. For example, in the case of malignant pleural disease, mesothelioma or lung cancer, administration is preferably by intrapleural administration (see Adusumilli et al., *Science Translational Medicine* 6(261):261ra151 (2014)). One skilled in the art can select a suitable mode of administration based on the type of cancer and/or location of a tumor to be treated. The cells can be introduced by injection or catheter. In one embodiment, the cells are pleurally administered to the subject in need, for example, using an intrapleural catheter. Optionally, expansion and/or differentiation agents can be administered to the subject prior to, during or after administration of cells to increase production of the cells provided herein in vivo.

Proliferation of the cells provided herein is generally done ex vivo, prior to administration to a subject, and can be desirable in vivo after administration to a subject (see Kaiser et al., *Cancer Gene Therapy* 22:72-78 (2015)). Cell proliferation should be accompanied by cell survival to permit cell expansion and persistence, such as with T cells.

In some embodiments, cancers or tumors that can be treated with the fusion proteins, cells, or pharmaceutical compositions disclosed herein are solid tumors. Cancers or tumors to be treated using the fusion proteins, cells, or pharmaceutical compositions provided herein comprise cancers typically responsive to immunotherapy. In some embodiments, the cancer or tumor can be carcinomas, sarcoma, melanoma (e.g., cutaneous or intraocular malignant melanoma), glioma, glioblastoma, brain and spinal cord tumors, germ cell tumors, neuroendocrine tumors, carcinoid tumors, gastric cancer, esophageal cancer, liver cancer, lung cancer (e.g., small cell lung cancer, or non-small cell lung cancer), head and neck cancer, skin cancer, nasopharyngeal cancer, kidney cancer, colorectal cancer, breast cancer, pancreatic cancer, testicular cancer, cervical cancer, ovarian cancer, uterine cancer, prostate cancer (for example, hormone refractory prostate adenocarcinoma), bladder cancer, colon cancer, endocrine cancer, basal cell cancer, squamous cell cancer, dermatofibrosarcoma protuberans, mesothelioma, Merkel cell carcinoma, bone cancer, intestinal cancer, renal cancer (for example, clear cell carcinoma), throat cancer, rectal cancer, cancer of the anal region, brain cancer, stomach cancer, carcinoma of the fallopian tubes, carcinoma of the endometrium, carcinoma of the cervix, carcinoma of the vagina, carcinoma of the vulva, cancer of the small intestine, cancer of the thyroid gland, cancer of the parathyroid gland, cancer of the adrenal gland, sarcoma of soft tissue, cancer of the urethra, cancer of the penis, solid tumors of childhood, cancer of ureter, carcinoma of the renal pelvis, neoplasm of the central nervous system (CNS), spinal axis tumor, brain stem glioma, pituitary adenoma, Kaposi's sarcoma, epidermoid cancer, fibrosarcoma, myxosarcoma, liposarcoma, chondrosarcoma, osteogenic sarcoma, synovial sarcoma, chordoma, angiosarcoma, endotheliosarcoma, lymphangiosarcoma, lymphangioendotheliosarcoma, synovioma, Ewing's tumor, leiomyosarcoma, rhabdomyosarcoma, squamous cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, bile duct carcinoma, choriocarcinoma, seminoma, embryonal carcinoma, Wilm's tumor, epithelial carcinoma, glioma, astrocytoma, medulloblastoma, craniopharyngioma, ependymoma, pinealoma, hemangioblastoma, acoustic neuroma, oligodenroglioma, schwannoma, meningioma, neuroblastoma, or retinoblastoma.

In some embodiments, cancers or tumors that can be treated with the fusion proteins, cells, or pharmaceutical compositions disclosed herein are hematological cancers. In some embodiments, the hematological cancer can be lymphoma, leukemia, multiple myeloma (MM), or myelodysplastic syndrome (MDS). In some embodiments, the hematological cancer can be polycythemia vera, acute leukemia, acute myeloid leukemia (AML), acute lymphocytic leukemia, acute myeloblastic leukemia, acute promyelocytic leukemia, acute myelomonocytic leukemia, acute monocytic leukemia, acute erythroleukemia, chronic leukemia, chronic myeloid leukemia (CIVIL), chronic myelocytic leukemia, chronic lymphocytic leukemia, chronic myelomonocytic leukemia (CMML), natural killer cell leukemia (NK leukemia), Hodgkin's disease, non-Hodgkin's disease, Waldenstrom's macroglobulinemia, lymphocytic lymphoma, primary CNS lymphoma, T-cell lymphoma, natural killer cell lymphoma (NK lymphoma), cutaneous T-Cell lymphoma (CTCL), or peripheral T-cell lymphoma (PTCL).

In cancer treatment, eliminating cancer or tumor cells in a subject can occur, but any clinical improvement constitutes a benefit. An anti-tumor effect can be manifested by a decrease in tumor volume, a decrease in the number of tumor cells, a decrease in the number of metastases, an increase in life expectancy, or amelioration of various physiological symptoms associated with the cancerous condition. An anti-tumor effect can also be manifested by the ability of the cells or pharmaceutical compositions provided herein in prevention of the occurrence of tumor in the first place. In some embodiments, an "anti-tumor effect" can be manifested by the reduction in cancer-induced immunosuppression. Clinical improvement comprises decreased risk or rate of progression or reduction in pathological consequences of the cancer or tumor. It is also understood that a method of treating cancer can include any effect that ameliorates a sign or symptom associated with cancer. Such signs or symptoms include, but are not limited to, reducing tumor burden, including inhibiting growth of a tumor, slowing the growth rate of a tumor, reducing the size of a tumor, reducing the number of tumors, eliminating a tumor, all of which can be measured using routine tumor imaging techniques well known in the art. Other signs or symptoms associated with cancer include, but are not limited to, fatigue, pain, weight loss, and other signs or symptoms associated with various cancers.

In some embodiments, the methods or uses provided herein can reduce tumor burden. Thus, administration of the fusion proteins, cells or pharmaceutical compositions disclosed herein can reduce the number of tumor cells, reduce tumor size, and/or eradicate the tumor in the subject. Methods for monitoring patient response to administration of a pharmaceutical composition disclosed herein are known in the art and can be employed in accordance with methods disclosed herein. In some embodiments, methods known in the art can be employed to monitor the patient for response to administration of therapeutic methods disclosed herein. In some embodiments, methods known in the art can be used to monitor size of lesions, and/or size of lymph nodes. As a non-limiting example, in some embodiments, contrast-enhanced CT scans can detect and/or monitor lesions and/or lymph nodes in a patient. In some embodiments, administration of a pharmaceutical composition disclosed herein can reduce the size of lesions detected by CT scans in a patient. In some embodiments, administration of a pharmaceutical composition disclosed herein can cause shrinkage of abnormal lymph nodes. In some embodiments, the methods or uses provided herein can provide for increased or lengthened survival of a subject having cancer. In some embodiments, the methods or uses provided herein can provide for an increased immune response in the subject against the cancer.

In the methods disclosed herein, a therapeutically effective amount of the fusion proteins, cells or pharmaceutical compositions disclosed herein is administered to a subject in need of cancer treatment. The subject can be a mammal. In some embodiments, the subject is a human. Another group of suitable subjects can be a subject who has a history of cancer, but has been responsive to another mode of therapy. The prior therapy can have included, but is not restricted to, surgical resection, radiotherapy, and chemotherapy. In some embodiments, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts and are suitably defined for different types of cancers. Features typical of high-risk subgroups are those in which the tumor has invaded neighboring tissues, or who show involvement of lymph nodes.

The subject can have an advanced form of disease, in which case the treatment objective can include mitigation or reversal of disease progression, and/or amelioration of side effects. The subjects can have a history of the condition, for which they have already been treated, in which case the therapeutic objective can be to decrease or delay the risk of recurrence. Additionally, refractory or recurrent malignancies can be treated using the fusion proteins, genetically engineered cells or pharmaceutical compositions disclosed herein.

For treatment, the amount administered is an amount effective for producing the desired effect. An effective amount or therapeutically effective amount is an amount sufficient to provide a beneficial or desired clinical result upon treatment. An effective amount can be provided in a single administration or a series of administrations (one or more doses). An effective amount can be provided in a bolus or by continuous perfusion. In terms of treatment, an effective amount is an amount that is sufficient to palliate, ameliorate, stabilize, reverse or slow the progression of the disease, or otherwise reduce the pathological consequences of the disease. The effective amount can be determined by the physician for a particular subject. Several factors are typically considered when determining an appropriate dosage to achieve an effective amount, including for example, age, sex and weight of the subject, the condition being treated, and the severity of the condition.

Fusion proteins, cells, or pharmaceutical compositions provided herein can be administered with medical devices known in the art. For example, in some embodiments, a needleless hypodermic injection device can be used, such as the devices disclosed in U.S. Pat. Nos. 5,399,163; 5,383,851; 5,312,335; 5,064,413; 4,941,880; 4,790,824; or 4,596,556. Examples of well-known implants and modules for use described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Combination therapy using agents with different mechanisms of action can result in additive or synergetic effects. Combination therapy can allow for a lower dose of each agent than is used in monotherapy, thereby reducing toxic side effects and/or increasing the therapeutic index of the agent disclosed herein. Combination therapy can decrease the likelihood that resistant cancer cells will develop. In some embodiments, the additional therapy results in an increase in the therapeutic index of the cells or pharmaceutical compositions described herein. In some embodiments, the additional therapy results in a decrease in the toxicity and/or side effects of cells or pharmaceutical compositions described herein. In some embodiments, the fusion proteins, cells, or pharmaceutical compositions described herein can be administered in combination with an additional therapy. In some embodiments, the additional therapy can be surgical resection, radiotherapy, or chemotherapy.

The additional therapy can be administered prior to, concurrently with, or subsequent to administration of the fusion proteins, cells, or pharmaceutical compositions described herein. Combined administration can include co-administration, either in a single pharmaceutical formulation or using separate formulations, or consecutive administration in either order but generally within a time period such that all active agents can exert their biological activities simultaneously. A person skilled in the art can readily determine appropriate regimens for administering a pharmaceutical composition described herein and an additional therapy in combination, including the timing and dosing of an additional agent to be used in a combination therapy, based on the needs of the subject being treated.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

Particular embodiments of this invention are described herein, including the best mode known to the inventors for carrying out the invention. Upon reading the foregoing description, variations of the disclosed embodiments shall become apparent to individuals working in the art, and it is expected that those skilled artisans can employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference in its entirety as if each individual publication or patent application were specifically and individually indicated to be incorporated by reference. The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which need to be independently confirmed.

A number of embodiments of the invention have been described. Nevertheless, it will be understood that various modifications may be made without departing from the spirit and scope of the invention. Accordingly, the descriptions in the Experimental are intended to illustrate but not limit the scope of invention described in the claims.

5.8 Experimental

Figure 1:
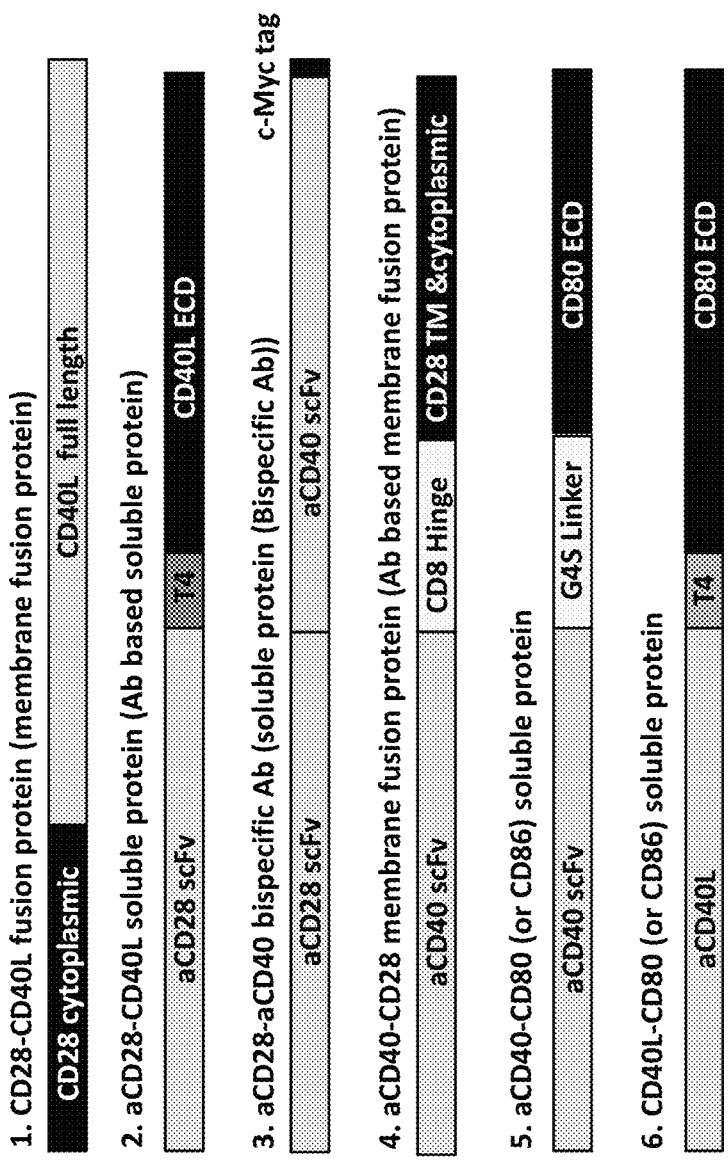
FIG. 1 is an illustrative diagram showing 4 different forms of LACO-Stim fusion protein constructs.

Costimulatory receptors or their ligands can be genetically introduced into immune effector cells (e.g., T cells) to enhance their effector functions, persistence and antitumor activity (Stephan M T et al., *Nat Med* (2007) 13(12):1440-1449; Topp M S et al. *J Exp Med* (2003) 198(6):947-955. Daniel-Meshulam I et al., *International Journal of Cancer* (2013) 133(12):2903-2913). However, T cells function inadequately within neoplastic lesions due to the expression paucity of the co-stimulatory receptors and ligands, as well as overexpression of inhibitory ligands (such as PD-L1) in the TME (Ankri C and Cohen C J, *Oncoimmunology* (2014) 3(1):e27399). Here, we have generated a panel of chimeric protein molecules called Lymphocytes-APCs Co-stimulators ("LACO-Stim"), including, for example: a. membrane fusion proteins composed of the extracellular domain of CD40 ligand (CD40L) and the cytoplasmic domain of CD28 and; b. soluble fusion proteins composed of the extracellular domain of CD40L and anti-CD28 antibodies (e.g., scFvs), c. bispecific antibodies against CD40 and CD28, d. membrane fusion proteins composed of anti-CD40 antibodies (e.g., scFvs) and the cytoplasmic domain CD28, e. soluble fusion proteins composed of anti-CD40 antibodies (e.g., scFvs) and the extracellular domain of CD80 (or CD86), and f soluble fusion proteins composed of the extracellular domain of CD40L and the extracellular domain of CD80 (or CD86) (FIG. 1). All the molecules were designed to target both CD28 signaling in T cells to boost T cell function and CD40 signaling in antigen presenting cells (APCs) such as dendritic cells, as well as CD40 signaling in macrophages and myeloid derived cells in the TEM to increase tumor antigen presentation ability of APCs and decrease suppressive effects of macrophages and myeloid derived cells in the TEM. The diagram is intended to illustrate, but not to limit, possible forms of LACO-Stim. It is understood that other T cell co-stimulatory receptors, including those disclosed herein or otherwise known in the art (e.g., 4-1BB, ICOS, CD27, OX40, DAP10, 2B4, CD30, CD2, LIGHT, GITR, TLR, DR3, and CD43) can be used to substitute CD28 as illustrated herein in forming a LACO-Stim molecule. It is also understood that other APC activators, including those disclosed herein or otherwise known in the art (e.g., CD80, CD86, CD91, DEC-205 and DC-SIGN) can be used to substitute CD40 as illustrated herein in forming a LACO-Stim molecule.

When co-introduced into human T cells with CARs or TCRs, the LACO-Stim molecules showed strong effects on increasing T cell anti-tumor functions and stimulating and maturation of APCs, macrophages and myeloid derived cells. It was found that T cells expressing the LACO-Stim molecules were able to overcome suppressive effect of TEM, such as PD1/PD-L1, Treg and TGF-beta suppressions. It was also found that LACO-Stim could orchestrate the interaction between T cells and APCs and promote epitope spreading capacity of APCs to further improve anti-tumor activities.

5.8.1 Materials and Method

Cell lines and primary human lymphocytes: A549-ESO-CBG was generated by lentivirally transducing A549 with Click beetle green (CBG) and EGFP, followed by lentiviral transduction of HLA-A2 and NY-ESO-1 antigen. Primary lymphocytes from normal donors were stimulated with CD3/CD28 Dynabeads (Life Technologies) as described (Liu X et al, *Cancer Res* (2015) 75(17):3596-3607) and cultured in R10 medium (RPMI-1640 supplemented with 10% FCS; Invitrogen). T cells were cryopreserved at day 10 in a solution of 90% FCS and 10% DMSO at 1e8 cells/vial.

Generation of TCR or CAR transferred T cells: An NY-ESO-1 8F TCR (Zhao Y et al, *J Immunol* (2005) 174(7):4415-4423) and a 4D5 ErBB2 (Her2/Neu) CAR (Liu X et al, 2015) were synthesized according to the relevant publications. For RNA electroporation, The in vitro transcription (IVT) vector was linearized by digestion with the proper restriction enzyme, and the mMESSAGE mMACHINE® T7 Ultra kit (Life Technologies) was used to generate the IVT RNA, according to the procedure provided with the kit. The frozen stimulated T cells were thawed and cultured in R/10 medium overnight before electroporation. Prior to electroporation, the T cells were washed three times with OPTI-MEM and re-suspended in OPTI-MEM at a final concentration of $1-3 \times 10^8$ cells/ml before electroporation. Subsequently, 0.1 ml of the T cells was mixed with the indicated IVT RNA and electroporated in a 2-mm cuvette (Harvard Apparatus BTX, Holliston, Mass.) using an ECM830 Electro Square Wave Porator (Harvard Apparatus BTX) (Zhao Y et al, *Cancer research* (2010) 70(22):9053-9061). For lentiviral transduction, the target genes were cloned into a lentiviral vector and T cells were transduced one day after anti-CD3/CD28 beads stimulation. A Her2 CAR and a NY-ESO-1 TCR were used as previously published (Liu X et al, 2015 and Zhao Y et al, 2005). One ScFv against CD28 (1412), and six ScFvs against CD40 (F2.103, F5.157, F5.55, 4D11, A40C and 119) were used to construct bispecific Ab or fusion proteins.

ELISA assays: Target cells were washed and suspended at $1 \times 10^6$ cells/mL in R10 medium. Of note, 100 µl of each type of target cells were added in triplicate to a 96-well round bottom plate (Corning). Effector T cells were washed and resuspended at $1 \times 10^6$ cells/mL in R10 medium and then 100 µl of T cells were combined with target cells in the indicated wells. The plates were incubated at 37° C. for 18 to 24 hours. After the incubation, supernatant was harvested and subjected to an ELISA assay (eBioscience).

Induce activation and maturation markers in immature human dendritic cells: 100 million PBMC can be suspended in 50 ml AIM-V, added to a T150 flask, and cultured at 37 C for 2 hrs to get adherent cells. After 2 hrs incubation, the flask is slightly shacked, and the suspension cells discarded. 20 ml AIM-V medium (Invitrogen) is added to the plastic-adherent cells from PBMCs and supplemented with 1,000 units/ml recombinant human GM-CSF and 500 units/ml rhIL-4. The cells are cultured in at 37° C. in a humidified $CO_2$ (5%) incubator. At day 3, GM-CSF and IL4 are added to the culture to 1000 u/ml and 500 u/ml respectively. 6 days later, recombinant human TNF-α, IL-6, IL-1β (10 ng/ml each) and peptide (10 ug/ml) are added to the immature dendritic cells (DC). At day 7, mature DCs are harvested, washed twice with AIM-V medium, and re-suspended in AIM-V medium supplemented with 5% human AB serum, at $4 \times 10^5$/ml.

5.8.2 Co-Expression of LACO-Stim Dramatically Improved CAR-T and TCR-T's Ability to Control Tumor Growth Four different forms of LACO-Stim were constructed that targeted both CD28 and CD40 (FIG. 1). 1) Fusion proteins composed of an extracellular domain of CD40L and the cytoplasmic domain of CD28; 2), Fusion proteins composed of an anti-CD28 scFv and CD40L extracellular region (Ab based soluble protein); 3) Bispecific antibodies composed of scFvs against both CD28 and CD40; and 4) Fusion proteins composed of an anti-CD40 scFv as extracellular region with CD28 intracellular region (Ab based membrane fusion protein). T cells were co-transferred with a Her2 CAR (4D5.BBZ) or a TCR against NY-ESO-1 and LACO-Stim as listed in Table 1 by RNA electroporation and CAR/LACO-Stim expression was examined by flow cytometry.

TABLE 1

Co-transfer T cells with a CAR/TCR and LACO-Stim

| EP# | CAR/TCR | LACO-Stim |
| --- | --- | --- |
| 1 | 4D5.BBZ | 1412-T4-CD40L |
| 2 | 4D5.BBZ | 1412-F2.103 |
| 3 | 4D5.BBZ | 1412-F5.157 |
| 4 | 4D5.BBZ | 1412-F5.77 |
| 5 | 4D5.BBZ | F2.103.BB |
| 6 | 4D5.BBZ | F5.157.BB |
| 7 | 4D5.BBZ | F5.77.BB |
| 8 | 4D5.BBZ | PD1-CD28 |
| 9 | 4D5.BBZ | |
| 10 | NO EP (T Cells) | |
| 11 | TCR | 1412-T4-CD40L |
| 12 | TCR | 1412-F2.103 |
| 13 | TCR | 1412-F5.157 |

TABLE 1-continued

Co-transfer T cells with a CAR/TCR and LACO-Stim

| EP# | CAR/TCR | LACO-Stim |
|---|---|---|
| 14 | TCR | 1412-F5.77 |
| 15 | TCR | F2.103.BB |
| 16 | TCR | F5.157.BB |
| 17 | TCR | F5.77.BB |
| 18 | TCR | PD1-CD28 |
| 19 | TCR | |

Figure 2:
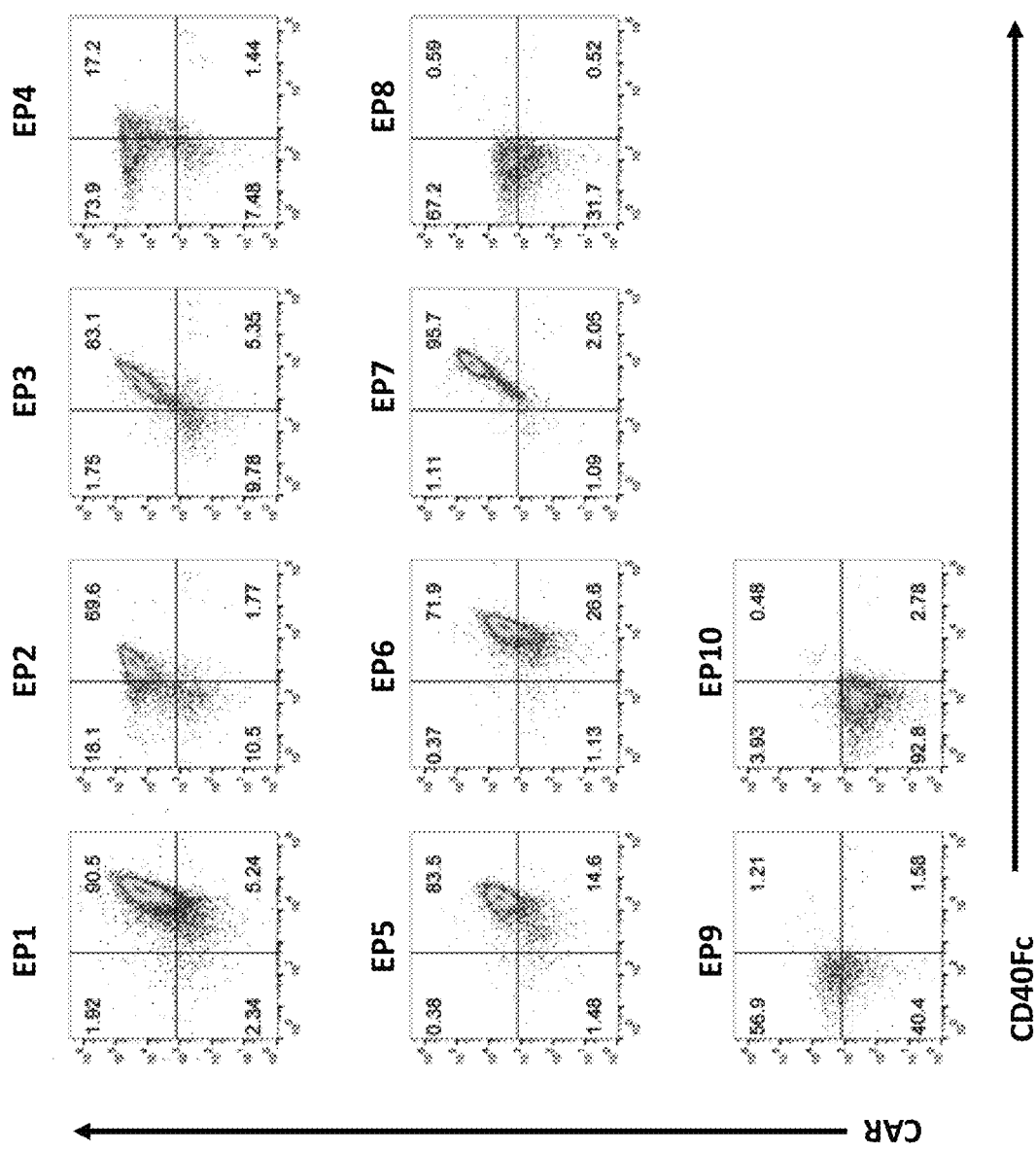
FIG. 2 shows CAR and CD40-Fc flow staining of transferred T cells. Flow cytometry detected CAR expression and binding of CD40 protein of T cells electroporated (EP) with RNA for a Her2 CAR and other constructs for different fusion proteins as indicated.

CAR staining and binding of CD40-Fc protein were detected for all the T cells co-transferred with CAR and LACO-Stim (FIG. 2). The T cell anti-tumor function was tested in an Incucyte Live-Cell Analysis System, a real-time quantitative live-cell imaging and analysis platform that enables visualization and quantification of cell behavior over time. Also used as a control was the PD1-CD28 switch receptor, a fusion protein composed of extracellular part of PD1 and intracellular part of CD28 that was previously used in an effort to rescue T cells from tumor immune suppression (Prosser M E et al, *Molecular immunology* (2012) 51(3-4): 263-272; Ankri C et al. *J Immunol* (2013) 191(8):4121-4129; Kobold S et al *J Natl Cancer Inst* (2015) 107(8); Liu X et al, *Cancer research* (2016) 76(6):1578-1590; Schlenker R et al: *Cancer research* (2017) 77(13):3577-3590).

Using a Her2 positive cancer line A549 that was transduced with HLA-A2 and NY-ESO-1 (A549-ESO) as targeting tumor cell line, it was found that compared with CAR alone or CAR co-expressed with a PD1-CD28 switch, T cells co-expressed with CAR and a LACO-Stim molecule (1412-T4-CD40L, 1412-F2.103, 1412-F5.157 or 1412-F5.77) showed improved ability to control the tumor growth, suggesting that soluble forms of LACO-Stim provided T cells with additional CD28 signaling for further T cell activation, proliferation and survival, which led to improved ability to control tumor growth (FIG. 3). When the LACO-Stim was co-introduced with an NY-ESO-1 TCR, it was found that all LACO-Stim molecules were able to help the TCR T cells to further suppress the tumor growth, compared with TCR alone or TCR co-transferred with PD1-CD28 (FIG. 4).

5.8.3 Co-Expression of LACO-Stim Further Improved CAR-T Cells' Ability to Control Tumor Growth when Tumor Cells Expressed CD40

In a separate experiment, T cells transferred with a Her2 CAR (4D5.BBZ) with LACO-Stim constructs (some new constructs for CD40L-CD28 or anti-CD40 scFv-CD28 membrane fusion proteins were added to the test), were tested against A549 tumor line transferred with either CD40, or PD-L1 or CD40+PD-L1. FIG. 5 shows CAR expression of transferred T cells and CD40 or PD-L1 expression on A549 tumor line. Cytokine productions (IFN-gamma and IL-2) for the T cells stimulated with above mentioned tumor lines were detected by ELISA assay, and it was found that most of LACO-Stim tested significantly promoted Her2 CART cells to produce both IFN-gamma (FIG. 6) and IL-2 (FIG. 7), especially when stimulated by A549 cell lines expressing CD40. CD40 was reported to be expressed in some cancers, including lung cancer (FIG. 8) and A549 was reported to express CD40, which explains even without transferring CD40 to A549 cell line, most LACO-Stim promoted Her2 CAR T cells to secrete much more cytokines than the T cells expressed only Her2 CAR. Using an Incucyte Live-Cell Analysis System, T cells that were co-transferred with 4D5.BBZ CAR and LACO-Stim as listed in Table 2 were tested on the four different A549 tumor lines, A549, A549-CD40, A549-PD-L1 and A549-CD40/PD-L1.

TABLE 2

Co-transfer T cells with a CAR and LACO-Stim

| EP# | CAR | LACO-Stim |
|---|---|---|
| 1 | CAR | F2.103.CD28 |
| 2 | CAR | F5.157.CD28 |
| 3 | CAR | F5.77.CD28 |
| 4 | CAR | F2.103.BB |
| 5 | CAR | 1412-T4-CD40L |
| 6 | CAR | 1412-F5.157 |
| 7 | CAR | PD1-CD28 |
| 8 | CAR | CAR alone |
| 9 | T Cell Alone | |

When targeting A549 tumor line expressing PD-L1, CART cells co-expressing LACO-Stim as well as CART cells co-expressing PD1-CD28 switch showed enhanced tumor inhibition as compared to CAR alone T cells, and CART cells co-expressing LACO-Stim, especially F5.77.28 (EP3) and 1412-T4-CD40L(EP5), showed stronger activity in tumor growth inhibition as compared to CART cells co-expressing PD1-CD28 switch (EP7) (FIGS. 9, 10, 11A and 11B). When A549 cells or A549 cells expressing CD40 were used as target tumors, most CART cells co-expressing CD28-CD40 LACO-Stim showed much stronger tumor inhibition than CAR alone T cells, whereas CART cells co-expressing the PD1-CD28 switch showed zero or minimal improvement in tumor growth inhibition, compared with CAR alone T cells (FIGS. 9, 10, 12A, 12B, 13A and 13B).

5.8.4 T Cells Co-Expressing LACO-Stim were Resistant to Tumor Microenvironment Inhibitions This experiment tested whether T cells receiving sufficient costimulatory signal from LACO-Stim to overcome tumor microenvironment associated inhibitions, such as PD1/PD-L1, Treg and TGF-beta (FIGS. 14-17). T cells were co-introduced with a CAR, a LACO-Stim molecule, and also PD1 (Table 3, EP1 to EP9). Same T cells not introduced with PD1 were used as controls (Table 3, EP11 to EP18).

TABLE 3

Co-transfer T cells with a CAR, LACO-Stim and PD1

| EP# | CAR | LACO-Stim | PD1 |
|---|---|---|---|
| 1 | CAR | | PD1 |
| 2 | CAR | PD1-CD28 | PD1 |
| 3 | CAR | 1412-T4-CD40L | PD1 |
| 4 | CAR | F2.103-CD28 | PD1 |
| 5 | CAR | F5.157-CD28 | PD1 |
| 6 | CAR | F5 77-CD28 | PD1 |
| 7 | CAR | F2.103-BB | PD1 |
| 8 | CAR | F5.77-BB | PD1 |
| 9 | CAR | F5.157-BB | PD1 |
| 10 | CAR | | |
| 11 | CAR | PD1-CD28 | |
| 12 | CAR | 1412-T4-CD40L | |
| 13 | CAR | F2.103-CD28 | |
| 14 | CAR | F5.157-CD28 | |
| 15 | CAR | F5 77-CD28 | |
| 16 | CAR | F2.103-BB | |
| 17 | CAR | F5.77-BB | |
| 18 | CAR | F5.157-BB | |

TABLE 3-continued

Co-transfer T cells with a CAR, LACO-Stim and PD1

| EP# | CAR | LACO-Stim | PD1 |
|---|---|---|---|
| 19 | CAR | 1412-F5.157 | |
| 20 | T cell Alone | | |

Using an Incucyte Live-Cell Analysis System, it was found that when tested against PD-L1 expressing A549 (A549-PD-L1), T cells co-transferred with a CAR and PD1 (EP1) suffered from strong suppression from the PD1/PD-L1 signaling pathway, evidenced by that those T cells nearly lost the ability to control tumor growth, similar to control T cells alone (EP20). In contrast, the T cells transferred with a CAR without PD1 (EP10) showed strong tumor growth inhibition against A549 expressing PD-L1, at the same level as the same CART cells against A549 without expressing PD-L1 (data not shown). When LACO-Stims were introduced into the PD1 expressing CART cells, by contrast, strong inhibition in tumor growth was observed. 1412-T4-CD40L (EP3) and F5.157-CD28 (EP5) completely protected PD1 expressing CART cells from the suppression from PD1/PD-L1 signaling (FIGS. 14-15). Others showed the protection at different levels. The PD1-CD28 switch (EP2) also showed complete protection of the T cells from PD1/PD-L1 inhibition.

When A549-CD40 or A549 were used as target cells, over expressing PD1 had minimal influence on the ability of T cells (expressing CAR alone or CAR/LACO-Stim) to control tumor growth. As shown, CART cells expressing PD1-CD28 switch had similar tumor controlling ability (EP2 or EP11) as compared with control cells expressing CAR alone (EP10). Meanwhile, most LACO-Stim transferred CART cells, expressing PD1 or not, showed strong tumor growth controlling ability compared with control cells expressing CAR alone (EP10) (FIGS. 14, 16&17).

The protection of T cells from PD1/PD-L1 inhibition by LACO-Stim expression was further confirmed by detecting IL-2 production of the T cells that were co-transferred with a Her2 CAR, LACO-Stim and PD1. The T cells were added to Her2-Fc, PD-L1-Fc and/or CD40-Fc proteins (at 10 ug/ml for each protein)-coated plates and cultured for 24 h. As shown in FIG. 18, expression of LACO-Stim promoted T cells to produce much more IL-2, even when the T cells were expressed exogenous PD1 and interacted with PD-L1, as long as CD40 was provided.

Regulatory T cells (Treg) are the major cell components of tumor microenvironment inhibitions. To test if LACO-Stim could rescue T cells from Treg inhibition, CD4/CD25 double positive Treg cells were added to CFSE labeled Her2 CART cells that were co-transferred with LACO-Stim and added to tissue culture plates that were pre-coated with Her2-Fc, PD-L1-Fc and/or CD40-Fc (at 10 ug/ml for each proteins). After 3 days, the T cells were harvested and subjected to flow cytometry analysis of CFSE dilution. The results showed that, when CD40 signal was provided, LACO-Stim could restore T cell proliferation in the presence of Treg to the same level where Tregs were absent (FIG. 19).

In a separate experiment, instead of adding Treg cells, TGF-beta was added to the T cells before the T cells were added to the tissue culture plates that were pre-coated with Her2-Fc, PD-L1-Fc and/or CD40-Fc (at 10 ug/ml for each protein). After 24 h, the culture supernatant was harvested and subjected to ELISA for IL-2 detection. The results showed that LACO-Stim expression promoted T cells to secrete high levels of IL-2 when CD40 signal was provided (FIG. 20).

In a further experiment, another set of CD40-CD28 LACO-Stim molecules using scFv from three different anti-CD40 antibodies (4D11, A40C and 119) were generated and co-transferred with 4D5.BBZ Her2 CAR into T cells, using PD1-CD28 and F5.77.CD28 as controls. As shown in FIG. 21A, all three LACO-Stims (4D11.CD28, A40C.CD28 and 119.CD28) enhanced CART's inhibition on tumor growth, when the tumor line A549 expressing CD40. When A549-PD-L1 cells were used as a target, CART cells with LACO-Stims (F5.77.CD28, A40C.CD28 and 119.CD28) showed strong inhibition on tumor growth (FIG. 21B).

Unlike A549 cells, which express CD40, PC3 cells were reported to be CD40 negative. PC3 cells were used in another set of experiments to confirm that expression of LACO-Stim could protect T cells from immunosuppressive effect in TME. An EGFP transduced PC3 cell line was transferred with either CD40, or PD-L1 or CD40 together with PD-L1 to generate PC3-CD40, PC3-PD-L1 and PC3-CD40-PD-L1 respectively. T cells were co-transferred with a Her2 CAR (4D5.BBZ) and PD1-CD28 switch receptor or two selected LACO-Stim (F5.77.CD28 and F2.103.CD28) and added to the PC3 cells described above. A group of T cells that were only transferred with a LACO-Stim molecule F5.77.CD28 was included in the experiment as control. The PC3 tumor growth was monitored using an Incucyte real time image system. As a positive control shown in FIG. 22A, when PC3 tumor expressed PD-L1, expression of the PD1-CD28 switch receptor significantly improved the CART tumor growth control, compared with CART Alone control. Meanwhile, CART cells expressing LACO-Stim F5.77.CD28 also showed efficient tumor growth control similar to the CART cells with PD1-CD28. When PC3-CD40 was used as target cell line, CART with F5.77.CD28 showed significantly higher activity in inhibiting tumor growth, as compared with CAR alone T cells and other groups, including CART with PD1-CD28 (FIG. 22B). When PC3 expressed both PD-L1 and CD40, both PD1-CD28 and F5.77.CD28 showed improved tumor growth control (FIG. 22C).

It was found that F5.77.CD28 LACO-Stim was able to enhance CART's ability to control tumor growth even without exogenous CD40 expression in PC3 (FIG. 22D). Together with the finding that F5.77.CD28 LACO-Stim was able to improve CART's ability to control tumor growth against PC3-PD-L1 tumors, these results indicated that after T cell-tumor interaction, tumors or T cells could be induced to express CD40, and the induced CD40 could engage with LACO-Stim molecules to improve T cells function. By contrast, the expression of PD1-CD28 switch appeared to have little effect on the ability of the CART cells to inhibit tumor growth unless the target cells were engineered to express PD-L1, indicating that although PD-L1 could be induced to express, the signal was not strong enough for the PD1-CD28 switch to improve T cell's activity in tumor growth control. It is noted that in all experiments, F5.77.CD28 expression alone (without CAR) did not affect T cells' function in tumor growth control, indicating that LACO-Stim alone could not non-specifically activate T cells.

5.8.5 LACO-Stims Promoted T Cell Proliferation

Increased T cell survival and proliferation contributed to the improved tumor growth control observed in the T cells expressing LACO-Stims. To confirm, T cell were transferred with F5.157.CD28, using T cell alone and PD1-CD28 as control, and stimulated with plate coated with OKT3 antibody, or in combination with PD-L1-Fc or CD40-Fc protein. T cell proliferation was monitored using Incucyte S3 real time imaging in the present of IncuCyte® NucLight Rapid Red Reagent. As shown in the FIG. 23 and FIG. 24, similarly low level of T cell proliferation was seen for T cell alone and T cells expressing PD1-CD28, which could be stimulated to some extent with OKT3 only or OKT3+CD40-Fc. Proliferation was further improved when T cells expressing PD1-CD28 were stimulated with OKT3+PD-L1-Fc. By contrast, T cells expressing a LACO-Stim F5.157.CD28 showed significant higher proliferation than other groups, including T cells expressing PD1-CD28 stimulated by OKT3+PD-L1, demonstrating that the LACO-Stim molecules effectively promoted T-cell proliferation.

In a further experiment, lentiviral construct was generated for T cells to permanently express a CD19 CAR and a LACO-Stim (FIG. 25). Lentiviral vectors that expressed either a CD19 CAR (CD19.BBZ) alone, a CD19 CAR and a PD1-CD28 switch receptor (CD19.BBZ+PD1-CD28), or a CD19 CAR and a LACO-Stim (CD19.BBZ+F5.157.CD28, FIG. 25) were generated and used to transduce T cells. The tumor growth control by the transduced T cells was tested in the Incucyte S3 real time imaging system using a CD19 positive leukemia cell line that expressing both EGFP and PD-L1 (Nalm6-GFP-PDL1) as target cells. As shown in FIG. 26, compared with the T cells that were only transduced with a CD19 CAR alone (CD19.BBZ), both PD1-CD28 and LACO-Stim F5.157.CD28 significantly improved the leukemia cell line growth control, again confirming that LACO-Stim expression could enhance T cells' function in inhibiting the growth of PD-L1 tumors.

5.8.6 LACO-Stims Promoted Dendritic Cells Epitope Spreading

This experiment showed that the CD28-CD40 LACO-Stims not only provided positive signal to increase T cell activities, but also activated myeloid cells, macrophages, and dendritic cells by promoting their maturation and decreasing their immunosuppressive status through the engagement of CD40 on those cells. Furthermore, engagement of CD40, together with cytokines and chemokines produced by LACO-Stims T cells, promoted the cross-presentation ability of macrophages and dendritic cells to increase epitope spreading.

Her2 CAR transferred T cells were co-transferred with LACO-Stim and co-cultured with K562 transferred with both Her2 and NY-ESO-1 antigens, in the present of dendritic cells cultured from an HLA-A201 positive donor and NY-ESO-1 TCR transferred T cells. Depending on the presence of the different cells, the cultures were grouped into three groups (as shown in FIG. 27). After 24 h co-culture, the cells were harvested and subjected to flow cytometry analysis to detect activated NY-ESO-1 TCR (vb8) positive CD8 T cells, which were the T cells activated by HLA-A201 positive dendritic cells cross-presenting NY-ESO-1, after subtracting 3-5% background that were activated Her2 CAR transferred T cells. As shown in FIG. 27, Her2 CAR T cells co-transferred with LACO-Stims showed significantly increased number of activated NY-ESO-1 TCR positive CD8 T cells, compared with CAR alone or CAR with PD1-CD28 switch receptor, demonstrating the LACO-Stim expression in T cells promoted cross-presentation of tumor antigens to the antigen specific T cells through the engagement of CD40 on the dendritic cells.

Therefore, as shown in FIG. 28, LACO-Stims (e.g., CD28-CD40 fusion proteins disclosed herein) could orchestrate T cells and APCs to facilitate and improve the antitumor activities of genetically modified T cells, providing a novel way to improve T cell therapy for cancer patients by providing more durable and efficacious treatment.

5.8.7 LACO-Stims Promoted Maturation of moDCs and Induces M1 Conversion of Macrophages T cells were transduced with lentiviral vectors carrying polynucleotide sequences encoding LACO-stim A40C.CD28 ("A40C"; SEQ ID NO:105), CD19 CAR (FMC63.BBZ; "FMC63"; SEQ ID NO:108), MSLN CAR (ss1.BBZ; "ss1"; SEQ ID NO:109), A40C-FMC63, or A40C-ss1. Expression of A40C, FMC63, and ss1 were confirmed by flow cytometry and shown in FIG. 29.

CD14+ monocytes were obtained from PBMCs of healthy donors by CD14 positive selection. Selected CD14+ monocytes were seeded in R10 completed medium and 100 ng/mL recombinant human GM-CSF and 20 ng/mL recombinant human IL-4 for 9 d to obtain monocyte-derived dendritic cell ("moDCs"). Selected CD14+ monocytes were seeded in R10 completed medium and 10 ng/mL recombinant human GM-CSF for 7 d to obtain M0 macrophages.

Autologous moDCs were co-cultured with LPS (long/mL), UTD, LACO-stim T, CAR-CD19 T, or LACO-stim-CAR-CD19 T, for 24 h. (moDC:T=1:5). moDCs were stained using mouse anti-human CD11b, CD80, CD83, CD86, and HLA-DR, to measure the levels of these maturation markers for moDC. As shown in FIG. 30, LACO-stim T cells mediated maturation of moDCs.

Cytokine secretion also indicated the maturation and activation of autologous moDCs induced by LACO-stim CAR T cells (FIG. 31). Autologous moDCs were co-cultured with LPS (10 ng/mL), UTD, LACO-stim T cells, CAR-CD19 T cells, LACO-stim-CAR-CD19 T cells, for 24 h. (moDC:T=1:5). Supernatant were assessed using ELISA to measure secretion of IL12p70, IL2, IFNγ, TNF-α, and IL1β. As shown, autologous moDCs co-cultured with LACO-stim T cells, especially LACO-stim-CAR-CD19 T cells, induced cytokines secretion.

Autologous M0 macrophages were co-cultured with LPS (10 ng/mL), IL-4 (20 ng/mL), IL-10 (20 ng/mL), UTD, LACO-stim T cells, CAR-CD19 T cells, LACO-stim-CAR-CD19 T cells, for 24 h (MAC:T=1:5). Macrophages were then subject to phenotypic analysis by staining using mouse anti-human CD11b, CD80, CD86, HLA-DR, CD206, CD163. As shown in FIG. 32, autologous LACO-stim T cells and LACO-stim-CAR-CD19 T cells induced conversion of M0 macrophage to M1 phenotype and suppressed the conversion to M2 phenotype.

Additionally, secretion of cytokines IL1β, IFN-L1, IFN-L23, IFNβ, and IL-10 was assessed by subjecting the supernatant from autologous macrophages co-cultured with LPS (10 ng/mL), UTD, LACO-stim T cells, CAR-CD19 T cells, or LACO-stim-CAR-CD19 T (24 h; MAC: T=1:5) to ELISA or BioLegend's LEGENDplex multiplex assay. As shown, autologous macrophages co-cultured with LACO-stim-CAR-CD19 induced cytokines secretion (FIG. 33).

The phagocytotic function of autologous monocyte-derived macrophages co-cultured with UTD, LACO-stim T cells, CAR-CD19 T cells, LACO-stim-CAR-CD19 T cells, or LACO-stim-CAR-MESO T cells (24 h) were measured by co-culturing with pHrodo red E. coli (K-12) for 2 h and flow cytometry. As shown, LACO-stim, LACO-stim-CAR-CD19 and LACO-stim-CAR-MESO suppressed the phagocytotic function of macrophages (FIG. 34).

To measure the non-CD19 specific tumor killing, autologous moDCs were co-cultured with non-CD19 expression tumor cell line (MOLM14-CBG) for 24 h; then, supplemented with UTD, LACO-stim T, CAR-CD19 T, or LACO-stim-CAR-CD19 T. The tumor cell line's total Green Object Integrated Intensity was recorded by Incucyte. As shown, autologous moDC(s) co-culture with LACO-stim-CAR-CD19 induce non-CD19 specific (MOLM14) killing (FIG. 35).

Similarly, macrophages were also co-cultured with MOLM14-CBG for 24 h; and then, supplemented with UTD, LACO-stim T, CAR-CD19 T, or LACO-stim-CAR-CD19 T. The tumor cell line's total Green Object Integrated Intensity was recorded by Incucyte. As shown, autologous macrophages co-cultured with LACO-stim-CAR-CD19 induced non-CD19 specific (MOLM14) killing (FIG. 36).

The activities of LACO-stim-CAR-T cells in promoting the maturation of moDCs were further confirmed. Autologous moDCs were co-cultured with tumor cell line for 24 h, supplemented with LPS (10 ng/mL), UTD, LACO-stim T cells, CAR-CD19 T cells, LACO-stim-CAR-CD19 T cells, CAR-MESO T cells, or LACO-stim-CAR-MESO T cells for 24 h. (moDC:tumor cell:T=1:1:5). moDCs were stained using mouse anti-human CD11b, CD80, CD83, CD86, and HLA-DR. As shown, LACO-stim T cells mediated maturation of moDCs; LACO-stim-CAR-CD19, and LACO-stim-CAR-MESO further stimulated the maturation (FIG. 37). Supernatants were also assessed using ELISA. As shown, production of cytokine, including IL12, IL2, IFNγ, TNF-α, and IL1β, was stimulated in the moDCs co-culture with tumor cell lines and LACO-stim T, LACO-stim-CAR-CD19 and LACO-stim-CAR-MESO (FIGS. 38A-38C).

Phenotypic analyses of macrophages upon cancer stimulation were also conducted. Autologous M0 macrophages were co-cultured with tumor cell line for 24 h. then supplemented with LPS (10 ng/mL), IL-4 (20 ng/mL), IL-10 (20 ng/mL), UTD, LACO-stim T cells, CAR-CD19 T cells, LACO-stim-CAR-CD19 T cells, CAR-MESO T cells, or LACO-stim-CAR-MESO T cells, for 24 h (MAC:tumor cell:T=1:1:5). Macrophages were stained using mouse anti-human CD11b, CD80, CD86, HLA-DR, CD206, CD163. As shown in FIGS. 39A-39B, after autologous macrophages were co-cultured with tumor cell line, LACO-stim T, LACO-stim-CAR-CD19 and LACO-stim-CAR-MESO induced the M1 conversion and suppressed the M2 conversion of the M0 macrophages.

Additionally, secretion of cytokines IL12p70, IL2, IFNγ, TNF-α, GM-CSF, IL8, IL1β, IFN-L1, IFN-L23, IFNβ, and IL-10 was assessed by subjecting the supernatant from autologous macrophages co-cultured with tumor cells LPS (10 ng/mL), UTD, LACO-stim T cells, CAR-CD19 T cells, or LACO-stim-CAR-CD19 T (24 h; MAC:T=1:1:5) to ELISA or BioLegend's LEGENDplex multiplex assay. As shown in FIGS. 40A-40C, after autologous macrophages were co-cultured with tumor cell line, LACO-stim-CAR-CD19 T induced cytokines secretion.

5.8.8 TriCD40L-CD28 LACO-Stim Molecules Enhanced Cytokine Secretion and Tumor Killing Effects of CAR T Cells T cells were co-electroporated with a 4D5-BBZ Her2 CAR (4D5) mRNA, a CD28-CD40 bispecific Ab (1412-4D11), CD40L, CD40L trimer-CD28 fusion protein (TriCD40L_8-28: CD40L trimer-CD8 transmembrane domain and CD28 cytoplasmic domain, SEQ ID NO:199; TriCD40L_28-28: CD40L trimer-CD28 transmembrane domain and CD28 cytoplasmic domain, SEQ ID NO:201), A40C-28 LACO-Stim, and/or a PD1-CD28 switch receptor (PD1-28) as indicated. CD40L expression was measured by cell cytometry and shown in FIG. 41. CD40 binding was measured by CD40-Fc detection using cell cytometry and shown in FIG. 42. CAR expression was measured by cell cytometry and shown in FIG. 43.

The T cells expressing indicated CARs, LACO-stim, LACO-stim-CARs, other molecules or other fusions were co-cultured with a tumor line A549-ESO with or without expressing CD40. IFN-gamma secretion and IL-2 secretion of T cells was measured by ELISA. As shown in FIG. 44 (IFN-gamma) and FIG. 45 (IL-2), co-expression of LACO-stim molecule TriCD40L_8-28, TriCD40L_28-28, or A40C-28 each stimulated IFN-gamma secretion and IL-2 secretion by the CAR T cell co-cultured with tumor cells (CD40-expressing or not).

Cytolytic activities of T cells co-electroporated with indicated CARs, LACO-stim, LACO-stim-CARs, other molecules or other fusions against tumor lines A549-ESO with or without expressing CD40 were measured. As shown in FIG. 46, co-expression of LACO-stim molecule TriCD40L_8-28, TriCD40L_28-28, or A40C-28 each significantly enhanced the tumor killing effects of the CART cells.

5.8.9 LACO-Stim Molecules Enhanced the Tumor Killing Effects of CAR-T Cells Targeting CD70

CD27 is a natural ligand for CD70. In this study, CARs targeting CD70, including CD27 CAR (SEQ ID NO:203) and LACO-Stim (A40C28)-CD27-CAR (SEQ ID NO:204) were constructed. As shown in FIG. 47, CD27-CAR was composed of CD27-full length (FL) and the ζ domain of CD3. A40C28-CD27-CAR was composed of CD8a signal peptide, A40C28, F2A, CD27-FL and the ζ domain of CD3.

786-O-CBG, cells derived from human renal carcinoma, were electroporated with 0 or 10 μg CD40 mRNA. The expression of CD40 was measured by flow cytometry using with PE-anti-CD40 antibody (FIG. 48A). A40C28 expression in T cells expressing A40C28-CD27-CAR was measured by flow cytometry using CD40-Fc and PE-anti-Fc antibody (FIG. 48B, upper). CD27-CAR expression was measured by flow cytometry using PE-anti-CD27 antibody (FIG. 48B, lower).

The CD70 expression levels of tumor cells were assessed by staining tumor cells with PE-anti-CD70 antibody by FACS and provided in the table below. The results are presented based on gene expression levels. To further evaluate the functions of the CD27-CAR and CD27 CAR+LACO, T cells transduced with CD27 CAR, or CD27 CAR+A40C.28 (CD27 CAR+LACO), or non-transduced (NTD) were stimulated with different tumor cells, and CD107a level was assessed by staining with PE-anti-CD107a and FITC-anti-CD8 antibodies and analyzed by FACS. The results shown percentage of CD107a positive T cells in the population of CD8 positive T cells.

TABLE 1

CD107a upregulation of T cells stimulated by the tumor cell lines

| Tumor Lines | CD70 | NTD | CD27 CAR | CD27 CAR + LACO |
|---|---|---|---|---|
| 786-O | + + + | 0.8 | 27.6 | 27.3 |
| Raji-CBG | + + + | 0.5 | 29.9 | 30.3 |
| Jeko-1-CBG | + + + | 0.9 | 23.1 | 34.4 |
| A498-CBG | + + + | 0.9 | 30.8 | 22.7 |
| U87-CBG | + + + | 1.3 | 37.8 | 32.0 |
| PC3-CBG | + + | 0.8 | 16.0 | 15.9 |
| U937 | + + | 0.2 | 7.1 | 9.0 |
| THP1 | + + | 1.7 | 20.2 | 22.2 |
| SKOV3-CBG | + | 0.3 | 3.2 | 3.3 |
| OVCAR3 | + | 0.3 | 8.8 | 6.9 |
| HS766T-CBG | + | 1.0 | 15.0 | 9.7 |
| A549-CBG | + | 0.2 | 4.4 | 3.3 |
| Detroit 562-CBG | − | 2.1 | 1.1 | 0.9 |
| H226 | − | 0.9 | 2.1 | 1.4 |
| Molm14-CBG | − | 2.1 | 0.8 | 0.7 |
| Nalm6-CBG | − | 1.0 | 0.7 | 0.7 |
| SupT1 | − | 0.2 | 0.2 | 0.2 |
| ASPC1 | − | 0.2 | 0.1 | 0.1 |

The killing effects of CD27-CAR T cells and A40C28-CD27-CAR T cells against C786-O-CBG electroporated with 0 or 10 μg CD40 mRNA were measured and shown in FIG. 49. C786-O-CBG cells (FIG. 49, upper panel) and C786-O-CBG cells electroporated with 10 μg CD40 mRNA (FIG. 49, lower panel) were cultured for 6 h in 37° C., 5% $CO_2$ incubator with UTD control, CD27-CAR T cells, or A40C28-CD27-CAR T cells at different Effect (E):Target (T) ratios (10:1, 3:1, 1:1 and 0.3:1). Killing curves were analyzed in incucyte for 72 h. As shown, co-expression of LACO-stim (A40C28) enhanced the anti-tumor effects of CD27-CAR T cells, especially at lower E:T ratio (FIG. 49).

Additionally, different CAR-T cells were incubated with 786-O-CBG cells with E:T=1:1 for 24 h, and the IL-2 levels (FIG. 50, upper panel) and IFN-gamma levels (FIG. 50, lower panel) in the supernatant were detected by ELISA. As shown in FIG. 50, co-expression of LACO-stim (A40C28) enhanced the cytokine release of CD27-CAR T cells. The same effect was observed with different tumor cell (FIGS. 51A and 51B).

The anti-tumor function of CD27-CAR T cells and A40C28-CD27-CAR T cells was also confirmed in mouse model. 1 million A549-CD70-CBG cells were inoculated into NSG-mouse by IH. After 13 days, the tumor size reached about 100 mm³. Then 3 million of CAR-T cells were injected into the mouse by IV. Tumor volume, weight of mouse, and average radiance of tumor were analyzed. As shown in FIG. 52, both CD27-CAR T cells and A40C28-CD27-CAR T cells reduced tumor burden compared to the control, as indicated by the average radiance of tumor.

5.8.10 Co-Expression of LACO-Stim Enhanced the Tumor Killing Effects of CAR-T Cells Having Targeting CD19

T cells were electroporated with CD19 CAR (FMC63.BBz; SEQ ID NO:108) mRNA, either alone or with LACO-stim 119.CD28 (119-28; SEQ ID NO:108) mRNA or A40C.CD28 (A40C-28; SEQ ID NO:105) mRNA, or switch receptor PD1-28 mRNA. The CAR expression was detected using an anti-mouse IgG Fab antibody one day after the electroporation, T cells without electroporation were used as a negative control (FIG. 53).

The percentage of CD107a expression was measured by cell cytometry in CD3+ T cells expressing the CD19 CAR (FMC63.BBz), either alone or with 119-28, A40C-28, or PD1-28, and cocultured with indicated tumor cell lines for 4 hours. As shown, stimulation by CD19-expressing tumor cells Nalm6, K-19 and Raji, but not K562 (which do not express CD19) activated the CD19 CART cells (FIG. 54).

Cytokine secretion by CD19 CART cells was also measured by ELISA. T cells were electroporated with CD19 CAR (FMC63.BBz) mRNA, either alone or with 119-28 mRNA, A40C-28 mRNA, or PD1-28 mRNA. One day after the electroporation, the CAR-T cells were overnight co-cultured with indicated tumor cell lines. The cytokine secretion in the culture supernatants was measured. As shown, co-culture with CD19 expression tumor cells stimulated IFN-gamma release (FIG. 55A) and IL2 release (FIG. 55B) by T cells expressing FMC63.BBz, and co-expression with LACO-stim further enhanced the secretion of both cytokines (FIGS. 55A and 55B)

A real-time, impedance-based cytotoxicity assay was used to evaluate the cytolytic activities of CD19-expressing A549 tumor cells when co-cultured with various CD19 CAR-T cells. A549 tumor cells were electroporated with 2 μg CD19 mRNA, and co-cultured with T cells electroporated with CD19 CAR (FMC63.BBz) mRNA, either alone or with 119-28 mRNA, A40C-28 mRNA, or PD1-28 mRNA over a 60-hour period at E:T ratio as 10:1. As shown in FIG. 56, the CD19 CAR T cells inhibited growth of CD19-expressing A549 tumor cells, and the co-expression of LACO-Stim resulted in a strong arresting effect.

The anti-tumor effects of T cells expressing CD19 CAR with or without LACO-stim were also measured using a mouse model. Specifically, T cells modified with CD19 CAR (FMC63.BBZ) or CD19 CAR and LACO (FMC63.BBZ+A40C-28) by electroporation were tested in Raji-CBG engrafted NSG mice. Mice were implanted with Raji-CBG tumor cells (1E6 cells/mouse, i.v.) on day 1. The mice were treated with T cells (i.v.) at day 4 and day 9 after Raji-CBG tumor inoculation at the dose of 2E7/mouse. Mice treated with non-transduced T cells or PBS served as control. Mice were imaged at the indicated time post tumor inoculation. As shown in FIG. 57, CD19 CAR-T cells induced regression of advanced tumors in Raji-CBG engrafted NSG mice, and the co-expression of LACO-stim further enhanced the anti-tumor effect of the CAR-T cells.

The CD19 CAR and LACO-stim can also be transduced to T cells using lentiviral vectors. T cells were transduced with lentiviral vectors carrying CD19 CAR (FMC63.BBz), FMC63.BBz-A40C-28, FMC63.BBz-119-28, or PD1-28, and the CAR expression was detected using an anti-mouse IgG Fab antibody, and the expression of A40C-28 and 119-28 was detected using CD40-Fc (FIG. 58).

5.8.11 Co-Expression of LACO-Stim Improved the Tumor Killing Effects of CAR-T Cells Having Targeting BCMA BCMA31 CART cells, LACO-BCMA31 CART cells, BCMA31-LACO CART cells, and B38M CART were generated as follows. First, lentiviruses were generated and transduced to T cells to express BCMA31.BBz (SEQ ID NO:205), LACO-BCMA31.BBz (SEQ ID NO:206), BCMA31-LACO.BBz (SEQ ID NO:207) and B38M.BBz. The expression of the CAR and LACO-stim in T cells was confirmed (FIGS. 59A-59B). As shown, expansion of the LACO-BCMA31 CART was much faster than that of BCMA31 CART and B38M CART (FIG. 60A), and the size of BCMA31 and B38M CART cells were larger than LACO-BCMA31 and NTD T cells (FIG. 60B).

We cocultured these T cells with a panel of tumor cells and examined the production of INF-γ and IL-2 by the T cells. LACO-BCMA31 produced significantly more IL-2 than other T cell types when cocultured with Jeko-1 and Raji (FIG. 61A). LACO-BCMA31 also produced significantly more INF-γ than other T cell types when cocultured with Nalm6, Jeko-1 and Raji (FIG. 61B).

We evaluated the function of these CART cells in vivo. Jeko-1 tumor cells were established in NSG mice by intravenous injection. Nine days later, T cells were injected intravenously. Bioluminescence imaging showed that BCMA31, LACO-BCMA31, BCMA31-LACO, and B38M T cells significantly reduced tumor growth. LACO-BCMA31 and BCMA31-LACO T cells had the greatest anti-tumor effect (FIGS. 62A-62B).

Next, we electroporated BCMA31.BBz, LACO, or both BCMA31.BBz and LACO mRNA into T cells for transient expression. The expression of CAR and LACO in the T cells was shown in FIG. 63 and Table 4 below.

TABLE 4

T cells electroporated with mRNA products

| | Constructs | BCMA CAR % | CAR MFI | LACO % | LACO MFI |
|---|---|---|---|---|---|
| 1 | BCMA31.BBz (10 μg) | 91.3% | 2238 | | |
| 2 | A40C.CD28 (10 μg) | | | 95.8% | 1244 |
| 3 | A40C.CD28-BCMA31.BBz (10 μg + 10 μg) | 90.5% | 2766 | 95.8% | 1234 |
| 4 | NTD | | | | |

We cocultured T cells with different tumor cells for four hours and then examined the activation of the T cells by tumor cells. CD107a were strongly activated in the BCMA31 T cells and BCMA31+LACO T cells when they were cocultured with BCMA+ tumor cells, including Nalm6, Jeko-1, RPMI-8226, and Raji (FIG. 64).

The cytotoxic T cell activities against the tumor cells were further confirmed by Incucyte Live-Cell Analysis System. BCMA31 T cells and BCMA+LACO T cells effectively controlled the growth of BCMA+ tumor cells compared with NTD and LACO alone T cells (FIGS. 65A-65D).

5.8.12 Co-Expression of LACO-Stim Improved the Tumor Killing Effects of CAR-T Cells Having Targeting Mesothelin The tumor killing effects of the provided mesothelin CARTs cells were measured in the tumor killing assay. Various mRNA-based anti-mesothelin CAR-T cells, including mock T cells (NO EP), T cells with A40C28 (SEQ ID NO:105), anti-mesothelin M12 CART cells (SEQ ID NO:208), M12 CART cells co-expressing A40C28 (SEQ ID NO:105), M32 CART cells (SEQ ID NO:209), and M32 CART cells co-expressing A40C28 were co-cultured with A549-GFP tumor cells that were electroporated with 0, 0.5 mg and 10 mg mesothelin mRNA at E/T ratio=3:1. As shown in FIG. 66, anti-mesothelin scFv-M12 and -M32 CART cells had low killing effect toward the A549 tumor cells with low mesothelin expression (0.5 mg group) and strong killing effect toward A549 tumor cells with high mesothelin expression (10 μg group), while A40C28 greatly improved the killing efficiency of CART cells to mesothelin-expressing tumor cells.

Lentivirus-based CART cells were generated using the following procedures: T cells were isolated from PBMC and activated by anti-CD3/CD28 beads (T cell:beads=1:3). At day 1, the activated T cells were transduced with lentivirus at a multiplicity of infection (MOI) of 3. At day 7, the transduction efficiency of T cell was evaluated by FACS staining. Generally, the transduction efficiency was between 10% to 70%. The CART cells were cultured up to day 14, which were used for functional study immediately or frozen and stored using liquid nitrogen.

The tumor killing effects of the lentivirus-based anti-mesothelin CART cells were measured. CART cells including mock T cells (UTD), M12 CART cells, M12+A40C28 CART cells (SEQ ID NO:210) were co-cultured with different cancer cells, including H226, OVCAR3 and MOLM14 that electroporated with 0 or 10 μg mesothelin mRNA at E/T ratio=2:1. As shown in FIG. 67, both M12 CART cells and M12+A40C28 CART cells showed strong killing effects toward mesothelin-expressing cancer cells, and the co-expression of A40C28 greatly improved the killing efficiency.

A second LACO molecule (1412-4D11; SEQ ID NO:211) was also prepared and used in the studies. Various mRNA-based anti-mesothelin CART cells were prepared, including mock T cells (NO EP), M12 CART cells, M12+1412-4D11 CART cells, M32 CART cells, and M32+1412-4D11 CART cells. These CART cells were co-cultured with A549-GFP tumor cells that were electroporated with 0 or 2 μg mesothelin mRNA at E/T ratio=10:1. As shown in FIG. 68, both M12 and M32 CART cells demonstrated effective killing toward the mesothelin-expressing A549 tumor cells (2 μg group), and the co-expression of 1412-4D11 greatly improved the killing efficiency of the CART cells.

5.8.13 Co-Expression of LACO-Stim Improved the Tumor Killing Effects of CAR-T Cells Having Targeting CD123

The cytolytic activities of the provided CD123 CARTs cells were measured in the tumor killing assay. LACO molecule A40C28 was used in this study. Various mRNA-based anti-CD123 CART cells, including mock T cells (NO EP), T cells expressing C5 CAR, C5 CAR with A40C28, C7 CAR, C7 CAR with A40C28, C11 CAR, and C11 CAR with A40C28, were co-cultured with tumor cells Molm-14, Nalm6, Jeko-1, at E/T ratio=10:1. As shown in FIG. 69, the co-expression of LACO (A40C28) improved the killing efficiency of provided CART cells against all tumor cells.

The cytolytic activity of the provided CD123 CARTs cells was further examined in A549 cells electroporated with 0, 0.1 μg or 10 μg CD123 mRNA. As shown in FIG. 70, the ectopic expression levels of CD123 in A549 cells correlated with cytolytic activities of the CD123 CARTs against such tumors. Again, the co-expression of LACO consistently enhanced the anti-tumor effects of the CART cells (FIG. 70).

IFN-γ release was detected by ELISA in the CART killing assays. As shown in FIG. 71, CD123 expressing cancer cells, such as MOLM14 cells, and especially AML cells (patient-001), promoted the release of IFN-γ by the CART cells; and the co-expression of LACO (A40C28) further enhanced such release.

5.8.14 Co-Expression of LACO-Stim Enhanced Activation of T Cells Expressing BITE T cells were electroporated with the mRNA as provided in the Table 5 below.

TABLE 5

T cells electroporated with various mRNA.

| T cell # | EP# | RNA |
|---|---|---|
| 1 | 1 | CD19-CD3 (Blina) 10 μg |
| 2 | 2 | 4D5-6-CD3 10 μg |
| 3 | 3 | A40C28 10 μg + GFP 5 μg |
| 4 | 4 | 4D11-1412 10 μg + GFP 5 μg |
| 5 | 5 | GFP 5 μg |
| 6 | 6 | CD19.BBz 10 μg |
| 7 | 7 | 4D5.BBz 10 μg |
| 8 | 8 | No EP |
| After EP, mix immediately, culture overnight ||| 
| 9 | 1 + 3 | Blina 10 μg & A40C28 10 μg + GFP 5 μg |
| 10 | 2 + 3 | 4D5-6-CD3 10 μg & A40C28 10 μg + GFP 5 μg |
| 11 | 1 + 4 | Blina 10 μg & 4D11-1412 10 μg + GFP 5 μg |
| 12 | 2 + 4 | 4D5-6-CD3 10 μg & 4D11-1412 10 μg + GFP 5 μg |
| 13 | 1 + 5 | Blina & 10 μg GFP 5 μg |
| 14 | 2 + 5 | 4D5-6-CD3 10 μg & GFP 5 μg |
| 15 | 4 + 6 | 4D11-1412 10 μg + GFP 5 μg & CD19.BBz 10 μg |
| 16 | 4 + 7 | 4D11-1412 10 μg + GFP 5 μg & 4D5.BBz 10 μg |
| 17 | 4 + 8 | 4D11-1412 10 μg + GFP 5 μg & No EP |

Note:
CD19 BiTE (Blina), Her2 BiTE (4D5-6-CD3), LACO-1 (A40C28; membrane bound), LACO-2 (4D11-1412; soluable) CD 19 CAR (FMC63.BBz), Her2 CAR (4D5.BBz)

The expression of GFP and LACO-stims of the T cells was detected by flow cytometry. The number in brackets shows T cell # in Table 5 above (FIG. 72). Note that for #9 and #10, mixing T cells expressing BiTEs (Blina or 4D5-6-CD3) with those expressing membrane bound form LACO-stim A40C-28, there was no CD40-Fc staining for GFP negative T cells expressing BiTEs. While for #11, #12, #15 and #16, mixing GFP negative T cells expressing BiTEs (Blina or 4D5-6-CD3) or CARs (CD19BBZ or 4D5BBZ) with those expressing soluble form LACO-stim 4D11-1412, there was strong CD40-Fc staining for those GFP negative T cells, indicating soluble LACO-Stim 4D11-1412 secreted by 4D11-1412 and GFP transferred T cells and loaded on the GFP negative T cells (FIG. 72). The detection of GFP and Blina or CD19 CAR (CD19-FC) of the T cells was shown in FIG. 73.

The T cells described in Table 5 above were stimulated with a CD19 positive tumor line Nalm6. GFP and CD107a expression of the T cells were detected by flow cytometry. As shown in FIG. 74, strong CD107a upregulation was observed for #1 and #6 T cells, which were transferred with either a CD19 BiTE (Blina) or a CD19 CAR, and GFP negative. The T cells transferred with LACO-Stim (A40C-28 or 4D11-1412) and GFP (#3 and #4), or GFP alone (#5) were CD107a negative, because they were unable to be activated by Nalm6. However, when these GFP positive T cells (including the LACO-expressing T cells) were mixed with T cells expressing a BiTE (Blina), they became tumor reactive as shown by high CD107a expressing (#9, #11, and #13), because the CD19 BiTEs (Blina) secreted from Blina transferred T cells were loaded onto those GFP positive T cells. This effect was not observed when these LACO-expressing GFP positive T cells were mixed with T cells expressing a CD19 CAR (#15). These results showed that T cells expressing LACO-Stim could be loaded with BiTEs, demonstrating that T cells expressing a LACO-Stim could be used in combination with a BiTE or BiTE-expressing T cells.

IL-2 secretion by the T cells described in Table 5 above stimulated with a CD19 positive tumor line Nalm6 was measured by ELISA. As shown in FIG. 75, there was no IL-2 secretion from the T cells transferred with LACO-Stim (A40C-28 or 4D11-1412) and GFP (#3 and #4), or GFP alone (#5). When those GFP positive T cells were mixed with T cells expressing a BiTEs (Blina), the GFP positive T cells secreted high levels of IL-2 (#9 and #11). Compared with T cells that were only transferred with GFP (#13), the T cells transferred with GFP and LACO-Stim (#9 and #11) secreted higher levels of IL-2. These results showed that the function of BiTE-loaded LACO-Stim-transferred T cells was superior to BiTE-loaded T cells without LACO-Stim. Moreover, When T cells transferred with CD19 CAR mixed with T cells transferred with soluble LACO-Stim 4D11-1412 (#15), the IL-2 secretion levels were higher than T cells transferred with only CD19 CAR (#6), confirming that soluble LACO-Stim could be loaded to a CART cells and enhanced CART cell function.

The GFP and Her2 BiTE (4D5-6-CD3) or CAR (4D5.BBZ) expression in the T cells described in Table 5 above was detected by flow cytometry and shown in FIG. 76. These T cells were stimulated with a Her2 positive tumor line SK-OV3. As shown in FIG. 77, strong CD107a upregulation was seen for #2 and #7, which was transferred with either a Her2 BiTE (4D5-6-CD3) or a Her2 CAR (4D5.BBZ) and GFP negative. The T cells transferred with LACO-Stim (A40C-28 or 4D11-1412) and GFP (#3 and #4), or GFP alone (#5) were unable to be activated by SK-OV3 and therefore CD107a negative. When these GFP positive T cells (including the LACO-expressing T cells) were mixed with T cells expressing a BiTEs (4D5-6-CD3), they became tumor reactive as shown by high CD107a expressing (#10, #12 and #14), because the BiTEs secreted from 4D5-6-CD3-transferred T cells were loaded onto these GFP positive T cells. By comparison, this effect was not observed when these LACO-expressing GFP positive T cells were mixed with T cells expressing a Her2 CAR (#16). Again, these results showed that T cells expressing LACO-Stim could be loaded with BiTEs, demonstrating that T cells expressing a LACO-Stim could be used in combination with a BiTE or BiTE-expressing T cells.

IL-2 secretion by the T cells described in Table 5 above stimulated with a Her2 positive tumor line SK-OV3 was measured by ELISA. As shown in FIG. 78, there was no IL-2 secretion of the T cells transferred with LACO-Stim (A40C-28 or 4D11-1412) and GFP (#3 and #4), or GFP alone (#5). When those GFP positive T cells were mixed with T cells expressing a BiTEs (4D5-6-CD3), the GFP positive T cells secreted high levels of IL-2 (#10 and #12). Compared with T cells that were only transferred with GFP (#14), the T cells transferred with GFP and LACO-Stim (#10 and #12) secreted higher levels of IL-2. These results also showed that the function of BiTE-loaded LACO-Stim-transferred T cells was superior to BiTE-loaded T cells without LACO-Stim. Moreover, When T cells transferred with Her2 CAR mixed with T cells transferred with soluble LACO-Stim 4D11-1412 (#16), the IL-2 secretion levels were higher than T cells transferred with only Her2 CAR (#7), confirming that soluble LACO-Stim could be loaded to a CART cells and enhanced CART cell function.

Taken together, this study confirmed that a synergistic effect could be achieved when LACO-expressing T cells were used in combination with BiTE or BiTE expressing T cells.

5.8.15 Exemplary Embodiments

Embodiment 1. A fusion protein comprising a first domain that activates an antigen-presenting cell (APC) and a second domain that activates an immune effector cell, wherein (i) the first domain comprises (a) a ligand that binds an activation receptor of the APC, or a receptor-binding fragment thereof, or (b) an antibody that binds an activation receptor of the APC, or an antigen-binding fragment thereof; and (ii) the second domain comprises (a) a co-stimulatory receptor of the immune effector cell, or a functional fragment thereof, (b) a co-stimulatory ligand of the immune effector cell, or a receptor-binding fragment thereof, or (c) an antibody that binds a co-stimulatory receptor of the immune effector cell, or an antigen-binding fragment thereof.

Embodiment 2. The fusion protein of Embodiment 1, wherein the APC is selected from the group consisting of a dendritic cell, a macrophage, a myeloid derived suppressor cell, a monocyte, a B cell, a T cell, and a Langerhans cell.

Embodiment 3. The fusion protein of Embodiment 1, wherein the activation receptor of the APC is selected from the group consisting of CD40, CD80, CD86, CD91, DEC-205 and DC-SIGN.

Embodiment 4. The fusion protein of Embodiment 3, wherein the first domain comprises the ligand that binds CD40, CD80, CD86, CD91, DEC-205 or DC-SIGN, or a receptor-binding fragment thereof.

Embodiment 5. The fusion protein of Embodiment 3, wherein the first domain comprises amino acids 119-261 of CD40 Ligand (CD40L).

Embodiment 6. The fusion protein of Embodiment 5, wherein the first domain comprises CD40L.

Embodiment 7. The fusion protein of any one of Embodiments 1 to 3, wherein the first domain comprises an antibody that binds the activation receptor of the APC, or an antigen-binding fragment thereof.

Embodiment 8. The fusion protein of Embodiment 7, wherein the first domain is an anti-CD40 antibody or an antigen-binding fragment thereof.

Embodiment 9. The fusion protein of Embodiment 7 or 8, wherein the first domain is a monoclonal antibody.

Embodiment 10. The fusion protein of any one of Embodiments 7 to 9, wherein the first domain is a chimeric, humanized, or human antibody.

Embodiment 11. The fusion protein of any one of Embodiments 7 to 10, wherein the first domain is a Fab, Fab', F(ab')2, Fv, scFv, (scFv)2, single chain antibody, dual variable region antibody, diabody, nanobody, or single variable region antibody.

Embodiment 12. The fusion protein of Embodiment 7, wherein the first domain is an anti-CD40 scFv having an amino acid sequence selected from the group consisting of SEQ ID NOs:75, 78, 81, 84, 87, and 90.

Embodiment 13. The fusion protein of any one of Embodiments 1 to 12, wherein the immune effector cell is selected from the group consisting of a T cell, an NK cell, an NKT cell, a macrophage, a neutrophil, and a granulocyte.

Embodiment 14. The fusion protein of any one of Embodiments 1 to 13 wherein the second domain comprises a cytoplasmic domain of the co-stimulatory receptor.

Embodiment 15. The fusion protein of Embodiment 14, wherein the co-stimulatory receptor is selected from the group consisting of CD28, 4-1BB, ICOS, CD27, OX40, DAP10, 2B4, CD30, CD2, LIGHT, GITR, TLR, DR3, and CD43.

Embodiment 16. The fusion protein of Embodiment 14, wherein the co-stimulatory receptor is CD28.

Embodiment 17. The fusion protein of Embodiment 14, wherein the co-stimulatory receptor is 4-1BB.

Embodiment 18. The fusion protein of any one of Embodiments 14 to 17, wherein the second domain further comprises the transmembrane domain of the co-stimulatory receptor.

Embodiment 19. The fusion protein of any one of Embodiments 1 to 13, wherein the second domain is a co-stimulatory ligand of the immune effector cell, or a receptor-binding fragment thereof.

Embodiment 20. The fusion protein of Embodiment 19, wherein the co-stimulatory ligand is selected from the group consisting of CD58, CD70, CD83, CD80, CD86, CD137L, CD252, CD275, CD54, CD49a, CD112, CD150, CD155, CD265, CD270, TL1A, CD127, IL-4R, GITR-L, TIM-4, CD153, CD48, CD160, CD200R, and CD44.

Embodiment 21. The fusion protein of any one of Embodiments 1 to 13, wherein the second domain is an antibody that binds the co-stimulatory receptor, or an antigen-binding fragment thereof.

Embodiment 22. The fusion protein of Embodiment 21, wherein the co-stimulatory receptor is selected from the group consisting of CD28, 4-1BB, ICOS, CD27, OX40, DAP10, 2B4, CD30, CD2, LIGHT, GITR, TLR, DR3, and CD43.

Embodiment 23. The fusion protein of Embodiment 21, wherein the co-stimulatory receptor is CD28.

Embodiment 24. The fusion protein of any one of Embodiments 21 to 23, wherein the second domain is a monoclonal antibody.

Embodiment 25. The fusion protein of any one of Embodiments 21 to 24, wherein the second domain is a chimeric, humanized, or human antibody.

Embodiment 26. The fusion protein of any one of Embodiments 21 to 25, wherein the second domain is a Fab, Fab', F(ab')2, Fv, scFv, (scFv)2, single chain antibody, dual variable region antibody, diabody, nanobody, or single variable region antibody.

Embodiment 27. The fusion protein of Embodiment 21, wherein the second domain is an anti-CD28 scFv having the amino acid sequence of SEQ ID NO:72.

Embodiment 28. The fusion protein of any one of Embodiments 1 to 27, wherein the N-terminus of the first domain is linked to the C-terminus of the second domain.

Embodiment 29. The fusion protein of any one of Embodiments 1 to 27, wherein the N-terminus of the second domain is linked to the C-terminus of the first domain.

Embodiment 30. The fusion protein of any one of Embodiments 1 to 29, wherein the first domain and the second domain are linked via a linker.

Embodiment 31. The fusion protein of Embodiment 1, wherein the first domain comprises CD40L or a receptor-binding fragment thereof, and the second domain comprises a CD28 cytoplasmic domain.

Embodiment 32. The fusion of protein of Embodiment 31, wherein the first domain comprises a CD40L.

Embodiment 33. The fusion of protein of Embodiment 31 or 32, wherein the N-terminus of the first domain is linked to the C-terminus of the second domain.

Embodiment 34. The fusion protein of Embodiment 1, wherein the first domain comprises CD40L or a receptor-binding fragment thereof and the second domain comprises an anti-CD28 antibody or an antigen-binding fragment thereof.

Embodiment 35. The fusion protein of Embodiment 34, wherein the N-terminus of the first domain is linked to the C-terminus of the second domain.

Embodiment 36. The fusion protein of Embodiment 34 or 35, wherein the two domains are linked via a T4 fibritin trimerization motif.

Embodiment 37. The fusion protein of Embodiment 1, wherein the first domain comprises an anti-CD40 antibody or an antigen-binding fragment thereof, and the second domain comprises an anti-CD28 antibody or an antigen-binding fragment thereof.

Embodiment 38. The fusion protein of Embodiment 37, wherein the N-terminus of the first domain is linked to the C-terminus of the second domain.

Embodiment 39. The fusion protein of Embodiment 1, wherein the first domain comprises an anti-CD40 antibody or an antigen-binding fragment thereof, and the second domain comprises a CD28 transmembrane region and a CD28 cytoplasmic domain.

Embodiment 40. The fusion protein of Embodiment 39, wherein the first and second domains are linked via a CD8 hinge, a CD28 hinge, or an IgG Fc region.

Embodiment 41. The fusion protein of Embodiment 39 or 40, wherein the N-terminus of the second domain is linked to the C-terminus of the first domain.

Embodiment 42. The fusion protein of Embodiment 1 having an amino acid sequence that is at least 85%, 90%, 95%, 98%, or 99% identical to SEQ ID NO:93.

Embodiment 43. The fusion protein of Embodiment 1 having an amino acid sequence that is at least 85%, 90%, 95%, 98%, or 99% identical to SEQ ID NO:94.

Embodiment 44. The fusion protein of Embodiment 1 having an amino acid sequence that is at least 85%, 90%, 95%, 98%, or 99% identical to SEQ ID NO:95.

Embodiment 45. The fusion protein of Embodiment 1 having an amino acid sequence that is at least 85%, 90%, 95%, 98%, or 99% identical to SEQ ID NO:96.

Embodiment 46. The fusion protein of Embodiment 1 having an amino acid sequence that is at least 85%, 90%, 95%, 98%, or 99% identical to SEQ ID NO:97.

Embodiment 47. The fusion protein of Embodiment 1 having an amino acid sequence that is at least 85%, 90%, 95%, 98%, or 99% identical to SEQ ID NO:98.

Embodiment 48. The fusion protein of Embodiment 1 having an amino acid sequence that is at least 85%, 90%, 95%, 98%, or 99% identical to SEQ ID NO:99.

Embodiment 49. The fusion protein of Embodiment 1 having an amino acid sequence that is at least 85%, 90%, 95%, 98%, or 99% identical to SEQ ID NO:100.

Embodiment 50. The fusion protein of Embodiment 1 having an amino acid sequence that is at least 85%, 90%, 95%, 98%, or 99% identical to SEQ ID NO:101.

Embodiment 51. The fusion protein of Embodiment 1 having an amino acid sequence that is at least 85%, 90%, 95%, 98%, or 99% identical to SEQ ID NO:102.

Embodiment 52. The fusion protein of Embodiment 1 having an amino acid sequence that is at least 85%, 90%, 95%, 98%, or 99% identical to SEQ ID NO:103.

Embodiment 53. The fusion protein of Embodiment 1 having an amino acid sequence that is at least 85%, 90%, 95%, 98%, or 99% identical to SEQ ID NO:104.

Embodiment 54. The fusion protein of Embodiment 1 having an amino acid sequence that is at least 85%, 90%, 95%, 98%, or 99% identical to SEQ ID NO:105.

Embodiment 55. The fusion protein of Embodiment 1 having an amino acid sequence that is at least 85%, 90%, 95%, 98%, or 99% identical to SEQ ID NO:106.

Embodiment 56. The fusion protein of Embodiment 1 having an amino acid sequence that is at least 85%, 90%, 95%, 98%, or 99% identical to SEQ ID NO:199.

Embodiment 57. The fusion protein of Embodiment 1 having an amino acid sequence that is at least 85%, 90%, 95%, 98%, or 99% identical to SEQ ID NO:201.

Embodiment 58. The fusion protein of Embodiment 1 having an amino acid sequence that is at least 85%, 90%, 95%, 98%, or 99% identical to SEQ ID NO:211.

Embodiment 59. The fusion protein of Embodiment 1 having an amino acid sequence selected from the group consisting of SEQ ID NOs:93-106, 199, 201 and 211.

Embodiment 60. A polynucleotide that encodes the fusion protein of any one of Embodiments 1 to 59.

Embodiment 61. A vector that comprises the polynucleotide of Embodiment 60.

Embodiment 62. The vector of Embodiment 61 that is a viral vector.

Embodiment 63. The vector of Embodiment 61 that is a retroviral vector, a lentiviral vector, an adenoviral vector, or an adeno-associated viral vector.

Embodiment 64. A genetically engineered immune effector cell that recombinantly expresses the fusion protein of any one of Embodiments 1 to 59, wherein the immune effector cell is selected from the group consisting of a T cell, an NK cell, an NKT cell, a macrophage, a neutrophil, and a granulocyte.

Embodiment 65. A genetically engineered immune effector cell comprising the polynucleotide of Embodiment 60 or the vector of any one of Embodiments 61 to 63, wherein the immune effector cell is selected from the group consisting of a T cell, an NK cell, an NKT cell, a macrophage, a neutrophil, and a granulocyte.

Embodiment 66. The cell of Embodiment 64 that further recombinantly expresses a chimeric antigen receptor (CAR), a T cell receptor (TCR) or a Bi-specific T-cell engager (BiTE), wherein the CAR, TCR or BiTE binds a tumor antigen or a viral antigen.

Embodiment 67. The cell of Embodiment 65, further comprising a polynucleotide that encodes a CAR, a TCR, or BiTE, wherein the CAR, TCR or BiTE binds a tumor antigen or a viral antigen.

Embodiment 68. The cell of Embodiment 66 or 67, wherein the CAR, TCR or BiTE binds a viral antigen selected from the group consisting of HPV, EBV, and HIV.

Embodiment 69. The cell of Embodiment 66 or 67, wherein the CAR, TCR or BiTE binds a tumor antigen selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin.

Embodiment 70. The cell of Embodiment 69, wherein the CAR has an amino acid sequence selected from the group consisting of SEQ ID NOs:107-121, and 203.

Embodiment 71. The cell of Embodiment 69, wherein the TCR has an amino acid sequence selected from the group consisting of SEQ ID NOs:122-129.

Embodiment 72. The cell of Embodiment 69, wherein the BiTE has an amino acid sequence selected from the group consisting of SEQ ID NO:130, 131, and 224.

Embodiment 73. The cell of any one of Embodiments 64 to 72, that is derived from a cell isolated from peripheral blood or bone marrow.

Embodiment 74. The cell of any one of Embodiments 64 to 72, that is derived from a cell differentiated in vitro from a stem or progenitor cell selected from the group consisting of a T cell progenitor cell, a hematopoietic stem and progenitor cell, a hematopoietic multipotent progenitor cell, an embryonic stem cell, and an induced pluripotent cell.

Embodiment 75. The cell of any of Embodiments 64 to 74 that is a T cell.

Embodiment 76. The T cell of Embodiment 75 that is a cytotoxic T cell, a helper T cell, or a gamma delta T, a CD4+/CD8+ double positive T cell, a CD4+ T cell, a CD8+ T cell, a CD4/CD8 double negative T cell, a CD3+ T cell, a naive T cell, an effector T cell, a cytotoxic T cell, a helper T cell, a memory T cell, a regulator T cell, a Th0 cell, a Th1 cell, a Th2 cell, a Th3 (Treg) cell, a Th9 cell, a Th17 cell, a Thαβ helper cell, a Tfh cell, a stem memory TSCM cell, a central memory TCM cell, an effector memory TEM cell, an effector memory TEMRA cell, or a gamma delta T cell.

Embodiment 77. A population of the genetically engineered immune effector cell of any one of Embodiments 64 to 72 that are derived from cells isolated from peripheral blood mononuclear cells (PBMC), peripheral blood leukocytes (PBL), tumor infiltrating lymphocytes (TIL), cytokine-induced killer cells (CIK), lymphokine-activated killer cells (LAK), or marrow infiltrate lymphocytes (MILs).

Embodiment 78. A pharmaceutical composition comprising the fusion protein of any one of Embodiments 1 to 59, and a pharmaceutically acceptable excipient.

Embodiment 79. A pharmaceutical composition comprising the cell or population of cells of any one of Embodiments 64 to 77, and a pharmaceutically acceptable excipient.

Embodiment 80. Use of the fusion protein of any one of Embodiments 1 to 56 in cancer treatment.

Embodiment 81. Use of the fusion protein of any one of Embodiments 1 to 56 for the preparation of a medicament for the treatment of cancer.

Embodiment 82. The use of Embodiment 80 or 81, wherein the fusion protein is used in combination with an immune effector cell.

Embodiment 83. The use of Embodiment 82, wherein the immune effector cell is selected from the group consisting of a CAR T cell, a TCRT cell, a TIL, a CIK, a LAK, and a MIL.

Embodiment 84. Use of the cell or population of cells of any one of Embodiments 64 to 77 in cancer treatment.

Embodiment 85. Use of the cell or population of cells of any one of Embodiments 64 to 77 for the preparation of a medicament for the treatment of cancer.

Embodiment 86. Use of the pharmaceutical composition of Embodiment 78 or 79 in cancer treatment.

Embodiment 87. Use of the pharmaceutical composition of Embodiment 78 or 79 for the preparation of a medicament for the treatment of cancer.

Embodiment 88. The use of any one of Embodiments 80 to 87, wherein the fusion protein, the cell, population of cells, or pharmaceutical composition is used in combination with an additional therapy.

Embodiment 89. A method of treating cancer in a subject in need thereof comprising administering a therapeutically effective amount of the fusion protein of any one of Embodiments 1 to 59 to the subject.

Embodiment 90. The method of Embodiment 89, further comprising administering a cell therapy to the subject.

Embodiment 91. The method of Embodiment 90, wherein the cell therapy is selected from the group consisting of a CAR T therapy, a TCRT therapy, a TIL therapy, a CIK therapy, a LAK therapy, and a MIL therapy.

Embodiment 92. A method of treating cancer in a subject in need thereof comprising administering a therapeutically effective amount of the cell or population of cells of any one of Embodiments 64 to 77 to the subject.

Embodiment 93. A method of treating cancer in a subject in need thereof comprising administering a therapeutically effective amount of the pharmaceutical composition of Embodiment 78 or 79 the subject.

Embodiment 94. The method of any one of Embodiments 89 to 93, further comprising administering an additional therapy to the subject.

Embodiment 95. The method of any one of Embodiments 89 to 94, wherein the subject is a human.

Embodiment 96. The use or method of any one of Embodiments 80 to 95, wherein the fusion protein, the cell, population of cells, or pharmaceutical composition reduces cancer-induced immunosuppression.

Embodiment 97. The use or method of any one of Embodiments 80 to 96, wherein the cancer is a hematological cancer.

Embodiment 98. The use or method of any one of Embodiments 80 to 96, wherein the cancer is a solid tumor.

Embodiment 99. A method of genetically engineering an immune effector cell comprising transferring the polynucleotide of Embodiment 60 into the cell.

Embodiment 100. The method of Embodiment 99, wherein the polynucleotide is transferred via electroporation.

Embodiment 101. The method of Embodiment 99, wherein the polynucleotide is transferred via viral transduction.

Embodiment 102. The method of Embodiment 101, comprising using a lentivirus, a retrovirus, an adenovirus, or an adeno-associated virus for the viral transduction.

Embodiment 103. The method of Embodiment 99, wherein the polynucleotide is transferred using a transposon system.

Embodiment 104. The method of Embodiment 103, wherein the transposon system is Sleeping Beauty or PiggyBac.

Embodiment 105. The method of Embodiment 99, wherein the polynucleotide is transferred using gene-editing.

Embodiment 106. The method of Embodiment 105, wherein the polynucleotide is transferred using a CRISPR-Cas system, a ZFN system, or a TALEN system.

Embodiment 107. The method of any one of Embodiments 99 to 106, wherein the immune effector cell is selected from the group consisting of a T cell, an NK cell, an NKT cell, a macrophage, a neutrophil, and a granulocyte cell.

6. REFERENCE TO SEQUENCE LISTING SUBMITTED ELECTRONICALLY

This application incorporates by reference a Sequence Listing with this application entitled "613A001US02.XML" created on Aug. 20, 2022 and having a size of 386,740 bytes.

What is claimed is:

1. A polynucleotide that encodes a fusion protein comprising a first domain that activates an antigen-presenting cell (APC) and a second domain that activates an immune effector cell, wherein
   (i) the first domain comprises an antibody that binds an activation receptor of the APC, or an antigen-binding fragment thereof; and
   (ii) the second domain comprises a co-stimulatory receptor of the immune effector cell, or a functional fragment thereof;
wherein the first domain is an anti-CD40 scFv having an amino acid sequence selected from the group consisting of SEQ ID NOs:75, 78, 81, 87, and 90.

2. The polynucleotide of claim 1, wherein the anti-CD40 scFv has the amino acid sequence of SEQ ID NO:75.

3. The polynucleotide of claim 1, wherein the anti-CD40 scFv has the amino acid sequence of SEQ ID NO:78.

4. The polynucleotide of claim 1, wherein the anti-CD40 scFv has the amino acid sequence of SEQ ID NO:81.

5. The polynucleotide of claim 1, wherein the anti-CD40 scFv has the amino acid sequence of SEQ ID NO:87.

6. The polynucleotide of claim 1, wherein the anti-CD40 scFv has the amino acid sequence of SEQ ID NO:90.

7. The polynucleotide of claim 1, wherein the second domain comprises a cytoplasmic domain of the co-stimulatory receptor, wherein the co-stimulatory receptor is selected from the group consisting of CD28, 4-1BB, ICOS, CD27, OX40, DAP10, 2B4, CD30, CD2, LIGHT, GITR, TLR, DR3, and CD43.

8. The polynucleotide of claim 7, wherein the second domain further comprises the transmembrane region of the co-stimulatory receptor.

9. The polynucleotide of claim 7, wherein the co-stimulatory receptor is CD28.

10. The polynucleotide of claim 1, wherein the first domain and the second domain are linked via a linker, and wherein the N-terminus of the first domain is linked to the C-terminus of the second domain.

11. The polynucleotide of claim 1, wherein the first domain and the second domain are linked via a linker, and wherein the N-terminus of the second domain is linked to the C-terminus of the first domain.

12. The polynucleotide of claim 1, wherein the second domain comprises a CD28 transmembrane region and a CD28 cytoplasmic domain.

13. The polynucleotide of claim 1, wherein the first and second domains are linked via a CD8 hinge, a CD28 hinge, or an IgG Fc region.

14. The polynucleotide of claim 1, wherein the fusion protein has an amino acid sequence that is at least 85%, at least 90%, at least 95%, at least 98%, at least 99%, or 100% identical to a sequence selected from the group consisting of SEQ ID NOs:98-103, and 105-106.

15. The polynucleotide of claim 1 wherein the fusion protein has an amino acid sequence that is at least 85%, at least 90%, at least 95%, at least 98%, at least 99%, or 100% identical to SEQ ID NO:105.

16. The polynucleotide of claim 1, wherein the fusion protein has the amino acid sequence of SEQ ID NO:98.

17. The polynucleotide of claim 1, wherein the fusion protein has the amino acid sequence of SEQ ID NO:99.

18. The polynucleotide of claim 1, wherein the fusion protein has the amino acid sequence of SEQ ID NO:100.

19. The polynucleotide of claim 1, wherein the fusion protein has the amino acid sequence of SEQ ID NO:101.

20. The polynucleotide of claim 1, wherein the fusion protein has the amino acid sequence of SEQ ID NO:102.

21. The polynucleotide of claim 1, wherein the fusion protein has the amino acid sequence of SEQ ID NO:103.

22. The polynucleotide of claim 1 wherein the fusion protein has the amino acid sequence of SEQ ID NO:105.

23. The polynucleotide of claim 1, wherein the fusion protein has the amino acid sequence of SEQ ID NO:106.

24. A vector that comprises the polynucleotide of claim 1.

25. A genetically engineered immune effector cell comprising the polynucleotide of claim 1, wherein the immune effector cell is selected from the group consisting of a T cell, an NK cell, an NKT cell, a macrophage, a neutrophil, and a granulocyte.

26. The cell of claim 25, further comprising a polynucleotide that encodes a CAR, a TCR, or bispecific T-cell engager, wherein the CAR, TCR or bispecific T-cell engager binds a tumor antigen or a viral antigen.

27. The cell of claim 26, wherein the CAR, TCR or bispecific T-cell engager binds a tumor antigen selected from the group consisting of Her2, NY-ESO-1, CD19, CD20, CD22, PSMA, c-Met, GPC3, IL13ra2, EGFR, CD123, CD7, GD2, PSCA, EBV16-E7, H3.3, EGFRvIII, BCMA, and Mesothelin.

28. The cell of claim 27, wherein the CAR has an amino acid sequence selected from the group consisting of SEQ ID NOs:107-121, and 203; the TCR has an amino acid sequence selected from the group consisting of SEQ ID NOs:122-129; or the bispecific T-cell engager has an amino acid sequence selected from the group consisting of SEQ ID NOs:130, 131, and 224.

29. The cell of claim 25, wherein the cell is derived from a cell isolated from peripheral blood or bone marrow, or is derived from a cell differentiated in vitro from a stem or progenitor cell selected from the group consisting of a T cell progenitor cell, a hematopoietic stem and progenitor cell, a hematopoietic multipotent progenitor cell, an embryonic stem cell, and an induced pluripotent cell.

30. The cell of claim 25 that is a T cell, wherein the T cell is a cytotoxic T cell, a helper T cell, or a gamma delta T, a CD4+/CD8+ double positive T cell, a CD4+ T cell, a CD8+ T cell, a CD4/CD8 double negative T cell, a CD3+ T cell, a naive T cell, an effector T cell, a cytotoxic T cell, a helper T cell, a memory T cell, a regulator T cell, a Th0 cell, a Th1 cell, a Th2 cell, a Th3 (Treg) cell, a Th9 cell, a Th17 cell, a Thαβ helper cell, a Tfh cell, a stem memory TSCM cell, a central memory TCM cell, an effector memory TEM cell, an effector memory TEMRA cell, or a gamma delta T cell.

31. A population of the genetically engineered immune effector cell of claim 25 that are derived from cells isolated from peripheral blood mononuclear cells (PBMC), peripheral blood leukocytes (PBL), tumor infiltrating lymphocytes (TIL), cytokine-induced killer cells (CIK), lymphokine-activated killer cells (LAK), or marrow infiltrate lymphocytes (MILs).

32. A method of treating cancer in a subject in need thereof comprising administering a therapeutically effective amount of the cells of claim 25 to the subject.

33. The method of claim 32, wherein the subject is a human.

34. A method of genetically engineering an immune effector cell comprising transferring the polynucleotide of claim 1 into the cell.

35. The method of claim 34, wherein the polynucleotide is transferred via electroporation, viral transduction, a transposon system, or gene editing.

36. The method of claim 34, wherein the immune effector cell is selected from the group consisting of a T cell, an NK cell, an NKT cell, a macrophage, a neutrophil, and a granulocyte cell.

* * * * *